12 Claims, No Drawings

(12) United States Patent
Chen et al.

(10) Patent No.: US 10,106,515 B2
(45) Date of Patent: Oct. 23, 2018

(54) 1-(CYCLOPENT-2-EN-1-YL)-3-(2-HYDROXY-3-(ARYLSULFONYL)PHENYL) UREA DERIVATIVES AS CXCR2 INHIBITORS

(71) Applicant: GLAXOSMITHKLINE INTELLECTUAL PROPERTY DEVELOPMENT LIMITED, Brentford, Middlesex (GB)

(72) Inventors: Weichun Chen, Shanghai (CN); Ebere F Igboko, Shanghai (CN); Xichen Lin, Shanghai (CN); Hongfu Lu, Shanghai (CN); Feng Ren, Shanghai (CN); Paul Bryan Wren, Uxbridge Middlesex (GB); Zhongmiao Xu, Shanghai (CN); Ting Yang, Shanghai (CN); Lingdong Zhu, Shanghai (CN)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/314,124

(22) PCT Filed: May 27, 2015

(86) PCT No.: PCT/EP2015/061618
§ 371 (c)(1),
(2) Date: Nov. 28, 2016

(87) PCT Pub. No.: WO2015/181186
PCT Pub. Date: Dec. 3, 2015

(65) Prior Publication Data
US 2017/0190681 A1 Jul. 6, 2017

(30) Foreign Application Priority Data

May 29, 2014 (WO) ............... PCT/CN2014/000545
Jul. 31, 2014 (WO) ............... PCT/CN2014/083380
Apr. 30, 2015 (WO) ............... PCT/CN2015/077947

(51) Int. Cl.
*C07D 307/18* (2006.01)
*C07D 241/04* (2006.01)

(52) U.S. Cl.
CPC ......... *C07D 307/18* (2013.01); *C07D 241/04* (2013.01); *C07C 2101/10* (2013.01)

(58) Field of Classification Search
None
See application file for complete search history.

(56) References Cited

FOREIGN PATENT DOCUMENTS

| WO | WO 2001/068084 A1 | 9/2001 |
| WO | WO 2007/124424 A2 | 11/2007 |
| WO | WO 2016/016178 A1 | 2/2016 |

OTHER PUBLICATIONS

Jamieson, et al., Inhibition of CXCR2 profoundly suppresses inflammation-driven and spontaneous tumorigenesis. The Journal of Clinical Investigation, 2012, 122, 3127-3144.*
Schinke et al., IL8-CXCR2 pathway inhibition as a therapeutic strategy against MDS and AML stem cells. Blood, 2015, 125, 3144-3152.*
Stadtmann et al., CXCR2: from bench to bedside. Frontier in Immunology, 2012, 3, 1-12.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*

* cited by examiner

*Primary Examiner* — Po-Chih Chen
(74) *Attorney, Agent, or Firm* — Leah M. Octavio; Andrea V. Lockenour

(57) ABSTRACT

The invention relates to 1-(3-sulfonylphenyl)-3-(cyclopent-2-en-1-yl)urea derivatives, and their use in treating or preventing diseases and conditions mediated by the CXCR2 receptor In addition, the invention relates to compositions containing the derivatives and processes for their preparation.

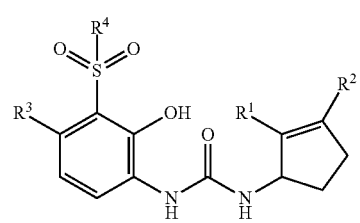

1-(CYCLOPENT-2-EN-1-YL)-3-(2-HYDROXY-3-(ARYLSULFONYL)PHENYL) UREA DERIVATIVES AS CXCR2 INHIBITORS

This application is a 371 of International Application No PCT/EP 2015/061618, filed 27 May 2015, which claims priority of PCT/CN2014/000545 filed 29 May 2014, PCT/CN2014/083380 filed 31 Jul. 2014 and PCT/CN2015/077947 filed 30 Apr. 2015.

FIELD OF INVENTION

The invention relates to 1-(cyclopent-2-en-1-yl)-3-(2-hydroxy-3-(arylsulfonyl)phenyl)urea derivatives and their use in treating or preventing diseases and conditions mediated by the CXCR2 receptor. In addition, the invention relates to compositions containing the derivatives and processes for their preparation.

BACKGROUND OF THE INVENTION

Chemokines are a family of low molecular weight chemotactic cytokines secreted by cells. Chemokines regulate a broad spectrum of cellular functions and exert their actions by binding to chemokine receptors which are G protein-coupled receptors. Chemokines are divided into different classes based on the positions of the N-terminal cysteine residues within the protein (Charo et al. (2006) *N. Engl. J. Med.* 354: 610-621). The CXC class of chemokines contains the CXC motif in which the first two cysteines are separated by a non-conserved amino acid. The CXC chemokines may be further divided into the ELR+ and the ELR− subclasses based on the presence or absence of the ELR (glutamic acid-leucine-arginine) motif before the first cysteine of the CXC motif. ELR+ CXC chemokines include interleukin-8 (IL-8; also known as CXCL8), GROα (CXCL1), GROβ (CXCL2), GROγ (CXCL3), neutrophil-activating protein-2 (NAP-2 or CXCL7), epithelial cell-derived neutrophil-activating peptide-78 (ENA-78 or CXCL5) and granulocyte chemotactic protein-2 (GCP-2 or CXCL6). An important function of ELR+ CXC chemokines is to recruit neutrophils to sites of inflammation and induce granule exocytosis and the respiratory burst. All ELR+ CXC chemokines bind to the chemokine receptor CXCR2 (also known as IL-8 receptor β), while IL-8 and GCP-2 bind to CXCR1 (also known as IL-8 receptor α).

CXCR2 is expressed on a variety of cells including neutrophils, keratinocytes, mast cells, eosinophils, macrophages, endothelial cells and neurons including sensory neurons. CXCR2 has been implicated in the pathology of various diseases including inflammatory diseases such as multiple sclerosis, rheumatoid arthritis, psoriasis, chronic obstructive pulmonary disease, inflammatory myopathies and atherosclerosis, neurodegenerative diseases such as Alzheimer's disease and Parkinson's disease, neurodegenerative infectious diseases such as HIV and cancer (Liu et al. (2010) *Nat. Neurosci.* 13:19-26; Mihara et al. (2005) *Eur. J. Immunol.* 35: 2573-82; Ono et al. (2003) *J. Allergy Clin. Immunol.* 111:1185-99; Xia & Hyman (2002) *J. Neuroimmunol.* 122: 55-64; Edman et al. (2008) *Stem Cells* 26:1891-1900; Dorsam & Gutkind (2007) *Nature Rev. Cancer* 7:79-94, Manjavachi et al. (2010), European Journal of Pain, 14: 23-31, Langford et al., J Neurovirol. (2002), 8(6):625-38, De Paepe et al., Acta Neuropathol. (2005), 109(6):576-82.)

Chemotherapy induced peripheral neuropathy (CIPN) is defined as the damage to the peripheral nervous system experienced by patients receiving chemotherapy treatment regimens. CIPN is a prevalent major dose-limiting side effect of many chemotherapeutic agents, including platinum compounds (for example, oxaliplatin), taxanes, *vinca* alkaloids, thalidomide and newer agents such as bortezomib [Balayssac, *Expert Opin. Drug Saf.*, 10, 407-417, 2011)]. This represents a significant limitation to treatment in many diverse cancers, as end-organ neurotoxicity and neuropathy can require discontinuation of effective therapy with a high impact on a patient's quality of life.

For example, oxaliplatin containing treatment regimens (e.g. 85 mg/m$^2$ every 2 weeks) produce an immediate 'cold' sensitive transient paraesthesia and limb muscular spasm in 95% of patients that develops into a symmetric, axonal, sensory distal primary neuropathy without motor involvement [Argyriou, *Cancer Treatment Reviews*, 43, 368-377 (2008)].

Oxaliplatin uptake and platinum accumulation within the dorsal root ganglion (DRG) and its sensory neurons is a major determinant of the neurotoxicity of oxaliplatin (Jong, *J. Pharmacol. Exp. Ther.*, 338(2):537-47 (2011). In addition, inflammatory cascade activation plays a role in the initiation and progression of CIPN with immune cell infiltration into the injured neuronal environment [Wang, *Cytokine*, 59, 3-9 (2012)].

The pro-inflammatory chemokine receptor CXCR2 is expressed in sensory neurons and its ligands have been implicated in regulating increases in sodium and potassium currents that govern neuronal excitability [Wang, Mol. Pain, 24, 38 (2008); Yang, *Mol. Pain*, 5, 26 (2009)]. In peripheral neuronal injuries, the recruitment of CXCR2+ pro-inflammatory secreting immune cells is also known to be involved in both acute and persistent pain and blocked by CXCR2 antagonism [Manjavachi, *Eur. J. Pain*, 14, 23-31 (2010); Kiguchi, *J. Pharmacol. Exp. Ther.*, 340, 577-587 (2012); Stadtmann & Zarbock, Front. Immunol., 3, 263 (2012)]. CXCR2 ligands have been shown to regulate the function of TRPv1 channels [Dong, *Neurosci. Bull.*, 28, 155-164 (2012)] involved in nociceptive processing and stimulate calcium influx and release of the pain mediating peptide calcitonin gene-related peptide (CGRP) in sensory neurons (Qin, *J. Neurosci. Res.*, 82, 51-62 (2005). Human peripheral nerve explants and Schwann cell cultures express [Ozaki, *NeuroReport*, 19, 31-35 (2008)] and secrete CXCR2 pro-inflammatory cytokines like IL-8 [Rutkowski, *J. Neuroimmunol.*, 101, 47-60 (1999)] which is significantly elevated in diabetic and alcoholic neuropathies and in length dependent small fiber neuropathy [AboElAsar, *Cytokine*, 59, 86-93 (2012)]; (Michalowska-Wender, *Folia Neuropathol.*, 45, 78-81 (2007); Üçeyler, *Neurology*, 74, 1806 (2010)]. The neuronal CXCR2 receptor system has also been shown to regulate re-myelination [Veenstra & Ransohoff, *J. Neuroimmunol.*, 246, 1-9 (2012)] and synaptic plasticity (Xiong, *J. Neurosci. Res.*, 71, 600-607 (2003) processes that govern neuronal communication.

The CXCR2 receptor and its ligands are also upregulated in colorectal cancer and have been implicated in chemoresistance [Acharyya, *Cell*, 150, 165-178 (2012)], tumor growth, vessel formation, cancer cell proliferation and neutrophil recruitment to the tumor microenvironment [Verbeke, *Cytokine & Growth Factor Review*, 22, 345-358 (2012)].

In light of the role that CXCR2 plays in the pathogenesis of various diseases, it is desirable to prepare compounds that inhibit CXCR2 activity, which may be used in the treatment or prevention of diseases mediated by CXCR2.

BRIEF SUMMARY OF THE INVENTION

According to a first aspect, the invention provides a compound of formula (I) or a pharmaceutically acceptable salt thereof,

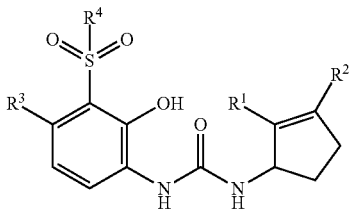

wherein $R^1$, $R^2$, $R^3$ and $R^4$ are defined herein.

Further aspects of the invention include:
i) methods of treating or preventing diseases mediated by CXCR2 using a compound of formula (I) or a pharmaceutically acceptable salt thereof; exemplary diseases include, but are not limited to, autoimmune or inflammatory diseases (e.g., multiple sclerosis, rheumatoid arthritis, psoriasis, chronic obstructive pulmonary disease), neurodegenerative diseases (e.g., Alzheimer's disease, Parkinson's disease), cancer, chronic obstructive pulmonary disease (COPD), chemotherapy induced peripheral neuropathy (CIPN), traumatic brain injury and spinal chord injury.
ii) pharmaceutical compositions comprising a) a compound of formula (I) or a pharmaceutically acceptable salt thereof and b) a pharmaceutically acceptable carrier or excipient; and
iii) uses of a compound of formula (I) or a pharmaceutically acceptable salt thereof for treating or preventing diseases mediated by CXCR2.

DETAILED DESCRIPTION OF THE INVENTION

According to a first aspect, the invention provides a compound of formula (I) or a pharmaceutically acceptable salt thereof,

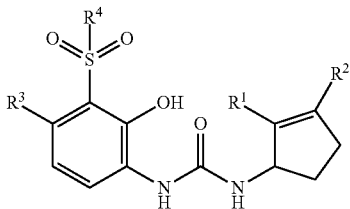

wherein
$R^1$ is H, $C_{1-3}$alkyl, $C_{1-3}$haloalkyl or halo;
$R^2$ is H, $C_{1-3}$alkyl, $C_{1-3}$haloalkyl or halo;
$R^3$ is fluoro, chloro or cyano; and
$R^4$ is selected from the group consisting of:
a) $C_{1-6}$alkyl optionally substituted by one or more substituents independently selected from the group consisting of: fluoro, $C_{1-3}$alkoxy, $C_{1-3}$fluoroalkyl, $C_{1-3}$fluoroalkoxy and hydroxy;
b) —$(CH_2)_n$—$N(R^{4a})(R^{4b})$; wherein
  n is 0, 1 or 2;
  the —$(CH_2)_n$— linker is optionally substituted by one or more groups independently selected from fluoro and methyl optionally substituted by one or more deuterium; and wherein $R^{4a}$ and $R^{4b}$ are independently $C_{1-3}$alkyl, or $R^{4a}$ and $R^{4b}$ may, together with the nitrogen to which they are attached, form a 4, 5 or 6-membered ring, which ring
  i) may contain one additional ring-heteroatom selected from nitrogen and oxygen;
  ii) may be saturated, or when the ring is a 5 or 6-membered, be unsaturated or aromatic;
  iii) may be substituted by one or more substituents independently selected from the group consisting of $C_{1-3}$alkyl optionally substituted by one or more deuterium, fluoro, $C_{1-3}$fluoroalkyl, hydroxy, $C_{1-3}$alkoxy, $C_{1-3}$alkoxyC_{1-3}alkyl and $C_{1-3}$fluoroalkoxy; or
  iv) may be ortho-fused to a further 5 or 6-membered ring which further ring may be saturated, unsaturated or aromatic; which further ring may contain one additional ring-heteroatom selected from nitrogen and oxygen; and which further ring may be independently substituted by one or more fluoro or methyl substituents;
c) —$(CH_2)_p$-heteroaryl; wherein
  p is 1 or 2;
  the —$(CH_2)_p$— linker is optionally substituted by one or more groups independently selected from fluoro and methyl optionally substituted by one or more deuterium;
  the heteroaryl is 5 or 6-membered and is attached to the —$(CH_2)_p$— via a ring carbon atom; and
  wherein the heteroaryl is optionally substituted by one or more substituents independently selected from the group consisting of $C_{1-3}$alkyl, fluoro, $C_{1-3}$fluoroalkyl; $C_{1-3}$alkoxy, $C_{1-3}$alkoxyC_{1-3}alkyl and $C_{1-3}$fluoroalkoxy; or wherein two substituents on adjacent ring-atoms, together with the interconnecting atoms form a further 5 or 6-membered ring ortho-fused to the heteroaryl group; which further ring is saturated, unsaturated or aromatic; and which further ring may contain one additional heteroatom selected from nitrogen and oxygen; and which further ring may be independently substituted by one or more fluoro or methyl substituents;
d) —$(CH_2)_q$-heterocyclyl; wherein
  q is 0, 1 or 2;
  the —$(CH_2)_q$— linker is optionally substituted by one or more groups independently selected from fluoro and methyl optionally substituted by one or more deuterium;
  the heterocyclyl group is 3, 4, 5 or 6-membered and is attached to the —$(CH_2)_q$— via a ring carbon atom;
  the heterocyclyl may be saturated or unsaturated; and
  wherein the heterocyclyl group is optionally substituted by one or more substituents independently selected from the group consisting of deuterium, $C_{1-3}$alkyl (optionally substituted by one or more deuterium), fluoro, $C_{1-3}$fluoroalkyl, hydroxy, $C_{1-3}$alkoxy, $C_{1-3}$alkoxy $C_{1-3}$alkyl, $C_{1-3}$fluoroalkoxy, $C_{3-6}$cycloalkyl and —$(CH_2)_s NR^{4c}R^{4d}$; or two substituents on the heterocyclyl group together with the interconnecting atom(s), form a further 5 or 6-membered ring which further ring may be saturated, unsaturated or aromatic (when the further ring is ortho-fused); and which further ring may contain one additional heteroatom selected from nitrogen and oxygen; and which further ring may be independently substituted by one or more fluoro or methyl substituents; wherein s is 0 or 1, and wherein $R^{4c}$ and $R^{4d}$ are independently $C_{1-3}$alkyl, or $R^{4c}$ and $R^{4d}$ may, together with the nitrogen to which they are attached, form a 4, 5 or 6-membered saturated ring which ring may be substituted by one or more fluoro substituent; and e) —(CH$_2$)$_r$—C$_{3-6}$cycloalkyl; wherein
r is 0, 1 or 2;
the —(CH$_2$)$_r$— linker is optionally substituted by one or more groups independently selected from fluoro and methyl optionally substituted by one or more deuterium; and
wherein the C$_{3-6}$cycloalkyl group is optionally substituted by one or more substituents independently selected from C$_{1-3}$alkyl (optionally substituted by one or more deuterium), fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy and —(CH$_2$)$_t$NR$^{4e}$R$^{4f}$; or wherein two substituents on the cycloalkyl group together with the interconnecting atom(s) form a further 5 or 6-membered ring which further ring may be saturated, unsaturated or aromatic (when the further ring is ortho-fused); and which further ring may contain one heteroatom selected from nitrogen and oxygen; and which further ring may be independently substituted by one or more fluoro or methyl substituents; wherein t is 0 or 1, and wherein R$^{4e}$ and R$^{4f}$ are independently C$_{1-3}$alkyl, or R$^{4e}$ and R$^{4f}$ may, together with the nitrogen to which they are attached, form a 4, 5 or 6-membered saturated ring which ring may be substituted by one or more fluoro substituent.

As used herein unless otherwise indicated, an alkyl substituent is a univalent radical derived by removal of a hydrogen atom from an acyclic alkane. For example, C$_{1-X}$alkyl refers to such an alkyl substituent containing 1 to X carbons. Such alkyl substituents include methyl and ethyl, may be straight chain (i.e. n-propyl, n-butyl, n-pentyl and n-hexyl) or branched chain (for example, isopropyl, isobutyl, secbutyl, tert-butyl, isopentyl and neopentyl). In an embodiment unless otherwise indicated, such an alkyl substituent is methyl, ethyl, n-propyl or isopropyl.

As used herein, a halo substituent refers to fluoro, chloro, bromo and iodo radicals. In an embodiment unless otherwise indicated such a halo substituent is fluoro or chloro.

As used herein unless otherwise indicated, a haloalkyl substituent is an alkyl group substituted by one or more halo substituents, which halo substituents may be the same or different. For example, C$_{1-X}$haloalkyl refers to such a haloalkyl substituent containing 1 to X carbons. Such haloalkyl substituents include monofluoromethyl, difluoromethyl, trifluoromethyl and 1-chloro-2-fluoroethyl. In an embodiment unless otherwise indicated such a haloalkyl substituent is monofluoromethyl, difluoromethyl or trifluoromethyl.

As used herein unless otherwise indicated, a fluoroalkyl substituent is an alkyl group substituted by one or more fluoro substituents. For example, C$_{1-X}$fluoroalkyl refers to such a fluoroalkyl substituent containing 1 to X carbons. Such fluoroalkyl substituents include monofluoromethyl, difluoromethyl and trifluoromethyl. In an embodiment unless otherwise indicated such a fluoroalkyl substituent is monofluoromethyl, difluoromethyl or trifluoromethyl.

As used herein unless otherwise indicated, an alkoxy substituent is a group of formula "R—O—" where R is alkyl as defined above. For example, C$_{1-X}$alkoxy refers to such an alkoxy substituent containing 1 to X carbons. Such alkoxy substituents include methoxy and ethoxy and may be straight chain (i.e. n-propoxy, n-butoxy, n-pentoxy and n-hexyloxy) or branched chain (for example, isopropoxy, isobutoxy, secbutoxy, tert-butoxy, isopentoxy and neopentoxy). In an embodiment unless otherwise indicated, such an alkoxy substituent is methoxy, ethoxy, n-propoxy or isopropoxy.

As used herein unless otherwise indicated, a haloalkoxy substituent is a group of formula "R—O—" where R is haloalkyl as defined above. For example, C$_{1-X}$haloalkoxy refers to such a haloalkoxy substituent containing 1 to X carbons. Such haloalkoxy substituents include monofluoromethoxy, difluoromethoxy, trifluoromethoxy and 1-chloro-2-fluoroethoxy and may be straight chain or branched chain. In an embodiment unless otherwise indicated, such a haloalkoxy substituent is monofluoromethoxy, difluoromethoxy or trifluoromethoxy.

As used herein unless otherwise indicated, a fluoroalkoxy substituent is a group of formula "R—O—" where R is fluoroalkyl. For example, C$_{1-X}$fluoroalkoxy refers to such a fluoroalkoxy substituent containing 1 to X carbons. Such fluoroalkoxy substituents include monofluoromethoxy, difluoromethoxy and trifluoromethoxy and may be straight chain or branched chain. In an embodiment unless otherwise indicated, such a haloalkoxy substituent is monofluoromethoxy, difluoromethoxy or trifluoromethoxy.

As used herein, unless otherwise indicated, heteroaryl is a univalent radical derived by removal of a hydrogen atom from a monocyclic 5 or 6-membered heteroaromatic ring, which ring consists of ring-carbon atoms and ring-heteroatoms selected from the group consisting of nitrogen, oxygen and sulphur, and which ring is aromatic. For example, heteroaryl is monocyclic heteroaryl consisting of 5 or 6 ring-atoms, 1 to 3 of which are ring-heteroatoms. Examples of heteroaryl are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, azepinyl, oxazepinyl, thiazepinyl and diazepinyl. In an embodiment the heteroaryl is pyridyl, pyrimidinyl or imidazolyl.

As used herein, unless otherwise indicated, heterocyclyl is a univalent radical derived by removal of a hydrogen atom from a 3, 4, 5 or 6-membered monocyclic heterocyclic ring, which ring consists of ring-carbon atoms and ring-heteroatoms selected from the group nitrogen, oxygen and sulfur; and which ring is saturated or unsaturated. For example, heterocyclyl is monocyclic saturated heterocyclyl consisting of 3 to 6 ring-atoms, 1 or 2 of which are ring-heteroatoms. Examples of monocyclic saturated heterocyclyl are pyrrolidinyl, dioxolanyl, imidazolidinyl, pyrazolidinyl, piperidinyl, dioxanyl, morpholino, dithianyl, thiomorpholino and piperazinyl. and which ring comprise one or two double bonds. For example, monocyclic unsaturated heterocyclyl is monocyclic unsaturated heterocyclyl consisting of 3 to 6 ring-atoms, 1 or 2 of which are ring-heteroatoms. Examples of monocyclic unsaturated heterocyclyl are 2H-pyrrolyl, 2-pyrrolinyl, 2-imidazolinyl, 2-pyrazolinyl, 2H-pyranyl and 4H-pyranyl. In an embodiment, the heterocycly is tetrahydrofuranyl, tetrahydropyranyl or piperidinyl As used herein, C$_{3-6}$cycloalkyl is a univalent radical derived by removal of a hydrogen atom from a 3, 4, 5 or 6-membered monocyclic cycloalkane. For example, C$_{3-6}$cycloalkyl is cycloalkyl consisting of 3 to 6 ring-carbon atoms. Examples of cycloalkyl are cyclopropyl, cyclobutyl, cyclopentyl and cyclohexyl.

As used herein, when two substituents on a ring together with their interconnecting atom(s) combine to form a further ring, this ring may be spiro fused or orthofused. A spiro-fused ring system consists of two rings which have only one carbon atom in common. An ortho-fused ring system consists of two rings which have only two atoms and one bond in common, for example naphthalene.

In an embodiment $R^1$ is methyl, fluoro or chloro. In a further embodiment $R^1$ is methyl or chloro.

In an embodiment $R^2$ is H, fluoro or chloro. In a further embodiment $R^2$ is H.

In an embodiment $R^3$ is chloro or cyano.

In an embodiment $R^3$ is chloro.

In an embodiment $R^3$ is cyano.

In an embodiment, when $R^4$ is alternative a), $R^4$ is $C_{1-4}$alkyl optionally substituted by one, two or three substituents independently selected from the group consisting of fluoro, $C_{1-3}$alkoxy and $C_{1-3}$fluoroalkyl.

In a further embodiment, when $R^4$ is alternative a), then $R^4$ is $C_{1-4}$alkyl optionally substituted by one, two or three fluoro.

In an embodiment, when $R^4$ is alternative b), $R^4$ is —N($R^{4a}$)($R^{4b}$), attached directly to the sulfone, wherein $R^{4a}$ and $R^{4b}$ are independently $C_{1-3}$alkyl, or $R^{4a}$ and $R^{4b}$ may, together with the nitrogen to which they are attached, form a 5 or 6-membered ring, which ring i) may contain one additional ring-heteroatom selected from nitrogen and oxygen; ii) may be saturated, unsaturated or aromatic; iii) may be substituted by one or more substituents independently selected from the group consisting of $C_{1-3}$alkyl (optionally substituted by one or more deuterium), fluoro, $C_{1-3}$fluoroalkyl; hydroxy, $C_{1-3}$alkoxy, $C_{1-3}$alkoxy$C_{1-3}$alkyl and $C_{1-3}$fluoroalkoxy; or iv) may be ortho-fused to a further 6-membered ring which further ring may be saturated, unsaturated or aromatic; which further ring may contain one additional ring-nitrogen atom; and which further ring may be independently substituted by one or more fluoro or methyl substituents.

In a further embodiment, when $R^4$ is alternative b), $R^4$ is —N($R^{4a}$)($R^{4b}$) attached directly to the sulfone; wherein $R^{4a}$ and $R^{4b}$ together with the nitrogen to which they are attached, form a pyrrolidine ring, a piperidine ring, a morpholine ring or a piperazine ring, any of which rings may be substituted by one or more substituents independently selected from $C_{1-3}$alkyl (optionally substituted by one or more deuterium), fluoro, $C_{1-3}$fluoroalkyl, hydroxy, $C_{1-3}$alkoxy, $C_{1-3}$alkoxy$C_{1-3}$alkyl and $C_{1-3}$fluoroalkoxy.

In an embodiment, when $R^4$ is alternative c), $R^4$ is —(CH$_2$)-heteroaryl; wherein the —(CH$_2$)— linker is optionally substituted by one or two groups independently selected from fluoro and methyl; and wherein the heteroaryl is optionally substituted by one or two substituents independently selected from $C_{1-3}$alkyl and fluoro.

In a further embodiment, when $R^4$ is alternative c), $R^4$ is —(CH$_2$)-heteroaryl; wherein the —(CH$_2$)— linker is optionally substituted by one or two groups independently selected from fluoro and methyl; and wherein the heteroaryl is optionally substituted by one or two substituents independently selected from $C_{1-3}$alkyl and fluoro; and wherein the heteroaryl is pyridyl, pyrimidinyl or imidazolyl.

In an embodiment, when $R^4$ is alternative d), $R^4$ is a 5 or 6-membered, saturated heterocyclyl group directly attached to the sulfone via a ring carbon atom, which heterocyclyl group is optionally substituted by one, two or three substituents independently selected from the group consisting of $C_{1-3}$alkyl (optionally substituted by one or more deuterium), fluoro, $C_{1-3}$fluoroalkyl, hydroxy, $C_{1-3}$alkoxy and —NR$^{4c}$R$^{4d}$, wherein R$^{4c}$ and R$^{4d}$ are independently $C_{1-3}$alkyl; and which heterocyclyl group contains one or two ring-heteroatoms independently selected from nitrogen and oxygen.

In a further embodiment, when $R^4$ is alternative d), $R^4$ is a 5 or 6-membered, saturated heterocyclyl directly attached to the sulfone via a ring carbon atom which heterocyclyl group is optionally substituted by one, two or three substituents independently selected from methyl, deuteromethyl and fluoro; and which heterocyclyl group contains one ring-heteroatom selected from nitrogen and oxygen.

In a still further embodiment, when $R^4$ is alternative d), $R^4$ is tetrahydrofuranyl, tetrahydropyranyl or piperidinyl directly attached to the sulfone via a ring carbon atom which heterocyclyl group is optionally substituted by one, two or three substituents independently selected from the group consisting of methyl, deuteromethyl and fluoro.

In an embodiment, when $R^4$ is alternative e), $R^4$ is a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —(CH$_2$)$_t$NR$^{4e}$R$^{4f}$; wherein t is 0 or 1, and wherein R$^{4e}$ and R$^{4f}$ are independently $C_{1-3}$alkyl, or R$^{4e}$ and R$^{4f}$ may, together with the nitrogen to which they are attached, form a 4, 5 or 6-membered saturated ring which ring may be substituted by one or more fluoro substituent.

In a further embodiment, when $R^4$ is alternative e), $R^4$ is $C_{4-6}$cycloalkyl directly attached to the sulfone; which cycloalkyl group is optionally substituted by one or two substituents independently selected from the group consisting of fluoro, hydroxy, methoxy and —NR$^{4e}$R$^{4f}$; and wherein R$^{4e}$ and R$^{4f}$ are independently $C_{1-2}$alkyl, or R$^{4e}$ and R$^{4f}$ may, together with the nitrogen to which they are attached, form a 4, 5 or 6-membered saturated ring which ring may be substituted by one or more fluoro substituent.

In an embodiment the compound has the formula (Ic)

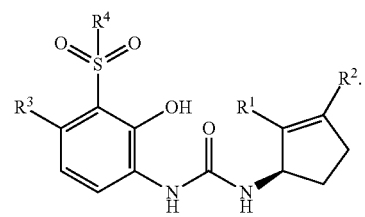

(Ic)

In an embodiment, $R^4$ is selected from the group consisting of:
a) $C_{1-4}$alkyl optionally substituted by one, two or three substituents independently selected from the group consisting of: fluoro, $C_{1-3}$alkoxy and $C_{1-3}$fluoroalkyl;
b) —N($R^{4a}$)($R^{4b}$), attached directly to the sulfone, wherein $R^{4a}$ and $R^{4b}$ are independently $C_{1-3}$alkyl, or $R^{4a}$ and $R^{4b}$ may, together with the nitrogen to which they are attached, form a 5 or 6-membered ring, which ring i) may contain one additional ring-heteroatom selected from nitrogen and oxygen; ii) may be saturated, unsaturated or aromatic; iii) may be substituted by one or more substituents independently selected from the group consisting of $C_{1-3}$alkyl (optionally substituted by one or more deuterium), fluoro, $C_{1-3}$fluoroalkyl; hydroxy, $C_{1-3}$alkoxy, $C_{1-3}$alkoxy$C_{1-3}$alkyl and $C_{1-3}$fluoroalkoxy; or iv) may be ortho-fused to a further 6-membered ring which further ring may be saturated, unsaturated or aromatic; which further ring may contain one additional ring-nitrogen atom; and which further ring may be independently substituted by one or more fluoro or methyl substituents;

c) —(CH$_2$)-heteroaryl; wherein the —(CH$_2$)— linker is optionally substituted by one or two groups independently selected from fluoro and methyl; and wherein the heteroaryl is optionally substituted by one or two substituents independently selected from C$_{1-3}$alkyl and fluoro;

d) a 5 or 6-membered, saturated heterocyclyl group directly attached to the sulfone via a ring carbon atom, which heterocyclyl group is optionally substituted by one, two or three substituents independently selected from the group consisting of C$_{1-3}$alkyl (optionally substituted by one or more deuterium), fluoro, C$_{1-3}$fluoroalkyl, hydroxy, C$_{1-3}$alkoxy and —NR$^{4c}$R$^{4d}$, wherein R$^{4c}$ and R$^{4d}$ are independently C$_{1-3}$alkyl; and which heterocyclyl group contains one or two ring-heteroatoms independently selected from nitrogen and oxygen; and e) a C$_{4-6}$cycloalkyl group directly attached to the sulfone; which cycloalkyl group is optionally substituted by one or two substituents independently selected from the group consisting of fluoro, C$_{1-3}$fluoroalkyl, hydroxy, C$_{1-3}$alkoxy and —(CH$_2$)$_t$NR$^{4e}$R$^{4f}$; wherein t is 0 or 1, and wherein R$^{4e}$ and R$^{4f}$ are independently C$_{1-3}$alkyl, or R$^{4e}$ and R$^{4f}$ may, together with the nitrogen to which they are attached, form a 4, 5 or 6-membered saturated ring which ring may be substituted by one or more fluoro substituent.

In a further embodiment R$^4$ is selected from the group consisting of:

a) C$_{1-4}$alkyl optionally substituted by one, two or three fluoro;

b) —N(R$^{4a}$)(R$^{4b}$) attached directly to the sulfone; wherein R$^{4a}$ and R$^{4b}$ together with the nitrogen to which they are attached, form a pyrrolidine ring, a piperidine ring, morpholine ring or a piperazine ring, any of which rings may be substituted by one or more substituents independently selected from the group consisting of C$_{1-3}$alkyl (optionally substituted by one or more deuterium), fluoro, C$_{1-3}$fluoroalkyl, hydroxy, C$_{1-3}$alkoxy, C$_{1-3}$alkoxyC$_{1-3}$alkyl and C$_{1-3}$fluoroalkoxy;

c) —(CH$_2$)-heteroaryl; wherein the —(CH$_2$)— linker is optionally substituted by one or two groups independently selected from fluoro and methyl; and wherein the heteroaryl is optionally substituted by one or two substituents independently selected from C$_{1-3}$alkyl and fluoro; and wherein the heteroaryl is pyridyl, pyrimidinyl or imidazolyl;

d) a 5 or 6-membered, saturated heterocyclyl directly attached to the sulfone, via a ring carbon atom which heterocyclyl group is optionally substituted by one, two or three substituents independently selected from methyl, deuteromethyl and fluoro; and which heterocyclyl group contains one ring-heteroatom selected from nitrogen and oxygen; and e) a C$_{4-6}$cycloalkyl directly attached to the sulfone; which cycloalkyl group is optionally substituted by one or two substituents independently selected from the group consisting of fluoro, hydroxy, methoxy and —NR$^{4e}$R$^{4f}$; and wherein R$^{4e}$ and R$^{4f}$ are independently C$_{1-2}$alkyl, or R$^{4e}$ and R$^{4f}$ may, together with the nitrogen to which they are attached, form a 4, 5 or 6-membered saturated ring which ring may be substituted by one or more fluoro substituent.

In an embodiment, R$^4$ is selected from the group consisting of:

a) C$_{1-6}$alkyl optionally substituted by one or more substituents independently selected from the group consisting of: fluoro, C$_{1-3}$alkoxy, C$_{1-3}$fluoroalkyl, C$_{1-3}$fluoroalkoxy and hydroxy;

d) —(CH$_2$)$_q$-heterocyclyl; wherein
q is 0, 1 or 2;
the —(CH$_2$)$_q$— linker is optionally substituted by one or more groups independently selected from fluoro and methyl optionally substituted by one or more deuterium;
the heterocyclyl group is 3, 4, 5 or 6-membered and is attached to the —(CH$_2$)$_q$— via a ring carbon atom;
the heterocyclyl may be saturated or unsaturated; and
wherein the heterocyclyl group is optionally substituted by one or more substituents independently selected from the group consisting of deuterium, C$_{1-3}$alkyl (optionally substituted by one or more deuterium), fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy, C$_{3-6}$cycloalkyl and —(CH$_2$)$_s$NR$^{4d}$R$^{4d}$; or two substituents on the heterocyclyl group together with the interconnecting atom(s), form a further 5 or 6-membered ring which further ring may be saturated, unsaturated or aromatic (when the further ring is ortho-fused); and which further ring may contain one additional heteroatom selected from nitrogen and oxygen; and which further ring may be independently substituted by one or more fluoro or methyl substituents; wherein s is 0 or 1, and wherein R$^{4c}$ and R$^{4d}$ are independently C$_{1-3}$alkyl, or R$^{4c}$ and R$^{4d}$ may, together with the nitrogen to which they are attached, form a 4, 5 or 6-membered saturated ring which ring may be substituted by one or more fluoro substituent; and e) —(CH$_2$)$_r$—C$_{3-6}$cycloalkyl; wherein
r is 0, 1 or 2;
the —(CH$_2$)$_r$— linker is optionally substituted by one or more groups independently selected from fluoro and methyl optionally substituted by one or more deuterium; and
wherein the C$_{3-6}$cycloalkyl group is optionally substituted by one or more substituents independently selected from the group consisting of C$_{1-3}$alkyl (optionally substituted by one or more deuterium), fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy and —(CH$_2$)$_t$NR$^{4e}$R$^{4f}$; or wherein two substituents on the cycloalkyl group together with the interconnecting atom(s) form a further 5 or 6-membered ring which further ring may be saturated, unsaturated or aromatic (when the further ring is ortho-fused); and which further ring may contain one heteroatom selected from nitrogen and oxygen; and which further ring may be independently substituted by one or more fluoro or methyl substituents; wherein t is 0 or 1, and wherein R$^{4e}$ and R$^{4f}$ are independently C$_{1-3}$alkyl, or R$^{4e}$ and R$^{4f}$ may, together with the nitrogen to which they are attached, form a 4, 5 or 6-membered saturated ring which ring may be substituted by one or more fluoro substituent.

In an embodiment, R$^4$ is selected from the group consisting of:

a) C$_{1-4}$alkyl optionally substituted by one, two or three substituents independently selected from the group consisting of: fluoro, C$_{1-3}$alkoxy and C$_{1-3}$fluoroalkyl;

d) a 5 or 6-membered, saturated heterocyclyl group directly attached to the sulfone via a ring carbon atom, which heterocyclyl group is optionally substituted by one, two or three substituents independently selected from the group consisting of C$_{1-3}$alkyl (optionally substituted by one or more deuterium), fluoro, C$_{1-3}$fluoroalkyl, hydroxy, C$_{1-3}$alkoxy and —NR$^{4d}$R$^{4d}$, wherein R$^{4c}$ and R$^{4d}$ are independently C$_{1-3}$alkyl; and which heterocyclyl group contains one or two ring-heteroatoms independently selected from nitrogen and oxygen; and e) a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —$(CH_2)_tNR^{4e}R^{4f}$; wherein t is 0 or 1, and wherein $R^{4e}$ and $R^{4f}$ are independently $C_{1-3}$alkyl, or $R^{4e}$ and $R^{4f}$ may, together with the nitrogen to which they are attached, form a 4, 5 or 6-membered saturated ring which ring may be substituted by one or more fluoro substituent.

In a further embodiment $R^4$ is selected from the group consisting of:

a) $C_{1-4}$alkyl optionally substituted by one, two or three fluoro;
d) a 5 or 6-membered, saturated heterocyclyl directly attached to the sulfone, via a ring carbon atom which heterocyclyl group is optionally substituted by one, two or three substituents independently selected from the group consisting of methyl, deuteromethyl and fluoro; and which heterocyclyl group contains one ring-heteroatom selected from nitrogen and oxygen; and
e) a $C_{4-6}$cycloalkyl directly attached to the sulfone; which cycloalkyl group is optionally substituted by one or two substituents independently selected from the group consisting of fluoro, hydroxy, methoxy and —$NR^{4e}R^{4f}$; and wherein $R^{4e}$ and $R^{4f}$ are independently $C_{1-2}$alkyl, or $R^{4e}$ and $R^{4f}$ may, together with the nitrogen to which they are attached, form a 4, 5 or 6-membered saturated ring which ring may be substituted by one or more fluoro substituent.

In an embodiment,
$R^1$ is methyl, fluoro or chloro;
$R^2$ is H, fluoro or chloro;
$R^3$ is chloro or cyano; and
$R^4$ is selected from the group consisting of:

a) $C_{1-4}$alkyl optionally substituted by one, two or three substituents independently selected from the group consisting of: fluoro, $C_{1-3}$alkoxy and $C_{1-3}$fluoroalkyl;
b) —$N(R^{4a})(R^{4b})$, attached directly to the sulfone, wherein $R^{4a}$ and $R^{4b}$ are independently $C_{1-3}$alkyl, or $R^{4a}$ and $R^{4b}$ may, together with the nitrogen to which they are attached, form a 5 or 6-membered ring, which ring i) may contain one additional ring-heteroatom selected from nitrogen and oxygen; ii) may be saturated, unsaturated or aromatic; iii) may be substituted by one or more substituents independently selected from the group consisting of $C_{1-3}$alkyl (optionally substituted by one or more deuterium), fluoro, $C_{1-3}$fluoroalkyl; hydroxy, $C_{1-3}$alkoxy, $C_{1-3}$alkoxy$C_{1-3}$alkyl and $C_{1-3}$fluoroalkoxy; or iv) may be ortho-fused to a further 6-membered ring which further ring may be saturated, unsaturated or aromatic; which further ring may contain one additional ring-nitrogen atom; and which further ring may be independently substituted by one or more fluoro or methyl substituents;
c) —$(CH_2)$-heteroaryl; wherein the —$(CH_2)$— linker is optionally substituted by one or two groups independently selected from fluoro and methyl; and wherein the heteroaryl is optionally substituted by one or two substituents independently selected from $C_{1-3}$alkyl and fluoro;
d) a 5 or 6-membered, saturated heterocyclyl group directly attached to the sulfone via a ring carbon atom, which heterocyclyl group is optionally substituted by one, two or three substituents independently selected from the group consisting of $C_{1-3}$alkyl (optionally substituted by one or more deuterium), fluoro, $C_{1-3}$fluoroalkyl, hydroxy, $C_{1-3}$alkoxy and —$NR^{4c}R^{4d}$, wherein $R^{4c}$ and $R^{4d}$ are independently $C_{1-3}$alkyl; and which heterocyclyl group contains one or two ring-heteroatoms independently selected from nitrogen and oxygen; and
e) a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —$(CH_2)_tNR^{4e}R^{4f}$; wherein t is 0 or 1, and wherein $R^{4e}$ and $R^{4f}$ are independently $C_{1-3}$alkyl, or $R^{4e}$ and $R^{4f}$ may, together with the nitrogen to which they are attached, form a 4, 5 or 6-membered saturated ring which ring may be substituted by one or more fluoro substituent.

In a further embodiment,
$R^1$ is methyl, fluoro or chloro;
$R^2$ is H, fluoro or chloro;
$R^3$ is chloro or cyano; and
$R^4$ is selected from the group consisting of:

a) $C_{1-4}$alkyl optionally substituted by one, two or three fluoro;
b) —$N(R^{4a})(R^{4b})$ attached directly to the sulfone; wherein $R^{4a}$ and $R^{4b}$ together with the nitrogen to which they are attached, form a pyrrolidine ring, a piperidine ring, morpholine ring or a piperazine ring, any of which rings may be substituted by one or more substituents independently selected from the group consisting of $C_{1-3}$alkyl (optionally substituted by one or more deuterium), fluoro, $C_{1-3}$fluoroalkyl, hydroxy, $C_{1-3}$alkoxy, $C_{1-3}$alkoxy$C_{1-3}$alkyl and $C_{1-3}$fluoroalkoxy;
c) —$(CH_2)$-heteroaryl; wherein the —$(CH_2)$— linker is optionally substituted by one or two groups independently selected from fluoro and methyl; and wherein the heteroaryl is optionally substituted by one or two substituents independently selected from $C_{1-3}$alkyl and fluoro; and wherein the heteroaryl is pyridyl, pyrimidinyl or imidazolyl;
d) a 5 or 6-membered, saturated heterocyclyl directly attached to the sulfone, via a ring carbon atom which heterocyclyl group is optionally substituted by one, two or three substituents independently selected from methyl, deuteromethyl and fluoro; and which heterocyclyl group contains one ring-heteroatom selected from nitrogen and oxygen; and
e) a $C_{4-6}$cycloalkyl directly attached to the sulfone; which cycloalkyl group is optionally substituted by one or two substituents independently selected from fluoro, hydroxy, methoxy and —$NR^{4e}R^{4f}$; and wherein $R^{4e}$ and $R^{4f}$ are independently $C_{1-2}$alkyl, or $R^{4e}$ and $R^{4f}$ may, together with the nitrogen to which they are attached, form a 4, 5 or 6-membered saturated ring which ring may be substituted by one or more fluoro substituent.

In an embodiment,
$R^1$ is methyl, fluoro or chloro;
$R^2$ is H, fluoro or chloro;
$R^3$ is chloro or cyano; and
$R^4$ is selected from the group consisting of:

a) $C_{1-6}$alkyl optionally substituted by one or more substituents independently selected from the group consisting of: fluoro, $C_{1-3}$alkoxy, $C_{1-3}$fluoroalkyl, $C_{1-3}$fluoroalkoxy and hydroxy;
d) —$(CH_2)_q$-heterocyclyl; wherein
q is 0, 1 or 2;
the —$(CH_2)_q$— linker is optionally substituted by one or more groups independently selected from fluoro and methyl optionally substituted by one or more deuterium;
the heterocyclyl group is 3, 4, 5 or 6-membered and is attached to the —$(CH_2)_q$— via a ring carbon atom;
the heterocyclyl may be saturated or unsaturated; and wherein the heterocyclyl group is optionally substituted by one or more substituents independently selected from the group consisting of deuterium, $C_{1-3}$alkyl (optionally substituted by one or more deuterium), fluoro, $C_{1-3}$fluoroalkyl, hydroxy, $C_{1-3}$alkoxy, $C_{1-3}$alkoxy$C_{1-3}$alkyl, $C_{1-3}$fluoroalkoxy, $C_{3-6}$cycloalkyl and —$(CH_2)_sNR^{4c}R^{4d}$; or two substituents on the heterocyclyl group together with the interconnecting atom(s), form a further 5 or 6-membered ring which further ring may be saturated, unsaturated or aromatic (when the further ring is ortho-fused); and which further ring may contain one additional heteroatom selected from nitrogen and oxygen; and which further ring may be independently substituted by one or more fluoro or methyl substituents; wherein s is 0 or 1, and wherein $R^{4c}$ and $R^{4d}$ are independently $C_{1-3}$alkyl, or $R^{4c}$ and $R^{4d}$ may, together with the nitrogen to which they are attached, form a 4, 5 or 6-membered saturated ring which ring may be substituted by one or more fluoro substituent; and e) —$(CH_2)_r$—$C_{3-6}$cycloalkyl; wherein
r is 0, 1 or 2;
the —$(CH_2)_r$— linker is optionally substituted by one or more groups independently selected from fluoro and methyl optionally substituted by one or more deuterium; and
wherein the $C_{3-6}$cycloalkyl group is optionally substituted by one or more substituents independently selected from the group consisting of $C_{1-3}$alkyl (optionally substituted by one or more deuterium), fluoro, $C_{1-3}$fluoroalkyl, hydroxy, $C_{1-3}$alkoxy, $C_{1-3}$alkoxy$C_{1-3}$alkyl, $C_{1-3}$fluoroalkoxy and —$(CH_2)_tNR^{4e}R^{4f}$; or wherein two substituents on the cycloalkyl group together with the interconnecting atom(s) form a further 5 or 6-membered ring which further ring may be saturated, unsaturated or aromatic (when the further ring is ortho-fused); and which further ring may contain one heteroatom selected from nitrogen and oxygen; and which further ring may be independently substituted by one or more fluoro or methyl substituents; wherein t is 0 or 1, and wherein $R^{4e}$ and $R^{4f}$ are independently $C_{1-3}$alkyl, or $R^{4e}$ and $R^{4f}$ may, together with the nitrogen to which they are attached, form a 4, 5 or 6-membered saturated ring which ring may be substituted by one or more fluoro substituent.

In an embodiment,
$R^1$ is methyl, fluoro or chloro;
$R^2$ is H, fluoro or chloro;
$R^3$ is chloro or cyano; and
$R^4$ is selected from the group consisting of:
a) $C_{1-4}$alkyl optionally substituted by one, two or three substituents independently selected from the group consisting of: fluoro, $C_{1-3}$alkoxy and $C_{1-3}$fluoroalkyl;
d) a 5 or 6-membered, saturated heterocyclyl group directly attached to the sulfone via a ring carbon atom, which heterocyclyl group is optionally substituted by one, two or three substituents independently selected from the group consisting of $C_{1-3}$alkyl (optionally substituted by one or more deuterium), fluoro, $C_{1-3}$fluoroalkyl, hydroxy, $C_{1-3}$alkoxy and —$NR^{4c}R^{4d}$, wherein $R^{4c}$ and $R^{4d}$ are independently $C_{1-3}$alkyl; and which heterocyclyl group contains one or two ring-heteroatoms independently selected from nitrogen and oxygen; and
e) a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —$(CH_2)_tNR^{4e}R^{4f}$; wherein t is 0 or 1, and wherein $R^{4e}$ and $R^{4f}$ are independently $C_{1-3}$alkyl, or $R^{4e}$ and $R^{4f}$ may, together with the nitrogen to which they are attached, form a 4, 5 or 6-membered saturated ring which ring may be substituted by one or more fluoro substituent.

In a further embodiment,
$R^1$ is methyl, fluoro or chloro;
$R^2$ is H, fluoro or chloro;
$R^3$ is chloro or cyano; and
$R^4$ is selected from the group consisting of:
a) $C_{1-4}$alkyl optionally substituted by one, two or three fluoro;
d) a 5 or 6-membered, saturated heterocyclyl directly attached to the sulfone, via a ring carbon atom which heterocyclyl group is optionally substituted by one, two or three substituents independently selected from methyl, deuteromethyl and fluoro; and which heterocyclyl group contains one ring-heteroatom selected from nitrogen and oxygen; and
e) a $C_{4-6}$cycloalkyl directly attached to the sulfone; which cycloalkyl group is optionally substituted by one or two substituents independently selected from the group consisting of fluoro, hydroxy, methoxy and —$NR^{4e}R^{4f}$; and wherein $R^{4e}$ and $R^{4f}$ are independently $C_{1-2}$alkyl, or $R^{4e}$ and $R^{4f}$ may, together with the nitrogen to which they are attached, form a 4, 5 or 6-membered saturated ring which ring may be substituted by one or more fluoro substituent.

In an embodiment,
$R^1$ is methyl or chloro;
$R^2$ is H;
$R^3$ is chloro or cyano; and
$R^4$ is selected from the group consisting of:
a) $C_{1-4}$alkyl optionally substituted by one, two or three substituents independently selected from the group consisting of: fluoro, $C_{1-3}$alkoxy and $C_{1-3}$fluoroalkyl;
b) —$N(R^{4a})(R^{4b})$, attached directly to the sulfone, wherein $R^{4a}$ and $R^{4b}$ are independently $C_{1-3}$alkyl, or $R^{4a}$ and $R^{4b}$ may, together with the nitrogen to which they are attached, form a 5 or 6-membered ring, which ring i) may contain one additional ring-heteroatom selected from nitrogen and oxygen; ii) may be saturated, unsaturated or aromatic; iii) may be substituted by one or more substituents independently selected from the group consisting of $C_{1-3}$alkyl (optionally substituted by one or more deuterium), fluoro, $C_{1-3}$fluoroalkyl; hydroxy, $C_{1-3}$alkoxy, $C_{1-3}$alkoxy$C_{1-3}$alkyl and $C_{1-3}$fluoroalkoxy; or iv) may be ortho-fused to a further 6-membered ring which further ring may be saturated, unsaturated or aromatic; which further ring may contain one additional ring-nitrogen atom; and which further ring may be independently substituted by one or more fluoro or methyl substituents;
c) —$(CH_2)$-heteroaryl; wherein the —$(CH_2)$— linker is optionally substituted by one or two groups independently selected from fluoro and methyl; and wherein the heteroaryl is optionally substituted by one or two substituents independently selected from $C_{1-3}$alkyl and fluoro;
d) a 5 or 6-membered, saturated heterocyclyl group directly attached to the sulfone via a ring carbon atom, which heterocyclyl group is optionally substituted by one, two or three substituents independently selected from the group consisting of $C_{1-3}$alkyl (optionally substituted by one or more deuterium), fluoro, $C_{1-3}$fluoroalkyl, hydroxy, $C_{1-3}$alkoxy and —$NR^{4c}R^{4d}$, wherein $R^{4c}$ and $R^{4d}$ are independently $C_{1-3}$alkyl; and which heterocyclyl group contains one or two ring-heteroatoms independently selected from nitrogen and oxygen; and
e) a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —$(CH_2)_tNR^{4e}R^{4f}$; wherein t is 0 or 1, and wherein $R^{4e}$ and $R^{4f}$ are independently $C_{1-3}$alkyl, or $R^{4e}$ and $R^{4f}$ may, together with the nitrogen to which they are attached, form a 4, 5 or 6-membered saturated ring which ring may be substituted by one or more fluoro substituent.

In a further embodiment, $R^1$ is methyl or chloro;

$R^2$ is H;

$R^3$ is chloro or cyano; and $R^4$ is selected from the group consisting of:
a) $C_{1-4}$alkyl optionally substituted by one, two or three fluoro;
b) —$N(R^{4a})(R^{4b})$ attached directly to the sulfone; wherein $R^{4a}$ and $R^{4b}$ together with the nitrogen to which they are attached, form a pyrrolidine ring, a piperidine ring, morpholine ring or a piperazine ring, any of which rings may be substituted by one or more substituents independently selected from the group consisting of $C_{1-3}$alkyl (optionally substituted by one or more deuterium), fluoro, $C_{1-3}$fluoroalkyl, hydroxy, $C_{1-3}$alkoxy, $C_{1-3}$alkoxy $C_{1-3}$alkyl and $C_{1-3}$fluoroalkoxy;
c) —$(CH_2)$-heteroaryl; wherein the —$(CH_2)$— linker is optionally-substituted by one or two groups independently selected from fluoro and methyl; and wherein the heteroaryl is optionally substituted by one or two substituents independently selected from $C_{1-3}$alkyl and fluoro; and wherein the heteroaryl is pyridyl, pyrimidinyl or imidazolyl;
d) a 5 or 6-membered, saturated heterocyclyl directly attached to the sulfone, via a ring carbon atom which heterocyclyl group is optionally substituted by one, two or three substituents independently selected from methyl, deuteromethyl and fluoro; and which heterocyclyl group contains one ring-heteroatom selected from nitrogen and oxygen; and
e) a $C_{4-6}$cycloalkyl directly attached to the sulfone; which cycloalkyl group is optionally substituted by one or two substituents independently selected from the group consisting of fluoro, hydroxy, methoxy and —$NR^{4e}R^{4f}$; and wherein $R^{4e}$ and $R^{4f}$ are independently $C_{1-2}$alkyl, or $R^{4e}$ and $R^{4f}$ may, together with the nitrogen to which they are attached, form a 4, 5 or 6-membered saturated ring which ring may be substituted by one or more fluoro substituent.

In an embodiment, $R^1$ is methyl or chloro;

$R^2$ is H;

$R^3$ is chloro or cyano; and $R^4$ is selected from the group consisting of:
a) $C_{1-6}$alkyl optionally substituted by one or more substituents independently selected from the group consisting of: fluoro, $C_{1-3}$alkoxy, $C_{1-3}$fluoroalkyl, $C_{1-3}$fluoroalkoxy and hydroxy;
d) —$(CH_2)_q$-heterocyclyl; wherein
q is 0, 1 or 2;
the —$(CH_2)_q$— linker is optionally substituted by one or more groups independently selected from fluoro and methyl optionally substituted by one or more deuterium;
the heterocyclyl group is 3, 4, 5 or 6-membered and is attached to the —$(CH_2)_q$— via a ring carbon atom;
the heterocyclyl may be saturated or unsaturated; and wherein the heterocyclyl group is optionally substituted by one or more substituents independently selected from the group consisting of deuterium, $C_{1-3}$alkyl (optionally substituted by one or more deuterium), fluoro, $C_{1-3}$fluoroalkyl, hydroxy, $C_{1-3}$alkoxy, $C_{1-3}$alkoxy $C_{1-3}$alkyl, $C_{1-3}$fluoroalkoxy, $C_{3-6}$cycloalkyl and —$(CH_2)_sNR^{4c}R^{4d}$; or two substituents on the heterocyclyl group together with the interconnecting atom(s), form a further 5 or 6-membered ring which further ring may be saturated, unsaturated or aromatic (when the further ring is ortho-fused); and which further ring may contain one additional heteroatom selected from nitrogen and oxygen; and which further ring may be independently substituted by one or more fluoro or methyl substituents; wherein s is 0 or 1, and wherein $R^{4c}$ and $R^{4d}$ are independently $C_{1-3}$alkyl, or $R^{4c}$ and $R^{4d}$ may, together with the nitrogen to which they are attached, form a 4, 5 or 6-membered saturated ring which ring may be substituted by one or more fluoro substituent; and
e) —$(CH_2)_r$—$C_{3-6}$cycloalkyl; wherein
r is 0, 1 or 2;
the —$(CH_2)_r$— linker is optionally substituted by one or more groups independently selected from fluoro and methyl optionally substituted by one or more deuterium; and
wherein the $C_{3-6}$cycloalkyl group is optionally substituted by one or more substituents independently selected from the group consisting of $C_{1-3}$alkyl (optionally substituted by one or more deuterium), fluoro, $C_{1-3}$fluoroalkyl, hydroxy, $C_{1-3}$alkoxy, $C_{1-3}$alkoxy$C_{1-3}$alkyl, $C_{1-3}$fluoroalkoxy and —$(CH_2)_tNR^{4e}R^{4f}$; or wherein two substituents on the cycloalkyl group together with the interconnecting atom(s) form a further 5 or 6-membered ring which further ring may be saturated, unsaturated or aromatic (when the further ring is ortho-fused); and which further ring may contain one heteroatom selected from nitrogen and oxygen; and which further ring may be independently substituted by one or more fluoro or methyl substituents; wherein t is 0 or 1, and wherein $R^{4e}$ and $R^{4f}$ are independently $C_{1-3}$alkyl, or $R^{4e}$ and $R^{4f}$ may, together with the nitrogen to which they are attached, form a 4, 5 or 6-membered saturated ring which ring may be substituted by one or more fluoro substituent.

In an embodiment, $R^1$ is methyl or chloro;

$R^2$ is H;

$R^3$ is chloro or cyano; and $R^4$ is selected from the group consisting of:
a) $C_{1-4}$alkyl optionally substituted by one, two or three substituents independently selected from the group consisting of: fluoro, $C_{1-3}$alkoxy and $C_{1-3}$fluoroalkyl;
d) a 5 or 6-membered, saturated heterocyclyl group directly attached to the sulfone via a ring carbon atom, which heterocyclyl group is optionally substituted by one, two or three substituents independently selected from the group consisting of $C_{1-3}$alkyl (optionally substituted by one or more deuterium), fluoro, $C_{1-3}$fluoroalkyl, hydroxy, $C_{1-3}$alkoxy and —$NR^{4d}R^{4d}$, wherein $R^{4c}$ and $R^{4d}$ are independently $C_{1-3}$alkyl; and which heterocyclyl group contains one or two ring-heteroatoms independently selected from nitrogen and oxygen; and
e) a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —(CH$_2$)$_t$NR$^{4e}$R$^{4f}$; wherein t is 0 or 1, and wherein R$^{4e}$ and R$^{4f}$ are independently C$_{1-3}$alkyl, or R$^{4e}$ and R$^{4f}$ may, together with the nitrogen to which they are attached, form a 4, 5 or 6-membered saturated ring which ring may be substituted by one or more fluoro substituent.

In a further embodiment,

R$^1$ is methyl or chloro;

R$^2$ is H;

R$^3$ is chloro or cyano; and

R$^4$ is selected from the group consisting of:

a) C$_{1-4}$alkyl optionally substituted by one, two or three fluoro;

d) a 5 or 6-membered, saturated heterocyclyl directly attached to the sulfone, via a ring carbon atom which heterocyclyl group is optionally substituted by one, two or three substituents independently selected from methyl, deuteromethyl and fluoro; and which heterocyclyl group contains one ring-heteroatom selected from nitrogen and oxygen; and e) a C$_{4-6}$cycloalkyl directly attached to the sulfone; which cycloalkyl group is optionally substituted by one or two substituents independently selected from the group consisting of fluoro, hydroxy, methoxy and —NR$^{4e}$R$^{4f}$; and wherein R$^{4e}$ and R$^{4f}$ are independently C$_{1-2}$alkyl, or R$^{4e}$ and R$^{4f}$ may, together with the nitrogen to which they are attached, form a 4, 5 or 6-membered saturated ring which ring may be substituted by one or more fluoro substituent.

In an embodiment, the compound is selected from the group consisting of:

(R)-1-(4-chloro-2-hydroxy-3-((4-methyltetrahydro-2H-pyran-4-yl)sulfonyl)phenyl)-3-(2-chlorocyclopent-2-en-1-yl)urea (Compound 40);

(R)-1-(3-(tert-butylsulfonyl)-4-cyano-2-hydroxyphenyl)-3-(2-methylcyclopent-2-en-1-yl)urea (Compound 191);

1-(4-chloro-2-hydroxy-3-((trans-3-(pyrrolidin-1-yl)cyclobutyl)sulfonyl)phenyl)-3-((R)-2-methylcyclopent-2-en-1-yl)urea (Compound 192);

1-(4-chloro-3-((trans-3-(dimethylamino)cyclobutyl)sulfonyl)-2-hydroxyphenyl)-3-((R)-2-methylcyclopent-2-en-1-yl)urea (Compound 193);

(R)-1-(4-chloro-3-((1,1-difluoroethyl)sulfonyl)-2-hydroxyphenyl)-3-(2-methylcyclopent-2-en-1-yl)urea (Compound 194);

1-(4-chloro-2-hydroxy-3-(((S)-3-methyltetrahydrofuran-3-yl)sulfonyl)phenyl)-3-((R)-2-methylcyclopent-2-en-1-yl)urea (Compound 195);

1-(4-chloro-2-hydroxy-3-(((R)-3-methyltetrahydrofuran-3-yl)sulfonyl)phenyl)-3-((R)-2-methylcyclopent-2-en-1-yl)urea (Compound 196);

1-(4-chloro-2-hydroxy-3-(((S)-3-methyltetrahydrofuran-3-yl)sulfonyl)phenyl)-3-((R)-2-chlorocyclopent-2-en-1-yl)urea (Compound 197); and 1-(4-chloro-2-hydroxy-3-(((R)-3-methyltetrahydrofuran-3-yl)sulfonyl)phenyl)-3-((R)-2-chlorocyclopent-2-en-1-yl)urea (Compound 198);

or a pharmaceutically acceptable salt thereof.

In an embodiment, the compound is 1-(4-chloro-2-hydroxy-3-(((R)-3-methyltetrahydrofuran-3-yl)sulfonyl)phenyl)-3-((R)-2-methylcyclopent-2-en-1-yl)urea (Compound 196) of formula (Ib) or a pharmaceutically acceptable salt thereof

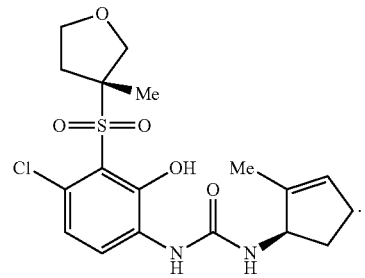

(Ib)

In an embodiment, the compound is 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof

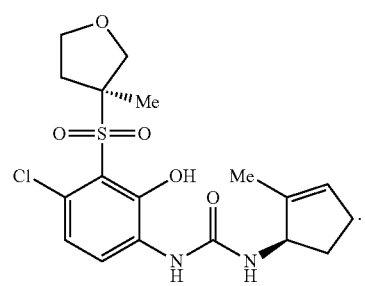

(Id)

The compounds defined in the first aspect may form acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Alternatively the compounds defined in the first aspect may form base addition salts formed with metal salts (such as sodium, potassium, aluminium, calcium, magnesium and zinc) and ammonium salts (such as isopropylamine, diethylamine, diethanolamine salts). For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In an embodiment the pharmaceutically acceptable salt is the piperazine salt. In a further embodiment, there is provided the piperazine salt of 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id)

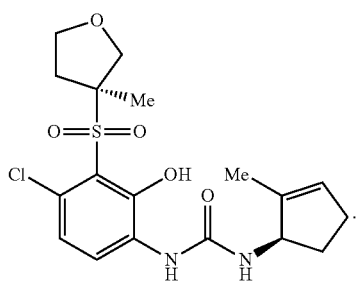
(Id)

It will be appreciated by those skilled in the art that certain protected derivatives of the compounds defined in the first aspect, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds defined in the first aspect. Therefore, in a further aspect, the invention provides a prodrug of a compound defined in the first aspect.

The compounds defined in the first aspect, their pharmaceutically acceptable salts or prodrugs, may exist in solvated or hydrated form. Therefore, in a further aspect, the invention provides a solvate or hydrate of a compound defined in the first aspect or a pharmaceutically acceptable salt thereof.

The compounds defined in the first aspect, their pharmaceutically acceptable salts, or solvates or hydrates, may exist in one or more polymorphic form. Therefore, in a further aspect, the invention provides a polymorph of a compound defined in the first aspect or their pharmaceutically acceptable salts, or a polymorph of a solvate or hydrate of a compound defined in the first aspect or a pharmaceutically acceptable salt thereof.

Hereinafter, compounds defined in the first aspect, their salts and prodrugs; any solvates or hydrates of any salt or prodrug; and any polymorph of any compound, salt, solvate or hydrate are referred to as "compounds of the invention". The term "compounds of the invention" also includes all embodiments described for the first aspect.

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention. In addition, the chiral compounds of the invention may be prepared by chiral synthesis.

The compounds of the invention may exist in one or more tautomeric forms. All tautomers and mixtures thereof are included in the scope of the present invention. For example, a claim to 2-hydroxyquinolinyl would also cover its tautomeric form, α-quinolinonyl.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$, $^{11}C$, $^{13}C$, $^{14}C$, $^{15}N$, $^{17}O$, $^{18}O$, $^{35}S$, $^8F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Experimental section hereafter using appropriate isotopic variations of suitable reagents.

Compounds of the invention may be prepared in a variety of ways. In the following reaction schemes and hereafter, unless otherwise stated $R^1$ to $R^4$ are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

Compounds of general formula (I) may be prepared by reacting isocyanate compounds of general formula (II) with anilines of general formula (III) according to reaction scheme 1. Typical reaction conditions comprise reacting (II) with (III) in DCM or pyridine at between 0° C. and 80° C. for approximately 12 to 72 hours.

Scheme 1

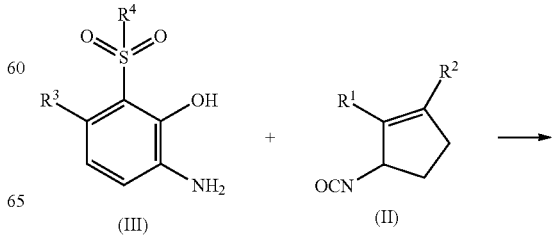

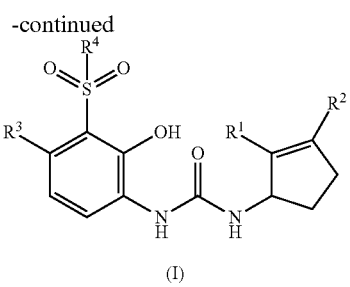

(I)

Alternatively protected versions of compounds of general formula (I) may be prepared followed by deprotection to give compounds of general formula (I). For example compounds of formula (Ia), i.e. compounds of general formula (I) where $R^4$ is piperidin-4-yl, may be prepared from the tert-butoxycarbonyl compound (IV) by reaction under trifluoroacetic acid (see reaction Scheme 2). Compounds of formula (Ia) may be converted to other compounds of formula (I) for example by alkylating on the piperidine nitrogen. Typical reaction conditions comprise treatment with base followed by addition of an alkylating agent. Conversion to compounds of formula (I) where the piperidine nitrogen is substituted by ethyl, may be acheived by reaction with acetaldehyde followed by addition of a reducing agent, such as sodium triacetoxyborohydride.

Scheme 2

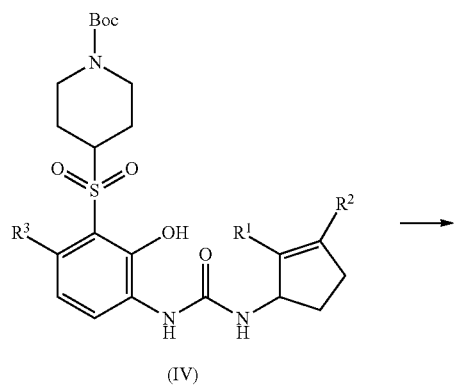

(IV)

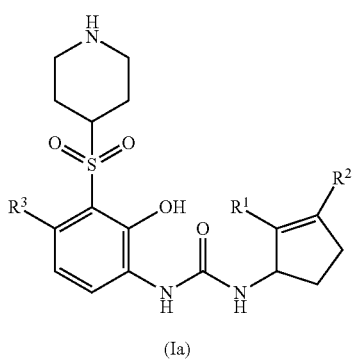

(Ia)

Compounds of general formula (II) may be prepared from compounds of general formula (V) by reaction with triphosgene or bis(trichloromethyl)carbonate according to reaction scheme 3. Typical reaction conditions comprise reacting (V) with bis(trichloromethyl)carbonate in DCM in the presence of aqueous sodium bicarbonate solution or reacting (V) with triphosgene in toluene at elevated temperature (e.g. 80° C.).

Scheme 3

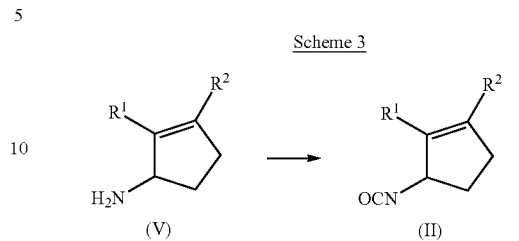

(V)                (II)

Alternatively isocyanate (II) may be generated in situ by reacting (V) with 4-nitrophenylcarbonochloridate and then reacting with compounds of formula (III) (see reaction scheme 1).

Compounds of general formula (V) may be prepared from compounds of general formula (VI) by reaction with isoindoline-1,3-dione to give (VII) followed by treatment with hydrazine according to reaction scheme 4. Typical reaction conditions are treating (VI) with triphenylphospine, isoindoline-1,3-dione and diisopropyl azodicarboxylate (DIAD), preferably at 0° C. followed by warming to room temperature, to give (VII). Compounds of formula (V) are then prepared by treating (VII) with hydrazine at elevated temperature.

Scheme 4

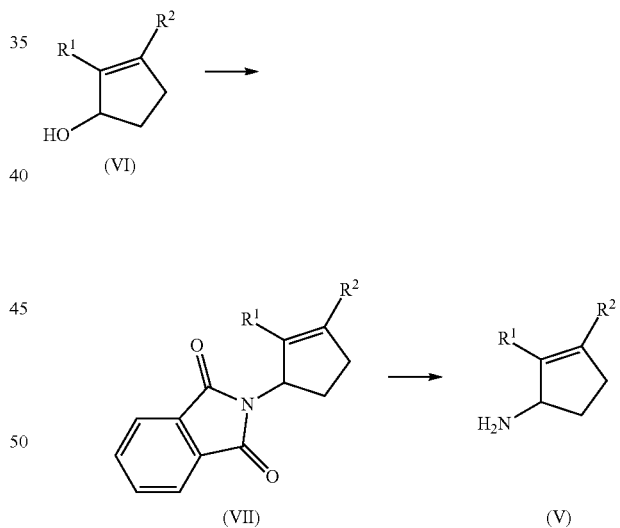

(VI)

(VII)                (V)

Compounds of formula (VI) may be prepared by a variety of procedures well known to the skilled chemist. For example, alcohols of formula (VI) may be prepared by reducing the corresponding ketone. Typical reaction conditions comprise treatment with sodium borohydride in the presence of cerium(III) chloride. Alternative reducing conditions are described in the experimental section hereinafter.

Compounds of formula (III) may be prepared from compounds of formula (VIII) according to reaction Scheme 5. Typical conditions comprise reaction of VIII with protic acid (such as sulfuric acid or hydrochloric acid) in a mixture of dioxane and water at elevated temperature.

Scheme 5

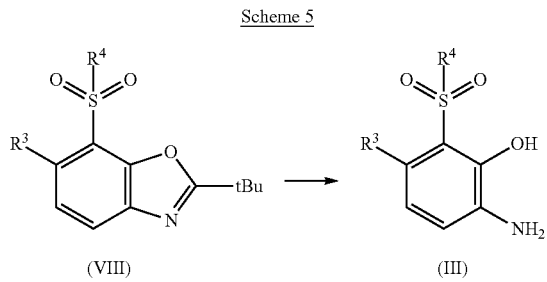

Compounds of formula (VIII) may be prepared from compounds of formula (IX) according to reaction Scheme 6 by treatment with an oxidising agent such as metachloroperbenzoic acid.

Scheme 6

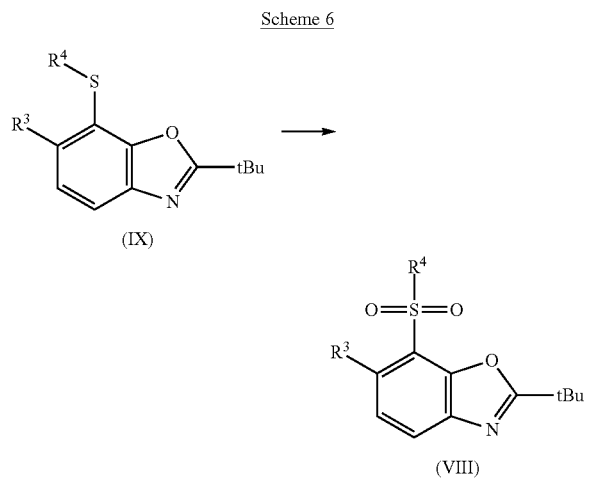

Compounds of formula (IX) may be prepared from compounds of formula (X) according to reaction Scheme 7 by reaction with an alkylating agent such as R⁴—X where X is a suitable leaving group such as bromo or methysulfonyl in the presence of a suitable base, such as potassium carbonate or triethylamine.

Scheme 7

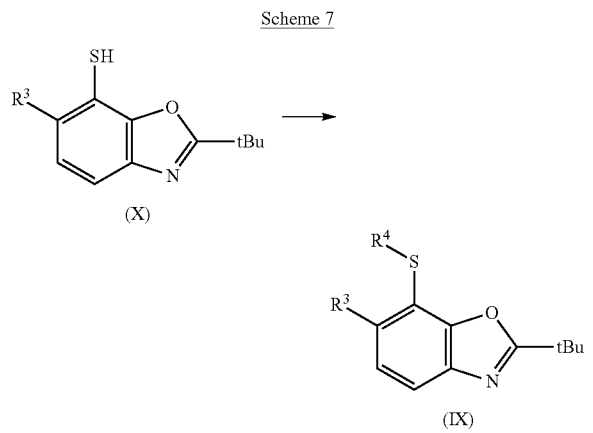

Compound of formula (X) where $R^3$ is chloro may be prepared by procedures described in US patent publication number US20070249672A1.

Compounds of formula (X) where $R^3$ is cyano may be prepared from the corresponding compound of formula (X) where $R^3$ is chloro by reaction with copper (II) cyanide at elevated temperature.

Compounds of formula (X) where $R^3$ is fluoro may be prepared by procedures described in US patent publication number US20070249672A1, International patent publication number WO0168033, and Busch-Petersen et al [Bioorganic and Medicinal Chemistry Letters, 16 (2006), 5513-5516].

Compounds of formula (IX) may be converted to other compounds of formula (IX) using procedures familiar to the skilled chemist. For example, compounds of formula (IXa) having a unsubstituted or partially substituted sp3 carbon attached to the sulfone moiety may be alkylated according to reaction scheme 8. Typical reaction conditions comprise treating (IXa) with a strong base (such as lithium bis(trimethylsilyl)amide, n-butyl lithium or lithhium diisopropylamide) followed by addition of an alkylating agent such as Rx-Y where Y is a good leaving group.

Scheme 8

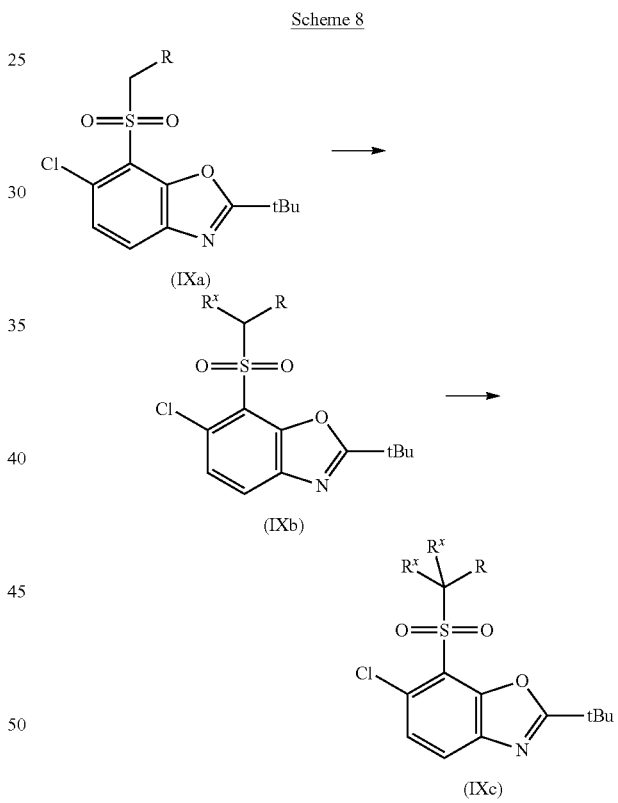

It will be appreciated by the skilled chemist that compounds of formula (I) may be converted to other compounds of formula (I) by methods known in the art.

The compounds of the invention may be useful in treating or preventing diseases mediated by CXCR2. Examples of such diseases include autoimmune or inflammatory diseases (such as multiple sclerosis, rheumatoid arthritis, psoriasis, Crohn's disease, inflammatory bowel disease, Sjorgen's syndrome, optic neuritis, chronic obstructive pulmonary disease and type I diabetes, neuromyelitis optica, Myasthenia Gavis, uveitis, Guillain-Barre syndrome, psoriatic arthritis, Gaves' disease, asthma, chronic obstructive pulmonary disease and allergy), neurodegenerative diseases (such as Alzheimer's disease and Parkinson's disease) and cancer. Further examples, of diseases mediated by CXCR2 are COPD, chemotherapy induced peripheral neuropathy (CIPN), traumatic brain injury and spinal chord injury.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, "prevent", "preventing" or "prevention" means the prophylactic administration of a drug to diminish the likelihood of the onset of or to delay the onset of a disease or biological manifestation thereof.

The compounds of the invention will normally, but not necessarily, be formulated into pharmaceutical compositions prior to administration to a patient by an appropriate route. Accordingly, in another aspect, the invention provides pharmaceutical compositions comprising a compound of the invention and one or more pharmaceutically-acceptable excipients.

As used herein, "pharmaceutically-acceptable excipient" means any pharmaceutically acceptable material present in the pharmaceutical composition or dosage form other than the compound or compounds of the invention. Typically the material gives form, consistency and performance to the pharmaceutical composition.

The pharmaceutical compositions of the invention typically contain one compound of the invention. However, in certain embodiments, the pharmaceutical compositions of the invention contain more than one compound of the invention. In addition, the pharmaceutical compositions of the invention may comprise one or more additional pharmaceutically active compounds.

It will be appreciated that the compounds of the combination or composition may be administered simultaneously (either in the same or different pharmaceutical formulations), separately or sequentially.

In one embodiment the compounds of the invention prevent or treat CIPN caused by the administration of chemotherapeutic agents. Accordingly, the compounds of the invention in preventing or treating CIPN may be administered in combination with a chemotherapeutic agent. In an embodiment, the compounds of the invention for the prevention or treatment of CIPN are combined with one or more primary chemotherapeutic agents, the active agent being selected from the following list: platinum compounds (for example, oxaliplatin), taxanes, *vinca* alkaloids, thalidomide and bortezomib. In a further embodiment, the primary chemotherapeutic agent is oxaliplatin.

Often chemotherapeutic agents are administered in combination with additional agents (eg, other chemotherapeutic agents, angiogenesis inhibitors) that provide increased treatment options for effective patient compliant anticancer treatment inclusive of treating refractory populations. In a further embodiment, the compounds of the invention are administered with a) a primary chemotherapeutic agent and b) an additional agent selected from the group consisting of bevacizumab, Irinotecan, capecitabine, cetuximab, panitumumab, regorafenib and Ziv-aflibercept.

Such pharmaceutical compositions of the invention may be prepared and packaged in bulk form wherein a safe and effective amount of a compound of the invention can be dispensed and then given to the patient such as with powders or syrups. Alternatively, the pharmaceutical compositions of the invention may be prepared and packaged as dosage forms wherein each physically discrete dosage form contains a safe and effective amount of a compound of the invention. Accordingly, in another aspect, the invention provides dosage forms comprising pharmaceutical compositions of the invention. Each discrete dosage form typically contains from 0.1 mg to 100 mg of a compound of the invention.

The compositions of the invention will typically be formulated into dosage forms which are adapted for administration to the patient by the desired route of administration. For example, dosage forms include those adapted for (1) oral administration such as tablets, capsules, caplets, pills, lozenges, powders, syrups, elixirs, suspensions, solutions, emulsions, sachets and cachets; (2) parenteral administration such as sterile solutions, suspensions, implants and powders for reconstitution; (3) transdermal administration such as transdermal patches; (4) rectal and vaginal administration such as suppositories, pessaries and foams; (5) inhalation and intranasal such as dry powders, aerosols, suspensions and solutions (sprays and drops); (6) topical administration such as creams, ointments, lotions, solutions, pastes, drops, sprays, foams and gels; (7) ocular administration such as drops, ointment, sprays, suspensions and inserts; (8) buccal and sublingual administration such as lozenges, patches, sprays, drops, chewing gums and tablets.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance. Certain pharmaceutically-acceptable excipients may be chosen for their ability to facilitate the release of the compound of the invention at the appropriate rate to treat of prevent the condition.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavouring agents, flavour masking agents, colouring agents, anticaking agents, humectants, chelating agents, plasticizers, viscosity increasing agents, rate modifying agents, antioxidants, preservatives, stabilizers, surfactants and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to determine suitable pharmaceutically-acceptable excipients in appropriate amounts for use with the compounds of the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press). The pharmaceutical compositions of the invention may be prepared using techniques and methods known to those skilled in the art. Some of the methods commonly used in the art are described in Remington's Pharmaceutical Sciences (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch and pre-gelatinized starch), gelatin, acacia, sodium alginate, alginic acid, tragacanth, guar gum, povidone, and cellulose and its derivatives (e.g. hydroxypropyl methyl cellulose). The oral solid dosage form may further comprise a disintegrant. Suitable disintegrants include starches, crospovidone, sodium starch glycolate, cros-carmellose, alginic acid, and sodium carboxymethyl cellulose. The oral solid dosage form may further comprise a lubricant. Suitable lubricants include stearic acid, magnesium stearate, calcium stearate, and sodium dodecyl sulphate. The oral solid dosage form may further comprise a glidant such as talc and colloidal silicon dioxide. The oral solid dosage form may further comprise an outer coating which may have cosmetic or functional properties.

It will be appreciated that the invention includes the following further aspects. The diseases and conditions described above extend, where appropriate, to these further aspects. In addtion the embodiments defined above in relation to the first aspect extend to these further apsects.

i) The use of a compound of the invention in the manufacture of a medicament for treating or preventing a disease or condition mediated by antagonism of the CXCR2 receptor. In an embodiment the use is treating or preventing a disease or condition selected from the list consisting of: autoimmune or inflammatory diseases, neurodegenerative diseases, cancer, chronic obstructive pulmonary disease (COPD), chemotherapy induced peripheral neuropathy (CIPN), traumatic brain injury and spinal chord injury. In an embodiment the use is treating Alzheimer's Disease. In another embodiment the use is treating multiple sclerosis. In another embodiment the use is treating COPD. In another embodiment the use is treating chemotherapy induced peripheral neuropathy (CIPN). In another embodiment the use is preventing CIPN. In an embodiment, there is provided the use of 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof for the manufacture of a medicament for treating or preventing CIPN. In an embodiment, there is provided the use of 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof for the manufacture of a medicament for preventing CIPN

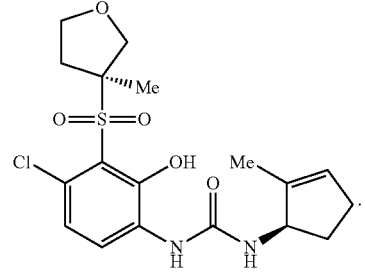

(Id)

ii) A method of treating or preventing a disease or condition mediated by antagonism of the CXCR2 receptor in a human comprising administering a compound of the invention. In an embodiment the method is treating or preventing a disease or condition selected from the list consisting of: autoimmune or inflammatory diseases, neurodegenerative diseases, cancer, chronic obstructive pulmonary disease (COPD), chemotherapy induced peripheral neuropathy (CIPN), traumatic brain injury and spinal chord injury. In an embodiment the method is treating Alzheimer's Disease. In another embodiment the method is treating multiple sclerosis. In another embodiment the method is treating COPD. In another embodiment the method is treating chemotherapy induced peripheral neuropathy (CIPN). In another embodiment the method is preventing CIPN. In another embodiment the use is preventing CIPN. In an embodiment, there is provided a method of treating or preventing a CIPN in a human comprising administering 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof. In an embodiment, there is provided a method of preventing a CIPN in a human comprising administering 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof.

iii) A pharmaceutical composition comprising a) a compound of the invention and b) one or more pharmaceutically acceptable excipients. In an embodiment, the compound is 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof.

iv) A pharmaceutical composition comprising a) 0.05 to 1000 mg of a compound of the invention and b) 0.1 to 2 g of one or more pharmaceutically acceptable excipients. In an embodiment, the compound is 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof.

v) A pharmaceutical composition for the treatment or prevention of a disease mediated by antagonisim of the CXCR2 receptor comprising a compound of the invention. In an embodiment the composition is for treating or preventing a disease or condition selected from the list consisting of: autoimmune or inflammatory diseases, neurodegenerative diseases, cancer, chronic obstructive pulmonary disease (COPD), chemotherapy induced peripheral neuropathy (CIPN), traumatic brain injury and spinal chord injury. In an embodiment the composition is for treating Alzheimer's Disease. In another embodiment the composition is for treating multiple sclerosis. In another embodiment the composition is for treating COPD. In another embodiment the composition is for treating chemotherapy induced peripheral neuropathy (CIPN). In another embodiment the composition is for preventing CIPN. In an embodiment, there is provided a composition for the treatment or prevention of CIPN comprising 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof. In an embodiment, there is provided a composition for the prevention of CIPN comprising 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof.

vi) A compound of the invention for use in therapy. In an embodiment, the compound is 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof.

vii) A compound of the invention for use in the treatment or prevention of a disease mediated by antagonism of the CXCR2 receptor. In an embodiment the use is treating or preventing a disease or condition selected from the list consisting of: autoimmune or inflammatory diseases, neurodegenerative diseases, cancer, chronic obstructive pulmonary disease (COPD), chemotherapy induced peripheral neuropathy (CIPN), traumatic brain injury and spinal chord injury. In an embodiment the use is the treatment of Alzheimer's Disease. In another embodiment the use is the treatment of multiple sclerosis. In another embodiment the use is the treatment of COPD. In another embodiment the use is the treatment of chemotherapy induced peripheral neuropathy (CIPN). In another embodiment the use is the prevention of CIPN. In an embodiment, there is provided 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof, for use in the treatment or prevention of CIPN. In an embodiment, there is provided 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) of formula (Id) or a pharmaceutically acceptable salt thereof, for use in the prevention of CIPN.

Supporting Compounds

Compounds of the invention and intermediates have been named using ACD/Name PRO 6.02 chemical naming software (Advanced Chemistry Development Inc., Toronto, Ontario, M5H2L3, Canada).

Abbreviations
  aq.—aqueous
  Conc.—concentrated
  DAST—diethylaminosulfur trifluoride
  DCM—dichloromethane
  DIAD—diisopropyl azodicarboxylate
  DIPEA—N-ethyl-N-isopropylpropan-2-amine
  DMAP—N,N-dimethylpyridin-4-amine
  DMF—N,N-dimethylformamide
  DMSO—dimethylsulphoxide
  DEA—diethyl amine
  DEAD—diethyl azodicarboxylate
  DIBAL-H—diisobutylaluminium hydride
  DMAP—4-dimethylaminopyridine
  EA—ethyl acetate
  EDC—1-ethyl-3-(3-dimethylaminopropyl)carbodiimide
  ES—electrospray
  HMPA—hexamethylphosphoramide
  IPA—isopropyl alcohol
  LCMS—liquid chromatography mass spectrometry
  LDA—lithium diisopropylamide
  LHMDS—lithium bis(trimethylsilyl)amide
  mCPBA—meta-chloroperoxybenzoic acid
  MDAP—mass directed automated preparative liquid chromatography
  MS—mass spectrometry
  MsCl—methanesulfonyl chloride
  NMP—N-methyl-2-pyrrolidone
  PCC—pyridinium chlorochromate
  PE—petroleum ether
  PPTS—pyridinium p-toluenesulfonate
  RT—room temperature
  SFC—supercritical fluid chromatography
  sat.—saturated
  TBAF—tetrabutylammonium fluoride
  TBME—tert-butyl methyl ether
  TEA—triethylamine
  TFA—trifluoroacetic acid
  THF—tetrahydrofuran
  HMPA—hexamethylphosphoramide LCMS Conditions:
1) Acidic Conditions:
Mobile phase: water containing 0.05% TFA/acetonitrile
Column: XBridge™ C18 30×100 mm—5 microns
Detection: MS and photodiode array detector (PDA)
2) Basic Conditions:
Mobile phase: water containing 0.08% $NH_4HCO_3$/acetonitrile
Column: XBridge™ C18 30×100 mm—5 microns;
Detection: MS and photodiode array detector (PDA)

MDAP Conditions:
1) Acidic Conditions:
Instrument: Waters instrument
Column: Sunfire Prep C18 column (5 um, 19×50 mm)
Mobile phase: water containing 0.05% TFA/acetonitrile.
2) Basic Conditions:
Instrumnet: Waters instrument
Column: Xbridge Prep C18 column (5 um, 19×50 mm)
Mobile phase: water containing 0.04% ammonia/acetonitrile.

Analytical SFC Conditions:
Instrument: SFC Method Station (Thar, Waters)
Other conditions, refer to each case Preparative-SFC Conditions:
Instrument: SFC-80 (Thar, Waters)
Column: Chiralpak AD-H 50*250 mm, 5 um (Deicel):
  Chiralpak AS-H 50*250 mm, 5 um (Deicel);
  Chiralpak OJ-H 50*250 mm, 5 um (Deicel);
  Chiralpak OZ-H 50*250 mm, 5 um (Deicel);
  Chiralpak IC 30*250 mm, 5 um (Deicel);
Column temperature: 40° C.
Mobile phase: Organic solvents: Methanol, EtOH or iPrOH
Additive: DEA (0~1%)
Organic solvents/$CO_2$: 10~50%
Flow: 50~80 g/min
Back pressure: 100 bar
Cycle time of stack injection: 6~20 min.

SUPPORTING COMPOUNDS/INTERMEDIATES

In the procedures that follow, after each starting material, reference to an intermediate is typically provided. This is provided merely for assistance to the skilled chemist. The starting material may not necessarily have been prepared from the batch referred to.

Intermediate 1:
(R)-1-chloro-5-isocyanatocyclopent-1-ene

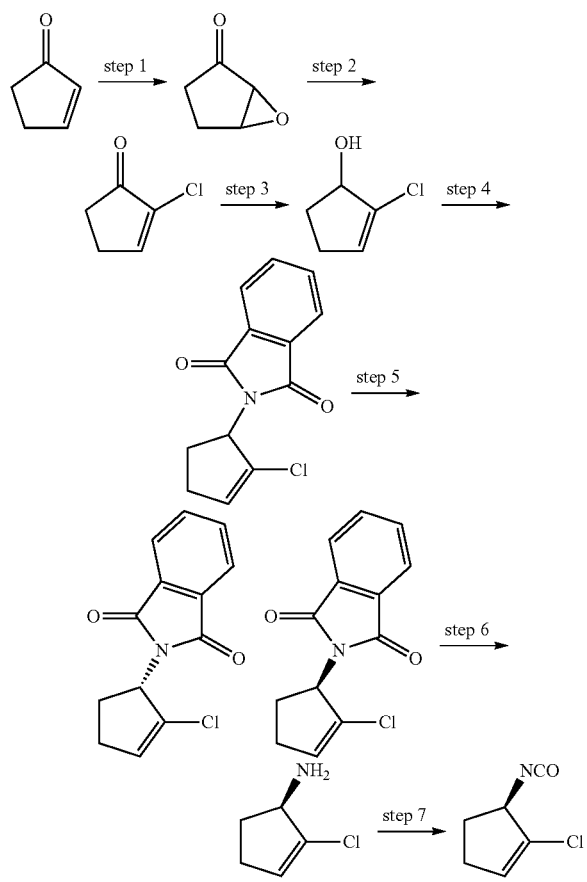

Step 1: To a solution of cyclopent-2-enone (1.2 g) in methanol (10 mL) was added hydrogen peroxide solution (30%, 0.5 g). The resulting mixture was stirred at RT overnight. Cold water (30 mL) was added and the resulting mixture was neutralized with sat. NaHCO$_3$ solution. The aqueous layer was extracted with DCM (2×100 mL). The combined organic layers were dried over Na$_2$SO$_4$, filtered and concentrated in vacuo to give 6-oxabicyclo[3.1.0]hexan-2-one (1.3 g) as a yellow oil.

Step 2: To a solution of 6-oxabicyclo[3.1.0]hexan-2-one (25 g) in methanol (10 mL) and water (3 mL) was added cerium(III) chloride heptahydrate (95 g). The resulting mixture was stirred at 70° C. for one hour. Cold water (30 mL) was added and the resulting mixture was neutralized with sat. NaHCO$_3$ solution. The aqueous layer was extracted with DCM (2×100 mL). The combined organic layers were dried over Na$_2$SO$_4$, filtered and concentrated in vacuo to give 2-chlorocyclopent-2-enone (29 g) as a yellow oil.

Step 3: To a solution of 2-chlorocyclopent-2-enone (600 mg) in methanol (20 mL) was added cerium(III) chloride heptahydrate (1918 mg) and NaBH$_4$ (195 mg). The resulting mixture was stirred at RT for one hour. Cold water (30 mL) was added and the resulting mixture was neutralized with sat. NaHCO$_3$ solution. The aqueous layer was extracted with DCM (2×100 mL). The combined organic layers were dried over Na$_2$SO$_4$, filtered and concentrated in vacuo to give 2-chlorocyclopent-2-enol (400 mg) as a yellow oil.

Step 4: To a solution of 2-chlorocyclopent-2-enol (20.0 g) and isoindoline-1,3-dione (37.2 g) in THF (200 mL) was added Ph$_3$P (66.4 g) and DIAD (49.2 mL) at 0° C. The mixture was stirred at RT overnight. The solvent was removed in vacuo and the residue was purified by column chromatography (eluting with PE:EA=10:1) to give 2-(2-chlorocyclopent-2-en-1-yl)isoindoline-1,3-dione (18.0 g) as a yellow solid. MS(ES$^+$) m/z 248 (MH$^+$).

Step 5: 2-(2-Chlorocyclopent-2-en-1-yl)isoindoline-1,3-dione (14 g) was purified by SFC to give (R)-2-(2-chlorocyclopent-2-en-1-yl)isoindoline-1,3-dione (5.0 g) as a white solid and (S)-2-(2-chlorocyclopent-2-en-1-yl)isoindoline-1,3-dione (5.5 g) as a yellow oil. (R)-2-(2-chlorocyclopent-2-en-1-yl)isoindoline-1,3-dione: Chiral HPLC (Column: AD-H (250*4.6 mm, 5 um); mobile phase: MeOH/CO$_2$=15%; Flow: 3.0 ml/min; Temperature: 40° C.): t$_R$=2.54 min, ee %=100%; $^1$H-NMR (400 MHz, CDCl$_3$) δ ppm 7.74-7.98 (m, 4H), 6.04 (d, J=2.2 Hz, 1H), 5.32 (dd, J=9.3, 1.9 Hz, 1H), 2.77 (ddd, J=9.4, 8.0, 3.0 Hz, 1H), 2.41-2.62 (m, 2H), 2.22-2.39 (m, 1H); (S)-2-(2-chlorocyclopent-2-en-1-yl)isoindoline-1,3-dione: Chiral HPLC (Column: AD-H (250*4.6 mm, 5 um); mobile phase: MeOH/CO$_2$=15%; flow: 3.0 ml/min; temperature: 40° C.): t$_R$=3.04 min, ee %=100%; $^1$H-NMR (400 MHz, CDCl$_3$) δ ppm 7.32-8.36 (m, 4H), 6.03 (d, J=2.2 Hz, 1H), 5.31 (dd, J=9.3, 1.8 Hz, 1H), 2.77 (ddd, J=9.4, 8.0, 3.0 Hz, 1H), 2.40-2.64 (m, 2H), 2.32 (ddd, J=14.2, 8.7, 3.8 Hz, 1H).

Step 6: To a solution of (R)-2-(2-chlorocyclopent-2-en-1-yl)isoindoline-1,3-dione (3.5 g) in ethanol (100 mL) was added hydrazine (85% in water, 0.7 mL). After refluxing for 3 hours, the reaction mixture was cooled to RT. The precipitate was filtered and rinsed with EtOH (10 mL). The filtrate was concentrated to remove half of solvent. To the solution was added HCl in ether (1 M, 20 mL) and concentrated to afford (R)-2-chlorocyclopent-2-enamine as a hydrochloride salt (2.0 g). $^1$H-NMR (400 MHz, DMSO-d$_6$) δ ppm 8.53 (s, 3H), 6.22 (s, 1H), 4.19 (d, J=5.8 Hz, 1H), 2.49-2.54 (m, 1H), 2.26-2.45 (m, 2H), 1.90-2.04 (m, 1H).

Step 7: To a solution of (R)-2-chlorocyclopent-2-enamine hydrochloride salt (600 mg) in toluene (15 mL) was added bis(trichloromethyl) carbonate (694 mg). The mixture was stirred at 120° C. for 4 hours. The mixture was then cooled to RT to afford a toluene solution of (R)-1-chloro-5-isocyanatocyclopent-1-ene. This solution should be synthesized freshly every time.

Intermediate 2:
(R)-5-isocyanato-1-methylcyclopent-1-ene

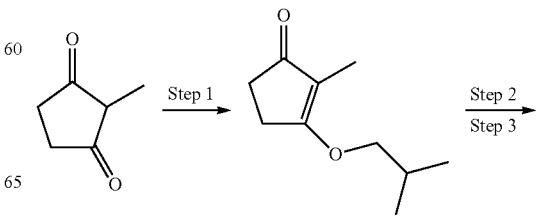

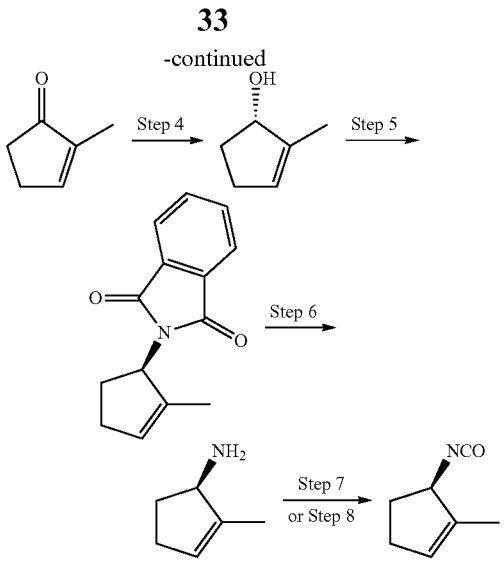

Step 1: A solution of 2-methylcyclopentane-1,3-dione (27.0 g), 2-methylpropan-1-ol (62.5 g) and TsOH (4.6 g) in benzene (500 mL) was heated to reflux overnight. The solvent was removed in vacuo and the residue was distilled under vacuum to give 3-isobutoxy-2-methylcyclopent-2-enone (34.5 g) as a yellow oil. $^1$H-NMR (400 MHz, CDCl$_3$) δ ppm 3.92 (d, J=6.6 Hz, 2H), 2.53-2.70 (m, 2H), 2.32-2.52 (m, 2H), 2.04 (dp, J=13.3, 6.7 Hz, 1H), 1.64 (t, J=1.5 Hz, 3H), 1.01 (d, J=6.7 Hz, 6H); MS(ES$^+$) m/z 169 (MH$^+$).

Step 2: To a solution of 3-isobutoxy-2-methylcyclopent-2-enone (34.5 g) in DCM (300 mL) was added DIBAL-H (1 M in hexane, 250 mL) dropwise at 0° C. The reaction mixture was stirred at this temperature for 90 mins. The reaction was quenched with water and then partitioned between DCM (200 mL) and HCl solution (1 M, 100 mL). The aqueous layer was extracted with DCM (2×200 mL). The combined organic layers were washed with sat. sodium bicarbonate solution (100 mL), brine (200 mL), dried over Na$_2$SO$_4$, filtered and concentrated in vacuo to give a mixture of 2-methylcyclopent-2-enol and 2-methylcyclopent-2-enone (27.0 g) as a yellow oil.

Step 3: The mixture of 2-methylcyclopent-2-enol and 2-methylcyclopent-2-enone from Step 2 (27.0 g) and manganese (IV) oxide (5.0 g) in diethyl ether (200 mL) was stirred at RT overnight. The mixture was filtered and the filtrate was concentrated in vacuo. The residue was distilled in vacuo to give 2-methylcyclopent-2-enone (16.5 g) as a colorless oil.

Step 4: To a solution of (R)-1-methyl-3,3-diphenylhexahydropyrrolo[1,2-c][1,3,2]oxazaborole (1 M in toluene, 31.8 mL) in absolute THF (20 mL) was added carefully 2-methylcyclopent-2-enone (15.3 g) and BH$_3$ (1 M in THF, 111 mL) and the mixture was stirred for one hour. Methanol (150 ml) was added followed by brine and the aqueous layer was extracted with DCM (2×200 mL). The combined organic layers were dried over Na$_2$SO$_4$, filtered and concentrated in vacuo to give (S)-2-methylcyclopent-2-enol (unknown ee %, 16.0 g) as a yellow oil.

Step 5: To a solution of (S)-2-methylcyclopent-2-enol (16.0 g) and isoindoline-1,3-dione (36.0 g) in THF (240 mL) was added triphenylphosphine (77.0 g) under N$_2$. The mixture was cooled to 0° C. Diisopropyl azodicarboxylate (63.4 mL) was added dropwise to the mixture. After stirring for 30 mins, the mixture was stirred at 0° C. overnight. The solvent was removed and the residue was purified by column chromatography (eluting with PE:EA=10:1) to give a crude product, which was purified by SFC to afford (R)-2-(2-methylcyclopent-2-en-1-yl)isoindoline-1,3-dione (10.6 g, >98% ee) as a white solid. Chiral HPLC (Column: AD-H, 4.6*250 mm, 5 μm, MeOH/CO$_2$=10%, column temperature: 40° C., CO$_2$ flow rate: 2.7 mL/min): t$_R$=2.17 min, ee %: >98%; $^1$H-NMR (400 MHz, CDCl$_3$) δ ppm 7.83 (dd, J=5.4, 3.1 Hz, 2H), 7.76-7.61 (m, 2H), 5.68 (s, 1H), 5.21 (d, J=7.4 Hz, 1H), 2.69 (dd, J=5.7, 3.5 Hz, 1H), 2.42-2.30 (m, 2H), 2.22-2.12 (m, 1H), 1.61 (s, 3H); MS (ES$^+$) m/z 228 (MH$^+$).

Step 6: To a solution of (R)-2-(2-methylcyclopent-2-en-1-yl)isoindoline-1,3-dione (10.7 g) in ethanol (150 mL) was added hydrazine (85% in water, 3.0 mL). After refluxing for 3 hours, the reaction mixture was cooled to RT. The precipitate was filtered and the filter cake was rinsed with EtOH (10 mL). To the filtrate was added HCl in dioxane (4 M, 5 mL) and the mixture was concentrated. The resulting residue was dissolved in water, then freeze dried to afford (R)-2-methylcyclopent-2-enamine as the hydrochloride salt (6.3 g) as a brown solid, which was used in the next step without purification.

Step 7: To a solution of (R)-2-methylcyclopent-2-enamine hydrochloride salt (420 mg) in toluene (30 mL) was added triphosgene (560 mg). The resulting mixture was stirred at 110° C. for 6 hours. The mixture was then cooled to RT to afford a toluene solution of (R)-5-isocyanato-1-methylcyclopent-1-ene. This solution should be synthesized freshly every time.

Step 8: To a solution of (R)-2-methylcyclopent-2-enamine hydrochloride salt (23 mg) in DCM (3 mL) and sat. NaHCO$_3$ aqueous solution (3 mL) was added bis(trichloromethyl) carbonate (18 mg) at 0° C. The mixture was stirred for 2 hours at 0° C. to 25° C. The resulting two layers were separated, and the aqueous layer extracted with DCM (60 mL). The combined organic layers were washed with brine (15 mL), dried over Na$_2$SO$_4$, filtered and concentrated under reduced pressure to give (R)-5-isocyanato-1-methylcyclopent-1-ene (20 mg) as a white solid, which was used directly in the next step without further purification. MS(ES$^+$) m/z 141 (MH$^+$) (M: the urea derivative with ammonium hydroxide).

Intermediate 3:
5-isocyanato-1-methylcyclopent-1-ene

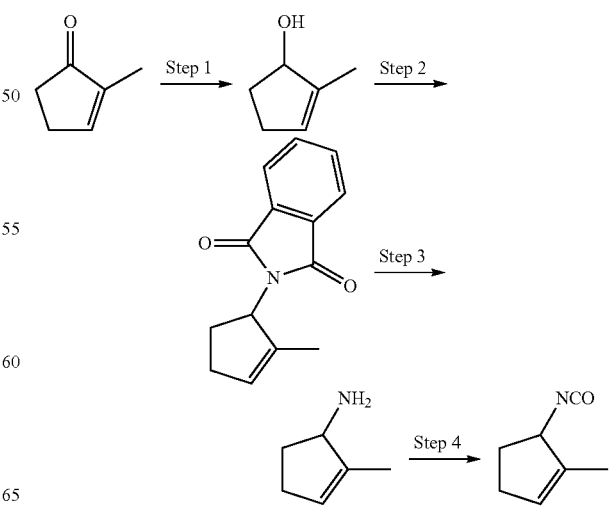

Step 1: To a solution of 2-methylcyclopent-2-enone (Intermediate 2, step 3, 20.0 g) in methanol (20 mL) was added cerium(III) chloride heptahydrate (78.0 g) and sodium tetrahydroborate (7.9 g). The resulting mixture was stirred at RT overnight. Cold water (30 mL) was added. The resulting mixture was neutralized with sat. NaHCO$_3$ solution. The aqueous layer was extracted with DCM (2×100 mL). The combined organic layers were dried over Na$_2$SO$_4$, filtered and concentrated in vacuo to give 2-methylcyclopent-2-enol (18.0 g) as a yellow oil.

Step 2: To a solution of 2-methylcyclopent-2-enol (3.0 g) and isoindoline-1,3-dione (6.8 g) in THF (5 mL) was added Ph$_3$P (14.4 g) under N2. The mixture was cooled to 0° C. DIAD (11.9 mL) was added dropwise into the mixture. After stirring for 30 mins, the mixture was stirred at 0° C. overnight. The solvent was removed in vacuo. The residue was purified by preparative TLC (PE) to give 2-(2-methylcyclopent-2-en-1-yl)isoindoline-1,3-dione (2.4 g) as yellow oil. MS(ES$^+$) m/z 228 (MH$^+$).

Step 3: To a solution of 2-(2-methylcyclopent-2-en-1-yl) isoindoline-1,3-dione (2.0 g) in ethanol (50 mL) was added hydrazine (85% in water, 0.5 mL). After refluxing for 4 hours, the reaction mixture was cooled to RT. The precipitate was filtered and the filter cake was rinsed with Et$_2$O (10 mL). To the filtrate was added HCl solution (4 M in dioxane, 5 mL). The resulting mixture was concentrated to afford 2-methylcyclopent-2-enamine as a hydrochloride salt (2.1 g), which was used in the next step without purification.

Step 4: To a solution of 2-methylcyclopent-2-enamine hydrochloride salt (0.8 g) in toluene (40 mL) was added triphosgene (0.4 g). The reaction mixture was stirred at 110° C. for 6 hours. The mixture was cooled to RT to afford a toluene solution of 5-isocyanato-1-methylcyclopent-1-ene. This solution was directly used for the next step without concentration and purification. This solution should be synthesized freshly every time.

Intermediate 4: 3-isocyanatocyclopent-1-ene

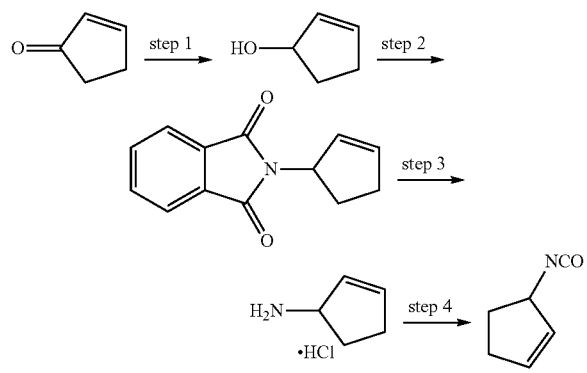

Step 1: To a stirred solution of cyclopent-2-enone (10.0 g) and CeCl$_3$ (47.7 g) in methanol (80 mL) was added NaBH$_4$ (5.1 g) at 0° C. The reaction mixture was stirred at the same temperature for 1 hour. The mixture was diluted with brine and extracted with EA (4×100 mL). The organic layer was washed with brine, dried over anhydrous magnesium sulfate, and evaporated. The residue was purified by column chromatography (eluting with hexane:EA=10:1) to give cyclopent-2-enol (8.8 g) as a yellow oil. $^1$H-NMR (400 MHz, CDCl$_3$) δ ppm 6.10-5.73 (m, 2H), 4.86 (d, J=5.6 Hz, 1H), 2.60-2.40 (m, 1H), 2.37-2.12 (m, 2H), 1.74-1.60 (m, 1H).

Step 2: To a solution of cyclopent-2-enol (8.8 g) and isoindoline-1,3-dione (23.1 g) in THF (150 mL) was added Ph$_3$P (41.2 g) under N$_2$. After cooling to 0° C., DIAD (30.5 mL) was added dropwise into the mixture, and the resulting mixture was stirred overnight. The solvent was removed in vacuo and the residue was purified by column chromatography (eluting with hexane:EA=30:1) to give 2-(cyclopent-2-en-1-yl)isoindoline-1,3-dione (6.1 g) as a white solid. MS(ES$^+$) m/z 214.2 (MH$^+$).

Step 3: 2-(Cyclopent-2-en-1-yl)isoindoline-1,3-dione (4.0 g) was dissolved in THF (20 mL) and hydrazine (85% in water, 1.1 g). The reaction mixture was then heated at reflux for 23 hours. After cooling to RT, the mixture was filtered and washing with cold Et$_2$O. HCl solution (2 M in dioxane, 10 mL) was added to the filtrate and the solution was concentrated in vacuo. The residue was washed with Et$_2$O (50 mL) to give cyclopent-2-enamine as a hydrochloride salt (0.9 g) as a light yellow solid. $^1$H-NMR (400 MHz, DMSO-d$_6$) δ ppm 8.26 (s, 5H), 6.34-6.00 (m, 2H), 5.77 (dd, J=5.3, 2.3 Hz, 2H), 4.14 (s, 2H), 2.51-2.46 (m, 2H), 2.39-2.25 (m, 2H), 2.25-2.10 (m, 2H), 1.77 (ddt, J=13.5, 8.8, 4.3 Hz, 2H).

Step 4: To a suspension of cyclopent-2-enamine hydrochloride salt (320 mg) in toluene (20 mL) was added triphosgene (476 mg). After stirring at 110° C. for 4 hours, the reaction mixture became clear. The reaction mixture was cooled to afford a toluene solution of 3-isocyanatocyclopent-1-ene. This solution should be synthesized freshly every time.

Intermediate 5:
(S)-1-chloro-5-isocyanatocyclopent-1-ene

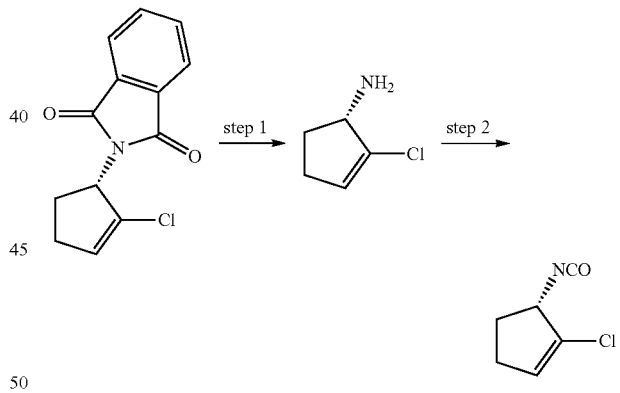

Step 1: To a solution of (S)-2-(2-chlorocyclopent-2-en-1-yl)isoindoline-1,3-dione (Intermediate 1, step 5, 5.5 g) in ethanol (120 mL) was added hydrazine (85% in water, 1.4 mL). After refluxing for 3 hours, the reaction mixture was cooled to RT. The precipitate was filtered and the filter cake was rinsed with EtOH (10 mL). To the filtrate was added HCl solution (4.0 M in dioxane, 5 mL) and the mixture was concentrated. The resulting residue was dissolved in water and freeze dried to afford (S)-2-chlorocyclopent-2-enamine as a hydrochloride salt (3.0 g) as a brown solid, which was used in the next step without purification. MS(ES$^+$) m/z 118 (MH$^+$).

Step 2: To a solution of (S)-2-chlorocyclopent-2-enamine hydrochloride salt (0.3 g) in toluene (20 mL) was added bis(trichloromethyl) carbonate (0.4 g) and the mixture was stirred at 110° C. for 6 hours. The mixture was cooled to RT to afford a toluene solution of (S)-5-isocyanato-1-methyl-cyclopent-1-ene. This solution should be synthesized freshly every time.

Intermediate 6:
1-chloro-3-isocyanato-2-methylcyclopent-1-ene

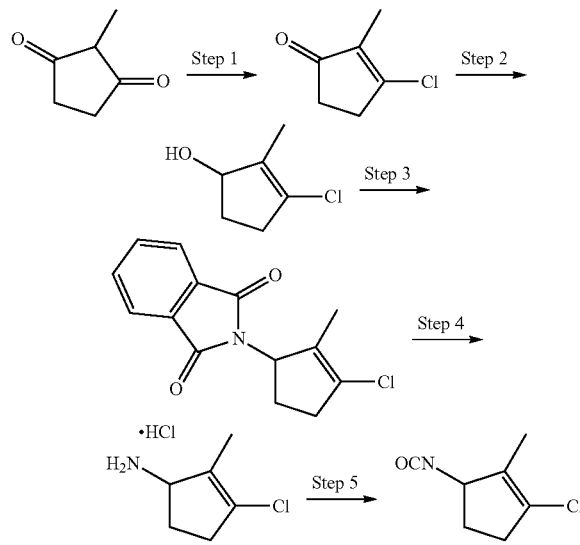

Step 1: To a stirred solution of 2-methylcyclopentane-1,3-dione (5.0 g) and DMF (0.3 mL) in DCM (80 mL) at 0° C. was added oxalyl dichloride (5.7 mL). After stirring for 0.5 hour, the mixture was diluted with brine and extracted with EA. The organic layer was washed with brine, dried over anhydrous magnesium sulfate and evaporated to give 3-chloro-2-methylcyclopent-2-enone (4.6 g) as a yellow oil. $^1$H-NMR (400 MHz, CDCl$_3$) δ ppm 2.72-2.86 (m, 2H), 2.45-2.60 (m, 2H), 1.79 (t, J=2.1 Hz, 3H).

Step 2: To a stirred solution of 3-chloro-2-methylcyclopent-2-enone (4.6 g) and CeCl$_3$ (13.8 g) in methanol (180 mL) was added NaBH$_4$ (1.5 g) at 0° C. The mixture was stirred at the same temperature until the reaction finished. The mixture was diluted with brine and extracted with EA. The organic layer was washed with brine, dried over anhydrous magnesium sulfate and evaporated. The residue was purified by column chromatography (eluting with hexane:EA=10:1) to give 3-chloro-2-methylcyclopent-2-enol (2.6 g) as a yellow oil. $^1$H-NMR (400 MHz, CDCl$_3$) δ ppm 4.51 (m, 1H), 3.78-2.29 (m, 4H), 1.78 (s, 3H).

Step 3: To a solution of 3-chloro-2-methylcyclopent-2-enol (2.6 g) and isoindoline-1,3-dione (4.3 g) in THF (100 mL) was added triphenylphosphine (7.7 g) under N2. The mixture was cooled to 0° C. and stirred for 30 mins. DIAD (5.7 mL) was added dropwise into the mixture and the mixture was stirred at 0° C. overnight. The solvent was removed in vacuo and the residue was purified by column chromatography (eluting with PE) to give 2-(3-chloro-2-methylcyclopent-2-en-1-yl)isoindoline-1,3-dione (1.7 g) as a white solid. MS(ES$^+$) m/z 262 (MH$^+$).

Step 4: To a solution of 2-(3-chloro-2-methylcyclopent-2-en-1-yl)isoindoline-1,3-dione (1.7 g) in THF (20 mL) was added hydrazine (85% in water, 0.3 mL). After heating under reflux for 4 hours, the reaction mixture was cooled to RT and filtered. HCl solution (4 M in dioxane) was added to the filtrate to adjust to acidic conditions. The mixture was concentrated to give 3-chloro-2-methylcyclopent-2-enamine as a hydrochloride salt (1.0 g), which was used in the next step without purification. $^1$H-NMR (400 MHz, CDCl$_3$) δ ppm 8.42 (s, 2H), 4.10 (s, 1H), 5.83 (s, 1H), 2.77-2.64 (m, 1H), 2.48 (d, J=18.4 Hz, 2H), 2.41-2.24 (m, 1H), 1.92-1.80 (m, 1H), 1.78 (s, 3H).

Step 5: To a solution of 3-chloro-2-methylcyclopent-2-enamine hydrochloride salt (980 mg) in toluene (10 mL) was added bis(trichloromethyl) carbonate (884 mg) at RT and the reaction mixture was heated under reflux for 5 hours. The mixture was cooled to RT to afford a toluene solution of 1-chloro-3-isocyanato-2-methylcyclopent-1-ene. This solution should be synthesized freshly every time.

Intermediate 7:
1-fluoro-3-isocyanato-2-methylcyclopent-1-ene

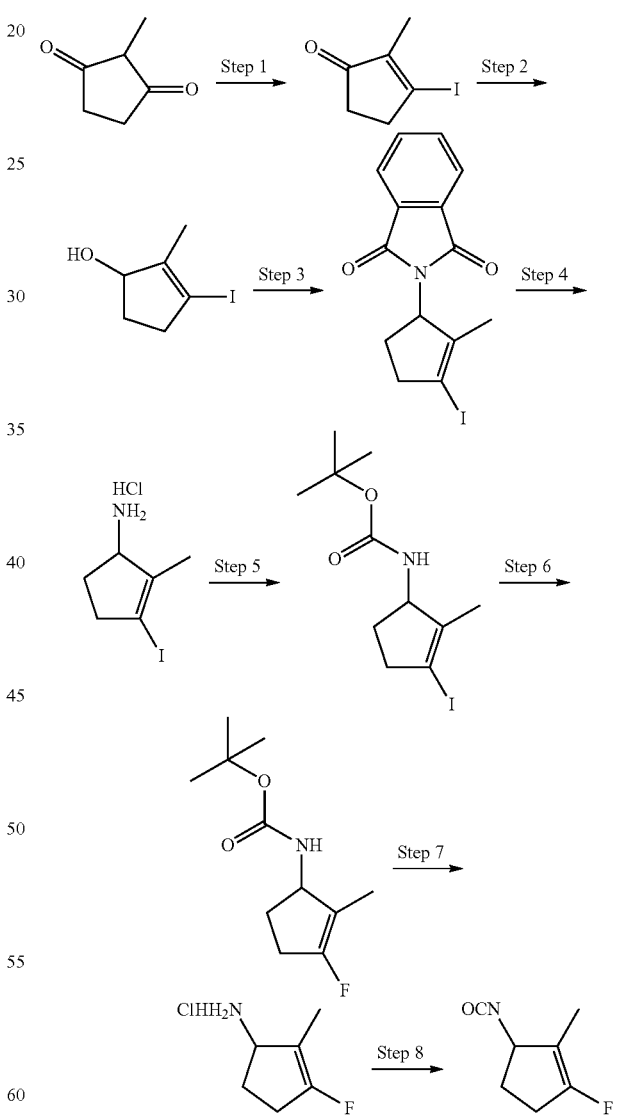

Step 1: Iodine (14.7 g) was added at RT to a stirred solution of triphenylphosphine (15.2 g) in acetonitrile (120 mL) and stirring was continued for 15 mins. TEA (8.1 mL) was added. After another 5 mins of stirring, 2-methylcyclopentane-1,3-dione (5.0 g) was added. The solution was heated under reflux until the reaction was complete. The solvent was evaporated in vacuo, and diethyl ether was added to the residue. The solvent was then decanted. This procedure was repeated three times. The combined organic layers were filtered through silica gel washing with diethyl ether. The solvent was then evaporated in vacuo to give 3-iodo-2-methylcyclopent-2-enone (9.4 g) as a yellow solid. ¹H-NMR (400 MHz, CDCl₃) δ ppm 3.00 (dd, J=4.6, 2.2 Hz, 2H), 2.53 (dd, J=5.9, 3.4 Hz, 2H), 1.81 (s, 3H).

Step 2: To a stirred solution of 3-iodo-2-methylcyclopent-2-enone (9.4 g) and cerium chloride (16.5 g) in methanol (80 mL) was added sodium borohydride (1.8 g) at 0° C. The reaction mixture was stirred at the same temperature until the reaction was complete. The mixture was diluted with brine and extracted with EA. The organic layer was washed with brine, dried over anhydrous magnesium sulfate and concentrated. The residue was purified by column chromatography (eluting with hexane:EA=10:1) to give 3-iodo-2-methylcyclopent-2-enol (9.8 g) as a yellow oil.

Step 3: To a solution of 3-iodo-2-methylcyclopent-2-enol (9.8 g) and isoindoline-1,3-dione (9.6 g) in THF (220 mL) was added triphenylphosphine (17.2 g) under N₂. The mixture was stirred for 30 mins at 0° C. and DIAD (12.7 mL) was added dropwise to the mixture. The mixture was stirred at 0° C. overnight. The solvent was removed under vacuum, and the residue was purified by preparative TLC (PE) to give 2-(3-iodo-2-methylcyclopent-2-en-1-yl)isoindoline-1,3-dione (5.3 g) as a white solid. MS(ES⁺) m/z 354 (MH⁺).

Step 4: To a solution of 2-(3-iodo-2-methylcyclopent-2-en-1-yl)isoindoline-1,3-dione (5.3 g) in ethanol (30 mL) was added hydrazine (85% in water, 0.5 mL). The mixture was heated under reflux for 4 hours. The reaction mixture was cooled to RT and filtered. To the filtrate was added HCl solution (4 M in dioxane) to adjust pH to acidic conditions. The mixture was concentrated to give 3-iodo-2-methylcyclopent-2-enamine as a hydrochloride salt (2.1 g). ¹H-NMR (400 MHz, DMSO-d₆) δ ppm 8.44 (s, 3H), 4.00 (s, 1H), 2.67-2.98 (m, 1H), 2.57 (m, 1H), 2.20-2.42 (m, 1H), 1.70-1.99 (m, 4H).

Step 5: TEA (3.4 mL) was added at RT to a stirred solution of 3-iodo-2-methylcyclopent-2-enamine hydrochloride salt (2.1 g) in DCM (30 mL) and stirring was continued for 15 mins. Di-tert-butyl dicarbonate (2.3 mL) was added. After completion of the reaction, water (10 mL) was added and the resulting mixture was extracted with DCM (2×100 mL). The combined organic layers were dried over Na₂SO₄, filtered and concentrated in vacuo. The residue was purified by column chromatography (eluting with PE:EA=15:1) to give tert-butyl (3-iodo-2-methylcyclopent-2-en-1-yl)carbamate (1.0 g) as a white solid. MS(ES⁺) m/z 268 (MH⁺).

Step 6: To a solution of tert-butyl (3-iodo-2-methylcyclopent-2-en-1-yl)carbamate (500 mg) and N-fluoro-N-(phenylsulfonyl)benzenesulfonamide (732 mg) in THF (50 mL) was added butyllithium solution (2.5 M in hexanes, 1.9 mL) at −78° C. under N₂. The resulting mixture was stirred for 1 hour at this temperature. NH₄Cl solution (15 mL) was added and the resulting mixture was extracted with DCM (2×40 mL). The combined organic layers were dried over Na₂SO₄, filtered and concentrated in vacuo. The residue was purified by column chromatography (eluting with PE) to give tert-butyl (3-fluoro-2-methylcyclopent-2-en-1-yl)carbamate (160 mg) as a colorless oil.

Step 7: Tert-butyl (3-fluoro-2-methylcyclopent-2-en-1-yl) carbamate (160 mg) was added at RT to a stirred solution of HCl solution (4 M in 1,4-dioxane, 10 mL). After stirring overnight, the mixture was concentrated in vacuo to give 3-fluoro-2-methylcyclopent-2-enamine as a hydrochloride salt (130 mg) as a white solid.

Step 8: To a solution of 3-fluoro-2-methylcyclopent-2-enamine hydrochloride salt (83 mg) in a mixture of DCM (3 mL) and sat. NaHCO₃ solution (3 mL) was added bis(trichloromethyl) carbonate (46 mg) at 0° C. The mixture was stirred for 50 minutes. The organic phase was separated, dried and concentrated to give 1-fluoro-3-isocyanato-2-methylcyclopent-1-ene (63 mg) as a light yellow oil, which was used without further purification.

Intermediate 8:
1-fluoro-5-isocyanatocyclopent-1-ene

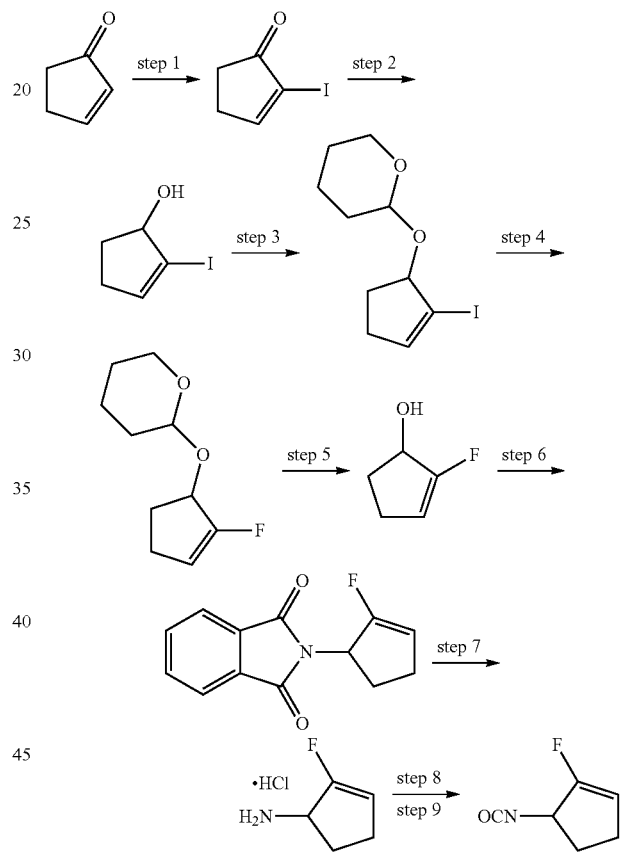

Step 1: To a stirred solution of cyclopent-2-enone (25.0 g) in THF—H₂O (v:v=1:1, 1000 mL) was added K₂CO₃ (50.5 g), then iodine (116.0 g) and then DMAP (37.2 g). Upon completion of the reaction, the mixture was diluted with EA (600 mL) and washed with sat. Na₂S₂O₃ (600 mL) and then HCl (0.1 M, 600 mL). The organic phase was dried over Na₂SO₄, filtered and concentrated under reduced pressure to give 2-iodocyclopent-2-enone (25.8 g) as a light yellow solid. MS(ES⁺) m/z 209 (MH⁺).

Step 2: To a solution of 2-iodocyclopent-2-enone (25.8 g) in methanol (450 mL) and THF (450 mL) was added cerium(III) chloride heptahydrate (55.5 g). Sodium borohydride (4.7 g) was then added portion-wise at 0° C. over 30 mins. The resulting mixture was stirred at RT for 3 hours. The reaction mixture was quenched with aq. HCl solution (0.5 M, 80 mL) to pH ~5, and then extracted with EA (2×300 mL). The combined organic phases were washed with brine (150 mL), sat. NaHCO₃ (150 mL) and then brine (150 mL) again. The resulting mixture was dried over sodium sulfate and concentrated under reduced pressure to afford 2-iodocyclopent-2-enol (18.5 g) as a light yellow solid. ¹H-NMR (400 MHz, CDCl₃) δ ppm 6.33-6.26 (m, 1H), 4.74-4.65 (m, 1H), 2.55-2.44 (m, 1H), 2.36-2.25 (m, 2H), 1.93 (s, 1H), 1.90-1.84 (m, 1H).

Step 3: To a mixture of 2-iodocyclopent-2-enol (18.0 g) in THF (120 mL) was added 3,4-dihydro-2H-pyran (14.4 g) and TsOH (1.3 g). The mixture was stirred and heated under reflux overnight. After cooling to RT, the mixture was diluted with EA (80 mL). The mixture was washed with sat. NaHCO₃ solution (80 mL). The organic phase was dried over Na₂SO₄, filtered and concentrated under reduced pressure. The residue was purified by column chromatography (eluting with PE:EA=18:1) to give 2-((2-iodocyclopent-2-en-1-yl)oxy)tetrahydro-2H-pyran (19.0 g) as a light yellow oil. ¹H-NMR (400 MHz, CDCl₃) δ ppm 6.32 (d, J=33.6 Hz, 1H), 4.77-4.82 (m, 1H), 3.84-3.97 (m, 1H), 3.46-3.60 (m, 1H), 2.43-2.55 (m, 1H), 2.17-2.39 (m, 2H), 1.91-2.05 (m, 1H), 1.76-1.91 (m, 2H), 1.62-1.75 (m, 2H), 1.52-1.61 (m, 3H).

Step 4: To a solution of 2-((2-iodocyclopent-2-en-1-yl)oxy)tetrahydro-2H-pyran (9.0 g) and N-fluoro-N-(phenylsulfonyl)benzenesulfonamide (11.6 g) in THF (200 mL) was added nBuLi (2.5 M in hexanes, 24.5 mL). The mixture was stirred at −78° C. overnight. Sat. NH₄Cl solution (40 mL) was added and the resulting mixture was extracted with EA (2×100 mL). The combined organic phases were dried over Na₂SO₄, filtered and concentrated under reduced pressure. The residue was purified by column chromatography (eluting with PE:EA=18:1) to give 2-((2-fluorocyclopent-2-en-1-yl)oxy)tetrahydro-2H-pyran (4.0 g) as a yellow oil. ¹H-NMR (400 MHz, CDCl₃) δ ppm 5.12-5.23 (m, 1H), 4.69-4.75 (m, 1H), 3.79-3.86 (m, 1H), 3.43-3.47 (m, 1H), 2.25-2.31 (m, 1H), 2.07-2.20 (m, 2H), 1.84-1.93 (m, 1H), 1.73-1.81 (m, 2H), 1.63-1.68 (m, 1H), 1.46-1.57 (m, 5H); MS(ES⁺) m/z 187 (MH⁺).

Step 5: To a solution of 2-((2-fluorocyclopent-2-en-1-yl)oxy)tetrahydro-2H-pyran (8.0 g) in methanol (30 mL) was added PPTS (5.4 g). The reaction mixture was stirred at 70° C. overnight. After cooling, the mixture was diluted with water (30 mL), and then extracted with DCM (2×80 mL). The combined organic layers were dried over Na₂SO₄, filtered and concentrated. The residue was purified by column chromatography (eluting with DCM) to give 2-fluorocyclopent-2-enol (2.1 g) as a light yellow oil. ¹H-NMR (400 MHz, CDCl₃) δ ppm 5.22 (t, J=2.3 Hz, 1H), 4.71-4.76 (m, 1H), 2.32-2.43 (m, 2H), 2.14-2.24 (m, 1H), 2.10 (s, 1H), 1.78-1.81 (m, 1H).

Step 6: To a solution of 2-fluorocyclopent-2-enol (2.0 g) and isoindoline-1,3-dione (3.0 g) in THF (300 mL) was added Ph₃P (6.5 g) under N₂. The reaction mixture was cooled to 0° C. DIAD (5.3 mL) was added dropwise and the mixture was stirred at 0° C. overnight. The mixture was concentrated under reduced pressure, and the residue was purified by column chromatography (eluting with PE:EA=15:1) to give 2-(2-fluorocyclopent-2-en-1-yl)isoindoline-1,3-dione (1.1 g) as a yellow solid. MS(ES⁺) m/z 232 (MH⁺).

Step 7: To a solution of 2-(2-fluorocyclopent-2-en-1-yl)isoindoline-1,3-dione (1.8 g) in absolute THF (20 mL) was added hydrazine (98% in H₂O, 0.4 g) carefully. The mixture was heated to 75° C. for 18 hours. Upon cooling to RT, the mixture was filtered and to the filtrate was added HCl solution (4 M in 1,4-dioxane, 2.2 mL). The mixture was stirred at RT for 3 hours, and concentrated under reduced pressure. The residue was washed with diethyl ether (3×30 mL) to give 2-fluorocyclopent-2-enamine as a hydrochloride salt (1.1 g) as a white solid. ¹H-NMR (400 MHz, DMSO-d₆) δ ppm 8.65 (s, 3H), 5.55 (s, 1H), 4.22 (s, 1H), 2.27-2.43 (m, 2H), 2.16-2.26 (m, 1H), 1.84-1.95 (m, 1H).

Step 8: To a solution of 2-fluorocyclopent-2-enamine hydrochloride salt (300 mg) in toluene (20 mL) was added triphosgene (388 mg). The reaction mixture was stirred at 110° C. for 6 hours. The mixture was then cooled to RT and directly used for the next step without concentration and purification.

Step 9: To a solution of 2-fluorocyclopent-2-enamine, hydrochloride (450 mg) in a mixture of DCM (15 mL) and sat. NaHCO₃ solution (15 mL) was added bis(trichloromethyl) carbonate (340 mg) at 0° C. and the mixture was stirred for 50 minutes. The organic phase was separated, dried and half of the solvent was removed. The resulting solution was used without further purification.

Intermediate 9:
1-fluoro-5-isocyanatocyclopent-1-ene

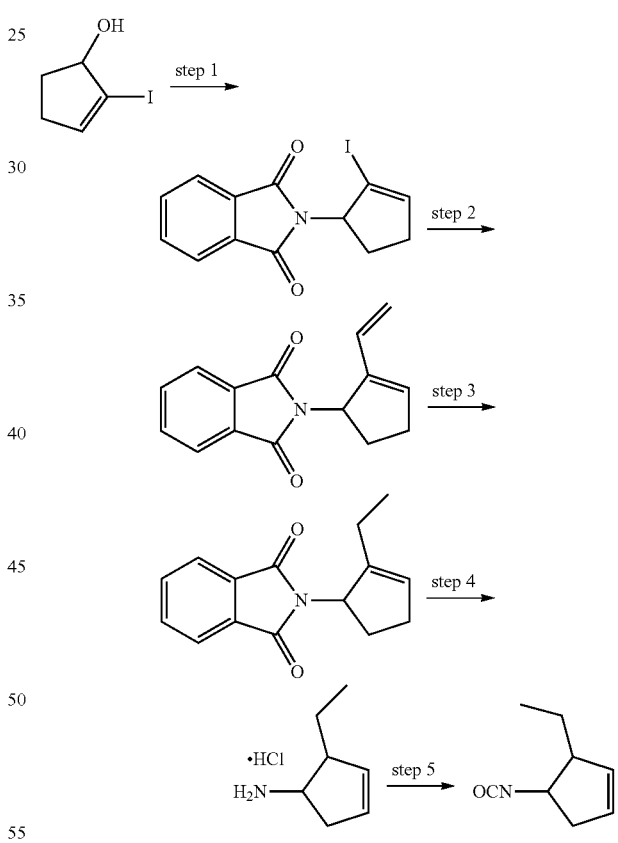

Step 1: To a solution of triphenylphosphine (2.5 g), 2-iodocyclopent-2-enol (Intermediate 8, Step 2, 1.0 g) and isoindoline-1,3-dione (1.4 g) in dry THF (30 mL) was added DIAD (1.8 mL) dropwise at 0° C. Then the resulting mixture was stirred at RT overnight. The mixture was diluted with EA (50 mL), and the organic phase was washed with water (20 mL) and brine (20 mL), dried over magnesium sulfate and then concentrated. The residue was purified by column chromatography (eluting with PE:EA=8:1) to afford 2-(2-iodocyclopent-2-en-1-yl)isoindoline-1,3-dione (460 mg) as a light yellow solid. MS(ES⁺) m/z 340 (MH⁺).

Step 2: To a solution of 2-(2-iodocyclopent-2-en-1-yl)isoindoline-1,3-dione (1500 mg), potassium carbonate (917 mg) and 2,4,6-trivinyl-1,3,5,2,4,6-trioxatriborinane, complexed with pyridine (1:1, 426 mg) in a mixture of toluene (20 mL), ethanol (15 mL) and water (10 mL) was added tetrakis(triphenylphosphine)palladium(0) (102 mg) under $N_2$. The resulting mixture was heated to 90° C. and stirred for 2 hours. The mixture was diluted with EA (20 mL) and the organic phase was washed with water and brine, dried over $MgSO_4$ and concentrated. The residue was purified by column chromatography (eluting with PE:EA=25:1) to afford 2-(2-vinylcyclopent-2-en-1-yl)isoindoline-1,3-dione (700 mg) as a yellow oil. $MS(ES^+)$ m/z 240 ($MH^+$).

Step 3: To a solution of 2-(2-vinylcyclopent-2-en-1-yl)isoindoline-1,3-dione (600 mg) in THF (50 mL) was added Pd/C (267 mg) under a nitrogen atmosphere. The resulting mixture was stirred at RT under hydrogen atmosphere for 15 hours. The mixture was filtered and the filtrate was concentrated to give 2-(2-ethylcyclopent-2-en-1-yl)isoindoline-1,3-dione (500 mg) as a colorless oil. $MS(ES^+)$ m/z 242 ($MH^+$).

Step 4: A mixture of 2-(2-ethylcyclopent-2-en-1-yl)isoindoline-1,3-dione (450 mg), ethanol (25 mL) and hydrazine (85% in water, 0.07 mL) was stirred whilst heating under reflux for 12 hours. After cooled to RT, the mixture was filtered and hydrochloric acid (4 M in dioxane, 1.0 mL) was added to the filtrate. The mixture was concentrated in vacuo and the residue was washed with cold water (100 mL) and dried under vacuum to give 2-ethylcyclopent-2-enamine as a hydrochloride salt (180 mg) as a white solid.

Step 5: To a solution of 2-ethylcyclopent-2-enamine hydrochloride salt (80 mg) and triphosgene (75 mg) was added toluene (9 mL). The resulting mixture was heated under reflux for 4 hours. After cooling to RT, the solution was directly used for the next step without further purification.

Intermediate 10:
1-chloro-5-isocyanatocyclopent-1-ene

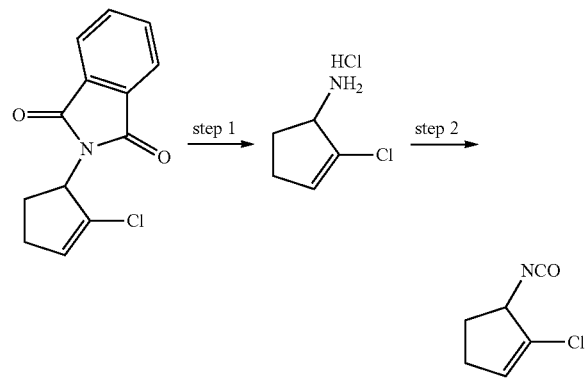

Step 1: 2-(2-Chlorocyclopent-2-en-1-yl)isoindoline-1,3-dione (Intermediate 5, Step 2, 9.0 g) was dissolved in absolute THF (100 mL), followed by careful addition of hydrazine (95% in $H_2O$, 2.5 g). The reaction mixture was heated at 60° C. overnight. Upon cooling to RT, the mixture was filtered and washing with cold THF. The combined filtrate and washings was concentrated in vacuo to give 2-chlorocyclopent-2-enamine as a hydrochloride salt (2.2 g) as a yellow solid. $MS(ES^+)$ m/z 118 ($MH^+$).

Step 2: To a solution of 2-chlorocyclopent-2-enamine hydrochloride salt (0.6 g) in toluene (32 mL) was added triphosgene (0.6 g) and the reaction mixture was stirred at 110° C. for 6 hours. The mixture was cooled to RT to give a toluene solution of the title compound that was directly used in the next step. This solution should be synthesized freshly every time.

Intermediate 11:
1-fluoro-5-isocyanatocyclopent-1-ene

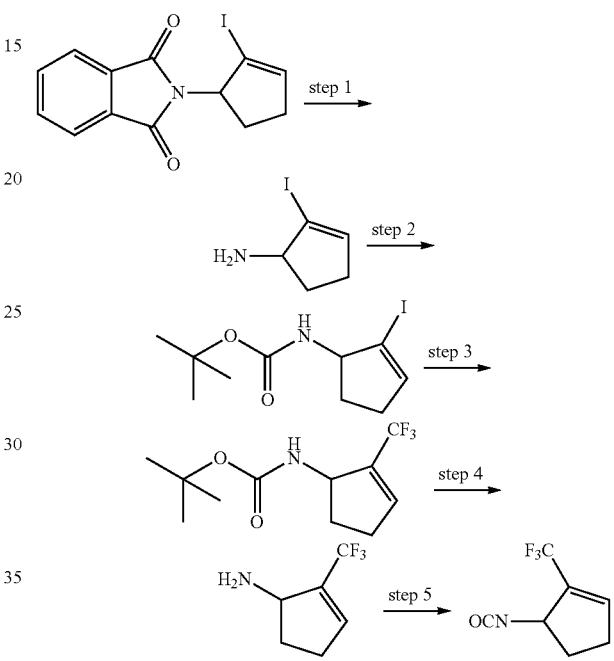

Step 1: To a solution of 2-(2-iodocyclopent-2-en-1-yl)isoindoline-1,3-dione (Intermediate 9, Step 1, 700 mg) in methanol (15 mL) was added hydrazine hydrate (155 mg) under a nitrogen atmosphere. After stirring at 75° C. overnight, the reaction mixture was cooled to RT. The mixture was filtered and the filtrate was concentrated in vacuo. The residue was treated with MeOH (5 mL) and evaporated. This procedure was repeated several times to afford 2-iodocyclopent-2-enamine (410 mg). $MS(ES^+)$ m/z 210 ($MH^+$).

Step 2: To a solution of 2-iodocyclopent-2-enamine (930 mg) in 1,4-dioxane (30 mL) was added TEA (0.3 mL) and di-tert-butyl dicarbonate (971 mg) and the mixture was stirred overnight. The mixture was concentrated and the residue was purified by column chromatography (eluting with EA:PE=1:20) to afford tert-butyl (2-iodocyclopent-2-en-1-yl)carbamate (1.0 g) as a white solid. $MS(ES^+)$ m/z 332 ($MH^+$).

Step 3: A solution of tert-butyl (2-iodocyclopent-2-en-1-yl)carbamate (50 mg), HMPA (0.2 mL), methyl 2,2-difluoro-2-(fluorosulfonyl)acetate (124 mg) and copper(I) iodide (185 mg) was stirred in DMF (2 mL) at 80° C. overnight. Cold water (30 mL) was added and the aqueous layer was extracted with DCM (2×100 mL). The combined organic layers were dried over $Na_2SO_4$, filtered and concentrated in vacuo to give tert-butyl (2-(trifluoromethyl)cyclopent-2-en-1-yl)carbamate (30 mg) as a white solid. $MS(ES^+)$ m/z 196 ($M+H+H-tBu^+$).

Step 4: A solution of tert-butyl (2-(trifluoromethyl)cyclopent-2-en-1-yl)carbamate (657 mg) and HCl (4 M in dioxane, 2.6 mL) was stirred in methanol (6 mL) at RT overnight. The solvent was removed under vacuum to give 2-(trifluoromethyl)cyclopent-2-enamine as a hydrochloride salt (450 mg) as a white solid. MS(ES$^+$) m/z 152 (MH$^+$).

Step 5: A solution of 2-(trifluoromethyl)cyclopent-2-enamine hydrochloride salt (49 mg) and bis(trichloromethyl) carbonate (31 mg) was stirred in toluene (5 mL) at 110° C. for 5 hours. The solvent was removed under vacuum to give the title compound (30 mg) as an oil.

Intermediate 12: 6-amino-3-chloro-2-((1,1,1-trifluoro-2-methylpropan-2-yl)sulfonyl) phenol

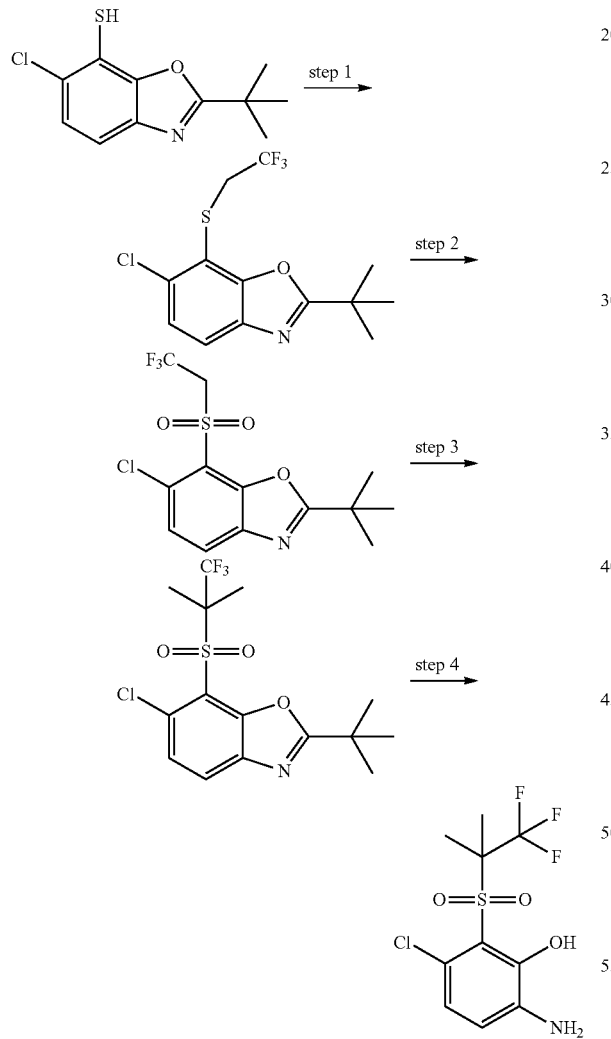

Step 1: To a solution of 2-(tert-butyl)-6-chlorobenzo[d]oxazole-7-thiol (7.0 g) (for preparation see US Patent Publication US2007/0249672) in DMF (70 mL), stirred at RT was added 1,1,1-trifluoro-2-iodoethane (6.7 g). The reaction mixture was stirred at 80° C. overnight. Upon cooling, the reaction mixture was washed with water (100 mL) and extracted with EA (2×100 mL). The combined organic layers were dried over anhydrous Na$_2$SO$_4$, filtered and concentrated to give 2-(tert-butyl)-6-chloro-7-((2,2,2-trifluoroethyl)thio)benzo[d]oxazole (9.0 g). MS(ES$^+$) m/z 324 (MH$^+$).

Step 2: To a solution of 2-(tert-butyl)-6-chloro-7-((2,2,2-trifluoroethyl)thio)benzo[d]oxazole (9.0 g) in anhydrous DCM (90 mL) stirred at RT was added mCPBA (14.4 g) and the reaction mixture was stirred at RT for 48 hours. The reaction mixture was filtered and the filtrate was washed with aq. Na$_2$S$_2$O$_3$ solution, and then NaOH solution. The organic layer was dried and concentrated to give 2-(tert-butyl)-6-chloro-7-((2,2,2-trifluoroethyl)sulfonyl)benzo[d]oxazole (7.0 g) which was used directly in the next step.

Step 3: To a solution of 2-(tert-butyl)-6-chloro-7-((2,2,2-trifluoroethyl)sulfonyl)benzo[d]oxazole (3.2 g) and iodomethane (12.8 g) in THF (50 mL) and HMPA (45 mL) was added lithium diisopropylamide (2 M in THF, 13.5 mL) and the mixture was stirred at −78° C. for 10 min. The mixture was quenched with NH$_4$Cl and then aq. HCl solution (10%). The resulting solution was extracted with EA. The organic layer was washed with brine, dried over Na$_2$SO$_4$ and concentrated to give a residue that was purified by column chromatography to afford 2-(tert-butyl)-6-chloro-7-((1,1,1-trifluoro-2-methylpropan-2-yl)sulfonyl)benzo[d]oxazole (3.0 g). MS(ES$^+$) m/z 384 (MH$^+$).

Step 4: To a solution of 2-(tert-butyl)-6-chloro-7-((1,1,1-trifluoro-2-methylpropan-2-yl)sulfonyl)benzo[d]oxazole (3.0 g) in 1,4-dioxane (30 mL) was added conc. HCl (7.5 mL) and the mixture was stirred at 100° C. for 24 hours. On cooling to RT, the pH was adjusted to ~8. The mixture was concentrated and the residue was purified by column chromatorgraphy to afford the title compound (1.2 g). MS(ES$^+$) m/z 318 (MH$^+$).

Intermediate 13:
6-amino-2-(tert-butylsulfonyl)-3-chlorophenol, trifluoroacetic acid salt

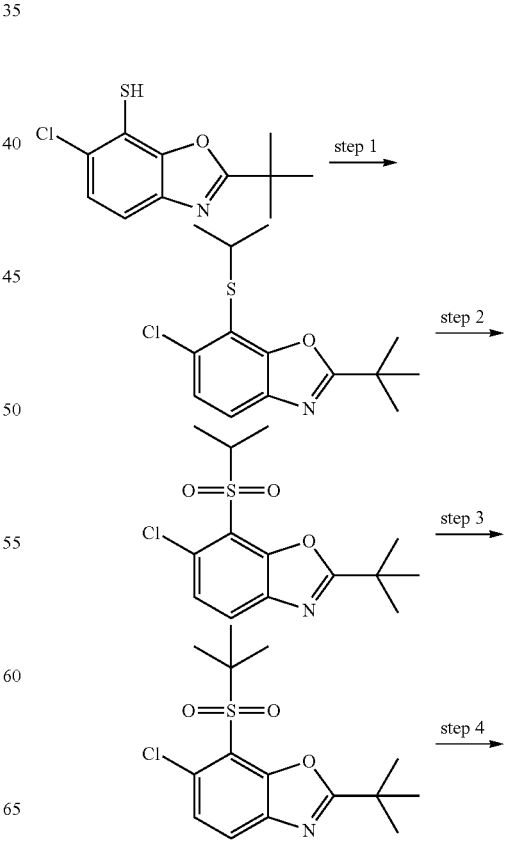

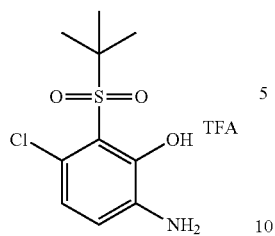

Step 1: To a solution of 2-(tert-butyl)-6-chlorobenzo[d]oxazole-7-thiol (3.0 g) in DMF (30 mL) was added 2-iodopropane (2.1 g). The mixture was stirred at 100° C. for 2 hours. The mixture was cooled to RT and concentrated. The crude product was purified by column chromatography to give 2-(tert-butyl)-6-chloro-7-(isopropylthio)benzo[d]oxazole (3.5 g).

Step 2: To a solution of 2-(tert-butyl)-6-chloro-7-(isopropylthio)benzo[d]oxazole (3.5 g) in DCM (40 mL) was added mCPBA (5.3 g) at 15° C. The mixture was stirred at 15° C. for 48 hours, and then quenched with sat. Na$_2$SO$_3$ solution. The organic layer was dried over Na$_2$SO$_4$ and concentrated. The residue was purified by column chromatography to afford 2-(tert-butyl)-6-chloro-7-(isopropylsulfonyl)benzo[d]oxazole (3.6 g). MS(ES$^+$) m/z 316 (MH$^+$).

Step 3: To a solution of 2-(tert-butyl)-6-chloro-7-(isopropylsulfonyl)benzo[d]oxazole (3.0 g) in THF (10 mL) was added LiHMDS (1.2 M in THF, 31.7 mL). The mixture was stirred at −78° C. for 10 mins. Iodomethane (6.7 g) was added. The mixture was stirred at −78° C. for 10 mins, and then quenched with aq. NH$_4$Cl and HCl solution (10%). The mixture was extracted with EA. The organic layer was washed with brine, dried over Na$_2$SO$_4$ and concentrated. The crude product was purified by column chromatography to afford 2-(tert-butyl)-7-(tert-butylsulfonyl)-6-chlorobenzo[d]oxazole (2.8 g). MS(ES$^+$) m/z 330 (MH$^+$).

Step 4: To a solution of 2-(tert-butyl)-7-(tert-butylsulfonyl)-6-chlorobenzo[d]oxazole (2.7 g) in 1,4-dioxane (10 mL) was added conc. HCl solution (3 mL) at 60° C. The mixture was stirred at 60° C. for 16 hours. The mixture was concentrated, and then dissolved in DCM. The pH was adjusted to ~9 and concentrated. The residue was purified by preparative HPLC (acidic condition) to afford the title compound (430 mg). MS(ES$^+$) m/z 264 (MH$^+$).

Intermediate 14: 6-amino-3-chloro-2-((2-(pyridin-2-yl)propan-2-yl)sulfonyl)phenol

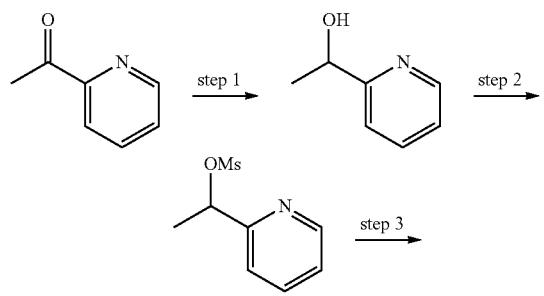

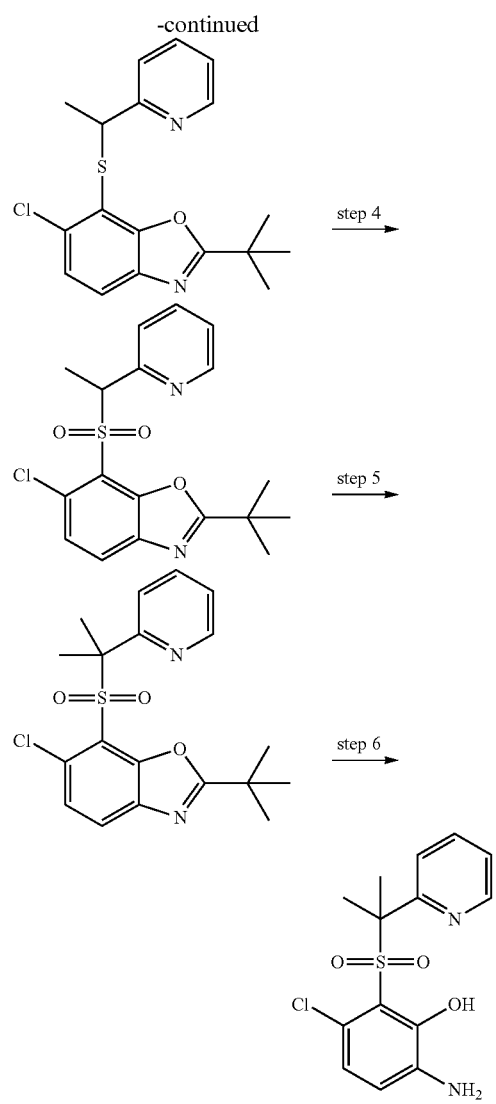

Step 1: To a solution of 1-(pyridin-2-yl)ethanone (5.0 g) in methanol (100 mL) at 0° C. was added sodium borohydride (3.1 g). The reaction mixture was stirred at 0° C. to RT for 2 hours. The mixture was quenched with water and then extracted with EA (3×100 mL). The combined organic layers were washed with brine, dried over sodium sulfate and filtered. The filtrate was concentrated to give 1-(pyridin-2-yl)ethanol (5.1 g) as a colorless oil.

Step 2: To an ice-cooled solution of 1-(pyridin-2-yl)ethanol (5.1 g) in DCM (80 mL) was added TEA (11.5 mL) followed by MsCl (3.5 mL). The reaction mixture was stirred at RT for 4 hours. Water (100 mL) was added. The organic layer was separated, dried over sodium sulfate and filtered. The filtrate was concentrated to afford 1-(pyridin-2-yl)ethyl methanesulfonate (7.8 g) as a yellow liquid oil. MS(ES$^+$) m/z 202 (MH$^+$).

Step 3: To a solution of 1-(pyridin-2-yl)ethyl methanesulfonate (2.8 g) and 2-(tert-butyl)-6-chlorobenzo[d]oxazole-7-thiol (3.0 g) in DMF (40 mL) was added potassium carbonate (2.7 g). The reaction mixture was stirred at 50° C. overnight. EA (100 mL) was added and the mixture was washed with brine for three times. The organic layer was dried over sodium sulfate and filtered. The filtrate was concentrated to afford 2-(tert-butyl)-6-chloro-7-((1-(pyridin-2-yl)ethyl)thio)benzo[d]oxazole (4.3 g) as a yellow vicious liquid. MS(ES⁺) m/z 347 (MH⁺).

Step 4: To a solution of 2-(tert-butyl)-6-chloro-7-((1-(pyridin-2-yl)ethyl)thio)benzo[d]oxazole (4.7 g) in DCM (100 mL) was added TFA (4.2 mL) at 0° C., followed by mCPBA (6.1 g) portionwise. The reaction mixture was warmed to RT and stirred overnight. Aq. NaHCO₃ and aq. Na₂SO₃ solution were added. The mixture was partitioned between DCM and water. The organic layer was washed with brine, dried over sodium sulfate and filtered. The filtrate was concentrated and purified by column chromatograpy (eluting with 0-50% EA in PE) to give 2-(tert-butyl)-6-chloro-7-((1-(pyridin-2-yl)ethyl)sulfonyl)benzo[d]oxazole (1.2 g) as a white solid. MS(ES⁺) m/z 379 (MH⁺).

Step 5: To a solution of 2-(tert-butyl)-6-chloro-7-((1-(pyridin-2-yl)ethyl)sulfonyl)benzo[d]oxazole (0.9 g) in THF (6 mL) was added LiHMDS (1.0 M in THF, 4.1 mL) dropwise at −70° C. The mixture was stirred at −70° C. for 30 mins, followed by addition of iodomethane (0.3 mL). Stirring was continued for another hour. Then the mixture was quenched with sat. ammonium chloride solution and extracted with EA (2×50 mL). The combined organic layers were washed with brine, dried over sodium sulfate and evaporated in vacuo. The resulting residue was purified by column chromatography (eluting with a gradient of 0-40% EA in PE) to afford 2-(tert-butyl)-6-chloro-7-((2-(pyridin-2-yl)propan-2-yl)sulfonyl)benzo[d]oxazole (0.7 g) as a white solid. MS(ES⁺) m/z 393 (MH⁺).

Step 6: To a solution of 2-(tert-butyl)-6-chloro-7-((2-(pyridin-2-yl)propan-2-yl)sulfonyl)benzo[d]oxazole (1.5 g) in 1,4-dioxane (6 mL) was added conc. hydrochloric acid (8 mL). After stirring at 110° C. for 4 hours, the reaction mixture was concentrated to the title compound (1.7 g) as a light brown solid. MS(ES⁺) m/z 327 (MH⁺).

Intermediate 15: 6-amino-3-chloro-2-((4-hydroxy-2-methylbutan-2-yl)sulfonyl)phenol

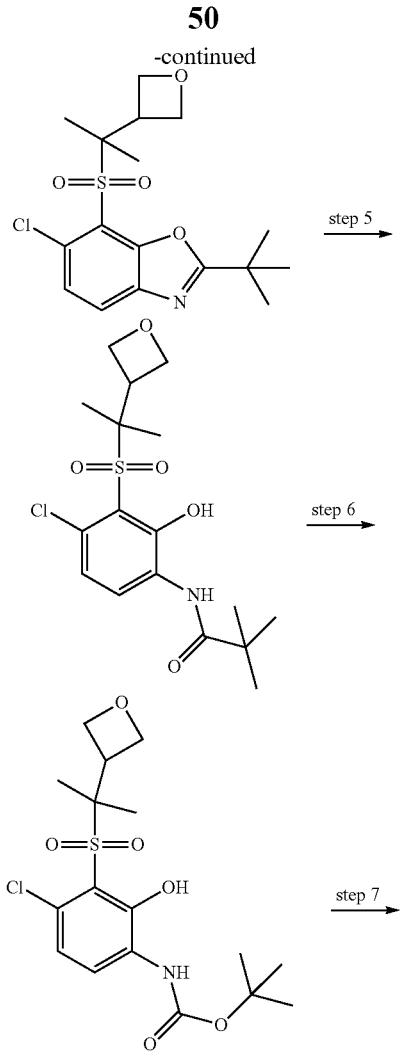

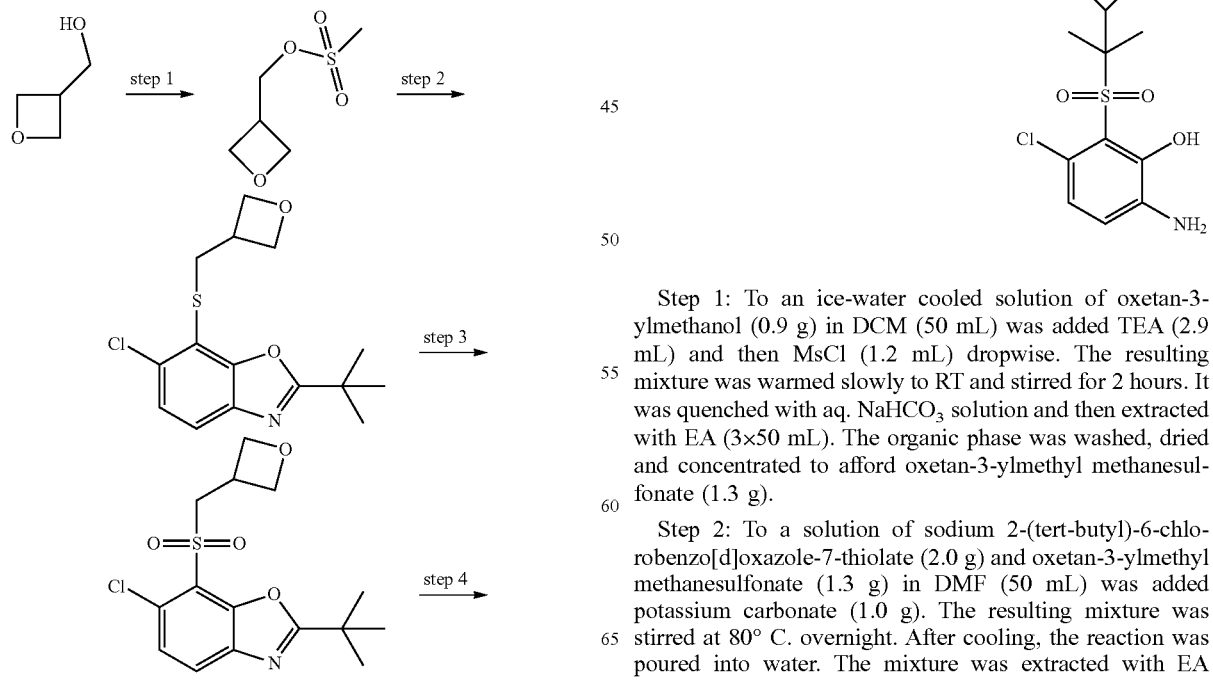

Step 1: To an ice-water cooled solution of oxetan-3-ylmethanol (0.9 g) in DCM (50 mL) was added TEA (2.9 mL) and then MsCl (1.2 mL) dropwise. The resulting mixture was warmed slowly to RT and stirred for 2 hours. It was quenched with aq. NaHCO₃ solution and then extracted with EA (3×50 mL). The organic phase was washed, dried and concentrated to afford oxetan-3-ylmethyl methanesulfonate (1.3 g).

Step 2: To a solution of sodium 2-(tert-butyl)-6-chlorobenzo[d]oxazole-7-thiolate (2.0 g) and oxetan-3-ylmethyl methanesulfonate (1.3 g) in DMF (50 mL) was added potassium carbonate (1.0 g). The resulting mixture was stirred at 80° C. overnight. After cooling, the reaction was poured into water. The mixture was extracted with EA (2×100 mL). The combined organic phases were washed, dried and concentrated to afford 2-(tert-butyl)-6-chloro-7-((oxetan-3-ylmethyl)thio)benzo[d]oxazole (2.3 g). MS(ES⁺) m/z 312 (MH⁺).

Step 3: To an ice-water cooled solution of 2-(tert-butyl)-6-chloro-7-((oxetan-3-ylmethyl)thio)benzo[d]oxazole (2.3 g) in DCM (50 mL) was added mCPBA (3.6 g). The resulting mixture was warmed to RT and stirred overnight. The mixture was quenched with aq. NaHCO₃ and Na₂S₂O₃ solution and then extracted with EA (2×100 mL). The organic phase was washed, dried and concentrated. The residue was purified with column chromatograph (eluting with 0-30% EA in PE) to afford 2-(tert-butyl)-6-chloro-7-((oxetan-3-ylmethyl)sulfonyl)benzo[d]oxazole (2.0 g).

Step 4: To a dry ice-ethanol cooled solution of iodomethane (0.4 mL) and 2-(tert-butyl)-6-chloro-7-((oxetan-3-ylmethyl)sulfonyl)benzo[d]oxazole (0.8 g) in THF (50 mL) was added LiHMDS (1 M in THF, 9.3 mL) dropwise. The resulting mixture was warmed up slowly and stirred for 3 hours. The mixture was quenched with aq. NH₄Cl solution. The mixture was extracted with EA (2×100 mL). The combined organic phases were washed, dried and concentrated to afford 2-(tert-butyl)-6-chloro-7-((2-(oxetan-3-yl)propan-2-yl)sulfonyl)benzo[d]oxazole (0.8 g).

Step 5: To a solution of 2-(tert-butyl)-6-chloro-7-((2-(oxetan-3-yl)propan-2-yl)sulfonyl)benzo[d]oxazole (300 mg) in ethanol (5 mL)/water (5 mL) was added sodium hydroxide (161 mg). The resulting reaction mixture was stirred at 60° C. for 2 hours. After the reaction was complete, the mixture was concentrated. The residue was diluted with water (50 mL), basified with aq. NaHCO₃ solution and extracted with EA (2×50 mL). The organic phase was washed, dried and concentrated to afford N-(4-chloro-2-hydroxy-3-((2-(oxetan-3-yl)propan-2-yl)sulfonyl)phenyl)pivalamide (0.3 g). MS(ES⁺) m/z 390 (MH⁺).

Step 6: To a solution of N-(4-chloro-2-hydroxy-3-((2-(oxetan-3-yl)propan-2-yl)sulfonyl)phenyl)pivalamide (0.3 g) in THF (10 mL) was added Boc₂O (0.4 mL) and DMAP (9.4 mg). The resulting reaction mixture was stirred at 60° C. for 4 hours. After the starting material was consumed, the mixture was cooled to RT. Hydrazine (0.1 g) was added. The resulting mixture was stirred at RT overnight. After the reaction was complete, the mixture was diluted with water (50 mL) and extracted with EA (2×50 mL). The organic phase was washed, dried and concentrated. The residue was purified by column chromatography (eluting with 0-30% EA in PE) to afford tert-butyl (4-chloro-2-hydroxy-3-((2-(oxetan-3-yl)propan-2-yl)sulfonyl)phenyl)carbamate (0.2 g). MS(ES⁺) m/z 428 (MNa⁺).

Step 7: To a solution of tert-butyl (4-chloro-2-hydroxy-3-((2-(oxetan-3-yl)propan-2-yl)sulfonyl)phenyl)carbamate (200 mg) in DCM (5 mL) was added TFA (0.4 mL). The reaction mixture was stirred at RT overnight and then diluted with water (20 mL), basified with aq. NaHCO₃ solution carefully. The mixture was extracted with EA (2×25 mL). The combined organic phases were washed, dried and concentrated to afford the title compound (150 mg). MS(ES⁺) m/z 306 (MH⁺).

Intermediate 16: 6-amino-3-chloro-2-((4-hydroxy-2-methylbutan-2-yl)sulfonyl)phenol

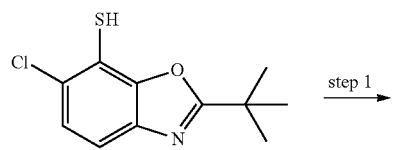

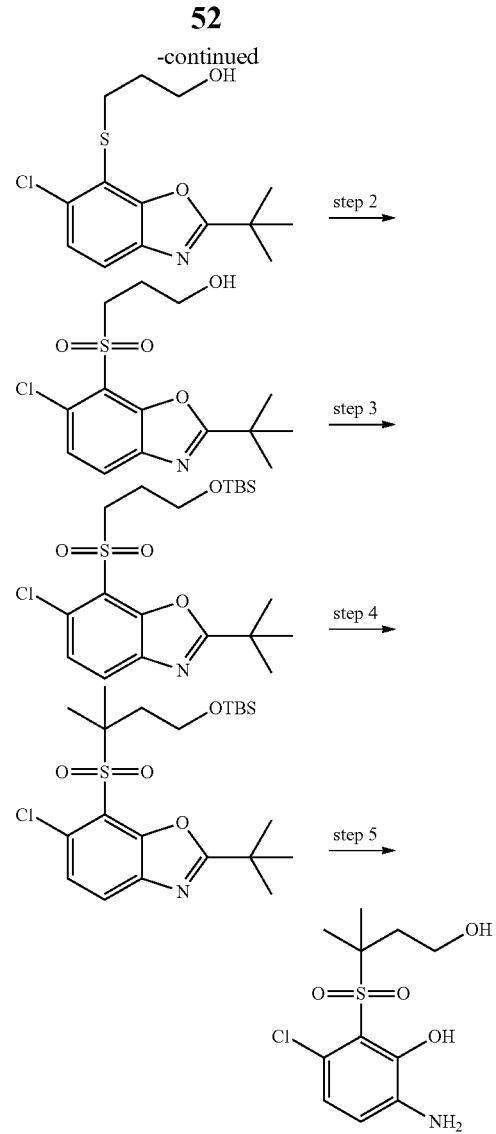

Step 1: A mixture of 2-(tert-butyl)-6-chlorobenzo[d]oxazole-7-thiol (7.0 g), 3-bromopropan-1-ol (4.0 g) and cesium carbonate (9.4 g) in THF (5 mL) was stirred at 100° C. under a nitrogen atmosphere for 5 hours. The mixture was filtered and the filtrate was concentrated and purified by column chromatography (eluting with PE:EA=10:1) to afford 3-((2-(tert-butyl)-6-chlorobenzo[d]oxazol-7-yl)thio)propan-1-ol (4.6 g). MS(ES⁺) m/z 300 (MH⁺).

Step 2: To a solution of 3-((2-(tert-butyl)-6-chlorobenzo[d]oxazol-7-yl)thio)propan-1-ol (1.0 g) in DCM (2 mL) was added mCPBA (1.7 g) at 0° C. The mixture was stirred at 30° C. for 18 hours. The reaction mixture was quenched with aq. Na₂SO₃ solution (50 mL). The organic phase was washed with aq. NaOH (1 M, 20 mL) and water (100 mL). The organic phase was dried over Na₂SO₄, filtered and concentrated to give 3-((2-(tert-butyl)-6-chlorobenzo[d]oxazol-7-yl)sulfonyl)propan-1-ol (1.0 g). MS(ES⁺) m/z 332 (MH⁺).

Step 3: A mixture of 3-((2-(tert-butyl)-6-chlorobenzo[d]oxazol-7-yl)sulfonyl)propan-1-ol (4.9 g), tert-butylchlorodimethylsilane (4.5 g) and 1H-imidazole (2.0 g) in DCM (50 mL) was stirred at 30° C. for 2 hours. The mixture was purified by column chromatography (eluting with PE:EA=10:1) to give 2-(tert-butyl)-7-((3-((tert-butyldimethylsilyl)oxy)propyl)sulfonyl)-6-chlorobenzo[d]oxazole (5.0 g). MS(ES⁺) m/z 446 (MH⁺).

Step 4: To a solution of 2-(tert-butyl)-7-((3-((tert-butyldimethylsilyl)oxy)propyl)sulfonyl)-6-chlorobenzo[d]oxazole (4.0 g) in THF (10 mL) was added NaHMDS (1 M in THF, 90 mL) at ~70° C. and the mixture was stirred at this temperature for 30 mins. MeI (5.6 mL) was added and the mixture was stirred at –70° C. for another 30 mins. The reaction was quenched with NH₄Cl solution (5 mL), and then extracted with EA (3×5 mL). The combined organic layers were dried over Na₂SO₄, filtered and concentrated. The residue was purified by column chromatography (eluting with PE:EA=10:1) to give 2-(tert-butyl)-7-((4-((tert-butyldimethylsilyl)oxy)-2-methylbutan-2-yl)sulfonyl)-6-chlorobenzo[d]oxazole (3.9 g). MS(ES⁺) m/z 474 (MH⁺).

Step 5: A solution of 2-(tert-butyl)-7-((4-((tert-butyldimethylsilyl)oxy)-2-methylbutan-2-yl)sulfonyl)-6-chlorobenzo[d]oxazole (5.0 g) in 1,4-dioxane (25 mL) and aq. HCl solution (37%, 25 mL) was stirred at 100° C. for 4 hours. Aq. NaOH solution was added to adjust the pH to ~8. The mixture was concentrated and purified by column chromatography (eluting with PE:EA=2:1) to give the title compound (1.2 g). MS(ES⁺) m/z 316 (MNa⁺).

Intermediate 17: 6-amino-3-chloro-2-((1-fluoro-2-methylpropan-2-yl)sulfonyl)phenol

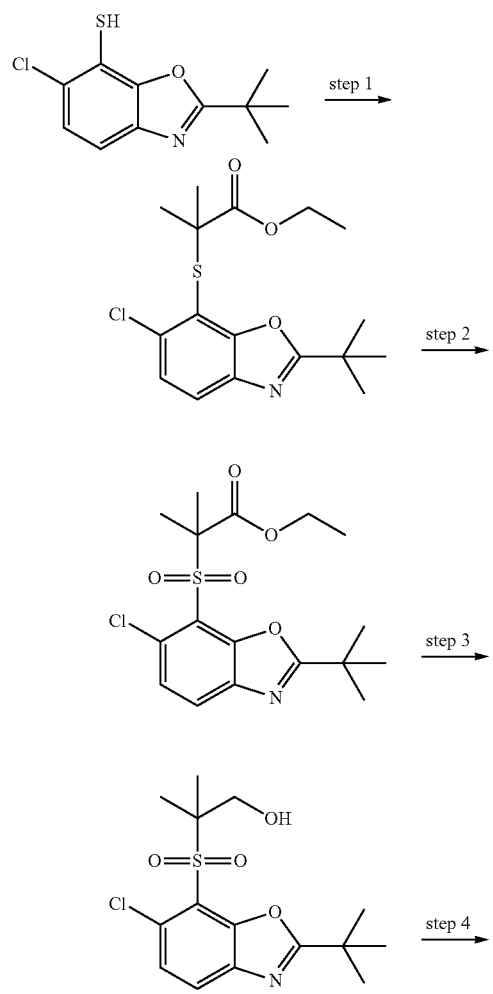

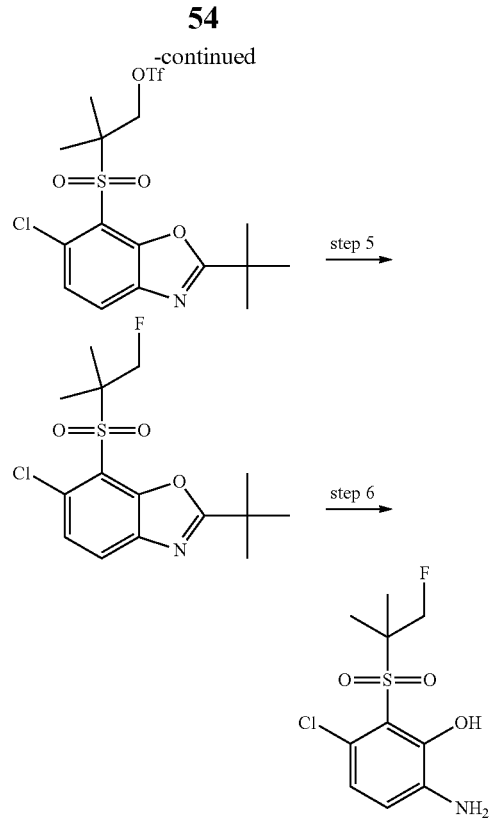

Step 1: A mixture of 2-(tert-butyl)-6-chlorobenzo[d]oxazole-7-thiol (15.0 g), ethyl 2-bromo-2-methylpropanoate (12.1 g) and potassium carbonate (17.2 g) in DMF (300 mL) was stirred at 100° C. for 3 hours. The reaction was filtered and concentrated. Water (200 mL) was added. The mixture was extracted with EA (3×10 mL). The combined organic phases were washed with water (3×100 mL), dried and concentrated to afford ethyl 2-((2-(tert-butyl)-6-chlorobenzo[d]oxazol-7-yl)thio)-2-methylpropanoate (20.0 g). MS(ES⁺) m/z 356 (MH⁺).

Step 2: To a solution of ethyl 2-((2-(tert-butyl)-6-chlorobenzo[d]oxazol-7-yl)thio)-2-methylpropanoate (20.0 g) in DCM (200 mL) was added mCPBA (28.5 g) at 0° C. After stirring at 25° C. for 18 hours, the mixture was filtered and quenched with aq. Na₂SO₃ solution (100 mL). The organic phase was washed with aq. NaOH solution (1 M, 2×50 mL) and water (3×50 mL). The resulting organic solution was dried and concentrated. The residue was purified by column chromatography (eluting with PE:EA=5:1) to afford ethyl 2-((2-(tert-butyl)-6-chlorobenzo[d]oxazol-7-yl)sulfonyl)-2-methylpropanoate (12.0 g). MS(ES⁺) m/z 388 (MH⁺).

Step 3: To a solution of ethyl 2-((2-(tert-butyl)-6-chlorobenzo[d]oxazol-7-yl)sulfonyl)-2-methylpropanoate (7.5 g) in THF (150 mL) was added DIBAL-H (1 M in hexane, 97 mL) at –70° C. The reaction mixture was stirred at 30° C. for 4 hours. MeOH (10 mL) was added slowly. The mixture was then concentrated. Water (200 mL) and EA (300 mL) were added. The mixture was filtered and the aqueous phase was extracted with EA (2×200 mL). The combined organic phases were drided and concentrated to afford 2-((2-(tert-butyl)-6-chlorobenzo[d]oxazol-7-yl)sulfonyl)-2-methylpropan-1-ol (5.0 g). MS(ES⁺) m/z 346 (MH⁺).

Step 4: To a solution of 2-((2-(tert-butyl)-6-chlorobenzo[d]oxazol-7-yl)sulfonyl)-2-methylpropan-1-ol (4.5 g) and pyridine (5.2 g) in DCM (100 mL) stirred at –10° C. was added trifluoromethanesulfonic anhydride (7.4 g) dropwise.

The reaction mixture was stirred at RT for 4 hours, and then quenched with water. The mixture was washed with water and HCl (1 M). The organic phase was dried and concentrated to give 2-((2-(tert-butyl)-6-chlorobenzo[d]oxazol-7-yl)sulfonyl)-2-methylpropyl trifluoromethanesulfonate (7.4 g).

Step 5: A solution of 2-((2-(tert-butyl)-6-chlorobenzo[d]oxazol-7-yl)sulfonyl)-2-methylpropyl trifluoromethanesulfonate (7.2 g) and tetrabutylammonium fluoride, 3H$_2$O (9.5 g) in acetonitrile (100 mL) was stirred at 80° C. for 4 hours. The solution was concentrated and the residue was poured into water. The mixture was filtered. After washing with water for three times, the solid was dried under reduced pressure to give 2-(tert-butyl)-6-chloro-7-((1-fluoro-2-methylpropan-2-yl)sulfonyl)benzo[d]oxazole (4.2 g). MS(ES$^+$) m/z 348 (MH$^+$).

Step 6: A solution of 2-(tert-butyl)-6-chloro-7-((1-fluoro-2-methylpropan-2-yl)sulfonyl)benzo[d]oxazole (4.0 g) in 1,4-dioxane (40 mL) and conc. HCl solution (20 mL) was stirred at 110° C. overnight. The pH of solution was adjusted to ~7 with aq. NaOH solution. The mixture was extracted with EA (3×100 mL). The organic layers were dried and concentrated. The residue was purified by column chromatography (eluting with EA:PE=1:5) to gvie the title compound (1.8 g). MS(ES$^+$) m/z 282 (MH$^+$).

Intermediate 18: 6-amino-3-chloro-2-((2-methyl-1-(pyrrolidin-1-yl)propan-2-yl)sulfonyl)phenol

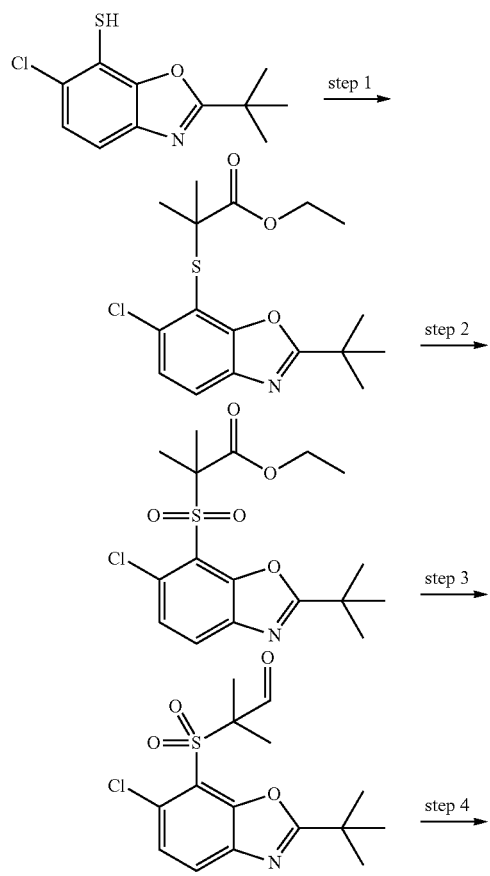

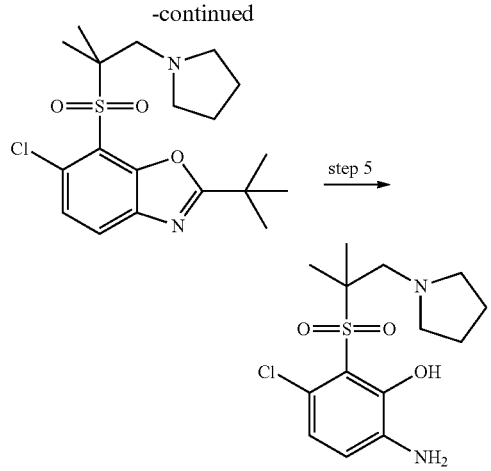

Step 1: Ethyl 2-bromo-2-methylpropanoate (4.4 g) was added to a solution of 2-(tert-butyl)-6-chlorobenzo[d]oxazole-7-thiol (5.0 g) and potassium carbonate (5.7 g) in acetonitrile (100 mL) at RT. After stirring at 80° C. for 4 hours, the mixture was filtered and the filltration was concentrated. The residue was purified by column chromatography (eluting with PE:EA=15:1) to afford ethyl 2-((2-(tert-butyl)-6-chlorobenzo[d]oxazol-7-yl)thio)-2-methylpropanoate (5.5 g) as a brown oil. MS(ES$^+$) m/z 356 (MH$^+$).

Step 2: mCPBA (9.5 g) was added to a solution of ethyl 2-((2-(tert-butyl)-6-chlorobenzo[d]oxazol-7-yl)thio)-2-methylpropanoate (5.5 g) in DCM (200 mL) at 0° C. After stirring at 25° C. for 12 hours, the reaction was quenched with aq. NaHCO$_3$ and Na$_2$S$_2$O$_3$ solution. The mixture was extracted with DCM (2×200 mL). The organic phases were washed, dried and concentrated. The residue was purified by column chromatography (eluting with PE:EA=10:1 to 4:1) to afford ethyl 2-((2-(tert-butyl)-6-chlorobenzo[d]oxazol-7-yl)sulfonyl)-2-methylpropanoate (4.4 g) as a brown oil. MS(ES$^+$) m/z 388 (MH$^+$).

Step 3: To a solution of ethyl 2-((2-(tert-butyl)-6-chlorobenzo[d]oxazol-7-yl)sulfonyl)-2-methylpropanoate (4.4 g) in DCM (200 mL) was added DIBAL-H (1 M in hexane, 25.0 mL) at −78° C. The reaction mixture was stirred at −78° C. for 0.5 hour. Aq. HCl solution (1 M) was added. The organic layer was separated, washed with brine (50 mL), dried over Na$_2$SO$_4$, filtered and concentrated. The residue was purified by column chromatography (eluting with PE:EA=10:1) to afford 2-((2-(tert-butyl)-6-chlorobenzo[d]oxazol-7-yl)sulfonyl)-2-methylpropanal (2.5 g) as a white solid. MS(ES$^+$) m/z 344 (MH$^+$).

Step 4: To a solution of 2-((2-(tert-butyl)-6-chlorobenzo[d]oxazol-7-yl)sulfonyl)-2-methylpropanal (2.0 g) and pyrrolidine (1.2 g) in DCE (15 mL) was added acetic acid (1.7 mL) at RT. After stirring at 25° C. for 1 hour, sodium triacetoxyborohydride (1.8 g) was added at 0° C. The mixture was stirred at RT for 12 hours. The reaction solution was combined with another batch of the same reaction using 2-((2-(tert-butyl)-6-chlorobenzo[d]oxazol-7-yl)sulfonyl)-2-methylpropanal (0.5 g) as starting material. The combined mixture was diluted with EA (100 mL). The organic phase was washed with sat. NaHCO$_3$ solution (50 mL) and brine (30 mL), dried over Na$_2$SO$_4$, filtered and concentrated. The residue was purified by column chromatography (eluting with PE:EA=12:1 to 4:1) to afford 2-(tert-butyl)-6-chloro- 7-((2-methyl-1-(pyrrolidin-1-yl)propan-2-yl)sulfonyl)benzo[d]oxazole (620 mg) as a white solid. MS(ES+) m/z 399 (MH+).

Step 5: To a solution of 2-(tert-butyl)-6-chloro-7-((2-methyl-1-(pyrrolidin-1-yl)propan-2-yl)sulfonyl)benzo[d]oxazole (550 mg) in 1,4-dioxane (10 mL) and water (5 mL) was added aq. HCl solution (35%, 5 mL) at RT. The reaction mixture was stirred at 120° C. for 12 hours. The reaction solution was combined with another batch of the same reaction using 2-(tert-butyl)-6-chloro-7-((2-methyl-1-(pyrrolidin-1-yl)propan-2-yl)sulfonyl)benzo[d]oxazole (50 mg) as starting material. The combined mixture was concentrated and the residue was dissolved in MeOH. Aq. NaHCO3 solution was added until pH=8. The mixture was filtered and washing with water and dried to afford the title compound (400 mg) as a gray solid. MS(ES+) m/z 333 (MH+).

Intermediate 19: 6-amino-3-chloro-2-((1-hydroxy-2-methylpropan-2-yl)sulfonyl)phenol

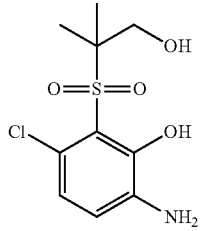

A mixture of 2-((2-(tert-butyl)-6-chlorobenzo[d]oxazol-7-yl)sulfonyl)-2-methylpropan-1-ol (Intermediate 17, Step 3, 2.0 g) in 1,4-dioxane (10 mL) and aq. HCl solution (37%, 10 mL) was stirred at 100° C. under a nitrogen atmosphere for 4 hours. After completion of the reaction, pH was adjusted to 8. The resulting mixture was purified by preparative HPLC to afford the title compound (410 mg). MS(ES+) m/z 280 (MH+).

Intermediate 20: 6-amino-3-chloro-2-((2-fluoropropan-2-yl)sulfonyl)phenol

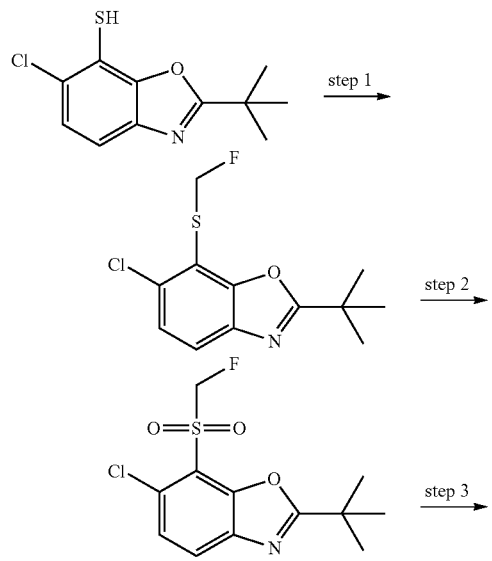

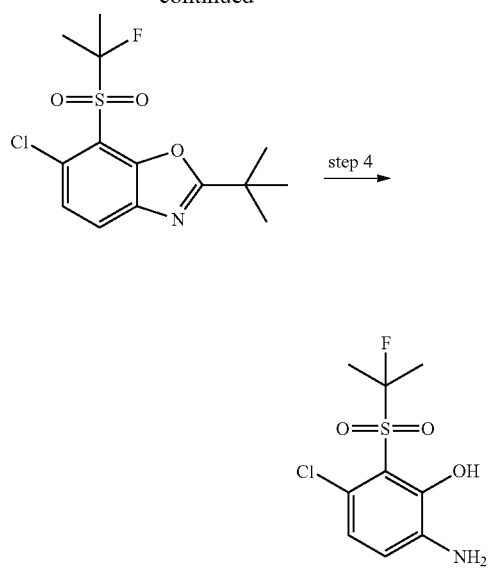

Step 1: To a solution of 2-(tert-butyl)-6-chlorobenzo[d]oxazole-7-thiol (10.0 g) and Cs2CO3 (16.2 g) in acetonitrile (20 mL) stirred at RT was added bromofluoromethane (5.6 g). The reaction mixture was stirred at RT for 1 hour. The mixture was filtered and the filtrate was concentrated. The residue was diluted with DCM (300 mL), and the mixture was washed with water (3×100 mL). The organic phase was dried and concentrated to give 2-(tert-butyl)-6-chloro-7-((fluoromethyl)thio)benzo[d]oxazole (11.0 g).

Step 2: To a solution of 2-(tert-butyl)-6-chloro-7-((fluoromethyl)thio)benzo[d]oxazole (11.0 g) in DCM (200 mL) stirred at RT was added mCPBA (24.5 g) portionwise. After stirring at RT overnight, the mixture was filtered and the filtrate was washed with sat. Na2S2O3 solution, then with aq. NaOH solution (1 M), dried and concentrated to give 2-(tert-butyl)-6-chloro-7-((fluoromethyl)sulfonyl)benzo[d]oxazole (10.3 g). MS(ES+) m/z 306 (MH+).

Step 3: To a solution of diisopropylamine (7.1 g) in THF (100 mL) stirred under a nitrogen atmosphere at −78° C. was added nBuLi (2.5 M in hexane, 28 mL) dropwise. The reaction mixture was stirred at −78° C. for 1 hour. This solution was then added to a solution of 2-(tert-butyl)-6-chloro-7-((fluoromethyl)sulfonyl)benzo[d]oxazole (10.7 g) in THF (200 mL) dropwise at −78° C. The mixture was stirred at −78° C. for another 1 hour. MeI (6.6 mL) was added dropwise. The resulting solution was warmed to RT, and then quenched with sat. NH4Cl solution. The mixture was extracted with EA. The organic layer was dried and concentrated. The residue was purified by column chromatography to give 2-(tert-butyl)-6-chloro-7-((2-fluoropropan-2-yl)sulfonyl)benzo[d]oxazole (2.1 g). MS(ES+) m/z 334 (MH+).

Step 4: A solution of 2-(tert-butyl)-6-chloro-7-((2-fluoropropan-2-yl)sulfonyl)benzo[d]oxazole (2.1 g) in 1,4-dioxane (20 mL) and conc. HCl solution (5 mL) was stirred at 120° C. overnight. The pH of the solution was adjusted to ~7 with NaOH solution and extracted with DCM. The organic layer was dried and concentrated. The residue was purified by column chromatography to give the title compound (1.0 g). MS(ES+) m/z 268 (MH+).

Intermediate 21:
6-amino-3-chloro-2-(isopropylsulfonyl)phenol

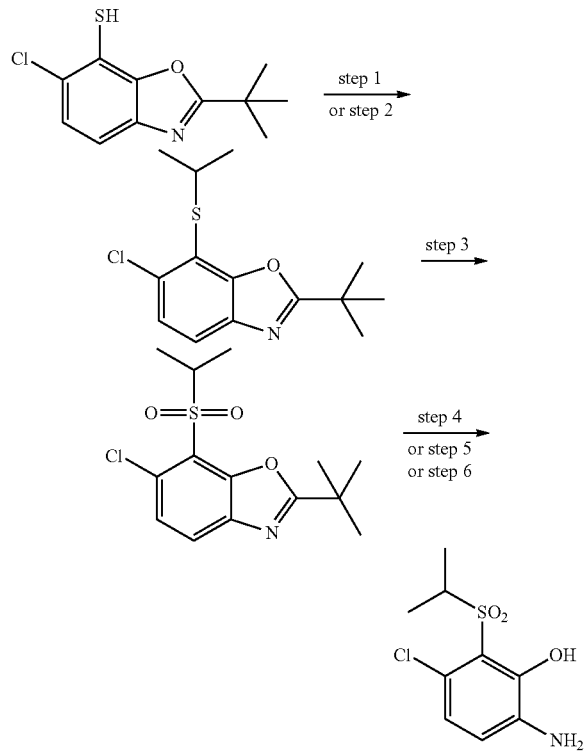

Step 1: To a suspension of 2-(tert-butyl)-6-chlorobenzo[d]oxazole-7-thiol (50.0 g) and 2-iodopropane (42.2 g) in acetonitrile (1 L) stirred in air at RT was added K$_2$CO$_3$ (42.9 g). After stirring at RT for 3 hours, the reaction mixture was concentrated. DCM (500 mL) and H$_2$O (500 mL) were then added. The organic layer was separated, and the aqueous phase was extracted with DCM (3×300 mL). The combined organic layers were dried over Na$_2$SO$_4$ and concentrated to give 2-(tert-butyl)-6-chloro-7-(isopropylthio)benzo[d]oxazole (52.0 g).

Step 2: To a solution of 2-(tert-butyl)-6-chlorobenzo[d]oxazole-7-thiol (15.0 g) and 2-bromopropane (5.8 mL) in DMF (100 mL) was added K$_2$CO$_3$ (17.2 g). The resulting mixture was stirred at 50° C. overnight. After completion of the reaction, the mixture was poured into water, extracted with ethyl acetate (2×500 mL). The combined organic phases were washed and dried. The solvent was removed to afford 2-(tert-butyl)-6-chloro-7-(isopropylthio)benzo[d]oxazole (16.0 g).

Step 3: To a suspension of 2-(tert-butyl)-6-chloro-7-(isopropylthio)benzo[d]oxazole (50.0 g) in DCM (1000 mL) stirred in air at RT was added mCPBA (89.0 g) portionwise. After stirring at RT for 16 hours, the mixture was filtered. The filtrate was treated with aq. Na$_2$SO$_3$ solution, and washed with aq. NaOH solution. The organic layer was separated, dried and concentrated to give 6-chloro-2-isopropyl-7-(isopropylsulfonyl)benzo[d]oxazole (50.0 g). MS(ES$^+$) m/z 316 (MH$^+$).

Step 4: To a solution of 6-chloro-2-isopropyl-7-(isopropylsulfonyl)benzo[d]oxazole (40.0 g) in 1,4-dioxane (500 mL) stirred in air at RT was added conc. HCl solution (100 mL) in portionwise. The reaction mixture was stirred at 110° C. for 16 hours. After cooling, the mixture was extracted with DCM. The pH was adjusted to ~8 with aq. NaOH solution. The aqueous phase was extracted with DCM. The organic phase was dried and concentrated to give the crude product, which was purified by crystallization to afford 6-amino-3-chloro-2-(isopropylsulfonyl)phenol (20.0 g). MS(ES$^+$) m/z 250 (MH$^+$).

Step 5: To a solution of 2-(tert-butyl)-6-chloro-7-(isopropylsulfonyl)benzo[d]oxazole (18.0 g) in 1,4-dioxane (500 mL) and water (500 mL) was added conc. HCl solution (34.6 mL). The resulting mixture was stirred at 100° C. overnight. The solvent was removed. The residue was basified with aq. NH$_3$.H$_2$O solution to pH=9, and then extracted with EA (2×500 mL). The combined organic phases were washed and dried. The solvent was removed to afford 6-amino-3-chloro-2-(isopropylsulfonyl)phenol (10.0 g). MS(ES$^+$) m/z 250 (MH$^+$).

Step 6: To a solution of 2-(tert-butyl)-6-chloro-7-(isopropylsulfonyl)benzo[d]oxazole (2.8 g) in 1,4-dioxane (20 mL) and water (5 mL) was added sulfuric acid (4.0 mL). The resulted mixture was stirred at 80° C. for 3 hours. Cold water (10 mL) was added and the mixture was washed with DCM (2×100 mL). Aq. NaOH solution (2 M) was added to the aqueous layer to adjust pH to 9. The aqueous layer was extracted with EA (2×100 mL). The combined organic layers were dried over Na$_2$SO$_4$, filtered and concentrated in vacuo. The residue was purified by preparative HPLC (C8, mobile phase 0.01% NH$_4$HCO$_3$/H$_2$O, CH$_3$OH, 30 mL/min) (40%~60%, 6 min; 60~70%, 6 min; 70%~95%, 1 min; 95%~95%, 1 min) to give the title compound (1.7 g) as a dark solid. MS(ES$^+$) m/z 250 (MH$^+$).

Intermediate 22: 6-amino-3-chloro-2-((1-(pyridin-2-yl)ethyl)sulfonyl)phenol

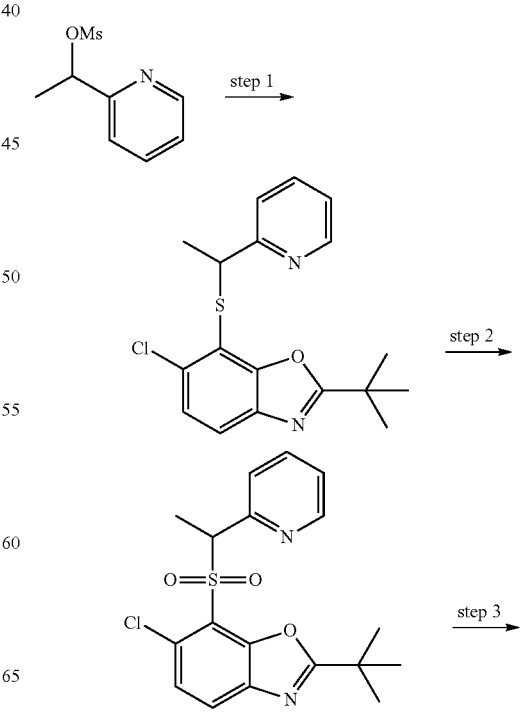

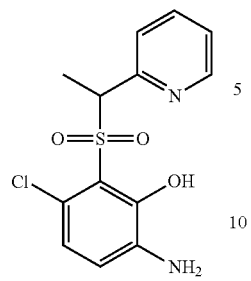

Step 1: To a solution of 1-(pyridin-2-yl)ethyl methanesulfonate (Intermediate 14, Step 2, 3.7 g), 2-(tert-butyl)-6-chlorobenzo[d]oxazole-7-thiol (4.0 g) in DMF (40 mL) was added potassium carbonate (3.7 g). The reaction mixture was stirred at 50° C. overnight. EA (100 mL) was added. The mixture was washed with brine three times. The organic layer was dried over sodium sulfate and filtered. The resulting filtrate was concentrated to afford 2-(tert-butyl)-6-chloro-7-((1-(pyridin-2-yl)ethyl)thio)benzo[d]oxazole (5.7 g) as a yellow vicious liquid. MS(ES$^+$) m/z 347 (MH$^+$).

Step 2: To a solution of 2-(tert-butyl)-6-chloro-7-((1-(pyridin-2-yl)ethyl)thio)benzo[d]oxazole (5.5 g) in DCM (100 mL) was added TFA (5 mL) at 0° C., and then mCPBA (7.2 g) portionwise. The reaction mixture was warmed to RT and stirred overnight. Aq. NaHCO$_3$ and aq. Na$_2$SO$_3$ solutions were added. The mixture was partitioned between DCM and water. The organic layer was washed with brine, dried over sodium sulfate and filtered. The filtrate was concentrated and purified by column chromatograpy (eluting with 0-50% EA in PE) to give 2-(tert-butyl)-6-chloro-7-((1-(pyridin-2-yl)ethyl)sulfonyl)benzo[d]oxazole (4.2 g) as a white solid. MS(ES$^+$) m/z 379 (MH$^+$).

Step 3: To a solution of 2-(tert-butyl)-6-chloro-7-((1-(pyridin-2-yl)ethyl)sulfonyl)benzo[d]oxazole (1.5 g) in 1,4-dioxane (6 mL) was added aq. HCl solution (37%, 8 mL). After stirring at 110° C. for 4 hours, the reaction mixture was concentrated to afford the title compound (1.6 g) as a light brown solid. MS(ES$^+$) m/z 313 (MH$^+$).

Intermediate 23: 6-amino-3-chloro-2-((1-(pyrimidin-2-yl)ethyl)sulfonyl)phenol

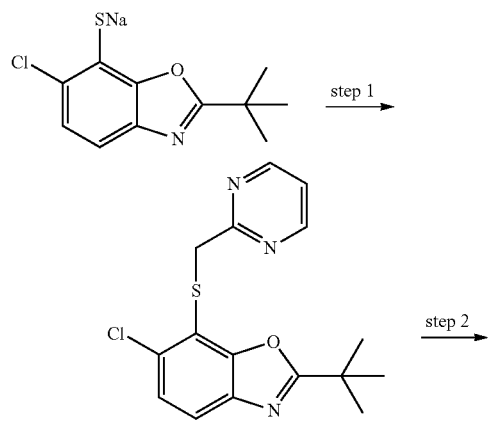

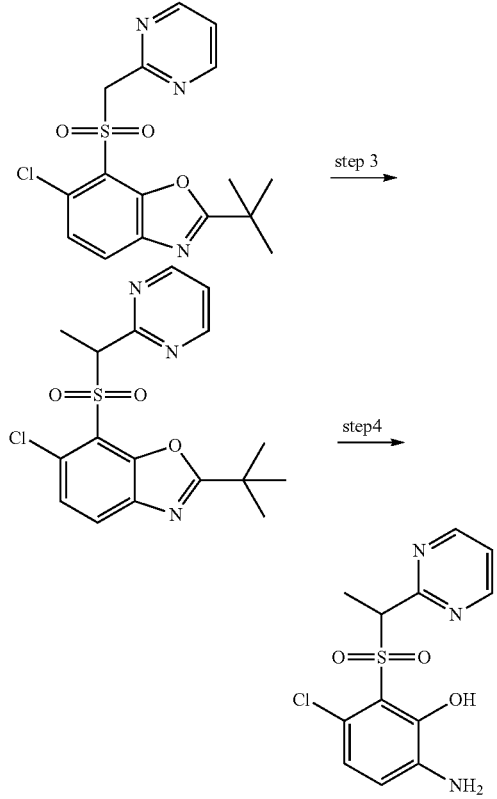

Step 1: To a mixture of sodium 2-(tert-butyl)-6-chlorobenzo[d]oxazole-7-thiolate (3.2 g) in DMF (25 mL) was added 2-(chloromethyl)pyrimidine.hydrochloride (2.0 g) and potassium carbonate (3.4 g). After stirring at 60° C. for 2 hours, the reaction mixture was poured into water (250 mL), and then extracted with EA (2×75 mL). The combined organic layers were concentrated, and the residue was purified by column chromatography (eluting with PE:EA=1:3) to give 2-(tert-butyl)-6-chloro-7-((pyrimidin-2-ylmethyl)thio)benzo[d]oxazole (2.6 g) as a brown solid. MS(ES$^+$) m/z 334 (MH$^+$).

Step 2: To a stirred solution of 2-(tert-butyl)-6-chloro-7-((pyrimidin-2-ylmethyl)thio)benzo[d]oxazole (2.6 g) and TFA (3.0 mL) in DCM (100 mL) at 0° C. was added a solution of mCPBA (5.9 g) in DCM (120 mL) slowly. The reaction mixture was stirred at 30° C. overnight. Aq. Na$_2$S$_2$O$_3$ solution (150 mL) and aq. Na$_2$CO$_3$ solution (200 mL) were added. The mixture was extracted with DCM (3×140 mL). The combined organic layers were dried over MgSO$_4$, filtered and concentrated under reduced pressure. The residue was purified by column chromatography (eluting with EA:PE=1:1) to give 2-(tert-butyl)-6-chloro-7-((pyrimidin-2-ylmethyl)sulfonyl)benzo[d]oxazole (660 mg) as a yellow solid. MS(ES$^+$) m/z 366 (MH$^+$).

Step 3: To a solution of 2-(tert-butyl)-6-chloro-7-((pyrimidin-2-ylmethyl)sulfonyl)benzo[d]oxazole (660 mg) in THF (20 mL) was added potassium tert-butoxide (211 mg) at RT. The mixture was stirred at this temperature for 1 hour. MeI (0.1 mL) was added. The mixture was stirred at RT for another 2 hours. Water (50 mL) was added. The mixture was extracted with EA (2×15 mL). The combined organic layers were dried over Na$_2$SO$_4$, filtered and concentrated in vacuo. The residue was purified by column chromatography (eluting with PE:EA=4:1) to give 2-(tert-butyl)-6-chloro-7-((1-

(pyrimidin-2-yl)ethyl)sulfonyl)benzo[d]oxazole (490 mg) as a yellow solid. MS(ES+) m/z 380 (MH+).

Step 4: A mixture of 2-(tert-butyl)-6-chloro-7-((1-(pyrimidin-2-yl)ethyl)sulfonyl)benzo[d]oxazole (490 mg) and conc. HCl solution (3 mL) in 1,4-dioxane (8 mL) was heated 85° C. overnight. Sat. NaHCO₃ solution (50 mL) was added. The mixture was extracted with EA (3×15 mL). The combined organic layers were dried over Na₂SO₄, filtered and concentrated under reduced pressure. The residue was purified by column chromatography (eluting with EA:PE=1:1) to give the title compound (333 mg) as a brown solid. MS(ES+) m/z 314 (MH+).

Intermediate 24: 4-amino-3-hydroxy-2-((1,1,1-trifluoro-2-methylpropan-2-yl)sulfonyl)benzonitrile

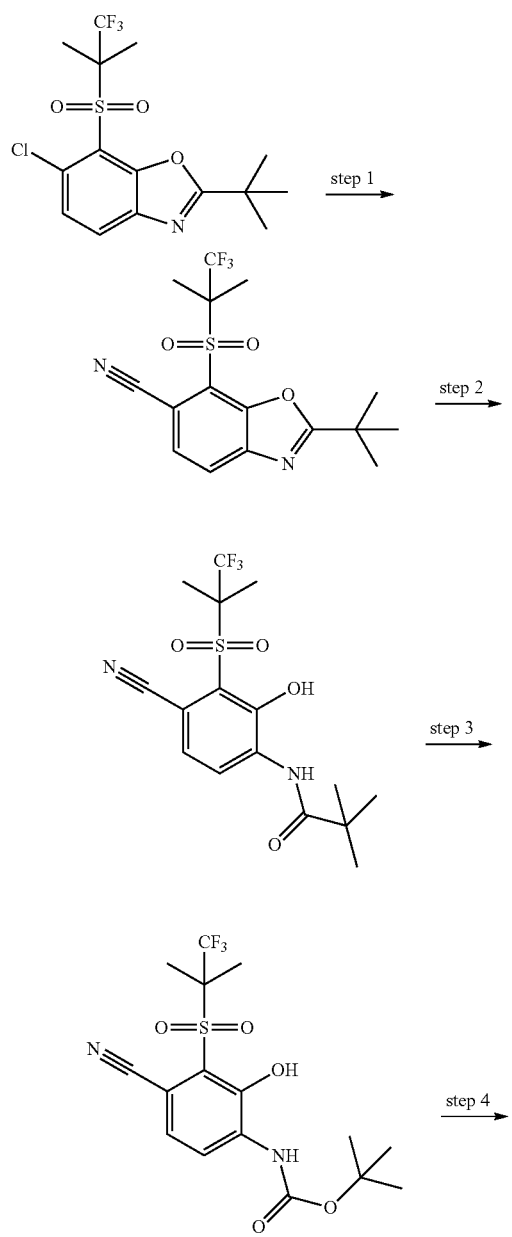

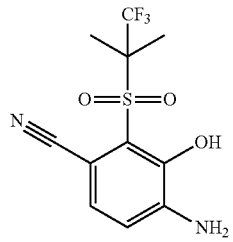

Step 1: To a solution of 2-(tert-butyl)-6-chloro-7-((1,1,1-trifluoro-2-methylpropan-2-yl)sulfonyl)benzo[d]oxazole (Intermediate 12, Step 3, 1000 mg) in NMP (10 mL) was added copper(I) cyanide (2334 mg). The mixture was stirred at 200° C. for 12 hours. EA (100 mL) was added. The organic layer was washed with sat. ammonia (3×100 mL). The organic layer were dried over Na₂SO₄, filtered and concentrated in vacuo. The residue was purified by column chromatography (eluting with PE:EA=5:1) to give 2-(tert-butyl)-7-((1,1,1-trifluoro-2-methylpropan-2-yl)sulfonyl)benzo[d]oxazole-6-carbonitrile (340 mg) as a white solid. MS(ES+) m/z 375 (MH+).

Step 2: To a stirred solution of 2-(tert-butyl)-7-((1,1,1-trifluoro-2-methylpropan-2-yl)sulfonyl)benzo[d]oxazole-6-carbonitrile (300 mg) in ethanol (2 mL) and water (2 mL) at 50° C. was added sodium hydroxide (160 mg). The mixture was stirred at this temperature for 2 hours. Cold water (50 mL) was added. The resulting mixture was neutralized with sat. NaHCO₃ solution. The aqueous layer was extracted with DCM (2×50 mL). The combined organic layers were dried over Na₂SO₄, filtered and concentrated in vacuo to give N-(4-cyano-2-hydroxy-3-((1,1,1-trifluoro-2-methylpropan-2-yl)sulfonyl)phenyl)pivalamide (300 mg) as a light yellow solid. MS(ES+) m/z 393 (MH+).

Step 3: To a solution of N-(4-cyano-2-hydroxy-3-((1,1,1-trifluoro-2-methylpropan-2-yl)sulfonyl)phenyl)pivalamide (380 mg) in THF (5 mL) was added Boc₂O (0.5 mL) and DMAP (11.8 mg). The resulting mixture was stirred at 50° C. for 3 hours. After cooling, hydrazine (85% in water, 0.4 mL) was added. The resulting mixture was stirred at RT overnight. The resulting solution was diluted with water (50 mL), and extracted with EA (2×50 mL). The combined organic phases were washed, dried and concentrated. The residue was purified by column chromatography (eluting with 0-50% EA in PE) to afford tert-butyl (4-cyano-2-hydroxy-3-((1,1,1-trifluoro-2-methylpropan-2-yl)sulfonyl)phenyl)carbamate (270 mg). MS(ES+) m/z 409 (MH+).

Step 4: To a solution of tert-butyl (4-cyano-2-hydroxy-3-((1,1,1-trifluoro-2-methylpropan-2-yl)sulfonyl)phenyl)carbamate (270 mg) in DCM (10 mL) was added TFA (0.5 mL). The resulting mixture was stirred at RT overnight, and then quenched with aq. NaHCO₃ solution till pH=8. The resulting solution was extracted with EA (2×50 mL). The combined organic phases were washed, dried and concentrated to afford the title compound (110 mg). MS(ES+) m/z 309 (MH+).

Intermediate 25: 6-amino-3-chloro-2-((1-(1-methyl-1H-imidazol-2-yl)ethyl)sulfonyl)phenol

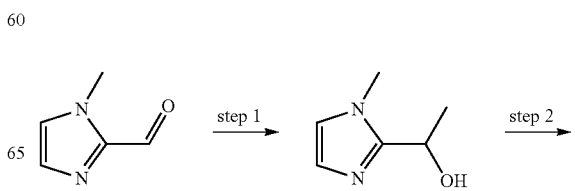

-continued

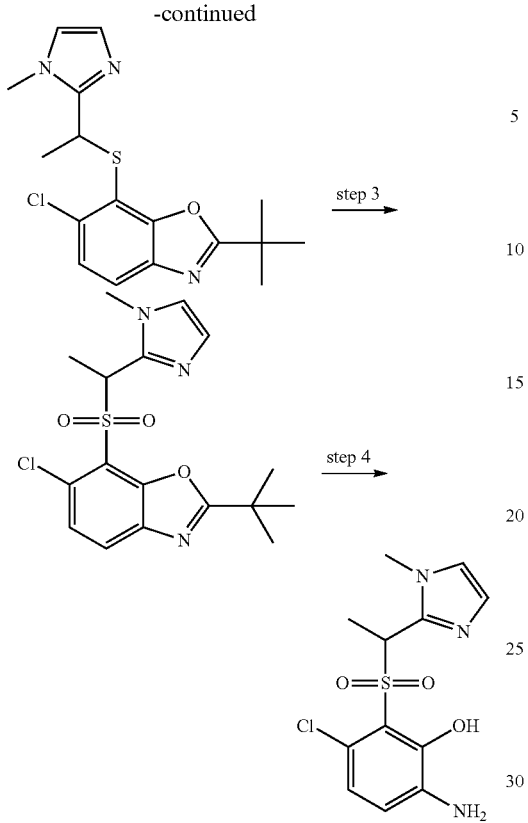

Step 1: To a solution of 1-methyl-1H-imidazole-2-carbaldehyde (10.0 g) in THF (100 mL) was added MeI (1.0 M in diethyl ether, 182 mL) at 0° C. The mixture was stirred at 0° C. for 3 hours, and then quenched with NH₄Cl solution (250 mL). The resulting mixture was extracted with EA (5×400 mL). The combined organic phases were dried and concentrated to afford 1-(1-methyl-1H-imidazol-2-yl)ethanol (11.0 g).

Step 2: To a solution of 2-(tert-butyl)-6-chlorobenzo[d]oxazole-7-thiol (5.9 g), 1-(1-methyl-1H-imidazol-2-yl)ethanol (6.5 g) and Ph₃P (13.4 g) in THF (65 mL) was added DEAD (8.1 mL) at 0° C. The reaction mixture was stirred at 20° C. for 18 hours. The solvent was removed. The residue was purified by column chromatography (eluting with PE:EA=2:1) to afford 2-(tert-butyl)-6-chloro-7-((1-(1-methyl-1H-imidazol-2-yl)ethyl)thio)benzo[d]oxazole (10.0 g). MS(ES⁺) m/z 350 (MH⁺).

Step 3: To a solution of TFA (2.4 mL) and 2-(tert-butyl)-6-chloro-7-((1-(1-methyl-1H-imidazol-2-yl)ethyl)thio)benzo[d]oxazole (6.0 g) in DCM (60 mL) was added mCPBA (3.9 g) at 0° C. After stirring at 25° C. for 18 hours, the reaction was quenched with aq. NaHSO₃ solution (20 mL), and then extracted with DCM (3×100 mL). After concentration, the residue was purified by preparative HPLC to afford 2-(tert-butyl)-6-chloro-7-((1-(1-methyl-1H-imidazol-2-yl)ethyl)sulfonyl)benzo[d]oxazole (2.5 g).

Step 4: To a solution of 2-(tert-butyl)-6-chloro-7-((1-(1-methyl-1H-imidazol-2-yl)ethyl)sulfonyl)benzo[d]oxazole (1.0 g) in 1,4-dioxane (2 mL) and water (2 mL) was added aq. HCl solution (37%, 4 mL). The mixture was stirred at 100° C. for 4 hours, and then concentrated. The pH was adjusted to 7-8. The resulting mixture was purified by preparative HPLC to afford the title compound (375 mg). MS(ES⁺) m/z 316 (MH⁺).

Intermediate 26: 6-amino-3-chloro-2-((1-hydroxypropan-2-yl)sulfonyl)phenol

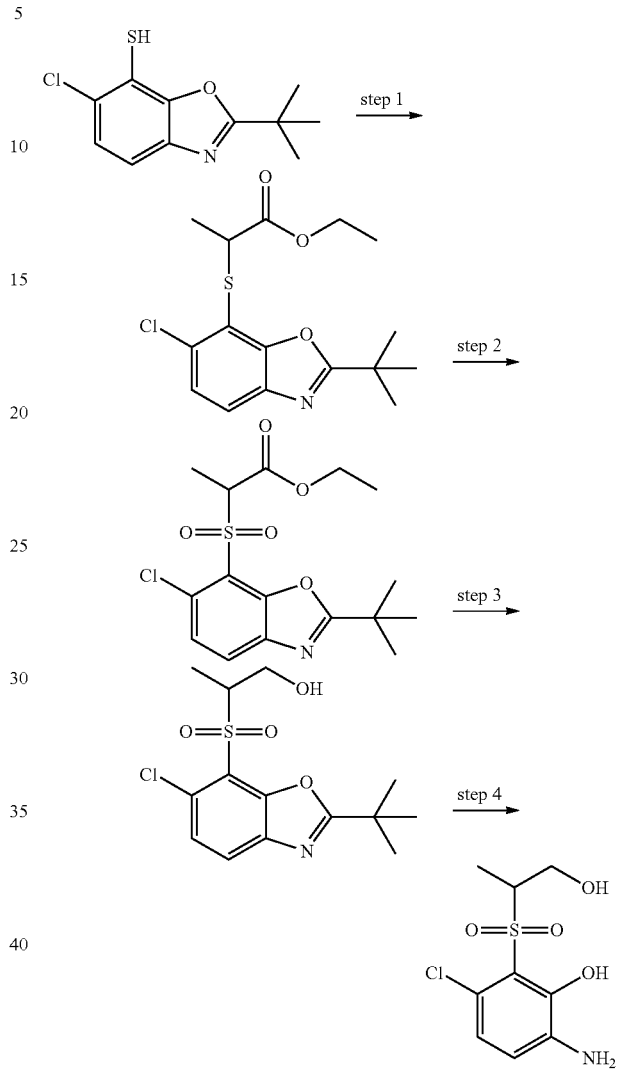

Step 1: To a solution of 2-(tert-butyl)-6-chlorobenzo[d]oxazole-7-thiol (1.2 g) in acetonitrile (30 mL) was added ethyl 2-bromopropanoate (1.0 g) and K₂CO₃ (1.4 g). After addition, it was stirred at 80° C. for 2 hours. The mixture was poured into water, and extracted with EA (2×80 mL). The combined organic phases were washed with brine, dried over Na₂SO₄, filtered and concentrated to afford the crude, which was purified by column chromatography (eluting with PE:EA=8:1) to give ethyl 2-((2-(tert-butyl)-6-chlorobenzo[d]oxazol-7-yl)thio)propanoate (1.5 g). MS(ES⁺) m/z 342 (MH⁺).

Step 2: To a solution of ethyl 2-((2-(tert-butyl)-6-chlorobenzo[d]oxazol-7-yl)thio)propanoate (1.4 g) in DCM (50 mL) was added mCPBA (2.5 g). The reaction mixture was stirred overnight at RT. The reaction was quenched with aq. NaHCO₃ and aq. Na₂S₂O₃ solutions. The mixture was extracted with EA (3×100 mL). The combined organic phases were washed with brine, dried over Na₂SO₄, filtered and concentrated to give the crude product, which was purified by column chromatography (eluting with PE:EA=10:1 to 10:3) to give ethyl 2-((2-(tert-butyl)-6-chlorobenzo[d]oxazol-7-yl)sulfonyl)propanoate (1.3 g). MS(ES⁺) m/z 374 (MH⁺).

Step 3: A solution of ethyl 2-((2-(tert-butyl)-6-chlorobenzo[d]oxazol-7-yl)sulfonyl)propanoate (1.3 g) in toluene (20 mL) was cooled to −78° C. DIBAL-H (1 M in hexane, 6.7 mL) was added. The reaction mixture was stirred for 4 hours, and then quenched with MeOH. The sat. NaHCO₃ solution was added. The resulting mixture was extracted with EA (3×50 mL). The combined organic phases were dried over Na₂SO₄, filtered and concentrated to give the residue, which was purified by column chromatography (eluting with PE:EA=6:1 to 4:1) to give 2-((2-(tert-butyl)-6-chlorobenzo[d]oxazol-7-yl)sulfonyl)propan-1-ol (800 mg). MS(ES⁺) m/z 332 (MH⁺).

Step 4: 2-((2-(Tert-butyl)-6-chlorobenzo[d]oxazol-7-yl)sulfonyl)propan-1-ol (260 mg) was dissolved in conc. HCl solution (5 mL) and water (5 mL). The reaction mixture was stirred overnight at 120° C. The solvent was evaporated to give the crude, which was combined with another batch of the same reaction using 2-((2-(tert-butyl)-6-chlorobenzo[d]oxazol-7-yl)sulfonyl)propan-1-ol (165 mg) as starting material. The combined mixture was purified by reversed phase chromatography eluting with water and acetonitrile to afford the title compound (90 mg). MS(ES⁺) m/z 266 (MH⁺).

Intermediate 27: 6-amino-3-chloro-2-((1,1-difluoroethyl)sulfonyl)phenol

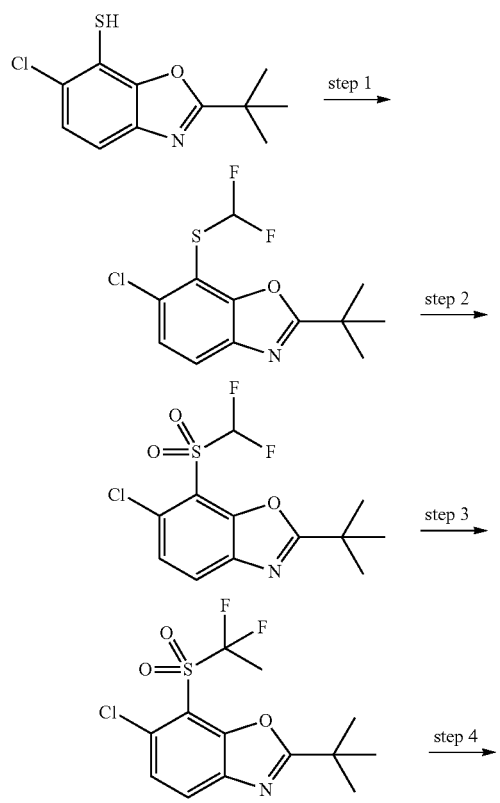

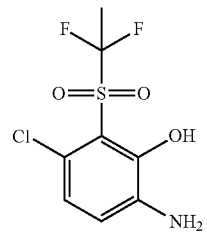

Step 1: To a solution of 2-(tert-butyl)-6-chlorobenzo[d]oxazole-7-thiol (6.0 g) and potassium hydroxide (13.9 g) in acetonitrile (80 mL) and water (80 mL) stirred at −78° C. was added diethyl (bromodifluoromethyl)phosphonate (11.9 g) in one portion. The reaction mixture was allowed to warm to RT and stirred for 30 mins. EA (200 mL) was added. The organic phase was separated. The aqueous phase was extracted with EA (2×100 mL). The combined organic layers were dried over sodium sulfate. The filtrate was concentrated to afford 2-(tert-butyl)-6-chloro-7-((difluoromethyl)thio)benzo[d]oxazole (7.2 g) as a colorless liquid. MS(ES⁺) m/z 292 (MH⁺).

Step 2: To a solution of 2-(tert-butyl)-6-chloro-7-((difluoromethyl)thio)benzo[d]oxazole (7.2 g) in DCM (200 mL) at 0° C. was added mCPBA (19.5 g). LCMS indicated that only sulfoxide formed. Additional mCPBA (19.5 g) was added. The reaction mixture was stirred at RT overnight. The desired product was observed with full conversion in LCMS. Aq. Na₂SO₃ solution was added. The organic phase was separated, and washed with sat. sodium carbonate solution and then brine. The resulting solution was dried over sodium sulfate and filtered. The filtrate was concentrated, and the residue was purified by column chromatography (eluting with a gradient of 0-60% EA in PE) to give 2-(tert-butyl)-6-chloro-7-((difluoromethyl)sulfonyl)benzo[d]oxazole (3.2 g) as a white solid. MS(ES⁺) m/z 324 (MH⁺).

Step 3: To a solution of 2-(tert-butyl)-6-chloro-7-((difluoromethyl)sulfonyl)benzo[d]oxazole (2.2 g) and MeI (4.2 mL) in THF (30 mL) and HMPA (27.0 mL) was added LDA (2 M in heptane, 13.5 mL). After stirring at −50° C. for 30 mins, the mixture was neutralized with sat. NH₄Cl solution and aq. HCl solution (10%). The mixture was extracted with EA (50 mL). The organic phase was washed with brine, dried over sodium sulfate and evaporated in vacuo. The residue was combined with another batch of the same reaction using 2-(tert-butyl)-6-chloro-7-((difluoromethyl)sulfonyl)benzo[d]oxazole (1.0 g) as starting material. The combined mixture was purified by column chromatography (eluting with 0-40% EA in PE) to afford 2-(tert-butyl)-6-chloro-7-((1,1-difluoroethyl)sulfonyl)benzo[d]oxazole (1.0 g) as a white solid. MS(ES⁺) m/z 338 (MH⁺).

Step 4: To a solution of 2-(tert-butyl)-6-chloro-7-((1,1-difluoroethyl)sulfonyl)benzo[d]oxazole (1.0 g) in 1,4-dioxane (20 mL) was added aq. hydrochloric acid (37%, 20 mL). The mixture was refluxed at 110° C. for 4 hours, and then concentrated. The residue was dissolved in EA (20 mL). The pH of the mixture was adjusted to 8 with TEA. The solvent was removed. The resulting residue was purified by column chromatography (eluting with 0-80% EA in PE) to afford the title compound (1.0 g) as a light brown solid. MS(ES⁺) m/z 272 (MH⁺).

Intermediate 28: 6-amino-3-chloro-2-((3-hydroxy-1-methylcyclobutyl)sulfonyl)phenol

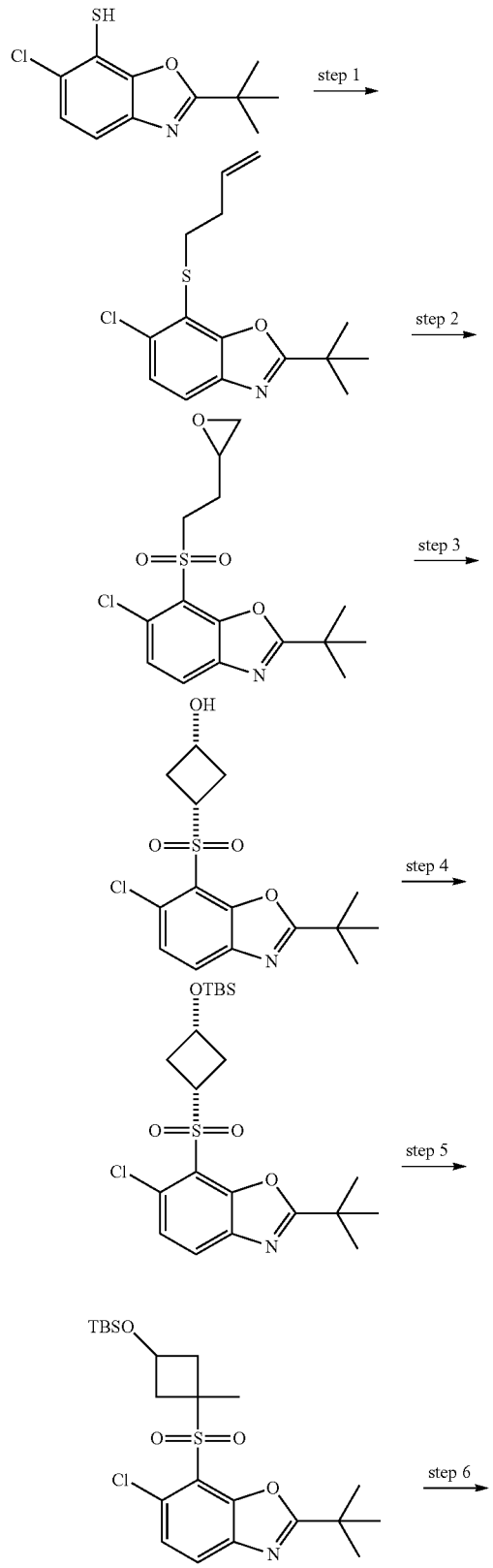

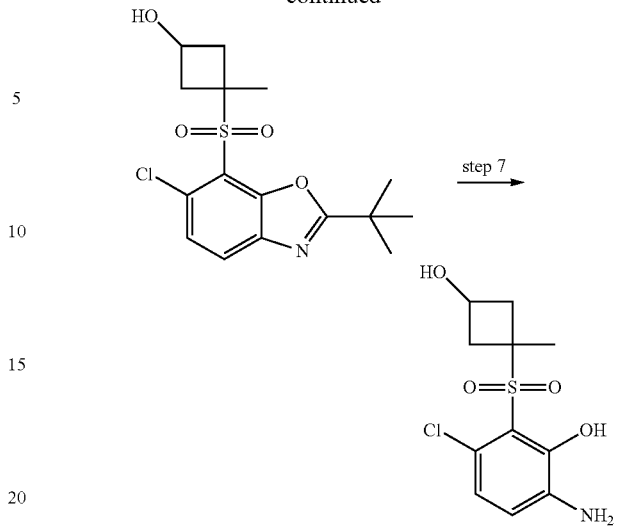

Step 1: To a solution of 2-(tert-butyl)-6-chlorobenzo[d]oxazole-7-thiol (25.0 g) in DMF (250 mL) was added 4-bromobut-1-ene (16.8 g) and then $K_2CO_3$ (21.4 g). The resulting mixture was stirred at 60° C. for 4 hours. After cooling, it was poured into water (1 L), and extracted with EA (2×200 mL). The combined organic layers were washed with water and brine. After drying over $Na_2SO_4$, the organic layer was concentrated to afford 7-(but-3-en-1-ylthio)-2-(tert-butyl)-6-chlorobenzo[d]oxazole (27.6 g). MS(ES$^+$) m/z 296 (MH$^+$).

Step 2: To an ice-water cooled solution of 7-(but-3-en-1-ylthio)-2-(tert-butyl)-6-chlorobenzo[d]oxazole (27.6 g) in DCM (400 mL) was added mCPBA (84.0 g) portionwise. After stirring at RT overnight, aq. $NaHCO_3$ and aq. $Na_2S_2O_3$ solutions were added. The mixture was extracted with DCM (2×500 mL). The combined organic layers were washed with water and brine, dried over $Na_2SO_4$, filtered and concentrated. The crude product was purified by column chromatography (eluting with PE:EA=1:0 to 7:3) to afford 2-(tert-butyl)-6-chloro-7-((2-(oxiran-2-yl)ethyl)sulfonyl)benzo[d]oxazole (26.0 g).

Step 3: To a solution of 2-(tert-butyl)-6-chloro-7-((2-(oxiran-2-yl)ethyl)sulfonyl)benzo[d]oxazole (10.0 g) in THF (200 mL) was added methylmagnesium bromide (3 M in ether, 38.8 mL) at −70° C. The mixture was warmed up slowly and stirred at RT overnight. The reaction mixture was poured into aq. $NH_4Cl$ solution, and extracted with EA (2×200 mL). The combined organic layers were washed with brine, dried over $Na_2SO_4$ and filtered. After removal of solvent, the crude product was purified by column chromatography (eluting with PE:EA=4:1 to 3:2) to afford cis-3-((2-(tert-butyl)-6-chlorobenzo[d]oxazol-7-yl)sulfonyl)cyclobutanol (7.2 g).

Step 4: To a solution of cis-3-((2-(tert-butyl)-6-chlorobenzo[d]oxazol-7-yl)sulfonyl)cyclobutanol (1.0 g) in DCM (50 mL) was added DMAP (0.036 g) and imidazole (0.4 g). After stirring for 10 mins, tert-butylchlorodimethylsilane (0.9 g) was added. The reaction mixture was quenched with sat. $NaHCO_3$ solution (30 mL), and extracted with EA for 3 times. The organic layers were washed with brine, dried over $Na_2SO_4$, filtered and concentrated in vacuo. The crude residue was purified by column chromatography (eluting with PE:EA=0:1 to 9:1) to give 2-(tertbutyl)-7-((cis-3-((tertbutyldimethylsilyl)oxy)cyclobutyl) sulfonyl)-6-chlorobenzo[d]oxazole (1.2 g). MS(ES+) m/z 458 (MH+).

Step 5: To a dry ice-ethanol cooled solution (temperature: −70° C.) of 2-(tert-butyl)-7-((cis-3-((tertbutyldimethylsilyl) oxy)cyclobutyl)sulfonyl)-6-chlorobenzo[d]oxazole (1.2 g) and MeI (0.2 mL) in THF (25 mL) was added LiHMDS (1 M in THF, 3.9 mL) dropwise at −70° C. The mixture was warmed up slowly, and stirred at RT for 3 hours. The reaction mixture was quenched with aq. NH4Cl solution, and extracted with EA (3×50 mL). The combined organic layers were washed with water and brine, dried (Na2SO4), filtered and concentrated to afford 2-(tert-butyl)-7-((-3-((tert-butyldimethylsilyl)oxy)-1-methylcyclobutyl)sulfonyl)-6-chlorobenzo[d]oxazole (1.2 g). MS(ES+) m/z 472 (MH+).

Step 6: To a solution of 2-(tert-butyl)-7-((3-((tert-butyldimethylsilyl)oxy)-1-methylcyclobutyl)sulfonyl)-6-chlorobenzo[d]oxazole (1.2 g) in THF (5 mL) was added TBAF (1 M in THF, 5.1 mL) dropwise. The mixture was stirred for 2 hours under a nitrogen atmosphere. The solvent was removed. The residue was purified by column chromatography (eluting with PE:EA=9:1 to 7:3) to afford 3-((2-(tert-butyl)-6-chlorobenzo[d]oxazol-7-yl)sulfonyl)-3-methylcyclobutanol (0.9 g).

Step 7: To a solution of 3-((2-(tert-butyl)-6-chlorobenzo[d]oxazol-7-yl)sulfonyl)-3-methylcyclobutanol (570 mg) in 1,4-dioxane (10 mL) and water (20 mL) was added conc. H2SO4 (0.8 mL) dropwise. The mixture was stirred at 120° C. overnight, and then basified with aq. NH3.H2O solution (7 M) to pH ~9. The mixture was purified by reversed phase chromatography (acidic condition), and then basified to afford the title compound (280 mg). MS(ES+) m/z 292 (MH+).

Intermediate 29: 6-amino-3-chloro-2-((3-methyltetrahydrofuran-3-yl)sulfonyl)phenol

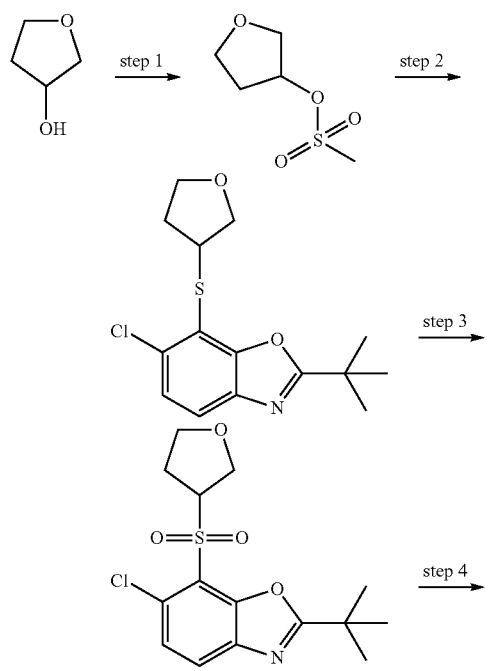

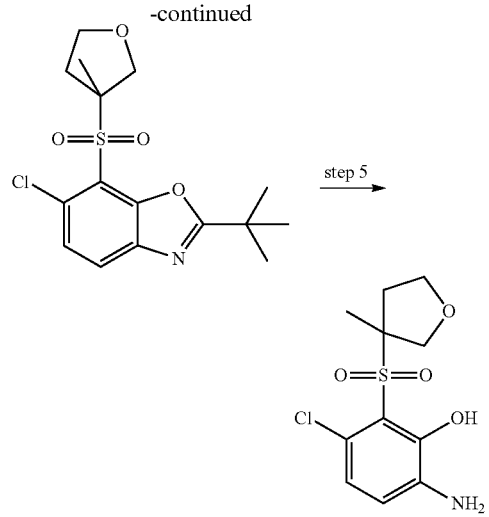

Step 1: To an ice-water cooled solution of tetrahydrofuran-3-ol (5.0 g) in DCM (100 mL) was added TEA (11.9 mL) and MsCl (4.9 mL). The resulting reaction mixture was stirred at 0° C. for 3 hours, and then quenched with aq. NaHCO3 solution. The mixture was extracted with EA (2×100 mL). The combined organic phases were washed, dried, filtered and concentrated to afford tetrahydrofuran-3-yl methanesulfonate (6.2 g).

Step 2: To a solution of sodium 2-(tert-butyl)-6-chlorobenzo[d]oxazole-7-thiolate (11.8 g) in DMF (100 mL) was added tetrahydrofuran-3-yl methanesulfonate (6.2 g) and K2CO3 (7.7 g). The resulting reaction mixture was stirred at 80° C. overnight. After cooling, it was poured into water (500 mL) and extracted with EA (2×150 mL). The combined organic phases were washed, dried and concentrated to afford 2-(tert-butyl)-6-chloro-7-((tetrahydrofuran-3-yl)thio) benzo[d]oxazole (11.4 g).

Step 3: To an ice-water cooled solution of 2-(tert-butyl)-6-chloro-7-((tetrahydrofuran-3-yl)thio)benzo[d]oxazole (7.4 g) in DCM (200 mL) was added mCPBA (11.7 g). The resulting mixture was stirred at RT for over 2 days, and then quenched with aq. NaHCO3 solution and aq. Na2S2O3 solution. The mixture was extracted with EA (2×200 mL). The combined organic phases were washed, dried and concentrated. The residue was purified by column chromatography (eluting with 0-40% EA in PE) to afford 2-(tert-butyl)-6-chloro-7-((tetrahydrofuran-3-yl)sulfonyl)benzo[d]oxazole (4.3 g). MS(ES+) m/z 344 (MH+).

Step 4: To a dry ice-ethanol cooled solution of 2-(tert-butyl)-6-chloro-7-((tetrahydrofuran-3-yl)sulfonyl)benzo[d] oxazole (4.3 g) and MeI (2.0 mL) in THF (100 mL) was added LiHMDS (1 M in THF, 31.3 mL). The resulting mixture was warmed up slowly and stirred at RT for 30 mins. Aq. NH4Cl solution was added. The mixture was extracted with EA (2×150 mL). The combined organic phases were washed, dried and concentrated to afford 2-(tert-butyl)-6-chloro-7-((3-methyltetrahydrofuran-3-yl) sulfonyl)benzo[d]oxazole (4.4 g). MS(ES+) m/z 358 (MH+).

Step 5: To a solution of 2-(tert-butyl)-6-chloro-7-((3-methyltetrahydrofuran-3-yl)sulfonyl)benzo[d]oxazole (4.4 g) in 1,4-dioxane (150 mL) was added aq. HCl solution (37%, 30.3 mL). The mixture was refluxed at 120° C. overnight, and then concentrated. The residue was dissolved in water (100 mL). The pH of the solution was adjusted to 8 with aq. NaHCO3 solution, and extracted with EA. The organic phase was washed and concentrated. The resulting residue was purified by column chromatography (eluting with a gradient of 0-80% EA in PE) to afford the title compound (2.4 g). MS(ES+) m/z 292 (MH+).

Intermediate 30: 6-amino-3-chloro-2-((4-methyltetrahydro-2H-pyran-4-yl)sulfonyl)phenol

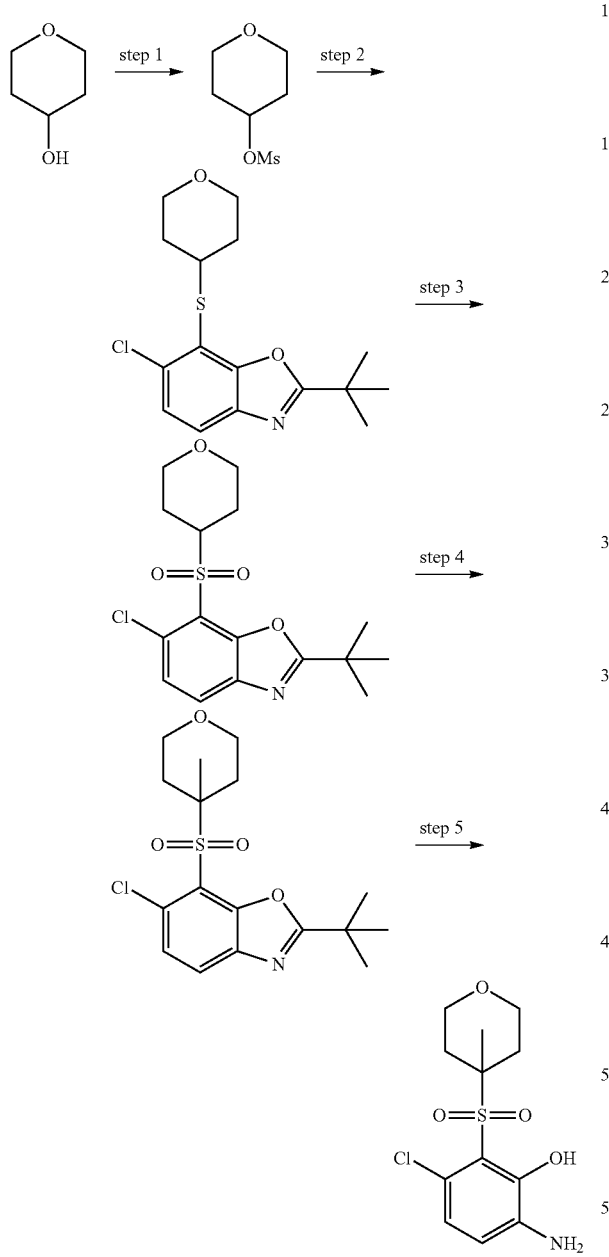

Step 1: To a solution of tetrahydro-2H-pyran-4-ol (10.0 g) in DCM (200 mL) was added TEA (12.9 g) and methanesulfonyl chloride (11.3 g). The mixture was stirred at 0° C. for 1 hour, and then washed with H$_2$O. The organic layer was dried over Na$_2$SO$_4$ and concentrated to afford tetrahydro-2H-pyran-4-yl methanesulfonate (15.5 g).

Step 2: To a solution of 2-(tert-butyl)-6-chlorobenzo[d]oxazole-7-thiol (18.0 g) and Cs$_2$CO$_3$ (12.1 g) in acetonitrile (5 mL) was added tetrahydro-2H-pyran-4-yl methanesulfonate (14.8 g). The mixture was stirred at 90° C. for 16 hours. After cooling to RT, the mixture was concentrated. The residue was partioned between EA (100 mL) and H$_2$O (100 mL). The organic layer was dried and concentrated to afford 2-(tert-butyl)-6-chloro-7-((tetrahydro-2H-pyran-4-yl)thio)benzo[d]oxazole (24.0 g). MS(ES+) m/z 326 (MH+).

Step 3: To a solution of 2-(tert-butyl)-6-chloro-7-((tetrahydro-2H-pyran-4-yl)thio)benzo[d]oxazole (24.0 g) in DCM (1000 mL) was added mCPBA (31.8 g). The mixture was stirred at 15° C. for 2 hours, and then quenched with aq. Na$_2$SO$_3$ solution. The pH was adjusted to ~7. The organic layer was dried and concentrated to afford 2-(tert-butyl)-6-chloro-7-((tetrahydro-2H-pyran-4-yl)sulfonyl)benzo[d]oxazole (18.0 g).

Step 4: To a solution of 2-(tert-butyl)-6-chloro-7-((tetrahydro-2H-pyran-4-yl)sulfonyl)benzo[d]oxazole (5.0 g) in THF (50 mL) was added BuLi (2.5 M in hexanes, 6.2 mL) at −78° C. under a nitrogen atmosphere. The mixture was stirred at −78° C. for 45 mins. MeI (2.2 g) was added. The reaction mixture was stirred at −78° C. for 1 hour, and then quenched with aq. NH$_4$Cl solution. The organic layer was dried and concentrated. The residue was purified by column chromatography to afford 2-(tert-butyl)-6-chloro-7-((4-methyltetrahydro-2H-pyran-4-yl)sulfonyl)benzo[d]oxazole (4.8 g). MS(ES+) m/z 372 (MH+).

Step 5: To a solution of 2-(tert-butyl)-6-chloro-7-((4-methyltetrahydro-2H-pyran-4-yl)sulfonyl)benzo[d]oxazole (1.0 g) in 1,4-dioxane (10 mL) was added aq. HCl solution (37%, 10 mL). After refluxed at 110° C. for 4 hours, the mixture was concentrated to afford the title compound (1.0 g) as a gray solid. MS(ES+) m/z 306 (MH+).

Intermediate 31: 6-amino-3-chloro-2-((4-d$_3$-methyltetrahydro-2H-pyran-4-yl)sulfonyl)phenol

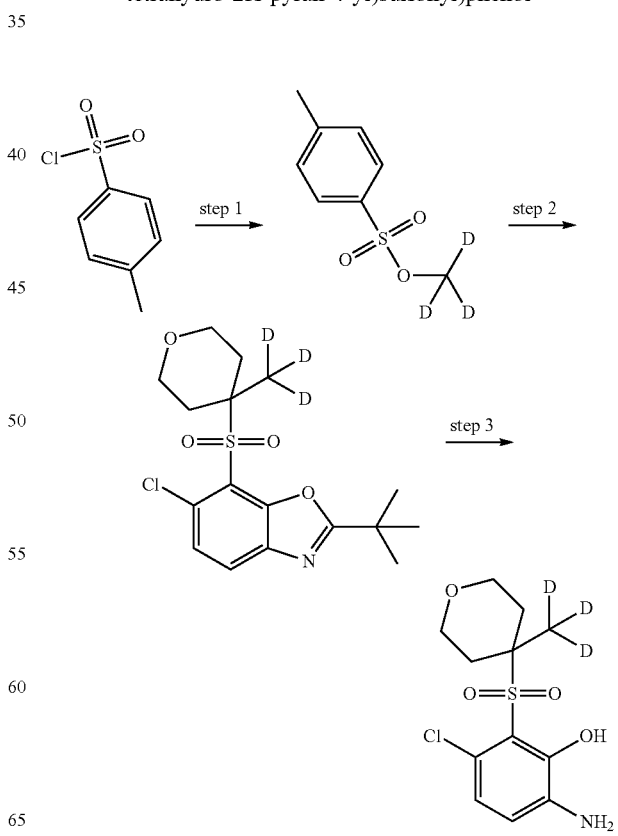

Step 1: To a mixture of NaOH (3.9 g) and [d₄]-methanol (1.0 g) in THF (10 mL) and water (10 mL) was added a solution of TsCl (10.6 g) in THF (16 mL) dropwise at ice-bath temperature. The reaction temperature was kept at −5-0° C. for 4 hours. The mixture was poured into ice-water, and then extracted with DCM (3×100 mL). The combined organic layers were washed, dried and concentrated to afford [d₃]-methyl p-toluenesulphonate (4.5 g). MS(ES⁺) m/z 190 (MH⁺).

Step 2: To a dry ice-ethanol cooled solution of 2-(tert-butyl)-6-chloro-7-((tetrahydro-2H-pyran-4-yl)sulfonyl)benzo[d]oxazole (Intermediate 30, Step 3, 0.9 g) and [d₃]-methyl p-toluenesulphonate (0.7 g) in THF (50 mL) was added LiHMDS (1 M in THF, 3.77 mL). The resulting mixture was warmed up slowly and stirred for 3 hours. Aq. NH₄Cl solution was added. The mixture was extracted with EA (2×100 mL). The combined organic layers were washed, dried and concentrated. The residue was purified by column chromatography (eluting with 0-30% EA in PE) to afford 2-(tert-butyl)-6-chloro-7-((4-d₃-methyltetrahydro-2H-pyran-4-yl)sulfonyl)benzo[d]oxazole (0.4 g). MS(ES⁺) m/z 375 (MH⁺).

Step 3: To a solution of 2-(tert-butyl)-6-chloro-7-((4-d₃-methyltetrahydro-2H-pyran-4-yl)sulfonyl)benzo[d]oxazole (0.4 g) in 1,4-dioxane (10 mL) and water (10 mL) was added conc. H₂SO₄ solution (0.6 mL). The resulting mixture was stirred at 120° C. overnight. The solvent was removed. The residue was basified with aq. NH₃·H₂O solution, and then purified with column chromatography (eluting with 10-40% EA in PE) to afford the title compound (0.2 g). MS(ES⁺) m/z 309 (MH⁺).

Intermediate 32: (±)-trans-6-amino-3-chloro-2-((3-hydroxycyclopentyl)sulfonyl)phenol

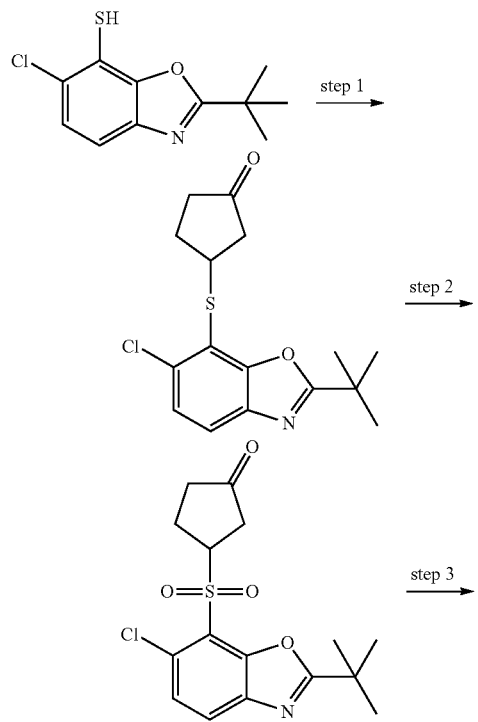

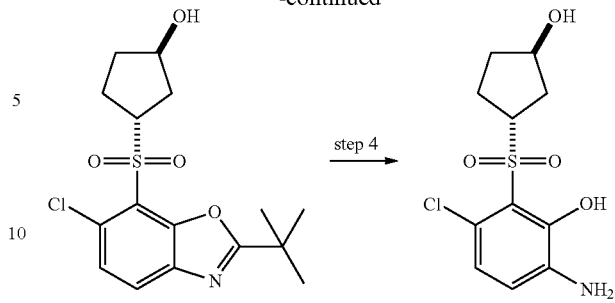

Step 1: To a solution of cyclopent-2-enone (0.5 g) in chloroform (30 mL) was added 2-(tert-butyl)-6-chlorobenzo[d]oxazole-7-thiol (1.3 g). The resulting mixture was stirred at RT for 18 hours. Diethyl ether (50 mL) was added. The organic phase was then washed with aq. NaOH solution (5% w/w, 2×20 mL), water (30 mL) and brine (30 mL). The resulting solution was dried over Na₂SO₄, filtered and concentrated under reduced pressure to give 3-((2-(tert-butyl)-6-chlorobenzo[d]oxazol-7-yl)thio)cyclopentanone (1.4 g) as a light yellow gel. MS(ES⁺) m/z 324 (MH⁺).

Step 2: To a solution of 3-((2-(tert-butyl)-6-chlorobenzo[d]oxazol-7-yl)thio)cyclopentanone (1.4 g) in DCM (10 mL) was added mCPBA (1.6 g) at 0° C. The resulting mixture was stirred at RT overnight. The mixture was washed with sat. K₂CO₃ solution (2×10 mL) and water (10 mL). The organic was dried over Na₂SO₄, filtered and concentrated under reduced pressure. The residue was purifed by column chromatography (eluting with PE:EA=2:1) to give 3-((2-(tertbutyl)-6-chlorobenzo[d]oxazol-7-yl)sulfonyl)cyclopentanone (800 mg) as a colorless gel. MS(ES⁺) m/z 356 (MH⁺).

Step 3: To a solution of 3-((2-(tert-butyl)-6-chlorobenzo[d]oxazol-7-yl)sulfonyl)cyclopentanone (200 mg) in THF (6 mL) at −78° C. was slowly added L-selectride (1.0 mL) with a syringe. The mixture was stirred under a nitrogen atmosphere at −78° C. for 2 hours. The mixture was then allowed to warm to RT and stirred for 18 hours. Water (5 mL) was carefully added. The mixture was adjusted to pH=6 with aq. HCl solution (4 M). The mixture was extracted with EA (2×15 mL). The organic layers were washed with brine (10 mL), dried over Na₂SO₄, filtered and concentrated under reduced pressure. The residue was purified by column chromatography (eluting with PE:EA=3:2) to give (±)-trans-3-((2-(tert-butyl)-6-chlorobenzo[d]oxazol-7-yl)sulfonyl)cyclopentanol (120 mg) as a colorless gel. MS(ES⁺) m/z 358 (MH⁺).

Step 4: (±)-Trans-3-((2-(tert-butyl)-6-chlorobenzo[d]oxazol-7-yl)sulfonyl)cyclopentanol (560 mg) was dissolved in 1,4-dioxane (5 mL), and then conc. HCl solution (4.8 mL) was added. The mixture was heated to 100° C. for 3 hours. The mixture was cooled to RT and evaporated under reduced pressure. The mixture was treated with sat. NaHCO₃ solution until pH=8 in ice bath.

The resulting mixture was extracted with DCM (5×20 mL). The combined organic phases were dried over sodium sulfate, filtered and concentrated under reduced pressure. The residue was purified by column chromatography (eluting with PE:EA=2:1) to give the title compound (350 mg) as a light yellow gel. ¹H-NMR (400 MHz, DMSO-d₆) δ ppm 10.49 (s, 1H), 6.87 (d, J=8.4 Hz, 1H), 6.80 (d, J=8.4 Hz, 1H), 4.41-4.27 (m, 2H), 3.79-3.62 (m, 1H), 2.33-2.14 (m, 3H), 2.01-1.89 (m, 2H), 1.89-1.77 (m, 1H); MS(ES⁺) m/z 292 (MH⁺).

Intermediate 33: (±)trans-6-amino-3-chloro-2-((2-hydroxycyclohexyl)sulfonyl)phenol

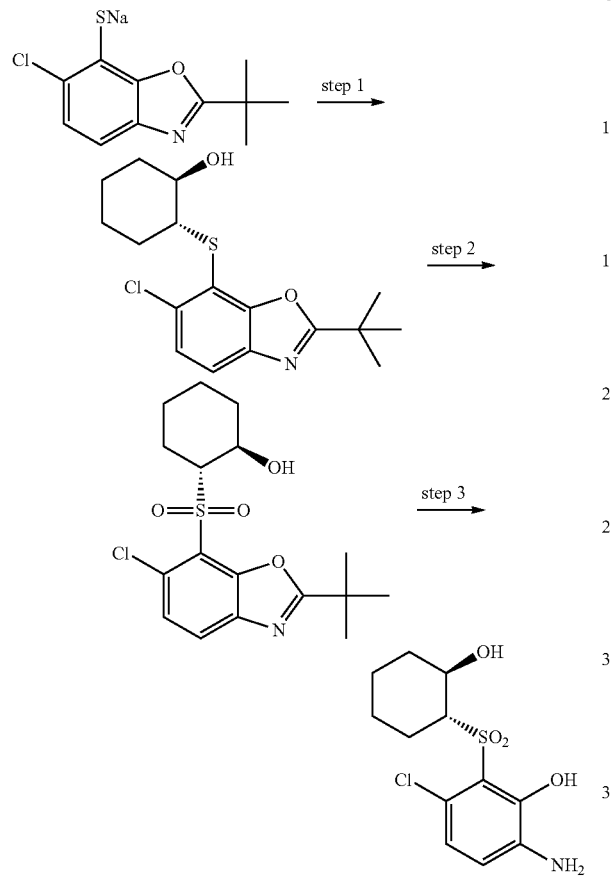

Step 1: To a solution of sodium 2-(tert-butyl)-6-chlorobenzo[d]oxazole-7-thiolate (350 mg) was added 7-oxabicyclo[4.1.0]heptane (143 mg). The resulting mixture was stirred at RT overnight. After concentration, the residue was combined with another batch of the same reaction using sodium 2-(tert-butyl)-6-chlorobenzo[d]oxazole-7-thiolate (30 mg) as starting material. The combined mixture was treated with aq. HCl solution (4 M) to adjust pH to 6, and then extracted with DCM (4×20 mL). The combined organic layers were dried over $Na_2SO_4$, filtered and concentrated to give (±)trans-2-((2-(tert-butyl)-6-chlorobenzo[d]oxazol-7-yl)thio)cyclohexanol (320 mg) as a light yellow gel. $MS(ES^+)$ m/z 340 $(MH^+)$.

Step 2: To a solution of (±)trans-2-((2-(tert-butyl)-6-chlorobenzo[d]oxazol-7-yl)thio)cyclohexanol (300 mg) in DCM (10 mL) was added mCPBA (335 mg) at 0° C. The resulting mixture was stirred at RT overnight. After completion of the reaction, the mixture was then washed with sat. $K_2CO_3$ solution (2×10 mL) and water (2×10 mL). The organic layer was dried over $Na_2SO_4$, and concentrated under reduced pressure. The residue was purifed by column chromatography (eluting with PE:EA=2:1) to give (±)trans-2-((2-(tert-butyl)-6-chlorobenzo[d]oxazol-7-yl)sulfonyl)cyclohexanol (150 mg) as a colorless gel. $MS(ES^+)$ m/z 372 $(MH^+)$.

Step 3: (±)Trans-2-((2-(tert-butyl)-6-chlorobenzo[d]oxazol-7-yl)sulfonyl)cyclohexanol (150 mg) was dissolved in 1,4-dioxane (2 mL), and then conc. HCl solution (1.2 mL) was added. The mixture was heated to 100° C. for 4 hours to give a brown solution. The mixture was cooled to RT. After concentration, the mixture was treated with sat. $NaHCO_3$ solution until pH=8 in an ice bath. The mixture was extracted with DCM (5×20 mL). The combined organic layers were dried over sodium sulfate, filtered and concentrated to give the title compound (130 mg) as a brown gel. $MS(ES^+)$ m/z 306 $(MH^+)$.

Intermediate 34: 6-amino-3-chloro-2-(((3R,4R)-4-fluorotetrahydrofuran-3-yl)sulfonyl)phenol

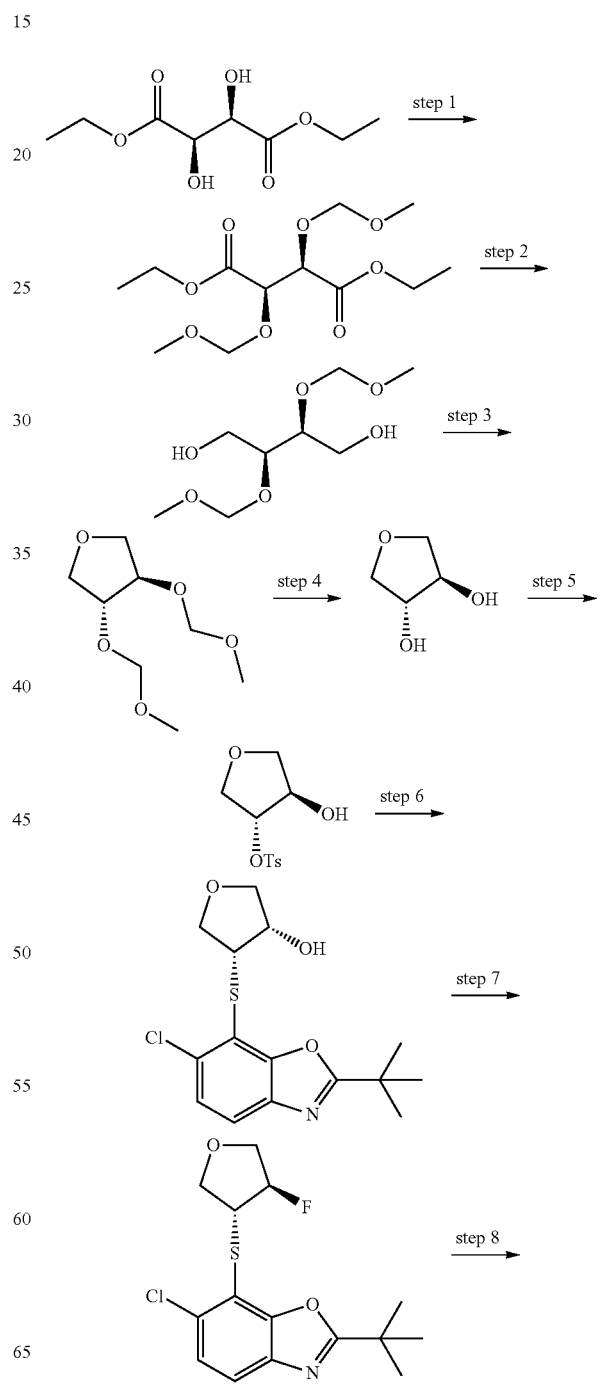

-continued

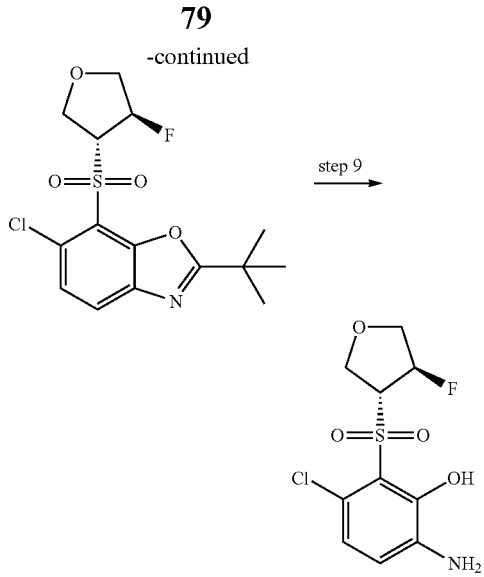

step 9

Step 1: To a mixture of (2R,3R)-diethyl 2,3-dihydroxysuccinate (100.0 g) and DIPEA (157.0 g) in DCM (200 mL) was added a solution of chloro(methoxy)methane (98.0 g) in DCM (100 mL) at 0° C. The mixture was stirred at 25° C. for 18 hours, and then t-BuOMe (1 L) was added. The mixture was filtered and the filtrate was evaporated to give (2R,3R)-diethyl 2,3-bis(methoxymethoxy)succinate (130.0 g) as a yellow oil.

Step 2: To a suspension of LiAlH$_4$ (23 g) in THF (900 mL) at 0° C. was added a solution of (2R,3R)-diethyl 2,3-bis(methoxymethoxy)succinate (120.0 g) in THF (100 mL) dropwise. The mixture was stirred at RT for 2 hours, and then quenched with water (25 mL). Aq. NaOH solution (15% w/w, 25 mL) was added, followed by addition of water (75 mL). The mixture was stirred overnight, and then filtered. The filtrate was evaporated to give (2S,3S)-2,3-bis(methoxymethoxy)butane-1,4-diol (70.0 g) as a white solid.

Step 3: A mixture of (2S,3S)-2,3-bis(methoxymethoxy)butane-1,4-diol (60.0 g), triphenylphosphine (90.0 g), DEAD (49.2 mL), THF (200 mL) and toluene (800 mL) was stirred at 20° C. for 36 hours. The solvent was evaporated and the residue was purified by column chromatography (eluting with PE:EA=4:1) to give the crude product (11.0 g) as a yellow oil. The crude oil was distilled by vacuum distillation and the fractions were collected at 75° C. to give (3S,4S)-3,4-bis(methoxymethoxy)tetrahydrofuran (7.5 g) as a colorless oil.

Step 4: A mixture of (3S,4S)-3,4-bis(methoxymethoxy)tetrahydrofuran (6.3 g), conc. HCl solution (4 mL) and methanol (12 mL) was stirred at 30° C. for 12 hours. The solvent was evaporated to give (3S,4S)-tetrahydrofuran-3,4-diol (3.3 g) as a colorless oil, which was solidified after a few minutes.

Step 5: To a solution of (3S,4S)-tetrahydrofuran-3,4-diol (1.5 g) in pyridine (15 mL) stirred at 0° C. was added 4-methylbenzene-1-sulfonyl chloride (1.7 mL). The reaction mixture was stirred at RT overnight. DCM (50 mL) was added. The pH value was adjusted to 4 by addition of aq. HCl solution (2 M). The organic layer was separated, washed with brine, dried over sodium sulfate and concentrated to afford (3S,4S)-4-hydroxytetrahydrofuran-3-yl 4-methylbenzenesulfonate (2.6 g) as an oil. MS(ES$^+$) m/z 281 (MH$^+$).

Step 6: To a solution of sodium 2-(tert-butyl)-6-chlorobenzo[d]oxazole-7-thiolate (2.6 g) and (3S,4S)-4-hydroxytetrahydrofuran-3-yl 4-methylbenzenesulfonate (2.6 g) in acetonitrile (10 mL) was added Cs$_2$CO$_3$ (1.6 g). The reaction mixture was stirred at 60° C. for 1 hour. The mixture was filtered and concentrated to afford (3S,4R)-4-((2-(tert-butyl)-6-chlorobenzo[d]oxazol-7-yl)thio)tetrahydrofuran-3-ol (3.3 g) as a colorless oil. MS(ES$^+$) m/z 328 (MH$^+$).

Step 7: To a solution of (3S,4R)-4-((2-(tert-butyl)-6-chlorobenzo[d]oxazol-7-yl)thio)tetrahydrofuran-3-ol (600 mg) in DCM (10 mL) stirred under a nitrogen atmosphere at −78° C. was added DAST (0.5 mL). The reaction mixture was allowed to warm to RT and stirred overnight. The mixture was washed with sat. sodium carbonate solution and brine. The organic phase was collected, dried over sodium sulfate and concentrated in vacuo to afford 2-(tert-butyl)-6-chloro-7-(((3R,4R)-4-fluorotetrahydrofuran-3-yl)thio)benzo[d]oxazole (604 mg) as a colorless oil. MS(ES$^+$) m/z 330 (MH$^+$).

Step 8: To a solution of 2-(tert-butyl)-6-chloro-7-(((3R,4R)-4-fluorotetrahydrofuran-3-yl)thio)benzo[d]oxazole (604 mg) in DCM (10 mL) was added mCPBA (1231 mg) at 0° C. The resulting mixture was stirred at RT overnight, and then quenched with aq. NaHCO$_3$ solution and aq. Na$_2$S$_2$O$_3$ solution. The mixture was extracted with EA (2×150 mL). The combined organic phases were washed, dried and concentrated. The residue was purified by column chromatography (eluting with PE:EA=7:3 to 1:1) to afford 2-(tert-butyl)-6-chloro-7-(((3R,4R)-4-fluorotetrahydrofuran-3-yl)sulfonyl)benzo[d]oxazole (660 mg) as a white solid. MS(ES$^+$) m/z 362 (MH$^+$).

Step 9: To a solution of 2-(tert-butyl)-6-chloro-7-(((3R,4R)-4-fluorotetrahydrofuran-3-yl)sulfonyl)benzo[d]oxazole (320 mg) in 1,4-dioxane (10 mL) was added conc. HCl solution (2 mL). After refluxing at 110° C. overnight, the mixture was concentrated and the resulting residue was purified by reversed phase chromatography (eluting with MeCN/H$_2$O (containing 0.1% TFA)=0:1 to 3:2) to afford the title compound (128 mg) as a gray solid. MS(ES$^+$) m/z 296 (MH$^+$).

Intermediate 35: trans-6-amino-3-chloro-2-((3-(difluoromethyl)cyclobutyl)sulfonyl)phenol

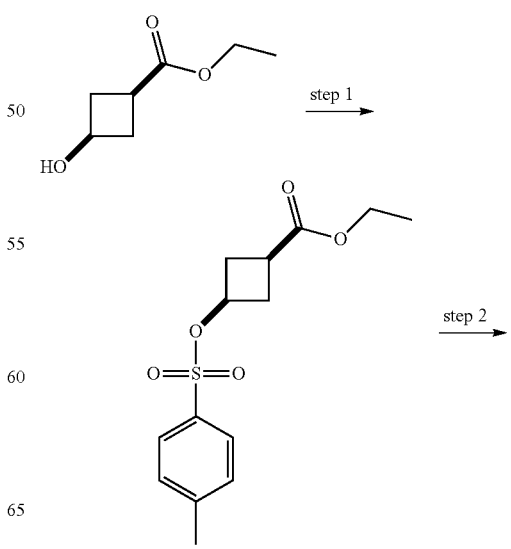

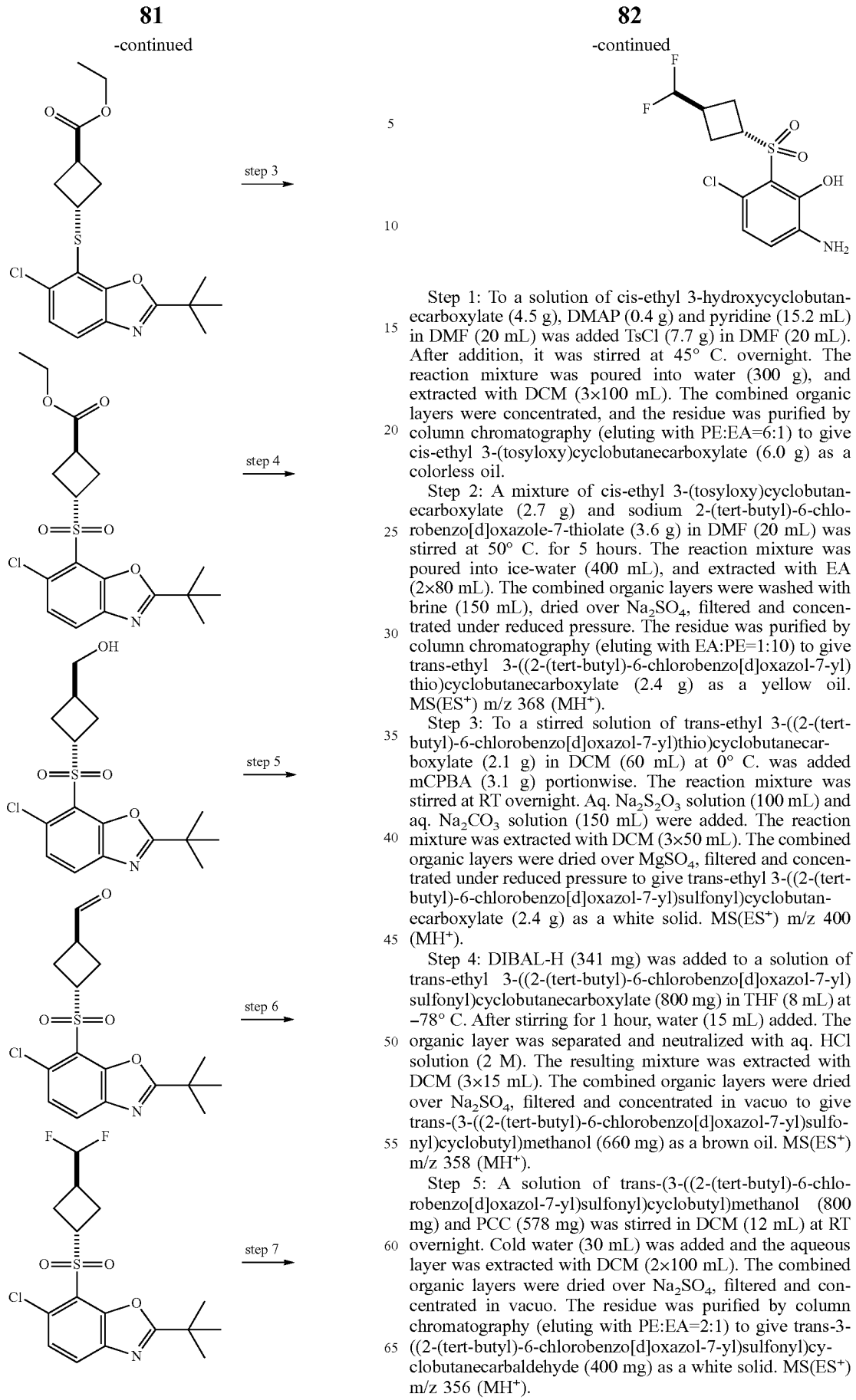

Step 1: To a solution of cis-ethyl 3-hydroxycyclobutanecarboxylate (4.5 g), DMAP (0.4 g) and pyridine (15.2 mL) in DMF (20 mL) was added TsCl (7.7 g) in DMF (20 mL). After addition, it was stirred at 45° C. overnight. The reaction mixture was poured into water (300 g), and extracted with DCM (3×100 mL). The combined organic layers were concentrated, and the residue was purified by column chromatography (eluting with PE:EA=6:1) to give cis-ethyl 3-(tosyloxy)cyclobutanecarboxylate (6.0 g) as a colorless oil.

Step 2: A mixture of cis-ethyl 3-(tosyloxy)cyclobutanecarboxylate (2.7 g) and sodium 2-(tert-butyl)-6-chlorobenzo[d]oxazole-7-thiolate (3.6 g) in DMF (20 mL) was stirred at 50° C. for 5 hours. The reaction mixture was poured into ice-water (400 mL), and extracted with EA (2×80 mL). The combined organic layers were washed with brine (150 mL), dried over $Na_2SO_4$, filtered and concentrated under reduced pressure. The residue was purified by column chromatography (eluting with EA:PE=1:10) to give trans-ethyl 3-((2-(tert-butyl)-6-chlorobenzo[d]oxazol-7-yl)thio)cyclobutanecarboxylate (2.4 g) as a yellow oil. MS(ES$^+$) m/z 368 (MH$^+$).

Step 3: To a stirred solution of trans-ethyl 3-((2-(tert-butyl)-6-chlorobenzo[d]oxazol-7-yl)thio)cyclobutanecarboxylate (2.1 g) in DCM (60 mL) at 0° C. was added mCPBA (3.1 g) portionwise. The reaction mixture was stirred at RT overnight. Aq. $Na_2S_2O_3$ solution (100 mL) and aq. $Na_2CO_3$ solution (150 mL) were added. The reaction mixture was extracted with DCM (3×50 mL). The combined organic layers were dried over $MgSO_4$, filtered and concentrated under reduced pressure to give trans-ethyl 3-((2-(tert-butyl)-6-chlorobenzo[d]oxazol-7-yl)sulfonyl)cyclobutanecarboxylate (2.4 g) as a white solid. MS(ES$^+$) m/z 400 (MH$^+$).

Step 4: DIBAL-H (341 mg) was added to a solution of trans-ethyl 3-((2-(tert-butyl)-6-chlorobenzo[d]oxazol-7-yl)sulfonyl)cyclobutanecarboxylate (800 mg) in THF (8 mL) at −78° C. After stirring for 1 hour, water (15 mL) added. The organic layer was separated and neutralized with aq. HCl solution (2 M). The resulting mixture was extracted with DCM (3×15 mL). The combined organic layers were dried over $Na_2SO_4$, filtered and concentrated in vacuo to give trans-(3-((2-(tert-butyl)-6-chlorobenzo[d]oxazol-7-yl)sulfonyl)cyclobutyl)methanol (660 mg) as a brown oil. MS(ES$^+$) m/z 358 (MH$^+$).

Step 5: A solution of trans-(3-((2-(tert-butyl)-6-chlorobenzo[d]oxazol-7-yl)sulfonyl)cyclobutyl)methanol (800 mg) and PCC (578 mg) was stirred in DCM (12 mL) at RT overnight. Cold water (30 mL) was added and the aqueous layer was extracted with DCM (2×100 mL). The combined organic layers were dried over $Na_2SO_4$, filtered and concentrated in vacuo. The residue was purified by column chromatography (eluting with PE:EA=2:1) to give trans-3-((2-(tert-butyl)-6-chlorobenzo[d]oxazol-7-yl)sulfonyl)cyclobutanecarbaldehyde (400 mg) as a white solid. MS(ES$^+$) m/z 356 (MH$^+$).

Step 6: To a stirred solution of trans-3-((2-(tert-butyl)-6-chlorobenzo[d]oxazol-7-yl)sulfonyl)cyclobutanecarbaldehyde (400 mg) in DCE (10 mL) cooled to −100° C. was added DAST (4 mL) over a period of 30 minutes. The reaction mixture was stirred at this temperature for 1 hour, and then at RT for 16 hours. The reaction mixture was quenched by a mixture of crushed ice and NaHCO$_3$. The organic layer was separated. The aqueous layer was extracted with DCM (2×50 mL). The combined organic layers were washed with brine (50 mL), dried over anhydrous Na$_2$SO$_4$ and concentrated. The residue was purified by column chromatography (eluting with PE:EA=5:1) to give trans-2-(tert-butyl)-6-chloro-7-((3-(difluoromethyl)cyclobutyl)sulfonyl)benzo[d]oxazole (401 mg) as a white solid. MS(ES$^+$) m/z 378 (MH$^+$).

Step 7: A solution of trans-2-(tert-butyl)-6-chloro-7-((3-(difluoromethyl)cyclobutyl)sulfonyl)benzo[d]oxazole (400 mg) in sulfuric acid (65%, 2 mL) and dioxane (4 mL) was stirred at 90° C. for 4 hours. The reaction mixture was purified by preparative HPLC (C8, mobile phase 0.01% CF$_3$COOH/H$_2$O, CH$_3$OH, 30 mL/min) (10%~55%, 5 min; 55~55%, 6 min; 40%~95%, 1 min; 95%~95%, 1 min) to give the title compound (120 mg) as a yellow solid. MS(ES$^+$) m/z 312 (MH$^+$).

Intermediate 36: trans-(R)-6-amino-3-chloro-2-((3-(3-fluoropyrrolidin-1-yl)cyclobutyl)sulfonyl)phenol

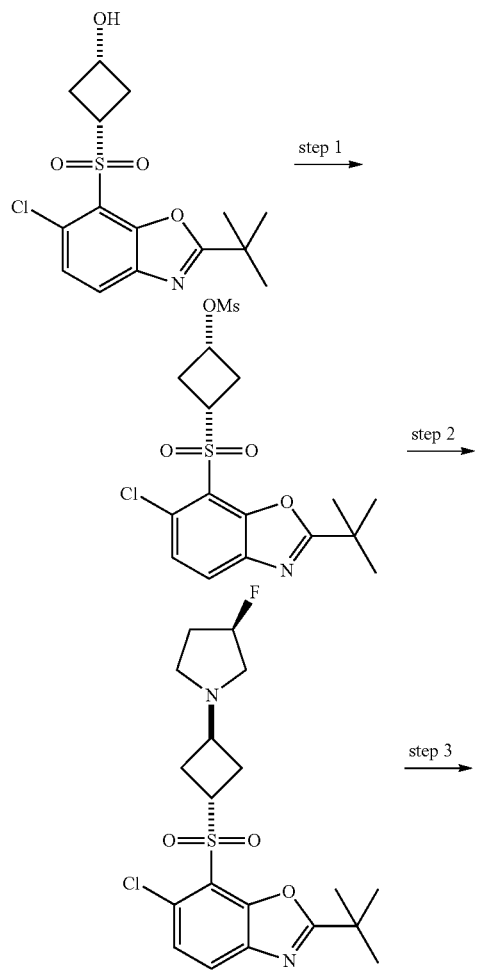

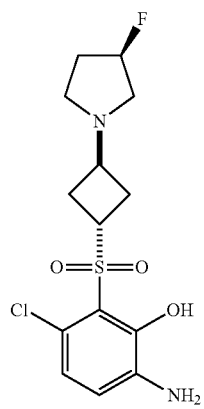

Step 1: To a solution of cis-3-((2-(tert-butyl)-6-chlorobenzo[d]oxazol-7-yl)sulfonyl)cyclobutanol (Intermediate 28, Step 3, 1.0 g) and N,N-diethylpropan-2-amine (0.9 mL) in DCM (20 mL) was added methanesulfonyl chloride (0.3 mL) at 0° C. The mixture was stirred at 0° C. for 4 hours. The reaction mixture was then poured into water and extracted with DCM (2×50 mL). The combined organic phases were washed, dried and concentrated to give cis-3-((2-(tert-butyl)-6-chlorobenzo[d]oxazol-7-yl)sulfonyl)cyclobutyl methanesulfonate (1.3 g) as a colorless solid. MS(ES$^+$) m/z 422 (MH$^+$).

Step 2: A solution of cis-3-((2-(tert-butyl)-6-chlorobenzo[d]oxazol-7-yl)sulfonyl)cyclobutyl methanesulfonate (2.2 g), potassium carbonate (1.1 g) and (R)-3-fluoropyrrolidine (0.7 g) in DMF (10 mL) was stirred at 80° C. for 2 days. Cold water (30 mL) was added and the resulting mixture was neutralized with sat. NaHCO$_3$ solution. The aqueous layer was extracted with DCM (2×100 mL). The combined organic layers were dried over Na$_2$SO$_4$, filtered and concentrated in vacuo. The residue was purified by preparative TLC (silica gel, GF254 10-40μ, 25×25 cm) with CHCl$_3$—AcOEt (8:1, twice) to give trans-(R)-2-(tert-butyl)-6-chloro-7-((3-(3-fluoropyrrolidin-1-yl)cyclobutyl)sulfonyl)benzo[d]oxazole (460 mg) as a yellow solid without further purification. MS(ES$^+$) m/z 415 (MH$^+$).

Step 3: Trans-(R)-2-(tert-butyl)-6-chloro-7-((3-(3-fluoropyrrolidin-1-yl)cyclobutyl)sulfonyl)benzo[d]oxazole (460 mg) was dissolved in 1,4-dioxane (20 mL) and water (4 mL). Conc. sulfuric acid (1.0 mL) was added. The mixture was heated to 100° C. overnight. The mixture was cooled to RT. The solvent was removed. The residue was then treated with 6 M NaOH until pH=12 in an ice bath. The mixture was extracted with EA (4×50 mL). The combined organic layers were dried over sodium sulfate, filtered and concentrated to give the title compound (200 mg) as an oil. MS(ES$^+$) m/z 349 (MH$^+$).

Intermediate 37: 6-amino-3-chloro-2-((trans-3-fluorocyclobutyl)sulfonyl)phenol

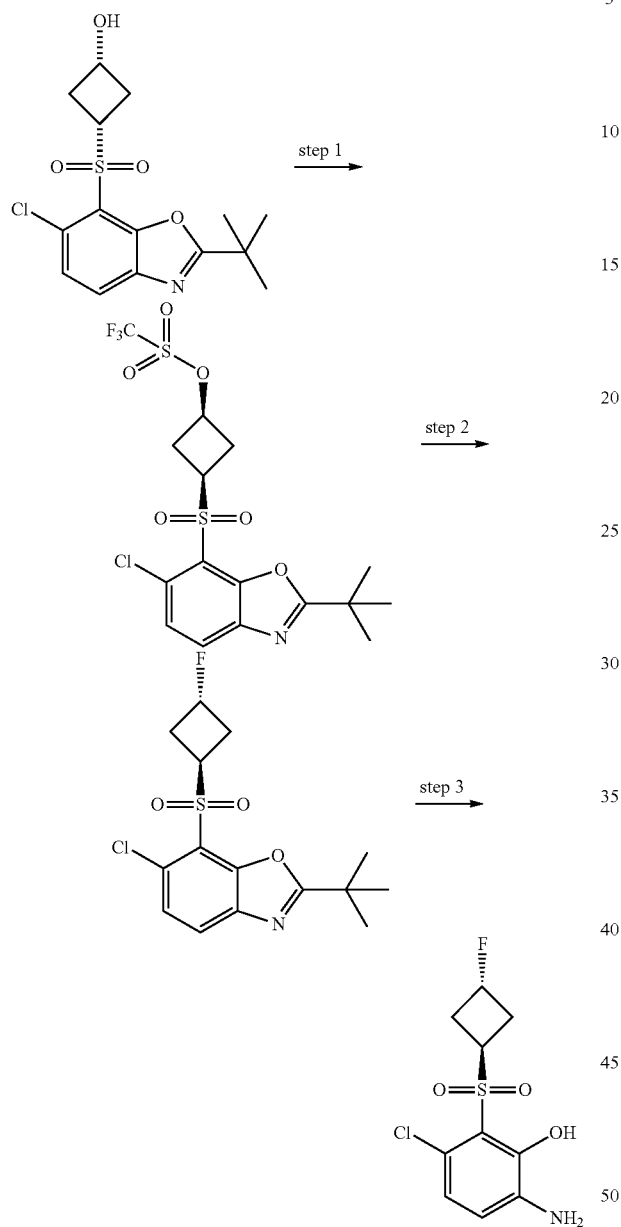

Step 1: To a solution of cis-3-((2-(tert-butyl)-6-chlorobenzo[d]oxazol-7-yl)sulfonyl)cyclobutanol (Intermediate 28, Step 3, 2.0 g) in DCM (8 mL) was added pyridine (0.9 mL) and triflic anhydride (11.6 mL) at −20° C. The reaction mixture was stirred at −20° C. to 10° C. for 2 hours. EA (50 mL) was added. The mixture was washed with brine, dried over anhydrous sodium sulfate, filtered and concentrated to afford cis-3-((2-(tert-butyl)-6-chlorobenzo[d]oxazol-7-yl)sulfonyl)cyclobutyl trifluoromethanesulfonate (2.8 g). MS(ES$^+$) m/z 476 (MH$^+$).

Step 2: To a solution of cis-3-((2-(tert-butyl)-6-chlorobenzo[d]oxazol-7-yl)sulfonyl)cyclobutyl trifluoromethanesulfonate (2.8 g) in DCM (15 mL) stirred at −15° C. was added tetra-n-butylammonium fluoride (3.0 g). The reaction mixture was stirred at RT overnight. The resulting mixture was washed with brine, dried over anhydrous sodium sulfate, filtered and concentrated to afford 2-(tert-butyl)-6-chloro-7-((trans-3-fluorocyclobutyl)sulfonyl)benzo[d]oxazole (2.0 g). MS(ES$^+$) m/z 346 (MH$^+$).

Step 3: To a solution of 2-(tert-butyl)-6-chloro-7-((trans-3-fluorocyclobutyl)sulfonyl)benzo[d]oxazole (2.0 g) in 1,4-dioxane (20 mL) was slowly added conc. sulfuric acid (4.6 mL). The reaction mixture was stirred under reflux overnight. The mixture was diluted with EA. The organic phase was separated, washed with water for 3 times, dried over Na$_2$SO$_4$, filtered and concentrated. The residue was purified by column chromatography (eluting with 0-40% EA in PE) to afford the title compound (1.2 g) as a white solid. MS(ES$^+$) m/z 280 (MH$^+$).

Intermediate 38: (±)trans-6-amino-3-chloro-2-((2-hydroxycyclopentyl)sulfonyl)phenol

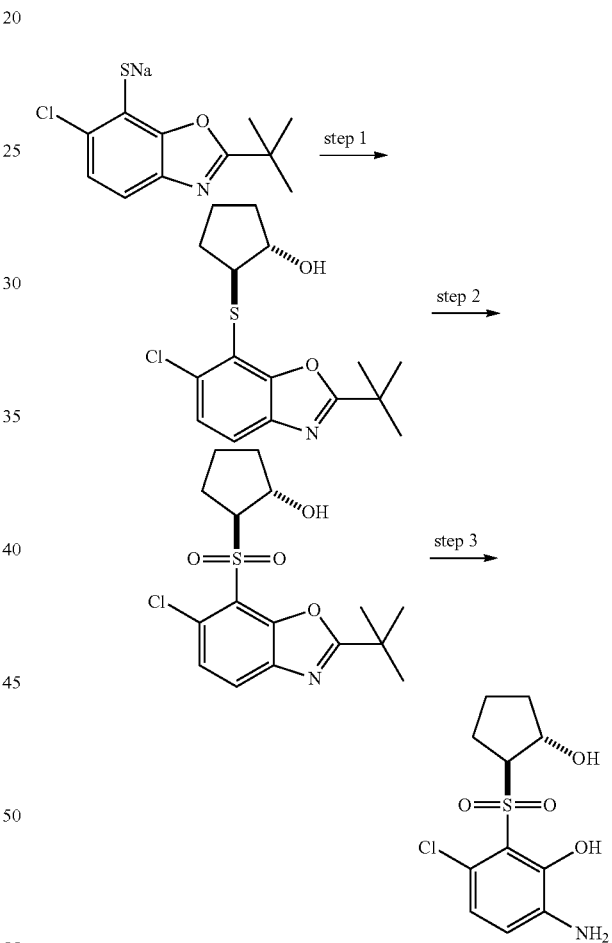

Step 1: To a solution of sodium 2-(tert-butyl)-6-chlorobenzo[d]oxazole-7-thiolate (300 mg) in ethanol (10 mL) was added 6-oxa-bicyclo[3.1.0]hexane (144 mg). The mixture was stirred at 25° C. for 2 hours. Water was added. The mixture was extracted with DCM. The organic phase was dried over Na$_2$SO$_4$, filtered and concentrated. The residue was purified by TLC (PE:EA=3:1) to yield (±)trans-2-((2-(tert-butyl)-6-chlorobenzo[d]oxazol-7-yl)thio)cyclopentanol (174 mg) as a yellow oil. $^1$H-NMR (500 MHz, CDCl$_3$) δ ppm 7.54 (d, J=8.4 Hz, 1H), 7.39 (d, J=8.5 Hz, 1H), 4.02 (dd, J=11.0, 4.8 Hz, 1H), 3.66 (dd, J=11.6, 6.9 Hz, 1H), 2.10-2.40 (m, 2H), 1.76-1.84 (m, 2H), 1.58-1.67 (m, 2H), 1.52 (s, 9H); MS(ES⁺) m/z 326 (MH⁺).

Step 2: To a solution of (±)trans-2-((2-(tert-butyl)-6-chlorobenzo[d]oxazol-7-yl)thio)cyclopentanol (214 mg) in DCM (20 mL) was added mCPBA (283 mg) at 0° C. After stirring at 20° C. overnight, the mixture was quenched with aq. Na₂S₂O₃ and aq. NaHCO₃ solutions, and then extracted with DCM (3×10 mL). The combined organic layers were dried over Na₂SO₄, filtered and concentrated. The residue was purified by preparative TLC (PE:EA=3:1) to give (±)trans-2-((2-(tert-butyl)-6-chlorobenzo[d]oxazol-7-yl)sulfonyl)cyclopentanol (180 mg) as a white solid. ¹H-NMR (500 MHz, CDCl₃) δ ppm 7.83 (d, J=8.5 Hz, 1H), 7.49 (d, J=8.4 Hz, 1H), 4.82 (q, J=6.5 Hz, 1H), 3.83-3.99 (m, 1H), 1.95-2.22 (m, 3H), 1.70-1.85 (m, 3H), 1.52 (s, 9H); MS(ES⁺) m/z 358 (MH⁺).

Step 3: To a solution of (±)trans-2-((2-(tert-butyl)-6-chlorobenzo[d]oxazol-7-yl)sulfonyl)cyclopentanol (230 mg) in 1,4-dioxane (6 mL) was added aq. HCl solution (12 M, 3 mL). The mixture was stirred at 110° C. for 4 hours. The mixture was concentrated. Aq. NaHCO₃ solution was added until pH=7. The mixture was extracted with DCM (3×20 mL). The combined organic layers were dried over Na₂SO₄, filtered and contrated to give the title compound (180 mg) as a red brown oil. ¹H-NMR (500 MHz, MeOD-d₄) δ ppm 6.79 (s, 2H), 4.48 (dd, J=10.2, 4.3 Hz, 1H), 3.93-4.09 (m, 1H), 1.60-2.00 (m, 6H); MS(ES⁺) m/z 292 (MH⁺).

Intermediate 39: (±)trans-6-amino-3-chloro-2-((2-hydroxycyclopentyl)sulfonyl)phenol

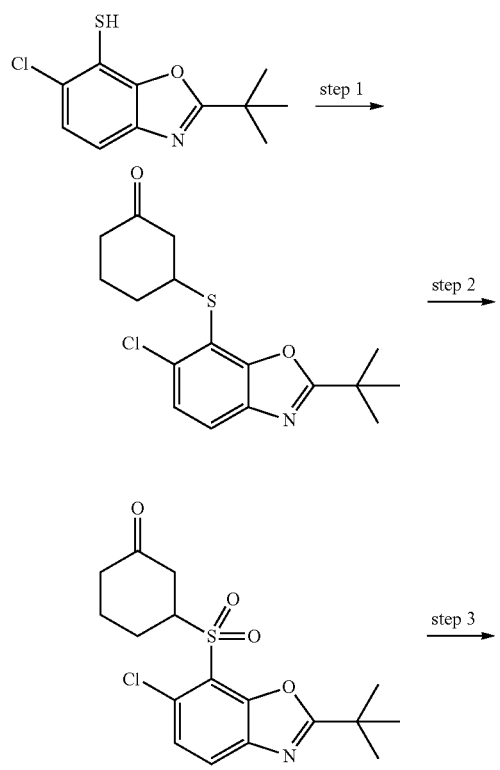

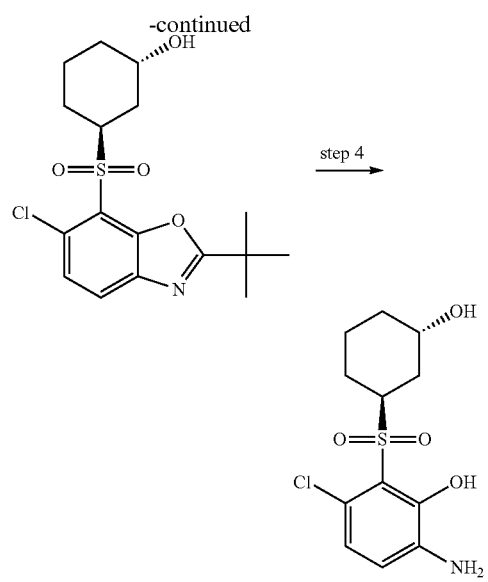

Step 1: To a solution of cyclohex-2-enone (0.5 g) and 2-(tert-butyl)-6-chlorobenzo[d]oxazole-7-thiol (1.2 g) in chloroform (5 mL) was added TEA (0.07 mL) at 0° C. The resulting mixture was stirred at RT for 18 hours. Diethyl ether (20 mL) was added. The organic phase was washed with 5% NaOH aqueous (2×10 mL), water (2×15 mL) and brine (15 mL). The organic phase was dried over Na₂SO₄, filtered and concentrated under reduced pressure to give 3-((2-(tert-butyl)-6-chlorobenzo[d]oxazol-7-yl)thio)cyclohexanone (1.3 g) as a light yellow gel. MS(ES⁺) m/z 338 (MH⁺).

Step 2: To a solution of 3-((2-(tert-butyl)-6-chlorobenzo[d]oxazol-7-yl)thio)cyclohexanone (1.3 g) in DCM (25 mL) was added mCPBA (1.5 g) at 0° C. The resulting mixture was stirred at RT overnight. The mixture was then washed with sat. K₂CO₃ solution (2×10 mL) and water (10 mL). The organic phase was dried over Na₂SO₄, filtered and concentrated under reduced pressure. The residue was purifed by column chromatography (eluting with PE:EA=3:1) to give 3-((2-(tert-butyl)-6-chlorobenzo[d]oxazol-7-yl)sulfonyl)cyclohexanone (900 mg) as a light yellow gel. MS(ES⁺) m/z 370 (MH⁺).

Step 3: To a solution of 3-((2-(tert-butyl)-6-chlorobenzo[d]oxazol-7-yl)sulfonyl)cyclohexanone (900 mg) in THF (30 mL) at −78° C. was slowly added L-selectride (1 M in THF, 4.4 mL) with a syringe, and stirred under a nitrogen atmosphere at −78° C. for 2 hours. The resulting mixture was then allowed to warm to RT and stirred for another 18 hours. Water (10 mL) was carefully added. The pH was adjusted to pH=6 with aq. HCl solution (4 M). The mixture was extracted with EA (2×25 mL). The organic layers were washed with brine (2×15 mL), dried over Na₂SO₄, filtered and concentrated under reduced pressure. The residue was combined another batch of the same reaction using 3-((2-(tert-butyl)-6-chlorobenzo[d]oxazol-7-yl)sulfonyl)cyclohexanone (170 mg) as starting material. The combined mixture was purified by column chromatography (eluting with PE:EA=3:1) to give (±)trans-3-((2-(tert-butyl)-6-chlorobenzo[d]oxazol-7-yl)sulfonyl)cyclohexanol (350 mg) as a colorless gel. MS(ES⁺) m/z 372 (MH⁺).

Step 4: (±)Trans-3-((2-(tert-butyl)-6-chlorobenzo[d]oxazol-7-yl)sulfonyl)cyclohexanol (270 mg) was dissolved in 1,4-dioxane (2 mL), and then conc. HCl solution (2.2 mL)

was added. The mixture was heated to 100° C. for 3 hours to give a brown solution. The reaction mixture was cooled to RT and evaporated under reduced pressure. The residue was then treated with sat. NaHCO₃ solution until pH=8 in an ice bath. The mixture was extracted with DCM (5×20 mL). The combined organic layers were dried over sodium sulfate, filtered and concentrated to give the title compound (200 mg) as a brown solid. MS(ES⁺) m/z 305 (MH⁺).

Intermediate 40: (±)trans-6-amino-3-chloro-2-((2-hydroxycyclopentyl)sulfonyl)phenol

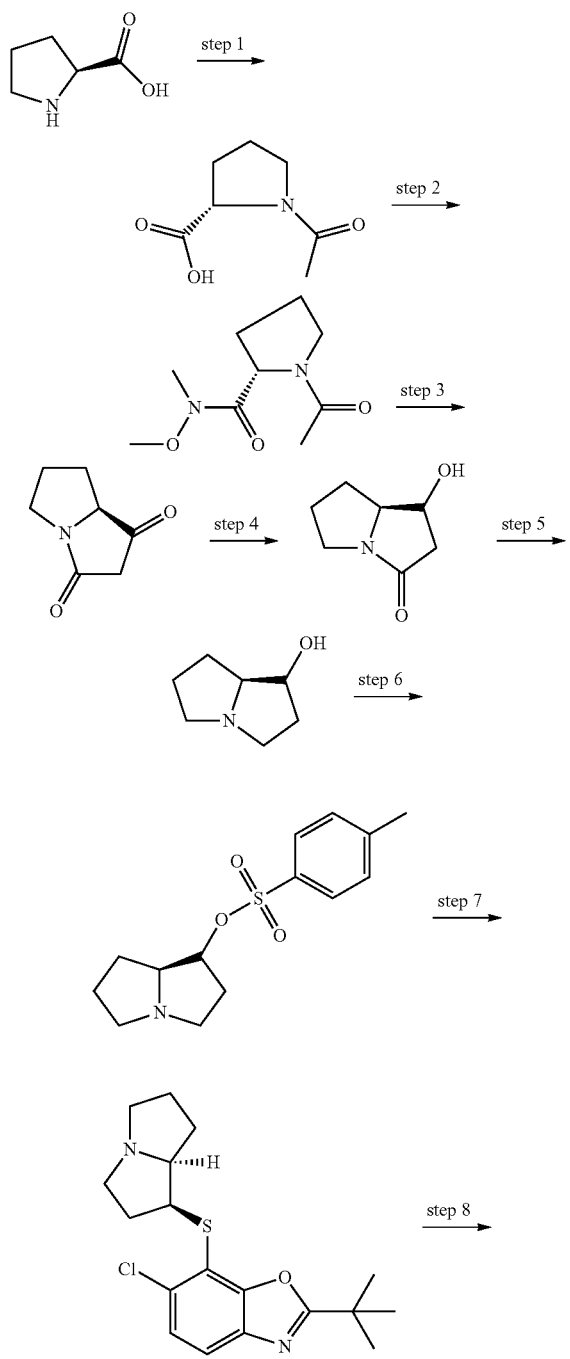

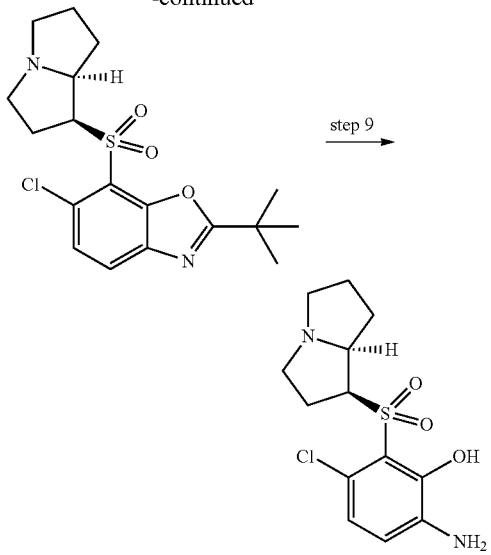

Step 1: To a solution of (S)-pyrrolidine-2-carboxylic acid (1.0 g) in DCM (20 mL) was added acetic anhydride (2.7 g). The resulting mixture was stirred at 30° C. overnight and concentrated in vacuo. Cold water (30 mL) was added, and the aqueous layer was extracted with DCM (2×100 mL). The combined organic layers were dried over Na₂SO₄, filtered and concentrated in vacuo. The residue was purified by preparative HPLC to give (S)-1-acetylpyrrolidine-2-carboxylic acid (500 mg) as a white solid. MS(ES⁺) m/z 158 (MH⁺).

Step 2: To a solution of (S)-1-acetylpyrrolidine-2-carboxylic acid (10.0 g) and 4-methylmorpholine (12.9 g) in DCM (100 mL) was dropwise added isobutyl carbonochloridate (9.6 g) at RT. After 20 mins, N,O-dimethylhydroxylamine, hydrochloride (9.3 g) was added. The mixture was stirred overnight, and then concentrated in vacuo. Brine (50 mL) was added and the aq. layer was extracted with DCM (3×50 mL). The combined organic layers were dried over Na₂SO₄, filtered and concentrated in vacuo. The residue was purified by column chromatography (eluting with DCM:methanol=20:1) to give (S)-1-acetyl-N-methoxy-N-methylpyrrolidine-2-carboxamide (8.1 g) as a colorless oil. MS(ES⁺) m/z 201 (MH⁺).

Step 3: To a solution of (S)-1-acetyl-N-methoxy-N-methylpyrrolidine-2-carboxamide (8.0 g) in THF (10 mL) was added LiHMDS (1 M in THF, 80 mL) dropwise at −78° C. After 2 hours, aq. HCl solution (1 M, 5 mL) was added dropwise, and the mixture was warmed to ambient temperature. The aq. layer was extracted with EA (3×50 mL). The combined organic layers were dried over Na₂SO₄, filtered and concentrated in vacuo to give (S)-tetrahydro-1H-pyrrolizine-1,3(2H)-dione (6.0 g) as a colorless oil.

Step 4: To a solution of (S)-tetrahydro-1H-pyrrolizine-1,3(2H)-dione (7.0 g) in ethanol (3 mL) and DCM (3 mL) was added sodium borohydride (1.6 g). The reaction mixture was stirred overnight. Cold water (10 mL) was added and the resulting mixture was extracted with EA (2×50 mL). The combined organic layers were dried over Na₂SO₄, filtered and concentrated in vacuo to give (1R,7aS)-1-hydroxytetrahydro-1H-pyrrolizin-3(2H)-one (2.7 g) as a light yellow oil.

Step 5: To a solution of (1R,7aS)-1-hydroxytetrahydro-1H-pyrrolizin-3(2H)-one (3.2 g) in THF (50 mL) was added LiAlH₄ (0.9 g). The reaction mixture was heated to reflux for 4 hours. After cooling to RT, water (50 mL) was added dropwise and stirred at RT for 1 hour. The solid was filtered and the organic layer was concentrated. The residue was purified by column chromatography (eluting with DCM: MeOH=10:1) to give (1R,7aS)-hexahydro-1H-pyrrolizin-1-ol (1.5 g) as a yellow oil. MS(ES⁺) m/z 128 (MH⁺).

Step 6: To a solution of (1R,7aS)-hexahydro-1H-pyrrolizin-1-ol (1.8 g) and DIPEA (1.8 g) in THF (50 mL) was added 4-methylbenzene-1-sulfonyl chloride (2.7 g). The reaction mixture was stirred at RT overnight. After cooling to RT, water (50 mL) was added dropwise. The aqueous layer was extracted with DCM (2×100 mL). The combined organic layers were dried over Na₂SO₄, filtered and concentrated in vacuo to give (1R,7aS)-hexahydro-1H-pyrrolizin-1-yl 4-methylbenzenesulfonate (1.1 g) as a yellow oil. MS(ES⁺) m/z 282 (MH⁺).

Step 7: A solution of (1R,7aS)-hexahydro-1H-pyrrolizin-1-yl 4-methylbenzenesulfonate (1.1 g) and sodium 2-(tert-butyl)-6-chlorobenzo[d]oxazole-7-thiolate (421 mg) in DMF (10 mL) was stirred at 50° C. overnight. Cold water (30 mL) was added. The resulting mixture was neutralized with sat. NaHCO₃ solution. The aq. layer was extracted with DCM (2×100 mL). The combined organic layers were dried over Na₂SO₄, filtered and concentrated in vacuo. The residue was purified by column chromatography (eluting with PE:EA=1:1) to give 2-(tert-butyl)-6-chloro-7-(((1S,7aS)-hexahydro-1H-pyrrolizin-1-yl)thio)benzo[d]oxazole (500 mg) as a yellow oil. MS(ES⁺) m/z 282 (MH⁺). MS(ES⁺) m/z 351 (MH⁺).

Step 8: A solution of 2-(tert-butyl)-6-chloro-7-(((1S,7aS)-hexahydro-1H-pyrrolizin-1-yl)thio)benzo[d]oxazole (500 mg), sodium tungstate dehydrate (470 mg) and aq. H₂O₂ solution (30%, 1 mL) in methanol (10 mL) was stirred at RT for 12 hours. Cold water (30 mL) was added. The resulting mixture was neutralized with sat. NaHCO₃ solution. The aq. layer was extracted with DCM (2×100 mL). The combined organic layers were dried over Na₂SO₄, filtered and concentrated in vacuo. The residue was purified by reversed phase chromatography (eluting with 0.01% CF₃COOH/H₂O, CH₃OH, 30 mL/min) (10%~55%, 5 min; 55~55%, 6 min; 40%~95%, 1 min; 95%~95%, 1 min) to give 2-(tert-butyl)-6-chloro-7-(((1S,7aS)-hexahydro-1H-pyrrolizin-1-yl)sulfonyl)benzo[d]oxazole (130 mg) as a yellow oil. MS(ES⁺) m/z 383 (MH⁺).

Step 9: A solution of 2-(tert-butyl)-6-chloro-7-(((1S,7aS)-hexahydro-1H-pyrrolizin-1-yl)sulfonyl)benzo[d]oxazole (130 mg) in sulfuric acid (65%, 2 mL) and dioxane (4 mL) was stirred at 90° C. for 4 hours. The reaction mixture was purified by reversed phase chromatography (mobile phase 0.01% CF₃COOH/H₂O, CH₃OH, 30 mL/min) (10%~55%, 5 min; 55~55%, 6 min; 40%~95%, 1 min; 95%~95%, 1 min) to give the title compound (100 mg) as a yellow solid. MS(ES⁺) m/z 317 (MH⁺).

Intermediate 41: 6-amino-3-chloro-2-(((3S,4R)-3-fluorotetrahydro-2H-pyran-4-yl)sulfonyl)phenol

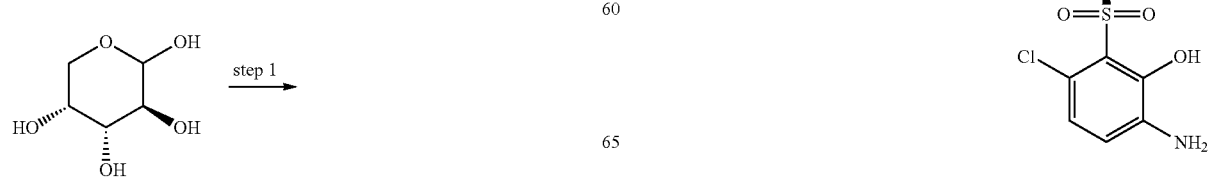

Step 1: A mixture of (3S,4R,5R)-tetrahydro-2H-pyran-2,3,4,5-tetraol (50.0 g) and DMAP (4.1 g) in pyridine (1000 mL) and Ac$_2$O (500 mL) was stirred at 28° C. for 18 hours. The mixture was concentrated, and then dissolved in toluene (200 mL). The mixture was washes with aq. HCl solution (1 M, 2×100 mL), dried and concentrated to afford (3S,4R,5R)-tetrahydro-2H-pyran-2,3,4,5-tetrayl tetraacetate (92.0 g).

Step 2: To a solution of (3S,4R,5R)-tetrahydro-2H-pyran-2,3,4,5-tetrayl tetraacetate (60.0 g) in DCM (600 mL) was added tribromophosphine (28.6 mL) and water (20.4 mL) at 0° C. The reaction mixture was stirred at 25° C. for 2 hours, and then quenched with water (500 mL). The mixture was extracted with DCM (3×200 mL). The combined organic phases were washed with aq. NaHCO$_3$ solution (2×300 mL), dried and concentrated to afford (3S,4R,5R)-2-bromotetrahydro-2H-pyran-3,4,5-triyl triacetate (58.0 g).

Step 3: To a solution of (3S,4R,5R)-2-bromotetrahydro-2H-pyran-3,4,5-triyl triacetate (58.7 g) in acetic acid (880 mL) was added copper(II) sulfate, 5H$_2$O (11.7 g) in water (100 mL) and zinc (113 g) at 0° C. The reaction mixture was stirred at 0° C. for 1 hour. DCM (200 mL) was added. After filtration, the mixture was extracted with DCM (2×400 mL). The combined organic phases were dried and concentrated. The residue was purified by column chromatography (eluting with PE:EA=10:1) to afford (3R,4S)-3,4-dihydro-2H-pyran-3,4-diyl diacetate (28.0 g).

Step 4: A solution of (3R,4S)-3,4-dihydro-2H-pyran-3,4-diyl diacetate (23.0 g) in methanol was hydrogenated using H-cube (settings: 20° C., 50 psi) and 17.5 g of 10% Pd/C as the catalyst. The mixture was filtered and concentrated to afford (3R,4S)-tetrahydro-2H-pyran-3,4-diyl diacetate (19.0 g).

Step 5: A mixture of (3R,4S)-tetrahydro-2H-pyran-3,4-diyl diacetate (19.0 g) and sodium methoxide (20.3 g) in methanol (190 mL) was stirred at 17° C. for 18 hours, and then quenched with aq. HCl solution (1 M, 10 mL). The mixture was concentrated and treated with EA (3×300 mL) at 45° C. for 30 mins. The combined organic phases were washed with sat. NaHCO$_3$ solution (500 mL), dried and concentrated to afford (3R,4S)-tetrahydro-2H-pyran-3,4-diol (8.0 g).

Step 6: To a mixture of (3R,4S)-tetrahydro-2H-pyran-3,4-diol (8.7 g) in pyridine (90 ml) was added 4-methylbenzene-1-sulfonyl chloride (14.0 g) at 0° C. The mixture was stirred at 15° C. for 8 hours. The mixture was quenched with aq. HCl solution (6 M), and then extracted with DCM (3×100 mL). The combined organic phases were dried and concentrated to afford (3R,4S)-3-hydroxytetrahydro-2H-pyran-4-yl 4-methylbenzenesulfonate (11.0 g).

Step 7: To a solution of DAST (10.9 mL) in DCM (100 mL) was added a solution of (3R,4S)-3-hydroxytetrahydro-2H-pyran-4-yl 4-methylbenzenesulfonate (4.5 g) in DCM (50 mL) dropwise at −30° C. The mixture was stirred at −30° C. for 30 mins, and then stirred at RT overnight. The mixture was quenched with MeOH, and then concentrated. The residue was purified by column chromatography (eluting with EA:PE=1:4) to give (3S,4S)-3-fluorotetrahydro-2H-pyran-4-yl 4-methylbenzenesulfonate (850 mg) as a colorless oil. MS(ES$^+$) m/z 275 (MH$^+$).

Step 8: A mixture of (3S,4S)-3-fluorotetrahydro-2H-pyran-4-yl 4-methylbenzenesulfonate (800 mg), sodium 2-(tert-butyl)-6-chlorobenzo[d]oxazole-7-thiolate (923 mg), Cs$_2$CO$_3$ (665 mg) and acetonitrile (50 mL) was stirred at 100° C. for 6 hours. The mixture was filtered and concentrated. The residue was purified by column chromatography (eluting with EA:PE=1:10) to give 2-(tert-butyl)-6-chloro-7-(((3S,4R)-3-fluorotetrahydro-2H-pyran-4-yl)thio)benzo[d]oxazole (750 mg) as a colorless oil, which was solidified after a day. MS(ES$^+$) m/z 344 (MH$^+$).

Step 9: A mixture of 2-(tert-butyl)-6-chloro-7-(((3S,4R)-3-fluorotetrahydro-2H-pyran-4-yl)thio)benzo[d]oxazole (500 mg) and mCPBA (753 mg) in DCM (20 mL) was stirred at 15° C. for 12 hours. The mixture was quenched with NaHSO$_3$ solution. The organic phase was washed with aq. NaOH solution (1 M), dried and concentrated to give 2-(tert-butyl)-6-chloro-7-(((3S,4R)-3-fluorotetrahydro-2H-pyran-4-yl)sulfonyl)benzo[d]oxazole (520 mg) as a colorless oil, which was solidified after a day. MS(ES$^+$) m/z 376 (MH$^+$).

Step 10: A solution of 2-(tert-butyl)-6-chloro-7-(((3S,4R)-3-fluorotetrahydro-2H-pyran-4-yl)sulfonyl)benzo[d]oxazole (500 mg) in 1,4-dioxane (9 mL) and water (9 mL) was stirred at 100° C. for 12 hours. The solvent was removed and the mixture was neutralized by aq. NaOH solution. After concentration, the residue was purified by preparative HPLC to give the title compound (106 mg) as a white solid. MS(ES$^+$) m/z 310 (MH$^+$).

Intermediate 42: (R)-6-amino-3-chloro-2-((2-(tetrahydrofuran-3-yl)propan-2-yl)sulfonyl)phenol

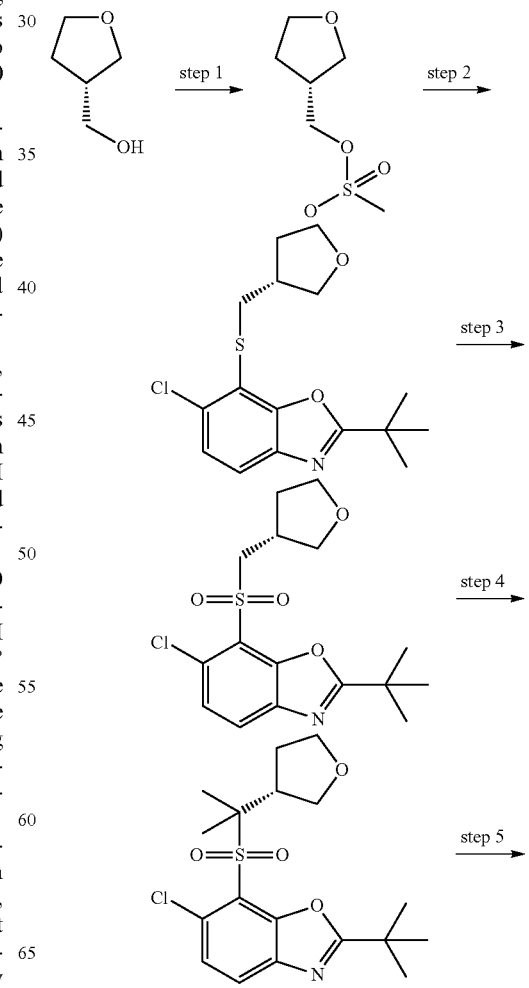

-continued

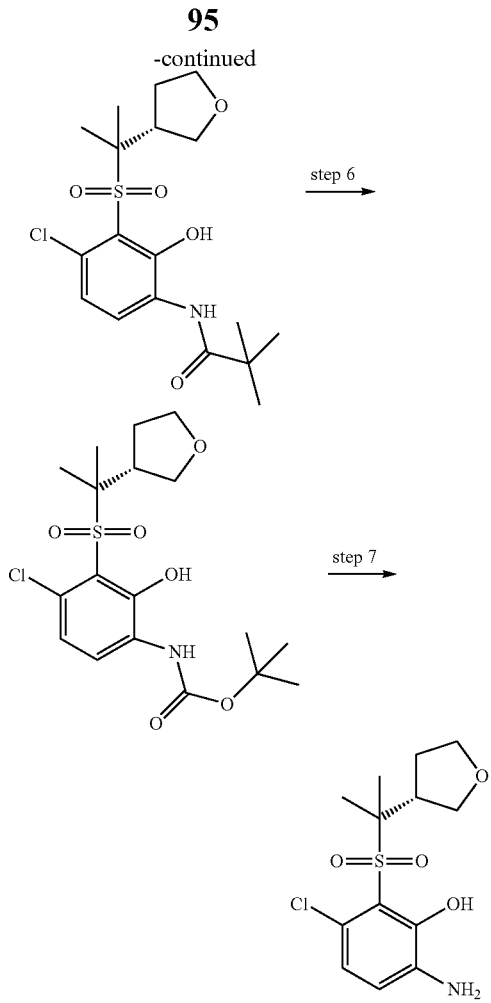

Step 1: To an ice-water cooled (0° C.) solution of (S)-(tetrahydrofuran-3-yl)methanol (1.0 g) in DCM (50 mL) was added TEA (2.7 mL) and MsCl (1.1 mL). The mixture was stirred at 0° C. for 3 hours, and then quenched with aq. NaHCO$_3$ solution. The resulting mixture was extracted with EA (3×100 mL). The combined organic phases were washed, dried and concentrated to afford (R)-(tetrahydrofuran-3-yl)methyl methanesulfonate (1.7 g).

Step 2: To a solution of sodium 2-(tert-butyl)-6-chlorobenzo[d]oxazole-7-thiolate (3.0 g) in DMF (100 mL) was added (R)-(tetrahydrofuran-3-yl)methyl methanesulfonate (1.7 g) and K$_2$CO$_3$ (2.0 g). The resulting reaction mixture was stirred at 80° C. overnight. After cooling, the mixture was poured into water (500 mL) and extracted with EA (2×150 mL). The combined organic phases were washed, dried and concentrated to afford (R)-2-(tert-butyl)-6-chloro-7-(((tetrahydrofuran-3-yl)methyl)thio)benzo[d]oxazole (1.8 g). MS(ES$^+$) m/z 326 (MH$^+$).

Step 3: To an ice-water cooled solution of (R)-2-(tert-butyl)-6-chloro-7-(((tetrahydrofuran-3-yl)methyl)thio)benzo[d]oxazole (1.8 g) in DCM (50 mL) was added mCPBA (2.7 g). The resulting mixture was warmed up slowly and stirred at RT overnight. After completion of the reaction, the mixture was quenched with aq. NaHCO$_3$ solution and aq. Na$_2$S$_2$O$_3$ solution. The resulting mixture was extracted with EA (2×150 mL). The combined organic phases were washed, dried and concentrated to afford (R)-2-(tert-butyl)-6-chloro-7-(((tetrahydrofuran-3-yl)methyl)sulfonyl)benzo[d]oxazole (1.9 g). MS(ES$^+$) m/z 358 (MH$^+$).

Step 4: To a dry ice-ethanol cooled solution of (R)-2-(tert-butyl)-6-chloro-7-(((tetrahydrofuran-3-yl)methyl)sulfonyl)benzo[d]oxazole (1.9 g) and MeI (0.7 mL) in THF (50 mL) was added LiHMDS (1 M in THF, 13.3 mL). The resulting mixture was warmed up slowly and stirred at RT for 30 mins. After completion of the reaction, the mixture was quenched with aq. NH$_4$Cl solution. The mixture was extracted with EA (2×150 mL). The combined organic phases were washed, dried and concentrated to afford (R)-2-(tert-butyl)-6-chloro-7-((2-(tetrahydrofuran-3-yl) propan-2-yl)sulfonyl)benzo[d]oxazole (2.0 g). MS(ES$^+$) m/z 386 (MH$^+$).

Step 5: To a solution of (R)-2-(tert-butyl)-6-chloro-7-((2-(tetrahydrofuran-3-yl)propan-2-yl)sulfonyl)benzo[d]oxazole (2.0 g) in ethanol (25 mL) and water (25 mL) was added NaOH (1.0 g). The resulting mixture was stirred at 60° C. for 3 hours, and then concentrated. The residue was dissolved in water (50 mL) and acidified with aq. citric acid to pH=6. The mixture was extracted with EA (2×50 mL). The combined organic phases were washed, dried and concentrated to afford (R)—N-(4-chloro-2-hydroxy-3-((2-(tetrahydrofuran-3-yl)propan-2-yl)sulfonyl)phenyl)pivalamide (2.0 g). MS(ES$^+$) m/z 404 (MH$^+$).

Step 6: To a solution of (R)—N-(4-chloro-2-hydroxy-3-((2-(tetrahydrofuran-3-yl)propan-2-yl)sulfonyl)phenyl) pivalamide (2.0 g) in THF (50 mL) was added di-tert-butyl dicarbonate (2.3 mL) and DMAP (0.06 g). The resulting mixture was stirred at 60° C. for 4 hours. After cooling, hydrazine (0.8 g) was added. The mixture was stirred at RT overnight. The mixture was diluted with water (100 mL), and extracted with EA (2×100 mL). The combined organic layers were washed, dried and concentrated. The residue was purified with column chromatography (eluting with 0-30% EA in PE) to afford (R)-tert-butyl (4-chloro-2-hydroxy-3-((2-(tetrahydrofuran-3-yl)propan-2-yl)sulfonyl) phenyl)carbamate (1.0 g). MS(ES$^+$) m/z 442 (MNa$^+$).

Step 7: To a solution of (R)-tert-butyl (4-chloro-2-hydroxy-3-((2-(tetrahydrofuran-3-yl)propan-2-yl)sulfonyl) phenyl)carbamate (1.0 g) in DCM (30 mL) was added TFA (1.8 mL). The resulting mixture was stirred at RT overnight. Water (50 mL) was added. The mixture was basified with aq. NaHCO$_3$ solution carefully, and extracted with EA (2×50 mL). The combined organic phases were washed, dried and concentaretd to afford the title compound (0.7 g). MS(ES$^+$) m/z 342 (MNa$^+$).

Intermediate 43: (S)-6-amino-3-chloro-2-((2-(tetrahydrofuran-3-yl)propan-2-yl)sulfonyl)phenol

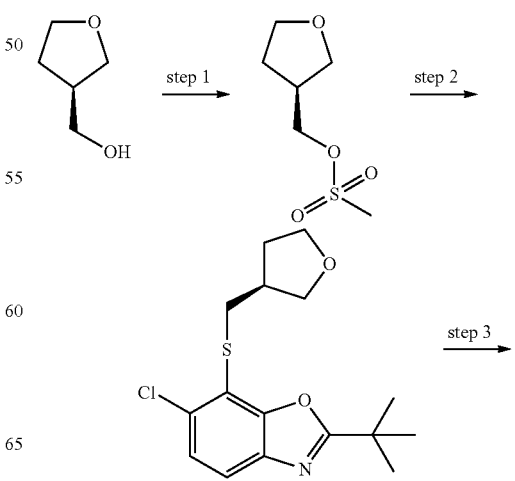

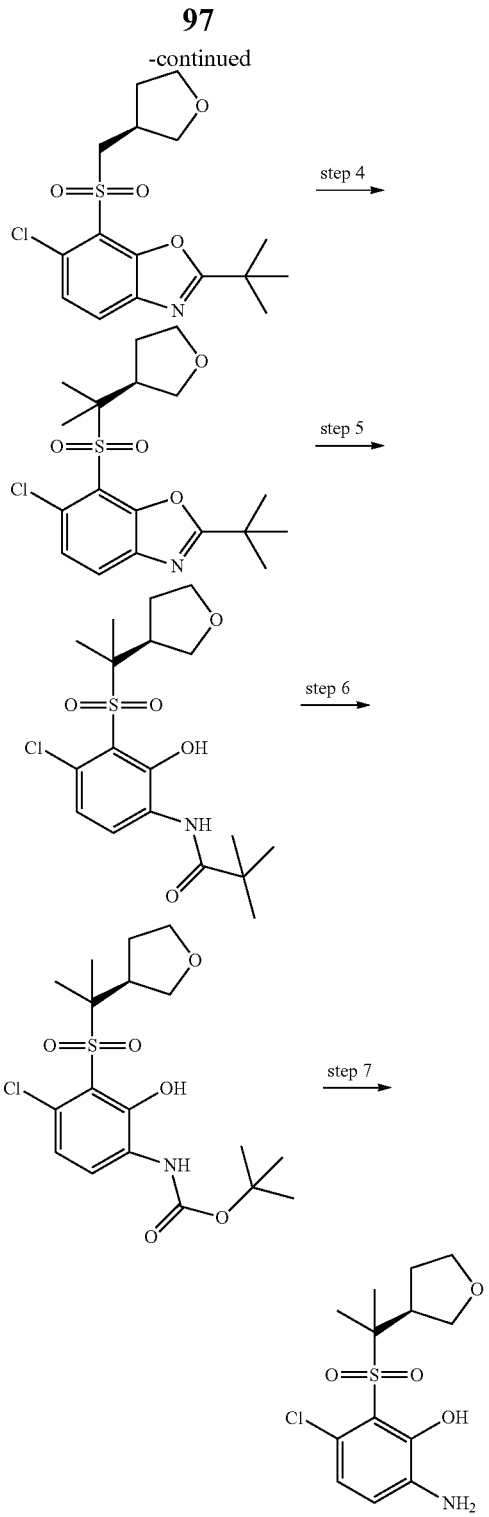

Step 1: To an ice-water cooled (0° C.) solution of (R)-(tetrahydrofuran-3-yl)methanol (1.0 g) in DCM (50 mL) was added TEA (2.7 mL) and MsCl (1.1 mL). The resulting mixture was stirred at 0° C. for 3 hours, and then quenched with aq. NaHCO₃ solution. The mixture was extracted with EA (2×100 mL). The combined organic phases were washed, dried and concentrated to afford (S)-(tetrahydrofuran-3-yl)methyl methanesulfonate (1.5 g).

Step 2: To a solution of sodium 2-(tert-butyl)-6-chlorobenzo[d]oxazole-7-thiolate (2.6 g) in DMF (100 mL) was added (S)-(tetrahydrofuran-3-yl)methyl methanesulfonate (1.5 g) and K₂CO₃ (1.7 g). The resulting mixture was stirred at 80° C. overnight. After cooling, the mixture was poured into water (500 mL), and extracted with EA (2×150 mL). The combined organic phases were washed, dried and concentrated to afford (S)-2-(tert-butyl)-6-chloro-7-(((tetrahydrofuran-3-yl)methyl)thio)benzo[d]oxazole (2.5 g). MS(ES⁺) m/z 326 (MH⁺).

Step 3: To an ice-water cooled solution of (S)-2-(tert-butyl)-6-chloro-7-(((tetrahydrofuran-3-yl)methyl)thio)benzo[d]oxazole (2.5 g) in DCM (50 mL) was added mCPBA (2.9 g). The resulting mixture was warmed up slowly and stirred at RT overnight. After completion of the reaction, the mixture was quenched with aq. NaHCO₃ solution and aq. Na₂S₂O₃ solution, and then extracted with EA (2×150 mL). The combined organic layers were washed, dried and concentrated to afford (S)-2-(tert-butyl)-6-chloro-7-(((tetrahydrofuran-3-yl)methyl)sulfonyl)benzo[d]oxazole (2.7 g). MS(ES⁺) m/z 358 (MH⁺).

Step 4: To a dry ice-ethanol cooled solution of (S)-2-(tert-butyl)-6-chloro-7-(((tetrahydrofuran-3-yl)methyl)sulfonyl)benzo[d]oxazole (2.7 g) in THF (100 mL) was added MeI (1.0 mL) and LiHMDS (1 M in THF, 16.6 mL). The resulting mixture was warmed up slowly and stirred at RT for 30 mins. After completion of the reaction, the mixture was quenched with aq. NH₄Cl solution, and then extracted with EA (2×150 mL). The combined organic phases were washed, dried and concentrated to afford (S)-2-(tert-butyl)-6-chloro-7-((2-(tetrahydrofuran-3-yl)propan-2-yl)sulfonyl)benzo[d]oxazole (2.8 g), which was used in the next step without purification. MS(ES⁺) m/z 386 (MH⁺).

Step 5: To a solution of (S)-2-(tert-butyl)-6-chloro-7-((2-(tetrahydrofuran-3-yl)propan-2-yl)sulfonyl)benzo[d]oxazole (2.8 g) in ethanol (25 mL) and water (25 mL) was added NaOH (1.5 g). The resulting mixture was stirred at 60° C. for 3 hours. After the mixture was concentrated, the residue was dissolved in water (50 mL). The mixture was acidified with aq. citric acid to pH=6, and then extracted with EA (2×100 mL). The combined organic layers were washed, dried and concentrated to afford (S)—N-(4-chloro-2-hydroxy-3-((2-(tetrahydrofuran-3-yl)propan-2-yl)sulfonyl)phenyl)pivalamide (2.5 g). MS(ES⁺) m/z 404 (MH⁺).

Step 6: To a solution of (S)—N-(4-chloro-2-hydroxy-3-((2-(tetrahydrofuran-3-yl)propan-2-yl)sulfonyl)phenyl)pivalamide (2.5 g) in THF (50 mL) was added di-tert-butyl dicarbonate (2.9 mL) and DMAP (0.08 g). The resulting mixture was stirred at 60° C. for 4 hours. After cooling, hydrazine (1.0 g) was added. The mixture was stirred at RT overnight, and then diluted with water (100 mL). The resulting mixture was extracted with EA (2×100 mL). The combined organic layers were washed, dried and concentrated. The residue was purified with column chromatography (eluting with 0-30% EA in PE) to afford (S)-tert-butyl (4-chloro-2-hydroxy-3-((2-(tetrahydrofuran-3-yl)propan-2-yl)sulfonyl)phenyl)carbamate (1.0 g). MS(ES⁺) m/z 442 (MNa⁺).

Step 7: To a solution of (S)-tert-butyl (4-chloro-2-hydroxy-3-((2-(tetrahydrofuran-3-yl)propan-2-yl)sulfonyl)phenyl)carbamate (1.0 g) in DCM (25 mL) was added TFA (1.8 mL). The resulting mixture was stirred at RT overnight. Water (50 mL) was added. The mixture was basified with aq. NaHCO₃ solution carefully, and extracted with EA (2×50 mL). The combined organic phases were washed, dried and concentrated to afford the title compound (0.5 g). MS(ES⁺) m/z 342 (MNa⁺).

Intermediate 44:
6-amino-2-(tert-butylsulfonyl)-3-chlorophenol

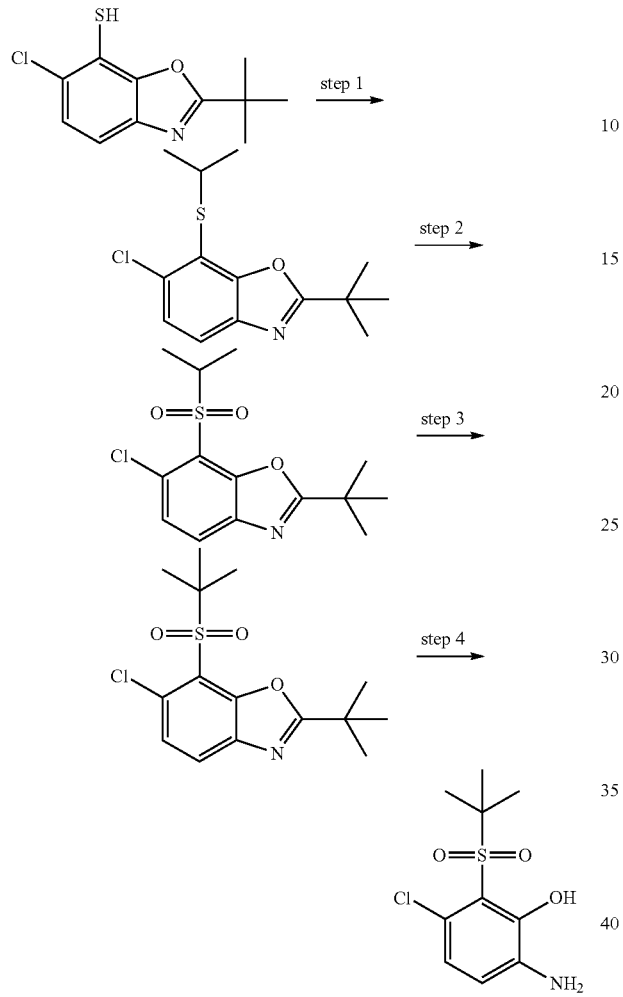

Step 1: To a solution of 2-(tert-butyl)-6-chlorobenzo[d]oxazole-7-thiol (3.0 g) in DMF (30 mL) was added 2-iodopropane (2.1 g). The mixture was stirred at 100° C. for 2 hours. After cooling, the solvent was removed. The residue was purified by column chromatography to give 2-(tert-butyl)-6-chloro-7-(isopropylthio)benzo[d]oxazole (3.5 g).

Step 2: To a solution of 2-(tert-butyl)-6-chloro-7-(isopropylthio)benzo[d]oxazole (3.5 g) in DCM (40 mL) was added mCPBA (5.3 g) at 15° C. The mixture was stirred at 15° C. for 48 hours, and then quenched with sat. Na$_2$SO$_3$ solution. The organic layer was dried over Na$_2$SO$_4$, filtered and concentrated. The residue was purified by column chromatography to afford 2-(tert-butyl)-6-chloro-7-(isopropylsulfonyl)benzo[d]oxazole (3.6 g). MS(ES$^+$) m/z 316 (MH$^+$).

Step 3: To a solution of 2-(tert-butyl)-6-chloro-7-(isopropylsulfonyl)benzo[d]oxazole (3.0 g) in THF (10 mL) was added LiHMDS (1 M in THF, 31.7 mL). The mixture was stirred at −78° C. for 10 mins, and then iodomethane (6.74 g) was added. The mixture was stirred at −78° C. for 10 mins, and then quenched with aq. NH$_4$Cl solution and aq. HCl solution (10%). The mixture was extracted with EA. The organic layer was washed with brine, dried over Na$_2$SO$_4$ and concentrated. The crude product was purified by column chromatography to afford 2-(tert-butyl)-7-(tert-butylsulfonyl)-6-chlorobenzo[d]oxazole (2.8 g). MS(ES$^+$) m/z 330 (MH$^+$).

Step 4: To a solution of 2-(tert-butyl)-7-(tert-butylsulfonyl)-6-chlorobenzo[d]oxazole (2.7 g) in 1,4-dioxane (10 mL) was added conc. HCl solution (3 mL) at 60° C. The mixture was stirred at this temperature for 16 hours. The mixture was concentrated, and then dissolved in DCM. The pH was adjusted to ~9. The resulting mixture was concentrated. The residue was purified by preparative HPLC (acid condition with TFA) to afford the title compound (430 mg). MS(ES$^+$) m/z 263 (MH$^+$).

Intermediate 45: 6-amino-3-chloro-2-((2-(tetrahydrofuran-3-yl)propan-2-yl)sulfonyl)phenol

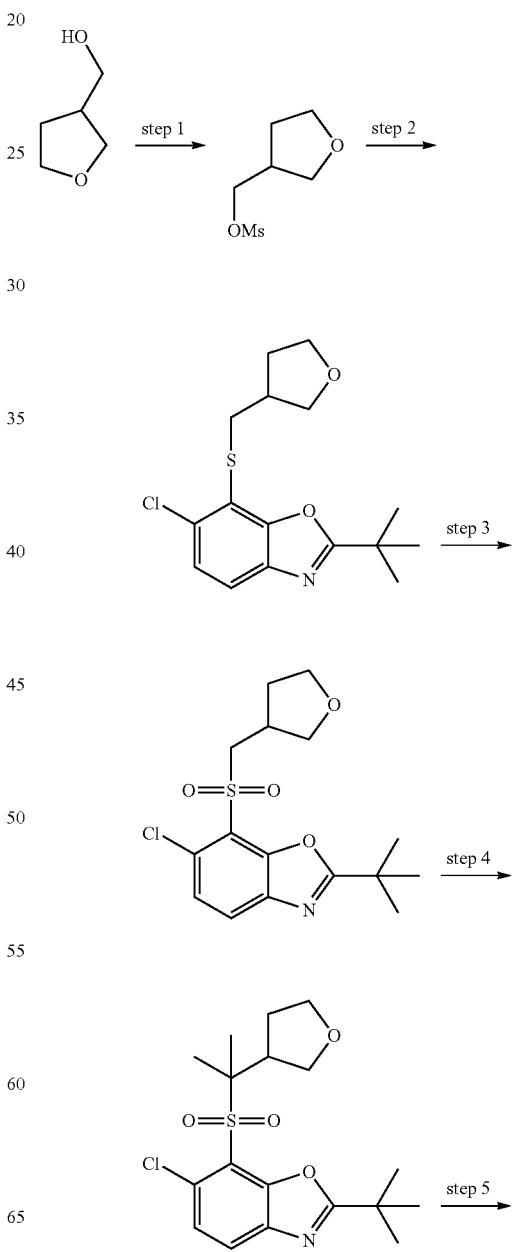

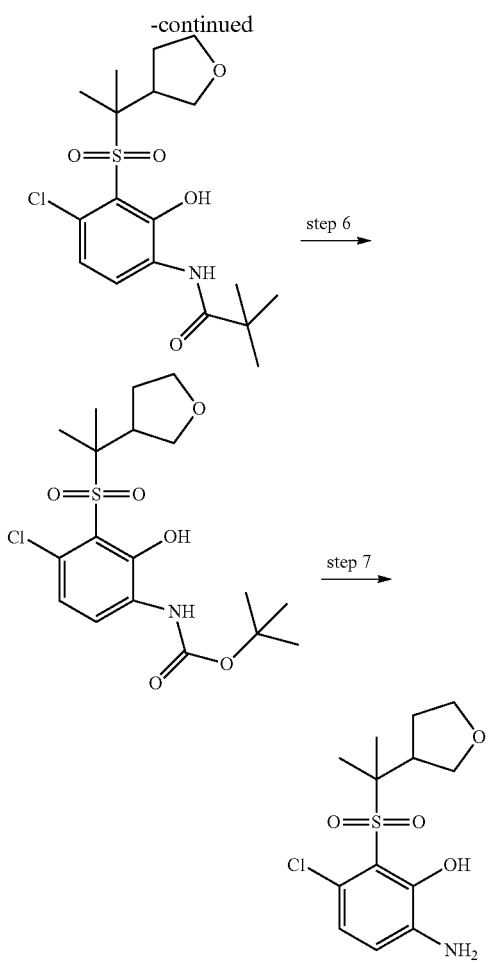

Step 1: To an ice-water cooled solution of (tetrahydrofuran-3-yl)methanol (2.0 g) in DCM (50 mL) was added TEA (5.5 mL) and then MsCl (2.3 mL) dropwise. The resulting mixture was warmed up slowly and stirred at RT for 2 hours. The mixture was quenched with aq. NaHCO$_3$ solution, extracted with EA (3×100 mL). The combined organic layers were washed, dried and concentrated to afford (tetrahydrofuran-3-yl)methyl methanesulfonate (3.2 g).

Step 2: To a solution of sodium 2-(tert-butyl)-6-chlorobenzo[d]oxazole-7-thiolate (4.5 g) and (tetrahydrofuran-3-yl)methyl methanesulfonate (3.1 g) in DMF (50 mL) was added potassium carbonate (2.4 g). The resulting mixture was stirred at 80° C. overnight. After cooling, the mixture was poured into water, extracted with EA (2×100 mL). The combined organic layers were washed, dried and concentrated to afford 2-(tert-butyl)-6-chloro-7-(((tetrahydrofuran-3-yl)methyl)thio)benzo[d]oxazole (5.0 g). MS(ES$^+$) m/z 326 (MH$^+$).

Step 3: To an ice-water cooled solution of 2-(tert-butyl)-6-chloro-7-(((tetrahydrofuran-3-yl)methyl)thio)benzo[d]oxazole (5.0 g) in DCM (50 mL) was added mCPBA (9.5 g). The resulting mixture was warmed up slowly and stirred at RT overnight. The mixture was quenched with aq. NH$_4$Cl solution, and extracted with EA (2×100 mL). The combined organic phases were washed, dried and concentrated. The residue was purified by column chromatography (eluting with 0-30% EA in PE) to afford 2-(tert-butyl)-6-chloro-7-(((tetrahydrofuran-3-yl)methyl)sulfonyl)benzo[d]oxazole (3.6 g). MS(ES$^+$) m/z 358 (MH$^+$).

Step 4: To a cooled (−70° C.) solution of 2-(tert-butyl)-6-chloro-7-(((tetrahydrofuran-3-yl)methyl)sulfonyl)benzo[d]oxazole (1.2 g) and MeI (0.4 mL) in THF (50 mL) was added LiHMDS (1 M in THF, 8.4 mL). The resulting mixture was warmed up slowly, and stirred at RT for 30 mins. The mixture was quenched with aq. NH$_4$Cl solution, extracted with EA (2×100 mL). The combined organic phases were washed, dried and concentrated to afford 2-(tert-butyl)-6-chloro-7-((2-(tetrahydrofuran-3-yl)propan-2-yl)sulfonyl)benzo[d]oxazole (1.2 g). MS(ES$^+$) m/z 386 (MH$^+$).

Step 5: To a solution of 2-(tert-butyl)-6-chloro-7-((2-(tetrahydrofuran-3-yl)propan-2-yl)sulfonyl)benzo[d]oxazole (1.2 g) in ethanol (15 mL) and water (15 mL) was added sodium hydroxide (0.6 g). The resulting mixture was stirred at 60° C. for 3 hours. The solvent was removed. The residue was diluted with water (50 mL), acidified with aq. citric acid to pH=6, and then extracted with EA (2×50 mL). The combined organic phases were washed, dried and concentrated to afford N-(4-chloro-2-hydroxy-3-((2-(tetrahydrofuran-3-yl)propan-2-yl)sulfonyl)phenyl)pivalamide (1.2 g). MS(ES$^+$) m/z 404 (MH$^+$).

Step 6: To a solution of N-(4-chloro-2-hydroxy-3-((2-(tetrahydrofuran-3-yl)propan-2-yl)sulfonyl)phenyl)pivalamide (1.2 g) in THF (10 mL) was added Boc$_2$O (1.4 mL) and DMAP (0.04 g). The resulting mixture was stirred at 50° C. overnight. The mixture was diluted with water (10 mL). To the mixture was added hydrazine (0.5 g). The resulting mixture was stirred for 5 hours, diluted with water (100 mL), and then extracted with EA (2×100 mL). The combined organic phases were washed, dried and concentrated. The residue was purified by column chromatography (eluting with 0-30% EA in PE) to afford tert-butyl (4-chloro-2-hydroxy-3-((2-(tetrahydrofuran-3-yl)propan-2-yl)sulfonyl)phenyl)carbamate (0.9 g). MS(ES$^+$) m/z 442 (MNa$^+$).

Step 7: To a solution of tert-butyl (4-chloro-2-hydroxy-3-((2-(tetrahydrofuran-3-yl)propan-2-yl)sulfonyl)phenyl)carbamate (0.9 g) in DCM (20 mL) was added TFA (1.7 mL). The resulting mixture was stirred at RT overnight. The mixture was basified with aq. NaHCO$_3$ solution to pH=8, and then extracted with EA (2×50 mL). The combined organic phases were washed, dried and concentrated to afford the title compound (0.6 g). MS(ES$^+$) m/z 320 (MH$^+$).

Intermediate 46: 6-amino-3-chloro-2-((2-(tetrahydro-2H-pyran-4-yl)propan-2-yl)sulfonyl)phenol

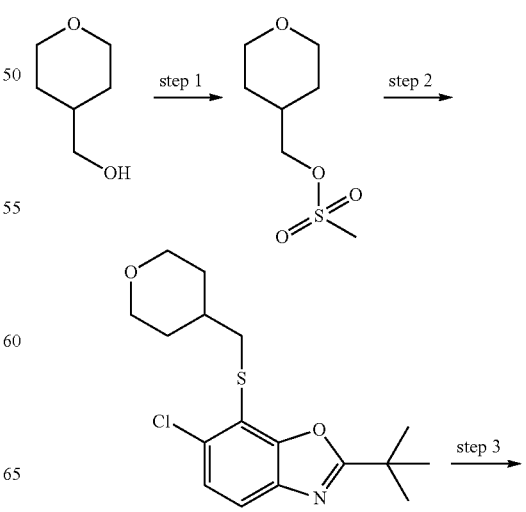

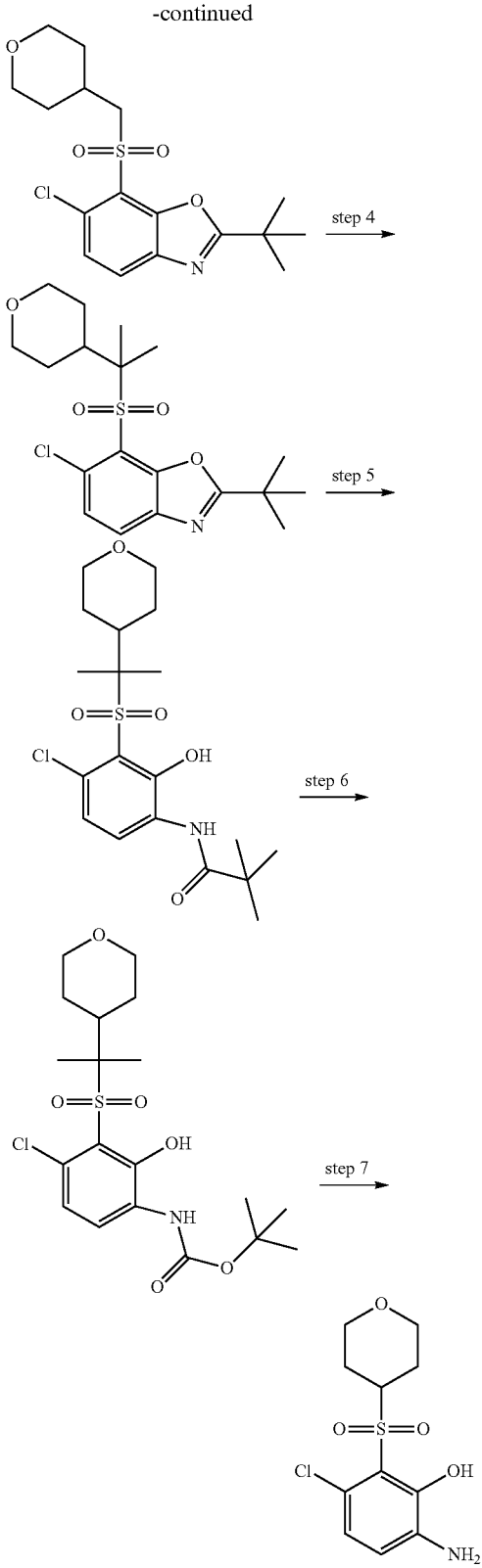

-continued

Step 1: To an ice-water cooled (0° C.) solution of (tetrahydro-2H-pyran-4-yl)methanol (2.0 g) in DCM (50 mL) was added TEA (4.8 mL) and MsCl (2.0 mL). The resulting mixture was stirred at 0° C. for 3 hours, and then quenched with aq. NaHCO$_3$ solution. The mixture was extracted with EA (3×100 mL). The combined organic layers were washed, dried and concentrated to afford (tetrahydro-2H-pyran-4-yl)methyl methanesulfonate (3.0 g).

Step 2: To a solution of sodium 2-(tert-butyl)-6-chlorobenzo[d]oxazole-7-thiolate (3.3 g) in DMF (100 mL) was added (tetrahydro-2H-pyran-4-yl)methyl methanesulfonate (2.0 g) and K$_2$CO$_3$ (2.1 g). The resulting reaction mixture was stirred at 80° C. overnight. After cooling, the mixture was poured into water (500 mL), and extracted with EA (2×150 mL). The combined organic layers were washed, dried and concentrated to afford 2-(tert-butyl)-6-chloro-7-(((tetrahydro-2H-pyran-4-yl)methyl)thio)benzo[d]oxazole (3.4 g).

Step 3: To an ice-water cooled solution of 2-(tert-butyl)-6-chloro-7-(((tetrahydro-2H-pyran-4-yl)methyl)thio)benzo[d]oxazole (3.4 g) in DCM (100 mL) was added mCPBA (4.9 g). The resulting mixture was warmed up and stirred at RT overnight. The mixture was quenched with aq. NaHCO$_3$ solution and Na$_2$S$_2$O$_3$ solution, and then extracted with EA (2×100 mL). The combined organic layers were washed, dried and concentrated to afford 2-(tert-butyl)-6-chloro-7-(((tetrahydro-2H-pyran-4-yl)methyl)sulfonyl)benzo[d]oxazole (3.3 g). MS(ES$^+$) m/z 372 (MH$^+$).

Step 4: To a dry ice-ethanol cooled solution of 2-(tert-butyl)-6-chloro-7-(((tetrahydro-2H-pyran-4-yl)methyl)sulfonyl)benzo[d]oxazole (2.0 g) and MeI (0.7 mL) in THF (50 mL) was added LiHMDS (1 M in THF, 13.5 mL). The resulting mixture was warmed up slowly and stirred at RT for 1 hour. The mixture was quenched with aq. NH$_4$Cl solution, and extracted with EA (2×100 mL). The combined organic layers were washed, dried and concentrated to afford 2-(tert-butyl)-6-chloro-7-((2-(tetrahydro-2H-pyran-4-yl)propan-2-yl)sulfonyl)benzo[d]oxazole (2.0 g). MS(ES$^+$) m/z 400 (MH$^+$).

Step 5: To a solution of 2-(tert-butyl)-6-chloro-7-((2-(tetrahydro-2H-pyran-4-yl)propan-2-yl)sulfonyl)benzo[d]oxazole (2.0 g) in ethanol (25 mL) and water (25 mL) was added sodium hydroxide (1.0 g). The resulting mixture was stirred at 60° C. for 2 hours. The solvent was removed. The residue was diluted with water (100 mL), acidified with aq. citric acid to pH=6, and then extracted with EA (2×100 mL). The combined organic phases were washed, dried and concentrated to afford N-(4-chloro-2-hydroxy-3-((2-(tetrahydro-2H-pyran-4-yl)propan-2-yl)sulfonyl)phenyl)pivalamide (1.5 g).

Step 6: To a solution of N-(4-chloro-2-hydroxy-3-((2-(tetrahydro-2H-pyran-4-yl)propan-2-yl)sulfonyl)phenyl)pivalamide (1.5 g) in THF (25 mL) was added di-tert-butyl dicarbonate (1.7 mL) and DMAP (0.04 g). The resulting mixture was stirred at 60° C. for 4 hours. After cooling, hydrazine (0.6 g) was added. The mixture was continued to stir at RT overnight. The resulting mixture was diluted with water (100 mL), and extracted with EA (2×100 mL). The combined organic layers were washed, dried and concentrated. The residue was purified by column chromatography (eluting with 0-30% EA in PE) to afford tert-butyl (4-chloro-2-hydroxy-3-((2-(tetrahydro-2H-pyran-4-yl)propan-2-yl)sulfonyl)phenyl)carbamate (0.8 g). MS(ES$^+$) m/z 456 (MNa$^+$).

Step 7: To a solution of tert-butyl (4-chloro-2-hydroxy-3-((2-(tetrahydro-2H-pyran-4-yl)propan-2-yl)sulfonyl)phenyl)carbamate (0.8 g) in DCM (20 mL) was added TFA (1.4 mL). The resulting mixture was stirred at RT for 3 hours. The resulting mixture was poured into aq. NaHCO$_3$ solution carefully, and extracted with EA (2×50 mL). The combined organic phases were washed, dried and concentrated to afford the title compound (0.5 g). MS(ES$^+$) m/z 356 (MNa$^+$).

Intermediate 47: 6-amino-3-chloro-2-((2-(oxetan-3-yl)propan-2-yl)sulfonyl)phenol

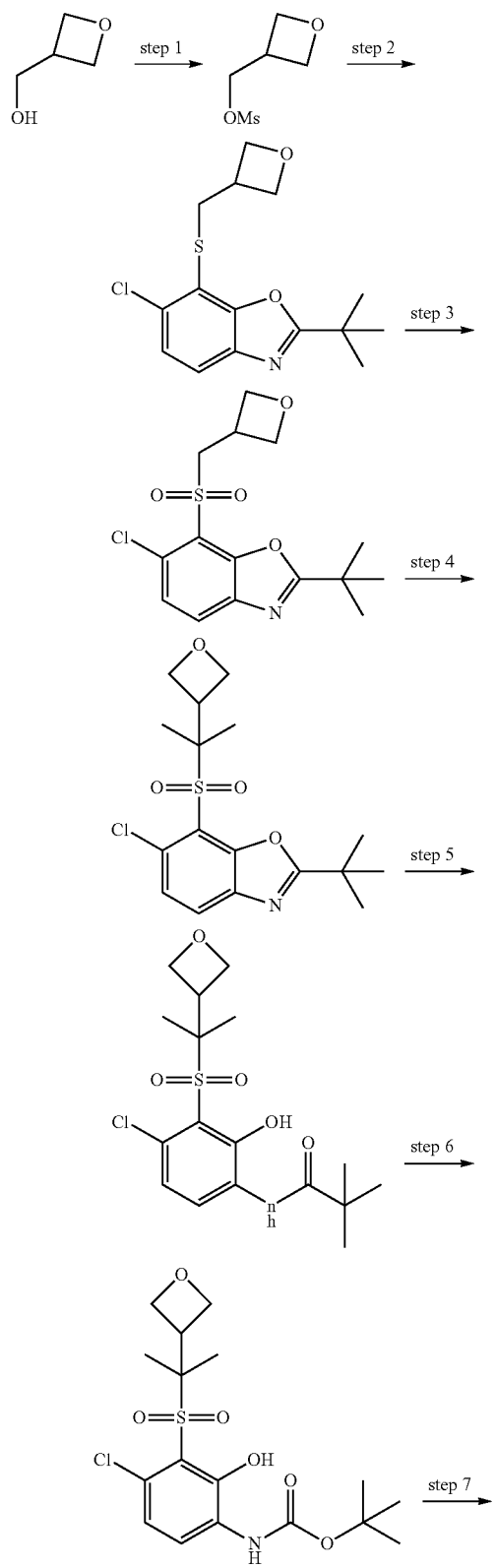

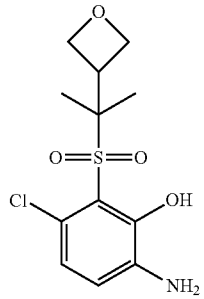 [SMILES: CC(C)(C1COC1)S(=O)(=O)c1c(Cl)ccc(N)c1O]

Step 1: To an ice-water cooled solution of oxetan-3-ylmethanol (0.9 g) in DCM (50 mL) was added TEA (2.9 mL), and then MsCl (1.2 mL) dropwise. The resulting mixture was warmed up slowly and stirred at RT for 2 hours. The mixture was quenched with aq. NaHCO$_3$ solution, and extracted with EA (3×50 mL). The combined organic layers were washed, dried and concentrated to afford oxetan-3-ylmethyl methanesulfonate (1.3 g).

Step 2: To a solution of sodium 2-(tert-butyl)-6-chlorobenzo[d]oxazole-7-thiolate (2.0 g) and oxetan-3-ylmethyl methanesulfonate (1.3 g) in DMF (50 mL) was added potassium carbonate (1.0 g). The resulting mixture was stirred at 80° C. overnight. After cooling, the mixture was poured into water, and extracted with EA (2×100 mL). The combined organic layers were washed, dried and concentrated to afford 2-(tert-butyl)-6-chloro-7-((oxetan-3-ylmethyl)thio)benzo[d]oxazole (2.3 g). MS(ES$^+$) m/z 312 (MH$^+$).

Step 3: To an ice-water cooled solution of 2-(tert-butyl)-6-chloro-7-((oxetan-3-ylmethyl)thio)benzo[d]oxazole (2.3 g) in DCM (50 mL) was added mCPBA (3.6 g). The resulting mixture was warmed up slowly and stirred at RT overnight. The mixture was then quenched with aq. NaHCO$_3$ and Na$_2$S$_2$O$_3$ solutions, extracted with EA (2×100 mL). The combined organic layers were washed, dried and concentrated. The residue was purified by column chromatography (eluting with PE:EA=1:0-7:3) to afford 2-(tert-butyl)-6-chloro-7-((oxetan-3-ylmethyl)sulfonyl)benzo[d]oxazole (2.0 g). MS(ES$^+$) m/z 344 (MH$^+$).

Step 4: To a dry ice-ethanol cooled solution of iodomethane (0.4 mL) and 2-(tert-butyl)-6-chloro-7-((oxetan-3-ylmethyl)sulfonyl)benzo[d]oxazole (0.8 g) in THF (50 mL) was added LiHMDS (1 M in THF, 9.3 mL) dropwise. The resulting mixture was warmed up slowly and stirred for 3 hours. The mixture was quenched with aq. NH$_4$Cl solution, extracted with EA (2×100 mL). The combined organic layers were washed, dried and concentrated to afford 2-(tert-butyl)-6-chloro-7-((2-(oxetan-3-yl)propan-2-yl)sulfonyl) benzo[d]oxazole (0.8 g).

Step 5: To a solution of 2-(tert-butyl)-6-chloro-7-((2-(oxetan-3-yl)propan-2-yl)sulfonyl)benzo[d]oxazole (600 mg) in ethanol (5 mL) and water (5 mL) was added NaOH (323 mg). The resulting mixture was stirred at 60° C. for 3 hours. The reaction mixture was diluted with water (50 mL), and then extracted with EA (3×50 mL). The combined organic layers were washed, dried and concentrated to afford N-(4-chloro-2-hydroxy-3-((2-(oxetan-3-yl)propan-2-yl)sulfonyl)phenyl)pivalamide (600 mg). MS(ES$^+$) m/z 390 (MH$^+$).

Step 6: To a solution of N-(4-chloro-2-hydroxy-3-((2-(oxetan-3-yl)propan-2-yl)sulfonyl)phenyl)pivalamide (400 mg) in THF (5 mL) was added DMAP (125 mg) and Boc$_2$O (0.2 mL). The mixture was stirred at 60° C. for 2 hours.

Hydrazine (0.2 mL) was added. The resulting mixture was stirred at RT overnight. The mixture was then diluted with water (50 mL), extracted with EA (2×250 mL). The combined organic layers were washed, dried and concentrated. The residue was purified by column chromatography (eluting with PE:EA=1:0-7:3) to afford tert-butyl (4-chloro-2-hydroxy-3-((2-(oxetan-3-yl)propan-2-yl)sulfonyl)phenyl)carbamate (200 mg). MS(ES+) m/z 428 (MNa+).

Step 7: To a solution of tert-butyl (4-chloro-2-hydroxy-3-((2-(oxetan-3-yl)propan-2-yl)sulfonyl)phenyl)carbamate (200 mg) in DCM (10 mL) was added TFA (0.4 mL). After stirring at RT overnight, the reaction mixture was basified with aq. NaHCO$_3$ solution carefully. The mixture was extracted with EA (3×50 mL). The combined organic layers were washed, dried and concentrated. The residue was purified by solumn chromatography (eluting with PE:EA=9:1 to 3:2) to afford the title compound (50 mg). MS(ES+) m/z 306 (MH+).

Intermediate 48: 6-amino-3-chloro-2-((1-fluoro-2-methylpropan-2-yl)sulfonyl)phenol

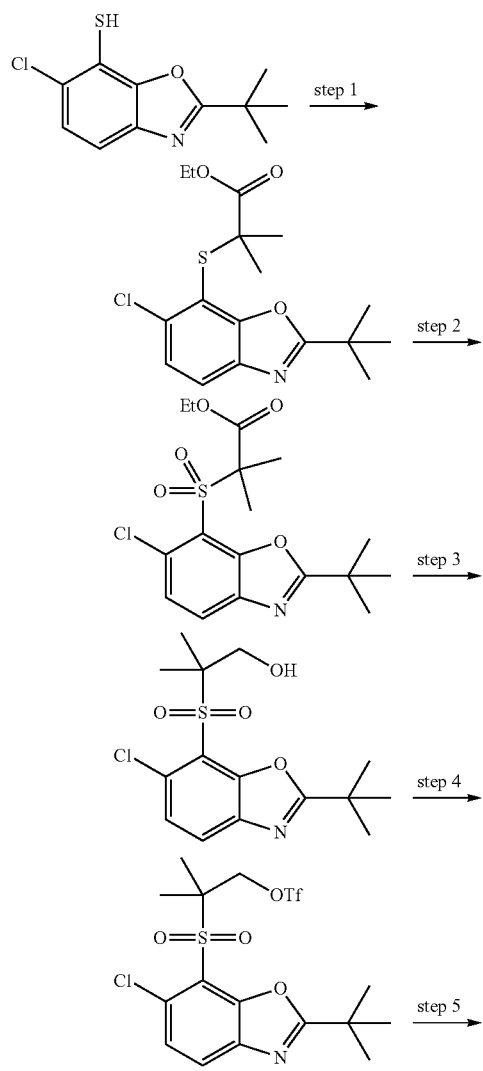

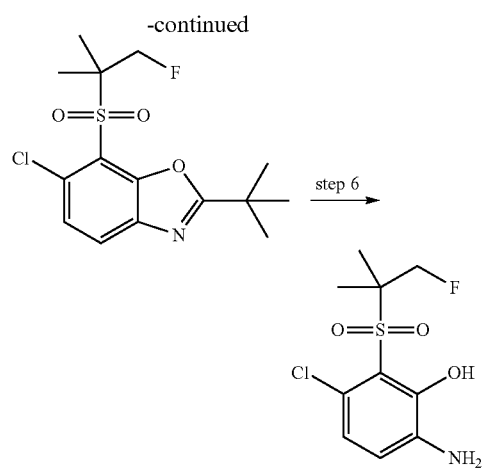

Step 1: To a solution of sodium 2-(tert-butyl)-6-chlorobenzo[d]oxazole-7-thiolate (11.0 g) in DMF (80 mL) was added ethyl 2-bromo-2-methylpropanoate (9.0 g) and K$_2$CO$_3$ (2.9 g). The mixture was stirred at 60° C. for 3 hours. EA (200 mL) was added and the mixture was washed by brine (3×150 mL). The organic layer was dried over sodium sulfate, filtered and concentrated to afford ethyl 2-((2-(tert-butyl)-6-chlorobenzo[d]oxazol-7-yl)thio)-2-methylpropanoate (14.8 g) as a white solid.

Step 2: To a solution of ethyl 2-((2-(tert-butyl)-6-chlorobenzo[d]oxazol-7-yl)thio)-2-methylpropanoate (14.8 g) in DCM (200 mL) was added mCPBA (20.6 g). The mixture was stirred at RT overnight. Aq. Na$_2$SO$_3$ solution was added. The organic phase was separated, and then washed with sat. sodium carbonate solution and brine. The resulting organic phase was dried over sodium sulfate, filtered and concentrated. The residue was purified by column chromatography (eluting with PE:EA=1:0-3:2) to give ethyl 2-((2-(tert-butyl)-6-chlorobenzo[d]oxazol-7-yl)sulfonyl)-2-methylpropanoate (10.3 g) as a white solid.

Step 3: To a solution of ethyl 2-((2-(tert-butyl)-6-chlorobenzo[d]oxazol-7-yl)sulfonyl)-2-methylpropanoate (5.0 g) in THF (130 mL) stirred under a nitrogen atmosphere at −50° C. was added DIBAL-H (1 M in hexane, 64.5 mL). The reaction mixture was allowed to warm to RT and stirred overnight. The reaction mixture was quenched with sat. ammonium chloride, and then partitioned between EA (150 mL) and sodium hydroxide solution (2 M, 150 mL). The organic phase was washed with brine (150 mL), dried over sodium sulphate and evaporated in vacuo to give 2-((2-(tert-butyl)-6-chlorobenzo[d]oxazol-7-yl)sulfonyl)-2-methylpropan-1-ol (4.5 g) as a white solid.

Step 4: To a solution of 2-((2-(tert-butyl)-6-chlorobenzo[d]oxazol-7-yl)sulfonyl)-2-methylpropan-1-ol (5.2 g) in DCM (100 mL) stirred under a nitrogen atmosphere at RT was added pyridine (2.1 mL) and triflic anhydride (1 M in DCM, 19.4 mL). The mixture was stirred at RT for 1 hour, and then partitioned between DCM (100 mL) and brine (100 mL). The organic phase was dried over sodium sulphate and evaporated in vacuo to give 2-((2-(tert-butyl)-6-chlorobenzo[d]oxazol-7-yl)sulfonyl)-2-methylpropyl trifluoromethanesulfonate (6.5 g) as a white solid.

Step 5: To a solution of 2-((2-(tert-butyl)-6-chlorobenzo[d]oxazol-7-yl)sulfonyl)-2-methylpropyl trifluoromethanesulfonate (6.5 g) in THF (100 mL) at −15° C. was added TBAF (1 M in THF, 27.2 mL) dropwise. The mixture was allowed to warm to 30° C. gradually and stirred for 2 hours.

The solvent was evaporated and the residue was partitioned between EA (100 mL) and brine (100 mL). The organic phase was dried over sodium sulphate and evaporated in vacuo. The resulting residue was purified by column chromatography (eluting with PE:EA=1:0-1:1) to afford 2-(tert-butyl)-6-chloro-7-((1-fluoro-2-methylpropan-2-yl)sulfonyl)benzo[d]oxazole (2.4 g) as a white solid.

Step 6: To a solution of 2-(tert-butyl)-6-chloro-7-((1-fluoro-2-methylpropan-2-yl)sulfonyl)benzo[d]oxazole (2.4 g) in 1,4-dioxane (20 mL) was added conc. HCl solution (20 mL). The mixture was refluxed at 110° C. for 4 hours, and then concentrated. The residue was dissolved in EA (20 mL). The pH of the solution was adjusted to 8 with TEA. The mixture was concentated. The resulting residue was purified by column chromatography (eluting with PE:EA=1:0 to 1:4) to afford the title compound (1.9 g) as a white solid. MS(ES+) m/z 282 (MH+).

Intermediate 49: 6-amino-3-chloro-2-((difluoro(pyridin-2-yl)methyl)sulfonyl)phenol

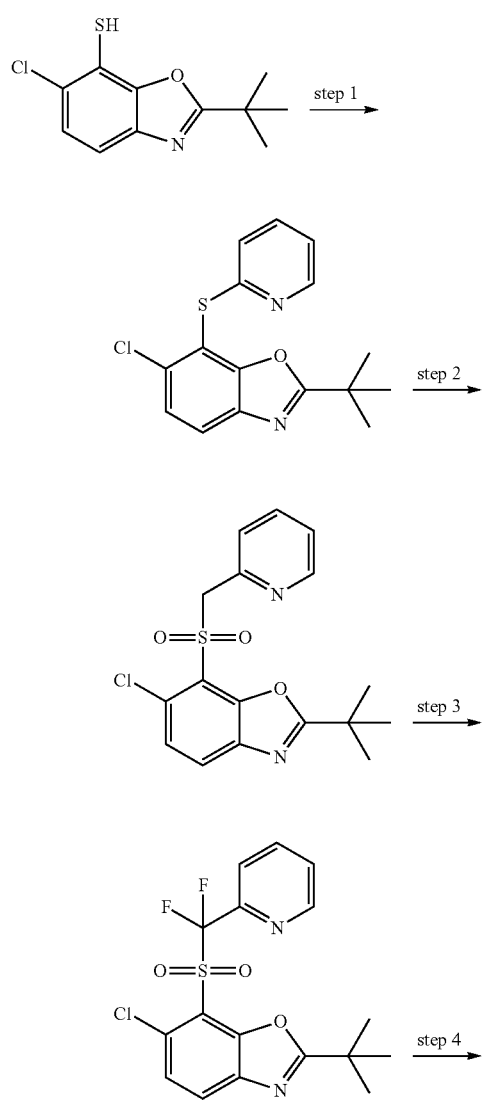

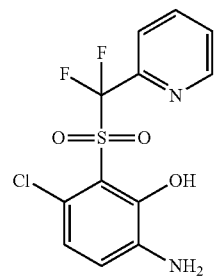

Step 1: To a solution of 2-(chloromethyl)pyridine hydrochloride salt (1.8 g) and sodium 2-(tert-butyl)-6-chlorobenzo[d]oxazole-7-thiolate (2.6 g) in DMF (30 mL) was added $K_2CO_3$ (4.2 g). The mixture was stirred at 60° C. for 3 hours, and then poured into ice-water. The crude product was extracted with EA (3×30 mL). The combined organic layers were washed with brine, dried over $Na_2SO_4$, filtered and concentrated. The residue was purified by column chromatography (eluting with PE:EA=3:1) to give 2-(tert-butyl)-6-chloro-7-((pyridin-2-ylmethyl)thio)benzo[d]oxazole (2.4 g). MS(ES+) m/z 333 (MH+).

Step 2: To a solution of 2-(tert-butyl)-6-chloro-7-((pyridin-2-ylmethyl)thio)benzo[d]oxazole (2.4 g) in TFA (10 mL) was added $H_2O_2$ (0.5 mL). The mixture was stirred at RT overnight. The mixture was quenched with aq. $NaHCO_3$ and $Na_2S_2O_3$ solutions, and then extracted with EA (3×100 mL). The combined organic layers were washed, dried, filtered and concentrated. The crude was purified by column chromatography (PE:EA=10:1-10:3) to give 2-(tert-butyl)-6-chloro-7-((pyridin-2-ylmethyl)sulfonyl)benzo[d]oxazole (2.2 g). MS(ES+) m/z 365 (MH+).

Step 3: A solution of 2-(tert-butyl)-6-chloro-7-((pyridin-2-ylmethyl)sulfonyl)benzo[d]oxazole (2.0 g) in THF (30 mL) was cooled to −78° C. LiHMDS (1 M in THF, 24.1 mL) was added slowly. The mixture was continued to stir for 1.5 hours. N-fluoro-N-(phenylsulfonyl)benzenesulfonamide (3.8 g) in THF (20 mL) was added dropwise. The mixture was stirred for 2 hours at −78° C., and then quenched with water. The resulting solution was extracted with EA (3×50 mL). The combined organic layers were dried over $Na_2SO_4$, filtered and concentrated to give the residue, which was purified by column chromatography (PE:EA=2:1) to afford 2-(tert-butyl)-6-chloro-7-((difluoro(pyridin-2-yl)methyl)sulfonyl)benzo[d]oxazole (1.8 g). MS(ES+) m/z 401 (MH+).

Step 4: 2-(Tert-butyl)-6-chloro-7-((difluoro(pyridin-2-yl)methyl)sulfonyl)benzo[d]oxazole (1.8 g) was dissolved in 1,4-dioxane (30 mL) and water (15 mL). Conc. HCl solution (8 mL) was added. The mixture was stirred at 110° C. for 4 hours. The solvent was removed. The residue was washed with a mixture of dioxane and diethyl ether to give the title compound (1.4 g). MS(ES+) m/z 335 (MH+).

Intermediate 50: 6-amino-3-chloro-2-((fluoro(pyridin-2-yl)methyl)sulfonyl)phenol

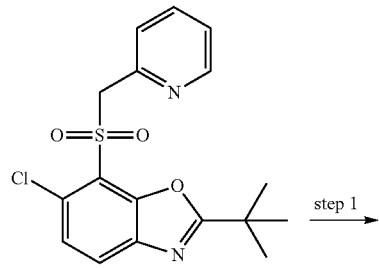

step 1

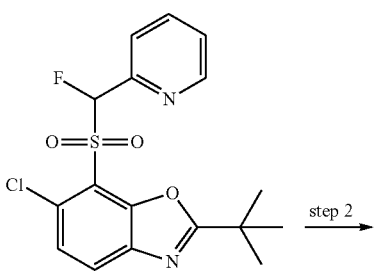

step 2

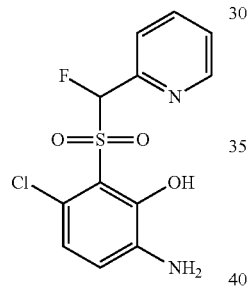

Intermediate 51: 6-amino-3-chloro-2-((6-methyl-2-oxaspiro[3.3]heptan-6-yl)sulfonyl)phenol

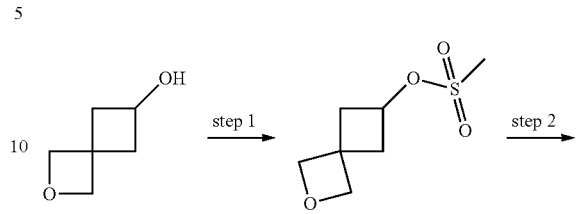

step 1 ... step 2

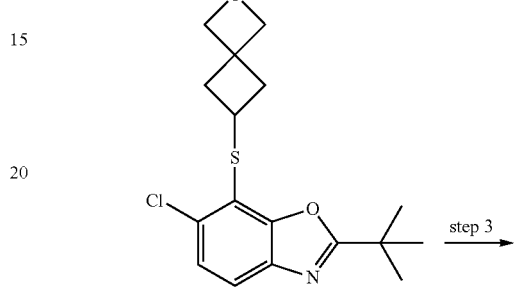

step 3

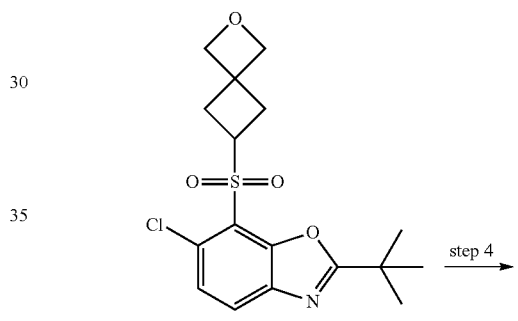

step 4

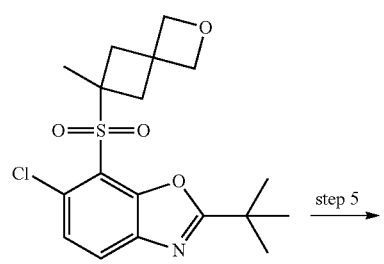

step 5

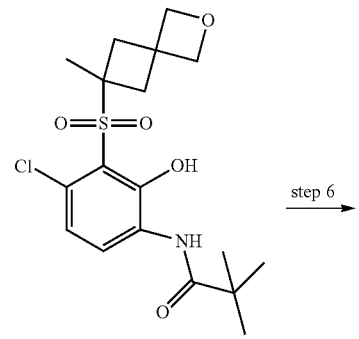

step 6

Step 1: A solution of 2-(tert-butyl)-6-chloro-7-((pyridin-2-ylmethyl)sulfonyl)benzo[d]oxazole (Intermediate 49, Step 2, 1.2 g) in THF (30 mL) was cooled to −78° C. LiHMDS (0.5 g) was added dropwise. The mixture was continued to stir for 1.5 hours. N-fluoro-N-(phenylsulfonyl)benzenesulfonamide (0.9 g) was added dropwise. The mixture was stirred for 2 hours at −78° C., and then quenched with water. The resulting solution was extracted with EA (3×50 mL). The combined organic layers were dried over Na$_2$SO$_4$, filtered and concentrated. The residue was combined with another batch of the same reaction using 2-(tert-butyl)-6-chloro-7-((pyridin-2-ylmethyl)sulfonyl)benzo[d]oxazole (305 mg) as starting material. The combined mixture was purified by column chromatography (eluting with PE:EA=2:1) to give 2-(tert-butyl)-6-chloro-7-((fluoro(pyridin-2-yl)methyl)sulfonyl)benzo[d]oxazole (0.9 g). MS(ES$^+$) m/z 383 (MH$^+$).

Step 2: To a solution of 2-(tert-butyl)-6-chloro-7-((fluoro(pyridin-2-yl)methyl)sulfonyl)benzo[d]oxazole (1.0 g) in 1,4-dioxane (20 mL) and water (10 mL) was added conc. HCl solution (8 mL). The mixture was stirred for 4 hours at 110° C. The solvent was evaporated. The residue was purified by preparative HPLC to give the title compound (450 mg). MS(ES$^+$) m/z 317 (MH$^+$).

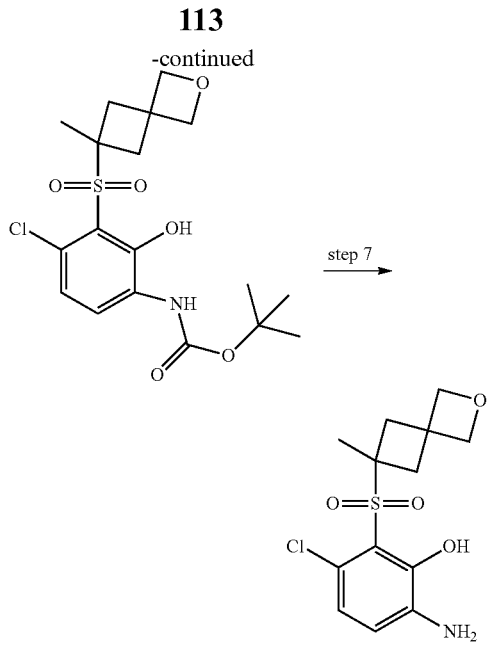

Step 1: To an ice-water cooled solution of 2-oxaspiro[3.3] heptan-6-ol (2.0 g) in DCM (50 mL) was added TEA (4.9 mL) and then MsCl (2.0 mL) dropwise. The resulting mixture was warmed up slowly and stirred at RT for 2 hours. The mixture was quenched with aq. NaHCO₃ solution, and extracted with EA (3×100 mL). The combined organic phases were washed, dried and concentrated to afford 2-oxaspiro[3.3]heptan-6-yl methanesulfonate (3.0 g).

Step 2: To a solution of sodium 2-(tert-butyl)-6-chlorobenzo[d]oxazole-7-thiolate (4.0 g) in DMF (150 mL) was added 2-oxaspiro[3.3]heptan-6-yl methanesulfonate (2.9 g) and potassium carbonate (2.1 g). The resulting mixture was stirred at 80° C. overnight. After cooling, the mixture was poured into water (300 mL), and extracted with EA (3×100 mL). The combined organic phases were washed, dried and concentrated to afford 7-(2-oxaspiro[3.3]heptan-6-ylthio)-2-(tert-butyl)-6-chlorobenzo[d]oxazole (5.0 g). MS(ES⁺) m/z 338 (MH⁺).

Step 3: To a solution of 7-(2-oxaspiro[3.3]heptan-6-ylthio)-2-(tert-butyl)-6-chlorobenzo[d]oxazole (5.0 g) in DCM (100 mL) stirred at 0° C. was added mCPBA (6.4 g) portionwise. The mixture was warmed up slowly and stirred at RT overnight. The mixture was quenched with aq. NaHCO₃ solution and sat. Na₂S₂O₃ solution, and then extracted with EA (2×150 mL). The combined organic phases were washed, dried and concentrated. The residue was purified by column chromatography (eluting with 0-30% EA in PE) to afford 7-(2-oxaspiro[3.3]heptan-6-ylsulfonyl)-2-(tert-butyl)-6-chlorobenzo[d]oxazole (4.6 g).

Step 4: To a cooled (−70° C.) solution of 7-(2-oxaspiro[3.3]heptan-6-ylsulfonyl)-2-(tert-butyl)-6-chlorobenzo[d]oxazole (1.1 g) and MeI (0.3 mL) in THF (50 mL) was added LiHMDS (1 M in THF, 4.5 mL). The resulting mixture was warmed up slowly, and stirred at RT for 60 mins. The mixture was quenched with aq. NH₄Cl solution, and extracted with EA (2×100 mL). The combined organic phases were washed, dried and concentrated to afford 2-(tert-butyl)-6-chloro-7-((6-methyl-2-oxaspiro[3.3]heptan-6-yl)sulfonyl)benzo[d]oxazole (1.0 g). MS(ES⁺) m/z 384 (MH⁺).

Step 5: To a solution of 2-(tert-butyl)-6-chloro-7-((6-methyl-2-oxaspiro[3.3]heptan-6-yl)sulfonyl)benzo[d]oxazole (1.0 g) in ethanol (10 mL) and water (10 mL) was added NaOH (0.5 g). The resulting mixture was stirred at 60° C. for 60 mins. The solvent was removed under reduced pressure. The residue was diluted with water (50 mL), acidified with aq. citric acid to pH=6, and then extracted with EA (3×50 mL). The combined organic phases were washed, dried and concentrated to afford N-(4-chloro-2-hydroxy-3-((6-methyl-2-oxaspiro[3.3]heptan-6-yl)sulfonyl)phenyl)pivalamide (1.0 g). MS(ES⁺) m/z 402 (MH⁺).

Step 6: To a solution of N-(4-chloro-2-hydroxy-3-((6-methyl-2-oxaspiro[3.3]heptan-6-yl)sulfonyl)phenyl)pivalamide (1.0 g) in THF (10 mL) was added Boc₂O (1.2 mL) and DMAP (0.03 g). The resulting mixture was stirred at 50° C. overnight. The mixture was diluted with water (10 mL). Hydrazine (0.4 g) was added. The resulting mixture was stirred for another 5 hours. The mixture was then diluted with water (100 mL), and extracted with EA (2×100 mL). The combined organic phases were washed, dried and concentrated. The residue was purified by column chromatography (eluting with 0-30% EA in PE) to afford tert-butyl (4-chloro-2-hydroxy-3-((6-methyl-2-oxaspiro[3.3]heptan-6-yl)sulfonyl)phenyl)carbamate (0.6 g). MS(ES⁺) m/z 418 (MH⁺).

Step 7: To a solution of tert-butyl (4-chloro-2-hydroxy-3-((6-methyl-2-oxaspiro[3.3]heptan-6-yl)sulfonyl)phenyl) carbamate (0.6 g) in DCM (10 mL) was added TFA (1.1 mL). The resulting mixture was stirred at RT for 3 hours. The mixture was poured into aq. NaHCO₃ solution carefully, and extracted with EA (2×50 mL). The combined organic phases were washed, dried and concentrated to afford the title compound (0.4 g). MS(ES⁺) m/z 318 (MH⁺).

Intermediate 52: 6-amino-3-chloro-2-((3-methyltetrahydro-2H-pyran-3-yl)sulfonyl)phenol

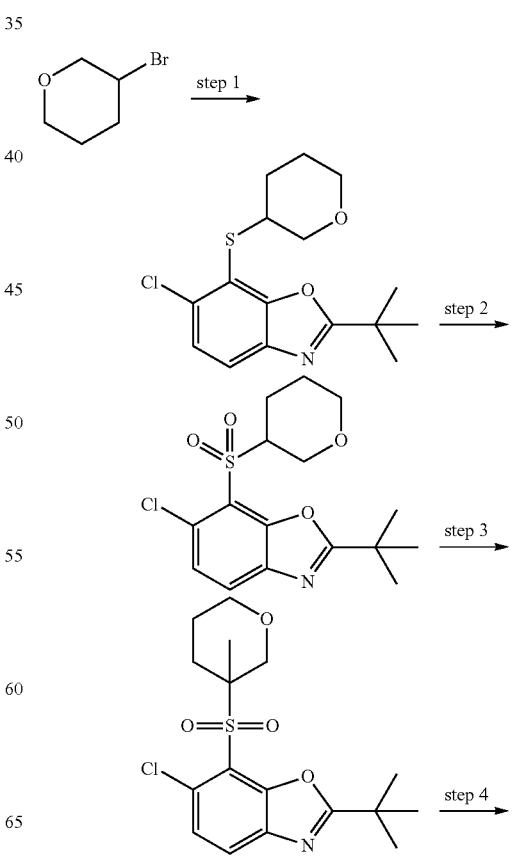

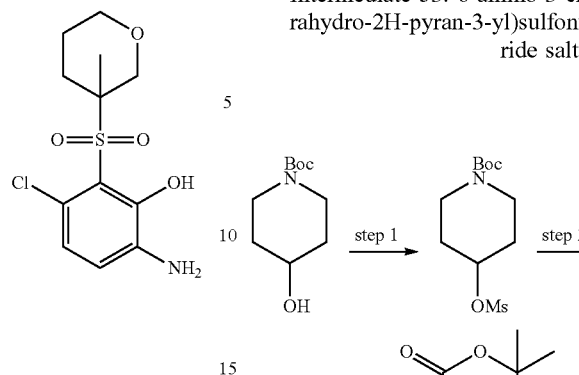

Step 1: 3-Bromotetrahydro-2H-pyran (1.9 g) was added to a solution of sodium 2-(tert-butyl)-6-chlorobenzo[d]oxazole-7-thiolate (3.0 g) and potassium carbonate (3.1 g) in acetonitrile (50 mL) at RT. The mixture was stirred at 80° C. for 12 hours, and then filtered. The filtrate was concentrated. The residue was purified by column chromatography (eluting with PE:EA=15:1) to afford 2-(tert-butyl)-6-chloro-7-((tetrahydro-2H-pyran-3-yl)thio)benzo[d]oxazole (2.0 g) as a yellow oil. MS(ES$^+$) m/z 326 (MH$^+$).

Step 2: mCPBA (1.1 g) was added to a solution of 2-(tert-butyl)-6-chloro-7-((tetrahydro-2H-pyran-3-yl)thio)benzo[d]oxazole (0.6 g) in DCM (50 mL) at 0° C. The mixture was stirred at 25° C. overnight. The resulting solution was combined with another batch of the same reaction using 2-(tert-butyl)-6-chloro-7-((tetrahydro-2H-pyran-3-yl)thio)benzo[d]oxazole (300 mg) as starting material. The combined mixture was quenched with sat. NaHCO$_3$ solution and Na$_2$S$_2$O$_3$ solution. The organic layer was seperated, washed with brine (20 mL), dried over Na$_2$SO$_4$ and concentrated. The residue was purified by column chromatography (eluting with PE:EA=8:1 to 4:1) to afford 2-(tert-butyl)-6-chloro-7-((tetrahydro-2H-pyran-3-yl)sulfonyl)benzo[d]oxazole (0.5 g) as a white solid. MS(ES$^+$) m/z 358 (MH$^+$).

Step 3: LiHMDS (1 M in TFA, 1.7 mL) was added dropwise to a solution of 2-(tert-butyl)-6-chloro-7-((tetrahydro-2H-pyran-3-yl)sulfonyl)benzo[d]oxazole (500 mg) and iodomethane (793 mg) in THF (50 mL) at −78° C. The mixture was stirred at −78° C. for 1 hour, and then quenched with water (30 mL). The resulting mixture was extracted with EA (80 mL). The organic phase was washed with brine (20 mL) and dried over Na$_2$SO$_4$. The solvent was removed to give 2-(tert-butyl)-6-chloro-7-((3-methyltetrahydro-2H-pyran-3-yl)sulfonyl)benzo[d]oxazole (500 mg) as a yellow solid. MS(ES$^+$) m/z 372 (MH$^+$).

Step 4: Aq. HCl solution (35%, 3 mL) was added to a solution of 2-(tert-butyl)-6-chloro-7-((3-methyltetrahydro-2H-pyran-3-yl)sulfonyl)benzo[d]oxazole (500 mg) in 1,4-dioxane (6 mL) and water (3 mL) at RT. The mixture was stirred at 120° C. for 12 hours, and then concentrated. The residue was washed with a mixture of dioxane and diethyl ether to give the title compound (250 mg) as a brown solid. MS(ES$^+$) m/z 306 (MH$^+$).

Intermediate 53: 6-amino-3-chloro-2-((3-methyltetrahydro-2H-pyran-3-yl)sulfonyl)phenol, hydrochloride salt

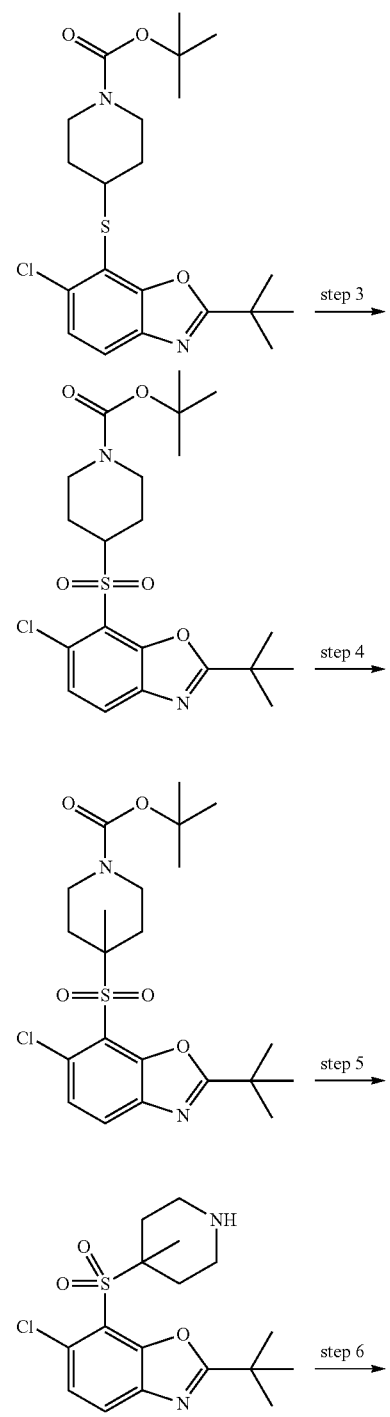

-continued

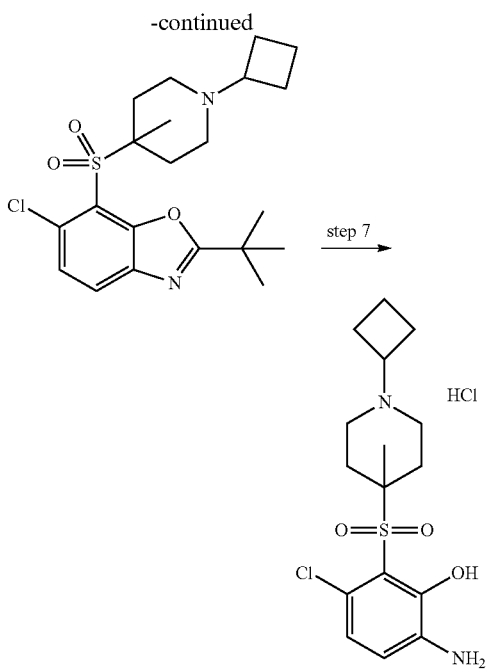

Step 1: To a solution of tert-butyl 4-hydroxypiperidine-1-carboxylate (10.0 g) in DCM (100 mL) was added TEA (13.9 mL) and then MsCl (4.7 mL) in an ice bath. The mixture was stirred at RT for 4 hours. Water (100 mL) was added. The organic layer was separated, dried over sodium sulfate, filtered and concentrated to afford tert-butyl 4-((methylsulfonyl)oxy)piperidine-1-carboxylate (13.9 g) as a white solid. MS(ES$^+$) m/z 302 (MNa$^+$).

Step 2: To a solution of sodium 2-(tert-butyl)-6-chlorobenzo[d]oxazole-7-thiolate (12.0 g) and tert-butyl 4-((methylsulfonyl)oxy)piperidine-1-carboxylate (13.9 g) in DMF (100 mL) was added potassium carbonate (6.3 g). The mixture was stirred at 80° C. for 2 hours. EA (200 mL) was added. The solution was washed with brine (4×200 mL). The organic layer was dried over sodium sulfate and concentrated to afford tert-butyl 4-((2-(tert-butyl)-6-chlorobenzo[d]oxazol-7-yl)thio)piperidine-1-carboxylate (19.3 g) as a yellow liquid. MS(ES$^+$) m/z 369 (M-tBu+H+H$^+$).

Step 3: To a solution of tert-butyl 4-((2-(tert-butyl)-6-chlorobenzo[d]oxazol-7-yl)thio)piperidine-1-carboxylate (19.3 g) in DCM (50 mL) was added mCPBA (20.4 g) at 0° C. The resulting mixture was stirred at RT overnight, quenched with aq. NaHCO$_3$ solution and aq. Na$_2$S$_2$O$_3$ solution, and then extracted with EA (2×150 mL). The combined organic phases were washed, dried and concentrated. The residue was purified by recrystallization in methanol/H$_2$O to afford tert-butyl 4-((2-(tert-butyl)-6-chlorobenzo[d]oxazol-7-yl)sulfonyl)piperidine-1-carboxylate (14.0 g). MS(ES$^+$) m/z 479 (MH$^+$).

Step 4: To a dry ice-ethanol cooled solution of tert-butyl 4-((2-(tert-butyl)-6-chlorobenzo[d]oxazol-7-yl)sulfonyl)piperidine-1-carboxylate (3.0 g) and MeI (0.6 mL) in THF (50 mL) was added LiHMDS (1 M in THF, 9.9 mL). The resulting mixture was warmed up slowly and stirred for 3 hours. The mixture was quenched with aq. NH$_4$Cl solution, extracted with EA (2×100 mL). The combined organic phases were washed, dried and concentrated. The residue was purified by column chromatography (eluting with 0-40% EA in PE) to afford tert-butyl 4-((2-(tert-butyl)-6-chlorobenzo[d]oxazol-7-yl)sulfonyl)-4-methylpiperidine-1-carboxylate (2.7 g). MS(ES$^+$) m/z 415 (M-tBu+H+H$^+$).

Step 5: To an ice-water cooled solution of tert-butyl 4-((2-(tert-butyl)-6-chlorobenzo[d]oxazol-7-yl)sulfonyl)-4-methylpiperidine-1-carboxylate (2.7 g) in DCM (50 mL) was added TFA (4.4 mL). The resulting mixture was warmed up slowly and stirred at RT overnight. The mixture was quenched with aq. NaHCO$_3$ solution carefully, and extracted with DCM (2×100 mL). The combined organic layers were washed, dried and concentrated to afford 2-(tert-butyl)-6-chloro-7-((4-methylpiperidin-4-yl)sulfonyl)benzo[d]oxazole (2.0 g). MS(ES$^+$) m/z 371 (MH$^+$).

Step 6: A solution of 2-(tert-butyl)-6-chloro-7-((4-methylpiperidin-4-yl)sulfonyl)benzo[d]oxazole (0.4 g) and cyclobutanone (0.3 mL) in DCM (8 mL) and acetonitrile (8 mL) was stirred for 1 hour. Sodium triacetoxyborohydride (0.7 g) was added portionwise. The mixture was stirred at RT for 3 days. EA (50 mL) was added. The organic phase was washed with brine, dried over sodium sulfate and concentrated. The residue was purified by column chromatography (eluting with 0-40% EA in PE) to give 2-(tert-butyl)-6-chloro-7-((1-cyclobutyl-4-methylpiperidin-4-yl)sulfonyl)benzo[d]oxazole (0.4 g) as a white solid. MS(ES$^+$) m/z 425 (MH$^+$).

Step 7: To a solution of 2-(tert-butyl)-6-chloro-7-((1-cyclobutyl-4-methylpiperidin-4-yl)sulfonyl)benzo[d]oxazole (0.4 g) in 1,4-dioxane (10 mL) was added conc. HCl solution (10 mL). The mixture was refluxed for 2 hours, and then concentrated to afford the title compound (0.4 g) as a brown solid. MS(ES$^+$) m/z 359 (MH$^+$).

Intermediate 54: amino-3-chloro-2-((4-(2-fluoroethyl)tetrahydro-2H-pyran-4-yl)sulfonyl)phenol

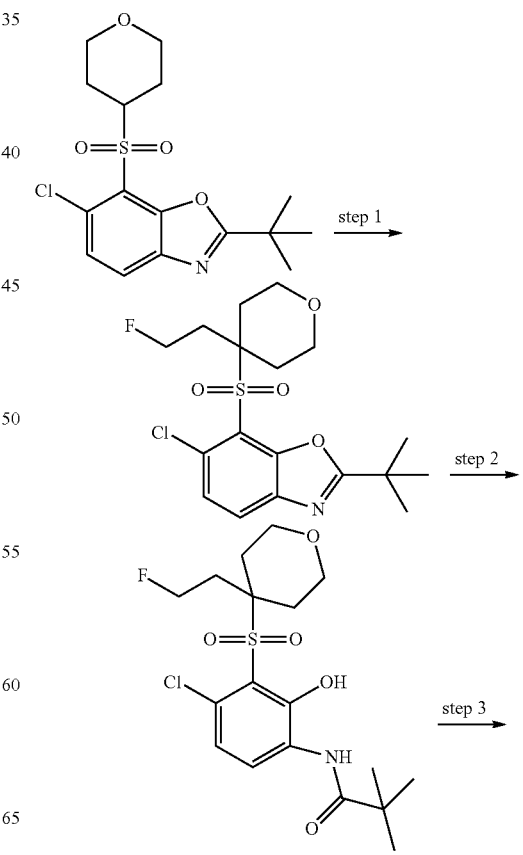

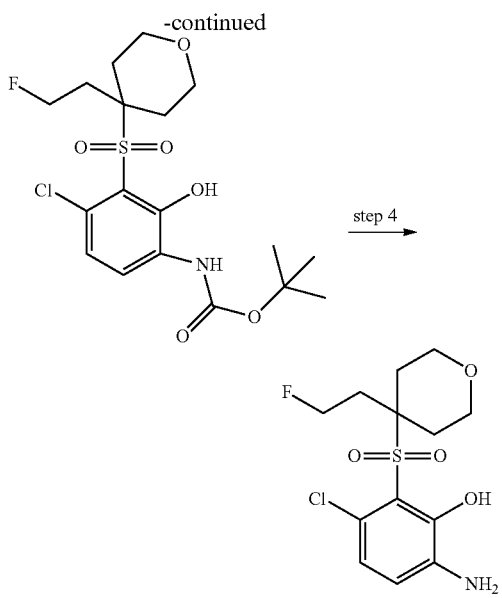

step 4 →

Step 1: To a cooled (−70° C.) solution of 2-(tert-butyl)-6-chloro-7-((tetrahydro-2H-pyran-4-yl)sulfonyl)benzo[d]oxazole (Intermediate 30, Step 3, 2.0 g) and 1-bromo-2-fluoroethane (1.1 g) in THF (50 mL) was added LiHMDS (1 M in THF, 8.4 mL). The resulting mixture was warmed up slowly and stirred at RT for 30 mins. The mixture was quenched with aq. NH₄Cl solution, and extracted with EA (3×50 mL). The combined organic phases were washed, dried and concentrated to afford 2-(tert-butyl)-6-chloro-7-((4-(2-fluoroethyl)tetrahydro-2H-pyran-4-yl)sulfonyl)benzo[d]oxazole (2.2 g), which was used in the next step without purification. MS(ES⁺) m/z 404 (MH⁺).

Step 2: To a solution of 2-(tert-butyl)-6-chloro-7-((4-(2-fluoroethyl)tetrahydro-2H-pyran-4-yl)sulfonyl)benzo[d]oxazole (2.2 g) in ethanol (15 mL) and water (15 mL) was added sodium hydroxide (1.1 g). The resulting mixture was stirred at 60° C. for 2 hours, and then concentrated. The residue was diluted with water (50 mL), acidified with aq. citric acid to pH=6 and extracted with EA (3×50 mL). The combined organic phases were washed, dried and concentrated to afford N-(4-chloro-3-((4-(2-fluoroethyl)tetrahydro-2H-pyran-4-yl)sulfonyl)-2-hydroxyphenyl)pivalamide (2.0 g). MS(ES⁺) m/z 444 (MNa⁺).

Step 3: To a solution of N-(4-chloro-3-((4-(2-fluoroethyl)tetrahydro-2H-pyran-4-yl)sulfonyl)-2-hydroxyphenyl)pivalamide (2.0 g) in THF (10 mL) was added Boc₂O (2.2 mL) and DMAP (0.06 g). The resulting mixture was stirred at 50° C. overnight, and then diluted with water (10 mL). Hydrazine (0.8 g) was added. The resulting mixture was stirred for another 5 hours. Water (100 mL) was added. The mixture was extracted with EA (2×100 mL). The combined organic phases were washed, dried and concentrated. The residue was purified with column chromatography (eluting with 0-30% EA in PE) to afford tert-butyl (4-chloro-3-((4-(2-fluoroethyl)tetrahydro-2H-pyran-4-yl)sulfonyl)-2-hydroxyphenyl)carbamate (0.6 g). MS(ES⁺) m/z 460 (MNa⁺).

Step 4: To a solution of tert-butyl (4-chloro-3-((4-(2-fluoroethyl)tetrahydro-2H-pyran-4-yl)sulfonyl)-2-hydroxyphenyl)carbamate (0.6 g) in DCM (10 mL) was added TFA (1.1 mL). The resulting mixture was stirred at RT overnight, and then basified with aq. NaHCO₃ solution to pH=8. The mixture was extracted with EA (2×50 mL). The combined organic phases were washed, dried and concentrated to afford the title compound (0.4 g). MS(ES⁺) m/z 360 (MNa⁺).

Intermediate 55: 6-amino-3-chloro-2-((4-(fluoromethyl)tetrahydro-2H-pyran-4-yl)sulfonyl)phenol

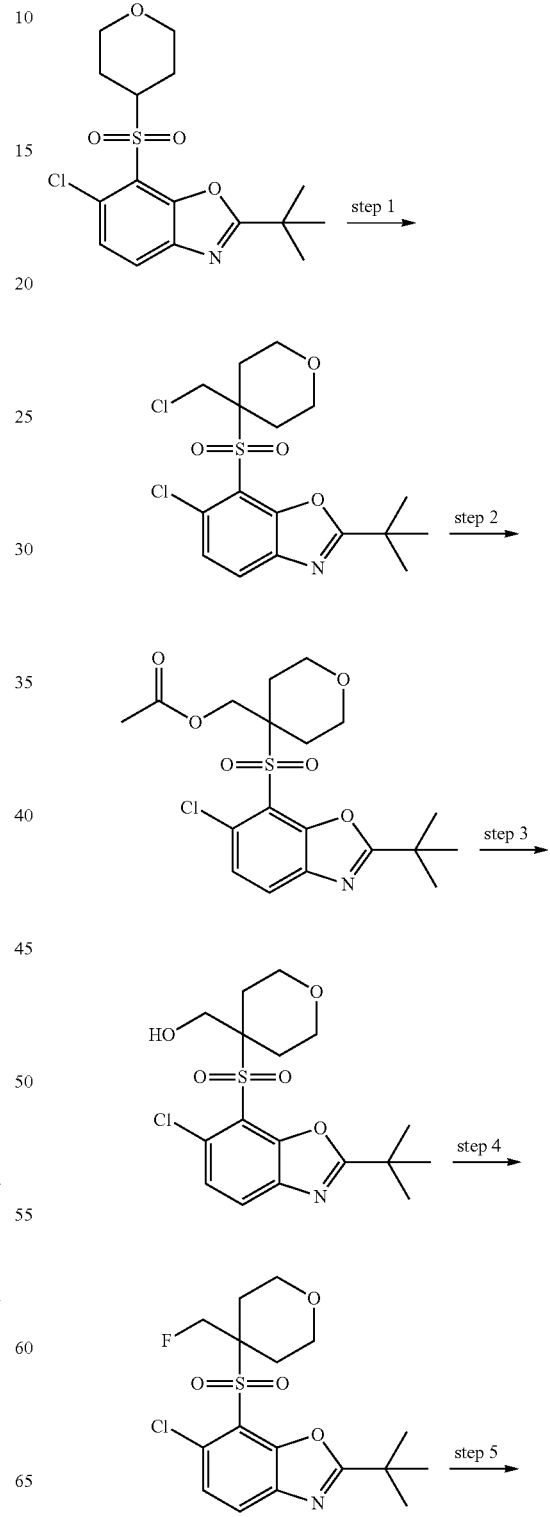

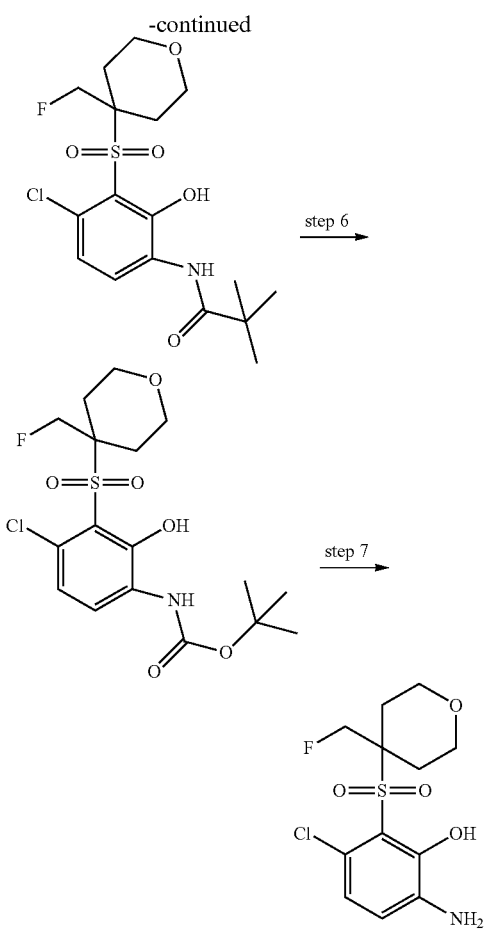

Step 1: To a dry ice-ethanol cooled solution of 2-(tert-butyl)-6-chloro-7-((tetrahydro-2H-pyran-4-yl)sulfonyl)benzo[d]oxazole (Intermediate 30, Step 3, 2.5 g) and bromochloromethane (0.7 mL) in THF (100 mL) was added LiHMDS (1 M in THF, 10.5 mL). The resulting mixture was warmed up slowly and stirred for 1 hour. The mixture was quenched with aq. NH$_4$Cl solution, and extracted with EA (2×100 mL). The combined organic layers were washed, dried and concentrated. The residue was purified by column chromatography (eluting with 10-30% EA in PE) to afford 2-(tert-butyl)-6-chloro-7-((4-(chloromethyl)tetrahydro-2H-pyran-4-yl)sulfonyl)benzo[d]oxazole (1.6 g). MS(ES$^+$) m/z 406 (MH$^+$).

Step 2: A mixture of 2-(tert-butyl)-6-chloro-7-((4-(chloromethyl)tetrahydro-2H-pyran-4-yl)sulfonyl)benzo[d]oxazole (3.0 g) and potassium acetate (7.3 g) in DMSO (50 mL) was stirred at 120° C. for 3 days. The mixture was diluted with water (500 mL), and extracted with EA (2×150 mL). The combined organic layers were washed, dried and concentrated to afford (4-((2-(tert-butyl)-6-chlorobenzo[d]oxazol-7-yl)sulfonyl)tetrahydro-2H-pyran-4-yl)methyl acetate (1.3 g). MS(ES$^+$) m/z 430 (MH$^+$).

Step 3: To a suspension of (4-((2-(tert-butyl)-6-chlorobenzo[d]oxazol-7-yl)sulfonyl)tetrahydro-2H-pyran-4-yl) methyl acetate (1.0 g) in methanol (25 mL) was added K$_2$CO$_3$ (0.3 g). The mixture was stirred at RT for 30 mins. Water (50 mL) was added. The mixture was extracted with EA (2×50 mL). The combined organic phases were washed, dried and concentrated to afford (4-((2-(tert-butyl)-6-chlorobenzo[d]oxazol-7-yl)sulfonyl)tetrahydro-2H-pyran-4-yl) methanol (0.9 g). MS(ES$^+$) m/z 388 (MH$^+$).

Step 4: To a dry ice-ethanol cooled (−70° C.) solution of (4-((2-(tert-butyl)-6-chlorobenzo[d]oxazol-7-yl)sulfonyl)tetrahydro-2H-pyran-4-yl)methanol (1.0 g) in DCM (30 mL) was added DAST (2.7 mL) dropwise. The mixture was stirred at RT for 8 days, and then poured into aq. NaHCO$_3$ solution carefully. The resulting mixture was extracted with EA (3×50 mL). The combined organic phases were washed, dried and concentrated. The residue was purified by column chromatography (eluting with 0-30% EA in PE) to afford 2-(tert-butyl)-6-chloro-7-((4-(fluoromethyl)tetrahydro-2H-pyran-4-yl)sulfonyl)benzo[d]oxazole (0.3 g). MS(ES$^+$) m/z 390 (MH$^+$).

Step 5: To a solution of 2-(tert-butyl)-6-chloro-7-((4-(fluoromethyl)tetrahydro-2H-pyran-4-yl)sulfonyl)benzo[d]oxazole (250 mg) in ethanol (5 mL) and water (5 mL) was added sodium hydroxide (128 mg). The resulting mixture was stirred at 60° C. for 2 hours. The solvent was removed. The residue was diluted with water (25 mL), acidified with aq. citric acid to pH=7, and extracted with EA (2×25 mL). The combined organic phases were washed, dried and concentrated to afford N-(4-chloro-3-((4-(fluoromethyl)tetrahydro-2H-pyran-4-yl)sulfonyl)-2-hydroxyphenyl)pivalamide (0.2 g). MS(ES$^+$) m/z 408 (MH$^+$).

Step 6: To a solution of N-(4-chloro-3-((4-(fluoromethyl)tetrahydro-2H-pyran-4-yl)sulfonyl)-2-hydroxyphenyl)pivalamide (220 mg) in THF (10 mL) was added Boc$_2$O (0.3 mL) and DMAP (6.6 mg). The resulting mixture was stirred at 60° C. for 4 hours. After cooling, hydrazine (86 mg) was added. The mixture was stirred at RT overnight, and then diluted with water (50 mL). The resulting mixture was extracted with EA (2×50 mL). The combined organic phases were washed, dried and concentrated. The residue was purified by column chromatography (eluting with 0-30% EA in PE) to afford tert-butyl (4-chloro-3-((4-(fluoromethyl)tetrahydro-2H-pyran-4-yl)sulfonyl)-2-hydroxyphenyl)carbamate (150 mg). MS(ES$^+$) m/z 446 (MNa$^+$).

Step 7: To a solution of tert-butyl (4-chloro-3-((4-(fluoromethyl)tetrahydro-2H-pyran-4-yl)sulfonyl)-2-hydroxyphenyl)carbamate (150 mg) in DCM (5 mL) was added TFA (0.3 mL). The resulting mixture was stirred at RT overnight. The mixture was basified with aq. NaHCO$_3$ solution carefully, and then extracted with EA (2×50 mL). The combined organic phases were washed, dried and concentrated to afford the title compound (100 mg). MS(ES$^+$) m/z 324 (MH$^+$).

Intermediate 56: 6-amino-3-chloro-2-((1-cyclobutyl-4-fluoropiperidin-4-yl)sulfonyl)phenol, hydrochloride salt

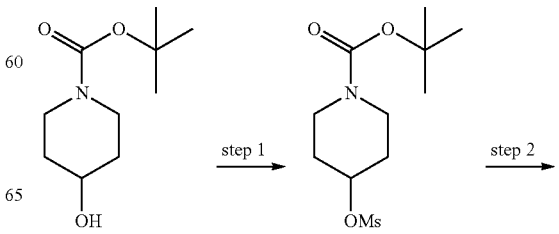

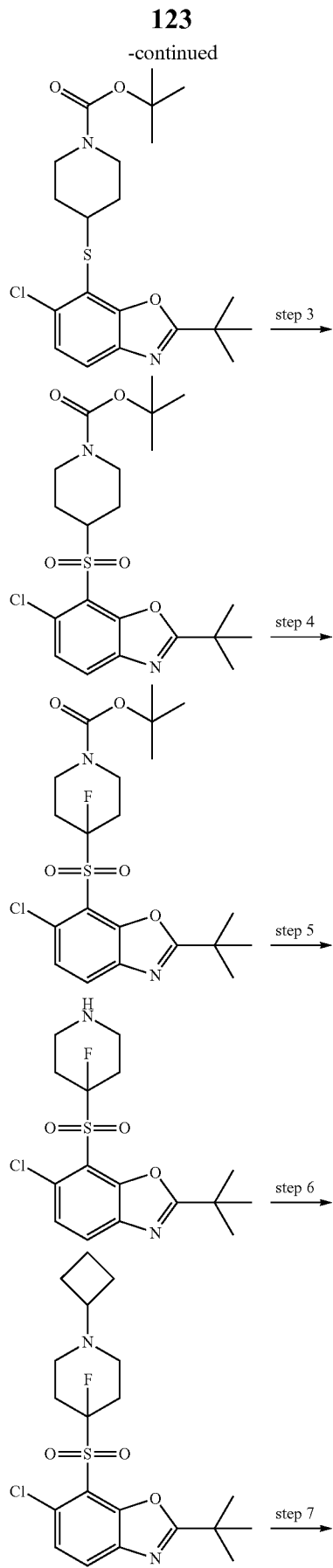

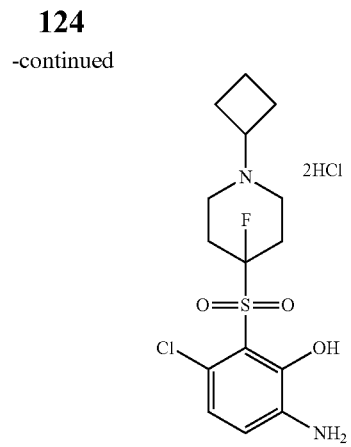

Step 1: To a solution of tert-butyl 4-hydroxypiperidine-1-carboxylate (10.0 g) in DCM (100 mL) was added TEA (13.9 mL), followed by addition of MsCl (4.7 mL) in an ice bath. The mixture was stirred at RT for 4 hours. Water (100 mL) was added. The organic layer was separated, dried over sodium sulfate, filtered and concentrated to afford tert-butyl 4-((methylsulfonyl)oxy)piperidine-1-carboxylate (13.9 g) as a white solid. MS(ES$^+$) m/z 302 (M+Na$^+$).

Step 2: To a solution of sodium 2-(tert-butyl)-6-chlorobenzo[d]oxazole-7-thiolate (12.0 g) and tert-butyl 4-((methylsulfonyl)oxy)piperidine-1-carboxylate (13.9 g) in DMF (100 mL) was added potassium carbonate (6.3 g). The mixture was stirred at 80° C. for 2 hours. EA (200 mL) was added. The organic phase was washed with brine (4×200 mL). The combined organic layers were dried over sodium sulfate, filtered and concentrated to afford tert-butyl 4-((2-(tert-butyl)-6-chlorobenzo[d]oxazol-7-yl)thio)piperidine-1-carboxylate (19.3 g) as a yellow oil. MS(ES$^+$) m/z 369 (M-t-Bu+H+H$^+$).

Step 3: To a solution of tert-butyl 4-((2-(tert-butyl)-6-chlorobenzo[d]oxazol-7-yl)thio)piperidine-1-carboxylate (19.3 g) in DCM (50 mL) was added mCPBA (20.4 g) at 0° C. After stirring at RT overnight, the mixture was quenched with aq. NaHCO$_3$ solution and aq. Na$_2$S$_2$O$_3$ solution, and then extracted with EA (2×150 mL). The combined organic layers were washed, dried and concentrated. The crude was purified by recrystallization in methanol/H$_2$O to afford tert-butyl 4-((2-(tert-butyl)-6-chlorobenzo[d]oxazol-7-yl)sulfonyl)piperidine-1-carboxylate (14.0 g). MS(ES$^+$) m/z 479 (MNa$^+$).

Step 4: To a solution of tert-butyl 4-((2-(tert-butyl)-6-chlorobenzo[d]oxazol-7-yl)sulfonyl)piperidine-1-carboxylate (3.0 g) in THF (60 mL) was added BuLi (1.6 M in n-hexane, 12.3 mL) at −78° C. dropwise. After 1 hour, a solution of N-fluorobenzenesulfonimide (4.1 g) in THF (8 mL) was added dropwise. The mixture was warmed up to ambient temperature, and stirred for 1 hour. The mixture was then quenched by addition of water (0.5 mL). The mixture was partitioned between sat. NH$_4$Cl solution and EA. The organic phase was washed with brine, dried over sodium sulfate, filtered and concentrated in vacuo. The residue was purified by column chromatography (eluting with PE:EA=1:0-3:2) to afford tert-butyl 4-((2-(tert-butyl)-6-chlorobenzo[d]oxazol-7-yl)sulfonyl)-4-fluoropiperidine-1-carboxylate (1.5 g) as a white solid. MS(ES$^+$) m/z 475 (MH$^+$).

Step 5: To a solution of tert-butyl 4-((2-(tert-butyl)-6-chlorobenzo[d]oxazol-7-yl)sulfonyl)-4-fluoropiperidine-1-carboxylate (1.5 g) in DCM (20 mL) was added TFA (4 mL). The mixture was stirred at RT for 30 mins. The mixture was adjusted to pH-8 by addition of sat. sodium carbonate solution. The organic layer was separated, dried over sodium sulfate, filtered and concentrated to afford 2-(tert-butyl)-6-chloro-7-((4-fluoropiperidin-4-yl)sulfonyl)benzo[d]oxazole (1.2 g) as a white solid. MS(ES+) m/z 375 (MH+).

Step 6: A solution of 2-(tert-butyl)-6-chloro-7-((4-fluoropiperidin-4-yl)sulfonyl)benzo[d]oxazole (0.5 g) and cyclobutanone (0.3 mL) in DCM (8 mL) and acetonitrile (8 mL) was stirred for 1 hour. Sodium triacetoxyborohydride (0.8 g) was added portionwise. The reaction mixture was stirred at RT for 3 days. EA (50 mL) was added. The mixture was washed with brine. The organic phase was dried over sodium sulfate, and the solvent was evaporated. The resulting residue was purified by column chromatography (eluting with PE:EA=1:0-3:2) to give 2-(tert-butyl)-6-chloro-7-((1-cyclobutyl-4-fluoropiperidin-4-yl)sulfonyl)benzo[d]oxazole (0.5 g) as a white solid. MS(ES+) m/z 429 (MH+).

Step 7: To a solution of 2-(tert-butyl)-6-chloro-7-((1-cyclobutyl-4-fluoropiperidin-4-yl)sulfonyl)benzo[d]oxazole (0.5 g) in 1,4-dioxane (10 mL) was added HCl solution (10 M, 10 mL). The reaction mixture was refluxed for 2 hours. The mixture was concentrated to afford the title compound (470 mg) as a brown solid. MS(ES+) m/z 363 (MH+).

Intermediate 57: 6-amino-3-chloro-2-((3-fluorotetrahydrofuran-3-yl)sulfonyl)phenol

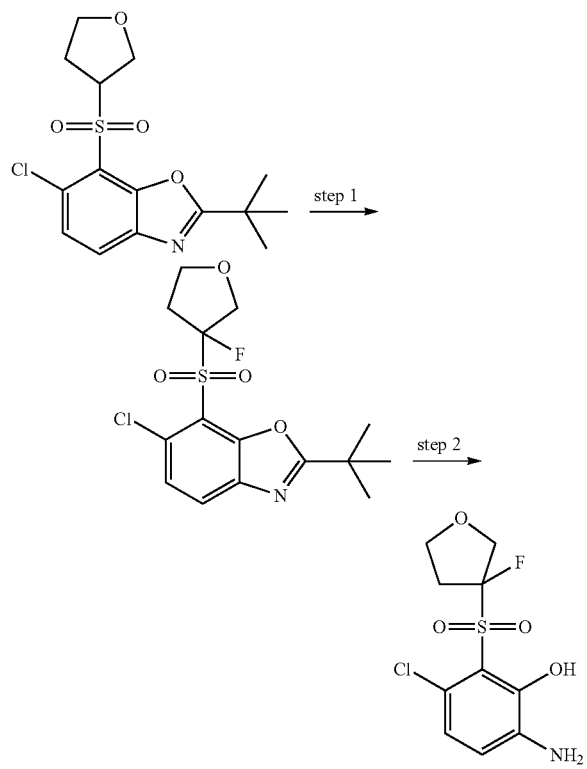

Step 1: To a dry ice-ethanol cooled (−70° C.) solution of 2-(tert-butyl)-6-chloro-7-((tetrahydrofuran-3-yl)sulfonyl)benzo[d]oxazole (Intermediate 29, Step 3, 0.8 g) and N-fluoro-N-(phenylsulfonyl)benzenesulfonamide (1.1 g) in THF (25 mL) was added LiHMDS (1 M in THF, 3.5 mL). The resulting mixture was stirred and warmed up slowly. After stirring for 1 hour, the mixture was quenched with aq. NH4Cl solution, extracted with EA (2×100 mL). The combined organic phases were washed, dried and concentrated. The residue was purified with column chromatography (eluting with 0-30% EA in PE) to afford 2-(tert-butyl)-6-chloro-7-((3-fluorotetrahydrofuran-3-yl)sulfonyl)benzo[d]oxazole (0.8 g). MS(ES+) m/z 362 (MH+).

Step 2: To a solution of 2-(tert-butyl)-6-chloro-7-((3-fluorotetrahydrofuran-3-yl)sulfonyl)benzo[d]oxazole (0.8 g) in 1,4-dioxane (10 mL) and water (10 mL) was added conc. H2SO4 (1.2 mL). The resulting mixture was stirred at 120° C. overnight, and then concentrated under reduced pressure. The residue was basified with aq. NH3.H2O solution, and purified by reversed phase chromatography (under acidic condition). The collected fractions were basified with aq. NaHCO3 solution to afford the title compound (0.3 g). MS(ES+) m/z 296 (MH+).

Intermediate 58: 6-amino-3-chloro-2-((4-fluorotetrahydro-2H-pyran-4-yl)sulfonyl)phenol

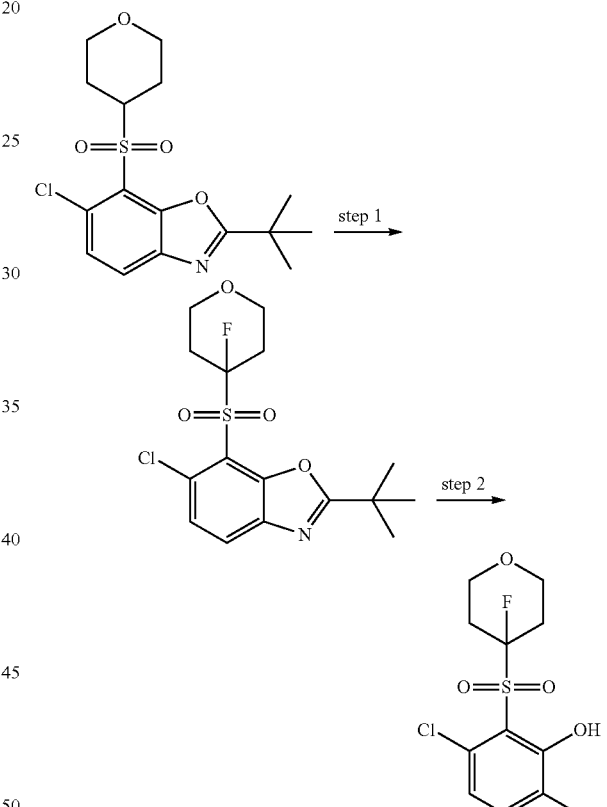

Step 1: To a solution of 2-(tert-butyl)-6-chloro-7-((tetrahydro-2H-pyran-4-yl)sulfonyl)benzo[d]oxazole (Intermediate 30, Step 3, 2.3 g) in THF (50 mL) was added LiHMDS (1 M in THF, 9.4 mL) at −78° C. dropwise. After 1 hour, a solution of N-fluorobenzenesulfonimide (3.0 g) in THF (8 mL) was added dropwise. The mixture was warmed up to ambient temperature, and stirred for 1 hour. The resulting mixture was quenched by addition of water (0.5 mL), and then partitioned between sat. NH4Cl solution and EA. The organic phase was washed with brine, dried over sodium sulfate, filtered and concentrated in vacuo. The residue was purified by column chromatography (eluting with EA:PE=0: 100-40:60) to afford 2-(tert-butyl)-6-chloro-7-((4-fluorotetrahydro-2H-pyran-4-yl)sulfonyl)benzo[d]oxazole (1.4 g) as a white solid. MS(ES+) m/z 376 (MH+).

Step 2: To a solution of 2-(tert-butyl)-6-chloro-7-((4-fluorotetrahydro-2H-pyran-4-yl)sulfonyl)benzo[d]oxazole (1.4 g) in 1,4-dioxane (10 mL) was added aq. HCl solution (37%, 10 mL). After refluxed at 110° C. overnight, the mixture was concentrated to afford the title compound (1.2 g) as a gray solid. MS(ES$^+$) m/z 310 (MH$^+$).

Intermediate 59: 6-amino-3-chloro-2-((3,3-difluorocyclobutyl)sulfonyl)phenol

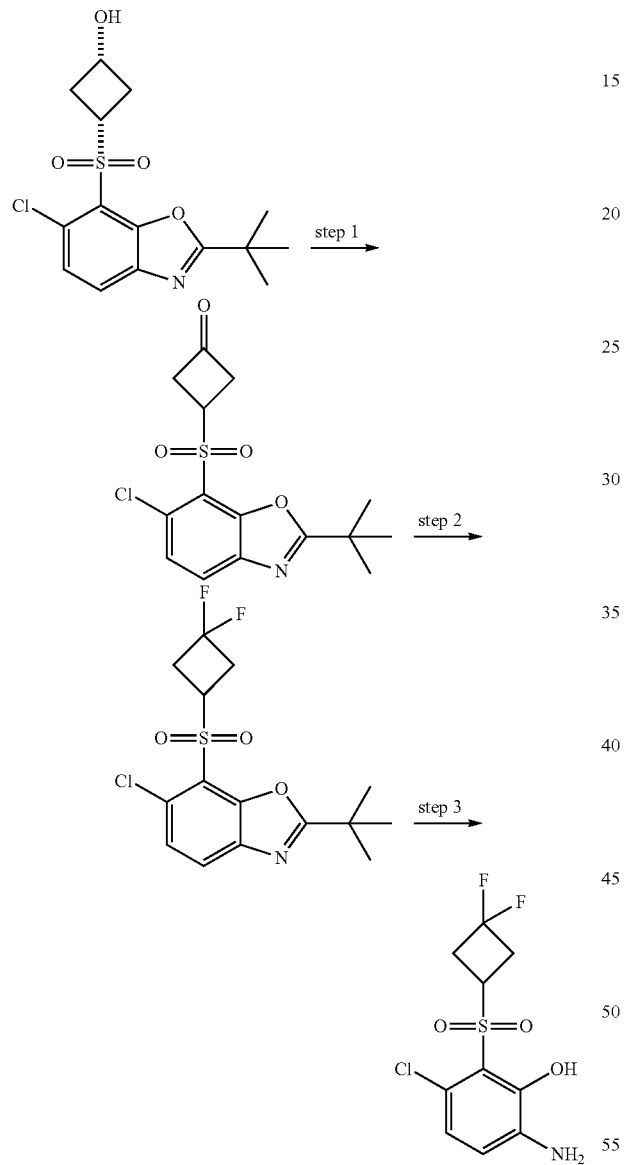

Step 1: To a solution of cis-3-((2-(tert-butyl)-6-chlorobenzo[d]oxazol-7-yl)sulfonyl)cyclobutanol (Intermediate 28, Step 3, 1.0 g) in water (2 mL), acetonitrile (1 mL) and DCM (1 mL) stirred at RT was added ruthenium(III) chloride (6.0 mg). Sodium periodate (1.9 g) was then added over 5 mins. The mixture was stirred at RT overnight. Cold water (20 mL) was added. The resulting mixture was extracted with DCM (2×30 mL). The combined organic layers were washed with sat. NaHCO$_3$ solution and brine, dried over Na$_2$SO$_4$, filtered and concentrated in vacuo to give 3-((2-(tert-butyl)-6-chlorobenzo[d]oxazol-7-yl)sulfonyl)cyclobutanone (900 mg) as a yellow oil. MS(ES$^+$) m/z 342 (MH$^+$).

Step 2: To a stirred solution of 3-((2-(tert-butyl)-6-chlorobenzo[d]oxazol-7-yl)sulfonyl)cyclobutanone (800 mg) in 1,2-dichloroethane (10 mL) cooled to −100° C. was added DAST (0.9 mL) over 30 mins. The mixture was stirred at this temperature for 1 hour, and then warmed up to RT. The mixture was stirred at RT for 16 hours, and then quenched by addition of crushed ice (30 g) and solid NaHCO$_3$ (5 g). The aq. layer was extracted with DCM (2×50 mL). The combined organic layers were washed with brine (50 mL), dried over anhydrous Na$_2$SO$_4$, filtered and concentrated under reduced pressure. The residue was purified by column chromatography (eluting with PE:EA=5:1) to give 2-(tert-butyl)-6-chloro-7-((3,3-difluorocyclobutyl)sulfonyl)benzo[d]oxazole (500 mg) as a white solid. MS(ES$^+$) m/z 364 (MH$^+$).

Step 3: A solution of 2-(tert-butyl)-6-chloro-7-((3,3-difluorocyclobutyl)sulfonyl)benzo[d]oxazole (500 mg) in sulfuric acid (65%, 2 mL) and dioxane (4 mL) was stirred at 90° C. for 4 hours. The mixture was purified by reversed phase chromatography (C18, mobile phase 0.01% CF$_3$COOH/H$_2$O, CH$_3$OH, 30 mL/min, 10%~55%, 5 min; 55~55%, 6 min; 40%~95%, 1 min; 95%~95%, 1 min) to give the title compound (350 mg) as a yellow solid. MS(ES$^+$) m/z 298 (MH$^+$).

Intermediate 60: 2-(2-oxaspiro[3.3]heptan-6-ylsulfonyl)-6-amino-3-chlorophenol

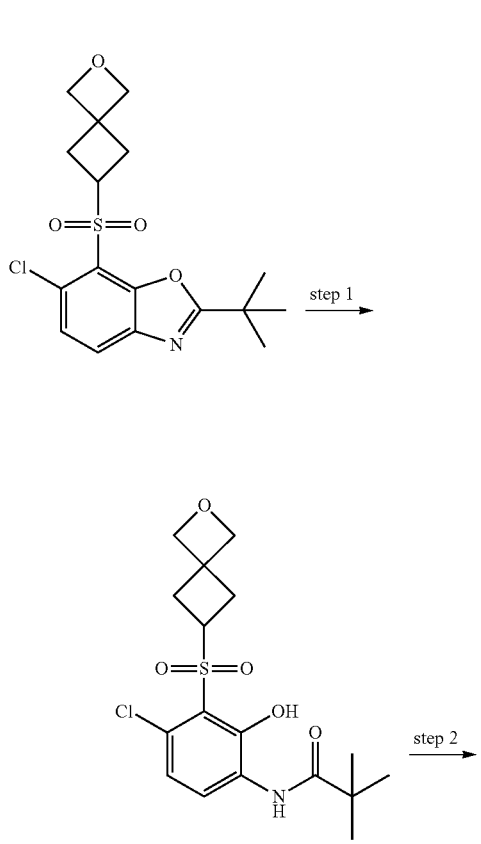

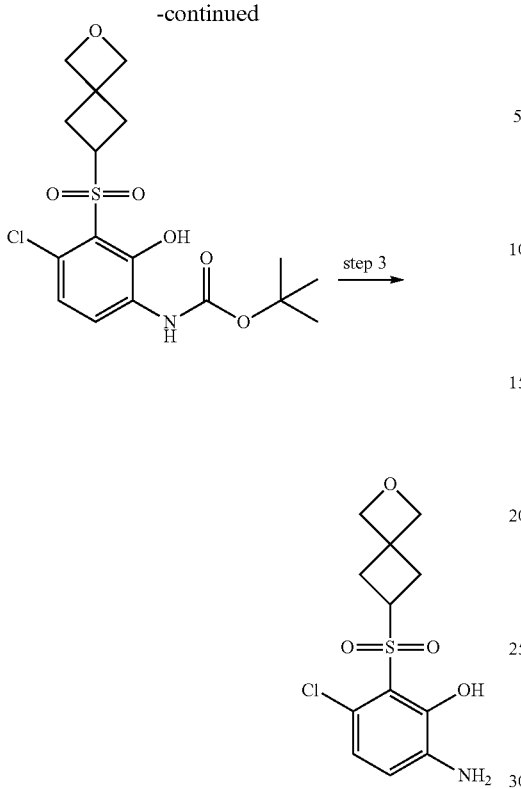

Step 1: To a solution of 7-(2-oxaspiro[3.3]heptan-6-ylsulfonyl)-2-(tert-butyl)-6-chlorobenzo[d]oxazole (Intermediate 51, Step 3, 1.0 g) in ethanol (10 mL) and water (10 mL) was added sodium hydroxide (0.5 g). The resulting mixture was stirred at 60° C. for 4 hours. The mixture was concentrated under reduced pressure. The residue was diluted with water (100 mL), and acidified with aq. citric acid to pH=5. The mixture was extracted with EA (2×50 mL). The combined organic layers were washed, dried, filtered and concentrated to afford N-(3-(2-oxaspiro[3.3]heptan-6-ylsulfonyl)-4-chloro-2-hydroxphenyl)pivalamide (1.0 g). MS(ES⁺) m/z 388 (MH⁺).

Step 2: To a solution of N-(3-(2-oxaspiro[3.3]heptan-6-ylsulfonyl)-4-chloro-2-hydroxyphenyl)pivalamide (1.0 g) in THF (10 mL) was added Boc₂O (1.2 mL) and DMAP (0.03 g). The resulting mixture was stirred at 50° C. overnight, and then diluted with water (10 mL). To the mixture was added hydrazine (0.4 mL). The resulting mixture was stirred for 5 hours, and then diluted with water (100 mL). The mixture was extracted with EA (2×100 mL). The combined organic layers were washed, dried and concentrated. The residue was purified by column chromatography (eluting with PE:EA=1:0-7:3) to afford tert-butyl (3-(2-oxaspiro[3.3]heptan-6-ylsulfonyl)-4-chloro-2-hydroxyphenyl)carbamate (450 mg). MS(ES⁺) m/z 404 (MH⁺).

Step 3: To a solution of tert-butyl (3-(2-oxaspiro[3.3]heptan-6-ylsulfonyl)-4-chloro-2-hydroxyphenyl)carbamate (450 mg) in DCM (20 mL) was added TFA (0.9 mL). The resulting mixture was stirred at 25° C. overnight. The mixture was basified with aq. NaHCO₃ solution, and extracted with EA (2×50 mL). The combined organic layers were washed, dried and concentrated to afford the title compound (250 mg). MS(ES⁺) m/z 304 (MH⁺).

Intermediate 61: 6-amino-3-chloro-2-((tetrahydro-2H-pyran-3-yl)sulfonyl)phenol

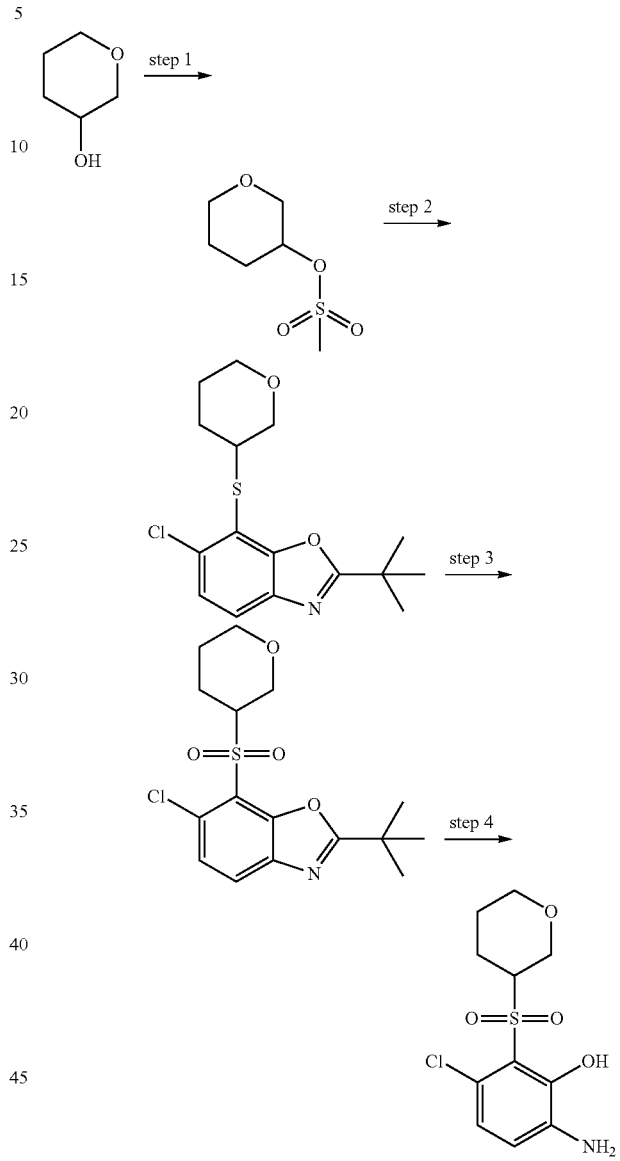

Step 1: To a solution of tetrahydro-2H-pyran-3-ol (2.0 g) in DCM (100 mL) was added TEA (4.0 g) and methanesulfonyl chloride (2.7 g) at 0° C. under a nitrogen atmosphere. The resulting mixture was stirred at this temperature for 30 mins, and then quenched with aq. NaHCO₃ solution. The mixture was extracted with DCM (2×50 mL). The combined organic phases were washed, dried and concentrated to afford tetrahydro-2H-pyran-3-yl methanesulfonate (3.2 g) as a brown oil.

Step 2: Tetrahydro-2H-pyran-3-yl methanesulfonate (2.0 g) was added to a solution of sodium 2-(tert-butyl)-6-chlorobenzo[d]oxazole-7-thiolate (2.6 g) and potassium carbonate (2.7 g) in DMF (30 mL) at RT. The mixture was stirred at 80° C. for 12 hours. The reaction mixture was combined with another batch of the same reaction using sodium 2-(tert-butyl)-6-chlorobenzo[d]oxazole-7-thiolate (0.1 g) as starting material. The combined mixture was diluted with EA (200 mL), washed with water (2×40 mL) and brine (40 mL), dried over $Na_2SO_4$ and concentrated. The residue was purified by column chromatography (eluting with PE:EA=15:1) to afford 2-(tert-butyl)-6-chloro-7-((tetrahydro-2H-pyran-3-yl)thio)benzo[d]oxazole (1.0 g) as a colorless oil. $MS(ES^+)$ m/z 326 ($MH^+$).

Step 3: mCPBA (1513 mg) was added to a solution of 2-(tert-butyl)-6-chloro-7-((tetrahydro-2H-pyran-3-yl)thio)benzo[d]oxazole (800 mg) in DCM (50 mL) at 0° C. The mixture was stirred at 25° C. overnight, and then combined with another batch of the same reaction using 2-(tert-butyl)-6-chloro-7-((tetrahydro-2H-pyran-3-yl)thio)benzo[d]oxazole (150 mg) as starting material. The combined mixture was quenched with sat. $NaHCO_3$ solution and $Na_2S_2O_3$ solution. The organic layer was separated, washed with brine (50 mL), dried over $Na_2SO_4$ and concentrated. The residue was purified by column chromatography (eluting with PE:EA=8:1 to 4:1) to afford 2-(tert-butyl)-6-chloro-7-((tetrahydro-2H-pyran-3-yl)sulfonyl)benzo[d]oxazole (900 mg) as a white solid. $MS(ES^+)$ m/z 310 ($MH^+$).

Step 4: Aq. HCl solution (35%, 1 mL) was added to a solution of 2-(tert-butyl)-6-chloro-7-((tetrahydro-2H-pyran-3-yl)sulfonyl)benzo[d]oxazole (400 mg) in 1,4-dioxane (2 mL) and water (1 mL) at RT. The mixture was stirred at 120° C. for 12 hours, and then combined with another batch of the same reaction using 2-(tert-butyl)-6-chloro-7-((tetrahydro-2H-pyran-3-yl)sulfonyl)benzo[d]oxazole (50 mg) as starting material. The combined solution was concentrated. The residue was purified by preparative HPLC (Instrument: gilson281; Column: Shimadzu Shim-Pack, PRC-ODS, 20×250 mm, 15 μm, two connected in series; Mobile Phase: ACN, water (0.05% TFA); Flow Rate: 30 mL/min; Detective Wavalength (nm): 214/254; Retention Time (min): 8.5 min) to afford the title compound (200 mg) as a brown solid. $MS(ES^+)$ m/z 292 ($MH^+$).

Intermediate 62: 6-amino-3-chloro-2-((1-(2,2,2-trifluoroethyl)piperidin-4-yl)sulfonyl)phenol, hydrochloride salt

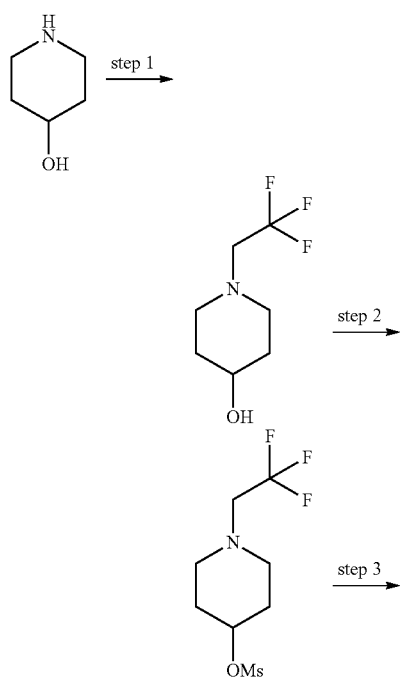

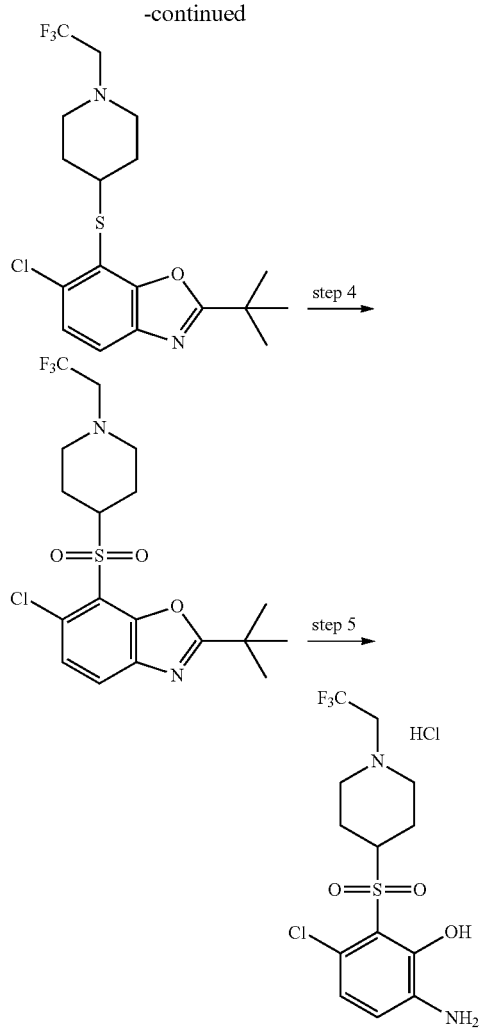

Step 1: To a solution of piperidin-4-ol (1.0 g) and 2,2,2-trifluoroethyl trifluoromethanesulfonate (1.6 mL) in DMF (50 mL) was added $Cs_2CO_3$ (6.4 g). The solution was stirred at 90° C. for 3 hours. The reaction mixture was filtered to afford 1-(2,2,2-trifluoroethyl)piperidin-4-ol solution (0.2 M in DMF, 50 mL). $MS(ES^+)$ m/z 184 ($MH^+$).

Step 2: To a solution of 1-(2,2,2-trifluoroethyl)piperidin-4-ol (0.2 M in DMF, 50 mL) was added TEA (2.1 mL), then followed by MsCl (0.8 mL) under an ice bath temperature. After stirring at RT for 4 hours, the mixture was concentrated to afford 1-(2,2,2-trifluoroethyl)piperidin-4-yl methanesulfonate (2.6 g) as a yellow oil. $MS(ES^+)$ m/z 262 ($MH^+$).

Step 3: To a solution of 1-(2,2,2-trifluoroethyl)piperidin-4-yl methanesulfonate (2.6 g), sodium 2-(tert-butyl)-6-chlorobenzo[d]oxazole-7-thiolate (3.1 g) in DMF (50 mL) was added $K_2CO_3$ (2.1 g). The mixture was stirred at 90° C. for 2 hours. EA (150 mL) was added. The mixture was washed by brine for three times. The organic layer was dried over sodium sulfate, filtered and concentrated to afford 2-(tert-butyl)-6-chloro-7-((1-(2,2,2-trifluoroethyl)piperidin-4-yl)thio)benzo[d]oxazole (4.0 g). $MS(ES^+)$ m/z 407 ($MH^+$).

Step 4: To a solution of 2-(tert-butyl)-6-chloro-7-((1-(2,2,2-trifluoroethyl)piperidin-4-yl)thio)benzo[d]oxazole (6.3 g) and TFA (7 mL) in DCM (30 mL) stirred at 0° C. was portionwise added mCPBA (3.5 g). The mixture was stirred at RT overnight. The solvent was removed. The residue was purified by reversed phase column chromatography (eluting with ACN and water) to afford 2-(tert-butyl)-6-chloro-7-((1-(2,2,2-trifluoroethyl)piperidin-4-yl)sulfonyl)benzo[d]oxazole (751 mg). MS(ES+) m/z 439 (MH+).

Step 5: To a solution of 2-(tert-butyl)-6-chloro-7-((1-(2,2,2-trifluoroethyl)piperidin-4-yl)sulfonyl)benzo[d]oxazole (751 mg) in 1,4-dioxane (10 mL) was added conc. HCl solution (10 mL). The mixture was stirred under reflux for 3 hours, and then concentrated to afford the title compound (320 mg). MS(ES+) m/z 373 (MH+).

Intermediate 63: 6-amino-3-chloro-2-((1-(2,2-difluoroethyl)piperidin-4-yl)sulfonyl)phenol

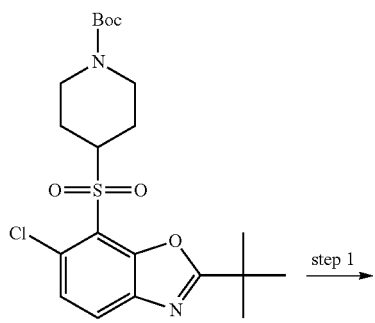

step 1

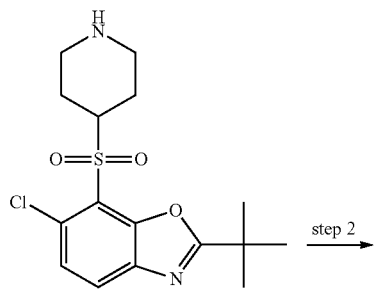

step 2

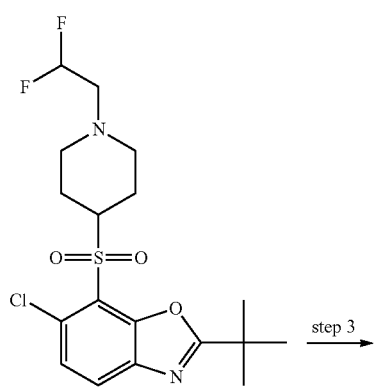

step 3

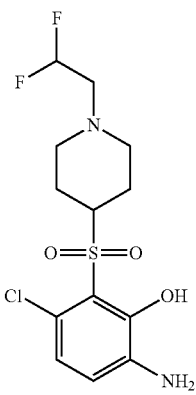

Step 1: To a stirred solution of tert-butyl 4-((2-(tert-butyl)-6-chlorobenzo[d]oxazol-7-yl)sulfonyl)piperidine-1-carboxylate (Intermediate 56, Step 3, 1100 mg) in DCM (20 mL) at RT was added 2,2,2-trifluoroacetic acid (0.5 mL). The mixture was stirred at this temperature for 2 hours. Cold water (50 mL) was added. The resulting mixture was neutralized with sat. NaHCO₃ solution. The aq. layer was extracted with DCM (2×50 mL). The combined organic layers were dried over Na₂SO₄, filtered and concentrated in vacuo to give 2-(tert-butyl)-6-chloro-7-(piperidin-4-ylsulfonyl)benzo[d]oxazole (650 mg) as a light yellow solid. MS(ES+) m/z 357 (MH+).

Step 2: Potassium carbonate (0.1 g) was added to a solution of 2-(tert-butyl)-6-chloro-7-(piperidin-4-ylsulfonyl)benzo[d]oxazole (0.3 g) and 1,1-difluoro-2-iodoethane (0.2 g) in DMF (4 mL) at RT. The mixture was stirred at 70° C. for 16 hours. Cold water (30 mL) was added. The aq. layer was extracted with DCM (2×50 mL). The combined organic layers were dried over Na₂SO₄, filtered and concentrated in vacuo to give 2-(tert-butyl)-6-chloro-7-((1-(2,2-difluoroethyl)piperidin-4-yl)sulfonyl)benzo[d]oxazole (270 mg) as a light yellow solid. MS(ES+) m/z 421 (MH+).

Step 3: To a solution of 2-(tert-butyl)-6-chloro-7-((1-(2,2-difluoroethyl)piperidin-4-yl)sulfonyl)benzo[d]oxazole (0.3 g) in 1,4-dioxane (2 mL) was added sulfuric acid (65%, 0.06 mL). The resulting mixture was stirred for 1 hour at 100° C. Cold water (30 mL) was added. The resulting mixture was neutralized with sat. NaHCO₃ solution. The aq. layer was extracted with DCM (2×50 mL). The combined organic layers were dried over Na₂SO₄, filtered and concentrated in vacuo to give the title compound (170 mg) as a dark solid. MS(ES+) m/z 355 (MH+).

Intermediate 64: 6-amino-3-chloro-2-((1-cyclobutylpiperidin-4-yl)sulfonyl)phenol-d1, hydrochloride salt

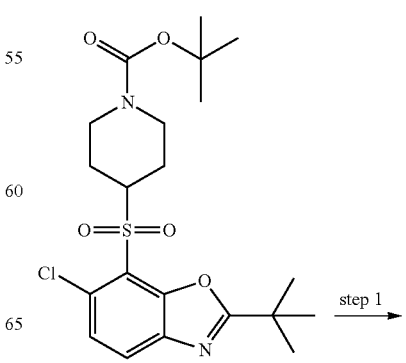

step 1

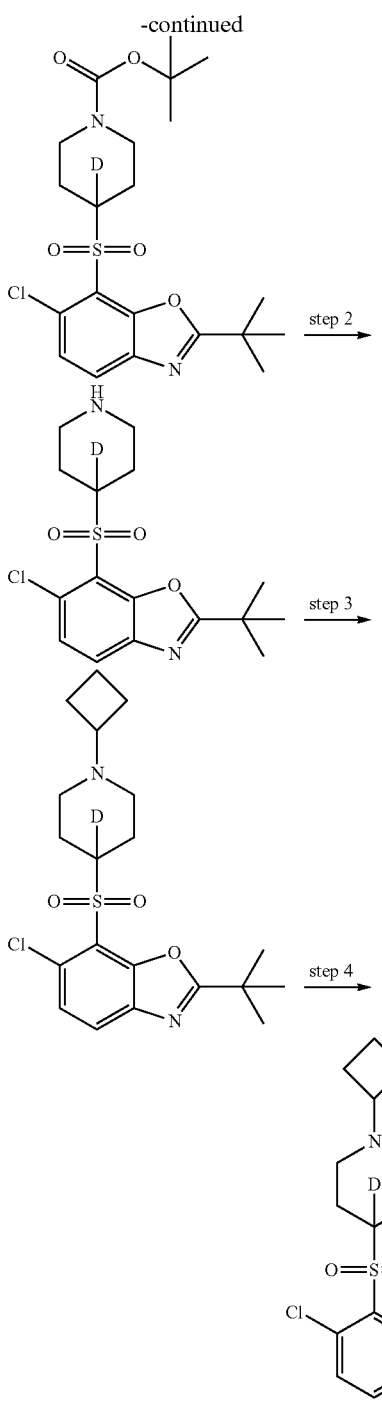

4-((2-(tert-butyl)-6-chlorobenzo[d]oxazol-7-yl)sulfonyl)piperidine-1-carboxylate-d₁ (2.3 g) as a white solid. MS(ES⁺) m/z 402 (M-tBu+H+H⁺).

Step 2: To a solution of tert-butyl 4-((2-(tert-butyl)-6-chlorobenzo[d]oxazol-7-yl)sulfonyl)piperidine-1-carboxylate-di (2.3 g) in DCM (10 mL) was added TFA (2 mL). The mixture was stirred at RT for 2 hours. The mixture was washed with sat. sodium carbonate solution. The organic layer was separated, dried over sodium sulfate and concentrated to afford 2-(tert-butyl)-6-chloro-7-(piperidin-4-ylsulfonyl)benzo[d]oxazole-d₁ (1.8 g) a brown solid. MS(ES⁺) m/z 358 (MH⁺).

Step 3: A solution of 2-(tert-butyl)-6-chloro-7-(piperidin-4-ylsulfonyl)benzo[d]oxazole-di (0.4 g) and cyclobutanone (0.3 mL) in DCM (8 mL) and acetonitrile (8 mL) was stirred for 1 hour. Sodium triacetoxyborohydride (0.7 g) was added portionwise. The mixture was stirred at RT for over 3 days. EA (50 mL) was added. The mixture was washed with brine, dried over sodium sulfate and concentrated to give 2-(tert-butyl)-6-chloro-7-((1-cyclobutyl-4-methylpiperidin-4-yl)sulfonyl)benzo[d]oxazole-di (0.5 g) as a white solid. MS(ES⁺) m/z 412 (MH⁺).

Step 4: To a solution of 2-(tert-butyl)-6-chloro-7-((1-cyclobutylpiperidin-4-yl)sulfonyl)benzo[d]oxazole-di (0.5 g) in 1,4-dioxane (10 mL) was added aq. HCl solution (10 M, 10 mL). The mixture was refluxed for 2 hours, and then concentrated to afford the title compound (470 mg) as a brown solid. MS(ES⁺) m/z 346 (MH⁺).

Intermediate 65: 6-amino-3-chloro-2-((1-cyclobutylpiperidin-4-yl)sulfonyl)phenol, hydrochloride salt

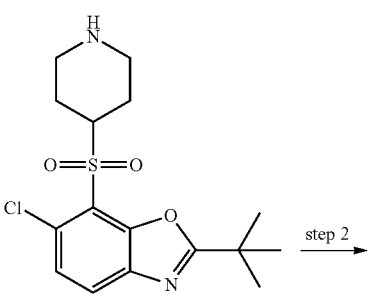

Step 1: To a solution of tert-butyl 4-((2-(tert-butyl)-6-chlorobenzo[d]oxazol-7-yl)sulfonyl)piperidine-1-carboxylate (Intermediate 56, Step 3, 3.0 g) in THF (45 mL) was added BuLi (1.6 M in n-hexane, 12.3 mL) dropwise at −70° C. The mixture was stirred at −70° C. for 30 mins. Methanol-d₄ (0.9 g) was added. The resulting mixture was continued to stir for another 1 hour. The mixture was quenched with sat. ammonium chloride solution, and extracted with EA (2×50 mL). The combined organic layers were washed with brine, dried over sodium sulfate, and evaporated in vacuo. The residue was purified by column chromatography (eluting with a gradient of 0-40% EA in PE) to afford tert-butyl

138

Intermediate 66: 6-amino-3-chloro-2-((1-(2-fluoro-ethyl)piperidin-4-yl)sulfonyl)phenol

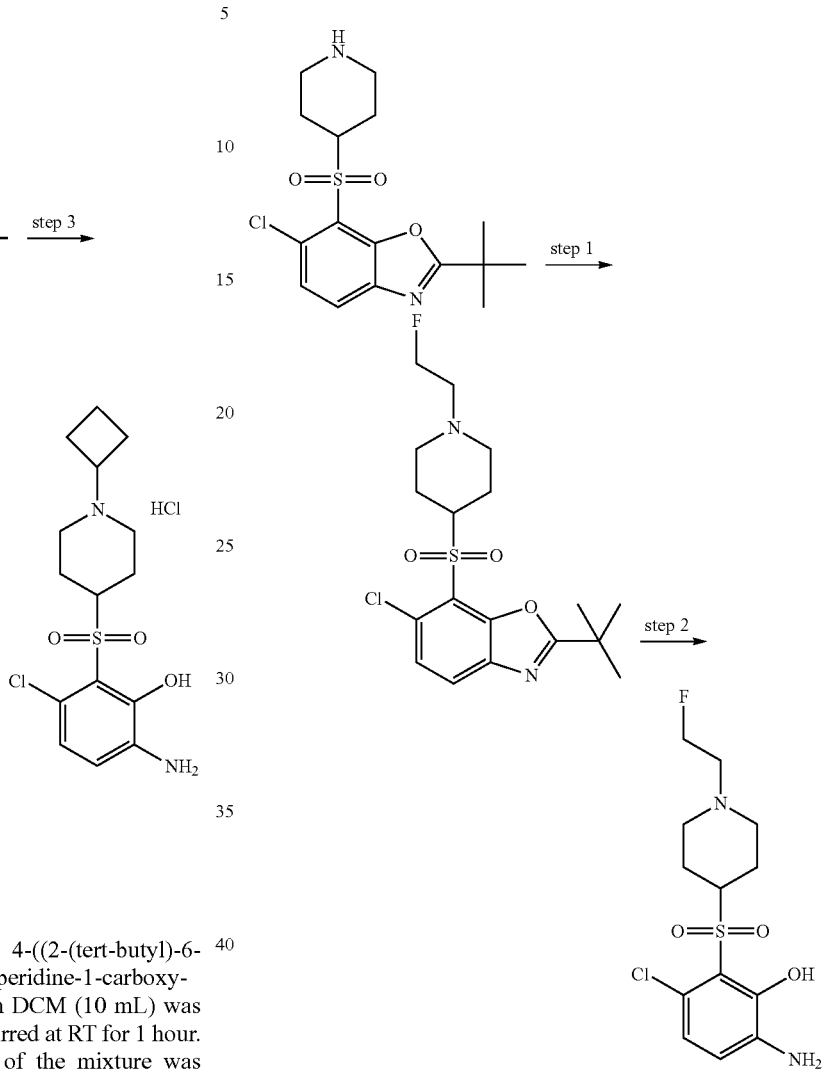

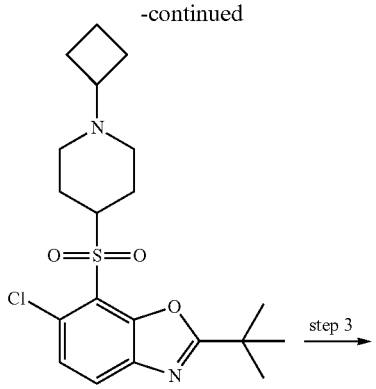

Step 1: To a solution of tert-butyl 4-((2-(tert-butyl)-6-chlorobenzo[d]oxazol-7-yl)sulfonyl)piperidine-1-carboxylate (Intermediate 56, Step 3, 1.1 g) in DCM (10 mL) was added TFA (2 mL). The mixture was stirred at RT for 1 hour. DCM (40 mL) was added. The pH of the mixture was adjusted to 8 with sat. sodium carbonate solution. The organic layer was dried over sodium sulfate and concentrated to afford 2-(tert-butyl)-6-chloro-7-(piperidin-4-ylsulfonyl)benzo[d]oxazole (0.9 g) as a brown solid. MS(ES$^+$) m/z 357 (MH$^+$).

Step 2: A solution of 2-(tert-butyl)-6-chloro-7-(piperidin-4-ylsulfonyl)benzo[d]oxazole (0.4 g) and cyclobutanone (0.3 mL) in DCM (8 mL) and acetonitrile (8 mL) was stirred for 1 hour. Sodium triacetoxyborohydride (0.7 g) was added portionwise. The mixture was stirred at RT overnight. EA (50 mL) was added. The mixture was washed with brine, dried over sodium sulfate and concentrated to give 2-(tert-butyl)-6-chloro-7-((1-cyclobutylpiperidin-4-yl)sulfonyl)benzo[d]oxazole (450 mg) as a white solid. MS(ES$^+$) m/z 411 (MH$^+$).

Step 3: To a solution of 2-(tert-butyl)-6-chloro-7-((1-cyclobutylpiperidin-4-yl)sulfonyl)benzo[d]oxazole (0.5 g) in 1,4-dioxane (10 mL) was added aq. HCl solution (10 M, 10 mL). The mixture was refluxed for 2 hours, and then concentrated to afford the title compound (630 mg) as a brown solid. MS(ES$^+$) m/z 345 (MH$^+$).

Step 1: Potassium carbonate (0.1 g) was added to a solution of 2-(tert-butyl)-6-chloro-7-(piperidin-4-ylsulfonyl)benzo[d]oxazole (Intermediate 65, Step 1, 0.3 g) and 1-bromo-2-fluoroethane (0.1 g) in DMF (3 mL) at RT. The mixture was stirred at 30° C. for 3 hours. The mixture was poured into ice-water (50 mL), and extracted with EA (4×50 mL). The combined organic phases were washed with brine (80 mL), dried over Na$_2$SO$_4$ and concentrated under reduced pressure. The residue was purified by column chromatography (eluting with EA:PE=1:0) to give 2-(tert-butyl)-6-chloro-7-((1-(2-fluoroethyl)piperidin-4-yl)sulfonyl)benzo[d]oxazole (230 mg) as a light yellow solid. MS(ES$^+$) m/z 403 (MH$^+$).

Step 2: To a solution of 2-(tert-butyl)-6-chloro-7-((1-(2-fluoroethyl)piperidin-4-yl)sulfonyl)benzo[d]oxazole (220 mg) in 1,4-dioxane (2 mL) was added sulfuric acid (65%, 0.05 mL). The resulting mixture was stirred for 1 hour at 100° C. After cooling to RT, cold water (30 mL) was added. The resulting mixture was neutralized with sat. Na$_2$CO$_3$ solution. The aq. layer was extracted with EA (2×100 mL). The combined organic layers were dried over Na$_2$SO$_4$, filtered and concentrated in vacuo to give the title compound (120 mg) as a dark solid. MS(ES$^+$) m/z 337 (MH$^+$).

Intermediate 67: 6-amino-3-chloro-2-((octahydroindolizin-7-yl)sulfonyl)phenol, TFA salt

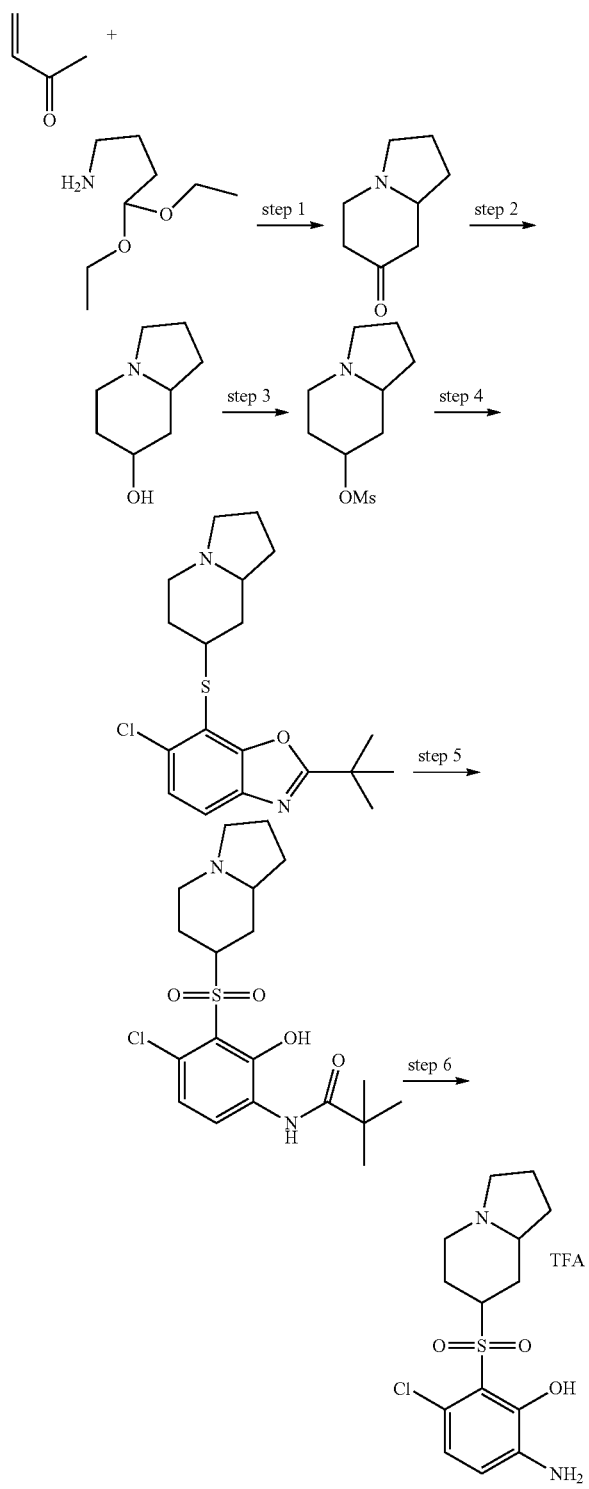

Step 1: To a stirred solution of 4,4-diethoxybutan-1-amine (16.0 g) in diethyl ether (60 mL) at 0° C. was added freshly distilled but-3-en-2-one (9.0 g) dropwise. The mixture was maintained at 0° C. for 1 hour. The amine was extracted into aq. HCl solution (2.5 M, 250 mL). The acidic aq. phase was heated on a steam-bath for 2 hours, and then concentrated under reduced pressure. The residue was distilled under vacuum (70° C. at 2 mmHg) to give hexahydroindolizin-7 (1H)-one (2.6 g) as a colorless oil. $^1$H-NMR (400 MHz, CDCl$_3$) δ ppm 3.33 (dd, J=9.5, 7.6 Hz, 1H), 3.16 (t, J=8.7 Hz, 1H), 2.67-2.56 (m, 1H), 2.53 (d, J=12.7 Hz, 1H), 2.40-2.18 (m, 5H), 2.05-1.90 (m, 2H), 1.89-1.77 (m, 1H), 1.60-1.47 (m, 1H); MS(ES$^+$) m/z 140 (MH$^+$).

Step 2: To a suspension of LiAlH$_4$ (1.2 g) in THF (50 mL) was added a solution of hexahydroindolizin-7(1H)-one (2.6 g) in THF (50 mL) dropwise at 0° C. The mixture was stirred at RT for 3 hours. After cooling, the excess reagent was decomposed by addition of water (0.3 mL). The mixture was stirred at RT for another 1 hour. The mixture was filtered through a pad of celite, dried over Na$_2$SO$_4$ and concentrated to give octahydroindolizin-7-ol (2.5 g) as a light yellow oil. MS(ES$^+$) m/z 142 (MH$^+$).

Step 3: To a solution of octahydroindolizin-7-ol (2.5 g) in DCM (40 mL) was added TEA (4.9 mL), then followed by MsCl (1.5 mL) in an ice bath. The mixture was stirred at RT for 4 hours. Water (100 mL) was added. The organic layer was separated, dried over sodium sulfate, filtered and concentrated to afford octahydroindolizin-7-yl methanesulfonate (3.7 g) as a yellow oil.

Step 4: To a solution of octahydroindolizin-7-yl methanesulfonate (3.6 g), 2-(tert-butyl)-6-chlorobenzo[d]oxazole-7-thiol (2.0 g) in DMF (25 mL) was added potassium carbonate (2.3 g). The mixture was stirred at 90° C. for 2 hours. EA (150 mL) was added. The mixture was washed with brine for three times. The organic layer was dried over sodium sulfate, filtered and concentrated. The residue was purified by column chromatography (eluting with MeOH:DCM=0:1 to 15:85) to afford 2-(tert-butyl)-6-chloro-7-((octahydroindolizin-7-yl)thio)benzo[d]oxazole (1.7 g) as a yellow vicious liquid. MS(ES$^+$) m/z 365 (MH$^+$).

Step 5: To a solution of 2-(tert-butyl)-6-chloro-7-((octahydroindolizin-7-yl)thio)benzo[d]oxazole (200 mg) and H$_2$O$_2$ (0.3 mL) in methanol (4 mL) was added in sodium tungstate dihydrate (9 mg). After stirred at RT overnight, the reaction mixture was quenched with sat. sodium hyposulfite, and partitioned between EA (25 mL) and sat. sodium carbonate (25 mL). The organic phase was washed with brine (25 mL), dried over sodium sulphate, filtered and concentrated. The resulting residue was purified by reversed phase chromatography (C18, 0-50% MeCN:H$_2$O (0.1% TFA): 0:1 to 1:1) to afford N-(4-chloro-2-hydroxy-3-((octahydroindolizin-7-yl)sulfonyl)phenyl)pivalamide (150 mg) as a white solid. MS(ES$^+$) m/z 415 (MH$^+$).

Step 6: To a solution of N-(4-chloro-2-hydroxy-3-((octahydroindolizin-7-yl)sulfonyl)phenyl)pivalamide (150 mg) in 1,4-dioxane (4 mL) was added conc. HCl (2 mL) in 1,4-dioxane (4 mL). The mixture was stirred at 100° C. overnight, and concentrated. The resulting residue was purified by reversed phase chromatography (C18, MeCN:H$_2$O (0.1% TFA): 0:1 to 1:1) to afford the title compound (144 mg) as a white solid. MS(ES$^+$) m/z 331 (MH$^+$).

Intermediate 68: 6-amino-3-chloro-2-((3-fluoroazetidin-1-yl)sulfonyl)phenol

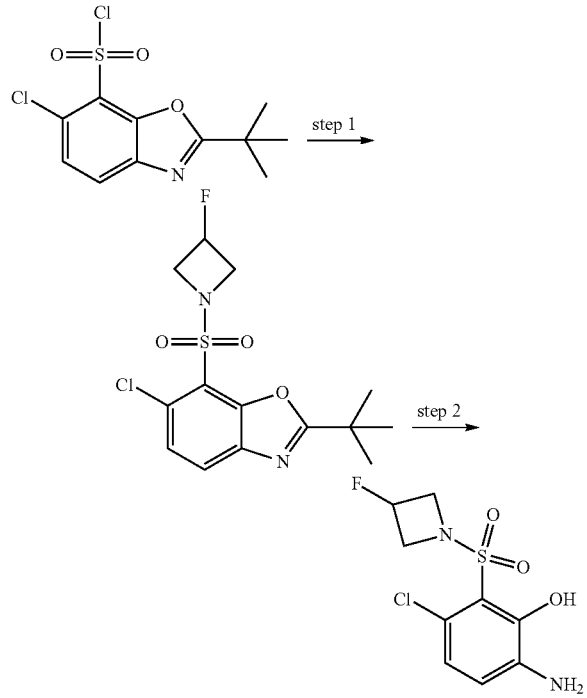

Step 1: A solution of 2-(tert-butyl)-6-chlorobenzo[d]oxazole-7-sulfonyl chloride (600 mg), 3-fluoroazetidine, hydrochloride (174 mg) and DIPEA (504 mg) in THF (6 mL) was stirred at RT for 6 hours. Cold water (30 mL) was added. The aq. layer was extracted with DCM (2×100 mL). The combined organic layers were dried over Na$_2$SO$_4$, filtered and concentrated under reduced pressure. The residue was purified by column chromatography (eluting with PE:EA=3:1) to give 2-(tert-butyl)-6-chloro-7-((3-fluoroazetidin-1-yl)sulfonyl)benzo[d]oxazole (220 mg) as a yellow gel. MS(ES$^+$) m/z 347 (MH$^+$).

Step 2: A solution of sulfuric acid (65%, 1 mL) and 2-(tert-butyl)-6-chloro-7-((3-fluoroazetidin-1-yl)sulfonyl)benzo[d]oxazole (200 mg) in dioxane (4 mL) was stirred at 90° C. for 4 hours. Cold water (30 mL) was added. The resulting mixture was extracted with DCM (2×100 mL). The combined organic layers were dried over Na$_2$SO$_4$, filtered and concentrated in vacuo to give the title compound (150 mg) as a yellow solid. MS(ES$^+$) m/z 281 (MH$^+$).

Intermediate 69: (R)-6-amino-3-chloro-2-((3-fluoropyrrolidin-1-yl)sulfonyl)phenol

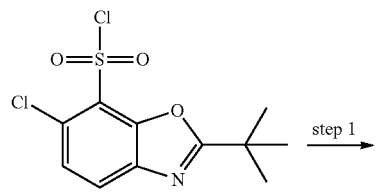

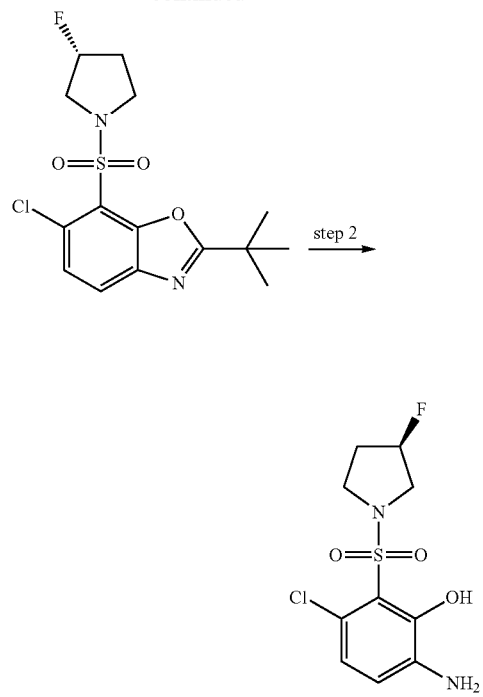

Step 1: A solution of 2-(tert-butyl)-6-chlorobenzo[d]oxazole-7-sulfonyl chloride (600 mg), (R)-3-fluoropyrrolidine (173 mg) and DIPEA (0.7 mL) was stirred in THF (6 mL) at RT for 6 hours. Cold water (30 mL) was added. The aq. layer was extracted with DCM (2×100 mL). The combined organic layers were dried over Na$_2$SO$_4$, filtered and concentrated in vacuo. The residue was purified by column chromatography (eluting with PE:EA=10:1) to give (R)-2-(tert-butyl)-6-chloro-7-((3-fluoropyrrolidin-1-yl)sulfonyl)benzo[d]oxazole (500 mg) as an oil. MS(ES$^+$) m/z 361 (MH$^+$).

Step 2: (R)-2-(tert-butyl)-6-chloro-7-((3-fluoropyrrolidin-1-yl)sulfonyl)benzo[d]oxazole (50 mg) was dissolved in 1,4-dioxane (5 mL) and water (1 mL). Conc. sulfuric acid (0.1 mL) was added. The mixture was heated to 100° C. overnight to afford a brown solution. The mixture was cooled to RT, evaporated in vacuo, and then treated with aq. NaOH solution (6 M) until pH=12 in an ice bath. The mixture was extracted with EA (4×~50 mL). The combined organic layers were dried over sodium sulfate, filtered and concentrated to afford the title compound (20 mg) as an oil. MS(ES$^+$) m/z 295 (MH$^+$).

Intermediate 70: 6-amino-3-chloro-2-((3,3-difluoropyrrolidin-1-yl)sulfonyl)phenol

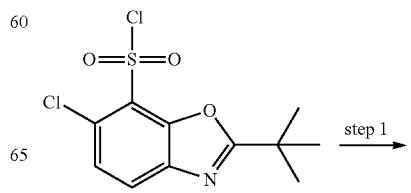

-continued

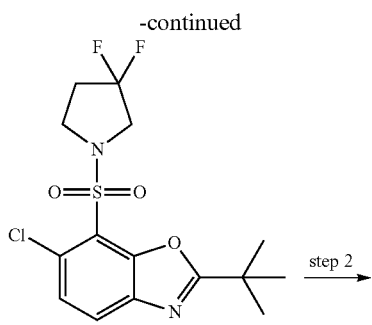

step 2

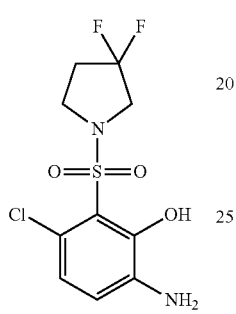

Step 1: To a solution of TEA (0.8 mL) and 3,3-difluoro-pyrrolidine (215 mg) in THF (10 mL) was added 2-(tert-butyl)-6-chlorobenzo[d]oxazole-7-sulfonyl chloride (618 mg) in small portion at RT. The mixture was stirred overnight. Cold water (30 mL) was added. The resulting mixture was extracted with DCM (2×100 mL). The combined organic layers were dried over Na$_2$SO$_4$, filtered and concentrated in vacuo. The residue was purified by column chromatography (eluting with PE:EA=1:1) to give 2-(tert-butyl)-6-chloro-7-((3,3-difluoropyrrolidin-1-yl)sulfonyl) benzo[d]oxazole (253 mg) as a yellow solid. MS(ES$^+$) m/z 379 (MH$^+$).

Step 2: A solution of 2-(tert-butyl)-6-chloro-7-((3,3-difluoropyrrolidin-1-yl)sulfonyl)benzo[d]oxazole (253 mg) in sulfuric acid (65%, 2 mL) and 1,4-dioxane (8 mL) was stirred at 90° C. overnight. The residue was purified by reversed phase chromatography (C8, mobile phase 0.01% CF$_3$COOH/H$_2$O, CH$_3$OH, 30 mL/min) (10%~55%, 5 min; 55~55%, 6 min; 40%~95%, 1 min; 95%~95%, 1 min) to give the title compound (108 mg) as a yellow solid. MS(ES$^+$) m/z 313 (MH$^+$).

Intermediate 71: 1-((3-amino-6-chloro-2-hydroxyphenyl)sulfonyl)piperidin-4-ol

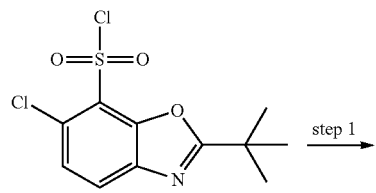

step 1

-continued

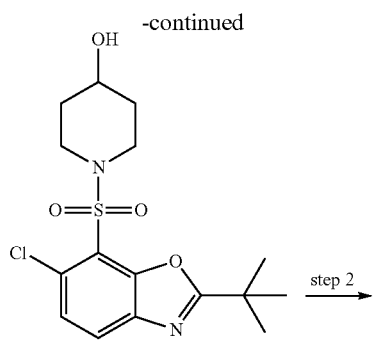

step 2

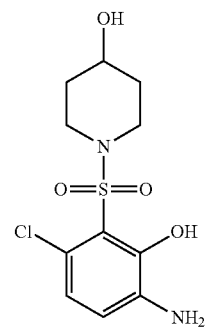

Step 1:

To a solution of TEA (0.8 mL) and piperidin-4-ol (203 mg) in THF (10 mL) was added 2-(tert-butyl)-6-chlorobenzo[d]oxazole-7-sulfonyl chloride (618 mg) in small portion at RT. The mixture was stirred overnight. Cold water (30 mL) was added. The resulting mixture was extracted with DCM (2×100 mL). The combined organic layers were dried over Na$_2$SO$_4$, filtered and concentrated in vacuo. The residue was purified by column chromatography (eluting with PE:EA=5:1) to give 1-((2-(tert-butyl)-6-chlorobenzo[d]oxazol-7-yl) sulfonyl)piperidin-4-ol (300 mg) as a yellow solid. MS(ES$^+$) m/z 373 (MH$^+$).

Step 2: A solution of 1-((2-(tert-butyl)-6-chlorobenzo[d] oxazol-7-yl)sulfonyl)piperidin-4-ol (300 mg) in sulfuric acid (65%, 2 mL) and 1,4-dioxane (8 mL) was stirred at 90° C. overnight. The residue was purified by reversed phase chromatography (C8, mobile phase 0.01% CF$_3$COOH/H$_2$O, CH$_3$OH, 30 mL/min) (10%~55%, 5 min; 55~55%, 6 min; 40%~95%, 1 min; 95%~95%, 1 min) to give the title compound (153 mg) as a yellow solid. MS(ES$^+$) m/z 307 (MH$^+$).

Intermediate 72: 2-((1H-pyrrolo[2,3-b]pyridin-1-yl) sulfonyl)-6-amino-3-chlorophenol

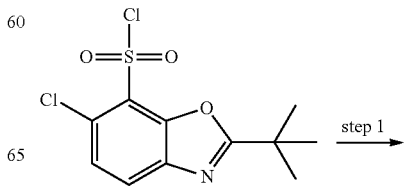

step 1

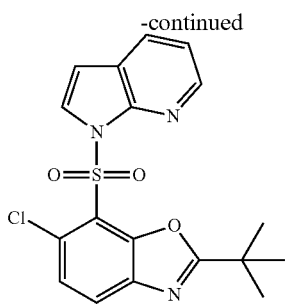

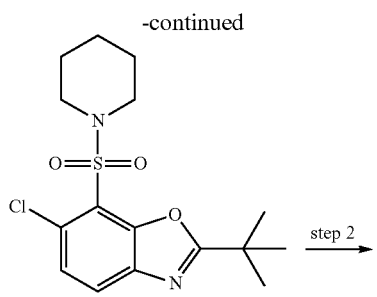

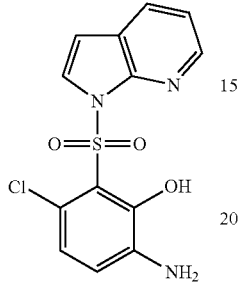

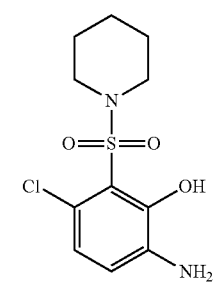

Step 1: To a mixture of sodium hydride (244 mg) in THF (5 mL) under a nitrogen atomsphere at 0° C. was added a solution of 1H-pyrrolo[2,3-b]pyridine (600 mg) in THF (8 mL) slowly. The mixture was stirred at RT for 20 mins. A solution of 2-(tert-butyl)-6-chlorobenzo[d]oxazole-7-sulfonyl chloride (1565 mg) in THF (15 mL) was added slowly. After addition, the mixture was stirred at RT for 1 hour. NH₄Cl (aq., 75 mL) was added. The resulting mixture was extracted with EA (3×40 mL). The combined organic layers were dried over MgSO₄, filtered and concentrated under reduced pressure. The residue was purified by column chromatography (eluting with EA:PE=1:5) to give 7-((1H-pyrrolo[2,3-b]pyridin-1-yl)sulfonyl)-2-(tert-butyl)-6-chlorobenzo[d]oxazole (1.5 g) as a yellow solid. MS(ES⁺) m/z 390 (MH⁺).

Step 2: 7-((1H-pyrrolo[2,3-b]pyridin-1-yl)sulfonyl)-2-(tert-butyl)-6-chlorobenzo[d]oxazole (1.3 g) was dissolved in 1,4-dioxane (10 mL) and water (10 mL). Conc. sulfuric acid (4.4 mL) was added. The mixture was heated to 100° C. overnight. After cooling, the mixture was combined with another batch of the same reaction using 7-((1H-pyrrolo[2,3-b]pyridin-1-yl)sulfonyl)-2-(tert-butyl)-6-chlorobenzo[d]oxazole (200 mg) as starting material. The mixture was treated with sodium carbonate to pH=8 in an ice bath. The mixture was extracted with EA (4×50 mL). The combined organic layers were dried over sodium sulfate, filtered and concentrated. The residue was purified by preparative HPLC to afford the title compound (350 mg) as a brown solid. MS(ES⁺) m/z 324 (MH⁺).

Intermediate 73:
6-amino-3-chloro-2-(piperidin-1-ylsulfonyl)phenol

Step 1: To a solution of TEA (303 mg) and piperidine (204 mg) in THF (30 mL) was added 2-(tert-butyl)-6-chlorobenzo[d]oxazole-7-sulfonyl chloride (616 mg). The mixture was stirred for 4 hours. Cold water (30 mL) was added. The resulting mixture was extracted with DCM (2×100 mL). The combined organic layers were dried over Na₂SO₄, filtered and concentrated in vacuo. The residue was purified by column chromatography (eluting with PE:EA=1:1) to give 2-(tert-butyl)-6-chloro-7-(piperidin-1-ylsulfonyl)benzo[d]oxazole (300 mg) as a yellow solid. MS(ES⁺) m/z 357 (MH⁺).

Step 2: To a solution of 2-(tert-butyl)-6-chloro-7-(piperidin-1-ylsulfonyl)benzo[d]oxazole (300 mg) in 1,4-dioxane (4 mL) was added sulfuric acid (65%, 2 mL). The resulting mixture was stirred for 1 hour at 100° C. After cooling to RT, cold water (30 mL) was added. The resulting mixture was neutralized with sat. Na₂CO₃ solution. The aq. layer was extracted with EA (2×100 mL). The combined organic layers were dried over Na₂SO₄, filtered and concentrated in vacuo to give the title compound (150 mg) as a dark solid. MS(ES⁺) m/z 291 (MH⁺).

Intermediate 74: 6-amino-3-chloro-2-(((7S,8aS)-7-fluorohexahydropyrrolo[1,2-a]pyrazin-2(1H)-yl)sulfonyl)phenol

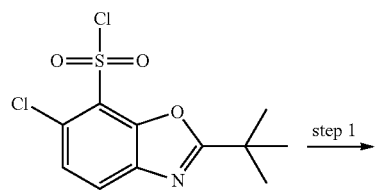

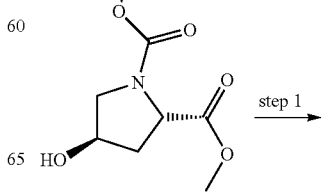

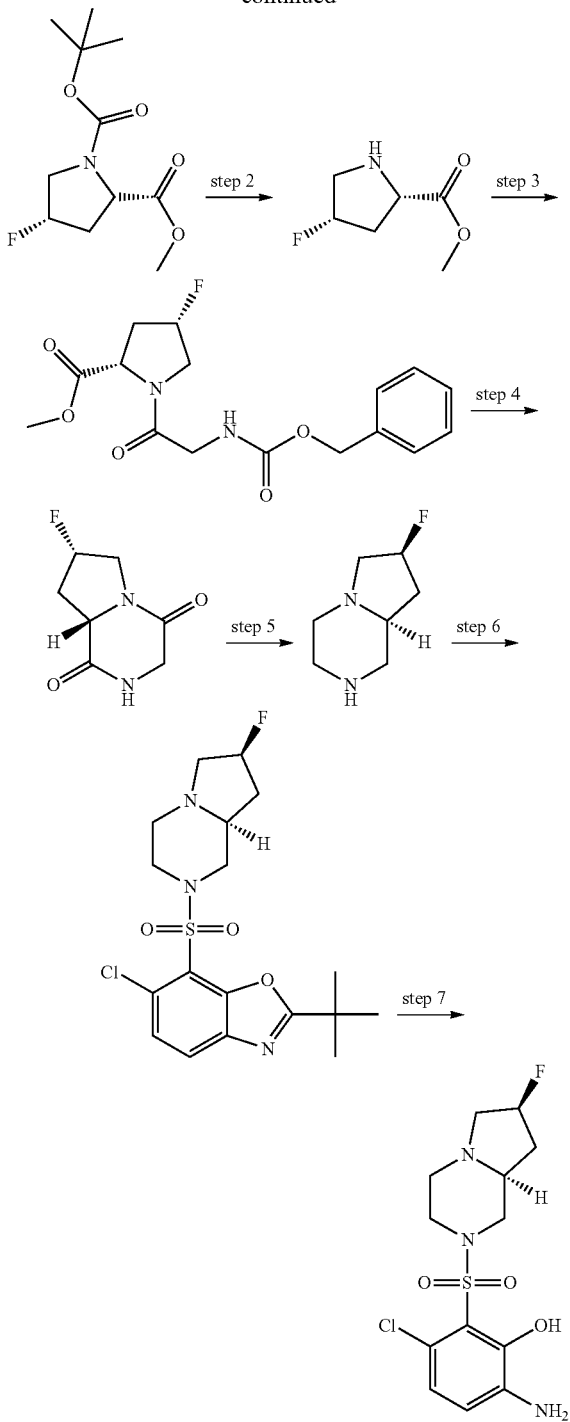

chromatography (eluting with PE:EA=5:1) to give (2S,4S)-1-tert-butyl 2-methyl 4-fluoropyrrolidine-1,2-dicarboxylate (526 mg) as a white solid. $^1$H-NMR (400 MHz, CDCl$_3$) δ ppm 5.20 (d, J=52.8 Hz, 1H), 4.49 (dd, J=46.7, 9.4 Hz, 1H), 3.98-3.49 (m, 5H), 2.60-2.22 (m, 2H), 1.45 (dd, J=22.4, 10.7 Hz, 9H).

Step 2: A mixture of (2S,4S)-1-tert-butyl 2-methyl 4-fluoropyrrolidine-1,2-dicarboxylate (526 mg) and HCl solution (1 M in 1,4-dioxane, 20 mL) was stirred at RT for 2 hours. The solvent was removed in vacuo to give (2S,4S)-methyl 4-fluoropyrrolidine-2-carboxylate, hydrochloride (400 mg) as a white solid. $^1$H-NMR (500 MHz, DMSO-d$_6$) δ ppm 10.02 (s, 1H), 5.45 (dt, J=52.4, 3.8 Hz, 1H), 4.65 (d, J=7.1 Hz, 1H), 3.78 (s, 3H), 3.67-3.42 (m, 2H), 2.45 (m, 1H).

Step 3: A solution of (2S,4S)-methyl 4-fluoropyrrolidine-2-carboxylate, hydrochloride (370 mg), TEA (0.3 mL) and 2-(((benzyloxy)carbonyl)amino)acetic acid (422 mg) was stirred in DCM (20 mL) at RT for 10 mins. Then bis(2-oxooxazolidin-3-yl)phosphinic chloride (513 mg) was added. The mixture was stirred at RT overnight. Cold water (30 mL) was added. The aq. layer was extracted with DCM (2×100 mL). The combined organic layers were dried over Na$_2$SO$_4$, filtered and concentrated in vacuo. The residue was purified by column chromatography (eluting with PE:EA=1:1) to give (2S,4S)-methyl 1-(2-(((benzyloxy)carbonyl)amino)acetyl)-4-fluoropyrrolidine-2-carboxylate (570 mg) as a yellow oil. MS(ES$^+$) m/z 339 (MH$^+$).

Step 4: A solution of (2S,4S)-methyl 1-(2-(((benzyloxy)carbonyl)amino)acetyl)-4-fluoropyrrolidine-2-carboxylate (620 mg) and Pd/C (20 mg) was stirred in methanol (40 mL) under H$_2$ at RT overnight. Cold water (30 mL) was added and the aq. layer was washed with DCM (2×100 mL), and then concentrated in vacuo to give (7S,8aS)-7-fluorohexahydropyrrolo[1,2-a]pyrazine-1,4-dione (300 mg) as a white solid. MS(ES$^+$) m/z 173 (MH$^+$).

Step 5: To a suspension of LiAlH$_4$ (55 mg) in THF (20 mL) was added (7S,8aS)-7-fluorohexahydropyrrolo[1,2-a]pyrazine-1,4-dione (250 mg) in THF (2 mL) dropwise at 0° C. The resulting mixture was stirred at 75° C. for 30 mins. The reaction mixture was cooled to 0° C., and water (2 mL) was added slowly. The mixture was stirred for 10 mins and then dried over MgSO$_4$. The resulting mixture was filtered through a pad of celite, and washed with THF (20 mL). The filtrate was concentrated under vacuum to give (7S,8aS)-7-fluorooctahydropyrrolo[1,2-a]pyrazine (100 mg) as a yellow oil. MS(ES$^+$) m/z 145 (MH$^+$).

Step 6: A solution of 2-(tert-butyl)-6-chlorobenzo[d]oxazole-7-sulfonyl chloride (1385 mg), (7S,8aS)-7-fluorooctahydropyrrolo[1,2-a]pyrazine (700 mg) and DIPEA (1.7 mL) was stirred in THF (15 mL) at RT for 6 hours. Cold water (30 mL) was added. The aq. layer was extracted with DCM (2×100 mL). The combined organic layers were dried over Na$_2$SO$_4$, filtered and concentrated in vacuo. The residue was purified by column chromatography (eluting with PE:EA=10:1) to give 2-(tert-butyl)-6-chloro-7-(((7S,8aS)-7-fluorohexahydropyrrolo[1,2-a]pyrazin-2(1H)-yl)sulfonyl)benzo[d]oxazole (400 mg) as a brown oil. MS(ES$^+$) m/z 412 (MH$^+$).

Step 7: 2-(Tert-butyl)-6-chloro-7-(((7S,8aS)-7-fluorohexahydropyrrolo[1,2-a]pyrazin-2(1H)-yl)sulfonyl)benzo[d]oxazole (130 mg) was dissolved in 1,4-dioxane (8 mL) and water (2 mL). Conc. H$_2$SO$_4$ (0.02 mL) was added. The mixture was heated to 100° C. overnight to give a brown solution. The reaction mixture was cooled to RT and evaporated in vacuo. The residue was treated with aq. NaOH solution (6 M) until pH=12 in an ice bath. The resulting mixture was extracted with EA (4×~50 mL). The combined Step 1: To a stirred solution of (2S,4R)-1-tert-butyl 2-methyl 4-hydroxypyrrolidine-1,2-dicarboxylate (1.0 g) in DCE (30 mL) cooled to −100° C. was added DAST (0.6 mL) over a period of 30 mins. The mixture was stirred at this temperature for 1 hour, and then at RT for 16 hours. The mixture was quenched by addition of crushed ice (30 g) and solid NaHCO$_3$ (5 g). The organic layer was separated. The aq. layer was extracted with DCM (2×50 mL). The combined organic layers were washed with brine (50 mL), dried over anhydrous Na$_2$SO$_4$. The solvent was removed under reduced pressure. The residue was purified by column Intermediate 75: (S)-6-amino-3-chloro-2-((8a-methylhexahydropyrrolo[1,2-a]pyrazin-2(1H)-yl)sulfonyl)phenol

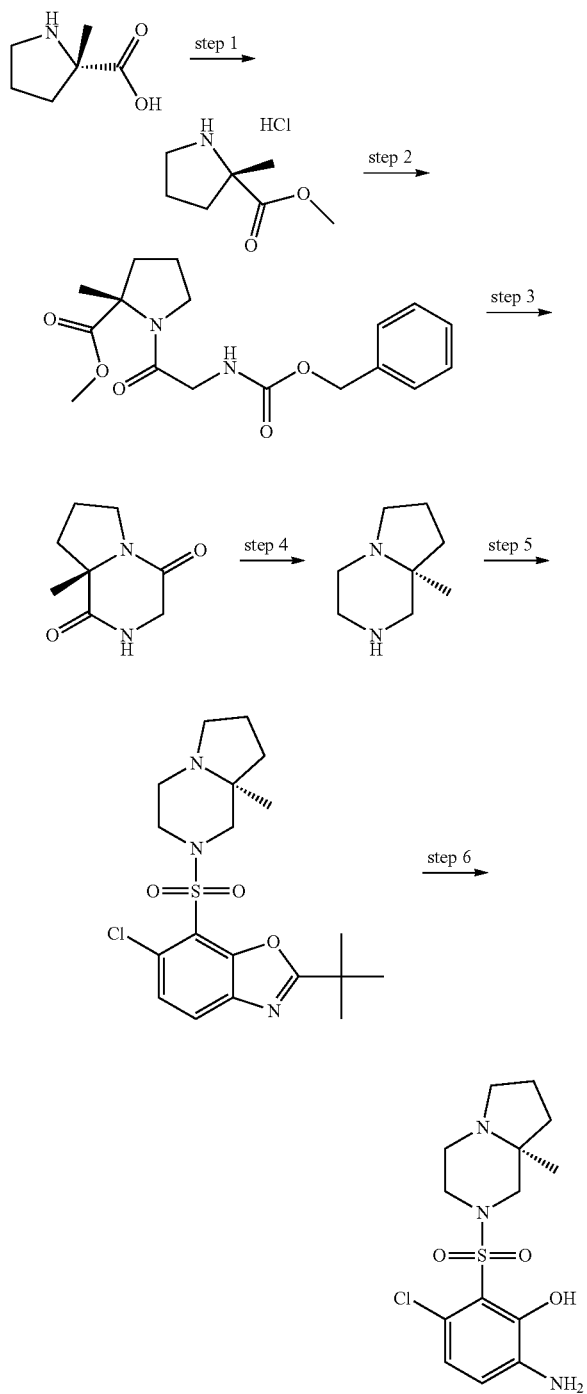

Step 1: To a solution of (S)-2-methylpyrrolidine-2-carboxylic acid (1.0 g) in methanol (10 mL) was added sulfurous dichloride (4.6 g). The resulting mixture was stirred for 3 hours. The solvent was concentrated under vacuum to give (S)-methyl 2-methylpyrrolidine-2-carboxylate, hydrochloride (1.1 g) as a white solid. $^1$H-NMR (400 MHz, CDCl$_3$) δ ppm 10.56 (s, 1H), 9.53 (s, 1H), 3.86 (s, 3H), 3.69-3.51 (m, 2H), 2.50-2.32 (m, 1H), 2.28-1.92 (m, 3H), 1.86 (d, J=6.5 Hz, 3H); MS(ES$^+$) m/z 144 (MH$^+$).

Step 2: A solution of (S)-methyl 2-methylpyrrolidine-2-carboxylate, hydrochloride (840 mg), TEA (2.3 mL) and 2-(((benzyloxy)carbonyl)amino)acetic acid (1467 mg) was stirred in DCM (20 mL) at RT for 10 mins. Then bis(2-oxooxazolidin-3-yl)phosphinic chloride (1785 mg) was added. The mixture was stirred at RT overnight. Cold water (30 mL) was added. The aq. layer was extracted with DCM (2×100 mL). The combined organic layers were dried over Na$_2$SO$_4$, filtered and concentrated in vacuo. The residue was purified by column chromatography (eluting with PE:EA=1:1) to give (S)-methyl 1-(2-(((benzyloxy)carbonyl)amino)acetyl)-2-methylpyrrolidine-2-carboxylate (1.3 g) as an oil. MS(ES$^+$) m/z 335 (MH$^+$).

Step 3: A solution of (S)-methyl 1-(2-(((benzyloxy)carbonyl)amino)acetyl)-2-methylpyrrolidine-2-carboxylate (1.3 g) and Pd/C (0.404 g) was stirred in methanol (46 mL) under a hydrogen atmosphere at RT overnight. Cold water (30 mL) was added. The aq. layer was washed with DCM (2×100 mL), and then concentrated in vacuo to give (S)-8a-methylhexahydropyrrolo[1,2-a]pyrazine-1,4-dione (1.1 g) as a white solid. MS(ES$^+$) m/z 169 (MH$^+$).

Step 4: To a suspension of LiAlH$_4$ (812 mg) in THF (15 mL) was added (S)-8a-methylhexahydropyrrolo[1,2-a]pyrazine-1,4-dione (900 mg) in THF (2 mL) dropwise at 0° C. The resulting mixture was stirred at 75° C. for 30 mins. The reaction mixture was cooled to 0° C., and water (2 mL) was added slowly. The mixture was stirred for 10 mins and then dried over MgSO$_4$. The resulting mixture was filtered through a pad of celite, and washed with THF (20 mL). The filtrate was concentrated under vacuum to give (S)-8a-methyloctahydropyrrolo[1,2-a]pyrazine (580 mg) as a yellow oil. MS(ES$^+$) m/z 141 (MH$^+$).

Step 5: A solution of 2-(tert-butyl)-6-chlorobenzo[d]oxazole-7-sulfonyl chloride (1385 mg), (S)-8a-methyloctahydropyrrolo[1,2-a]pyrazine (700 mg) and DIPEA (1.7 mL) was stirred in THF (15 mL) at RT for 6 hours. Cold water (30 mL) was added and the aq. layer was extracted with DCM (2×100 mL). The combined organic layers were dried over Na$_2$SO$_4$, filtered and concentrated in vacuo. The residue was purified by column chromatography (eluting with PE:EA=10:1) to give (S)-2-(tert-butyl)-6-chloro-7-((8a-methylhexahydropyrrolo[1,2-a]pyrazin-2(1H)-yl)sulfonyl)benzo[d]oxazole (400 mg) as a brown oil. MS(ES$^+$) m/z 412 (MH$^+$).

Step 6: (S)-2-(tert-butyl)-6-chloro-7-((8a-methylhexahydropyrrolo[1,2-a]pyrazin-2(1H)-yl)sulfonyl)benzo[d]oxazole (320 mg) was dissolved in 1,4-dioxane (20 mL) and water (5 mL). Conc. H$_2$SO$_4$ (0.04 mL) was added. The mixture was heated to 100° C. overnight to afford a brown solution. The reaction mixture was cooled to RT and evaporated in vacuo. The residue was treated with aq. NaOH solution (6 M) until pH=12 in an ice bath. The mixture was extracted with EA (4×~50 mL). The combined organic layers were dried over sodium sulfate, filtered and concentrated to give the title compound (260 mg) as an oil. MS(ES$^+$) m/z 346 (MH$^+$).

Intermediate 76: 4-amino-2-(tert-butylsulfonyl)-3-hydroxybenzonitrile

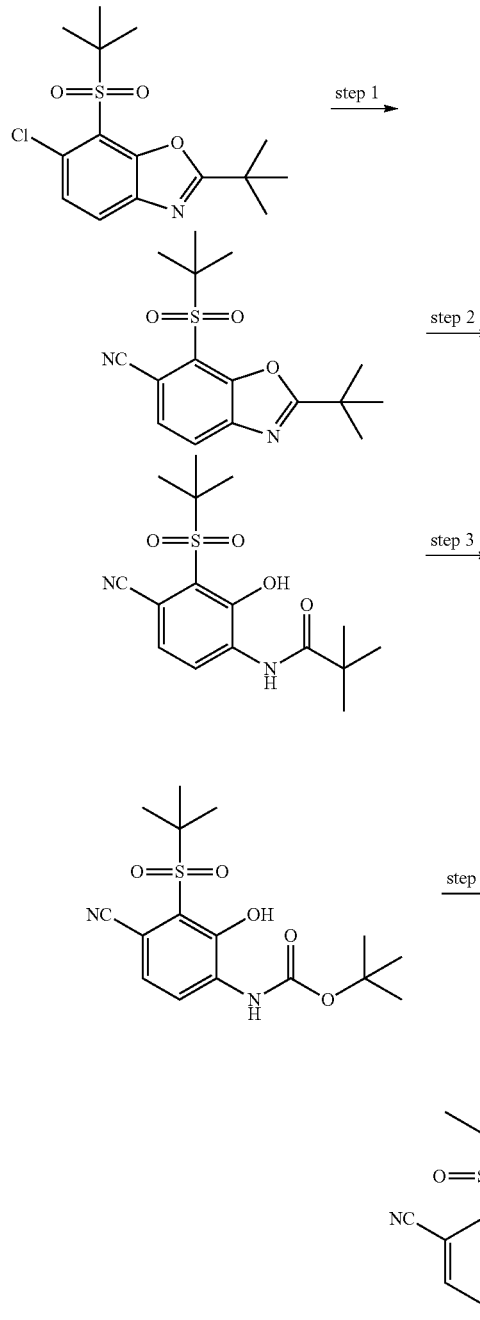

Step 1: The reaction was carried out in five batches (600 mg each) for microwave synthesis, and then combined for purification: A mixture of 2-(tert-butyl)-7-(tert-butylsulfonyl)-6-chlorobenzo[d]oxazole (Intermediate 44, Step 3, 0.6 g) and copper(I) cyanide (1.6 g) in NMP (4 mL) was stirred at 180° C. in the microwave for 90 mins. After cooling, the five batches were combined, and diluted with EA (100 mL) and water (100 mL). After filtration, the organic layer was separated, washed, dried, filtered and concentrated. The residue was purified by column chromatography (eluting with PE:EA=1:0 to 7:3) to afford 2-(tert-butyl)-7-(tertbutylsulfonyl)benzo[d]oxazole-6-carbonitrile (1.0 g). MS(ES⁺) m/z 321 (MH⁺).

Step 2: To a solution of 2-(tert-butyl)-7-(tert-butylsulfonyl)benzo[d]oxazole-6-carbonitrile (1.0 g) in ethanol (25 mL) and water (25 mL) was added sodium hydroxide (0.3 g). The resulting mixture was stirred at 60° C. for 1 hour, and then concentrated under reduced pressure. The residue was diluted with water (50 mL), acidified with aq. citric acid to pH=6, and extracted with EA (2×50 mL). The combined organic layers were washed, dried, filtered and concentrated to afford N-(3-(tert-butylsulfonyl)-4-cyano-2-hydroxyphenyl)pivalamide (1.1 g). MS(ES⁺) m/z 361 (MH⁺).

Step 3: To a solution of N-(3-(tert-butylsulfonyl)-4-cyano-2-hydroxyphenyl)pivalamide (1.2 g) in THF (30 mL) was added DMAP (0.04 g) and Boc₂O (1.6 mL). The mixture was stirred at 60° C. for 2 hours. To the mixture was added hydrazine.H₂O (1.6 mL). The resulting mixture was stirred at RT overnight, diluted with water (50 mL), and extracted with EA (2×100 mL). The combined organic layers were washed, dried, filtered and concentrated. The residue was purified by column chromatography (eluting with PE:EA=1:0 to 7:3) to afford tert-butyl (3-(tert-butylsulfonyl)-4-cyano-2-hydroxyphenyl)carbamate (1.2 g). MS(ES⁺) m/z 355 (MH⁺).

Step 4: To a solution of tert-butyl (3-(tert-butylsulfonyl)-4-cyano-2-hydroxyphenyl)carbamate (1.2 g) in DCM (25 mL) was added TFA (2.6 mL). The resulting mixture was stirred at RT overnight. DCM was removed. The residue was basified with aq. NaHCO₃ solution (pH=8), and extracted with EA (2×50 mL). The combined organic layers were washed, dried, filtered and concentrated to afford the title compound (0.8 g). MS(ES⁺) m/z 255 (MH⁺).

Intermediate 77: 6-amino-3-chloro-2-((cis-3-hydroxycyclobutyl)sulfonyl)phenol

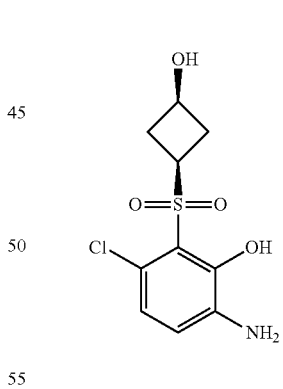

A mixture of cis-3-((2-(tert-butyl)-6-chlorobenzo[d]oxazol-7-yl)sulfonyl)cyclobutanol (Intermediate 28, Step 3, 1.2 g) and conc. H₂SO₄ (1.9 mL) in 1,4-dioxane (5 mL) and water (10 mL) was stirred at 120° C. for 6 hours. The resulting mixture was concentrated under reduced pressure. The residue was treated with aq. NaHCO₃ solution to pH=8, and then extracted with EA (2×50 mL). The combined organic phases were washed, dried and concentrated to afford the title compound (0.7 g). MS(ES⁺) m/z 278 (MH⁺).

Intermediate 78: 6-amino-3-chloro-2-(((1r,3r)-3-(pyrrolidin-1-yl)cyclobutyl)sulfonyl)phenol

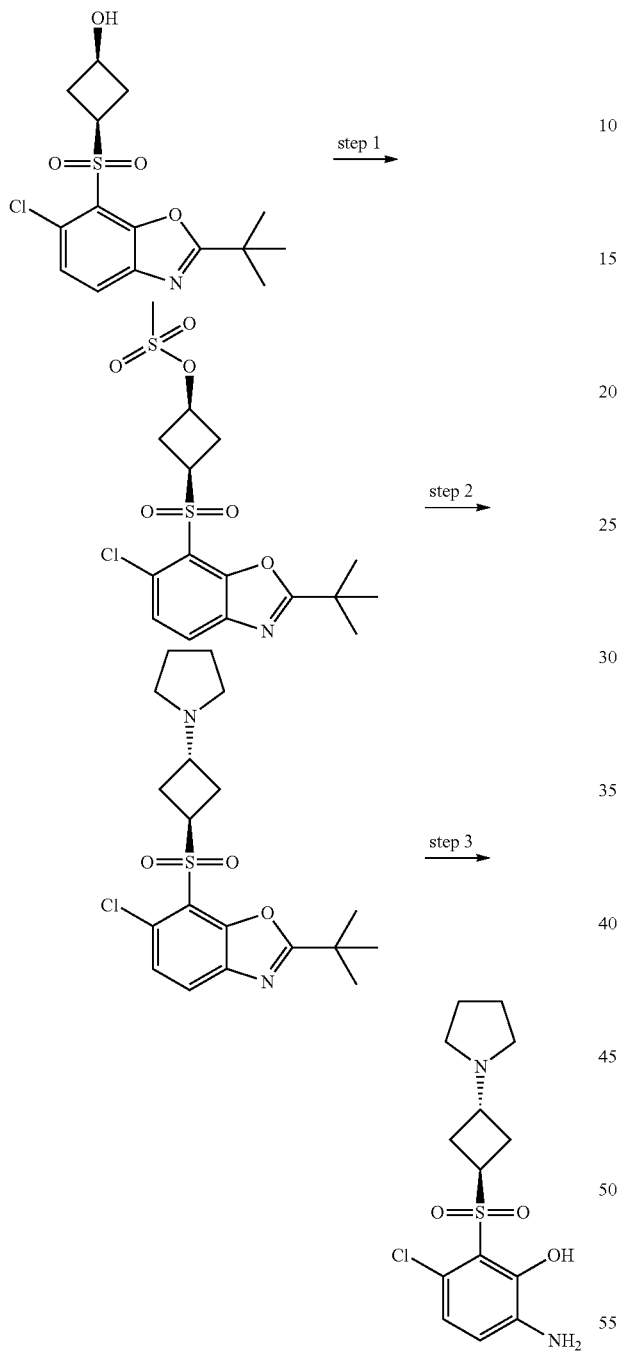

Step 1: To a solution of cis-3-((2-(tert-butyl)-6-chlorobenzo[d]oxazol-7-yl)sulfonyl)cyclobutanol (Intermediate 28, Step 3, 3.0 g) in DCM (30 mL) was added TEA (2.6 g) and methanesulfonyl chloride (1.2 g) at 0° C. under a nitrogen atmosphere. The resulting mixture was stirred at this temperature for 30 mins. The mixture was quenched with aq. NaHCO$_3$ solution, extracted with DCM (2×30 mL). The combined organic phases were washed, dried and concentrated to afford cis-3-((2-(tert-butyl)-6-chlorobenzo[d]oxazol-7-yl)sulfonyl)cyclobutyl methanesulfonate (2.6 g). MS(ES$^+$) m/z 422 (MH$^+$).

Step 2: To a solution of cis-3-((2-(tert-butyl)-6-chlorobenzo[d]oxazol-7-yl)sulfonyl)cyclobutyl methanesulfonate (2.4 g) in DMF (30 mL) was added potassium carbonate (1.6 g) and pyrrolidine (0.5 g). The mixture was stirred at 80° C. overnight. Water (20 mL) was added. The crude product was extracted with EA (3×80 mL). The combined organic phases were washed with brine, filtered and concentrated to give the crude product, which was purified by column chromatography (eluting with PE:EA=2:1) to 2-(tert-butyl)-6-chloro-7-((trans-3-(pyrrolidin-1-yl)cyclobutyl)sulfonyl)benzo[d]oxazole (2.0 g). MS(ES$^+$) m/z 397 (MH$^+$).

Step 3: 2-(Tert-butyl)-6-chloro-7-((trans-3-(pyrrolidin-1-yl)cyclobutyl)sulfonyl)benzo[d]oxazole (2.0 g) was dissolved in HCl in dioxane (50 mL) and water (50 mL). The reaction mixture was stirred overnight at 120° C. The solvent was removed to give the crude product (1.5 g), which was combined with another batch of the same reaction using 2-(tert-butyl)-6-chloro-7-((trans-3-(pyrrolidin-1-yl)cyclobutyl)sulfonyl)benzo[d]oxazole (1.3 g) as starting material. The mixture was purified by preparative HPLC to afford the title compound (614 mg). MS(ES$^+$) m/z 331 (MH$^+$).

Intermediate 79: 6-amino-2-(((1r,4r)-4-(azetidin-1-yl)cyclohexyl)sulfonyl)-3-chlorophenol

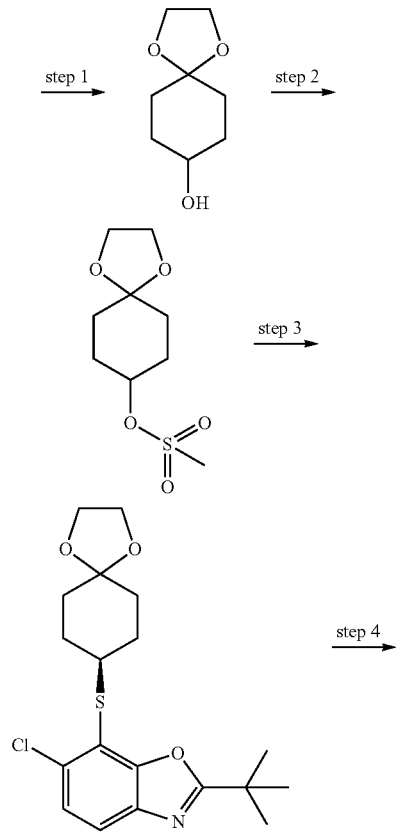

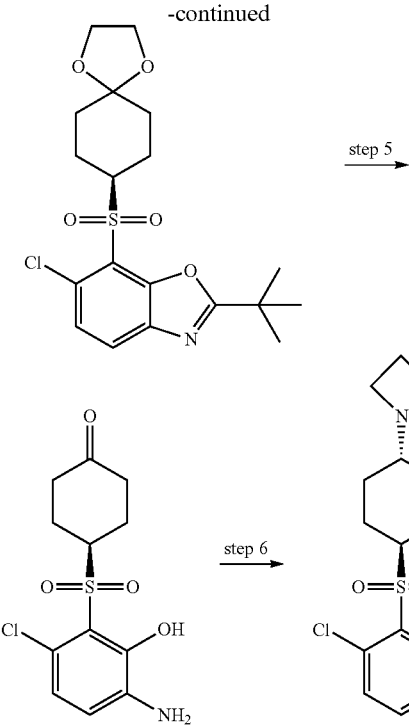

Step 1: To a solution of 1,4-dioxaspiro[4.5]decan-8-one (1.0 g) in methanol (3 mL) was added NaBH₄ (0.2 g). The mixture was stirred at 30° C. for 1 hour, and then poured into H₂O (20 mL).

The mixture was extracted with EA (10 mL). The organic layer was washed with brine, dried over Na₂SO₄, and concentrated to afford 1,4-dioxaspiro[4.5]decan-8-ol (750 mg).

Step 2: To a solution of 1,4-dioxaspiro[4.5]decan-8-ol (750 mg) in DCM (5 mL) was added TEA (959 mg) and methanesulfonyl chloride (652 mg). The mixture was stirred at 5° C. for 16 hours, and then washed with H₂O. The organic layer was dried over Na₂SO₄ and concentrated to afford 1,4-dioxaspiro[4.5]decan-8-yl methanesulfonate (1.0 g).

Step 3: To a solution of 2-(tert-butyl)-6-chlorobenzo[d]oxazole-7-thiol (270 mg) in DMF (5 mL) was added 1,4-dioxaspiro[4.5]decan-8-yl methanesulfonate (264 mg). The mixture was stirred at 100° C. for 2 hours. After cooling, the mixture was concentrated. The crude product was purified by column chromatography to afford 7-(1,4-dioxaspiro[4.5]decan-8-ylthio)-2-(tert-butyl)-6-chlorobenzo[d]oxazole (350 mg). MS(ES⁺) m/z 382 (MH⁺).

Step 4: To a solution of 7-(1,4-dioxaspiro[4.5]decan-8-ylthio)-2-(tert-butyl)-6-chlorobenzo[d]oxazole (200 mg) in DCM (4 mL) was added mCPBA (226 mg) at 15° C. The mixture was stirred at 15° C. for 48 hours, and then quenched with sat. Na₂SO₃ solution. The organic layer was dried over Na₂SO₄ and concentrated to afford 7-(1,4-dioxaspiro[4.5]decan-8-ylthio)-2-(tert-butyl)-6-chlorobenzo[d]oxazole (220 mg). MS(ES⁺) m/z 398 (MH⁺).

Step 5: To a solution of 7-(1,4-dioxaspiro[4.5]decan-8-ylsulfonyl)-2-(tert-butyl)-6-chlorobenzo[d]oxazole (6.8 g) in 1,4-dioxane (30 mL) was added aq. HCl solution (1 mL) at 60° C. The mixture was stirred at 60° C. for 16 hours, and then concentrated. The residue was dissolved in DCM, and the pH was adjusted to ~9. After concentration, the crude was purified by column chromatography to afford 4-((3-amino-6-chloro-2-hydroxyphenyl)sulfonyl)cyclohexanone (3.2 g). MS(ES⁺) m/z 304 (MH⁺).

Step 6: To a solution of 4-((3-amino-6-chloro-2-hydroxyphenyl)sulfonyl)cyclohexanone (1.2 g) in DCM (50 mL) was added azetidine, hydrochloride salt (1.8 g). The mixture was stirred at 30° C. for 1 hour. Sodium triacetoxyborohydride (2.5 g) was added. The mixture was stirred at 30° C. for 3 hours, and then concentrated. The residue was purified by SFC to afford the title compound (560 mg). MS(ES⁺) m/z 345 (MH⁺).

Intermediate 80 & 131: 6-amino-3-chloro-2-((trans-4-(pyrrolidin-1-yl)cyclohexyl)sulfonyl)phenol, trifluoroacetic acid salt and 6-amino-3-chloro-2-((cis-4-(pyrrolidin-1-yl)cyclohexyl)sulfonyl)phenol, trifluoroacetic acid salt

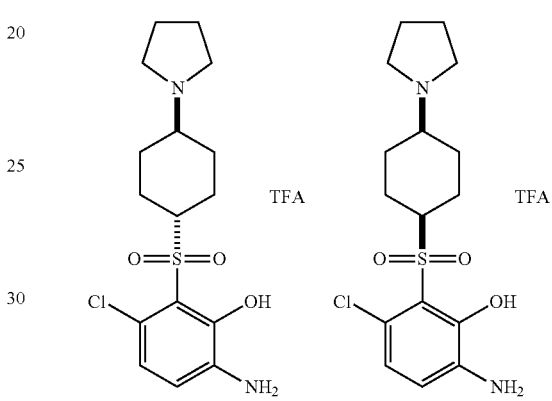

To a solution of 4-((3-amino-6-chloro-2-hydroxyphenyl)sulfonyl)cyclohexanone (Intermediate 79, Step 5, 3.0 g) in DCM (50 mL) was added pyrrolidine (0.7 g). The mixture was stirred at 30° C. for 1 hour. Sodium triacetoxyborohydride (6.3 g) was added. The mixture was stirred at 30° C. for 3 hours, and then concentrated. The residue was purified by column chromatography, SFC, and preparative HPLC (acidic condition) to afford 6-amino-3-chloro-2-((trans-4-(pyrrolidin-1-yl)cyclohexyl)sulfonyl)phenol, trifluoroacetic acid salt (Intermediate 80, 460 mg) and 6-amino-3-chloro-2-((cis-4-(pyrrolidin-1-yl)cyclohexyl)sulfonyl)phenol, trifluoroacetic acid salt (intermediate 131, 20 mg). MS(ES⁺) m/z 359 (MH⁺).

Intermediate 81: (S)-6-amino-3-chloro-2-((tetrahydrofuran-3-yl)sulfonyl)phenol

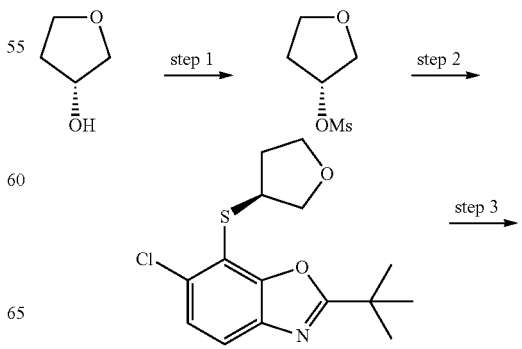

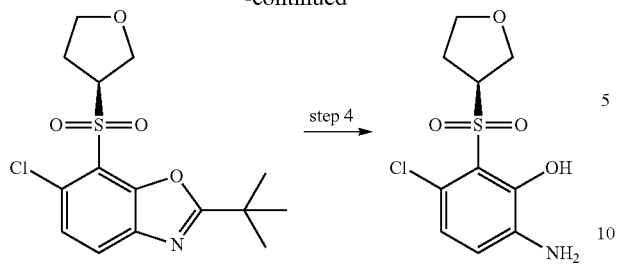

Step 1: To a solution of (R)-tetrahydrofuran-3-ol (0.5 g) and TEA (1.7 mL) in DCM (10 mL) was added MsCl (0.5 mL) under an ice-water bath. The reaction mixture was stirred at RT for 4 hours. Water (100 mL) was added. The organic layer was separated, dried over sodium sulfate, filtered and concentrated to afford (R)-tetrahydrofuran-3-yl methanesulfonate (1.0 g) as a yellow oil.

Step 2: To a solution of (R)-tetrahydrofuran-3-yl methanesulfonate (1.0 g), 2-(tert-butyl)-6-chlorobenzo[d]oxazole-7-thiol (1.3 g) in DMF (15 mL) was added potassium carbonate (1.5 g). The reaction mixture was stirred at 90° C. for 2 hours. EA (50 mL) was added. The mixture was washed with brine for three times. The organic layer was dried over sodium sulfate and filtered. The resulting filtrate was concentrated to afford (S)-2-(tert-butyl)-6-chloro-7-((tetrahydrofuran-3-yl)thio)benzo[d]oxazole (1.7 g) as a yellow vicious liquid. MS(ES$^+$) m/z 312 (MH$^+$).

Step 3: To a solution of (S)-2-(tert-butyl)-6-chloro-7-((tetrahydrofuran-3-yl)thio)benzo[d]oxazole (1.7 g) in DCM (40 mL) was added mCPBA (2.7 g). The reaction mixture was stirred at RT overnight. Aq. NaHCO$_3$ solution and aq. Na$_2$SO$_3$ solution was added. The organic phase was separated, washed with sat. sodium carbonate solution and dried over sodium sulfate. The solution was filtered and the filtrate was concentrated to give (S)-2-(tert-butyl)-6-chloro-7-((tetrahydrofuran-3-yl)sulfonyl)benzo[d]oxazole (1.9 g) as a white solid. MS(ES$^+$) m/z 344 (MH$^+$).

Step 4: To a solution of (S)-2-(tert-butyl)-6-chloro-7-((tetrahydrofuran-3-yl)sulfonyl)benzo[d]oxazole (1.9 g) in 1,4-dioxane (6 mL) was added conc. HCl (8 mL). After stirring at 110° C. for 4 hours, the reaction mixture was concentrated to afford the title compound (1.1 g) as a light brown solid.

Intermediate 82: 6-amino-3-chloro-2-((2-(tetrahydro-2H-pyran-4-yl)propan-2-yl)sulfonyl)phenol

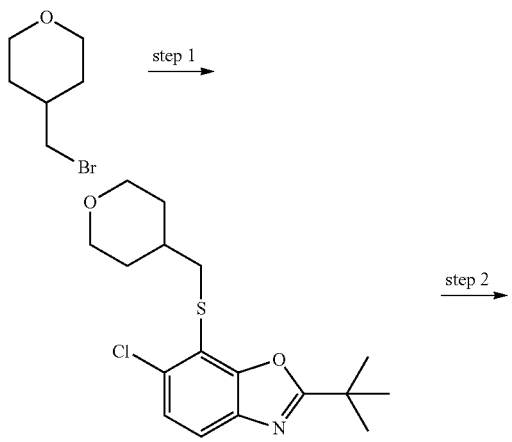

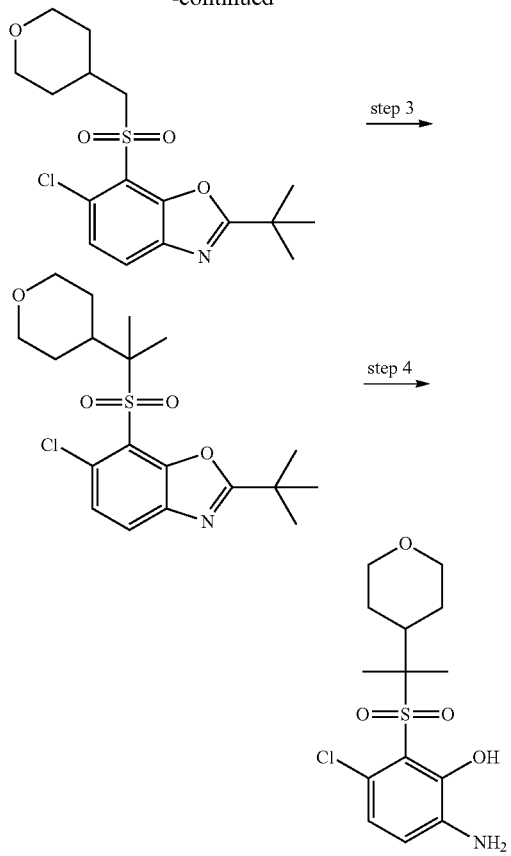

Step 1: To a solution of 2-(tert-butyl)-6-chlorobenzo[d]oxazole-7-thiol (2.0 g) in DMF (20 mL) was added 4-(bromomethyl)tetrahydro-2H-pyran (1.5 g) and potassium carbonate (2.3 g). The mixture was stirred at 95° C. for 16 hours, and then concentrated. The residue was partioned between EA and water. The organic layer was dried and concentrated to afford 2-(tert-butyl)-6-chloro-7-(((tetrahydro-2H-pyran-4-yl)methyl)thio)benzo[d]oxazole (2.8 g). MS(ES$^+$) m/z 340 (MH$^+$).

Step 2: To a solution of 2-(tert-butyl)-6-chloro-7-(((tetrahydro-2H-pyran-4-yl)methyl)thio)benzo[d]oxazole (2.6 g) in DCM (30 mL) was added mCPBA (3.3 g) at 15° C. The mixture was stirred at 15° C. for 48 hours. The mixture was quenched with sat. Na$_2$SO$_3$ solution. The organic layer was dried over Na$_2$SO$_4$ and concentrated. The residue was purified by column chromatography to afford 2-(tert-butyl)-6-chloro-7-(((tetrahydro-2H-pyran-4-yl)methyl)sulfonyl)benzo[d]oxazole (1.4 g). MS(ES$^+$) m/z 372 (MH$^+$).

Step 3: To a solution of 2-(tert-butyl)-6-chloro-7-(((tetrahydro-2H-pyran-4-yl)methyl)sulfonyl)benzo[d]oxazole (750 mg) in THF (10 mL) was added LiHMDS (1.2 M in THF, 13.5 mL). The mixture was stirred at −78° C. for 10 mins. Iodomethane (2863 mg) was added. The mixture was stirred at −78° C. for 30 mins, and then quenched with NH$_4$Cl. The resulting mixture was extracted with EA. The organic layer was washed with brine, dried over Na$_2$SO$_4$ and concentrated. The crude product was purified by column chromatography to afford 2-(tert-butyl)-6-chloro-7-((2-(tetrahydro-2H-pyran-4-yl)propan-2-yl)sulfonyl)benzo[d]oxazole (800 mg). MS(ES$^+$) m/z 400 (MH$^+$).

Step 4: To a solution of 2-(tert-butyl)-6-chloro-7-((2-(tetrahydro-2H-pyran-4-yl)propan-2-yl)sulfonyl)benzo[d]

oxazole (1.0 g) in 1,4-dioxane (10 mL) was added aq. HCl solution (37%, 3 mL) at 100° C. The mixture was stirred at this temperature for 6 hours. After cooling, the pH was adjusted to ~8. The mixture was concentrated and dissolved in DCM. The organic phase was washed with water (2×30 mL), dried and concentrated. The residue was purified by preparative HPLC (under acidic condition) to afford the title compound (30 mg). MS(ES$^+$) m/z 356 (MNa$^+$).

Intermediate 83: 6-amino-3-chloro-2-((1,1-difluoroethyl)sulfonyl)phenol

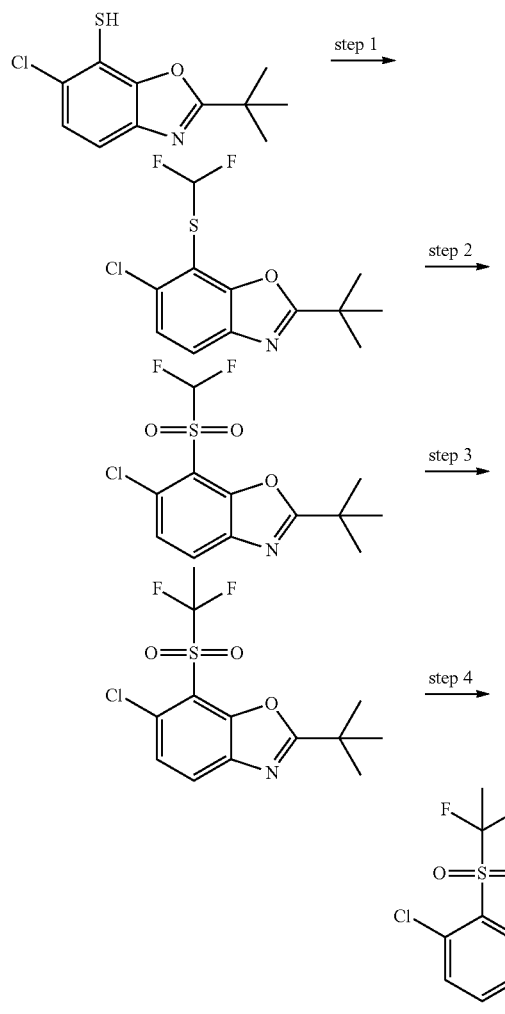

Step 1: To a solution of 2-(tert-butyl)-6-chlorobenzo[d]oxazole-7-thiol (6.0 g) and potassium hydroxide (13.9 g) in acetonitrile (80 mL) and water (80 mL) stirred at −78° C. was added diethyl (bromodifluoromethyl)phosphonate (11.9 g) in one portion. The mixture was allowed to warm to RT and stirred for 30 mins. EA (200 mL) was added. The organic phase was separated. The aqueous phase was extracted with EA (2×100 mL). The organic layers were combined, dried over sodium sulfate, filtered and concentrated to afford 2-(tert-butyl)-6-chloro-7-((difluoromethyl)thio)benzo[d]oxazole (7.2 g) as a colorless oil. MS(ES$^+$) m/z 292 (MH$^+$).

Step 2: To a solution of 2-(tert-butyl)-6-chloro-7-((difluoromethyl)thio)benzo[d]oxazole (7.2 g) in DCM (200 mL) at 0° C. was added mCPBA (19.5 g) and stirred for 2 hours. As the starting material was not consumed totally, additional mCPBA (19.5 g) was added. The mixture was stirred at RT overnight. Then aq. Na$_2$SO$_3$ solution was added. The organic phase was separated, washed with sat. sodium carbonate solution and brine. The resulting solution was dried over sodium sulfate, filtered and concentrated. The residue was purified by column chromatography (eluting with PE:EA=1:0-2:3) to give 2-(tert-butyl)-6-chloro-7-((difluoromethyl)sulfonyl)benzo[d]oxazole (3.2 g) as a white solid. MS(ES$^+$) m/z 324 (MH$^+$).

Step 3: To a solution of 2-(tert-butyl)-6-chloro-7-((difluoromethyl)sulfonyl)benzo[d]oxazole (2.2 g) and iodomethane (4.2 mL) in THF (30 mL) and HMPA (27 mL) was added LDA (2 M in THF, 13.5 mL). The mixture was stirred at −50° C. for 30 mins. The mixture was then neutralized with sat. NH$_4$Cl solution and 10% HCl solution. EA (50 mL) was added. The organic layers were washed with brine, dried over sodium sulfate and concentrated in vacuo. The crude product was combined with another batch of the same reaction using 2-(tert-butyl)-6-chloro-7-((difluoromethyl)sulfonyl)benzo[d]oxazole (1.0 g) as starting material. The crude product was purified by column chromatography (eluting with PE:EA=1:0-3:2) to afford 2-(tert-butyl)-6-chloro-7-((1,1-difluoroethyl)sulfonyl)benzo[d]oxazole (1.0 g) as a white solid. MS(ES$^+$) m/z 338 (MH$^+$).

Step 4: To a solution of 2-(tert-butyl)-6-chloro-7-((1,1-difluoroethyl)sulfonyl)benzo[d]oxazole (1.0 g) in 1,4-dioxane (20 mL) was added conc. HCl solution (20 mL). The mixture was refluxed at 110° C. for 4 hours, and then concentrated. The resulting residue was dissolved in EA (20 mL). The pH of the solution was adjusted to 8 with TEA. The mixture was concentrated. The residue was purified by column chromatography (eluting with PE:EA=1:0 to 1:4) to afford the title compound (1.0 g) as a light brown solid. MS(ES$^+$) m/z 272 (MH$^+$).

Intermediate 84: 6-amino-3-chloro-2-((5,6,7,8-tetrahydroimidazo[1,2-a]pyridin-6-yl)sulfonyl)phenol, trifluoroacetic acid salt

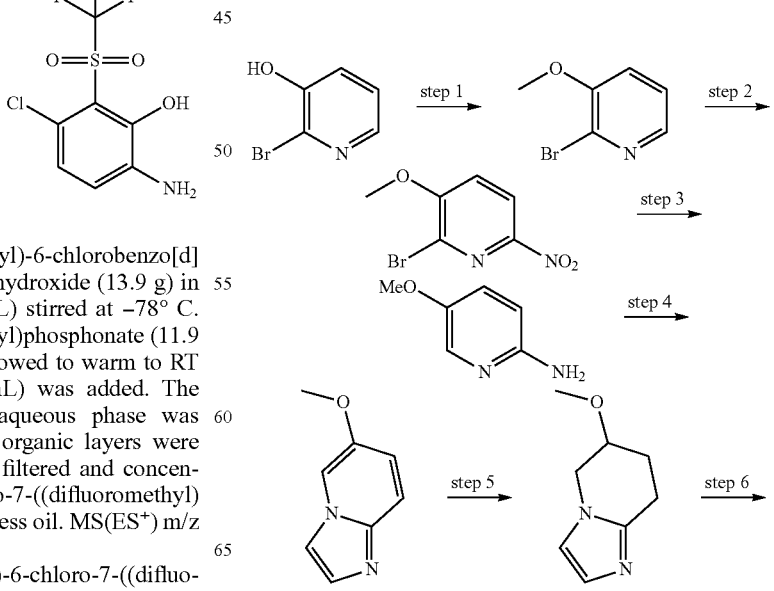

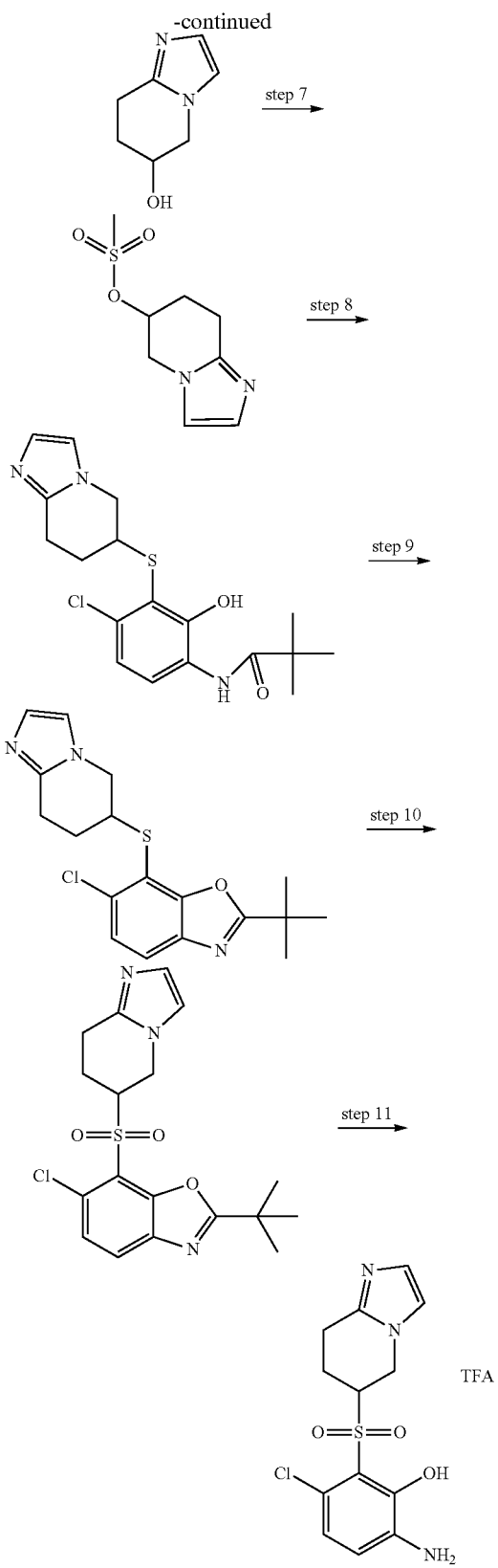

trated in vacuo. The residue was dissolved in Et$_2$O. The mixture was filtered and concentrated to afford 2-bromo-3-methoxypyridine (35.0 g). MS(ES$^+$) m/z 188 (MH$^+$).

Step 2: To a solution of 2-bromo-3-methoxypyridine (0.1 g) in conc. sulfuric acid (2 mL) was added nitric acid (0.1 g). The mixture was stirred at 55° C. for 3 hours. After cooling, the mixture was poured into water (10 mL). The mixture was filtered. The solid was washed with water, and then redissolved in DCM. The solution was dried over Na$_2$SO$_4$ and concentrated in vacuo to afford 2-bromo-3-methoxy-6-nitropyridine (60 mg). MS(ES$^+$) m/z 233 (MH$^+$).

Step 3: To a solution of 2-bromo-3-methoxy-6-nitropyridine (33.0 g) in methanol (400 mL) and EA (100 mL) was added potassium acetate (15.3 g) and Pd/C (1.5 g). The mixture was stirred at 50° C. for 48 hours under H$_2$ (50 psi). The mixture was filtered. The filtrate was concentrated in vacuo to afford 5-methoxypyridin-2-amine (16.0 g).

Step 4: To a solution of 5-methoxypyridin-2-amine (15.0 g) in methanol (40 mL) and water (20 mL) was added 2-chloroacetaldehyde (25.0 g) and sodium bicarbonate (10.2 g). The mixture was stirred under reflux for 2 hours, and then concentrated. The residue was partioned between EA and aq. NaHCO$_3$ solution. The organic layer was concentrated and purified by column chromatography to afford 6-methoxy-imidazo[1,2-a]pyridine (15.0 g).

Step 5: To a solution of 6-methoxyimidazo[1,2-a]pyridine (15.0 g) in methanol (200 mL) was added Pd(OH)$_2$ (1.4 g) and AcOH (0.6 mL). The mixture was stirred at 60° C. for 16 hours under H$_2$ (40 psi). The mixture was filtered. The filtrate was concentrated in vacuo to afford 6-methoxy-5,6,7,8-tetrahydroimidazo[1,2-a]pyridine (16.0 g). MS(ES$^+$) m/z 153 (MH$^+$).

Step 6: 6-Methoxy-5,6,7,8-tetrahydroimidazo[1,2-a]pyridine (3.8 g) was added to aq. HBr solution (48%, 1.4 mL). The mixture was stirred at 100° C. for 72 hours, and then concentrated. The residue was purified by preparative HPLC to afford 5,6,7,8-tetrahydroimidazo[1,2-a]pyridin-6-ol (3.6 g)

Step 7: To a solution of 5,6,7,8-tetrahydroimidazo[1,2-a]pyridin-6-ol (100 mg) in DCM (5 mL) was added TEA (146 mg) and methanesulfonyl chloride (99 mg). The mixture was stirred at 5° C. for 16 hours, and then washed with water. The organic layer was dried over Na$_2$SO$_4$ and concentrated to afford 5,6,7,8-tetrahydroimidazo[1,2-a]pyridin-6-yl methanesulfonate (125 mg). MS(ES$^+$) m/z 217 (MH$^+$).

Step 8: To a solution of 5,6,7,8-tetrahydroimidazo[1,2-a]pyridin-6-yl methanesulfonate (2.0 g) in DMF (20 mL) was added 2-(tert-butyl)-6-chlorobenzo[d]oxazole-7-thiol (2.2 g) and potassium carbonate (2.6 g). The mixture was stirred at 95° C. for 16 hours, and then concentrated. The resulting mixture was partitioned between EA and water. The organic layer was dried and concentrated to afford the crude product, which was purified by preparative HPLC to afford N-(4-chloro-2-hydroxy-3-((5,6,7,8-tetrahydroimidazo[1,2-a]pyridin-6-yl)thio)phenyl)pivalamide (950 mg). MS(ES$^+$) m/z 380 (MH$^+$).

Step 9: To a solution of N-(4-chloro-2-hydroxy-3-((5,6,7,8-tetrahydroimidazo[1,2-a]pyridin-6-yl)thio)phenyl)pivalamide (800 mg) in toluene (5 mL) stirred in air was added p-toluenesulfonic acid monohydrate (401 mg) in one charge. The reaction mixture was stirred at 85° C. for 20 hours, and then concentrated. The residue was dissolved in EA. The resulting mixture was washed with sat. NaHCO$_3$ solution, dried and concentrated to afford 2-(tert-butyl)-6-chloro-7-((5,6,7,8-tetrahydroimidazo[1,2-a]pyridin-6-yl)thio)benzo[d]oxazole (880 mg). MS(ES$^+$) m/z 362 (MH$^+$).

Step 1: To a solution of 2-bromopyridin-3-ol (40.0 g) in methanol (400 mL) and DCM (800 mL) was added (diazomethyl)trimethylsilane (2 M in hexane, 230 mL). The mixture was stirred at 13° C. for 3 hours, and then concen- Step 10: To a solution of 2-(tert-butyl)-6-chloro-7-((5,6,7,8-tetrahydroimidazo[1,2-a]pyridin-6-yl)thio)benzo[d]oxazole (400 mg) in DCM (10 mL) was added mCPBA (477 mg) at 30° C. The mixture was stirred at 30° C. for 16 hours. The resulting mixture was quenched with sat. Na$_2$SO$_3$ solution. The pH was adjusted to ~10. The mixture was washed with water (2×30 mL). The organic layer was dried and concentrated to afford 2-(tert-butyl)-6-chloro-7-((5,6,7,8-tetrahydroimidazo[1,2-a]pyridin-6-yl)sulfonyl)benzo[d]oxazole (270 mg). MS(ES$^+$) m/z 394 (MH$^+$).

Step 11: To a solution of 2-(tert-butyl)-6-chloro-7-((5,6,7,8-tetrahydroimidazo[1,2-a]pyridin-6-yl)sulfonyl)benzo[d]oxazole (270 mg) in 1,4-dioxane (6 mL) was added aq. HCl solution (37%, 2 mL) at 100° C. The mixture was stirred at this temperature for 4 hours. After cooling, the pH of the mixture was adjusted to ~8. The resulting mixture was concentrated. The residue was dissolved in DCM and filtered. The filtrate was concentrated. The residue was purified by preparative HPLC (under acidic condition) to afford the title compound (170 mg). MS(ES$^+$) m/z 328 (MH$^+$).

Intermediate 85: 6-amino-3-chloro-2-((octahydroindolizin-7-yl)sulfonyl)phenol, hydrochloride salt

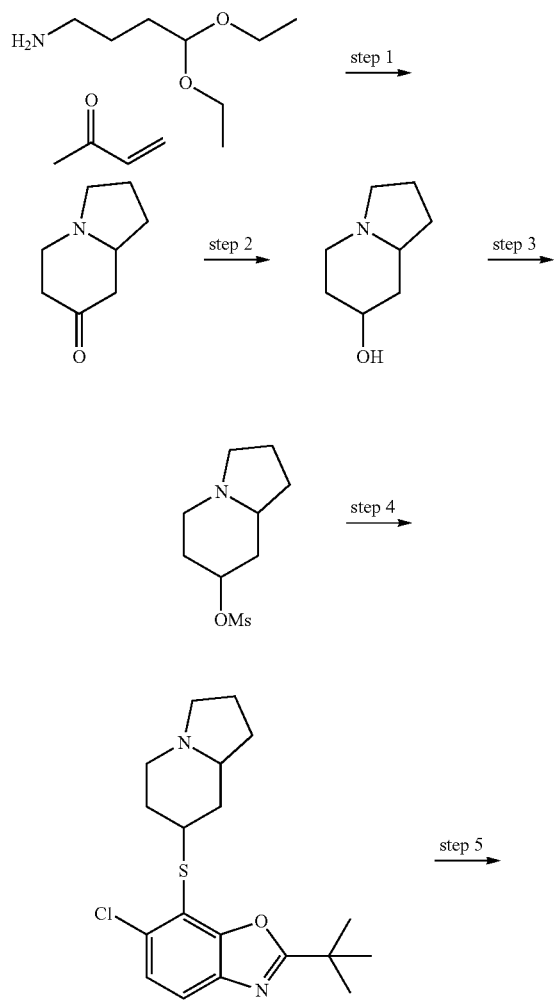

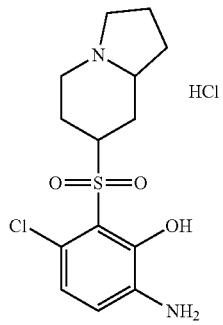

Step 1: To a solution of 4,4-diethoxybutan-1-amine (50.0 g) in diethyl ether (120 mL) stirred under a nitrogen atmosphere at 0° C. was added but-3-en-2-one (21.7 g) dropwise. After stirring for 1 hour, aq. HCl solution (37%, 127 mL) was added dropwise. The reaction mixture was stirred at 100° C. for 2 hours. After cooling, the mixture was concentrated. Water was added. The pH was adjusted to 8-10 with sat. K$_2$CO$_3$ solution. The resulting mixture was extracted with DCM (2×100 mL). The combined organic layers were dried and concentrated. The residue was distilled to afford hexahydroindolizin-7(1H)-one (10.5 g) as a colorless liquid.

Step 2: To a solution of hexahydroindolizin-7(1H)-one (10.0 g) in methanol (80 mL) stirred in air at 0° C. was added NaBH$_4$ (1.4 g) portionwise. The reaction mixture was stirred at 20° C. for 1 hour. Water was added. The mixture was extracted with DCM (4×30 mL). The organic layers were dried and concentrated to give octahydroindolizin-7-ol (8.2 g). MS(ES$^+$) m/z 142 (MH$^+$).

Step 3: To a solution of octahydroindolizin-7-ol (2.0 g) in DCM (20 mL) was added TEA (2.0 mL), and then followed by addition of MsCl (1.1 mL) under ice bath temperature. The reaction mixture was stirred at RT for 4 hours. Water (100 mL) was added. The organic layer was separated, dried over sodium sulfate and filtered. The resulting filtrate was concentrated to afford octahydroindolizin-7-yl methanesulfonate (1.6 g) as a yellow liquid oil. MS(ES$^+$) m/z 220 (MH$^+$).

Step 4: To a solution of octahydroindolizin-7-yl methanesulfonate (3.1 g), sodium 2-(tert-butyl)-6-chlorobenzo[d]oxazole-7-thiolate (3.4 g) in DMF (25 mL) was added potassium carbonate (2.2 g). The reaction mixture was stirred at 90° C. for 2 hours. EA (150 mL) was added. The mixture was washed with brine for three times. The organic layer was dried with sodium sulfate and filtered. The filtrate was concentrated and the resulting residue was purified by column chromatography (eluting with 0-15% methol/DCM) to afford 2-(tert-butyl)-6-chloro-7-((octahydroindolizin-7-yl)thio)benzo[d]oxazole (0.6 g) as a yellow vicious liquid. MS(ES$^+$) m/z 365 (MH$^+$).

Step 5: To a solution of 2-(tert-butyl)-6-chloro-7-((octahydroindolizin-7-yl)sulfonyl)benzo[d]oxazole (0.1 g) in 1,4-dioxane (6 mL) was added aq. HCl solution (37%, 6 mL). The mixture was refluxed for 4 hours. The mixture was concentrated to afford the title compound (107 mg) as a light brown solid. MS(ES$^+$) m/z 331 (MH$^+$).

Intermediate 86: 6-amino-3-chloro-2-((tetrahydro-2H-pyran-4-yl)sulfonyl)phenol

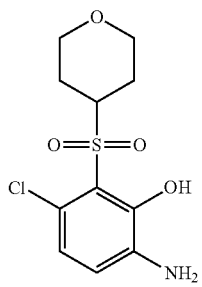 [SMILES: Nc1ccc(Cl)c(S(=O)(=O)C2CCOCC2)c1O]

To a solution of 2-(tert-butyl)-6-chloro-7-((tetrahydro-2H-pyran-4-yl)sulfonyl)benzo[d]oxazole (Intermediate 30, Step 3, 3.0 g) in 1,4-dioxane (20 mL) was added aq. HCl solution (37%, 20 mL). After refluxing at 110° C. for 4 hours, the mixture was concentrated to afford the title compound (3.2 g) as a light brown solid. MS(ES$^+$) m/z 292 (MH$^+$).

Intermediate 87: 6-amino-3-chloro-2-((3,3-difluoroazetidin-1-yl)sulfonyl)phenol

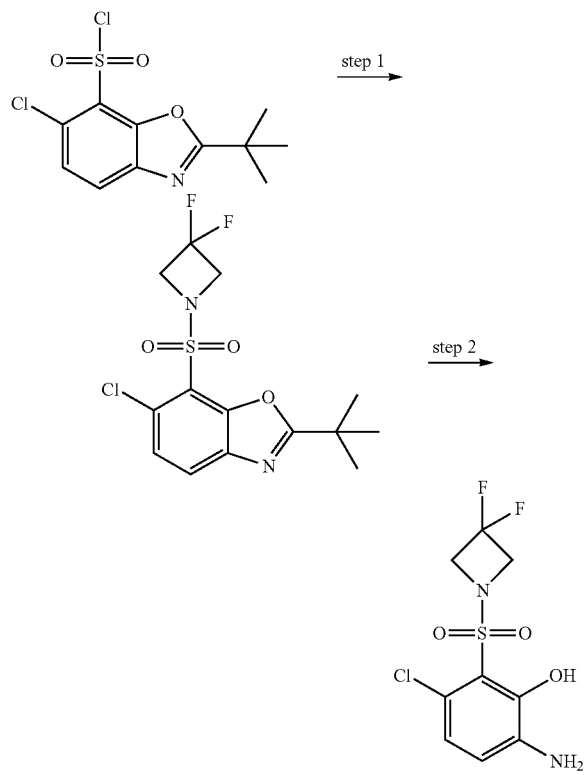

Step 1: A solution of 2-(tert-butyl)-6-chlorobenzo[d]oxazole-7-sulfonyl chloride (600 mg), 3,3-difluoroazetidine (362 mg) and DIPEA (0.3 mL) was stirred in THF (10 mL) at RT for 2 hours. Cold water (30 mL) was added. The aq. layer was extracted with DCM (2×100 mL). The combined organic layers were dried over Na$_2$SO$_4$, filtered and concentrated in vacuo. The residue was purified by column chromatography (eluting with PE:EA=10:1) to give 2-(tert-butyl)-6-chloro-7-((3,3-difluoroazetidin-1-yl)sulfonyl)benzo[d]oxazole (495 mg) as an oil. MS(ES$^+$) m/z 365 (MH$^+$).

Step 2: 2-(Tert-butyl)-6-chloro-7-((3,3-difluoroazetidin-1-yl)sulfonyl)benzo[d]oxazole (395 mg) was dissolved in 1,4-dioxane (20 mL) and water (4 mL). Conc. sulfuric acid (1.0 mL) was added. The mixture was heated to 100° C. overnight to give a brown solution. After cooling, the mixture was concentrated, and then treated with aq. NaOH solution (6 M) until pH=12 in an ice bath. The mixture was extracted with EA (4×~50 mL). The combined organic layers were dried over sodium sulfate, filtered and concentrated to give the title compound (257 mg) as an oil. MS(ES$^+$) m/z 299 (MH$^+$).

Intermediate 88: 6-amino-3-chloro-2-((3-fluoroazetidin-1-yl)sulfonyl)phenol

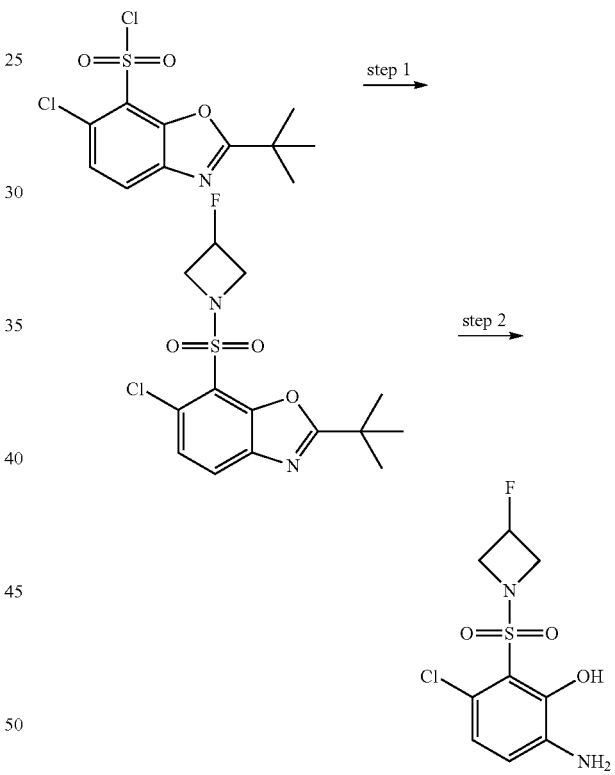

Step 1: A solution of 2-(tert-butyl)-6-chlorobenzo[d]oxazole-7-sulfonyl chloride (600 mg), 3-fluoroazetidine, hydrochloride (174 mg) and DIPEA (503 mg) in THF (6 mL) was stirred at RT for 6 hours. Cold water (30 mL) was added. The aqueous layer was extracted with DCM (2×100 mL). The combined organic layers were dried over Na$_2$SO$_4$, filtered and concentrated under reduced pressure. The residue was purified by column chromatography (eluting with PE:EA=3:1) to give 2-(tert-butyl)-6-chloro-7-((3-fluoroazetidin-1-yl)sulfonyl)benzo[d]oxazole (550 mg) as a yellow gel. MS(ES$^+$) m/z 347 (MH$^+$).

Step 2: 2-(Tert-butyl)-6-chloro-7-((3-fluoroazetidin-1-yl)sulfonyl)benzo[d]oxazole (450 mg) was dissolved in 1,4-dioxane (35 mL) and water (7 mL). Conc. sulfuric acid (1.2 mL) was added. The mixture was heated to 100° C. overnight to give a brown solution. After cooling, the mixture was concentrated in vacuo. The residue was treated with aq. NaOH solution (6 M) until pH=12 in an ice bath. The resulting mixture was extracted with EA (4×~50 mL). The combined organic layers were dried over sodium sulfate, filtered and concentrated to give the title compound (333 mg) as an oil. MS(ES⁺) m/z 281 (MH⁺).

Intermediate 89: (R)-6-amino-3-chloro-2-((3-fluoro-pyrrolidin-1-yl)sulfonyl)phenol

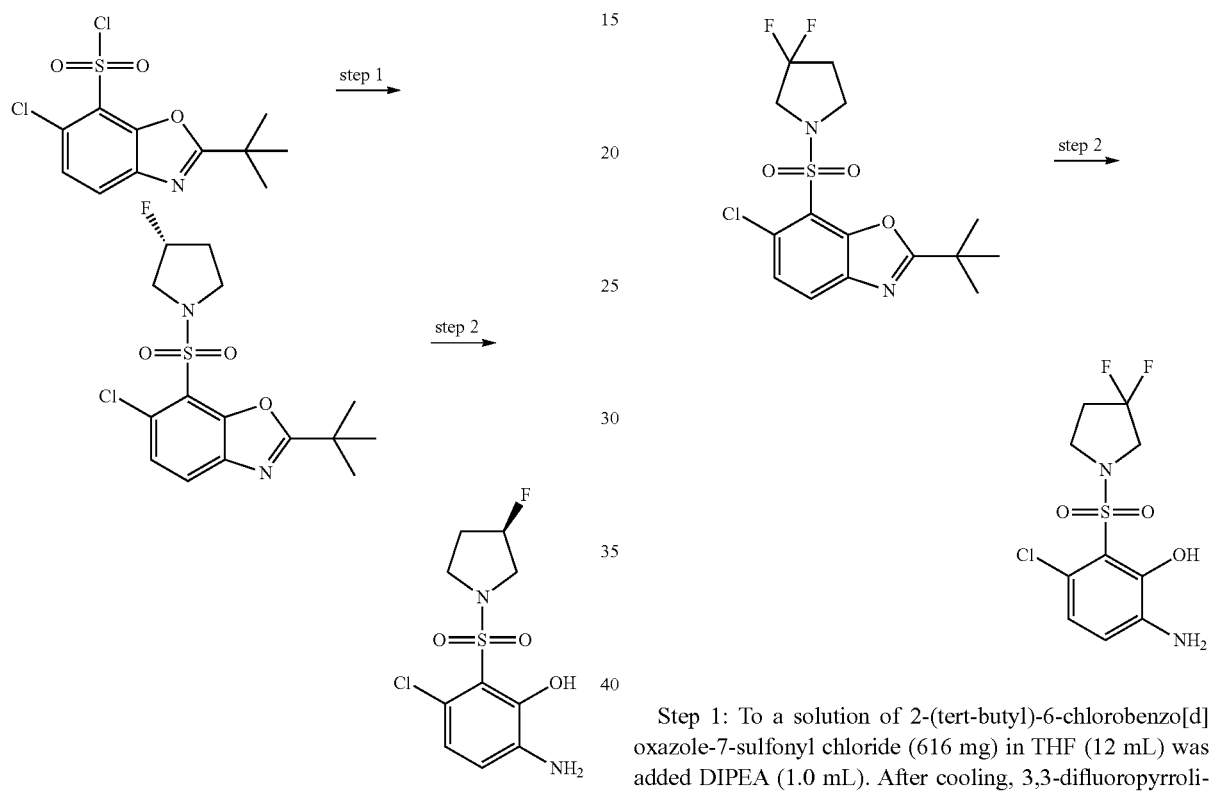

Step 1: A solution of 2-(tert-butyl)-6-chlorobenzo[d]oxazole-7-sulfonyl chloride (600 mg), (R)-3-fluoropyrrolidine (173 mg) and DIPEA (503 mg) was stirred in THF (6 mL) at RT for 6 hours. Cold water (30 mL) was added. The aqueous layer was extracted with DCM (2×100 mL). The combined organic layers were dried over Na₂SO₄, filtered and concentrated in vacuo. The residue was purified by column chromatography (eluting with PE:EA=10:1) to give (R)-2-(tert-butyl)-6-chloro-7-((3-fluoropyrrolidin-1-yl)sulfonyl)benzo[d]oxazole (344 mg) as an oil. MS(ES⁺) m/z 361 (MH⁺).

Step 2: (R)-2-(tert-butyl)-6-chloro-7-((3-fluoropyrrolidin-1-yl)sulfonyl)benzo[d]oxazole (290 mg) was dissolved in 1,4-dioxane (15 mL) and water (3 mL). Conc. sulfuric acid (0.8 mL) was added. The mixture was heated to 100° C. overnight to give a brown solution. After cooling, the mixture was concentrated in vacuo. The residue was treated with aq. NaOH solution (6 M) until pH=12 in an ice bath. The resulting mixture was extracted with EA (4×~50 mL). The combined organic layers were dried over sodium sulfate, filtered and concentrated to give the title compound (200 mg) as an oil. MS(ES⁺) m/z 295 (MH⁺).

Intermediate 90: 6-amino-3-chloro-2-((3,3-difluoro-pyrrolidin-1-yl)sulfonyl)phenol

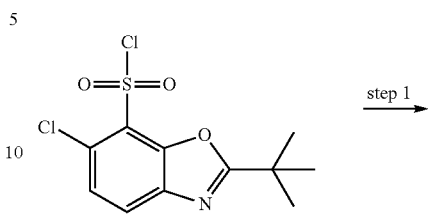

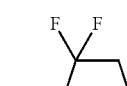

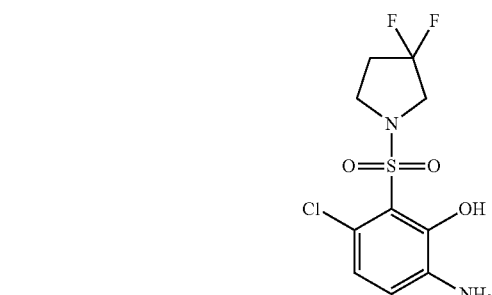

Step 1: To a solution of 2-(tert-butyl)-6-chlorobenzo[d]oxazole-7-sulfonyl chloride (616 mg) in THF (12 mL) was added DIPEA (1.0 mL). After cooling, 3,3-difluoropyrrolidine, hydrochloride (287 mg) was added potionwise over 2 minutes. The resulting mixture was stirred at RT overnight, and then concentrated under reduced pressure. The resiude was diluted with water (20 mL) and extracted with EA (4×30 mL). The combined organic layers were dried over sodium sulfate, filtered and concentrated. The crude product was purified by column chromatography (eluting with PE:EA=10:1) to give 2-(tert-butyl)-6-chloro-7-((3,3-difluoropyrrolidin-1-yl)sulfonyl)benzo[d]oxazole (410 mg) as a light yellow solid. MS(ES⁺) m/z 379 (MH⁺).

Step 2: 2-(Tert-butyl)-6-chloro-7-((3,3-difluoropyrrolidin-1-yl)sulfonyl)benzo[d]oxazole (410 mg) was dissolved in 1,4-dioxane (15 mL) and water (3 mL). Conc. sulfuric acid (1.2 mL) was added. The mixture was heated to 100° C. overnight to give a brown solution. After cooling, the mixture was concentrated in vacuo. The residue was treated with aq. NaOH solution (6 M) until pH=12 in an ice bath. The mixture was extracted with EA (4×~50 mL). The combined organic layers were dried over sodium sulfate, filtered and concentrated to give the title compound (330 mg) as a yellow oil. MS(ES⁺) m/z 313 (MH⁺).

Intermediate 91: 6-amino-3-chloro-2-((4,4-difluoropiperidin-1-yl)sulfonyl)phenol

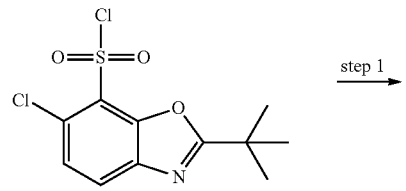

step 1

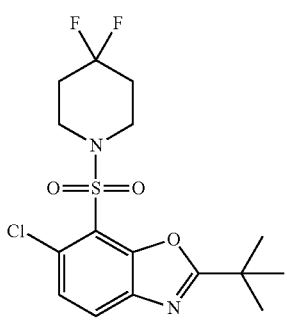

step 2

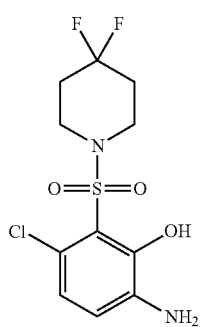

Step 1: To a solution of 2-(tert-butyl)-6-chlorobenzo[d]oxazole-7-sulfonyl chloride (616 mg) in THF (20 mL) was added DIPEA (1.0 mL). After cooling to 0° C., 4,4-difluoropiperidine, hydrochloride (315 mg) was added potionwise over 2 mins. The resulting mixture was stirred at RT overnight, and then concentrated under reduced pressure. The residue was diluted with water (20 mL) and extracted with EA (3×30 mL). The combined organic layers were dried over sodium sulfate, filtered and concentrated. The crude product was purified by column chromatography (eluting with PE:EA=5:1) to give 2-(tert-butyl)-6-chloro-7-((4,4-difluoropiperidin-1-yl)sulfonyl)benzo[d]oxazole (620 mg) as a light yellow solid. MS(ES$^+$) m/z 393 (MH$^+$).

Step 2: 2-(Tert-butyl)-6-chloro-7-((4,4-difluoropiperidin-1-yl)sulfonyl)benzo[d]oxazole (620 mg) was dissolved in 1,4-dioxane (15 mL) and water (3 mL). Conc. sulfuric acid (1.7 mL) was added. The mixture was heated to 100° C. overnight to give a brown solution. After cooling, the mixture was concentrated in vacuo. The residue was treated with aq. NaOH solution (6 M) until pH=12 in an ice bath. The mixture was extracted with EA (3×~50 mL). The combined organic layers were dried over sodium sulfate, filtered and concentrated to give the title compound (500 mg) as a yellow oil. MS(ES$^+$) m/z 327 (MH$^+$).

Intermediate 92: 6-amino-3-chloro-2-(pyrrolidin-1-ylsulfonyl)phenol

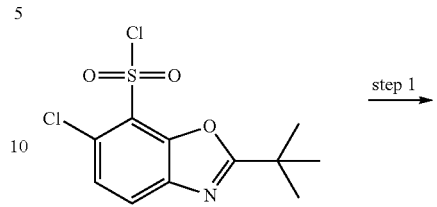

step 1

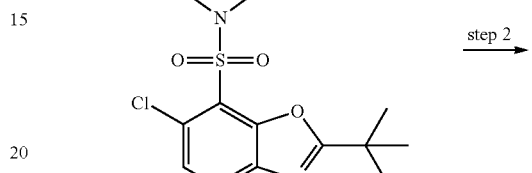

step 2

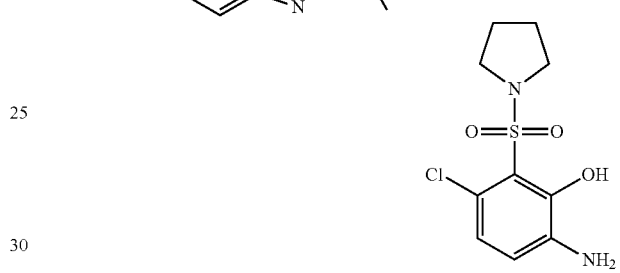

Step 1: To a solution of TEA (0.6 mL) and pyrrolidine (142 mg) in THF (10 mL) was added 2-(tert-butyl)-6-chlorobenzo[d]oxazole-7-sulfonyl chloride (616 mg) in small portion at RT. The mixture was stirred overnight. Cold water (30 mL) was added. The resulting mixture was extracted with DCM (2×100 mL). The combined organic layers were dried over Na$_2$SO$_4$, filtered and concentrated in vacuo to give 2-(tert-butyl)-6-chloro-7-(pyrrolidin-1-ylsulfonyl)benzo[d]oxazole (600 mg) as a yellow solid. MS(ES$^+$) m/z 343 (MH$^+$).

Step 2:
To a solution of 2-(tert-butyl)-6-chloro-7-(pyrrolidin-1-ylsulfonyl)benzo[d]oxazole (520 mg) in 1,4-dioxane (10 mL) was added HCl (37%, 6 mL). The resulting mixture was stirred for 15 hours at 100° C. The reaction mixture was concentrated in vacuo. The residue was purified by column chromatography (eluting with PE:EA=5:1) to give the title compound (250 mg) as a yellow solid. $^1$H-NMR (400 MHz, CDCl$_3$) δ ppm 6.84 (d, J=8.4 Hz, 1H), 6.75 (d, J=8.4 Hz, 1H), 3.45-3.39 (m, 4H), 1.96-1.91 (m, 4H); MS(ES$^+$) m/z 277 (MH$^+$)

Intermediate 93: 6-amino-3-chloro-2-((5,6-dihydroimidazo[1,2-a]pyrazin-7(8H)-yl)sulfonyl)phenol

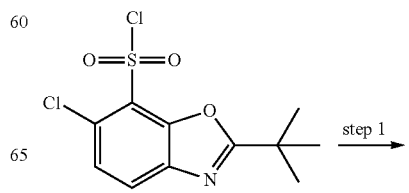

step 1

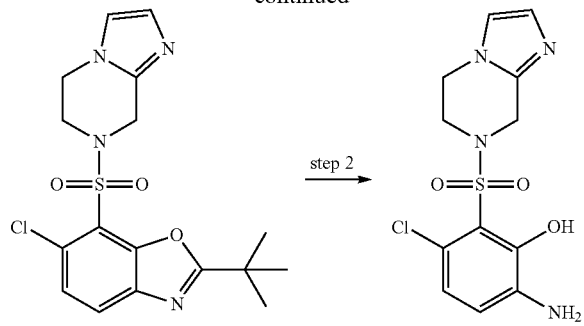

Step 1: To a solution of TEA (0.7 mL) and 5,6,7,8-tetrahydroimidazo[1,2-a]pyrazine (200 mg) in THF (10 mL) was added 2-(tert-butyl)-6-chlorobenzo[d]oxazole-7-sulfonyl chloride (500 mg) in small portion at RT. The mixture was stirred overnight. Cold water (30 mL) was added. The resulting mixture was extracted with DCM (2×100 mL). The combined organic layers were dried over Na$_2$SO$_4$, filtered and concentrated in vacuo. The residue was purified by column chromatography (eluting with PE:EA=1:1) to give 2-(tert-butyl)-6-chloro-7-((5,6-dihydroimidazo[1,2-a]pyrazin-7(8H)-yl)sulfonyl)benzo[d]oxazole (562 mg) as a yellow solid. MS(ES$^+$) m/z 395 (MH$^+$).

Step 2: 2-(Tert-butyl)-6-chloro-7-((5,6-dihydroimidazo[1,2-a]pyrazin-7(8H)-yl)sulfonyl)benzo[d]oxazole (520 mg) was dissolved in 1,4-dioxane (5 mL). Conc. HCl solution (2.4 mL) was added. The mixture was heated to 100° C. for 3 hours to give a brown solution. The mixture was cooled to RT and concentrated under reduced pressure. The residue was treated with sat. NaHCO$_3$ solution until pH=8 in an ice bath. The mixture was extracted with DCM (5×20 mL). The combined organic layers were dried over sodium sulfate, filtered and concentrated to give the title compound (320 mg) as a brown solid. MS(ES$^+$) m/z 329 (MH$^+$).

Intermediate 94:
6-amino-3-chloro-2-(morpholinosulfonyl)phenol

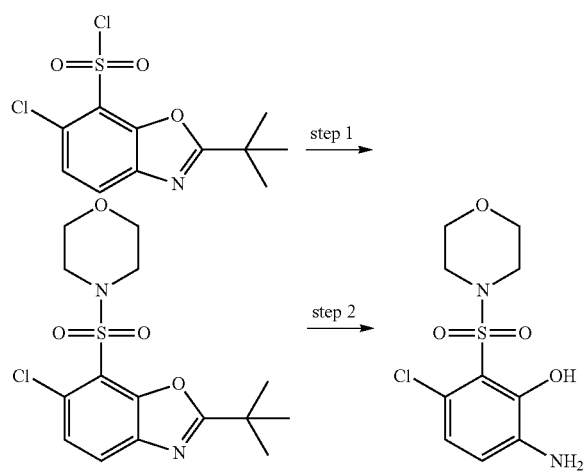

Step 1: To a solution of TEA (0.5 mL) and morpholine (113 mg) in THF (10 mL) was added 2-(tert-butyl)-6-chlorobenzo[d]oxazole-7-sulfonyl chloride (400 mg) in small portion at RT. The mixture was stirred overnight. Cold water (30 mL) was added. The resulting mixture was extracted with DCM (2×100 mL). The combined organic layers were dried over Na$_2$SO$_4$, filtered and concentrated in vacuo. The residue was purified by column chromatography (eluting with PE:EA=5:1) to give 2-(tert-butyl)-6-chloro-7-(morpholinosulfonyl)benzo[d]oxazole (370 mg) as a yellow solid. MS(ES$^+$) m/z 359 (MH$^+$).

Step 2: 2-(Tert-butyl)-6-chloro-7-(morpholinosulfonyl)benzo[d]oxazole (540 mg) was dissolved in 1,4-dioxane (15 mL) and water (3 mL). Conc. sulfuric acid (1.6 mL) was added. The mixture was heated to 100° C. overnight to give a brown solution. After cooling, the mixture was concentrated in vacuo. The residue was treated with aq. NaOH solution (6 M) until pH=12 in an ice bath. The mixture was extracted with EA (4×~50 mL). The combined organic layers were dried over sodium sulfate, filtered and concentrated to give the title compound (440 mg) as a yellow oil. MS(ES$^+$) m/z 293 (MH$^+$).

Intermediate 95: 6-amino-3-chloro-2-((4-ethyltetrahydro-2H-pyran-4-yl)sulfonyl)phenol

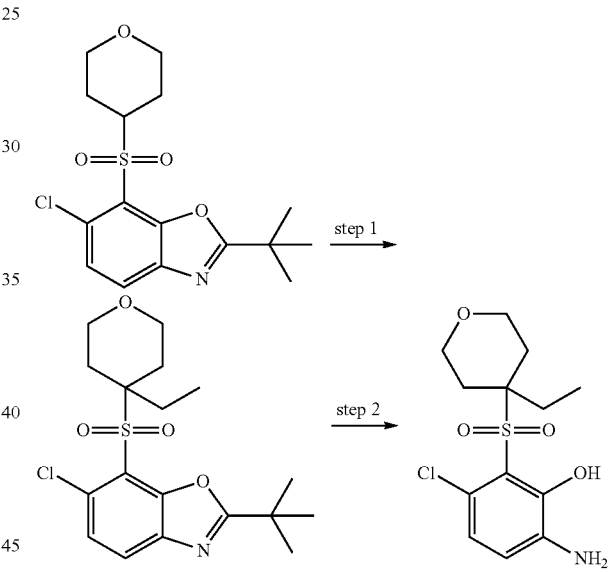

Step 1: To a dry ice-ethanol cooled solution of 2-(tert-butyl)-6-chloro-7-((tetrahydro-2H-pyran-4-yl)sulfonyl)benzo[d]oxazole (Intermediate 30, Step 3, 0.8 g) and iodoethane (0.3 mL) in THF (25 mL) was added LiHMDS (1 M in THF, 4.5 mL). The resulting mixture was warmed up slowly and stirred for 3 hours. The mixture was quenched with aq. NH$_4$Cl solution, and then extracted with EA (2×100 mL). The combined organic phases were washed, dried and concentrated to afford 2-(tert-butyl)-6-chloro-7-((4-ethyltetrahydro-2H-pyran-4-yl)sulfonyl)benzo[d]oxazole (0.8 g). MS(ES$^+$) m/z 386 (MH$^+$).

Step 2: To a solution of 2-(tert-butyl)-6-chloro-7-((4-ethyltetrahydro-2H-pyran-4-yl)sulfonyl)benzo[d]oxazole (0.8 g) in 1,4-dioxane (10 mL) and water (10 mL) was added conc. H$_2$SO$_4$ (1.1 mL). The resulting mixture was stirred at 120° C. overnight. The mixture was concentrated under reduced pressure. The residue was basified with aq. NaHCO$_3$ solution, and extracted with EA (3×50 mL). The combined organic phases were washed, dried and concentrated. The residue was purified with column chromatogra- Intermediate 96: 3-amino-6-chloro-N,N-diethyl-2-hydroxybenzenesulfonamide

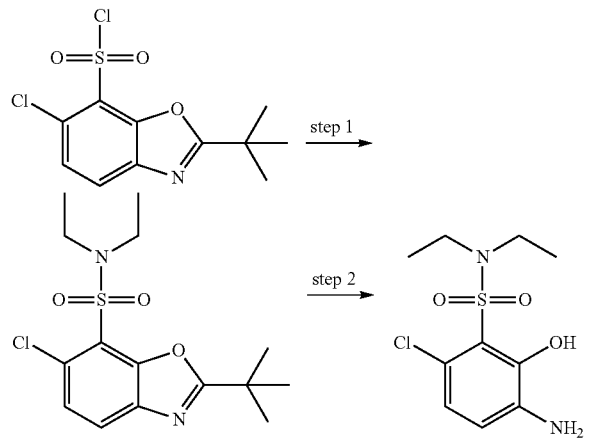

Step 1: A solution of 2-(tert-butyl)-6-chlorobenzo[d]oxazole-7-sulfonyl chloride (400 mg), TEA (263 mg) and diethylamine (114 mg) was stirred in THF (6 mL) at RT for 6 hours. Cold water (30 mL) was added. The aq. layer was extracted with DCM (2×100 mL). The combined organic layers were dried over $Na_2SO_4$, filtered and concentrated in vacuo. The residue was purified by column chromatography (eluting with PE:EA=10:1) to give 2-(tert-butyl)-6-chloro-N,N-diethylbenzo[d]oxazole-7-sulfonamide (263 mg) as an oil. MS(ES$^+$) m/z 345 (MH$^+$).

Step 2: 2-(Tert-butyl)-6-chloro-N,N-diethylbenzo[d]oxazole-7-sulfonamide (300 mg) was dissolved in 1,4-dioxane (15 mL) and water (3 mL). Conc. sulfuric acid (0.8 mL) was added. The mixture was heated to 100° C. overnight to give a brown solution. After cooling, the reaction mixture was concentrated in vacuo, and then treated with aq. NaOH solution (6 M) until pH=12 in an ice bath. The mixture was extracted with EA (4×~50 mL). The combined organic layers were dried over sodium sulfate, filtered and concentrated. The residue was purified by column chromatography (eluting with PE:EA=6:1) to give the title compound (190 mg) as a white oil. MS(ES$^+$) m/z 279 (MH$^+$).

Intermediate 97: (S)-6-amino-3-chloro-2-((1-methoxypropan-2-yl)sulfonyl)phenol

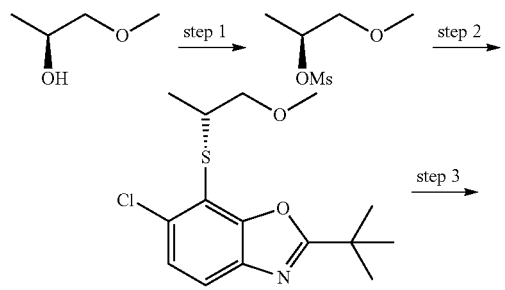

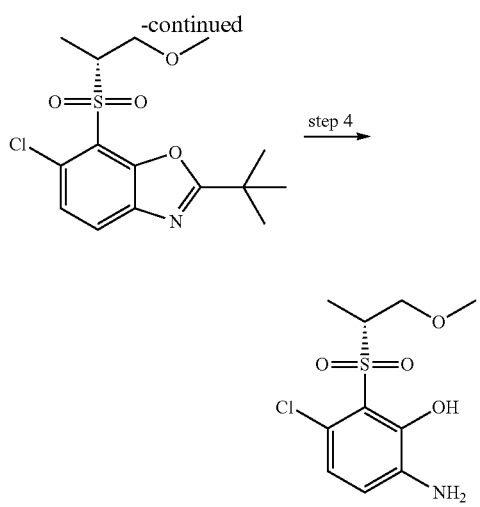

Step 1: To a solution of (S)-1-methoxypropan-2-ol (5.4 g) and TEA (12.1 g) in THF (20 mL) was added methanesulfonyl chloride (8.3 g) at 0° C. The mixture was stirred at 0° C. for 4 hours. The resulting solution was poured into water, and extracted with EA (2×50 mL). The combined organic phases were washed, dried and concentrated to give (S)-1-methoxypropan-2-yl methanesulfonate (10.8 g) as a light yellow liquid. $^1$H-NMR (400 MHz, CDCl$_3$) δ ppm 4.86-4.90 (m, 1H), 3.46-3.53 (m, 2H), 3.39 (s, 3H), 3.05 (s, 3H), 1.39 (d, J=6.5 Hz, 3H).

Step 2: $K_2CO_3$ (2.6 g) was added to a solution of sodium 2-(tert-butyl)-6-chlorobenzo[d]oxazole-7-thiolate (5.0 g) and (S)-1-methoxypropan-2-yl methanesulfonate (3.2 g) in DMF (25 mL) at RT. The reaction mixture was stirred at 50° C. for 3 hours. The resulting solution was poured into ice-water (50 mL), and extracted with EA (4×30 mL). The combined organic phases were washed with brine (8 mL), dried over $Na_2SO_4$ and concentrated under reduced pressure. The residue was purified by column chromatography (eluting with EA:PE=1:30) to give (R)-2-(tert-butyl)-6-chloro-7-((1-methoxypropan-2-yl)thio)benzo[d]oxazole (4.1 g) as a light yellow solid. MS(ES$^+$) m/z 314 (MH$^+$).

Step 3: To a solution of (R)-2-(tert-butyl)-6-chloro-7-((1-methoxypropan-2-yl)thio)benzo[d]oxazole (4.0 g) in DCM (20 mL) was added mCPBA (8.8 g) at 0° C. The resulting mixture was stirred at RT for 3 hours. Cold water (30 mL) was added. The solution was neutralized with sat. NaHCO$_3$ solution. The aqueous layer was extracted with DCM (2×80 mL). The combined organic layers were dried over $Na_2SO_4$, filtered and concentrated in vacuo. The residue was purified by column chromatography (eluting with PE:EA=5:1) to give (R)-2-(tert-butyl)-6-chloro-7-((1-methoxypropan-2-yl)sulfonyl)benzo[d]oxazole (4.0 g) as a colorless liquid. MS(ES$^+$) m/z 346 (MH$^+$).

Step 4: To a solution of aq. sulfuric acid (65%, 0.6 mL) in 1,4-dioxane (2 mL) was added (R)-2-(tert-butyl)-6-chloro-7-((1-methoxypropan-2-yl)sulfonyl)benzo[d]oxazole (2.0 g). The resulting mixture was stirred for 1 hour at 100° C. Cold water (50 mL) was added. The solution was neutralized with sat. NaHCO$_3$ solution. The aqueous layer was extracted with DCM (3×50 mL). The combined organic layers were dried over $Na_2SO_4$, filtered and concentrated in vacuo to give the title compound (1.1 g) as a dark solid. MS(ES$^+$) m/z 280 (MH$^+$).

Intermediate 98: 4-amino-2-((2-fluoropropan-2-yl)sulfonyl)-3-hydroxybenzonitrile

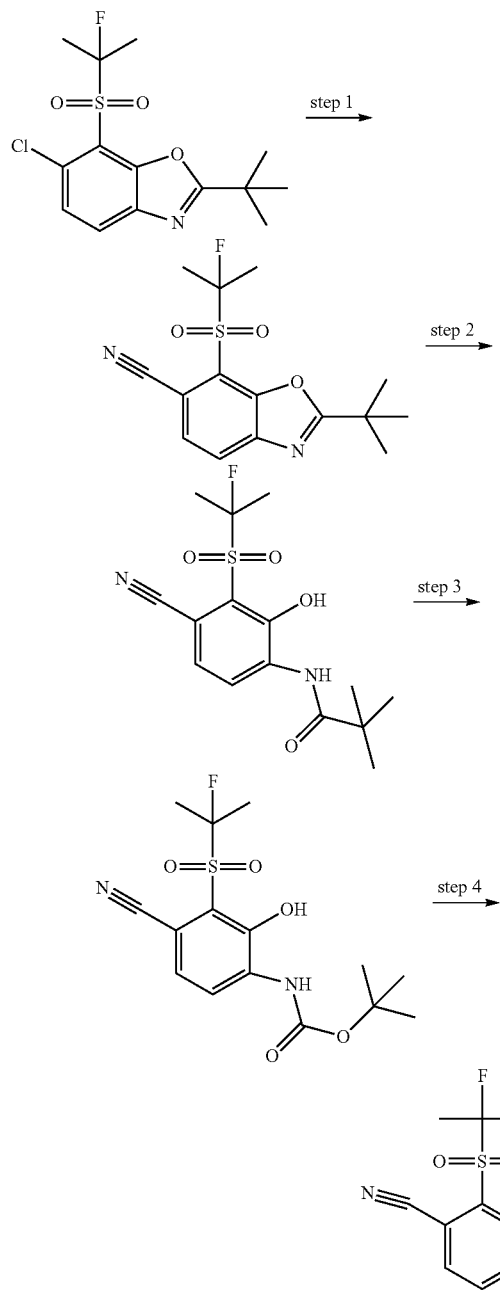

Step 1: A suspension of copper(I) cyanide (2.5 g) in NMP (10 mL) was heated to 200° C. A solution of 2-(tert-butyl)-6-chloro-7-((2-fluoropropan-2-yl)sulfonyl)benzo[d]oxazole (Intermediate 20, Step 3, 1.2 g) in NMP (10 mL) was added. The resulting mixture was stirred at 200° C. for 2 hours. After cooling, the mixture was diluted with EA (150 mL), and then washed with ammonium hydroxide (2×100 mL). The organic layer was dried over Na₂SO₄, filtered and concentrated under reduced pressure. The residue was purified by column chromatography (eluting with PE:EA=6:1) to give 2-(tert-butyl)-7-((2-fluoropropan-2-yl)sulfonyl)benzo[d]oxazole-6-carbonitrile (220 mg) as an off-white solid. $^1$H-NMR (400 MHz, CDCl₃) δ ppm 8.05 (d, J=8.2 Hz, 1H), 7.87 (d, J=8.2 Hz, 1H), 1.86 (s, 3H), 1.81 (s, 3H), 1.54 (s, 8H); MS(ES⁺) m/z 342 (MNH₄⁺).

Step 2: To a solution of 2-(tert-butyl)-7-((2-fluoropropan-2-yl)sulfonyl)benzo[d]oxazole-6-carbonitrile (510 mg) in ethanol (10 mL) and water (10 mL) was added NaOH (126 mg). The resulting mixture was stirred at 60° C. for 1 hour. The reaction mixture was diluted with water (50 mL), acidified with aq. citric acid to pH=6 and extracted with EA (2×50 mL). The combined organic phases were washed, dried and concentrated to afford N-(4-cyano-3-((2-fluoropropan-2-yl)sulfonyl)-2-hydroxyphenyl)pivalamide (530 mg). MS(ES⁺) m/z 343 (MH⁺).

Step 3: To a solution of N-(4-cyano-3-((2-fluoropropan-2-yl)sulfonyl)-2-hydroxyphenyl)pivalamide (330 mg) in THF (25 mL) was added DMAP (11.8 mg) and di-tert-butyl dicarbonate (421 mg). The resulting mixture was stirred at 50° C. for 3 hours. After cooling, hydrazine.H₂O (241 mg) was added. The resulting mixture was stirred at RT overnight. The resulting solution was diluted with water (50 mL), and extracted with EA (2×50 mL). The combined organic phases were washed, dried and concentrated. The residue was purified by column chromatography (eluting with 0-50% EA in PE) to afford tert-butyl (4-cyano-3-((2-fluoropropan-2-yl)sulfonyl)-2-hydroxyphenyl)carbamate (230 mg). MS(ES⁺) m/z 359 (MH⁺).

Step 4: To a solution of tert-butyl (4-cyano-3-((2-fluoropropan-2-yl)sulfonyl)-2-hydroxyphenyl)carbamate (0.2 g) in DCM (10 mL) was added TFA (0.5 mL). The resulting mixture was stirred at RT overnight. After concentration under reduced pressure, the residue was diluted with water (50 mL), basified with aq. NaHCO₃ solution, and extracted with EA (2×50 mL). The combined organic phases were washed, dried and concentrated to afford the title compound (130 mg). MS(ES⁺) m/z 259 (MH⁺).

Intermediate 99: 6-amino-3-chloro-2-((cis-3-ethoxycyclobutyl)sulfonyl)phenol

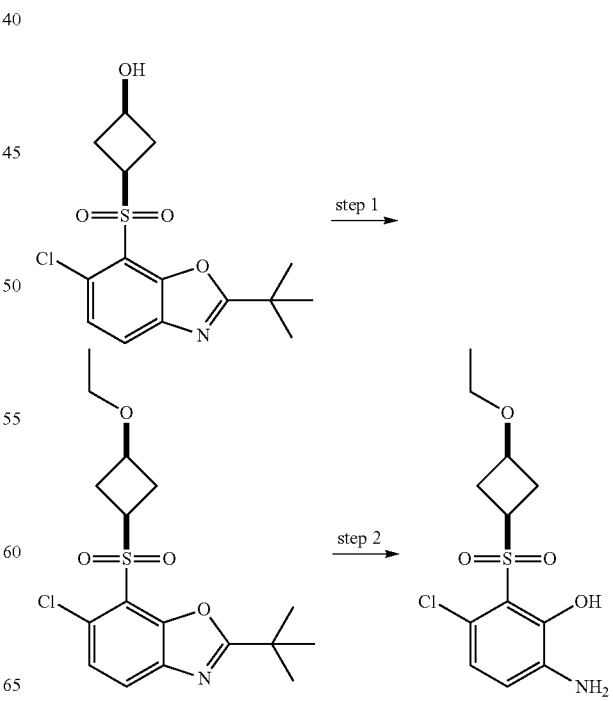

Step 1: To a solution of cis-3-((2-(tert-butyl)-6-chlorobenzo[d]oxazol-7-yl)sulfonyl)cyclobutanol (Intermediate 28, Step 3, 520 mg) in THF (50 mL) was added NaH (73 mg) at 0° C. After stirring for 30 mins, iodoethane (0.2 mL) was added. The reaction mixture was warmed up slowly and stirred at RT over 3 days. The reaction mixture was quenched with aq. NH$_4$Cl solution, and then extracted with EA (2×50 mL). The combined organic layers were washed, dried, filtered and concentrated. The residue was purified by column chromatography (eluting with PE:EA=4:1 to 3:2) to afford 2-(tert-butyl)-6-chloro-7-((cis-3-ethoxycyclobutyl)sulfonyl)benzo[d]oxazole (100 mg). MS(ES$^+$) m/z 372 (MH$^+$).

Step 2: To a solution of 2-(tert-butyl)-6-chloro-7-((cis-3-ethoxycyclobutyl)sulfonyl)benzo[d]oxazole (100 mg) in 1,4-dioxane (5 mL) was added conc. HCl solution (5 mL). The reaction mixture was heated at 120° C. overnight. The solution was cooled down to RT and purified by reversed phase chromatography (eluting with ACN and water) to afford the title compound (80 mg). MS(ES$^+$) m/z 306 (MH$^+$).

Intermediate 100: 6-amino-3-chloro-2-((1-ethoxy-2-methylpropan-2-yl)sulfonyl)phenol

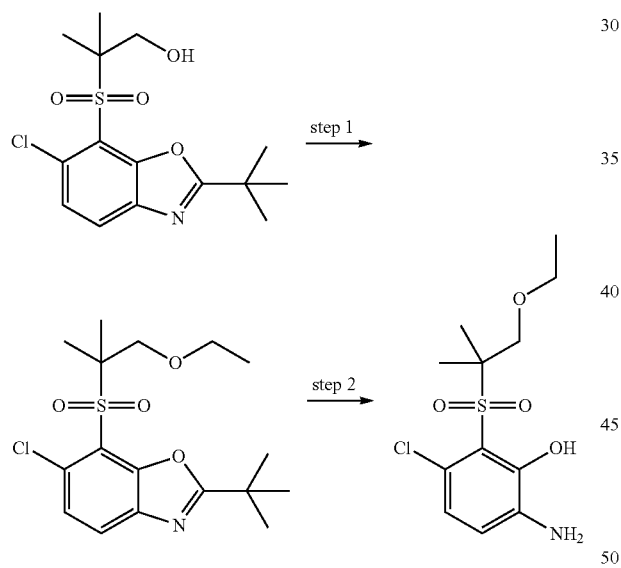

Step 1: To a solution of 2-((2-(tert-butyl)-6-chlorobenzo[d]oxazol-7-yl)sulfonyl)-2-methylpropan-1-ol (Intermediate 17, Step 3, 2.0 g) and iodoethane (1.8 g) in THF (15 mL) was added NaH (0.7 g) at 0° C. The reaction mixture was stirred at 30° C. for 4 hours, and then quenched with MeOH (5 mL). The resulting mixture was concentrated to afford 2-(tert-butyl)-6-chloro-7-((1-ethoxy-2-methylpropan-2-yl)sulfonyl)benzo[d]oxazole (2.0 g). MS(ES$^+$) m/z 374 (MH$^+$).

Step 2: A solution of 2-(tert-butyl)-6-chloro-7-((1-ethoxy-2-methylpropan-2-yl)sulfonyl)benzo[d]oxazole (2.0 g) in 1,4-dioxane (20 mL) and aq. HCl solution (37%, 20 mL) was stirred at 100° C. for 4 hours. The mixture was concentrated. The pH was adjusted to 8. The resulting mixture was purified by preparative HPLC to afford the title compound (620 mg). MS(ES$^+$) m/z 308 (MH$^+$).

Intermediate 101: cis-6-amino-3-chloro-2-((3-(dimethylamino)cyclopentyl)sulfonyl)phenol

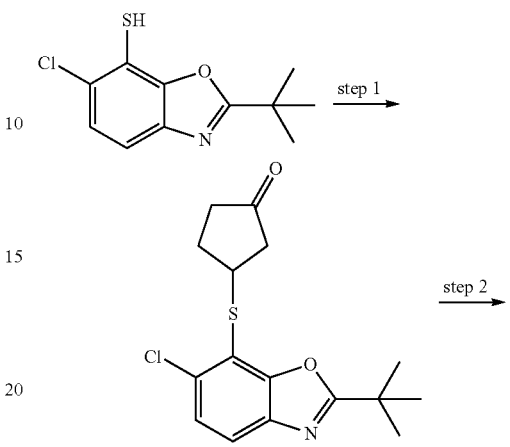

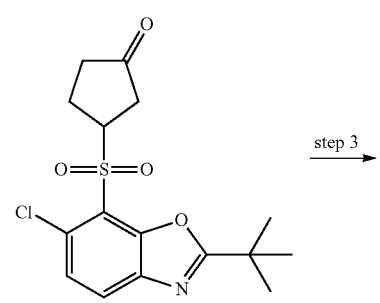

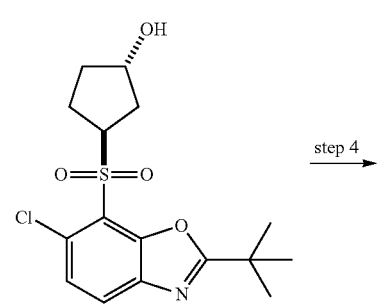

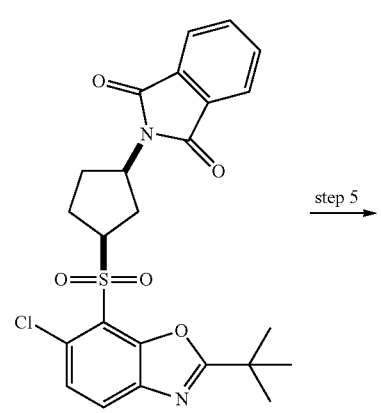

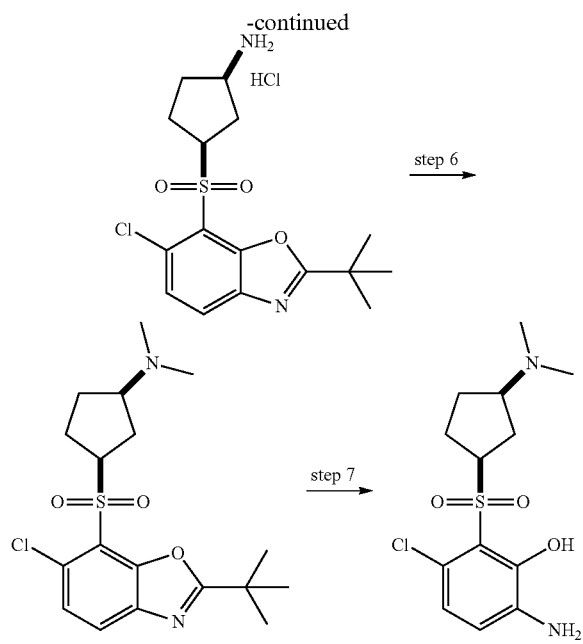

Step 1: To a solution of cyclopent-2-enone (0.5 g) in chloroform (30 mL) was added 2-(tert-butyl)-6-chlorobenzo[d]oxazole-7-thiol (1.3 g). The resulting mixture was stirred at RT for 18 hours. Diethyl ether (50 mL) was added. The mixture was washed with aq. NaOH solution (5%, 2×20 mL), water (30 mL) and brine (30 mL). The organic phase was dried over Na$_2$SO$_4$ and concentrated under reduced pressure to give 3-((2-(tert-butyl)-6-chlorobenzo[d]oxazol-7-yl)thio)cyclopentanone (1.4 g) as a light yellow gel. MS(ES$^+$) m/z 324 (MH$^+$).

Step 2: To a solution of 3-((2-(tert-butyl)-6-chlorobenzo[d]oxazol-7-yl)thio)cyclopentanone (1.4 g) in DCM (10 mL) was added mCPBA (1.6 g) at 0° C. The resulting mixture was stirred at RT overnight, and then washed with sat. K2CO3 solution (2×10 mL) and water (10 mL). The organic phase was dried over Na$_2$SO$_4$ and concentrated under reduced pressure. The residue was purifed by column chromatography (eluting with PE:EA=2:1) to give 3-((2-(tert-butyl)-6-chlorobenzo[d]oxazol-7-yl)sulfonyl)cyclopentanone (800 mg) as a colorless gel. MS(ES$^+$) m/z 356 (MH$^+$).

Step 3: To a solution of 3-((2-(tert-butyl)-6-chlorobenzo[d]oxazol-7-yl)sulfonyl)cyclopentanone (6.8 g) in THF (6 mL) at −78° C. was slowly added L-selectride (1 M in THF, 34.4 mL) with a syringe. The mixture was stirred under a nitrogen atmosphere at −78° C. for 2 hours. The mixture was allowed to warm to RT and stirred for 18 hours. Water (5 mL) was carefully added.

The pH was adjusted to 6 with addition of aq. HCl solution (4 M). The resulting mixture was extracted with EA (2×15 mL). The organic layers were washed with brine (10 mL), dried over Na$_2$SO$_4$, filtered and concentrated under reduced pressure. The residue was purified by column chromatography (eluting with PE:EA=3:2) to give trans-3-((2-(tert-butyl)-6-chlorobenzo[d]oxazol-7-yl)sulfonyl)cyclopentanol (5.0 g) as a colorless gel. MS(ES$^+$) m/z 358 (MH$^+$).

Step 4: DIAD (1.1 mL) was added to a solution of trans-3-((2-(tert-butyl)-6chlorobenzo[d]oxazol-7-yl)sulfonyl)cyclopentanol (1.0 g), isoindoline-1,3-dione (0.5 g) and triphenylphosphine (1.1 g) in THF at 0° C. The mixture was stirred at RT overnight. Cold water (30 mL) was added. The aqueous layer was extracted with DCM (2×100 mL). The combined organic layers were dried over Na$_2$SO$_4$, filtered and concentrated in vacuo. The residue was purified by column chromatography (eluting with PE:EA=40:1) to give 2-(cis-3-((2-(tert-butyl)-6-chlorobenzo[d]oxazol-7-yl)sulfonyl)cyclopentyl)isoindoline-1,3-dione (1.1 g) as a white solid. MS(ES$^+$) m/z 487 (MH$^+$).

Step 5: 2-(Cis-3-((2-(tert-butyl)-6-chlorobenzo[d]oxazol-7-yl)sulfonyl)cyclopentyl)isoindoline-1,3-dione (900 mg) was dissolved in absolute ethanol (12 mL) and THF (12 mL), followed by careful addition of hydrazine (98% in water, 69 mg). The flask was then heated to 80° C. for 18 hours. Upon cooling to RT, the resulting solid was filtered. The filtrate was added HCl solution (4 M in 1,4-dioxane, 1.9 mL), and then stirred at RT for 3 hours. The mixture was concentrated under reduced pressure. The residue was washed with Et$_2$O (3×3 mL) to give cis-3-((2-(tert-butyl)-6-chlorobenzo[d]oxazol-7-yl)sulfonyl)cyclopentanamine, hydrochloride (275 mg) as a yellow solid. MS(ES$^+$) m/z 357 (MH$^+$).

Step 6: To a stirred solution of cis-3-((2-(tert-butyl)-6-chlorobenzo[d]oxazol-7-yl)sulfonyl)cyclopentanamine, hydrochloride (265 mg), acetic acid (0.04 mL) and formaldehyde (0.5 mL) in DMF (8 mL) at 0° C. was added sodium triacetoxyborohydride (157 mg). The reaction mixture was stirred at RT for 3 hours. The mixture was quenched with aq. NaHCO$_3$ solution (75 mL). The mixture was extracted with EA (5×55 mL). The combined organic layers were washed with brine, dried over MgSO$_4$, filtered and concentrated under reduced pressure. The residue was purified by column chromatography (eluting with MeOH:DCM=1:20) to give cis-3-((2-(tert-butyl)-6-chlorobenzo[d]oxazol-7-yl)sulfonyl)-N,N-dimethylcyclopentanamine (80 mg) as a yellow solid. MS(ES$^+$) m/z 385 (MH$^+$).

Step 7: Cis-3-((2-(tert-butyl)-6-chlorobenzo[d]oxazol-7-yl)sulfonyl)-N,N-dimethylcyclopentanamine (91 mg) was dissolved in 1,4-dioxane (5 mL) and water (1 mL). Conc. sulfuric acid (0.2 mL) was added. The mixture was heated to 100° C. overnight. After cooling to RT, the mixture was concentrated in vacuo. Aq. NaOH solution (6 M) was added until pH=12 in an ice bath. The mixture was extracted with EA (4×50 mL). The combined organic layers were dried over sodium sulfate, filtered and concentrated to give the title compound (77 mg) as an oil. MS(ES$^+$) m/z 319 (MH$^+$).

Intermediate 102: (±)cis-6-amino-3-chloro-2-((2-(dimethylamino)cyclopentyl)sulfonyl)phenol

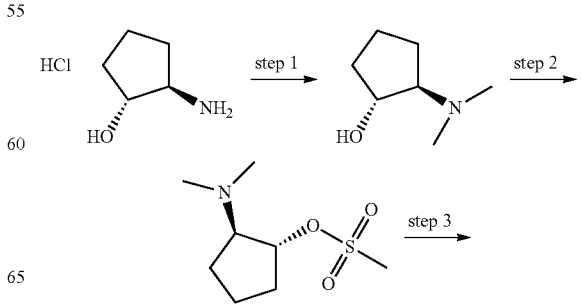

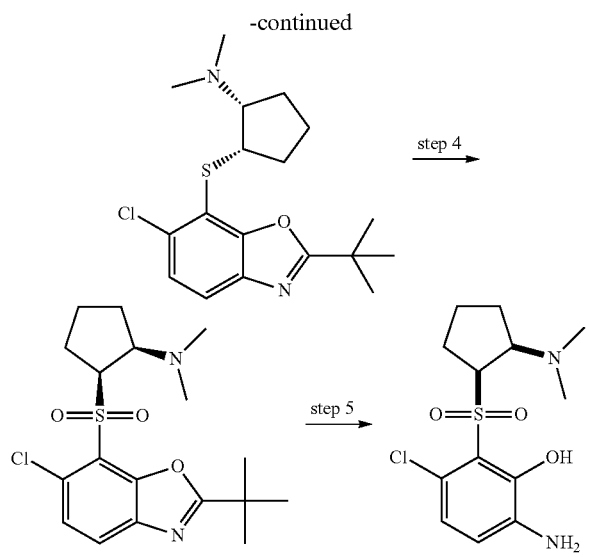

Step 1: To a precooled solution of formaldehyde (25.5 mL) and formic acid (25.5 mL) was added (±)trans-2-aminocyclopentanol, hydrochloride (1.2 g). The solution was heated to 100° C. overnight. After cooling, aq. HCl solution (6 M, 50 mL) was added. The solution was then concentrated to remove the excess formaldehyde and formic acid. The remaining solid was recrystalized from EA and ethanol. The residue was treated with aq. NaOH solution, extracted with ether, dried over $K_2CO_3$ and concentrated to afford (±)trans-2-(dimethylamino)cyclopentanol (874 mg) as a light yellow oil. $^1$H-NMR (500 MHz, $CDCl_3$) δ ppm 4.06 (dd, J=12.6, 5.5 Hz, 1H), 3.54 (s, 1H), 2.44-2.52 (m, 1H), 2.29 (s, 6H), 1.41-1.98 (m, 6H); MS($ES^+$) m/z 130 ($MH^+$).

Step 2: To a solution of (±)trans-2-(dimethylamino)cyclopentanol (874 mg) in DCM (10 mL) were added DIPEA (3.4 mL) and methanesulfonyl chloride (0.8 mL). The mixture was stirred at 25° C. for 4 hours. Water was added. The mixture was extracted with DCM. The organic phase was dried over $Na_2SO_4$ and concentrated to afford (±)trans-2-(dimethylamino)cyclopentyl methanesulfonate (884 mg) as a red brown vicious liquid. $^1$H-NMR (400 MHz, $CDCl_3$) δ ppm 4.15 (dt, J=7.4, 4.5 Hz, 1H), 2.87 (td, J=7.9, 4.8 Hz, 1H), 2.30 (d, J=5.8 Hz, 9H), 2.16 (dd, J=13.8, 8.4 Hz, 1H), 1.98-1.92 (m, 2H), 1.79-1.84 (m, 1H), 1.67-1.73 (m, 1H), 1.47-1.56 (m, 1H).

Step 3: To a solution of 2-(tert-butyl)-6-chlorobenzo[d]oxazole-7-thiol (824 mg) in DMF (20 mL), $K_2CO_3$ (589 mg) and (±)trans-2-(dimethylamino)cyclopentyl methanesulfonate (884 mg) were added. The mixture stirred at 90° C. for 2 hours. EA (20 mL) was added. The mixture was washed with brine (3×10 mL), dried over $Na_2SO_4$ and concentrated. The residue was purified by reversed phase column chromatography (C18, mobile phase 0.01% $CF_3COOH/H_2O$, $CH_3OH$, 30 mL/min) (5%~50%, 5 min; 50~50%, 10 min; 50%~95%, 5 min; 95%~95%, 1 min) to give (±)cis-2-((2-(tert-butyl)-6-chlorobenzo[d]oxazol-7-yl)thio)-N,N-dimethylcyclopentanamine (1.3 g) as a yellow solid. $^1$H-NMR (500 MHz, $CDCl_3$) δ ppm 7.59 (d, J=8.4 Hz, 1H), 7.42 (d, J=8.5 Hz, 1H), 4.20 (dd, J=7.1, 4.0 Hz, 1H), 3.21 (d, J=4.8 Hz, 1H), 3.04 (s, 3H), 2.88 (s, 3H), 2.28 (d, J=4.9 Hz, 1H), 1.98-2.19 (m, 2H), 1.85-1.93 (m, 2H), 1.73-1.82 (m, 1H), 1.51 (s, 9H); MS($ES^+$) m/z 353 ($MH^+$).

Step 4: To a solution of (±)cis-2-((2-(tert-butyl)-6-chlorobenzo[d]oxazol-7-yl)thio)-N,N-dimethylcyclopentanamine (320 mg) in DCM (10 mL), mCPBA (313 mg) and 2,2,2-trifluoroacetic acid (207 mg) were added. The mixture was stirred at 18° C. for 2 days. The mixture was quenched with aq. $Na_2S_2O_3$ solution and aq. $NaHCO_3$ solution. The resulting mixture was extracted with DCM (3×4 mL), dried over $Na_2SO_4$ and concentrated. The residue was purified by column chromatography (eluting with DCM:MeOH=10:1) to give (±)cis-2-((2-(tert-butyl)-6-chlorobenzo[d]oxazol-7-yl)sulfonyl)-N,N-dimethylcyclopentanamine (145 mg) as a purple oil. $^1$H-NMR (500 MHz, $CDCl_3$) δ ppm 7.80 (d, J=8.4 Hz, 1H), 7.47 (d, J=8.4 Hz, 1H), 4.12 (dd, J=14.3, 7.1 Hz, 1H), 3.68 (s, 1H), 2.24 (d, J=19.5 Hz, 6H), 2.05 (s, 2H), 1.93 (s, 2H), 1.79 (s, 2H), 1.52 (s, 9H); MS($ES^+$) m/z 385 ($MH^+$).

Step 5: To a solution of (±)cis-2-((2-(tert-butyl)-6-chlorobenzo[d]oxazol-7-yl)sulfonyl)-N,N-dimethylcyclopentanamine (180 mg) in 1,4-dioxane (4 mL) was added aq. HCl solution (12 M, 4 mL). The mixture was stirred at 110° C. for 4 hours, and then concentrated. Aq. $NaHCO_3$ solution was added until pH=7. The resulting mixture was extracted with DCM (3×2 mL). The combined organic phases were dried over $Na_2SO_4$ and concentrated to give the title compound (130 mg) as a brown oil. $^1$H-NMR (400 MHz, $CDCl_3$) δ ppm 6.85 (d, J=8.4 Hz, 1H), 6.78 (d, J=8.4 Hz, 1H), 4.20 (d, J=16.7 Hz, 2H), 2.26 (s, 6H), 1.97-2.06 (m, 3H), 1.79 (d, J=6.3 Hz, 3H); MS($ES^+$) m/z 319 ($MH^+$).

Intermediate 103: 6-amino-3-chloro-2-(((1s,4s)-4-(dimethylamino)cyclohexyl)sulfonyl)phenol

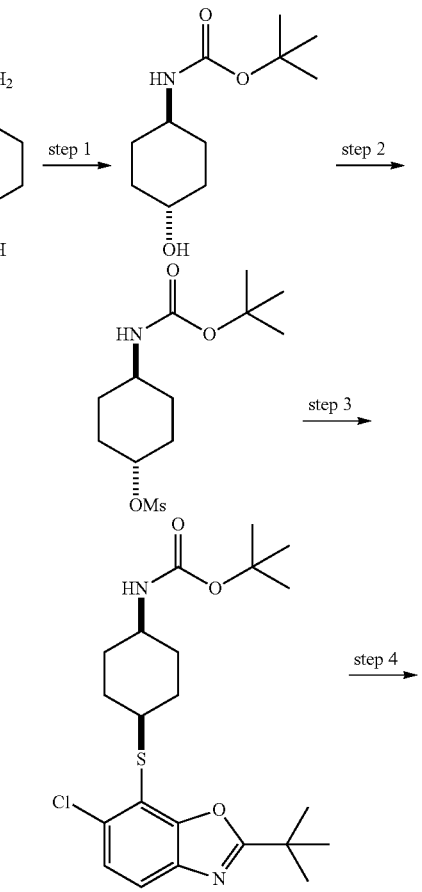

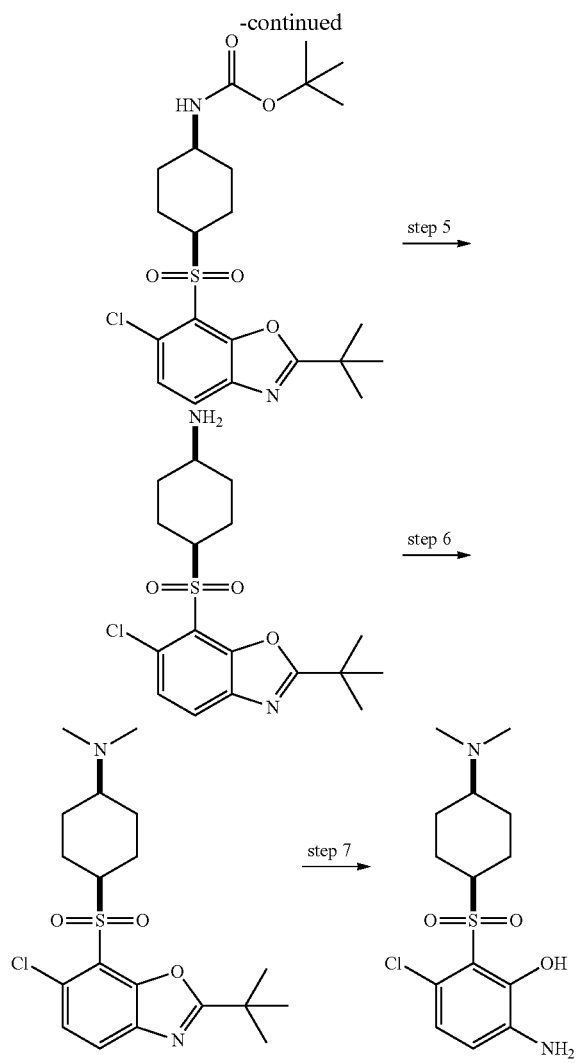

Step 1: To a stirred mixture of (1r,4r)-4-aminocyclohexanol (3.0 g) and DIPEA (5.0 mL) in DCM (100 mL) was added Boc$_2$O (6.4 mL) slowly. The reaction mixture was stirred at RT for 3 hours. The mixture was concentrated under reduced pressure to give tert-butyl ((1r,4r)-4-hydroxycyclohexyl)carbamate (5.7 g) as a pink solid. MS(ES$^+$) m/z 160 (M-t-Bu+H+H$^+$).

Step 2: To a stirred solution of tert-butyl ((1r,4r)-4-hydroxycyclohexyl)carbamate (5.0 g) and DIPEA (6.1 mL) in DCM (80 mL) at 0° C. was added methanesulfonyl chloride (2.4 mL) slowly. The reaction mixture was kept at this temperature for 1 hour. The solution was quenched with aq. NaHCO$_3$ solution (60 mL). The mixture was extracted with DCM (3×50 mL). The combined organic layers were dried over MgSO$_4$, filtered and concentrated under reduced pressure to give (1r,4r)-4-((tert-butoxycarbonyl)amino)cyclohexyl methanesulfonate (8.4 g) as a yellow solid. $^1$H-NMR (400 MHz, CDCl$_3$) δ ppm 4.62 (m, 1H), 3.47 (s, 1H), 2.71 (s, 3H), 2.11 (m, 4H), 1.68 (m, 2H), 1.44 (s, 9H), 1.25 (m, 2H).

Step 3: K$_2$CO$_3$ (3.5 g) was added to a solution of 2-(tert-butyl)-6-chlorobenzo[d]oxazole-7-thiol (3.1 g) and (1r,4r)-4-((tertbutoxycarbonyl)amino)cyclohexyl methanesulfonate (3.7 g) in DMF (80 mL) at RT. The reaction mixture was stirred at 80° C. for 2 hours. The reaction solution was combined with another batch using (1r,4r)-4-((tert-butoxycarbonyl)amino)cyclohexyl methanesulfonate (293 mg) as starting material. The combined mixture was poured into ice-water (400 mL), and extracted with EA (4×150 mL). The combined organic layers were washed with brine (80 mL), dried over Na$_2$SO$_4$, filtered and concentrated under reduced pressure to give tert-butyl ((1s,4s)-4-((2-(tert-butyl)-6-chlorobenzo[d]oxazol-7-yl)thio)cyclohexyl)carbamate (6.2 g) as a brown oil. MS(ES$^+$) m/z 383 (M-t-Bu+H+H$^+$).

Step 4: To a stirred solution of tert-butyl ((1s,4s)-4-((2-(tert-butyl)-6-chlorobenzo[d]oxazol-7-yl)thio)cyclohexyl)carbamate (6.0 g) in DCM (100 mL) at 0° C. was added a solution of mCPBA (4.7 g) in DCM (80 mL) over 10 mins. The reaction mixture was stirred at RT for 3 hours. Sat. Na$_2$S$_2$O$_3$ solution and sat. Na$_2$CO$_3$ solution were added. The reaction mixture was extracted with DCM (4×100 mL). The combined organic layer was dried over MgSO$_4$, filtered and concentrated under reduced pressure to give tert-butyl ((1s,4s)-4-((2-(tert-butyl)-6-chlorobenzo[d]oxazol-7-yl)sulfonyl)cyclohexyl)carbamate (4.8 g) as a brown solid. MS(ES$^+$) m/z 415 (M-t-Bu+H+H$^+$).

Step 5: To a stirred solution of tert-butyl ((1s,4s)-4-((2-(tert-butyl)-6-chlorobenzo[d]oxazol-7-yl)sulfonyl)cyclohexyl)carbamate (4.4 g) in DCM (25 mL) at 0° C. was added trifluoroacetic acid (7.2 mL). The reaction mixture was stirred at RT for 3 hours. The reaction mixture was combined with another batch of the same reaction using tert-butyl ((1s,4s)-4-((2-(tert-butyl)-6-chlorobenzo[d]oxazol-7-yl)sulfonyl)cyclohexyl)carbamate (400 mg) as starting material. The mixture was added ice-water (60 mL). Aq. NaHCO$_3$ solution was added to adjust pH to 8. The mixture was extacted with DCM (3×35 mL). The combined organic layers were dried over MgSO$_4$, filtered and concentrated under reduced pressure. The residue was purifed by column chromatography (eluting with MeOH:DCM=1:30) to give (1s,4s)-4-((2-(tert-butyl)-6-chlorobenzo[d]oxazol-7-yl)sulfonyl)cyclohexanamine (2.5 g) as a yellow solid. MS(ES$^+$) m/z 371 (MH$^+$).

Step 6: To a stirred solution of (1s,4s)-4-((2-(tert-butyl)-6-chlorobenzo[d]oxazol-7-yl)sulfonyl)cyclohexanamine (2.0 g), acetic acid (0.3 mL) and formaldehyde (4.0 mL) in methanol (40 mL) at 0° C. was added sodium cyanoborohydride (0.5 g). The reaction mixture was stirred at RT for 3 hours. The mixture was quenched with aq. NaHCO$_3$ solution (75 mL). The mixture was combined with another batch of the same reaction using (1s,4s)-4-((2-(tert-butyl)-6-chlorobenzo[d]oxazol-7-yl)sulfonyl)cyclohexanamine (500 mg) as starting material. The combined mixture was extracted with EA (5×55 mL). The combined organic layers were washed with brine, dried over MgSO$_4$, filtered and concentrated under reduced pressure. The residue was purified by column chromatography (eluting with MeOH:DCM=1:20) to give (1s,4s)-4-((2-(tert-butyl)-6-chlorobenzo[d]oxazol-7-yl)sulfonyl)-N,N-dimethylcyclohexanamine (1.8 g) as a yellow solid. MS(ES$^+$) m/z 399 (MH$^+$).

Step 7: A mixture of (1s,4s)-4-((2-(tert-butyl)-6-chlorobenzo[d]oxazol-7-yl)sulfonyl)-N,N-dimethylcyclohexanamine (1.6 g) and conc. HCl (10 mL) in 1,4-dioxane (40 mL) was heated 90° C. overnight. The mixture was combined with another batch of the same reaction using (1s,4s)-4-((2-(tert-butyl)-6-chlorobenzo[d]oxazol-7-yl)sulfonyl)-N,N-dimethylcyclohexanamine (200 mg) as starting material. The combined mixture was concentrated under reduced pressure. To the residue was added sat. NaHCO$_3$ solution (50 mL). The mixture was extracted with EA (5×35 mL). The combined organic layers were dried over Na$_2$SO$_4$, filtered and concentrated under reduced pressure. The residue was purified by column chromatography (eluting with MeOH: DCM=1:10) to give the title compound (900 mg) as a yellow solid. $^1$H-NMR (400 MHz, DMSO-d$_6$) δ ppm 6.84 (m, 2H), 3.66 (m, 1H), 2.17 (s, 6H), 2.03 (m, 3H), 1.90 (m, 2H), 1.57 (m, 2H), 1.45 (m, 2H); MS(ES$^+$) m/z 333 (MH$^+$).

Intermediate 104: 6-amino-3-chloro-2-((trans-3-((dimethylamino)methyl)cyclobutyl)sulfonyl)phenol

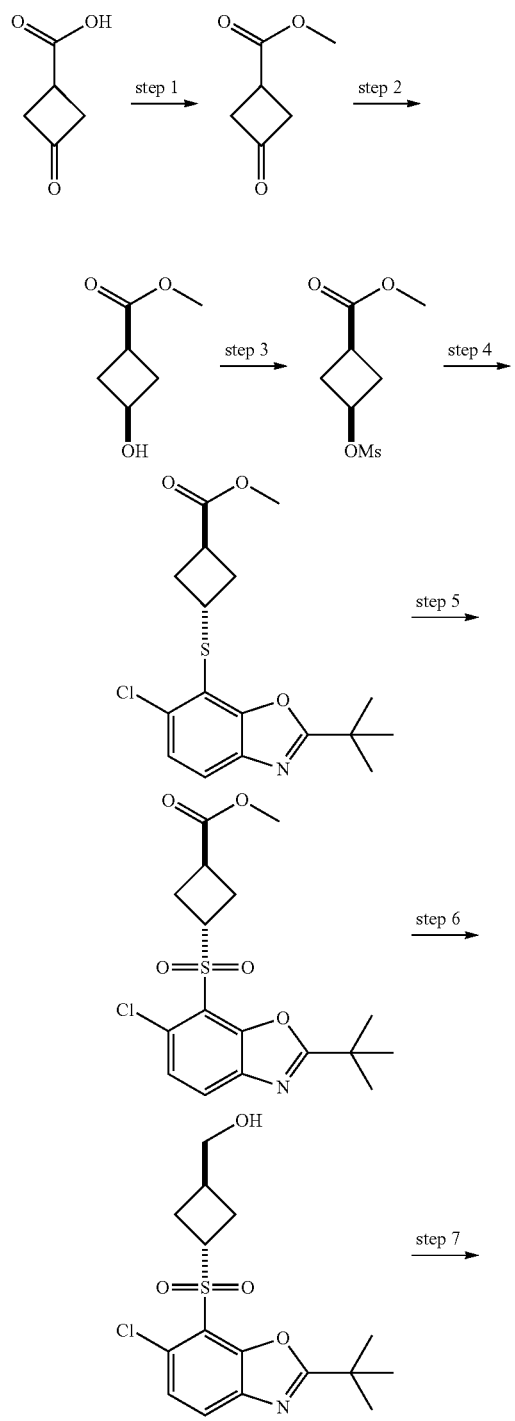

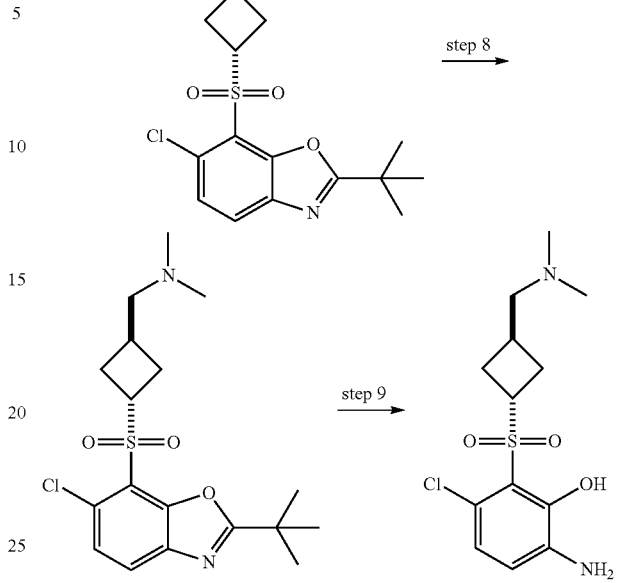

Step 1: A mixture of 3-oxocyclobutanecarboxylic acid (10.0 g), MeOH (3.6 mL), DMAP (1.1 g) and EDC (25.2 g) in DCM (100 mL) was stirred at 25° C. for 18 hours. The mixture was washed with water (8×200 mL). The combined aqueous phases were extracted with DCM (3×300 mL). The combined organics were dried, filtered and concentrated to methyl 3-oxocyclobutanecarboxylate (10.0 g).

Step 2: To a solution of methyl 3-oxocyclobutanecarboxylate (5.0 g) in methanol (30 mL) was added NaBH$_4$ (1.5 g) at 0° C. The reaction mixture was stirred at 25° C. for 30 mins, and then quenched with NH$_4$Cl solution (50 mL). The mixture was extracted with EA (3×150 mL). The combined organic phases were dried, filtered and concentrated to give cis-methyl 3-hydroxycyclobutanecarboxylate (4.3 g).

Step 3: To a solution of cis-methyl 3-hydroxycyclobutanecarboxylate (4.3 g) and TEA (9.2 mL) in DCM (40 mL) was added methanesulfonyl chloride (4.5 g) at 0° C. The reaction mixture was stirred at 25° C. for 2 hours, and then quenched with water (100 mL). The aqueous phase was extracted with DCM (3×150 mL). The combined organic layers were dried, filtered and concentrated to afford cis-methyl 3-((methylsulfonyl)oxy)cyclobutanecarboxylate (6.0 g).

Step 4: A mixture of 2-(tert-butyl)-6-chlorobenzo[d]oxazole-7-thiol (5.2 g), cis-methyl 3-((methylsulfonyl)oxy)cyclobutanecarboxylate (4.9 g) and Cs$_2$CO$_3$ (7.0 g) in acetonitrile (50 mL) was stirred at 100° C. for 4 hours. The reaction mixture was filtered and concentrated. The residue was purified by MDAP to afford trans-methyl 3-((2-(tert-butyl)-6-chlorobenzo[d]oxazol-7-yl)thio)cyclobutanecarboxylate (2.0 g).

Step 5: To a solution of trans-methyl 3-((2-(tert-butyl)-6-chlorobenzo[d]oxazol-7-yl)thio)cyclobutanecarboxylate (2.0 g) in dichloromethane (DCM) (20 mL) was added mCPBA (2.9 g) at 0° C. The reaction was stirred at 25° C. for 18 hours. The mixture was quenched with aq. Na$_2$SO$_3$ solution (50 mL), and then extracted with DCM (3×50 mL). The combined organic layers were washed with aq. NaOH solution (1 M, 2×10 mL) and water (50 mL), dried, filtered and concentrated to afford trans-methyl 3-((2-(tert-butyl)-6- chlorobenzo[d]oxazol-7-yl)sulfonyl)cyclobutanecarboxylate (1.1 g). MS(ES+) m/z 386 (MH+).

Step 6: To a mixture of LiAlH4 (79 mg) in THF (8 mL) was added a solution of trans-methyl 3-((2-(tert-butyl)-6-chlorobenzo[d]oxazol-7-yl)sulfonyl)cyclobutanecarboxylate (400 mg) in THF (4 mL). Then the mixture was stirred at 0° C. under a nitrogen atmosphere for 30 hours. The reaction mixture was quenched with water (3 mL). The organic phase was filtered and purified by column chromatography (eluting with PE:EA=2:1) to afford (trans-3-((2-(tert-butyl)-6-chlorobenzo[d]oxazol-7-yl)sulfonyl)cyclobutyl)methanol (300 mg). MS(ES+) m/z 358 (MH+).

Step 7: To a solution of (trans-3-((2-(tert-butyl)-6-chlorobenzo[d]oxazol-7-yl)sulfonyl)cyclobutyl)methanol (200 mg) in DCM (5 mL) was added Dess-Martin periodinane (474 mg) at 0° C. The reaction mixture was stirred at 30° C. for 18 hours. The obtained mixture was filtered and concentrated to afford trans-3-((2-(tert-butyl)-6-chlorobenzo[d]oxazol-7-yl)sulfonyl)cyclobutanecarbaldehyde (200 mg). MS(ES+) m/z 356 (MH+).

Step 8: A mixture of trans-3-((2-(tert-butyl)-6-chlorobenzo[d]oxazol-7-yl)sulfonyl)cyclobutanecarbaldehyde (200 mg) and dimethylamine (307 mg) in DCM (2 mL) was stirred at RT for 30 mins, and then sodium triacetoxyborohydride (238 mg) was added. The mixture was stirred at 30° C. in air for 2 hours. The solvent was removed to afford 1-(trans-3-((2-(tert-butyl)-6-chlorobenzo[d]oxazol-7-yl)sulfonyl)cyclobutyl)-N,N-dimethylmethanamine (200 mg). MS(ES+) m/z 385 (MH+).

Step 9: A mixture of 1-(trans-3-((2-(tert-butyl)-6-chlorobenzo[d]oxazol-7-yl)sulfonyl)cyclobutyl)-N,N-dimethylmethanamine (200 mg) and conc. HCl (0.4 mL) in 1,4-dioxane (1 mL) and water (1 mL) was stirred at 100° C. for 4 hours. The solvent was removed. The pH was adjusted to 8-9. The resulting mixture was purified by preparative TLC (DCM:MeOH=10:1) to afford the title compound (70 mg). MS(ES+) m/z 319 (MH+).

Intermediate 105: 6-amino-3-chloro-2-(((1s,3s)-3-((dimethylamino)methyl)cyclobutyl)sulfonyl)phenol

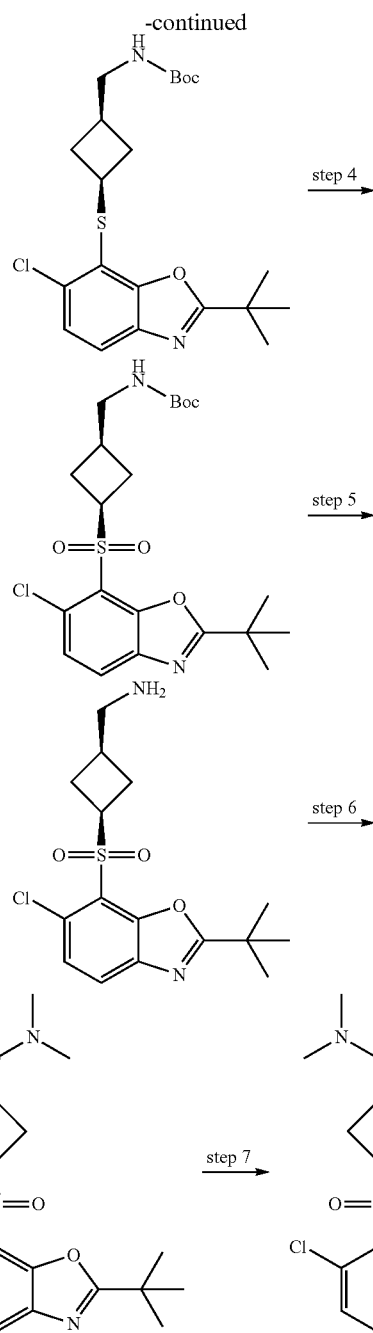

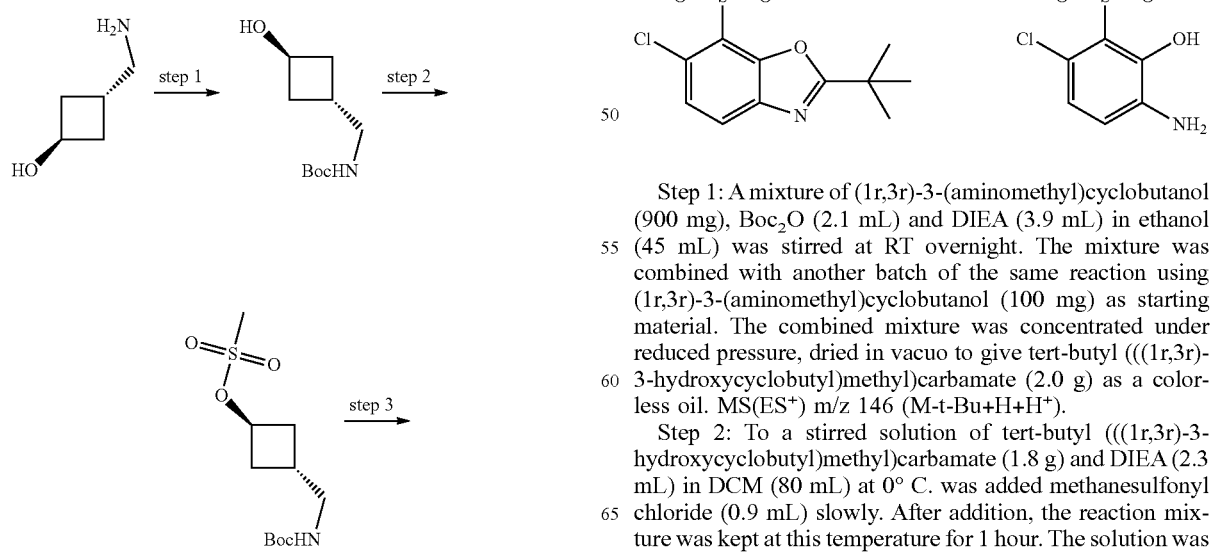

Step 1: A mixture of (1r,3r)-3-(aminomethyl)cyclobutanol (900 mg), Boc2O (2.1 mL) and DIEA (3.9 mL) in ethanol (45 mL) was stirred at RT overnight. The mixture was combined with another batch of the same reaction using (1r,3r)-3-(aminomethyl)cyclobutanol (100 mg) as starting material. The combined mixture was concentrated under reduced pressure, dried in vacuo to give tert-butyl (((1r,3r)-3-hydroxycyclobutyl)methyl)carbamate (2.0 g) as a colorless oil. MS(ES+) m/z 146 (M-t-Bu+H+H+).

Step 2: To a stirred solution of tert-butyl (((1r,3r)-3-hydroxycyclobutyl)methyl)carbamate (1.8 g) and DIEA (2.3 mL) in DCM (80 mL) at 0° C. was added methanesulfonyl chloride (0.9 mL) slowly. After addition, the reaction mixture was kept at this temperature for 1 hour. The solution was quenched with aq. NaHCO3 solution (60 mL). The mixture was combined with another batch of the same reaction using tert-butyl (((1r,3r)-3-hydroxycyclobutyl)methyl)carbamate (100 mg) as starting material. The combined mixture was extracted with DCM (2×50 mL). The combined organic layers was dried over MgSO$_4$, filtered and concentrated under reduced pressure to give (1r,3r)-3-(((tert-butoxycarbonyl)amino)methyl)cyclobutyl methanesulfonate (3.3 g) as a yellow oil. MS(ES$^+$) m/z 224 (M-t-Bu+H+H$^+$).

Step 3: K$_2$CO$_3$ (3.0 g) was added to a solution of 2-(tert-butyl)-6-chlorobenzo[d]oxazole-7-thiol (2.6 g) and (1r,3r)-3-(((tert-butoxycarbonyl)amino)methyl)cyclobutyl methanesulfonate (3.0 g) in DMF (30 mL) at RT. The mixture was stirred at 80° C. for 2 hours. The reaction solution was combined with another batch of the same reaction using (1r,3r)-3-(((tert-butoxycarbonyl)amino)methyl)cyclobutyl methanesulfonate (300 mg) as starting material. The combined mixture was poured into ice-water (200 mL), and extracted with EA (4×100 mL). The combined organic layers were washed with brine (80 mL), dried over Na$_2$SO$_4$ and concentrated under reduced pressure to give tert-butyl (((1s,3s)-3-((2-(tert-butyl)-6-chlorobenzo[d]oxazol-7-yl)thio)cyclobutyl)methyl)carbamate (5.0 g) as a brown oil. MS(ES$^+$) m/z 369 (M-t-Bu+H+H$^+$).

Step 4: To a stirred solution of tert-butyl (((1s,3s)-3-((2-(tert-butyl)-6-chlorobenzo[d]oxazol-7-yl)thio)cyclobutyl)methyl)carbamate (4.5 g) in DCM (100 mL) at 0° C. was added a solution of mCPBA (3.7 g) in DCM (50 mL) over 10 mins. After addition, the reaction mixture was stirred at RT for 2 hours. Aq. Na$_2$S$_2$O$_3$ solution and aq. Na$_2$CO$_3$ solution were added. The reaction mixture was combined with another batch of the same reaction using tert-butyl (((1s,3s)-3-((2-(tert-butyl)-6-chlorobenzo[d]oxazol-7-yl)thio)cyclobutyl)methyl)carbamate (500 mg) as starting material. The combined mixture was extracted with DCM (4×80 mL). The combined organic layers were dried over MgSO$_4$, filtered and concentrated under reduced pressure. The residue was purifed by column chromatography (eluting with EA:PE=1:5) to give tert-butyl (((1s,3s)-3-((2-(tert-butyl)-6-chlorobenzo[d]oxazol-7-yl)sulfonyl)cyclobutyl)methyl)carbamate (2.2 g) as a white solid. MS(ES$^+$) m/z 401 (M-t-Bu+H+H$^+$).

Step 5: To a stirred solution of tert-butyl (((1s,3s)-3-((2-(tert-butyl)-6-chlorobenzo[d]oxazol-7-yl)sulfonyl)cyclobutyl)methyl)carbamate (1.8 g) in DCM (30 mL) at 0° C. was added trifluoroacetic acid (3.0 mL). After addition, the reaction mixture was stirred at RT overnight. The mixture was combined with another batch of the same reaction using tert-butyl (((1s,3s)-3-((2-(tert-butyl)-6-chlorobenzo[d]oxazol-7-yl)sulfonyl)cyclobutyl)methyl)carbamate (350 mg) as starting material. The combined mixture was concentrated under reduced pressure. To the residue was added ice-water (100 mL). NaHCO$_3$ was added to adjust the pH to 7-8. The mixture was extracted with EA (3×35 mL). The combined organic layers were dried over MgSO$_4$, filtered and concentrated under reduced pressure to give ((1s,3s)-3-((2-(tert-butyl)-6-chlorobenzo[d]oxazol-7-yl)sulfonyl)cyclobutyl)methanamine (2.0 g) as a yellow solid. MS(ES$^+$) m/z 357 (MH$^+$).

Step 6: To a stirred solution of ((1s,3s)-3-((2-(tert-butyl)-6-chlorobenzo[d]oxazol-7-yl)sulfonyl)cyclobutyl)methanamine (1.9 g) and formaldehyde (1.4 mL) in methanol (30 mL) at 0° C. was added sodium cyanoborohydride (0.4 g) portionwise. After addition, the reaction mixture was stirred at RT for 2 hours. The mixture was quenched with NaHCO$_3$, and then combined with another batch of the same reaction using ((1s,3s)-3-((2-(tert-butyl)-6-chlorobenzo[d]oxazol-7-yl)sulfonyl)cyclobutyl)methanamine (150 mg) as starting material. The combined mixture was extracted with EA (4×40 mL). The combined organic phases were washed with brine, dried over MgSO$_4$, filtered and concentrated under reduced pressure to give 1-((1s,3s)-3-((2-(tert-butyl)-6-chlorobenzo[d]oxazol-7-yl)sulfonyl)cyclobutyl)-N, N-dimethylmethanamine (2.2 g) as a yellow solid. MS(ES$^+$) m/z 385 (MH$^+$).

Step 7: A mixture of 1-((1s,3s)-3-((2-(tert-butyl)-6-chlorobenzo[d]oxazol-7-yl)sulfonyl)cyclobutyl)-N,N-dimethylmethanamine (2.2 g) and conc. HCl solution (6 mL) in 1,4-dioxane (30 mL) was heated 90° C. overnight. After cooling, ice-water (40 mL) was added. The pH of the mixture was adjusted to 8 by addition of sat. NaHCO$_3$ solution. The mixture was extracted with EA (6×30 mL). The combined organic layers were dried over MgSO$_4$, filtered and concentrated. The residue was purified by column chromatography (eluting with methanol:DCM=1:10) to give the title compound (375 mg) as a grey solid. MS(ES$^+$) m/z 319 (MH$^+$).

Intermediate 106: 6-amino-3-chloro-2-((trans-3-(dimethylamino)cyclobutyl)sulfonyl)phenol

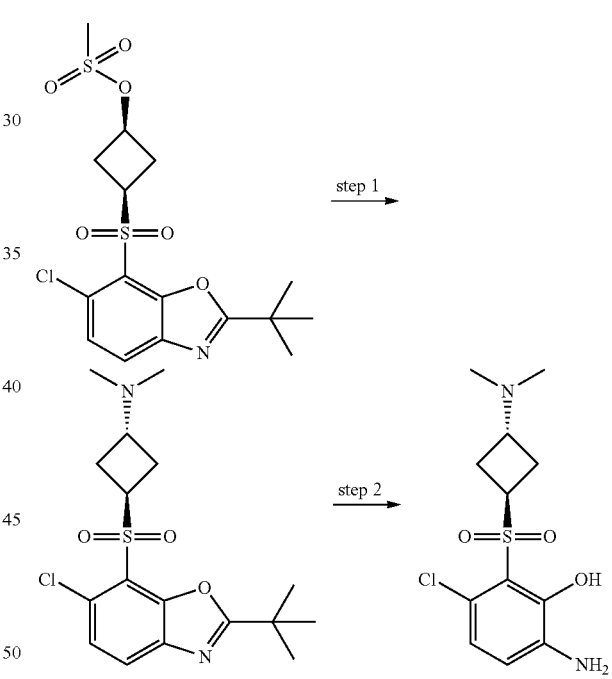

Step 1: Potassium carbonate (262 mg) was added to a solution of cis-3-((2-(tert-butyl)-6-chlorobenzo[d]oxazol-7-yl)sulfonyl)cyclobutyl methanesulfonate (Intermediate 36, Step 1, 200 mg) and dimethylamine hydrochloride (77 mg) in DMF (3 mL) at RT. The reaction mixture was stirred at 100° C. for 12 hours, and then combined with another batch of the same reaction using cis-3-((2-(tert-butyl)-6-chlorobenzo[d]oxazol-7-yl)sulfonyl)cyclobutyl methanesulfonate (200 mg) as starting material. The combined mixture was diluted with EA (50 mL). The organic phase was washed with water (2×20 mL) and brine (20 mL), dried over Na$_2$SO$_4$ and concentrated to give trans-3-((2-(tert-butyl)-6-chlorobenzo[d]oxazol-7-yl)sulfonyl)-N,N-dimethylcyclobutanamine (250 mg) as a brown oil. MS(ES$^+$) m/z 371 (MH$^+$).

Step 2: Aq. HCl solution (35%, 5 mL) was added to a solution of trans-3-((2-(tert-butyl)-6-chlorobenzo[d]oxazol-7-yl)sulfonyl)-N,N-dimethylcyclobutanamine (550 mg) in 1,4-dioxane (10 mL) and water (10 mL) at RT. The reaction mixture was stirred at 120° C. for 3 hours, and then combined with another batch of the same reaction using trans-3-((2-(tert-butyl)-6-chlorobenzo[d]oxazol-7-yl)sulfonyl)-N,N-dimethylcyclobutanamine (400 mg) as starting material. The combined mixture was concentrated. The residue was dissolved in MeOH. Aq. NaHCO$_3$ solution was added until pH=8. The mixture was concentrated. The resulting residue was purified by column chromatography (eluting with DCM:MeOH=50:1) to afford the title compound (220 mg) as a black oil. MS(ES$^+$) m/z 305 (MH$^+$).

Intermediate 107: 6-amino-3-chloro-2-((1-(dimethylamino)-2-methylpropan-2-yl)sulfonyl)phenol, trifluoroacetic acid salt

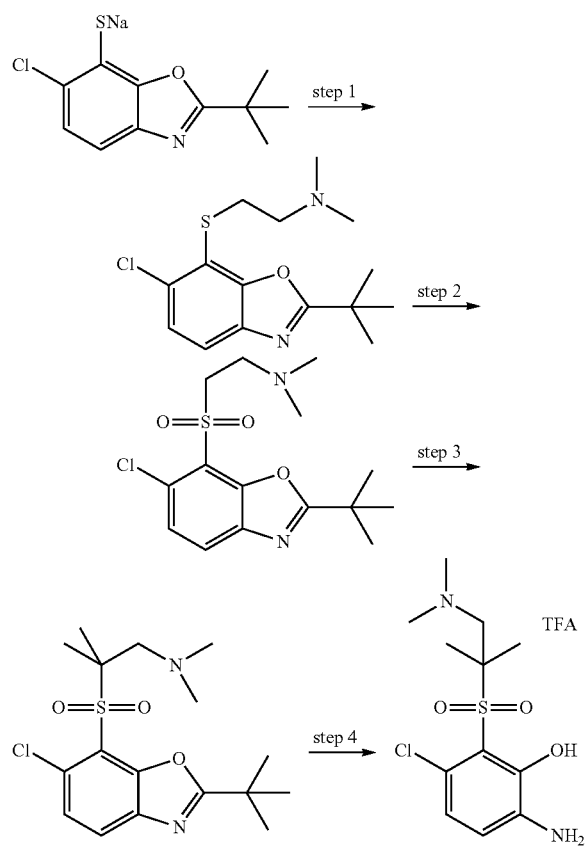

Step 1: 2-Chloro-N,N-dimethylethanamine, hydrochloride (1.6 g) was added to a solution of sodium 2-(tert-butyl)-6-chlorobenzo[d]oxazole-7-thiolate (2.6 g) and potassium carbonate (4.1 g) in acetonitrile (50 mL) at RT. The reaction mixture was stirred at 80° C. for 1 hour. The solvent was removed. The residue was purified by column chromatography (eluting with PE:EA=8:1 to 1:1) to afford 2-((2-(tert-butyl)-6-chlorobenzo[d]oxazol-7-yl)thio)-N,N-dimethylethanamine (1.5 g) as a brown oil. MS(ES$^+$) m/z 313 (MH$^+$).

Step 2: H$_2$O$_2$ (30%, 1 mL) was added to a solution of 2-((2-(tert-butyl)-6-chlorobenzo[d]oxazol-7-yl)thio)-N,N-dimethylethanamine (800 mg) in TFA (10 mL) at 0° C. The reaction mixture was stirred at 25° C. overnight. The reaction solution was combined with another two batches of the same reactions using 2-((2-(tert-butyl)-6-chlorobenzo[d]oxazol-7-yl)thio)-N,N-dimethylethanamine (100 mg and 300 mg) as starting materials. The combined mixture was quenched with aq. NaOH solution (10%) until pH=8. Aq. Na$_2$S$_2$O$_3$ was added. The mixture was extracted with DCM (2×50 mL). The combined organic layers were washed with brine, dried over Na$_2$SO$_4$ and concentrated to afford 2-((2-(tert-butyl)-6-chlorobenzo[d]oxazol-7-yl)sulfonyl)-N,N-dimethylethanamine (500 mg) as a yellow solid. MS(ES$^+$) m/z 345 (MH$^+$).

Step 3: LiHMDS (1 M in THF, 4.4 mL) was added dropwise to a solution of 2-((2-(tert-butyl)-6-chlorobenzo[d]oxazol-7-yl)sulfonyl)-N,N-dimethylethanamine (500 mg) in THF (50 mL) at −78° C. After 1 hour, iodomethane (823 mg) was added dropwise. After stirring at −78° C. for 1 hour, the reaction mixture was quenched by addition of sat. NH$_4$Cl solution (30 mL). The mixture was extracted with EA (100 mL). The organic layer was washed with brine (20 mL), dried over Na$_2$SO$_4$ and concentrated to afford 2-((2-(tert-butyl)-6-chlorobenzo[d]oxazol-7-yl)sulfonyl)-N,N,2-trimethylpropan-1-amine (400 mg) as a brown oil. MS(ES$^+$) m/z 373 (MH$^+$).

Step 4: Aq. HCl solution (35%, 2 mL) was added to a solution of 2-((2-(tert-butyl)-6-chlorobenzo[d]oxazol-7-yl)sulfonyl)-N,N,2-trimethylpropan-1-amine (300 mg) in 1,4-dioxane (4 mL) and water (2 mL) at RT. The reaction mixture was stirred at 120° C. for 12 hours, and then concentrated. The residue was purified by preparative HPLC to afford the title compound (170 mg) as a brown solid. MS(ES$^+$) m/z 307 (MH$^+$).

Intermediate 108: 6-amino-3-chloro-2-((2-(dimethylamino)-1,1-difluoroethyl)sulfonyl)phenol, trifluoroacetic acid salt

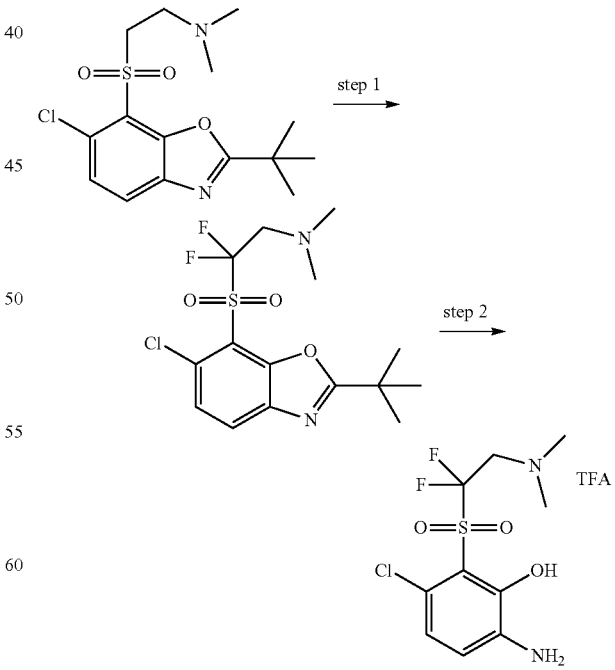

Step 1: LiHMDS (1 M in THF, 7.0 mL) was added dropwise to a solution of 2-((2-(tert-butyl)-6-chlorobenzo

[d]oxazol-7-yl)sulfonyl)-N,N-dimethylethanamine (0.8 g) in THF (20 mL) at −78° C. After 1 hour, N-fluoro-N-(phenylsulfonyl)benzenesulfonamide (1.8 g) in THF (5 mL) was added dropwise. After stirring at −78° C. for 1 hour, the reaction mixture was quenched with addition of sat. NH$_4$Cl solution (30 mL). The mixture was extracted with EA (100 mL). The organic layer was washed with brine (20 mL), dried over Na$_2$SO$_4$ and concentrated. The residue was purified by column chromatography (eluting with PE:EA=15:1) to afford 2-((2-(tert-butyl)-6-chlorobenzo[d]oxazol-7-yl)sulfonyl)-2,2-difluoro-N,N-dimethylethanamine (600 mg) as a brown oil. MS(ES$^+$) m/z 381 (MH$^+$).

Step 2: Aq. HCl solution (35%, 3 mL) was added to a solution of 2-((2-(tert-butyl)-6-chlorobenzo[d]oxazol-7-yl)sulfonyl)-2,2-difluoro-N,N-dimethylethanamine (600 mg) in 1,4-dioxane (6 mL) and water (3 mL) at RT. The reaction mixture was stirred at 120° C. for 12 hours, and then combined with another batch of the same reaction using 2-((2-(tert-butyl)-6-chlorobenzo[d]oxazol-7-yl)sulfonyl)-2,2-difluoro-N,N-dimethylethanamine (300 mg) as starting material. The combined solution was concentrated. The residue was purified by preparative HPLC to afford the title compound (390 mg) as a brown solid. MS(ES$^+$) m/z 307 (MH$^+$).

Intermediate 109: 3-amino-6-chloro-2-hydroxy-N,N-dimethylbenzenesulfonamide

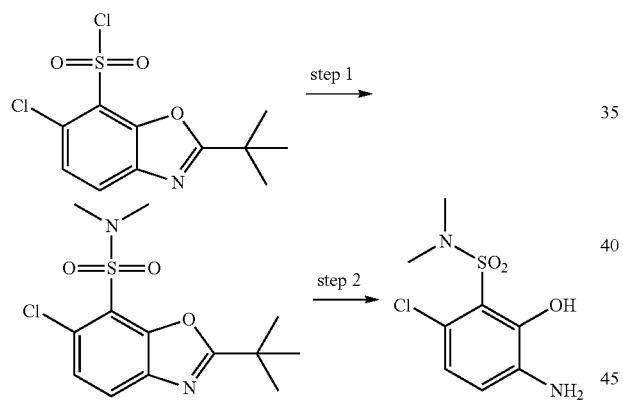

Step 1: To a solution of 2-(tert-butyl)-6-chlorobenzo[d]oxazole-7-sulfonyl chloride (250 mg) in THF (10 mL) was added TEA (0.3 mL). After cooling to 0° C., dimethylamine, hydrochloride (66 mg) was added potionwise over 2 minutes. The resulting mixture was stirred at RT overnight, and then concentrated under reduced pressure. The resiude was diluted with water (20 mL) and extracted with EA (3×20 mL). The combined organic layers were dried over sodium sulfate, filtered and concentrated. The residue was purified by column chromatography (eluting with PE:EA=5:1) to give 2-(tert-butyl)-6-chloro-N,N-dimethylbenzo[d]oxazole-7-sulfonamide (140 mg) as a light yellow solid. MS(ES$^+$) m/z 317 (MH$^+$).

Step 2: 2-(Tert-butyl)-6-chloro-N,N-dimethylbenzo[d]oxazole-7-sulfonamide (140 mg) was dissolved in 1,4-dioxane (5 mL) and water (1 mL). Conc. sulfuric acid (0.5 mL) was added. The mixture was heated to 100° C. overnight to give a brown solution. After cooling to RT, the mixture was concentrated under reduced pressure, and then treated with aq. NaOH solution (6 M) until pH=10 in an ice bath. The mixture was extracted with EA (4×50 mL). The combined organic layers were dried over sodium sulfate, filtered and concentrated to give the title compound (73 mg) as a brown solid. MS(ES$^+$) m/z 251 (MH$^+$).

Intermediate 110: 6-amino-3-chloro-2-(((1R,3s,5S)-8-methyl-8-azabicyclo[3.2.1]octan-3-yl)sulfonyl)phenol, trifluoroacetic acid salt

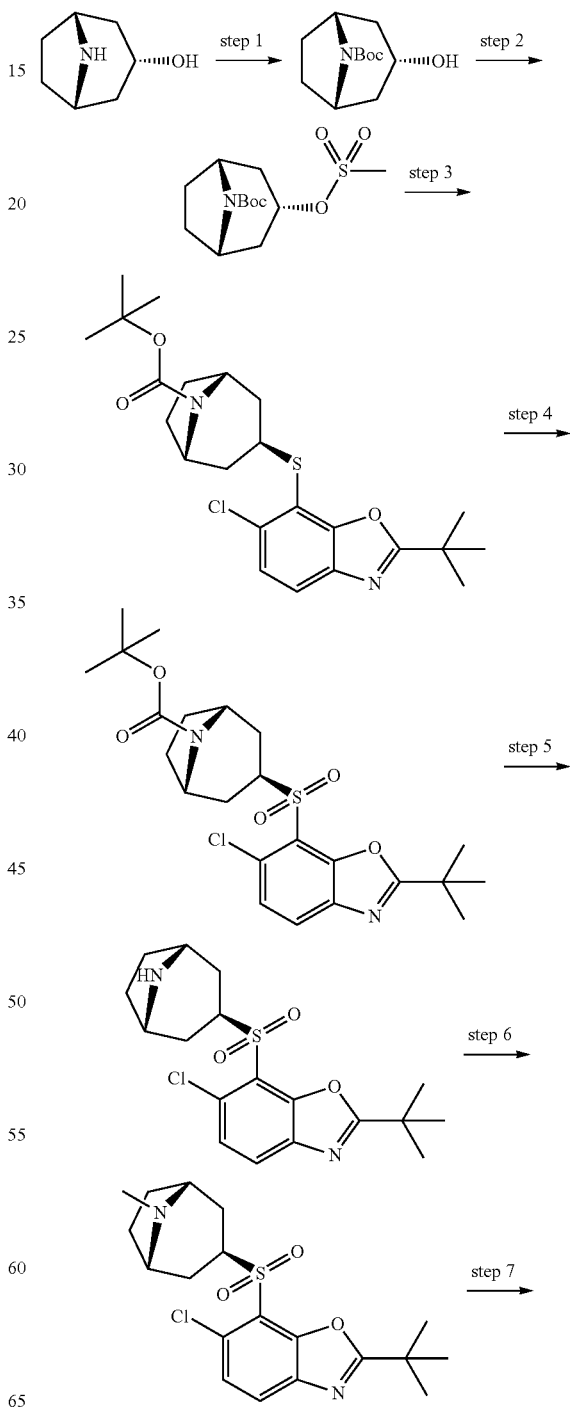

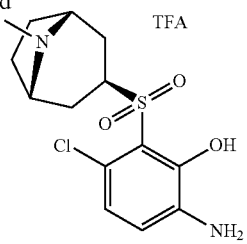

Step 1: To a solution of (1R,3r,5S)-8-azabicyclo[3.2.1]octan-3-ol (5.0 g) in ethanol (100 mL) was added TEA (11.0 mL) and Boc₂O (10.0 mL). The resulting mixture was stirred at 25° C. overnight, and then concentrated under reduced pressure to afford (1R,3r,5S)-tert-butyl 3-hydroxy-8-azabicyclo[3.2.1]octane-8-carboxylate (9.0 g).

Step 2: To a solution of (1R,3r,5S)-tert-butyl 3-hydroxy-8-azabicyclo[3.2.1]octane-8-carboxylate (9.0 g) in DCM (200 mL) was added TEA (11.0 mL) and MsCl (3.7 mL). The resulting mixture was stirred at 0° C. for 2 hours, and then diluted with water (100 mL). The reaction mixture was extracted with DCM (2×200 mL). The combined organic layers were washed, dried and concentrated to afford (1R,3r,5S)-tert-butyl 3-((methylsulfonyl)oxy)-8-azabicyclo[3.2.1]octane-8-carboxylate (12.0 g).

Step 3: To a solution of 2-(tert-butyl)-6-chlorobenzo[d]oxazole-7-thiol (9.5 g) in DMF (150 mL) was added K₂CO₃ (10.9 g) and (1R,3r,5S)-tert-butyl 3-((methylsulfonyl)oxy)-8-azabicyclo[3.2.1]octane-8-carboxylate (12.0 g). The resulting mixture was stirred at 85° C. overnight. After cooling, water was added. The mixture was extracted with EA (2×100 mL). The combined organic layers were washed with water and brine. After concentration, the residue was purified by column chromatography (eluting with 0-30% EA in PE) to afford (1R,3s,5S)-tert-butyl 3-((2-(tert-butyl)-6-chlorobenzo[d]oxazol-7-yl)thio)-8-azabicyclo[3.2.1]octane-8-carboxylate (10.2 g). MS(ES⁺) m/z 395 (M-t-Bu+H+H⁺).

Step 4: To a solution of (1R,3s,5S)-tert-butyl 3-((2-(tert-butyl)-6-chlorobenzo[d]oxazol-7-yl)thio)-8-azabicyclo[3.2.1]octane-8-carboxylate (10.2 g) in DCM (200 mL) was added mCPBA (12.7 g) at 0° C. The resulting mixture was warmed up slowly and stirred at RT overnight. The reaction mixture was quenched with aq. NaHCO₃ solution and aq. Na₂S₂O₃ solution. The mixture was extracted with DCM (2×200 mL). The combined organic layers were washed with water and brine. After concentration, the residue was purified by column chromatography (eluting with 10-30% EA in PE) to afford (1R,3s,5S)-tert-butyl 3-((2-(tert-butyl)-6-chlorobenzo[d]oxazol-7-yl)sulfonyl)-8-azabicyclo[3.2.1]octane-8-carboxylate (5.0 g). MS(ES⁺) m/z 427 (M-t-Bu+H+H⁺).

Step 5: To a solution of (1R,3s,5S)-tert-butyl 3-((2-(tert-butyl)-6-chlorobenzo[d]oxazol-7-yl)sulfonyl)-8-azabicyclo[3.2.1]octane-8-carboxylate (5.0 g) in DCM (100 mL) was added TFA (8.0 mL). The resulting mixture was stirred at RT overnight, and concentrated under reduced pressure to afford 7-((1R,3s,5S)-8-azabicyclo[3.2.1]octan-3-ylsulfonyl)-2-(tert-butyl)-6-chlorobenzo[d]oxazole, trifluoroacetic acid salt (5.0 g). MS(ES⁺) m/z 383 (MH⁺).

Step 6: To an ice-water cooled solution of 7-((1R,3s,5S)-8-azabicyclo[3.2.1]octan-3-ylsulfonyl)-2-(tert-butyl)-6-chlorobenzo[d]oxazole, trifluoroacetic acid salt (5.0 g), formaldehyde (2.8 mL) and AcOH (0.6 mL) in DMF (50 mL) was added sodium triacetoxyborohydride (4.3 g) portionwise. The reaction mixture was warmed up slowly and stirred at RT for 2 hours. The resulting mixture was quenched with aq. NaHCO₃ solution, and extracted with EA (2×100 mL). The combined organic phases were washed, dried and concentrated to afford 2-(tert-butyl)-6-chloro-7-(((1R,3s,5S)-8-methyl-8-azabicyclo[3.2.1]octan-3-yl)sulfonyl)benzo[d]oxazole (3.7 g). MS(ES⁺) m/z 397 (MH⁺).

Step 7: To a solution of 2-(tert-butyl)-6-chloro-7-(((1R,3s,5S)-8-methyl-8-azabicyclo[3.2.1]octan-3-yl)sulfonyl)benzo[d]oxazole (3.7 g) in 1,4-dioxane (50 mL) and water (100 mL) was added conc. HCl solution (2.8 mL). The mixture was stirred at 110° C. overnight, and then concentrated. The residue was purified by reversed phase chromatography (acidic condition) to afford the title compound (1.7 g). MS(ES⁺) m/z 331 (MH⁺).

Intermediate 111: 6-amino-3-chloro-2-((4-methyl-1-d₃-methylpiperidin-4-yl)sulfonyl)phenol, trifluoroacetic acid salt

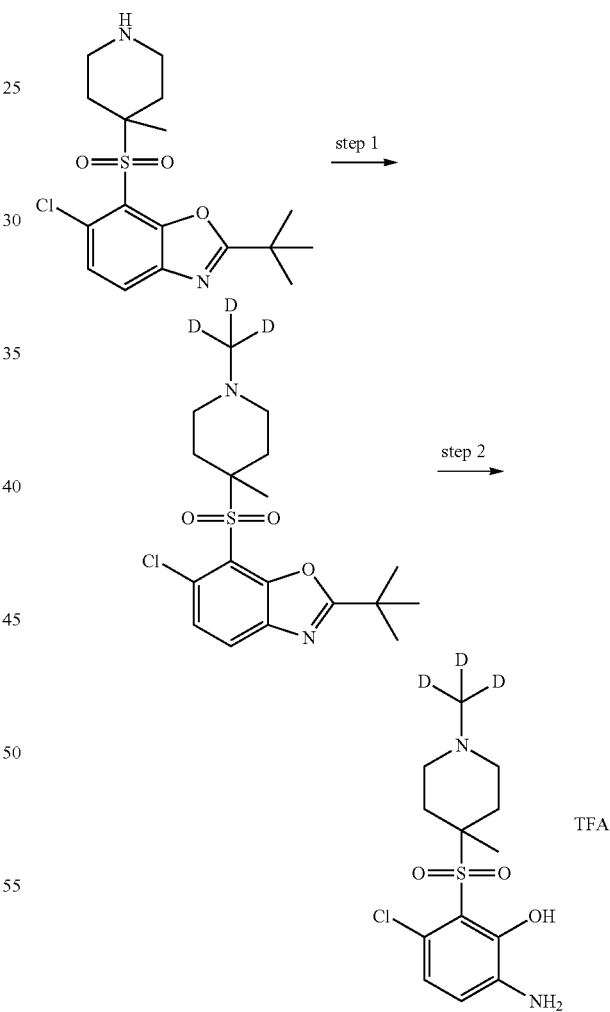

Step 1: To a solution of 2-(tert-butyl)-6-chloro-7-((4-methylpiperidin-4-yl)sulfonyl)benzo[d]oxazole (Intermediate 53, Step 5, 0.8 g) in DMF (10 mL) was added Cs₂CO₃ (1.3 g) and [d₃]methyl p-toluenesulphonate (Intermediate 31, Step 1, 0.6 g). The resulting mixture was stirred at RT overnight, and then diluted with water (50 mL). The mixture was extracted with EA (2×100 mL). The combined organic phases were washed, dried and concentrated. The residue was recrystallized from ethanol/water (1:1, v/v) to afford 2-(tert-butyl)-6-chloro-7-((1-d₃-methyl-methylpiperidin-4-yl)sulfonyl)benzo[d]oxazole (0.4 g). MS(ES⁺) m/z 388 (MH⁺).

Step 2: To a solution of 2-(tert-butyl)-6-chloro-7-((1-d₃-methyl-methylpiperidin-4-yl)sulfonyl)benzo[d]oxazole (0.4 g) in 1,4-dioxane (10 mL) and water (10 mL) was added conc. H₂SO₄ (0.6 mL). The resulting mixture was stirred at 120° C. overnight, and concentrated. The residue was basified with aq. NH₃.H₂O solution, and then purified with reversed phase chromatography (acidic condition) to afford the title compound (180 mg). MS(ES⁺) m/z 322 (MH⁺).

Intermediate 112: 6-amino-3-chloro-2-((7-methyl-7-azaspiro[3.5]nonan-2-yl)sulfonyl)phenol, trifluoroacetic acid salt

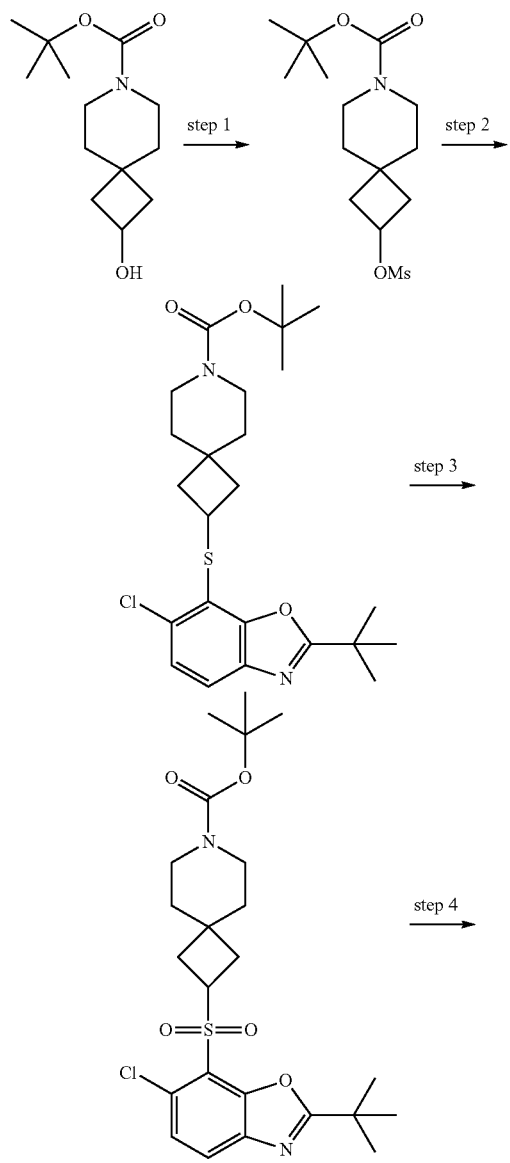

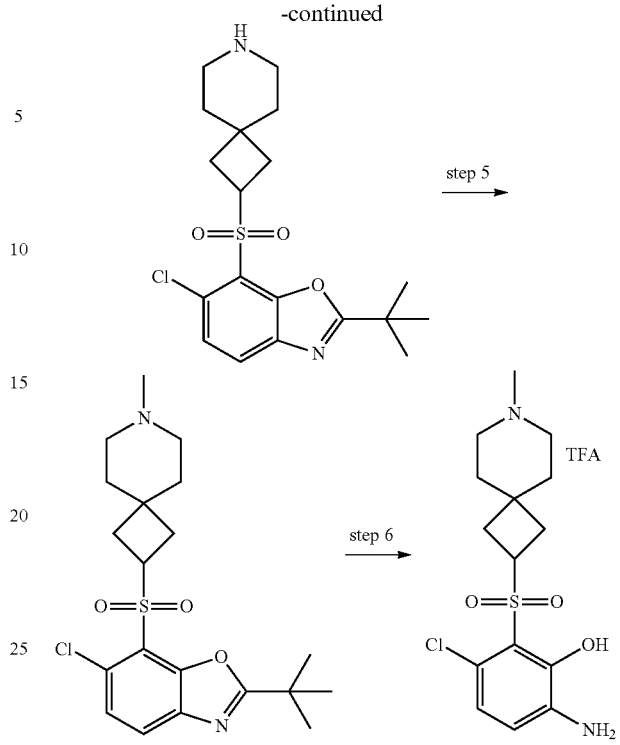

Step 1: To a solution of tert-butyl 2-hydroxy-7-azaspiro[3.5]nonane-7-carboxylate (1.9 g) and TEA (2.2 mL) in DCM (20 mL) was added methanesulfonyl chloride (1.1 g) at 0° C. The mixture was stirred at 20° C. for 2 hours, and then quenched with water (50 mL). The mixture was extracted with DCM (3×200 mL). The combined organic phases were dried and concentrated to afford tert-butyl 2-((methylsulfonyl)oxy)-7-azaspiro[3.5]nonane-7-carboxylate (2.4 g).

Step 2: A mixture of 2-(tert-butyl)-6-chlorobenzo[d]oxazole-7-thiol (2.2 g), tert-butyl 2-((methylsulfonyl)oxy)-7-azaspiro[3.5]nonane-7-carboxylate (2.4 g) and Cs₂CO₃ (1.0 g) in acetonitrile (20 mL) was stirred at 100° C. for 2 hours, and then filtered. After concentration, the residue was purified by column chromatography (eluting with PE:EA=20:1) to afford tert-butyl 2-((2-(tert-butyl)-6-chlorobenzo[d]oxazol-7-yl)thio)-7-azaspiro[3.5]nonane-7-carboxylate (2.6 g). MS(ES⁺) m/z 409 (M-t-Bu+H+H⁺).

Step 3: To a solution of tert-butyl 2-((2-(tert-butyl)-6-chlorobenzo[d]oxazol-7-yl)thio)-7-azaspiro[3.5]nonane-7-carboxylate (2.4 g) in DCM (20 mL) was added mCPBA (2.4 g) at 0° C. The reaction mixture was stirred at 20° C. for 18 hours, and then quenched with aq. Na₂SO₃ solution (50 mL). The resulting mixture was extracted with DCM (3×100 mL). The combined organic phases were concentrated and purified by column chromatography (eluting with PE:EA=5:1) to afford tert-butyl 2-((2-(tert-butyl)-6-chlorobenzo[d]oxazol-7-yl)sulfonyl)-7-azaspiro[3.5]nonane-7-carboxylate (2.3 g). MS(ES⁺) m/z 441 (M-t-Bu+H+H⁺).

Step 4: A solution of tert-butyl 2-((2-(tert-butyl)-6-chlorobenzo[d]oxazol-7-yl)sulfonyl)-7-azaspiro[3.5]nonane-7-carboxylate (2.3 g) in MeOH/HCl (20 mL) was stirred at 25° C. for 3 hours. The mixture was filtered and dried to afford 7-(7-azaspiro[3.5]nonan-2-ylsulfonyl)-2-(tert-butyl)-6-chlorobenzo[d]oxazole, hydrochloride (1.4 g). MS(ES⁺) m/z 397 (MH⁺).

Step 5: A mixture of 7-(7-azaspiro[3.5]nonan-2-ylsulfonyl)-2-(tert-butyl)-6-chlorobenzo[d]oxazole, hydrochloride (1.0 g) and formaldehyde (0.7 mL) in DCM (10 mL) was stirred at 25° C. for 30 mins. Sodium triacetoxyborohydride (1.0 g) was added at 10° C. The reaction mixture was combined with another batch of the same reaction using 7-(7-azaspiro[3.5]nonan-2-ylsulfonyl)-2-(tert-butyl)-6-chlorobenzo[d]oxazole, hydrochloride (200 mg) as starting material. The combined mixture was purified by column chromatography (eluting with DCM:MeOH=10:1) to afford 2-(tert-butyl)-6-chloro-7-((7-methyl-7-azaspiro[3.5]nonan-2-yl)sulfonyl)benzo[d]oxazole (1.3 g). MS(ES$^+$) m/z 411 (MH$^+$).

Step 6: A mixture of 2-(tert-butyl)-6-chloro-7-((7-methyl-7-azaspiro[3.5]nonan-2-yl)sulfonyl)benzo[d]oxazole (1.3 g) in 1,4-dioxane (3 mL) and water (3 mL). Aq. HCl solution (37%, 6 mL) was stirred at 120° C. for 18 hours, and then concentrated. The pH was adjusted to 7-8 with addition of TEA. The resulting mixture was purified by preparative HPLC to afford the title compound (420 mg). MS(ES$^+$) m/z 345 (MH$^+$).

Intermediate 113: 6-amino-3-chloro-2-((4-methyl-piperazin-1-yl)sulfonyl)phenol

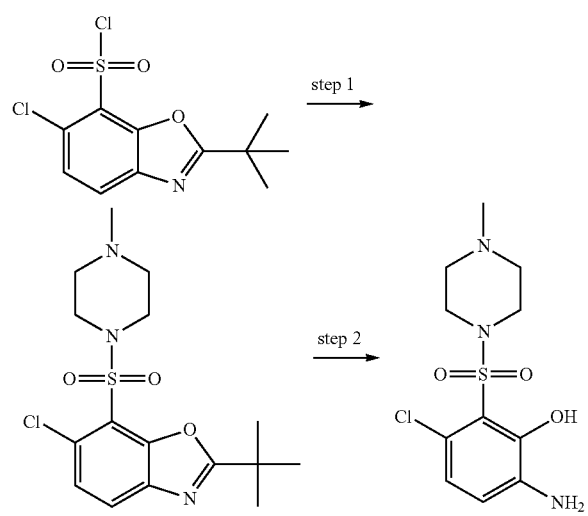

Step 1: To a solution of TEA (0.8 mL) and 1-methylpiperazine (241 mg) in THF (10 mL) was added 2-(tert-butyl)-6-chlorobenzo[d]oxazole-7-sulfonyl chloride (618 mg) portionwise at RT.

The mixture was stirred for 4 hours. Cold water (30 mL) was added. The resulting mixture was extracted with DCM (2×100 mL). The combined organic layers were dried over Na$_2$SO$_4$, filtered and concentrated in vacuo. The residue was purified by column chromatography (eluting with DCM:methanol=50:1) to give 2-(tert-butyl)-6-chloro-7-((4-methylpiperazin-1-yl)sulfonyl)benzo[d]oxazole (540 mg) as a yellow solid. MS(ES$^+$) m/z 372 (MH$^+$).

Step 2: To a solution of 2-(tert-butyl)-6-chloro-7-((4-methylpiperazin-1-yl)sulfonyl)benzo[d]oxazole (500 mg) in 1,4-dioxane (4 mL) was added aq. sulfuric acid solution (65%, 0.1 mL). The resulting mixture was stirred at 100° C. for 1 hour. After cooling, cold water (30 mL) was added. The resulting mixture was neutralized with sat. Na$_2$CO$_3$ solution. The aqueous layer was extracted with EA (2×100 mL). The combined organic layers were dried over Na$_2$SO$_4$, filtered and concentrated in vacuo to give the title compound (310 mg) as a dark solid. MS(ES$^+$) m/z 306 (MH$^+$).

Intermediate 114: trans-6-amino-3-chloro-2-((3-methoxycyclopentyl)sulfonyl)phenol

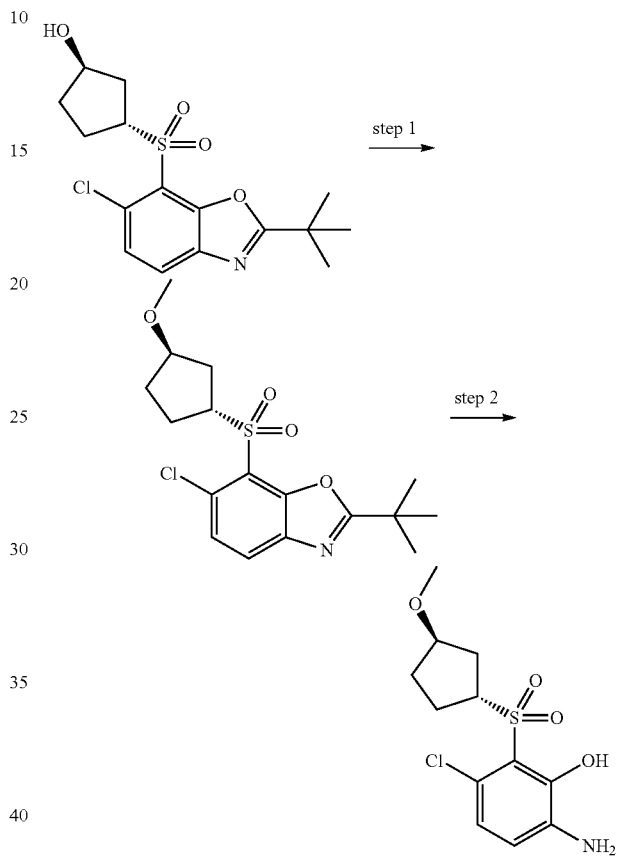

Step 1: To a suspension of NaH (33 mg) in DMF (4 mL) was added trans-3-((2-(tert-butyl)-6-chlorobenzo[d]oxazol-7-yl)sulfonyl)cyclopentanol (Intermediate 101, Step 3, 200 mg) at 0° C. After stirring at RT for 2 hours, iodomethane (0.1 mL) was added dropwise at 0° C. The resulting mixture was stirred at RT overnight. Cold water (30 mL) was added. The aqueous layer was extracted with DCM (2×100 mL). The combined organic layers were dried over Na$_2$SO$_4$, filtered and concentrated under reduced pressure. The residue was purified by column chromatography (eluting with PE:EA=5:1) to afford trans-2-(tert-butyl)-6-chloro-7-((3-methoxycyclopentyl)sulfonyl)benzo[d]oxazole (30 mg) as a white solid. MS(ES$^+$) m/z 372 (MH$^+$).

Step 2: Trans-2-(tert-butyl)-6-chloro-7-((3-methoxycyclopentyl)sulfonyl)benzo[d]oxazole (30 mg) was dissolved in 1,4-dioxane (4 mL). Conc. HCl solution (0.3 mL) was added. The mixture was heated to 100° C. for 4 hours to give a brown solution. The reaction mixture was cooled to RT, and then treated with sat. NaHCO$_3$ solution until pH=8 in an ice bath. The mixture was extracted with DCM (5×20 mL). The combined organic layers were dried over sodium sulfate, filtered and concentrated to give the title compound (25 mg) as a brown gel. MS(ES$^+$) m/z 306 (MH$^+$).

Intermediate 115: trans-6-amino-3-chloro-2-((2-methoxycyclopentyl)sulfonyl)phenol

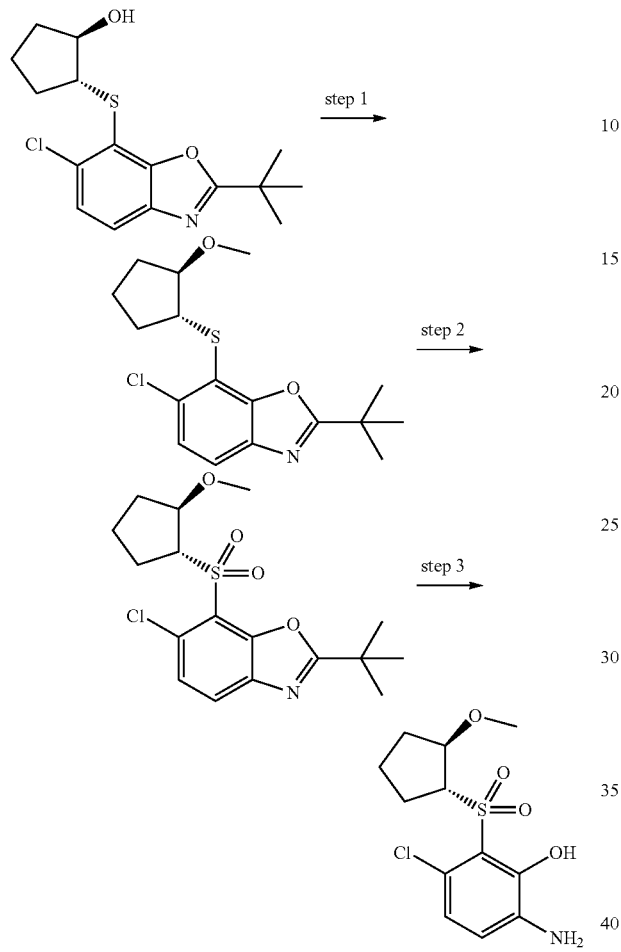

Step 1: To a suspension of trans-2-((2-(tert-butyl)-6-chlorobenzo[d]oxazol-7-yl)thio)cyclopentanol (Intermediate 38, Step 1, 220 mg) in DMF (3 mL) was added iodomethane (0.1 mL) at 0° C. The mixture was stirred at RT for 10 mins. NaH (29 mg) was added in one portion. The reaction mixture was stirred at 0° C. for another 30 mins, and then allowed to warm to RT, and stirred overnight. Cold water (10 mL) was added and the resulting mixture was extracted with DCM (2×20 mL). The combined organic layers were dried over $Na_2SO_4$, filtered and concentrated under reduced pressure. The residue was purified by column chromatography (eluting with PE:EA=5:1) to give trans-2-(tert-butyl)-6-chloro-7-((2-methoxycyclopentyl)thio)benzo[d]oxazole (200 mg) as a white solid. MS(ES⁺) m/z 340 (MH⁺).

Step 2: To a solution of trans-2-(tert-butyl)-6-chloro-7-((2-methoxycyclopentyl)thio)benzo[d]oxazole (220 mg) in DCM (10 mL) was added mCPBA (349 mg) at 0° C. The resulting mixture was stirred at RT for 48 hours, and then diluted with DCM (20 mL). The mixture was quenched with sat. $Na_2S_2O_3$ solution (10 mL) and washed with water (2×10 mL). The combined organic layers were dried over $Na_2SO_4$, filtered and concentrated under reduced pressure. The residue was purifed by column chromatography (eluting with PE:EA=4:1) to give trans-2-(tert-butyl)-6-chloro-7-((2-methoxycyclopentyl)sulfonyl)benzo[d]oxazole (200 mg) as a colorless gel. MS(ES⁺) m/z 372 (MH⁺).

Step 3: Trans-2-(tert-butyl)-6-chloro-7-((2-methoxycyclopentyl)sulfonyl)benzo[d]oxazole (200 mg) was dissolved in 1,4-dioxane (4 mL). Conc. HCl solution (2.0 mL) was added. The mixture was heated to 100° C. for 4 hours to give a brown solution. After cooling, the mixture was treated with sat. $NaHCO_3$ solution until pH=8 in an ice bath, and then extracted with DCM (5×20 mL). The combined organic layers were dried over sodium sulfate, filtered and concentrated to give the title compound (160 mg) as a brown gel. MS(ES⁺) m/z 306 (MH⁺).

Intermediate 116: 6-amino-3-chloro-2-(((3R,4S)-3-methoxytetrahydro-2H-pyran-4-yl)sulfonyl)phenol

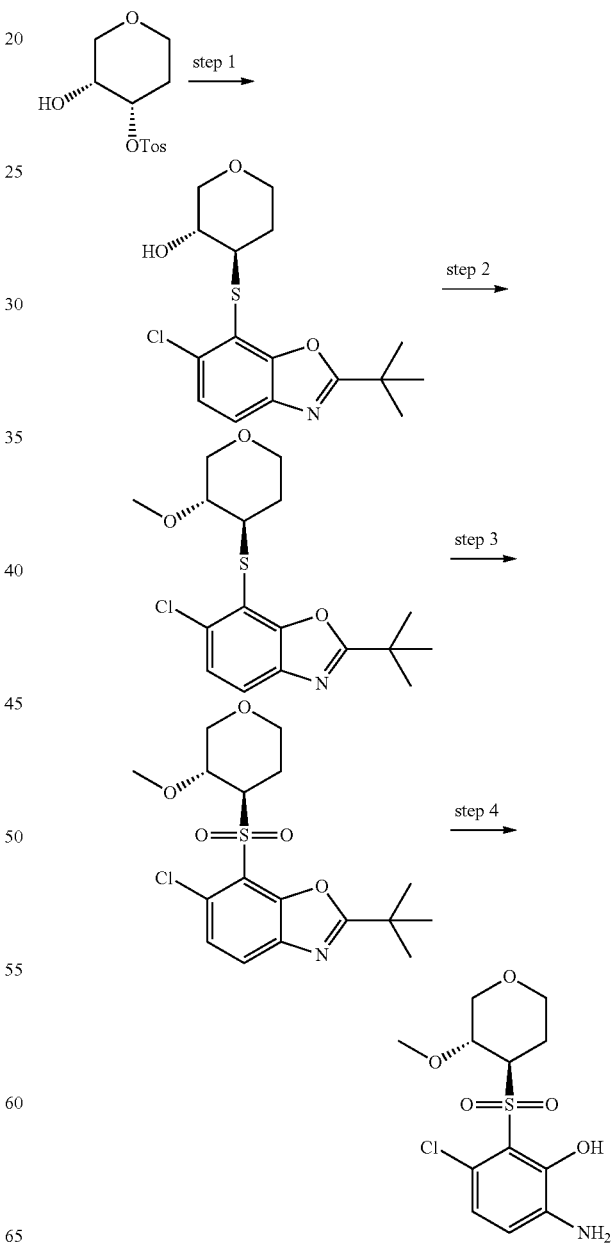

Step 1: A mixture of (3R,4S)-3-hydroxytetrahydro-2H-pyran-4-yl 4-methylbenzenesulfonate (Intermediate 41, Step 6, 5.0 g), 2-(tert-butyl)-6-chlorobenzo[d]oxazole-7-thiol, sodium salt (3.0 g) and Cs$_2$CO$_3$ (1.496 g) in acetonitrile (50 mL) was stirred at 100° C. under a nitrogen atmosphere for 6 hours. After filtration, the mixture was concentrated. The residue was purified by column chromatography (eluting with PE:EA=10:1) to afford (3R,4S)-4-((2-(tert-butyl)-6-chlorobenzo[d]oxazol-7-yl)thio)tetrahydro-2H-pyran-3-ol (1.1 g). MS(ES$^+$) m/z 342 (MH$^+$).

Step 2: A mixture of sodium hydride (0.4 g) in DMF (10 mL) was stirred at 10° C. under a nitrogen atmosphere for 10 mins. (3R,4S)-4-((2-(tert-butyl)-6-chlorobenzo[d]oxazol-7-yl)thio)tetrahydro-2H-pyran-3-ol (1.0 g) was added. After 20 mins, iodomethane (1.2 g) was added. The mixture was stirred for 1 hour. The reaction mixture was quenched with water (50 mL), and extracted with DCM (3×50 mL). The combined organic phases were washed with water (2×20 mL), dried and concentrated to afford 2-(tert-butyl)-6-chloro-7-(((3R,4S)-3-methoxytetrahydro-2H-pyran-4-yl)thio)benzo[d]oxazole (900 mg). MS(ES$^+$) m/z 356 (MH$^+$).

Step 3: To a solution of 2-(tert-butyl)-6-chloro-7-(((3R,4S)-3-methoxytetrahydro-2H-pyran-4-yl)thio)benzo[d]oxazole (1.1 g) in DCM (10 mL) was added mCPBA (1.3 g) at 0° C. The mixture was stirred at 10° C. for 18 hours. After filtration, the mixture was washed with aq. NaHSO$_3$ solution (100 mL) and aq. NaOH solution (1 M, 100 mL). The organic phase was separated, dried and concentrated to afford 2-(tert-butyl)-6-chloro-7-(((3R,4S)-3-methoxytetrahydro-2H-pyran-4-yl)sulfonyl)benzo[d]oxazole (1.0 g). MS(ES$^+$) m/z 388 (MH$^+$).

Step 4: A solution of 2-(tert-butyl)-6-chloro-7-(((3R,4S)-3-methoxytetrahydro-2H-pyran-4-yl)sulfonyl)benzo[d]oxazole (1.0 g) in 1,4-dioxane (4 mL) was stirred at 100° C. for 4 hours, and then concentrated. The pH was adjusted to 8-9. The resulting mixture was purified by preparative HPLC to afford the title compound (220 mg). MS(ES$^+$) m/z 322 (MH$^+$).

Intermediate 117: 6-amino-3-chloro-2-((cis-3-methoxycyclobutyl)sulfonyl)phenol

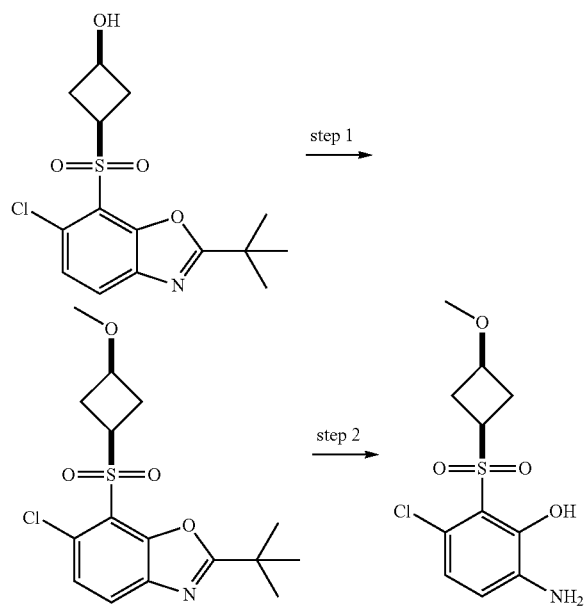

Step 1: To a solution of cis-3-((2-(tert-butyl)-6-chlorobenzo[d]oxazol-7-yl)sulfonyl)cyclobutanol (Intermediate 28, Step 3, 1.5 g) in THF (20 mL) was added NaH (0.2 g) at 0° C. After stirring for 30 mins, MeI (0.4 mL) was added. The reaction mixture was warmed up slowly and stirred at RT for 2 hours. After completion, the mixture was poured into aq. NH$_4$Cl solution and extracted with EA (2×50 mL). The combined organic phases were washed, dried and concentrated. The residue was purified by column chromatography (eluting with 20-40% EA in PE) to afford 2-(tert-butyl)-6-chloro-7-((cis-3-methoxycyclobutyl)sulfonyl)benzo[d]oxazole (0.7 g).

Step 2: A mixture of 2-(tert-butyl)-6-chloro-7-((cis-3-methoxycyclobutyl)sulfonyl)benzo[d]oxazole (0.7 g) and conc. H$_2$SO$_4$ solution (1.0 mL) in 1,4-dioxane (10 mL) and water (10 mL) was stirred at 120° C. overnight. The mixture was concentrated under reduced pressure. The residue was basified with aq. NaHCO$_3$ solution and extracted with EA (3×50 mL). The combined organic layers were washed, dried and concentrated to afford the title compound (0.4 g). MS(ES$^+$) m/z 292 (MH$^+$).

Intermediate 118: (±)trans-6-amino-3-chloro-2-((2-methoxycyclohexyl)sulfonyl)phenol

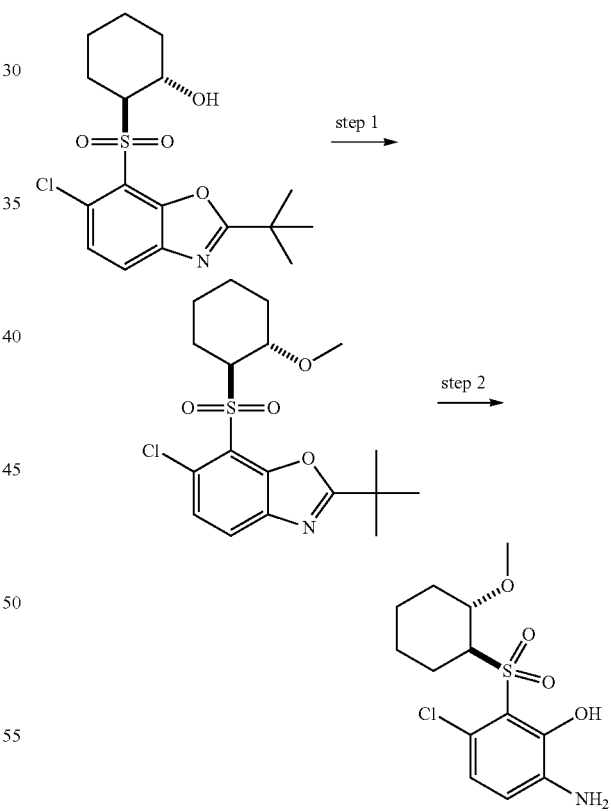

Step 1: To a solution of (±)trans-2-((2-(tert-butyl)-6-chlorobenzo[d]oxazol-7-yl)sulfonyl)cyclohexanol (Intermediate 33, Step 2, 400 mg) in DMF (3 mL) was added iodomethane (0.2 mL) at 0° C. The mixture was stirred at RT for 10 mins. NaH (69 mg) in one portion at 0° C. The resulting mixture was stirred at 0° C. for another 1 hour. The mixture was warmed to RT, and stirred overnight. Cold water (30 mL) was added. The resulting mixture was extracted with DCM (2×50 mL). The combined organic layers were dried over Na$_2$SO$_4$, filtered and concentrated under reduced pressure. The residue was purified by column chromatography (eluting with PE:EA=4:1) to afford (±)trans-2-(tert-butyl)-6-chloro-7-((2-methoxycyclohexyl) sulfonyl)benzo[d]oxazole (100 mg) as a light yellow gel. MS(ES$^+$) m/z 386 (MH$^+$).

Step 2: (±)trans-2-(tert-butyl)-6-chloro-7-((2-methoxycyclohexyl)sulfonyl)benzo[d]oxazole (100 mg) was dissolved in 1,4-dioxane (4 mL). Conc. HCl solution (8 µL) was added. The mixture was heated to 100° C. for 2.5 hours to give a brown solution. After cooling, the mixture was concentrated under reduced pressure, and then treated with sat. NaHCO$_3$ solution until pH=8 in an ice bath. The mixture was extracted with DCM (5×20 mL). The combined organic layers were dried over sodium sulfate, filtered and concentrated to give the title compound (80 mg) as a brown gel. MS(ES$^+$) m/z 320 (MH$^+$).

Intermediate 119: 6-amino-3-chloro-2-(((3S,4S)-4-methoxytetrahydrofuran-3-yl)sulfonyl)phenol and Intermediate 120: 6-amino-3-chloro-2-(((3R,4S)-4-methoxytetrahydrofuran-3-yl)sulfonyl)phenol

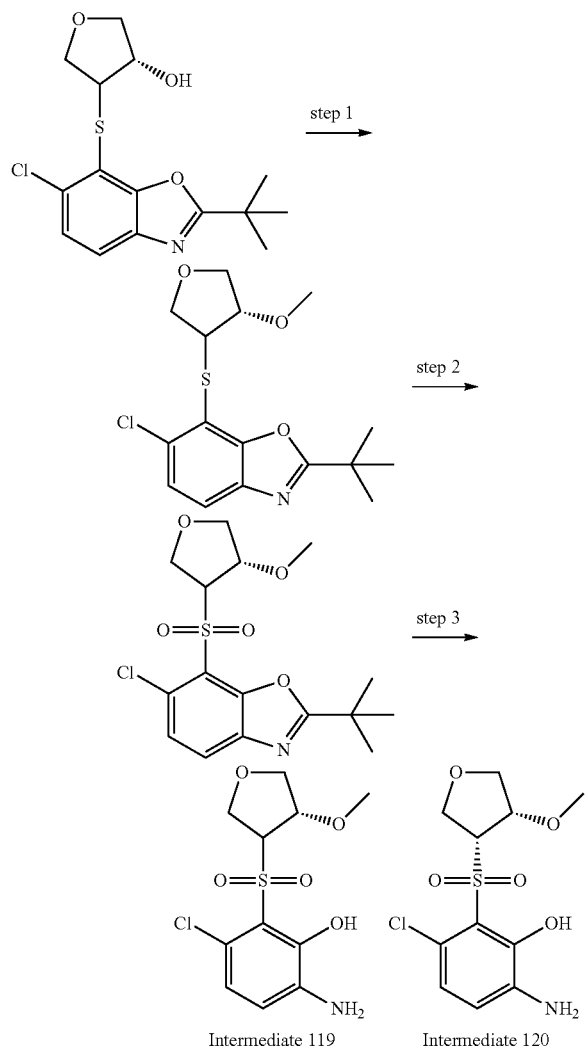

Step 1: To a solution of (3S)-4-((2-(tert-butyl)-6-chlorobenzo[d]oxazol-7-yl)thio)tetrahydrofuran-3-ol (Intermediate 34, Step 6, 600 mg) and methyl iodide (0.3 mL) in DMF (8 mL) stirred at 0° C. was added sodium hydride (73 mg). The mixture was stirred at RT for 1 hour. The mixture was quenched with sat. ammonium chloride solution. EA (20 mL) was added. The mixture was washed with brine (3×20 mL). The organic layers were dried over sodium sulfate and concentrated to afford 2-(tert-butyl)-6-chloro-7-(((4S)-4-methoxytetrahydrofuran-3-yl)thio)benzo[d]oxazole (626 mg) as a liquid oil. MS(ES$^+$) m/z 342 (MH$^+$).

Step 2: To a solution of 2-(tert-butyl)-6-chloro-7-(((4S)-4-methoxytetrahydrofuran-3-yl)thio)benzo[d]oxazole (626 mg) in DCM (20 mL) was added mCPBA (626 mg) at 0° C. The resulting mixture was stirred at RT overnight, and then quenched with aq. NaHCO$_3$ solutin and aq. Na$_2$S$_2$O$_3$ solution. The mixture was extracted with EA (2×150 mL). The combined organic phases were washed, dried and concentrated. The residue was purified by column chromatography (eluting with 30-50% EA in PE) to afford 2-(tert-butyl)-6-chloro-7-(((4S)-4-methoxytetrahydrofuran-3-yl)sulfonyl) benzo[d]oxazole (684 mg) as a white solid. MS(ES$^+$) m/z 374 (MH$^+$).

Step 3: To a solution of 2-(tert-butyl)-6-chloro-7-(((4S)-4-methoxytetrahydrofuran-3-yl)sulfonyl)benzo[d]oxazole (342 mg) in 1,4-dioxane (10 mL) was added aq. HCl solution (36%, 519 mg). After refluxing at 110° C. overnight, the mixture was concentrated. The residue was purified by reversed phase chromatography (eluting with 0-60% MeCN:H$_2$O (0.1% TFA)) to afford the title compounds (86 mg (Intermediate 119) and 140 mg (Intermediate 120)) as white solids. Intermediate 119: MS(ES$^+$) m/z 308 (MH$^+$). Intermediate 120: MS(ES$^+$) m/z 308 (MH$^+$).

Intermediate 121: 6-amino-3-chloro-2-((trans-3-(methoxymethyl)cyclobutyl)sulfonyl)phenol

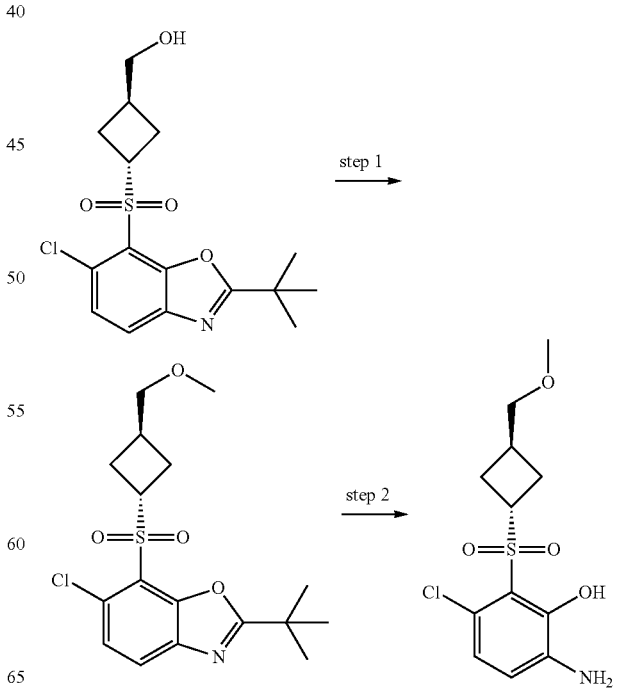

Step 1: To a mixture of NaH (22 mg) in DMF (3 mL) was added (trans-3-((2-(tert-butyl)-6-chlorobenzo[d]oxazol-7-yl)sulfonyl)cyclobutyl)methanol (Intermediate 104, Step 6, 200 mg) at 0° C. under a nitrogen atmosphere. After stirring for 30 mins, MeI (0.04 mL) was added. The mixture was stirred for 1 hour, and then quenched with water (5 mL). The resulting mixture was extracted with EA (3×20 mL). The combined organic layers were concentrated. The residue was purified by column chromatography (PE:EA=10:1) to afford 2-(tert-butyl)-6-chloro-7-((trans-3-(methoxymethyl)cyclobutyl)sulfonyl)benzo[d]oxazole (60 mg). MS(ES⁺) m/z 372 (MH⁺).

Step 2: A mixture of 2-(tert-butyl)-6-chloro-7-((trans-3-(methoxymethyl)cyclobutyl)sulfonyl)benzo[d]oxazole (60 mg) and aq. HCl solution (37%, 0.1 mL) in 1,4-dioxane (1 mL) and water (1 mL) was stirred at 100° C. for 4 hours. The mixture was concentrated. The pH was adjusted to 8-9. The organic phase was concentrated and purified by preparative TLC (eluting with PE:EA=3:1) to afford the title compound (35 mg). MS(ES⁺) m/z 306 (MH⁺).

Intermediate 122: 6-amino-3-chloro-2-((4-methoxypiperidin-1-yl)sulfonyl)phenol

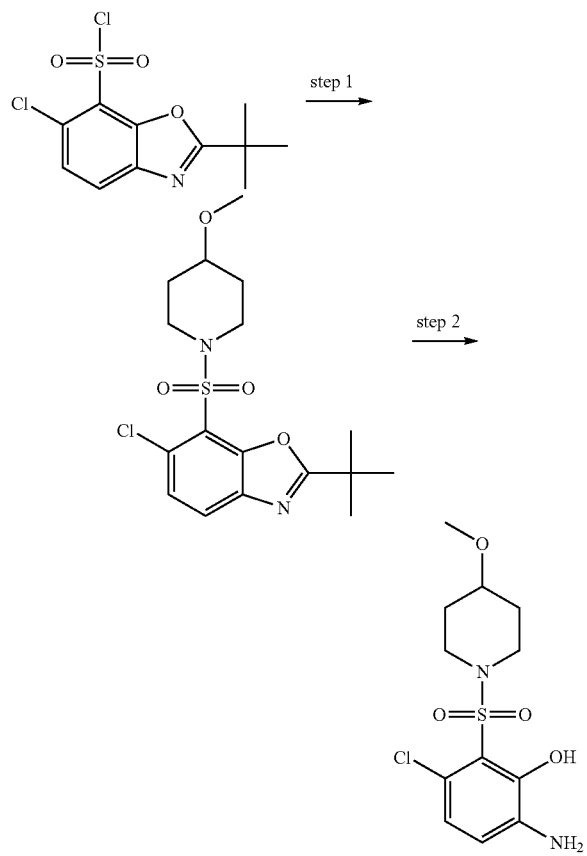

Step 1: To a solution of TEA (0.7 mL) and 4-methoxypiperidine (187 mg) in THF (10 mL) was added 2-(tert-butyl)-6-chlorobenzo[d]oxazole-7-sulfonyl chloride (500 mg) portionwise at RT. The mixture was stirred overnight. Cold water (30 mL) was added. The resulting mixture was extracted with DCM (2×100 mL). The combined organic layers were dried over Na₂SO₄, filtered and concentrated in vacuo to give 2-(tert-butyl)-6-chloro-7-((4-methoxypiperidin-1-yl)sulfonyl)benzo[d]oxazole (310 mg) as a yellow solid. MS(ES⁺) m/z 387 (MH⁺).

Step 2: To a solution of 2-(tert-butyl)-6-chloro-7-((4-methoxypiperidin-1-yl)sulfonyl)benzo[d]oxazole (391 mg) in water (1 mL) and 1,4-dioxane (5 mL) was added sulfuric acid (1982 mg). The mixture was stirred at 100° C. overnight. The solvent was removed in vacuo. The residue was purified by HPLC (C8, mobile phase 0.01% CF₃COOH, CH₃OH, 30 mL/min) (10%~55%, 5 min; 55~55%, 6 min; 40%~95%, 1 min; 95%~95%, 1 min) to give the title compound (272 mg) as a white solid. MS(ES⁺) m/z 321 (MH⁺).

Intermediate 123: 6-amino-3-chloro-2-((1-methoxy-2-methylpropan-2-yl)sulfonyl)phenol

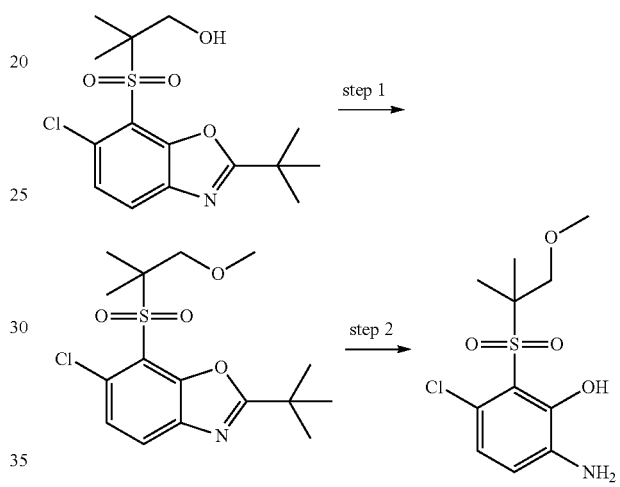

Step 1: To a mixture of NaH (0.2 g) in THF (15 mL) was added 2-((2-(tert-butyl)-6-chlorobenzo[d]oxazol-7-yl)sulfonyl)-2-methylpropan-1-ol (Intermediate 17, Step 3, 1.4 g). After stirring for 10 mins, MeI (0.3 mL) was added. The resulting mixture was stirred at 0° C. under a nitrogen atmosphere for 2 hours, and then quenched with water (10 mL). The mixture was extracted with EA (3×50 mL). The combined organic phases were dried and concentrated to afford 2-(tert-butyl)-6-chloro-7-((1-methoxy-2-methylpropan-2-yl)sulfonyl)benzo[d]oxazole (1.0 g). MS(ES⁺) m/z 360 (MH⁺).

Step 2: A solution of 2-(tert-butyl)-6-chloro-7-((1-methoxy-2-methylpropan-2-yl)sulfonyl)benzo[d]oxazole (900 mg) and aq. HCl solution (37%, 4.1 mL) in 1,4-dioxane (10 mL) and water (5 mL) was stirred at 100° C. for 4 hours, and then concentrated. The pH was adjusted to 8, and then purified by column chromatography (eluting with PE:EA=10:1) to afford the title compound (500 mg). MS(ES⁺) m/z 294 (MH⁺).

Intermediate 124: 6-amino-3-chloro-2-((1-methoxypropan-2-yl)sulfonyl)phenol

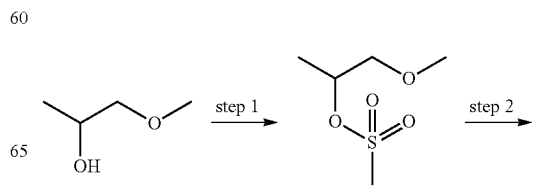

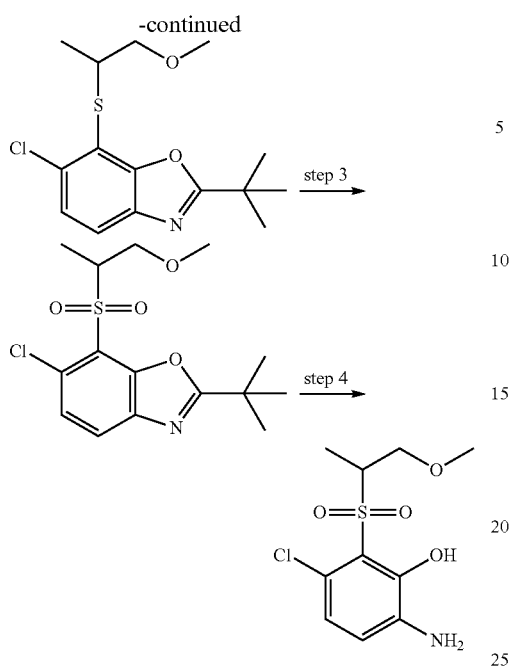

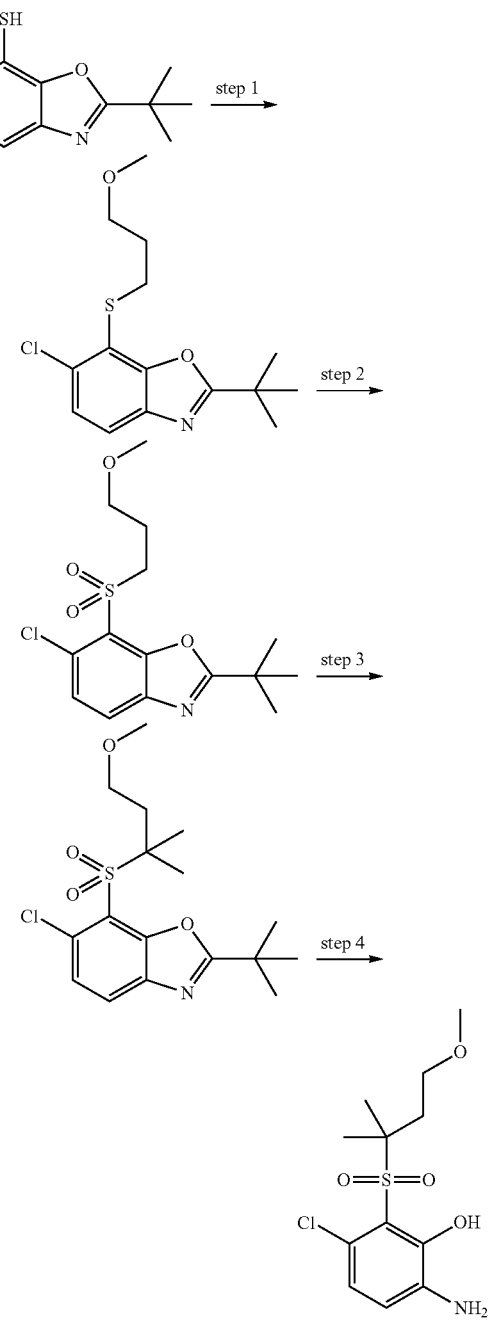

Intermediate 125: 6-amino-3-chloro-2-((4-methoxy-2-methylbutan-2-yl)sulfonyl)phenol Step 1: To a solution of 1-methoxypropan-2-ol (4.2 g) in DCM (50 mL) was added TEA (7.1 g). After stirring at 0° C. for 10 mins, methanesulfonyl chloride (6.9 g) was added dropwise. The mixture was stirred for another one hour, and then quenched with aq. NaHCO$_3$ solution. The resulting mixture was extracted with DCM (2×100 mL). The combined organic phases were washed, dried and concentrated to afford 1-methoxypropan-2-yl methanesulfonate (4.0 g).

Step 2: 1-Methoxypropan-2-yl methanesulfonate (1.0 g) was added to a solution of sodium 2-(tert-butyl)-6-chlorobenzo[d]oxazole-7-thiolate (1.5 g) and K$_2$CO$_3$ (1.6 g) in DMF (50 mL) at RT. The mixture was stirred at 80° C. for 4 hours. After cooling, the mixture was poured into water (100 mL), and then extracted with EA (2×100 mL). The combined organic phases were washed, dried and concentrated. The residue was purified by column chromatography (eluting with PE:EA=20:1) to afford 2-(tert-butyl)-6-chloro-7-((1-methoxypropan-2-yl)thio)benzo[d]oxazole (1.1 g) as a yellow oil. MS(ES$^+$) m/z 314 (MH$^+$).

Step 3: mCPBA (4.7 g) was added to a solution of 2-(tert-butyl)-6-chloro-7-((1-methoxypropan-2-yl)thio)benzo[d]oxazole (3.0 g) in DCM (70 mL) at 0° C. The mixture was stirred at 25° C. for 4 hours, and then quenched with aq. NaHCO$_3$ solution and aq. Na$_2$S$_2$O$_3$ solution. The resulting mixture was extracted with DCM (2×30 mL). The combined organic phases were washed, dried and concentrated. The residue was purified by column chromatography (eluting with PE:EA=10:1 to 4:1) to afford 2-(tert-butyl)-6-chloro-7-((1-methoxypropan-2-yl)sulfonyl)benzo[d]oxazole (3.1 g) as a yellow oil. MS(ES$^+$) m/z 346 (MH$^+$).

Step 4: To a solution of 2-(tert-butyl)-6-chloro-7-((1-methoxypropan-2-yl)sulfonyl)benzo[d]oxazole (1.0 g) in 1,4-dioxane (40 mL) and water (20 mL) was added aq. HCl solution (12 M, 25 mL). The mixture was stirred at 100° C. for 3 hours, and then concentrated. The residue was washed with PE to give the title compound (500 mg) as a white solid. MS(ES$^+$) m/z 280 (MH$^+$).

Step 1: A mixture of 2-(tert-butyl)-6-chlorobenzo[d]oxazole-7-thiol (6.0 g), 1-bromo-3-methoxypropane (4.8 g) and Cs$_2$CO$_3$ (3.4 g) in acetonitrile (50 mL) was stirred at 100° C. for 2 hours, and concentrated. The residue was purified by column chromatography (eluting with PE:EA=100:1) to afford 2-(tert-butyl)-6-chloro-7-((3-methoxypropyl)thio)benzo[d]oxazole (6.4 g). MS(ES$^+$) m/z 314 (MH$^+$).

Step 2: To a solution of 2-(tert-butyl)-6-chloro-7-((3-methoxypropyl)thio)benzo[d]oxazole (6.4 g) in DCM (60 mL) was added mCPBA (10.4 g) at 0° C. The mixture was stirred at 30° C. for 18 hours, and then filtered. Aq. Na₂SO₃ solution (100 mL) was added. The organic phase was washed by aq. NaOH solution (1 M, 50 mL) and water (2×100 mL), dried and concentrated to afford 2-(tert-butyl)-6-chloro-7-((3-methoxypropyl)sulfonyl)benzo[d]oxazole (5.2 g). MS(ES⁺) m/z 346 (MH⁺).

Step 3: To a solution of 2-(tert-butyl)-6-chloro-7-((3-methoxypropyl)sulfonyl)benzo[d]oxazole (4.3 g) in THF (15 mL) was added NaHMDS (1 M in THF, 62.2 mL) at −70° C. After stirring at −70° C. for 30 mins, MeI (3.9 mL) was added. The mixture was stirred at −70° C. for 30 mins, and then quenched with aq. NH₄Cl solution (5 mL). The resulting mixture was extracted with EA (3×5 mL). The combined organic phases were dried and concentrated. The residue was purified by column chromatography (eluting with PE:EA=10:1) to afford 2-(tert-butyl)-6-chloro-7-((4-methoxy-2-methylbutan-2-yl)sulfonyl)benzo[d]oxazole (4.0 g). MS(ES⁺) m/z 374 (MH⁺).

Step 4: A mixture of 2-(tert-butyl)-6-chloro-7-((4-methoxy-2-methylbutan-2-yl)sulfonyl)benzo[d]oxazole (1.0 g) and aq. HCl solution (37%, 5 mL) in 1,4-dioxane (5 mL) was stirred at 100° C. for 4 hours, and then concentrated. The residue was combined with another batch of the same reaction using 2-(tert-butyl)-6-chloro-7-((4-methoxy-2-methylbutan-2-yl)sulfonyl)benzo[d]oxazole (1.0 g) as starting material. The pH of the combined mixture was adjusted to 8, and then purified by preparative HPLC to afford the title compound (260 mg). MS(ES⁺) m/z 308 (MH⁺).

Intermediate 126: 6-amino-3-chloro-2-((4-(2-methoxyethyl)piperazin-1-yl)sulfonyl)phenol

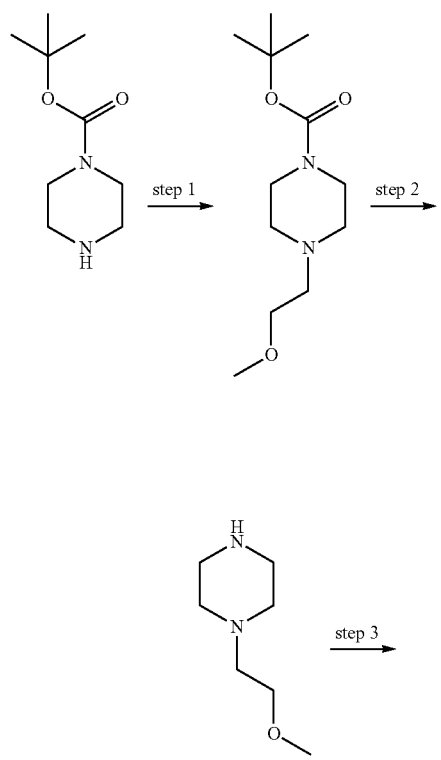

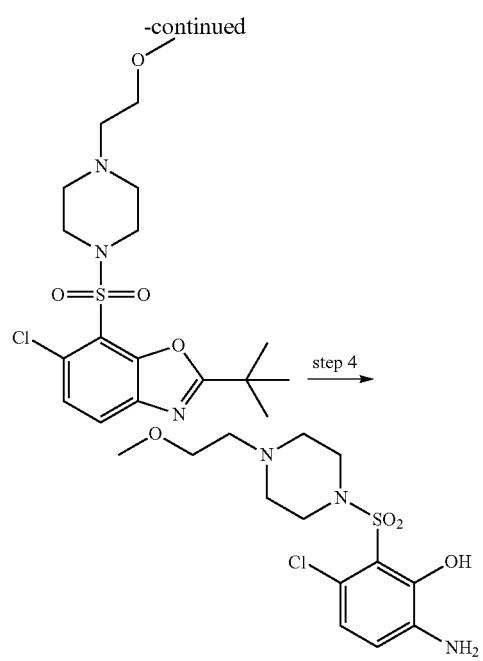

Step 1: A solution of tert-butyl piperazine-1-carboxylate (2.0 g) in acetonitrile (50 mL) was treated with K₂CO₃ (4.5 g) and 1-bromo-2-methoxyethane (1.6 g). The mixture was heated to 80° C. for 18 hours. After cooling, the mixture was diluted with water (20 mL) and extracted with DCM (3×30 mL). The combined organc layers were dried over MgSO₄, filtered and concentrated under reduced pressure. The residue was purified by column chromatography (eluting with 5% MeOH in DCM) to afford tert-butyl 4-(2-methoxyethyl)piperazine-1-carboxylate (2.4 g) as a colorless oil. MS(ES⁺) m/z 245 (MH⁺).

Step 2: Tert-butyl 4-(2-methoxyethyl)piperazine-1-carboxylate (2.4 g) was dissolved in HCl (4 M in dioxane, 24 mL). The resulting solution was stirred at RT for 3 hours, and then concentrated under reduced pressure. Ethanol was added. The solvent was evaporated. Ethanol and ether were added. The solid was collected by filtration to give 1-(2-methoxyethyl)piperazine, hydrochloride (1.8 g) as a white solid. ¹H-NMR (400 MHz, DMSO-d₆) δ ppm 11.82 (s, 1H), 9.90 (s, 2H), 3.72-3.76 (m, 2H), 3.65 (s, 2H), 3.32-3.50 (m, 8H), 3.29 (s, 3H); MS(ES⁺) m/z 145 (MH⁺).

Step 3: To a solution of 2-(tert-butyl)-6-chlorobenzo[d]oxazole-7-sulfonyl chloride (600 mg) in THF (20 mL) was added TEA (0.8 mL). After cooling to 0° C., 1-(2-methoxyethyl)piperazine, hydrochloride (528 mg) was added potionwise over 2 mins. The resulting mixture was stirred at RT overnight, and then concentrated under reduced pressure. The resiude was diluted with water (20 mL) and extracted with EA (3×20 mL). The combined organic layers were dried over sodium sulfate, filtered and concentrated. The residue was purified by column chromatography (eluting with PE:EA=1:2) to give 2-(tert-butyl)-6-chloro-7-((4-(2-methoxyethyl)piperazin-1-yl)sulfonyl)benzo[d]oxazole (465 mg) as a light yellow solid. MS(ES⁺) m/z 416 (MH⁺).

Step 4: To a solution of 2-(tert-butyl)-6-chloro-7-((4-(2-methoxyethyl)piperazin-1-yl)sulfonyl)benzo[d]oxazole (465 mg) in 1,4-dioxane (5 mL) was added conc. HCl solution (2.0 mL). The mixture was heated to 100° C. for 3 hours to give a brown solution. After cooling, the mixture was concentrated under reduced pressure, and then treated with sat. NaHCO₃ solution until pH=8 in an ice bath. The resulting mixture was extracted with DCM (5×20 mL). The combined organic layers were dried over sodium sulfate, filtered and concentrated to give the title compound (400 mg) as a brown solid. MS(ES⁺) m/z 350 (MH⁺).

Intermediate 126:
6-amino-3-chloro-2-(oxetan-3-ylsulfonyl)phenol

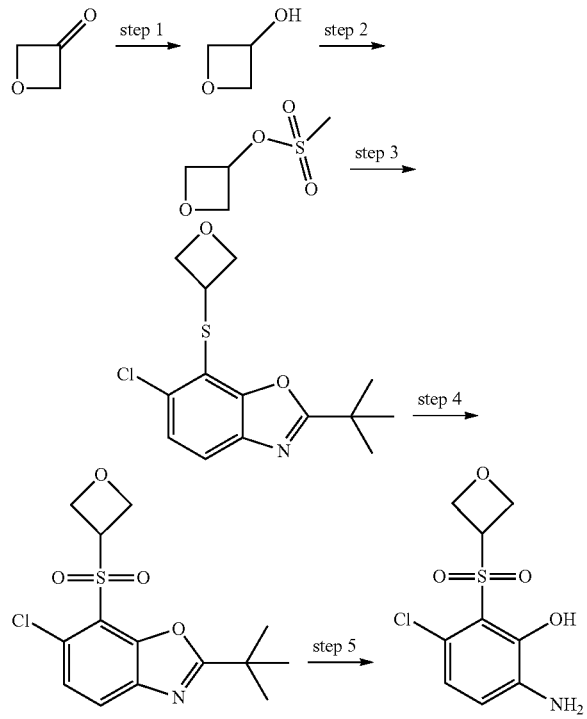

Step 1: To a suspension of oxetan-3-one (1.2 g) in THF (20 mL) was added NaBH₄ (0.8 g). The resulting mixture was stirred at 25° C. for 4 hours, and then quenched with aq. NH₄Cl solution (10 mL). The resulting solution was dried with Na₂SO₄ overnight. After filtration, the solvent was removed under reduced pressure to afford oxetan-3-ol (1.0 g).

Step 2: To an ice-water cooled solution of oxetan-3-ol (1.0 g) in DCM (50 mL) was added TEA (3.8 mL). MsCl (1.6 mL) was then added dropwise. The resulting mixture was warmed up slowly and stirred at RT for 2 hours. The mixture was then quenched with aq. NaHCO₃ solution and extracted with EA (3×50 mL). The combined organic phases were washed, dried and concentrated to afford oxetan-3-yl methanesulfonate (1.2 g).

Step 3: To a solution of sodium 2-(tert-butyl)-6-chlorobenzo[d]oxazole-7-thiolate (2.0 g) and oxetan-3-yl methanesulfonate (1.2 g) in DMF (50 mL) was added K₂CO₃ (1.0 g). The resulting mixture was stirred at 80° C. overnight. After cooling, the mixture was poured into water and extracted with EA (2×100 mL). The combined organic phases were washed, dried and concentrated to afford 2-(tert-butyl)-6-chloro-7-(oxetan-3-ylthio)benzo[d]oxazole (2.0 g). MS(ES⁺) m/z 298 (MH⁺).

Step 4: To an ice-water cooled solution of 2-(tert-butyl)-6-chloro-7-(oxetan-3-ylthio)benzo[d]oxazole (10.0 g) in DCM (250 mL) was added mCPBA (15.9 g). After addition, the mixture was warmed up slowly, and stirred at RT overnight. The reaction mixture was quenched with aq. NaHCO₃ solution and aq. Na₂S₂O₃ solution. The resulting mixture was extracted with EA (2×200 mL). The combined organic phases were washed, dried and concentrated. The residue was purified with column chromatography (eluting with 0-30% EA in PE) to afford 2-(tert-butyl)-6-chloro-7-(oxetan-3-ylsulfonyl)benzo[d]oxazole (7.7 g). MS(ES⁺) m/z 330 (MH⁺).

Step 5: To a solution of 2-(tert-butyl)-6-chloro-7-(oxetan-3-ylsulfonyl)benzo[d]oxazole (2.3 g) in 1,4-dioxane (25 mL) and water (50 mL) was added conc. H₂SO₄ (3.7 mL). The resulting mixture was stirred at 120° C. overnight, and then concentrated under reduced pressure to remove dioxane. The residue was basified with aq. NaHCO₃ solution to pH=8, and extracted with EA (2×100 mL). The combined organic phases were washed, dried and concentrated to afford the title compound (1.6 g). MS(ES⁺) m/z 264 (MH⁺).

Intermediate 127: 6-amino-3-chloro-2-((3-methyloxetan-3-yl)sulfonyl)phenol

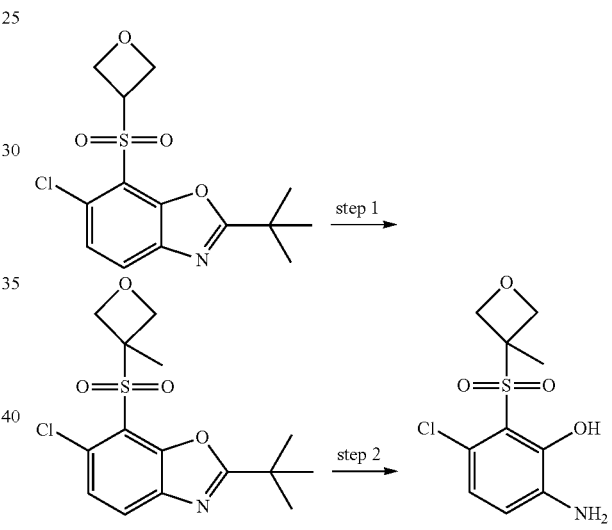

Step 1: To a solution of 2-(tert-butyl)-6-chloro-7-(oxetan-3-ylsulfonyl)benzo[d]oxazole (Intermediate 126, Step 4, 1.5 g) in THF (50 mL) was added LiHMDS (1.0 M in n-hexane, 9.1 mL) dropwise at −78° C. After 1 hour, a solution of methyl iodide (0.4 mL) in THF (8 mL) was added dropwise. The mixture was allowed to warm to ambient temperature, and stirred for 1 hour. The resulting mixture was quenched with water (0.5 mL), and then partitioned between sat. NH₄Cl solution and EA. The organic phase was washed with brine, dried over sodium sulfate, filtered and concentrated in vacuo. The residue was purified by column chromatography (eluting with 10-30% EA in PE) to afford 2-(tert-butyl)-6-chloro-7-((3-methyloxetan-3-yl)sulfonyl)benzo[d]oxazole (200 mg). MS(ES⁺) m/z 344 (MH⁺).

Step 2: To a solution of 2-(tert-butyl)-6-chloro-7-((3-methyloxetan-3-yl)sulfonyl)benzo[d]oxazole (0.2 g) in 1,4-dioxane (5 mL) and water (10 mL) was dropwise added conc. H₂SO₄ (0.3 mL). The mixture was stirred at 120° C. overnight, and then concentrated under reduced pressure. The residue was basified with aq. NaHCO₃ solution, and extracted with EA (2×50 mL). The combined organic phases were washed, dried and concentrated to afford the title compound (70 mg). MS(ES⁺) m/z 278 (MH⁺).

Intermediate 128: 6-amino-3-chloro-2-((3-fluorooxetan-3-yl)sulfonyl)phenol

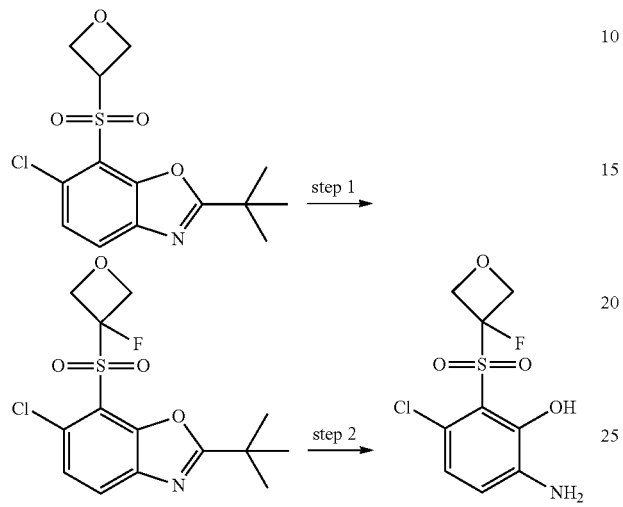

Step 1: To a solution of 2-(tert-butyl)-6-chloro-7-(oxetan-3-ylsulfonyl)benzo[d]oxazole (Intermediate 126, Step 4, 1.5 g) in THF (50 mL) was dropwise added LiHMDS (1.0 M in n-hexane, 9.1 mL) at −78° C. After 1 hour, a solution of N-fluoro-N-(phenylsulfonyl)benzenesulfonamide (1.4 g) in THF (8 mL) was added dropwise. The mixture was warmed to ambient temperature, and stirred for 1 hour. The mixture was quenched with water (0.5 mL), and partitioned between sat. NH₄Cl solution and EA. The organic phase was washed with brine, dried over sodium sulfate, filtered and concentrated in vacuo. The residue was purified by column chromatography (eluting with 10-30% EA in PE) to afford 2-(tert-butyl)-6-chloro-7-((3-fluorooxetan-3-yl)sulfonyl)benzo[d]oxazole (0.5 g). MS(ES⁺) m/z 348 (MH⁺).

Step 2: To a solution of 2-(tert-butyl)-6-chloro-7-((3-fluorooxetan-3-yl)sulfonyl)benzo[d]oxazole (0.5 g) in 1,4-dioxane (5 mL) and water (10 mL) was added conc. H₂SO₄ (0.8 mL). The mixture was stirred at 120° C. overnight, and then concentrated. The resulting mixture was basified with aq. NH₃.H₂O, and then purified by reversed phase chromatography (acidic condition) to afford the title compound (50 mg).

Intermediate 129: 6-amino-3-chloro-2-((3-(d3-methyl)tetrahydrofuran-3-yl)sulfonyl)phenol

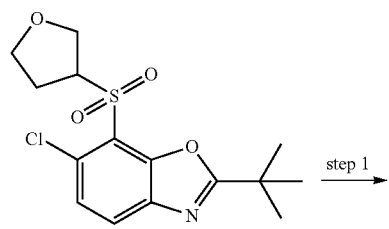

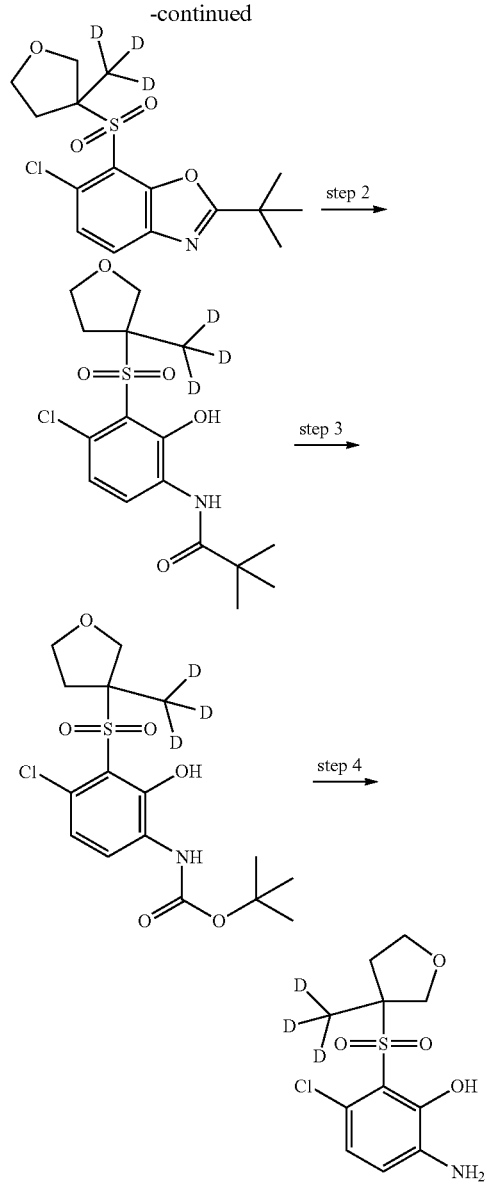

Step 1: To a dry ice-ethanol cooled solution of 2-(tert-butyl)-6-chloro-7-((tetrahydrofuran-3-yl)sulfonyl)benzo[d]oxazole (Intermediate 29, Step 3, 1.5 g) and [d₃]-methyl p-toluenesulphonate (Intermediate 31, Step 1, 1.2 g) in THF (15 mL) and HMPA (13.5 mL) was added LDA (2 M in THF, 3.3 mL) dropwise. After stirring for 10 mins, the mixture was quenched with aq. NH₄Cl solution at low temperature, and then extracted with EA (2×50 mL). The combined organic phases were washed, dried and concentrated. The residue was purified by column chromatography (eluting with 0-30% EA in PE) to afford 2-(tert-butyl)-6-chloro-7-((3-(d₃-methyl)tetrahydrofuran-3-yl)sulfonyl)benzo[d]oxazole (1.0 g). MS(ES⁺) m/z 361 (MH⁺).

Step 2: To a solution of 2-(tert-butyl)-6-chloro-7-((3-(d₃-methyl)tetrahydrofuran-3-yl)sulfonyl)benzo[d]oxazole (2.5 g) in ethanol (10 mL) and water (10 mL) was added sodium hydroxide (1.4 g). The mixture was stirred at 60° C. for 2 hours, and then concentrated. The residue was dissolved in water (50 mL), acidified with aq. citric acid to pH=6, and extracted with EA (2×50 mL). The combined organic phases were washed, dried and concentrated to afford N-(4-chloro-2-hydroxy-3-((3-(d₃-methyl)tetrahydrofuran-3-yl)sulfonyl)phenyl)pivalamide (2.5 g). MS(ES⁺) m/z 379 (MH⁺).

Step 3: To a solution of N-(4-chloro-2-hydroxy-3-((3-(d₃-methyl)tetrahydrofuran-3-yl)sulfonyl)phenyl)pivalamide (2.5 g) in THF (50 mL) was added DMAP (0.08 g) and Boc₂O (3.1 mL). The mixture was stirred at 60° C. for 2 hours. Hydrazine.H₂O (1.6 mL) was added. The resulting mixture was stirred at RT overnight, and then diluted with water (50 mL). The solution was extracted with EA (2×100 mL). The combined organic phases were washed, dried and concentrated. The residue was purified by column chromatography (eluting with 0-30% EA in PE) to afford tert-butyl (4-chloro-2-hydroxy-3-((3-(d₃-methyl)tetrahydrofuran-3-yl)sulfonyl)phenyl)carbamate (1.4 g). MS(ES⁺) m/z 417 (MNa⁺).

Step 4: To a solution of tert-butyl (4-chloro-2-hydroxy-3-((3-(d₃-methyl)tetrahydrofuran-3-yl)sulfonyl)phenyl)carbamate (1.4 g) in DCM (20 mL) was added TFA (2.7 mL). The resulting mixture was stirred at RT overnight, and then quenched with aq. NaHCO₃ solution carefully. The solution was extracted with DCM (2×50 mL). The combined organic phases were washed, dried and concentrated to afford the title compound (1.0 g). MS(ES⁺) m/z 295 (MH⁺).

Intermediate 130: (S)-6-amino-3-chloro-2-((1-methoxypropan-2-yl)sulfonyl)phenol

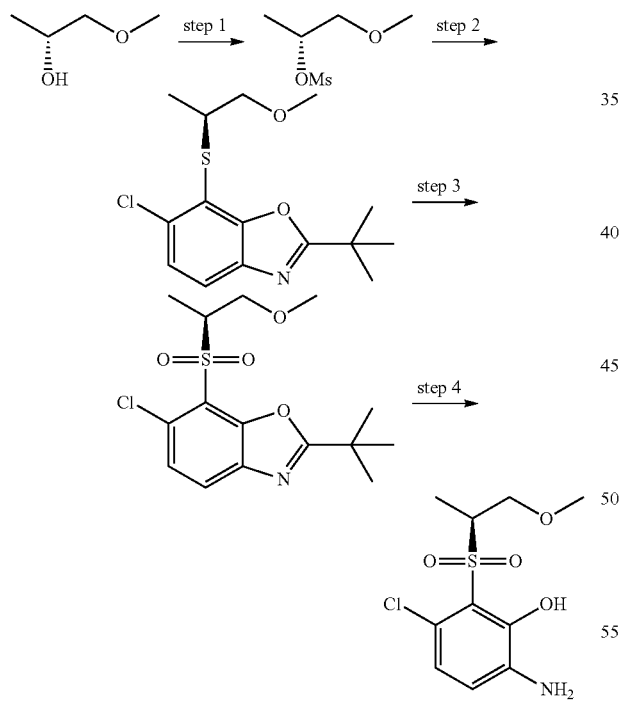

Step 1: To a solution of (R)-1-methoxypropan-2-ol (5.4 g) and TEA (12.1 g) in THF (20 mL) was added methanesulfonyl chloride (8.3 g) at 0° C. The mixture was stirred at 0° C. for 4 hours. The solution was poured into water, and extracted with EA (2×50 mL). The combined organic layers were washed, dried, filtered and concentrated to give (R)-1-methoxypropan-2-yl methanesulfonate (10.6 g) as a light yellow solid. ¹H-NMR (400 MHz, CDCl₃) δ ppm 4.87-4.90 (m, 1H), 3.42-3.55 (m, 2H), 3.39 (d, J=1.5 Hz, 3H), 3.05 (d, J=1.4 Hz, 3H), 1.39 (dd, J=6.5, 1.5 Hz, 3H).

Step 2: K₂CO₃ (2.6 g) was added to a solution of sodium 2-(tert-butyl)-6-chlorobenzo[d]oxazole-7-thiolate (5.0 g) and (R)-1-methoxypropan-2-yl methanesulfonate (3.2 g) in DMF (20 mL) at RT. The reaction mixture was stirred at 50° C. for 3 hours. The solution was poured into ice-water (50 mL), and extracted with EA (4×30 mL). The combined organic layers were washed with brine (8 mL), dried over Na₂SO₄, filtered and concentrated under reduced pressure. The residue was purified by column chromatography (eluting with PE:EA=30:1) to give (S)-2-(tert-butyl)-6-chloro-7-((1-methoxypropan-2-yl)thio)benzo[d]oxazole (4.0 g) as a light yellow liquid. MS(ES⁺) m/z 314 (MH⁺).

Step 3: To a solution of (S)-2-(tert-butyl)-6-chloro-7-((1-methoxypropan-2-yl)thio)benzo[d]oxazole (4.0 g) in DCM (20 mL) was added 3-hlorobenzoperoxoic acid (8.8 g) at 0° C. The resulting mixture was stirred at RT for 3 hours. Cold water (30 mL) was added. The resulting mixture was neutralized with sat. NaHCO₃ solution. The aqueous layer was extracted with DCM (2×80 mL). The combined organic layers were dried over Na₂SO₄, filtered and concentrated in vacuo. The residue was purified by column chromatography (eluting with PE:EA=5:1) to give (S)-2-(tert-butyl)-6-chloro-7-((1-methoxypropan-2-yl)sulfonyl)benzo[d]oxazole (4.0 g) as a colorless liquid. MS(ES⁺) m/z 346 (MH⁺).

Step 4: To a solution of sulfuric acid (0.5 mL) in 1,4-dioxane (8 mL) was added (S)-2-(tert-butyl)-6-chloro-7-((1-methoxpropan-2-yl)sulfonyl)benzo[d]oxazole (2.0 g). The resulting mixture was stirred for 1 hour at 100° C. Cold water (50 mL) was added. The resulting mixture was neutralized with sat. NaHCO₃ solution. The aqueous layer was extracted with DCM (3×50 mL). The combined organic layers were dried over Na₂SO₄, filtered and concentrated in vacuo to give the title compound (1.0 g) as a dark solid. MS(ES⁺) m/z 280 (MH⁺).

Supporting Compounds/Compounds
Method 1

Compound 1: 1-(4-chloro-2-hydroxy-3-((1,1,1-trifluoro-2-methylpropan-2-yl)sulfonyl)phenyl)-3-(cyclopent-2-en-1-yl)urea

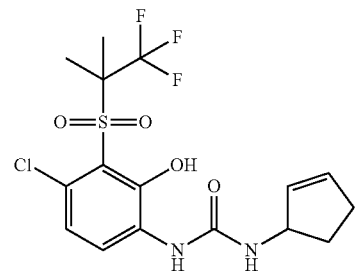 [SMILES: CC(C)(C(F)(F)F)S(=O)(=O)c1c(Cl)ccc(NC(=O)NC2C=CCC2)c1O]

To a solution of 6-amino-3-chloro-2-((1,1,1-trifluoro-2-methylpropan-2-yl)sulfonyl)phenol (Intermediate 12, 120 mg) in pyridine (5 mL) was added fresh 3-isocyanatocyclopent-1-ene solution (Intermediate 4, 0.08 M in toluene, 5 mL) and the resulting mixture was stirred at RT overnight. The mixture was quenched with ethanol (10 mL) and concentrated under reduced pressure. The residue was purified with MDAP (acidic condition) to afford the title compound (30 mg); ¹H-NMR (400 MHz, DMSO-d₆) δ ppm 10.35 (br. s., 1H), 8.31 (d, J=8.8 Hz, 1H), 8.22 (s, 1H), 7.17

(d, J=8.8 Hz, 1H), 7.12 (d, J=7.8 Hz, 1H), 5.89-5.96 (m, 1H), 5.66-5.75 (m, 1H), 4.64-4.74 (m, 1H), 2.16-2.45 (m, 3H), 1.63 (s, 6H), 1.43-1.57 (m, 1H); MS(ES$^+$) m/z 427 (MH$^+$).
Method 2

Compound 17: 1-(4-chloro-2-hydroxy-3-(isopropyl-sulfonyl)phenyl)-3-(3-fluoro-2-methylcyclopent-2-en-1-yl)urea

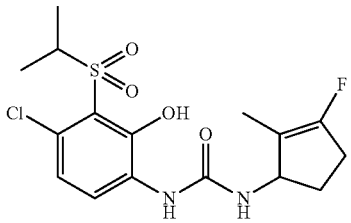 [SMILES: CC1=C(F)CCC1NC(=O)Nc1ccc(Cl)c(S(=O)(=O)C(C)C)c1O]

To a solution of 1-fluoro-3-isocyanato-2-methylcyclopent-1-ene (Intermediate 7, 63 mg) in DCM (10 mL) was added 6-amino-3-chloro-2-(isopropylsulfonyl)phenol (Intermediate 21, 111 mg) at 0° C. The resulting mixture was stirred at RT for 18 hours. The mixture was purificated by preparative HPLC (C8, mobile phase 0.01% NH$_4$HCO$_3$/H$_2$O, CH$_3$OH, 30 mL/min) (10%~40%, 5 min; 40~40%, 6 min; 40%~95%, 1 min; 95%~95%, 1 min) to give the title compound (4.5 mg) as a white solid. $^1$H-NMR (400 MHz, DMSO-d$_6$) δ ppm 8.18 (s, 2H), 7.14 (d, J=8.1 Hz, 1H), 6.75 (s, 1H), 4.53 (s, 1H), 4.06 (s, 1H), 2.32 (t, J=14.6 Hz, 3H), 1.54 (s, 1H), 1.53 (s, 3H), 1.21 (d, J=6.8 Hz, 6H); MS(ES$^+$) m/z 391 (MH$^+$).
Method 3

Compound 107: 1-(4-chloro-2-hydroxy-3-((4-methyltetrahydro-2H-pyran-4-yl)sulfonyl)phenyl)-3-(2-methylcyclopent-2-en-1-yl)urea

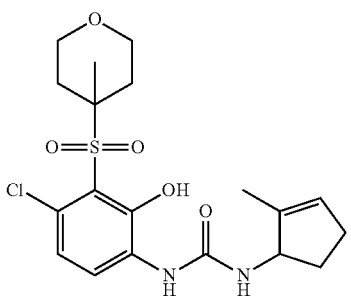

To a solution of 2-methylcyclopent-2-enamine, dihydrochloride (Intermediate 3, Step 3, 400 mg) and pyridine (0.6 mL) in DCM (5 mL) was added 4-nitrophenyl carbonochloridate (391 mg). After stirring at RT overnight, the mixture was concentrated under reduced pressure. The resulting residue was redissolved in DMF (5 mL). The above mixture was added to a solution of pyridine (0.6 mL) and 6-amino-3-chloro-2-((4-methyltetrahydro-2H-pyran-4-yl)sulfonyl)phenol (Intermediate 30, 350 mg) in DMF (5 mL). After stirring at 80° C. for 2 days, the mixture was concentrated and purified by MDAP to afford the title compound (16 mg) as a white solid. $^1$H-NMR (400 MHz, DMSO-d$_6$) δ ppm 10.29 (br. s., 1H), 8.38 (d, J=8.8 Hz, 1H), 8.15 (s, 1H), 7.09 (d, J=8.8 Hz, 1H), 7.04 (d, J=8.3 Hz, 1H), 5.50 (br. s., 1H), 4.47-4.60 (m, 1H), 3.84 (dd, J=11.7, 4.1 Hz, 2H), 3.48 (t, J=11.5 Hz, 2H), 2.10-2.35 (m, 3H), 2.04 (td, J=12.4, 5.0 Hz, 2H), 1.67 (s, 3H), 1.43-1.62 (m, 6H); MS(ES$^+$) m/z 429 (MH$^+$).
Method 4

Compound 45: (±)-trans-1-(4-chloro-2-hydroxy-3-((3-hydroxycyclopentyl)sulfonyl)phenyl)-3-((R)-2-methylcyclopent-2-en-1-yl)urea

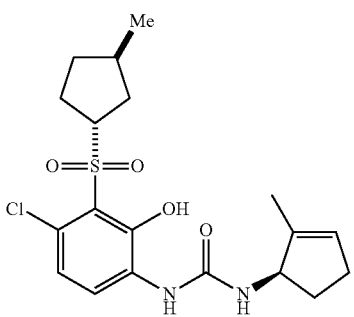

To a solution of (±)-trans-6-amino-3-chloro-2-((3-hydroxycyclopentyl)sulfonyl)phenol (Intermediate 32, 100 mg) in DCM (1 mL) was added (R)-5-isocyanato-1-methylcyclopent-1-ene (Intermediate 2, 80 mg) and pyridine (5 mL) at 0° C. The resulting mixture was stirred at 80° C. for 72 hours. The solvent was removed. The residue was purificated by MDAP (eluting with 0.01% CF$_3$COOH/H$_2$O and CH$_3$OH) to give the title compound (34 mg) as a gray solid. $^1$H-NMR (400 MHz, DMSO-d$_6$) δ ppm 10.81 (s, 1H), 8.35 (d, J=8.9 Hz, 1H), 8.16 (s, 1H), 7.10 (dd, J=18.7, 8.6 Hz, 2H), 5.51 (s, 1H), 4.90 (s, 1H), 4.53 (d, J=6.4 Hz, 1H), 4.22-4.13 (m, 2H), 2.38-1.92 (m, 5H), 1.81-1.72 (m, 3H), 1.67 (s, 3H), 1.64-1.45 (m, 2H); MS(ES$^+$) m/z 415 (MH$^+$).
Method 5

Compound 53: 1-(4-chloro-3-(((1S,7aS)-hexahydro-1H-pyrrolizin-1-yl)sulfonyl)-2-hydroxyphenyl)-3-((R)-2-methylcyclopent-2-en-1-yl)urea

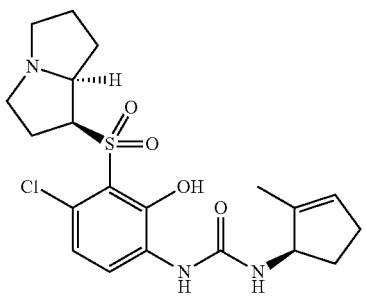 [SMILES: CC1=CCC[C@H]1NC(=O)Nc1ccc(Cl)c(S(=O)(=O)[C@H]2CCN3CCC[C@@H]23)c1O]

To a solution of (R)-5-isocyanato-1-methylcyclopent-1-ene (Intermediate 2, 58 mg) in pyridine (3 mL) was added 6-amino-3-chloro-2-(((1S,7aS)-hexahydro-1H-pyrrolizin-1-yl)sulfonyl)phenol (Intermediate 40, 100 mg) at 0° C. The resulting mixture was stirred at 50° C. for 18 hours. The mixture was concentrated under reduced pressure. The residue was purified by preparative HPLC (mobile phase 0.01% TFA/H$_2$O, CH$_3$CN, 50 mL/min) (10%~40%, 6 min;

40%~60%, 6 min; 60%~95%, 3 min; 95%~95%, 3 min) to afford the crude product (110 mg), which was purified again by preparative HPLC (mobile phase 0.01% NH$_4$HCO$_3$/H$_2$O, CH$_3$CN, 50 mL/min) (10%~40%, 6 min; 40%~60%, 6 min; 60%~95%, 3 min; 95%~95%, 3 min) to give the title compound (3.8 mg) as a white solid. $^1$H-NMR (400 MHz, DMSO-d$_6$) δ ppm 7.59-8.26 (m, 2H), 6.18-6.58 (m, 1H), 5.94 (s, 1H), 5.44 (s, 1H), 4.54 (s, 1H), 3.56-4.00 (m, 4H), 2.10-2.31 (m, 5H), 1.70-2.04 (m, 5H), 1.64 (s, 3H), 1.39-1.59 (m, 2H); MS(ES$^+$) m/z 440 (MH$^+$).

The following compounds (see Table 1) were prepared using similar procedures to that described for the above compounds from the starting materials shown.

TABLE 1

| No. | Structure | Name | Starting material and method | HNMR and LCMS |
|---|---|---|---|---|
| 2 | 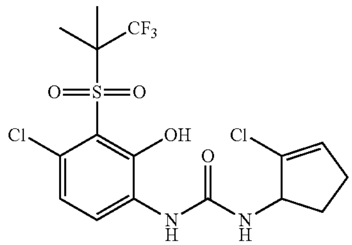 [SMILES: CC(C)(C(F)(F)F)S(=O)(=O)c1c(Cl)ccc(NC(=O)NC2CCC=C2Cl)c1O] | 1-(4-chloro-2-hydroxy-3-((1,1,1-trifluoro-2-methylpropan-2-yl)sulfonyl)phenyl)-3-(2-chlorocyclopent-2-en-1-yl)urea | Int 10 and 12, method 1 | $^1$H-NMR (400 MHz, DMSO-d$_6$) δ ppm 10.26 (br. s., 1H), 8.36 (d, J = 8.8 Hz, 1H), 8.29 (s, 1H), 7.36 (d, J = 8.8 Hz, 1H), 7.19 (d, J = 9.0 Hz, 1H), 5.93-6.03 (m, 1H), 4.67-4.80 (m, 1H), 2.22-2.45 (m, 3H), 1.56-1.73 (m, 7H); MS(ES$^+$) m/z 461 (MH$^+$). |
| 3 | 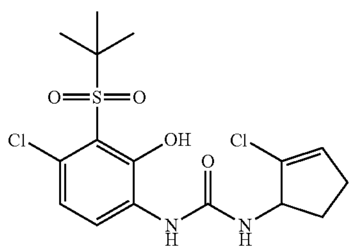 [SMILES: CC(C)(C)S(=O)(=O)c1c(Cl)ccc(NC(=O)NC2CCC=C2Cl)c1O] | 1-(3-(tert-butylsulfonyl)-4-chloro-2-hydroxyphenyl)-3-(2-chlorocyclopent-2-en-1-yl)urea | Int 10 and 13, method 1 | $^1$H-NMR (400 MHz, DMSO-d$_6$) δ ppm 10.43 (br. s., 1H), 8.39 (d, J = 8.8 Hz, 1H), 8.19 (s, 1H), 7.33 (d, J = 8.8 Hz, 1H), 7.13 (d, J = 8.8 Hz, 1H), 5.98 (br. s., 1H), 4.74 (br. s., 1H), 2.22-2.47 (m, 3H), 1.60-1.73 (m, 1H), 1.34 (s, 9H); MS(ES$^+$) m/z 407 (MH$^+$) |
| 4 | 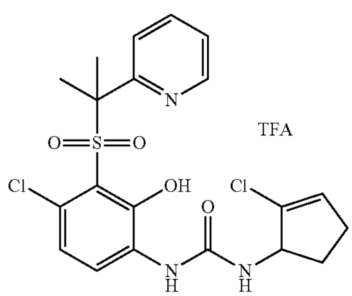 [SMILES: CC(C)(c1ccccn1)S(=O)(=O)c1c(Cl)ccc(NC(=O)NC2CCC=C2Cl)c1O] | 1-(4-chloro-2-hydroxy-3-((2-(pyridin-2-yl)propan-2-yl)sulfonyl)phenyl)-3-(2-chlorocyclopent-2-en-1-yl)urea, trifluoroacetic acid salt | Int 10 and 14, method 1 | $^1$H-NMR (400 MHz, DMSO-d$_6$) δ ppm 9.99 (br. s., 1H), 8.43 (d, J = 3.8 Hz, 1H), 8.31 (d, J = 8.8 Hz, 1H), 7.97 (s, 1H), 7.76-7.83 (m, 1H), 7.65 (d, J = 8.0 Hz, 1H), 7.38 (dd, J = 7.3, 5.0 Hz, 1H), 7.30 (d, J = 8.8 Hz, 1H), 6.97 (d, J = 8.8 Hz, 1H), 5.95-6.04 (m, 1H), 4.67-4.78 (m, 1H), 2.23-2.46 (m, 3H), 1.88 (s, 6H), 1.59-1.73 (m, 1H); MS(ES$^+$) m/z 470 (MH$^+$) |
| 5 | 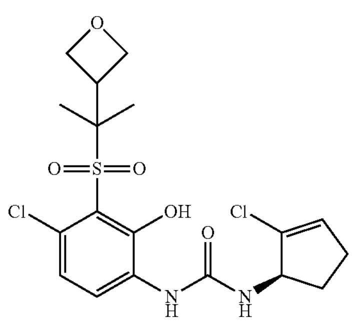 [SMILES: CC(C)(C1COC1)S(=O)(=O)c1c(Cl)ccc(NC(=O)N[C@@H]2CCC=C2Cl)c1O] | (R)-1-(4-chloro-2-hydroxy-3-((2-(oxetan-3-yl)propan-2-yl)sulfonyl)phenyl)-3-(2-chlorocyclopent-2-en-1-yl)urea | Int 1 and 15, method 1 | $^1$H-NMR (400 MHz, DMSO-d$_6$) δ ppm 10.28 (s, 1H), 8.40 (d, J = 8.8 Hz, 1H), 8.23 (s, 1H), 7.39 (d, J = 8.7 Hz, 1H), 7.16 (d, J = 8.9 Hz, 1H), 5.96-6.13 (m, 1H), 4.68-4.80 (m, 1H), 4.54-4.63 (m, 2H), 4.49 (t, J = 6.7 Hz, 2H), 3.42-3.71 (m, 1H), 2.21-2.45 (m, 3H), 1.57-1.72 (m, 1H), 1.40 (s, 6H); MS(ES$^+$) m/z 449 (MH$^+$). |
| 6 | 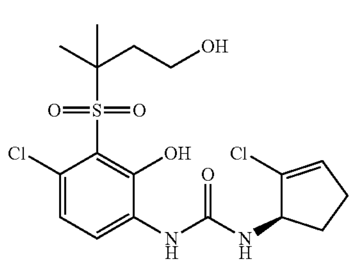 [SMILES: CC(C)(CCO)S(=O)(=O)c1c(Cl)ccc(NC(=O)N[C@@H]2CCC=C2Cl)c1O] | (R)-1-(4-chloro-2-hydroxy-3-((4-hydroxy-2-methylbutan-2-yl)sulfonyl)phenyl)-3-(2-chlorocyclopent-2-en-1-yl)urea | Int 1 and 16, method 1 | $^1$H-NMR (400 MHz, DMSO-d$_6$) δ ppm 8.36 (d, J = 8.8 Hz, 1H), 8.21 (s, 1H), 7.34 (d, J = 8.8 Hz, 1H), 7.08 (d, J = 8.8 Hz, 1H), 5.94-6.02 (m, 1H), 4.65-4.83 (m, 1H), 3.58 (t, J = 6.9 Hz, 2H), 2.35-2.46 (m, 2H), 2.20-2.35 (m, 1H), 1.91 (t, J = 6.8 Hz, 2H), 1.59-1.74 (m, 1H), 1.38 (s, 6H); MS(ES$^+$) m/z 437 (MH$^+$). |

TABLE 1-continued

| No. | Structure | Name | Starting material and method | HNMR and LCMS |
|---|---|---|---|---|
| 7 | 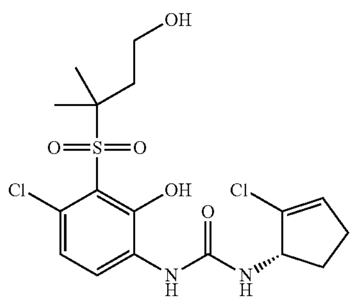 [SMILES: CC(C)(CCO)S(=O)(=O)c1c(Cl)ccc(NC(=O)N[C@H]2CCC=C2Cl)c1O] | (S)-1-(4-chloro-2-hydroxy-3-((4-hydroxy-2-methylbutan-2-yl)sulfonyl)phenyl)-3-(2-chlorocyclopent-2-en-1-yl)urea | Int 5 and 16, method 1 | $^1$H-NMR (400 MHz, DMSO-d$_6$) δ ppm 10.43 (s, 1H), 8.40 (d, J = 9.0 Hz, 1H), 8.21 (s, 1H), 7.36 (d, J = 8.8 Hz, 1H), 7.15 (d, J = 9.0 Hz, 1H), 5.96-6.01 (m, 1H), 4.69-4.79 (m, 1H), 4.61-4.69 (m, 1H), 3.52-3.61 (m, 2H), 2.21-2.45 (m, 3H), 1.89 (t, J = 6.9 Hz, 2H), 1.59-1.70 (m, 1H), 1.37 (s, 6H); MS(ES$^+$) m/z 437 (MH$^+$). |
| 8 | 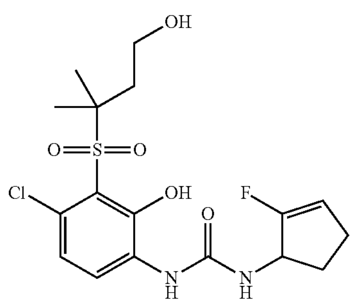 [SMILES: CC(C)(CCO)S(=O)(=O)c1c(Cl)ccc(NC(=O)NC2CCC=C2F)c1O] | 1-(4-chloro-2-hydroxy-3-((4-hydroxy-2-methylbutan-2-yl)sulfonyl)phenyl)-3-(2-fluorocyclopent-2-en-1-yl)urea | Int 8 and 16, method 1 | $^1$H-NMR (400 MHz, DMSO-d$_6$) δ ppm 10.43 (s, 1H), 8.38 (d, J = 8.8 Hz, 1H), 8.15 (s, 1H), 7.36 (d, J = 8.3 Hz, 1H), 7.14 (d, J = 8.8 Hz, 1H), 5.29-5.33 (m, 1H), 4.71-4.80 (m, 1H), 3.57 (t, J = 6.8 Hz, 2H), 2.09-2.45 (m, 4H), 1.89 (t, J = 6.8 Hz, 2H), 1.61 (dd, J = 13.6, 8.3 Hz, 1H), 1.37 (s, 6H); MS(ES$^+$) m/z 421 (MH$^+$). |
| 9 | 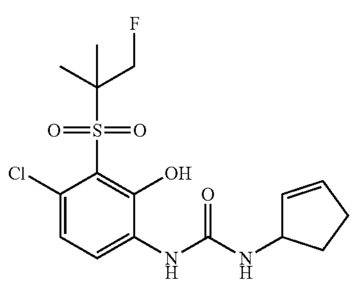 [SMILES: CC(C)(CF)S(=O)(=O)c1c(Cl)ccc(NC(=O)NC2C=CCC2)c1O] | 1-(4-chloro-3-((1-fluoro-2-methylpropan-2-yl)sulfonyl)-2-hydroxyphenyl)-3-(cyclopent-2-en-1-yl)urea | Int 4 and 17, method 1 | $^1$H-NMR (400 MHz, DMSO-d$_6$) δ ppm 10.31 (br. s., 1H), 8.28-8.43 (m, 1H), 8.01-8.18 (m, 1H), 7.01-7.21 (m, 2H), 5.84-6.03 (m, 1H), 5.61-5.83 (m, 1H), 4.54-4.83 (m, 3H), 2.12-2.45 (m, 3H), 1.29-1.54 (m, 7H); MS(ES$^+$) m/z 391 (MH$^+$). |
| 10 | 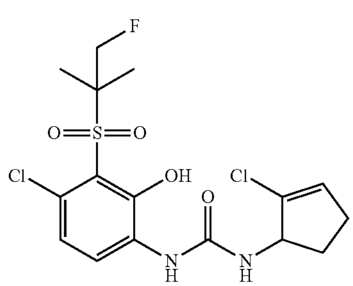 | 1-(4-chloro-3-((1-fluoro-2-methylpropan-2-yl)sulfonyl)-2-hydroxyphenyl)-3-(2-chlorocyclopent-2-en-1-yl)urea | Int 10 and 17, method 1 | $^1$H-NMR (400 MHz, DMSO-d$_6$) δ ppm 10.31 (br. s., 1H), 8.37 (d, J = 8.8 Hz, 1H), 8.20 (s, 1H), 7.34 (d, J = 8.8 Hz, 1H), 7.13 (d, J = 9.0 Hz, 1H), 5.95-6.01 (m, 1H), 4.69-4.80 (m, 2H), 4.62 (s, 1H), 2.23-2.46 (m, 3H), 1.60-1.73 (m, 1H), 1.40 (s, 6H); MS(ES$^+$) m/z 425 (MH$^+$). |
| 11 | 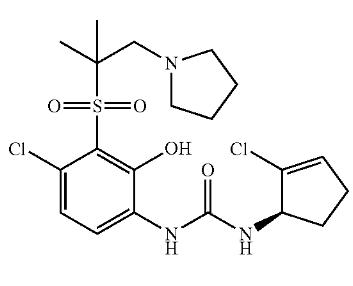 [SMILES: CC(C)(CN1CCCC1)S(=O)(=O)c1c(Cl)ccc(NC(=O)N[C@@H]2CCC=C2Cl)c1O] | (R)-1-(4-chloro-2-hydroxy-3-((2-methyl-1-(pyrrolidin-1-yl)propan-2-yl)sulfonyl)phenyl)-3-(2-chlorocyclopent-2-en-1-yl)urea | Int 1 and 18, method 1 | $^1$H-NMR (400 MHz, DMSO-d$_6$) δ ppm 8.12 (s, 1H), 8.00 (d, J = 8.5 Hz, 1H), 7.37 (d, J = 9.0 Hz, 1H), 6.42-6.56 (m, 1H), 5.93-6.00 (m, 1H), 4.62-4.81 (m, 1H), 3.25-3.10 (m, 4H), 2.18-2.45 (m, 4H), 1.91-2.02 (m, 4H), 1.54-1.71 (m, 1H), 1.42 (s, 3H), 1.41 (s, 3H); MS(ES$^+$) m/z 476 (MH$^+$). |

TABLE 1-continued

| No. | Structure | Name | Starting material and method | HNMR and LCMS |
|---|---|---|---|---|
| 12 | 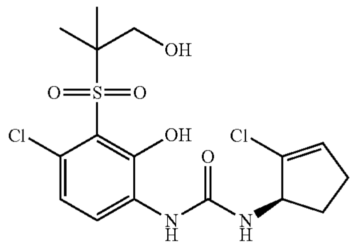 [SMILES: CC(C)(CO)S(=O)(=O)c1c(Cl)ccc(NC(=O)N[C@@H]2CCC=C2Cl)c1O] | (R)-1-(4-chloro-2-hydroxy-3-((1-hydroxy-2-methylpropan-2-yl)sulfonyl)phenyl)-3-(2-chlorocyclopent-2-en-1-yl)urea | Int 1 and 19, method 1 | $^1$H-NMR (400 MHz, DMSO-$d_6$) δ ppm 10.39 (br. s., 1H), 8.36 (d, J = 8.8 Hz, 1H), 8.20 (s, 1H), 7.35 (d, J = 8.5 Hz, 1H), 7.11 (d, J = 9.0 Hz, 1H), 5.95-6.01 (m, 1H), 4.69-4.76 (m, 1H), 3.63 (s, 2H), 2.22-2.46 (m, 3H), 1.59-1.70 (m, 1H), 1.33 (s, 6H); MS(ES$^+$) m/z 423 (MH$^+$). |
| 13 | 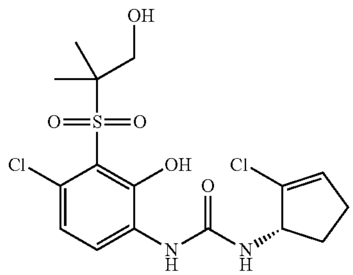 [SMILES: CC(C)(CO)S(=O)(=O)c1c(Cl)ccc(NC(=O)N[C@H]2CCC=C2Cl)c1O] | (S)-1-(4-chloro-2-hydroxy-3-((1-hydroxy-2-methylpropan-2-yl)sulfonyl)phenyl)-3-(2-chlorocyclopent-2-en-1-yl)urea | Int 5 and 19, method 1 | $^1$H-NMR (400 MHz, DMSO-$d_6$) δ ppm 10.39 (br. s., 1H), 8.36 (d, J = 8.8 Hz, 1H), 8.19 (s, 1H), 7.34 (d, J = 8.8 Hz, 1H), 7.10 (d, J = 8.8 Hz, 1H), 5.94-6.04 (m, 1H), 4.68-4.80 (m, 1H), 3.63 (m, 2H), 2.22-2.46 (m, 3H), 1.58-1.70 (m, 1H), 1.32 (s, 6H); MS(ES$^+$) m/z 423 (MH$^+$). |
| 14 | 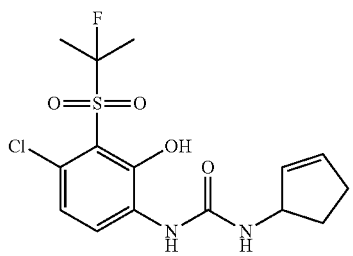 [SMILES: CC(C)(F)S(=O)(=O)c1c(Cl)ccc(NC(=O)NC2C=CCC2)c1O] | 1-(4-chloro-3-((2-fluoropropan-2-yl)sulfonyl)-2-hydroxyphenyl)-3-(cyclopent-2-en-1-yl)urea | Int 4 and 20, method 1 | $^1$H-NMR (400 MHz, DMSO-$d_6$) δ ppm 10.17 (s, 1H), 8.39 (d, J = 8.8 Hz, 1H), 8.16 (s, 1H), 7.08-7.22 (m, 2H), 5.93 (dd, J = 5.5, 2.0 Hz, 1H), 5.71 (dd, J = 5.4, 2.1 Hz, 1H), 4.64-4.73 (m, 1H), 2.32-2.46 (m, 1H), 2.15-2.32 (m, 2H), 1.75-1.83 (m, 3H), 1.68-1.75 (m, 3H), 1.41-1.55 (m, 1H); MS(ES$^+$) m/z 377 (MH$^+$). |
| 15 | 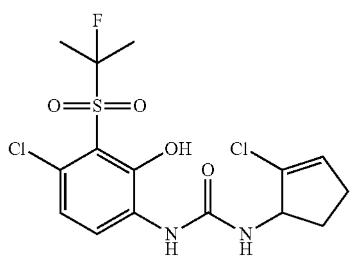 [SMILES: CC(C)(F)S(=O)(=O)c1c(Cl)ccc(NC(=O)NC2CCC=C2Cl)c1O] | 1-(4-chloro-3-((2-fluoropropan-2-yl)sulfonyl)-2-hydroxyphenyl)-3-(2-chlorocyclopent-2-en-1-yl)urea | Int 10 and 20, method 1 | $^1$H-NMR (400 MHz, DMSO-$d_6$) δ ppm 10.16 (br. s., 1H), 8.40 (d, J = 8.8 Hz, 1H), 8.22 (s, 1H), 7.36 (d, J = 8.8 Hz, 1H), 7.17 (d, J = 9.0 Hz, 1H), 5.95-6.02 (m, 1H), 4.69-4.79 (m, 1H), 2.23-2.46 (m, 3H), 1.78 (s, 3H), 1.73 (s, 3H), 1.60-1.71 (m, 1H); MS(ES$^+$) m/z 411 (MH$^+$). |
| 16 | 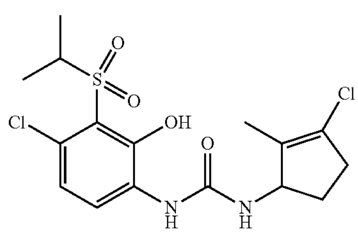 [SMILES: CC1=C(Cl)CCC1NC(=O)Nc1ccc(Cl)c(S(=O)(=O)C(C)C)c1O] | 1-(4-chloro-2-hydroxy-3-(isopropylsulfonyl)phenyl)-3-(3-chloro-2-methylcyclopent-2-en-1-yl)urea | Int 6 and 21, method 1 | $^1$H-NMR (400 MHz, DMSO-$d_6$) δ ppm 10.74 (s, 1H), 8.37 (d, J = 8.9 Hz, 1H), 8.15 (s, 1H), 7.23 (d, J = 8.4 Hz, 1H), 7.14 (d, J = 8.9 Hz, 1H), 4.64 (d, J = 6.3 Hz, 1H), 3.77-3.99 (m, 1H), 3.35 (s, 1H), 2.42-2.63 (m, 1H), 2.29-2.40 (m, 1H), 1.59-1.72 (m, 4H), 1.26 (d, J = 8.5 Hz, 6H); MS(ES$^+$) m/z 407 (MH$^+$). |
| 18 | 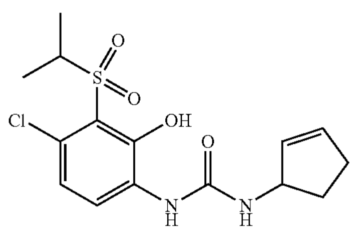 [SMILES: CC(C)S(=O)(=O)c1c(Cl)ccc(NC(=O)NC2C=CCC2)c1O] | 1-(4-chloro-2-hydroxy-3-(isopropylsulfonyl)phenyl)-3-(cyclopent-2-en-1-yl)urea | Int 4 and 21, method 2 | $^1$H-NMR (400 MHz, DMSO-$d_6$) δ ppm 10.73 (s, 1H), 8.35 (d, J = 8.9 Hz, 1H), 8.14 (s, 1H), 7.09-7.17 (m, 2H), 5.89-5.96 (m, 1H), 5.68-5.74 (m, 1H), 4.65-4.73 (m, 1H), 3.80-3.92 (m, 1H), 2.44-2.31 (m, 1H), 2.15-2.29 (m, 2H), 1.54-1.41 (m, 1H), 1.26 (d, J = 6.8 Hz, 6H); MS(ES$^+$) m/z 359 (MH$^+$). |

TABLE 1-continued

| No. | Structure | Name | Starting material and method | HNMR and LCMS |
|---|---|---|---|---|
| 19 | 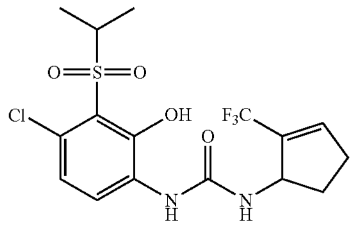 [SMILES: CC(C)S(=O)(=O)c1c(Cl)ccc(NC(=O)NC2CCC=C2C(F)(F)F)c1O] | 1-(4-chloro-2-hydroxy-3-(isopropylsulfonyl)phenyl)-3-(2-(trifluoromethyl)cyclopent-2-en-1-yl)urea | Int 11 and 21, method 1 | $^1$H-NMR (500 MHz, CDCl$_3$) δ ppm 10.93 (s, 1H), 8.38 (d, J = 8.8 Hz, 1H), 7.03 (d, J = 8.8 Hz, 1H), 6.91 (s, 1H), 6.58 (br. s., 1H), 5.15-5.21 (m, 1H), 4.82-4.88 (m, 1H), 3.85-3.93 (m, 1H), 2.44-2.66 (m, 3H), 1.85-1.94 (m, 1H), 1.39 (d, J = 6.9 Hz, 3H), 1.37 (d, J = 6.9 Hz, 3H); MS(ES$^+$) m/z 427 (MH$^+$). |
| 20 | 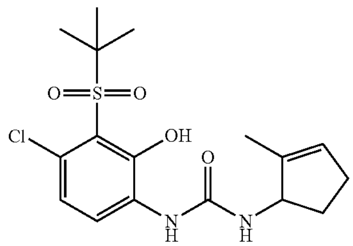 | 1-(4-chloro-2-hydroxy-3-(isopropylsulfonyl)phenyl)-3-(2-methylcyclopent-2-en-1-yl)urea | Int 3 and 21, method 3 | $^1$H-NMR (400 MHz, DMSO-d$_6$) δ ppm 10.74 (s, 1H), 8.37 (d, J = 8.8 Hz, 1H), 8.17 (s, 1H), 7.13 (d, J = 8.8 Hz, 1H), 7.07 (d, J = 8.5 Hz, 1H), 5.51 (s, 1H), 4.48-4.58 (m, 1H), 3.81-3.93 (m, 1H), 2.10-2.37 (m, 3H), 1.66 (s, 3H), 1.45-1.57 (m, 1H), 1.26 (d, J = 6.8 Hz, 6H); MS(ES$^+$) m/z 373 (MH$^+$). |
| 21 | 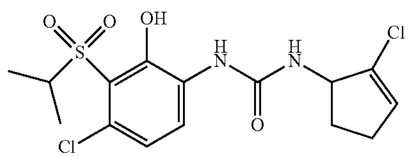 [SMILES: CC(C)S(=O)(=O)c1c(Cl)ccc(NC(=O)NC2CCC=C2Cl)c1O] | 1-(4-chloro-2-hydroxy-3-(isopropylsulfonyl)phenyl)-3-(2-chlorocyclopent-2-en-1-yl)urea | Int 10 and 21, method 2 | $^1$H-NMR (400 MHz, DMSO-d$_6$) δ ppm 10.72 (s, 1H), 8.36 (d, J = 8.8 Hz, 1H), 8.21 (s, 1H), 7.36 (d, J = 8.8 Hz, 1H), 7.15 (d, J = 8.8 Hz, 1H), 5.99 (s, 1H), 4.70-4.78 (m, 1H), 3.82-3.92 (m, 1H), 2.22-2.45 (m, 3H), 1.60-1.70 (m, 1H), 1.27 (d, J = 6.8 Hz, 6H); MS(ES$^+$) m/z 393 (MH$^+$). |
| 22 | 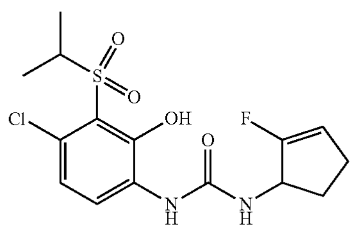 [SMILES: CC(C)S(=O)(=O)c1c(Cl)ccc(NC(=O)NC2CCC=C2F)c1O] | 1-(4-chloro-2-hydroxy-3-(isopropylsulfonyl)phenyl)-3-(2-fluorocyclopent-2-en-1-yl)urea | Int 8 and 21, method 2 | $^1$H-NMR (400 MHz, DMSO-d$_6$) δ ppm 10.72 (s, 1H), 8.32 (d, J = 8.8 Hz, 1H), 8.18 (s, 1H), 7.39 (d, J = 8.4 Hz, 1H), 7.11 (d, J = 8.8 Hz, 1H), 5.32 (s, 1H), 4.80-4.71 (m, 1H), 3.93-3.84 (m, 1H), 2.41-2.13 (m, 3H), 1.66-1.56 (m, 1H), 1.26 (d, J = 6.8 Hz, 6H); MS(ES$^+$) m/z 377 (MH$^+$). |
| 23 | 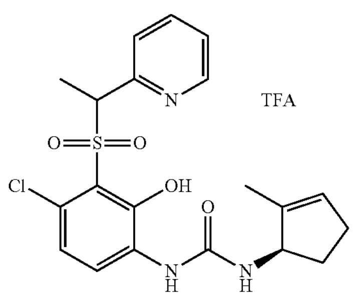 [SMILES: CC1=CCC[C@H]1NC(=O)Nc1ccc(Cl)c(S(=O)(=O)C(C)c2ccccn2)c1O ; "TFA"] | 1-(4-chloro-2-hydroxy-3-((1-(pyridin-2-yl)ethyl)sulfonyl)phenyl)-3-((R)-2-methylcyclopent-2-en-1-yl)urea, trifluoroacetic acid salt | Int 2 and 22, method 1 | $^1$H-NMR (400 MHz, DMSO-d$_6$) δ ppm 10.35 (br. s., 1H), 8.49 (d, J = 4.3 Hz, 1H), 8.29 (dd, J = 9.0, 3.5 Hz, 1H), 7.98 (s, 1H), 7.78 (t, J = 7.7 Hz, 1H), 7.41 (d, J = 7.8 Hz, 1H), 7.36 (dd, J = 7.3, 5.0 Hz, 1H), 7.09 (d, J = 8.8 Hz, 1H), 6.99 (d, J = 8.3 Hz, 1H), 5.50 (s, 1H), 5.20 (q, J = 7.0 Hz, 1H), 4.45-4.56 (m, 1H), 2.10-2.35 (m, 3H), 1.75 (d, J = 7.0 Hz, 3H), 1.65 (d, J = 7.0 Hz, 3H), 1.44-1.54 (m, 1H); MS(ES$^+$) m/z 436 (MH$^+$). |
| 24 | 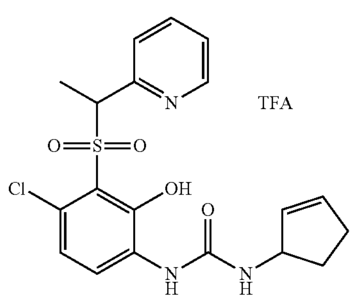 [SMILES: CC(c1ccccn1)S(=O)(=O)c1c(Cl)ccc(NC(=O)NC2C=CCC2)c1O ; "TFA"] | 1-(4-chloro-2-hydroxy-3-((1-(pyridin-2-yl)ethyl)sulfonyl)phenyl)-3-(cyclopent-2-en-1-yl)urea, trifluoroacetic acid salt | Int 4 and 22, method 1 | $^1$H-NMR (400 MHz, DMSO-d$_6$) δ ppm 10.34 (br. s., 1H), 8.48 (d, J = 4.5 Hz, 1H), 8.28 (d, J = 8.8 Hz, 1H), 7.95 (s, 1H), 7.74-7.81 (m, 1H), 7.41 (d, J = 7.5 Hz, 1H), 7.35 (dd, J = 7.2, 5.1 Hz, 1H), 7.08 (d, J = 8.8 Hz, 1H), 7.05 (d, J = 7.8 Hz, 1H), 5.89-5.94 (m, 1H), 5.66-5.73 (m, 1H), 5.19 (q, J = 7.0 Hz, 1H), 4.61-4.76 (m, 1H), 2.31-2.44 (m, 1H), 2.14-2.31 (m, 2H), 1.75 (d, J = 7.0 Hz, 3H), 1.40-1.51 (m, 1H); MS(ES$^+$) m/z 422 (MH$^+$). |

TABLE 1-continued

| No. | Structure | Name | Starting material and method | HNMR and LCMS |
|---|---|---|---|---|
| 25 | 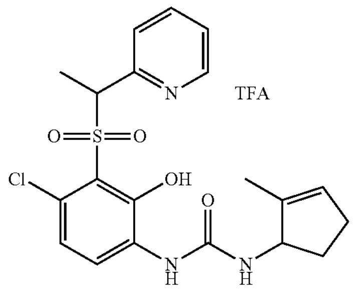 [SMILES: CC1=CCCC1NC(=O)Nc1ccc(Cl)c(S(=O)(=O)C(C)c2ccccn2)c1O ; "TFA"] | 1-(4-chloro-2-hydroxy-3-((1-(pyridin-2-yl)ethyl)sulfonyl)phenyl)-3-(2-methylcyclopent-2-en-1-yl)urea, trifluoroacetic acid salt | Int 3 and 22, method 1 | $^1$H-NMR (400 MHz, DMSO-$d_6$) δ ppm 8.49 (d, J = 4.3 Hz, 1H), 8.28 (dd, J = 8.9, 3.4 Hz, 1H), 7.97 (s, 1H), 7.78 (t, J = 7.7 Hz, 1H), 7.41 (d, J = 7.5 Hz, 1H), 7.35 (dd, J = 7.3, 4.8 Hz, 1H), 7.08 (d, J = 8.8 Hz, 1H), 6.97 (d, J = 8.0 Hz, 1H), 5.50 (br. s., 1H), 5.19 (q, J = 6.9 Hz, 1H), 4.51 (d, J = 4.5 Hz, 1H), 2.07-2.37 (m, 3H), 1.75 (d, J = 7.0 Hz, 3H), 1.65 (d, J = 6.5 Hz, 3H), 1.40-1.56 (m, 1H); MS(ES$^+$) m/z 436 (MH$^+$). |
| 26 | 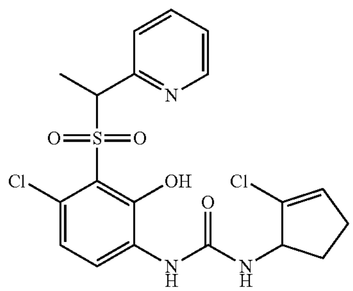 [SMILES: CC(c1ccccn1)S(=O)(=O)c1c(Cl)ccc(NC(=O)NC2CCC=C2Cl)c1O] | 1-(4-chloro-2-hydroxy-3-((1-(pyridin-2-yl)ethyl)sulfonyl)phenyl)-3-(2-chlorocyclopent-2-en-1-yl)urea | Int 10 and 22, method 1 | $^1$H-NMR (400 MHz, DMSO-$d_6$) δ ppm 8.49 (d, J = 4.5 Hz, 1H), 8.29 (d, J = 9.0 Hz, 1H), 8.03 (s, 1H), 7.78 (td, J = 7.7, 1.4 Hz, 1H), 7.41 (d, J = 7.8 Hz, 1H), 7.36 (dd, J = 7.4, 4.9 Hz, 1H), 7.28 (dd, J = 8.8, 2.8 Hz, 1H), 7.10 (d, J = 9.0 Hz, 1H), 5.95-6.01 (m, 1H), 5.20 (q, J = 7.0 Hz, 1H), 4.66-4.77 (m, 1H), 2.22-2.43 (m, 3H), 1.75 (d, J = 7.3 Hz, 3H), 1.57-1.68 (m, 1H); MS(ES$^+$) m/z 456 (MH$^+$). |
| 27 | 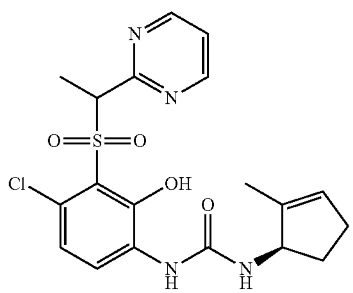 [SMILES: CC1=CCC[C@H]1NC(=O)Nc1ccc(Cl)c(S(=O)(=O)C(C)c2ncccn2)c1O] | 1-(4-chloro-2-hydroxy-3-((1-(pyrimidin-2-yl)ethyl)sulfonyl)phenyl)-3-((R)-2-methylcyclopent-2-en-1-yl)urea | Int 2 and 23, method 1 | $^1$H-NMR (400 MHz, DMSO-$d_6$) δ ppm 8.75 (d, J = 4.8 Hz, 2H), 8.12-8.30 (m, 1H), 8.02 (br. s., 1H), 7.45 (t, J = 4.6 Hz, 1H), 6.96 (d, J = 8.3 Hz, 1H), 6.92 (d, J = 8.0 Hz, 1H), 5.49 (br. s., 1H), 5.28-5.40 (m, 1H), 4.46-4.58 (m, 1H), 2.09-2.35 (m, 3H), 1.78 (d, J = 7.0 Hz, 3H), 1.66 (d, J = 6.3 Hz, 3H), 1.42-1.56 (m, 1H); MS(ES$^+$) m/z 437 (MH$^+$). |
| 28 | 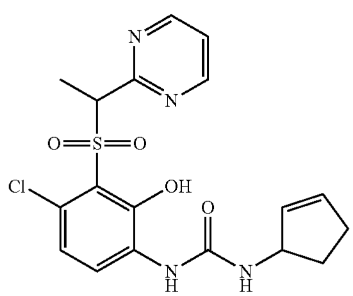 [SMILES: CC(c1ncccn1)S(=O)(=O)c1c(Cl)ccc(NC(=O)NC2C=CCC2)c1O] | 1-(4-chloro-2-hydroxy-3-((1-(pyrimidin-2-yl)ethyl)sulfonyl)phenyl)-3-(cyclopent-2-en-1-yl)urea | Int 4 and 23, method 1 | $^1$H-NMR (400 MHz, DMSO-$d_6$) δ ppm 10.28 (br. s., 1H), 8.75 (d, J = 4.8 Hz, 2H), 8.28 (d, J = 8.8 Hz, 1H), 7.95 (s, 1H), 7.47 (t, J = 4.9 Hz, 1H), 7.07 (d, J = 8.8 Hz, 1H), 7.03 (d, J = 7.8 Hz, 1H), 5.89-5.95 (m, 1H), 5.67-5.74 (m, 1H), 5.26 (q, J = 7.0 Hz, 1H), 4.62-4.71 (m, 1H), 2.31-2.44 (m, 1H), 2.15-2.31 (m, 2H), 1.81 (d, J = 7.0 Hz, 3H), 1.41-1.54 (m, 1H); MS(ES$^+$) m/z 423 (MH$^+$). |
| 29 | 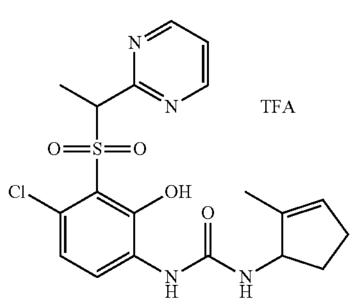 [SMILES: CC1=CCCC1NC(=O)Nc1ccc(Cl)c(S(=O)(=O)C(C)c2ncccn2)c1O ; "TFA"] | 1-(4-chloro-2-hydroxy-3-((1-(pyrimidin-2-yl)ethyl)sulfonyl)phenyl)-3-(2-methylcyclopent-2-en-1-yl)urea, trifluoroacetic acid salt | Int 3 and 23, method 1 | $^1$H-NMR (400 MHz, DMSO-$d_6$) δ ppm 10.30 (br. s., 1H), 8.76 (d, J = 4.8 Hz, 2H), 8.29 (dd, J = 8.9, 4.1 Hz, 1H), 7.98 (s, 1H), 7.47 (t, J = 4.9 Hz, 1H), 7.08 (d, J = 8.8 Hz, 1H), 6.97 (d, J = 8.3 Hz, 1H), 5.50 (br. s., 1H), 5.27 (q, J = 7.0 Hz, 1H), 4.47-4.59 (m, 1H), 2.06-2.36 (m, 3H), 1.81 (d, J = 7.0 Hz, 3H), 1.66 (d, J = 8.0 Hz, 3H), 1.44-1.56 (m, 1H); MS(ES$^+$) m/z 437 (MH$^+$). |

TABLE 1-continued

| No. | Structure | Name | Starting material and method | HNMR and LCMS |
|---|---|---|---|---|
| 30 | 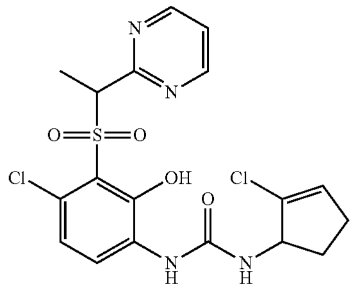 [SMILES: CC(c1ncccn1)S(=O)(=O)c1c(Cl)ccc(NC(=O)NC2CCC=C2Cl)c1O] | 1-(4-chloro-2-hydroxy-3-((1-(pyrimidin-2-yl)ethyl)sulfonyl)phenyl)-3-(2-chlorocyclopent-2-en-1-yl)urea | Int 10 and 23, method 1 | $^1$H-NMR (400 MHz, DMSO-$d_6$) δ ppm 10.27 (br. s., 1H), 8.75 (d, J = 4.8 Hz, 2H), 8.29 (d, J = 8.8 Hz, 1H), 8.03 (s, 1H), 7.47 (t, J = 4.4 Hz, 1H), 7.27 (d, J = 8.0 Hz, 1H), 7.09 (d, J = 8.8 Hz, 1H), 5.97 (br. s., 1H), 5.27 (q, J = 6.7 Hz, 1H), 4.65-4.78 (m, 1H), 2.21-2.44 (m, 3H), 1.82 (d, J = 7.0 Hz, 3H), 1.56-1.70 (m, 1H); MS(ES$^+$) m/z 457 (MH$^+$). |
| 31 | 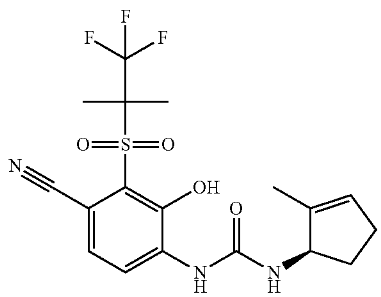 [SMILES: CC1=CCC[C@H]1NC(=O)Nc1ccc(C#N)c(S(=O)(=O)C(C)(C)C(F)(F)F)c1O] | (R)-1-(4-cyano-2-hydroxy-3-((1,1,1-trifluoro-2-methylpropan-2-yl)sulfonyl)phenyl)-3-(2-methylcyclopent-2-en-1-yl)urea | Int 2 and 24, method 1 | $^1$H-NMR (400 MHz, DMSO-$d_6$) δ ppm 8.66 (s, 1H), 8.46 (d, J = 8.6 Hz, 1H), 7.60 (d, J = 8.6 Hz, 1H), 7.30 (d, J = 8.3 Hz, 1H), 5.53 (s, 1H), 4.50-4.61 (m, 1H), 2.12-2.37 (m, 3H), 1.67 (s, 3H), 1.63 (s, 6H), 1.49-1.61 (m, 1H); MS(ES$^+$) m/z 432 (MH$^+$). |
| 32 | 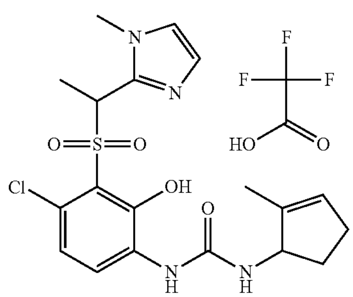 | 1-(4-chloro-2-hydroxy-3-((1-(1-methyl-1H-imidazol-2-yl)ethyl)sulfonyl)phenyl)-3-(2-methylcyclopent-2-en-1-yl)urea, trifluoroacetic acid salt | Int 3 and 25, method 1 | $^1$H-NMR (400 MHz, DMSO-$d_6$) δ ppm 8.44 (br. s., 1H), 8.07 (d, J = 8.3 Hz, 1H), 7.70-7.98 (m, 1H), 7.61 (br. s., 1H), 7.45 (s, 1H), 7.05-7.18 (m, 2H), 5.56-5.65 (m, 1H), 5.50-5.56 (m, 1H), 4.49-4.59 (m, 1H), 3.77-3.85 (m, 3H), 2.11-2.39 (m, 3H), 1.63-1.73 (m, 6H), 1.48-1.63 (m, 1H); MS(ES$^+$) m/z 439 (MH$^+$). |
| 33 | 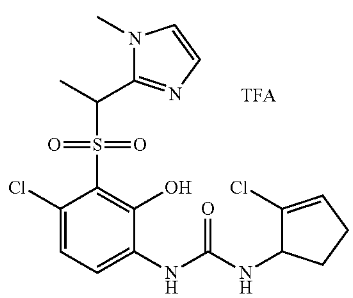 [SMILES: CC(c1nccn1C)S(=O)(=O)c1c(Cl)ccc(NC(=O)NC2CCC=C2Cl)c1O] | 1-(4-chloro-2-hydroxy-3-((1-(1-methyl-1H-imidazol-2-yl)ethyl)sulfonyl)phenyl)-3-(2-chlorocyclopent-2-en-1-yl)urea, trifluoroacetic acid salt | Int 10 and 25, method 1 | $^1$H-NMR (400 MHz, DMSO-$d_6$) δ ppm 8.47 (br. s., 1H), 8.12 (d, J = 8.5 Hz, 1H), 7.66 (br. s., 1H), 7.57 (br. s., 1H), 7.38-7.49 (m, 1H), 7.09 (dd, J = 8.8, 1.8 Hz, 1H), 6.00 (s, 1H), 5.64 (q, J = 6.8 Hz, 1H), 4.69-4.80 (m, 1H), 3.82 (s, 3H), 2.22-2.45 (m, 3H), 1.61-1.76 (m, 4H); MS(ES$^+$) m/z 459 (MH$^+$). |
| 34 | 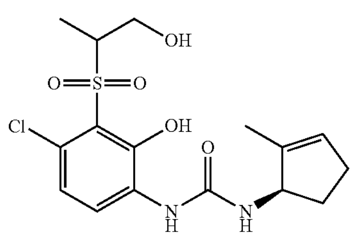 [SMILES: CC1=CCC[C@H]1NC(=O)Nc1ccc(Cl)c(S(=O)(=O)C(C)CO)c1O] | 1-(4-chloro-2-hydroxy-3-((1-hydroxypropan-2-yl)sulfonyl)phenyl)-3-((R)-2-methylcyclopent-2-en-1-yl)urea | Int 2 and 26, method 1 | $^1$H-NMR (400 MHz, DMSO-$d_6$) δ ppm 8.30 (d, J = 8.8 Hz, 1H), 8.12 (s, 1H), 6.94-7.16 (m, 2H), 5.51 (s, 1H), 4.53 (d, J = 6.0 Hz, 1H), 3.81-3.91 (m, 1H), 3.70-3.81 (m, 1H), 3.56-3.70 (m, 1H), 2.22-2.36 (m, 2H), 2.09-2.22 (m, 1H), 1.67 (s, 3H), 1.44-1.57 (m, 1H), 1.29 (d, J = 7.0 Hz, 3H); MS(ES$^+$) m/z 389 (MH$^+$). |

TABLE 1-continued

| No. | Structure | Name | Starting material and method | HNMR and LCMS |
|---|---|---|---|---|
| 35 | 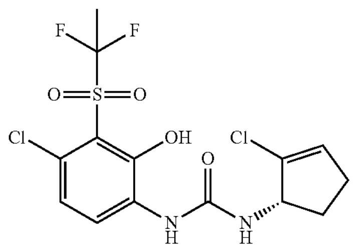 [SMILES: CC(F)(F)S(=O)(=O)c1c(Cl)ccc(NC(=O)N[C@H]2CCC=C2Cl)c1O] | (S)-1-(4-chloro-3-((1,1-difluoroethyl)sulfonyl)-2-hydroxyphenyl)-3-(2-chlorocyclopent-2-en-1-yl)urea | Int 5 and 27, method 1 | $^1$H-NMR (400 MHz, DMSO-d$_6$) δ ppm 10.40 (br. s., 1H), 8.34 (s, 1H), 8.31 (d, J = 8.8 Hz, 1H), 7.40 (d, J = 8.8 Hz, 1H), 7.21 (d, J = 8.8 Hz, 1H), 5.99 (s, 1H), 4.69-4.79 (m, 1H), 2.22-2.45 (m, 3H), 2.10 (t, J = 19.2 Hz, 3H), 1.61-1.72 (m, 1H); MS(ES$^+$) m/z 415 (MH$^+$). |
| 36 | 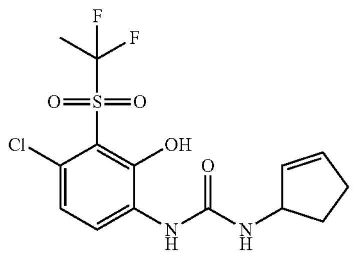 [SMILES: CC(F)(F)S(=O)(=O)c1c(Cl)ccc(NC(=O)NC2C=CCC2)c1O] | 1-(4-chloro-3-((1,1-difluoroethyl)sulfonyl)-2-hydroxyphenyl)-3-(cyclopent-2-en-1-yl)urea | Int 4 and 27, method 1 | $^1$H-NMR (400 MHz, DMSO-d$_6$) δ ppm 10.51 (br. s., 1H), 8.27 (s, 1H), 8.25 (d, J = 8.8 Hz, 1H), 7.17 (d, J = 8.8 Hz, 1H), 7.14 (d, J = 8.0 Hz, 1H), 5.94 (dd, J = 5.3, 2.0 Hz, 1H), 5.71 (dd, J = 5.4, 2.1 Hz, 1H), 4.65-4.73 (m, 1H), 2.31-2.45 (m, 1H), 2.17-2.31 (m, 2H), 2.09 (t, J = 19.2 Hz, 3H), 1.44-1.55 (m, 1H); MS(ES$^+$) m/z 381 (MH$^+$). |
| 37 | 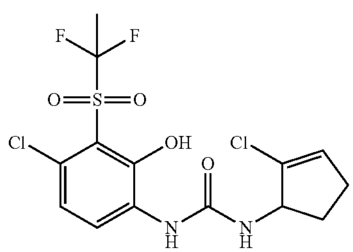 | 1-(4-chloro-3-((1,1-difluoroethyl)sulfonyl)-2-hydroxyphenyl)-3-(2-chlorocyclopent-2-en-1-yl)urea | Int 10 and 27, method 1 | $^1$H-NMR (400 MHz, DMSO-d$_6$) δ ppm 10.41 (br. s., 1H), 8.34 (s, 1H), 8.31 (d, J = 8.8 Hz, 1H), 7.39 (d, J = 8.8 Hz, 1H), 7.20 (d, J = 8.8 Hz, 1H), 5.96-6.03 (m, 1H), 4.69-4.79 (m, 1H), 2.24-2.45 (m, 3H), 2.10 (t, J = 19.3 Hz, 3H), 1.60-1.72 (m, 1H); MS(ES$^+$) m/z 415 (MH$^+$). |
| 38 | 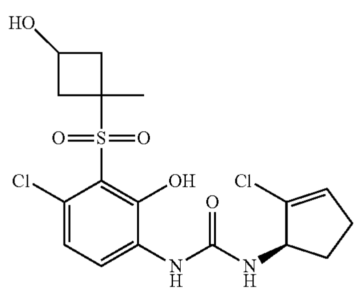 [SMILES: CC1(S(=O)(=O)c2c(Cl)ccc(NC(=O)N[C@@H]3CCC=C3Cl)c2O)CC(O)C1] | (R)-1-(4-chloro-2-hydroxy-3-((3-hydroxy-1-methylcyclobutyl)sulfonyl)phenyl)-3-(2-chlorocyclopent-2-en-1-yl)urea | Int 1 and 28, method 1 | $^1$H-NMR (400 MHz, DMSO-d$_6$) δ ppm 8.17-8.34 (m, 2H), 7.36 (d, J = 8.8 Hz, 1H), 6.98 (br. s., 1H), 5.94-6.02 (m, 1H), 5.48 (br. s., 1H), 4.68-4.79 (m, 1H), 4.13-4.24 (m, 1H), 3.08-3.25 (m, 1H), 2.53-2.63 (m, 2H), 2.18-2.49 (m, 5H), 1.56-1.77 (m, 1H), 1.50 (s, 1H), 1.25-1.43 (m, 2H); MS(ES$^+$) m/z 435 (MH$^+$). |
| 39 | 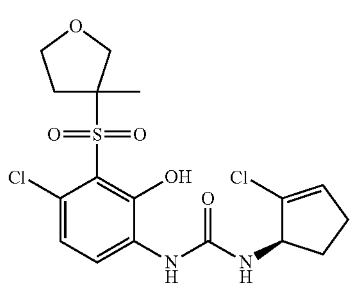 [SMILES: CC1(S(=O)(=O)c2c(Cl)ccc(NC(=O)N[C@@H]3CCC=C3Cl)c2O)CCOC1] | 1-(4-chloro-2-hydroxy-3-((3-methyltetrahydrofuran-3-yl)sulfonyl)phenyl)-3-((R)-2-chlorocyclopent-2-en-1-yl)urea | Int 1 and 29, method 1 | $^1$H-NMR (400 MHz, DMSO-d$_6$) δ ppm 10.49 (s, 1H), 8.37 (d, J = 8.8 Hz, 1H), 8.23 (s, 1H), 7.35 (d, J = 8.6 Hz, 1H), 7.16 (d, J = 8.8 Hz, 1H), 5.98 (d, J = 1.7 Hz, 1H), 4.70-4.79 (m, 1H), 4.34 (d, J = 10.0 Hz, 1H), 3.77-3.90 (m, 2H), 3.61 (d, J = 10.3 Hz, 1H), 2.68 (dt, J = 13.4, 7.8 Hz, 1H), 2.23-2.45 (m, 3H), 1.91-2.01 (m, 1H), 1.61-1.72 (m, 1H), 1.49 (s, 3H); MS(ES$^+$) m/z 435 (MH$^+$). |

TABLE 1-continued

| No. | Structure | Name | Starting material and method | HNMR and LCMS |
|---|---|---|---|---|
| 40 | 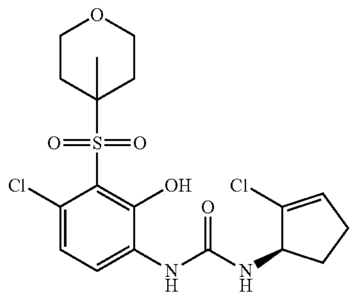 | (R)-1-(4-chloro-2-hydroxy-3-((4-methyltetrahydro-2H-pyran-4-yl)sulfonyl)phenyl)-3-(2-chlorocyclopent-2-en-1-yl)urea | Int 1 and 30, method 1 | $^1$H-NMR (400 MHz, DMSO-d$_6$) δ ppm 10.36 (br. s., 1H), 8.39 (d, J = 8.8 Hz, 1H), 8.20 (s, 1H), 7.35 (d, J = 8.8 Hz, 1H), 7.13 (d, J = 9.0 Hz, 1H), 5.96-6.02 (m, 1H), 4.69-4.80 (m, 1H), 3.84 (dd, J = 11.7, 4.4 Hz, 2H), 3.49 (t, J = 11.2 Hz, 2H), 2.22-2.46 (m, 3H), 2.04 (td, J = 12.5, 5.1 Hz, 2H), 1.61-1.74 (m, 1H), 1.58-1.61 (m, 1H), 1.54-1.58 (m, 1H), 1.50 (s, 3H); MS(ES$^+$) m/z 449 (MH$^+$). |
| 41 | 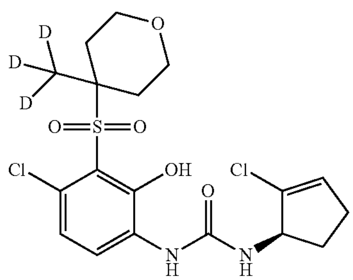 [SMILES: [2H]C([2H])([2H])C1(S(=O)(=O)c2c(Cl)ccc(NC(=O)N[C@@H]3CCC=C3Cl)c2O)CCOCC1] | (R)-1-(4-chloro-2-hydroxy-3-((4-d$_3$-methyl)tetrahydro-2H-pyran-4-yl)sulfonyl)phenyl)-3-(2-chlorocyclopent-2-en-1-yl)urea | Int 1 and 31, method 1 | $^1$H-NMR (400 MHz, DMSO-d$_6$) δ ppm 10.39 (s, 1H), 8.41 (d, J = 9.0 Hz, 1H), 8.20 (s, 1H), 7.35 (d, J = 8.8 Hz, 1H), 7.15 (d, J = 8.8 Hz, 1H), 5.96-6.01 (m, 1H), 4.69-4.79 (m, 1H), 3.84 (dd, J = 11.7, 4.4 Hz, 2H), 3.49-3.54 (m, 2H), 2.23-2.45 (m, 3H), 2.03 (td, J = 12.5, 5.0 Hz, 2H), 1.61-1.71 (m, 1H), 1.59 (s, 1H), 1.56 (s, 1H); MS(ES$^+$) m/z 452 (MH$^+$). |
| 42 | 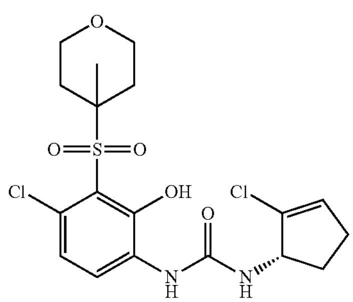 | (S)-1-(4-chloro-2-hydroxy-3-((4-methyltetrahydro-2H-pyran-4-yl)sulfonyl)phenyl)-3-(2-chlorocyclopent-2-en-1-yl)urea | Int 5 and 30, method 1 | $^1$H-NMR (400 MHz, DMSO-d$_6$) δ ppm 10.38 (s, 1H), 8.41 (d, J = 8.8 Hz, 1H), 8.21 (s, 1H), 7.36 (d, J = 8.8 Hz, 1H), 7.16 (d, J = 9.0 Hz, 1H), 5.99 (br. s., 1H), 4.67-4.83 (m, 1H), 3.84 (d, J = 7.5 Hz, 2H), 3.47-3.55 (m, 2H), 2.22-2.45 (m, 3H), 2.03 (dd, J = 11.8, 7.8 Hz, 2H), 1.54-1.72 (m, 3H), 1.50 (s, 3H); MS(ES$^+$) m/z 449 (MH$^+$). |
| 43 | 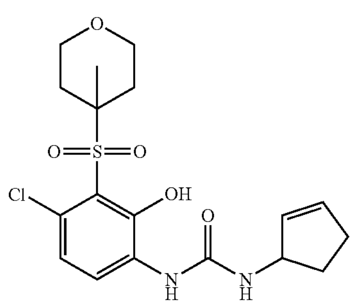 | 1-(4-chloro-2-hydroxy-3-((4-methyltetrahydro-2H-pyran-4-yl)sulfonyl)phenyl)-3-(cyclopent-2-en-1-yl)urea | Int 4 and 30, method 1 | $^1$H-NMR (400 MHz, DMSO-d$_6$) δ ppm 10.38 (s, 1H), 8.39 (d, J = 8.8 Hz, 1H), 8.11 (s, 1H), 7.14 (d, J = 8.8 Hz, 1H), 7.08-7.13 (m, 1H), 5.93 (dd, J = 5.5, 2.0 Hz, 1H), 5.71 (dd, J = 5.5, 2.0 Hz, 1H), 4.69 (dd, J = 5.0, 2.3 Hz, 1H), 3.84 (dd, J = 11.7, 4.1 Hz, 2H), 3.49 (t, J = 11.3 Hz, 2H), 2.31-2.45 (m, 1H), 2.14-2.31 (m, 2H), 2.03 (td, J = 12.5, 4.9 Hz, 2H), 1.40-1.63 (m, 6H); MS(ES$^+$) m/z 415 (MH$^+$). |
| 44 | 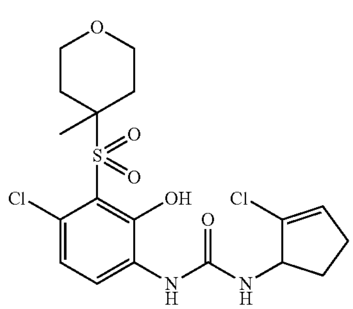 [SMILES: CC1(S(=O)(=O)c2c(Cl)ccc(NC(=O)NC3CCC=C3Cl)c2O)CCOCC1] | 1-(4-chloro-2-hydroxy-3-((4-methyltetrahydro-2H-pyran-4-yl)sulfonyl)phenyl)-3-(2-chlorocyclopent-2-en-1-yl)urea | Int 10 and 30, method 1 | $^1$H-NMR (400 MHz, DMSO-d$_6$) δ ppm 10.39 (s, 1H), 8.41 (d, J = 8.8 Hz, 1H), 8.20 (s, 1H), 7.35 (d, J = 8.8 Hz, 1H), 7.15 (d, J = 8.8 Hz, 1H), 5.98 (s, 1H), 4.68-4.82 (m, 1H), 3.84 (dd, J = 11.8, 4.3 Hz, 2H), 3.49 (t, J = 11.5 Hz, 2H), 2.34-2.46 (m, 2H), 2.24-2.34 (m, 1H), 2.04 (td, J = 12.4, 4.8 Hz, 2H), 1.54-1.73 (m, 3H), 1.50 (s, 3H); MS(ES$^+$) m/z 449 (MH$^+$). |

TABLE 1-continued

| No. | Structure | Name | Starting material and method | HNMR and LCMS |
|---|---|---|---|---|
| 46 | 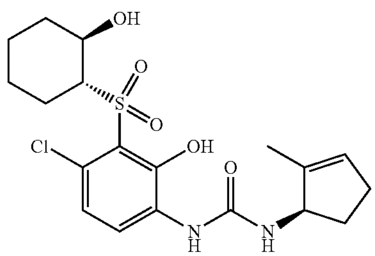 [SMILES: CC1=CCC[C@H]1NC(=O)Nc1ccc(Cl)c(S(=O)(=O)[C@@H]2CCCC[C@H]2O)c1O] | 1-(4-chloro-2-hydroxy-3-((trans-2-hydroxycyclohexyl)sulfonyl)phenyl)-3-((R)-2-methylcyclopent-2-en-1-yl)urea | Int 2 and 33, method 2 | $^1$H-NMR (400 MHz, DMSO-$d_6$) δ ppm 8.13 (s, 1H), 8.05 (s, 1H), 7.00 (d, J = 8.3 Hz, 1H), 6.60 (s, 1H), 5.48 (s, 1H), 4.48-4.58 (m, 1H), 3.67-3.77 (m, 1H), 3.25-3.40 (m, 2H), 2.06-2.35 (m, 4H), 1.82-1.91 (m, 1H), 1.70-1.78 (m, 1H), 1.56-1.67 (m, 4H), 1.43-1.54 (m, 1H), 1.28-1.39 (m, 1H), 1.11-1.27 (m, 3H); MS(ES$^+$) m/z 429 (MH$^+$). |
| 47 | 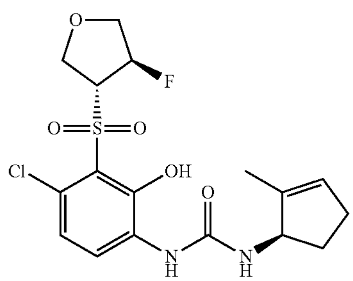 [SMILES: CC1=CCC[C@H]1NC(=O)Nc1ccc(Cl)c(S(=O)(=O)[C@@H]2COC[C@H]2F)c1O] | 1-(4-chloro-3-(((3R,4R)-4-fluorotetrahydrofuran-3-yl)sulfonyl)-2-hydroxyphenyl)-3-((R)-2-methylcyclopent-2-en-1-yl)urea | Int 2 and 34, method 1 | $^1$H-NMR (400 MHz, DMSO-$d_6$) δ ppm 11.0 (br. s., 1H), 8.32 (s, 1H), 8.15 (d, J = 8.8 Hz, 1H), 7.17 (d, J = 8.8 Hz, 1H), 7.08 (d, J = 8.3 Hz, 1H), 5.52-5.70 (m, 2H), 4.64-4.81 (m, 1H), 4.55 (d, J = 6.3 Hz, 1H), 4.36 (t, J = 9.2 Hz, 1H), 3.85-4.14 (m, 3H), 2.13-2.37 (m, 3H), 1.68 (s, 3H), 1.49-1.61 (m, 1H); MS(ES$^+$) m/z 419 (MH$^+$). |
| 48 | 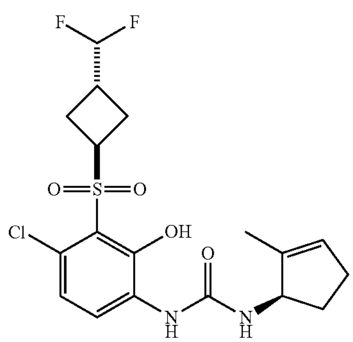 | 1-(4-chloro-3-((trans-3-(difluoromethyl)cyclobutyl)sulfonyl)-2-hydroxyphenyl)-3-((R)-2-methylcyclopent-2-en-1-yl)urea | Int 2 and 35, method 2 | $^1$H-NMR (400 MHz, DMSO-$d_6$) δ ppm 10.81 (s, 1H), 8.28 (d, J = 8.9 Hz, 1H), 8.21 (s, 1H), 7.12 (d, J = 8.9 Hz, 1H), 7.09 (d, J = 8.4 Hz, 1H), 6.21 (td, J = 56.7, 4.6 Hz, 1H), 5.52 (s, 1H), 4.59-4.47 (m, 2H), 2.95-2.78 (m, 1H), 2.59-2.51 (m, 2H), 2.40-2.32 (m, 2H), 2.30-2.13 (m, 3H), 1.66 (s, 3H), 1.56-1.46 (m, 1H); MS(ES$^+$) m/z 435 (MH$^+$). |
| 49 | 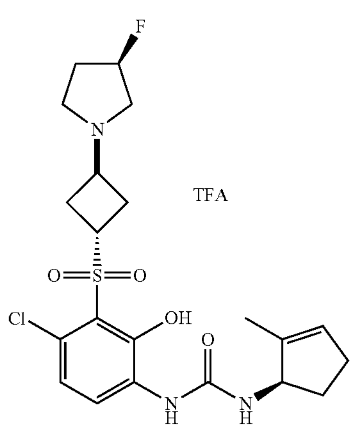 [SMILES: CC1=CCC[C@H]1NC(=O)Nc1ccc(Cl)c(S(=O)(=O)[C@H]2C[C@H](N3CC[C@@H](F)C3)C2)c1O] | trans-1-(4-chloro-3-((3-((R)-3-fluoropyrrolidin-1-yl)cyclobutyl)sulfonyl)-2-hydroxyphenyl)-3-((R)-2-methylcyclopent-2-en-1-yl)urea, trifluoroacetic acid salt | Int 2 and 36, method 2 | $^1$H-NMR (400 MHz, MeOD-$d_4$) δ ppm 8.30 (dd, J = 8.9, 2.8 Hz, 1H), 7.11 (dd, J = 8.8, 2.7 Hz, 1H), 5.56 (s, 1H), 5.41 (s, 1H), 4.66 (m, 1H), 4.47-4.18 (m, 1H), 3.94 (m, 1H), 3.68-3.44 (m, 3H), 2.99-2.90 (m, 1H), 2.89-2.69 (m, 3H), 2.49-2.34 (m, 4H), 2.27 (m, 1H), 1.75 (s, 3H), 1.72-1.60 (m, 2H); MS(ES$^+$) m/z 472 (MH$^+$). |

TABLE 1-continued

| No. | Structure | Name | Starting material and method | HNMR and LCMS |
|---|---|---|---|---|
| 50 | 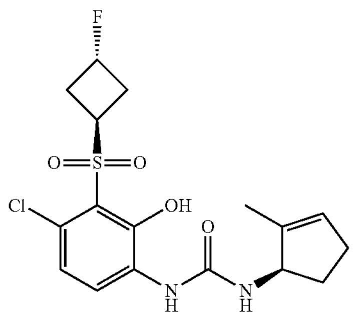 [SMILES: CC1=CCC[C@H]1NC(=O)Nc1ccc(Cl)c(S(=O)(=O)[C@H]2C[C@H](F)C2)c1O] | 1-(4-chloro-3-((trans-3-fluorocyclobutyl)sulfonyl)-2-hydroxyphenyl)-3-((R)-2-methylcyclopent-2-en-1-yl)urea | Int 2 and 37, method 1 | $^1$H-NMR (400 MHz, DMSO-$d_6$) δ ppm 10.77 (br. s., 1H), 8.26 (d, J = 8.8 Hz, 1H), 8.19 (s, 1H), 7.11 (d, J = 8.8 Hz, 1H), 7.07 (d, J = 8.3 Hz, 1H), 5.51 (br. s., 1H), 5.17-5.44 (m, 1H), 4.49-4.62 (m, 2H), 2.61-2.81 (m, 4H), 2.10-2.37 (m, 3H), 1.67 (s, 3H), 1.47-1.59 (m, 1H); MS(ES$^+$) m/z 403 (MH$^+$). |
| 51 | TFA | (±)trans-1-(4-chloro-2-hydroxy-3-((2-hydroxycyclopentyl)sulfonyl)phenyl)-3-((R)-2-methylcyclopent-2-en-1-yl)urea, trifluoroacetic acid salt | Int 2 and 38, method 2 | $^1$H-NMR (400 MHz, DMSO-$d_6$) δ ppm 10.75 (s, 1H), 8.34 (d, J = 8.8 Hz, 1H), 8.15 (s, 1H), 7.11 (d, J = 8.9 Hz, 1H), 7.07 (d, J = 8.4 Hz, 1H), 5.51 (s, 1H), 5.29 (d, J = 3.9 Hz, 1H), 4.58-4.49 (m, 1H), 4.37 (s, 1H), 4.03-3.96 (m, 1H), 2.35-2.12 (m, 3H), 2.11-2.00 (m, 1H), 1.91-1.80 (m, 2H), 1.79-1.68 (m, 2H), 1.67 (s, 3H), 1.64-1.57 (m, 1H), 1.56-1.46 (m, 1H); MS(ES$^+$) m/z 415 (MH$^+$). |
| 52 | 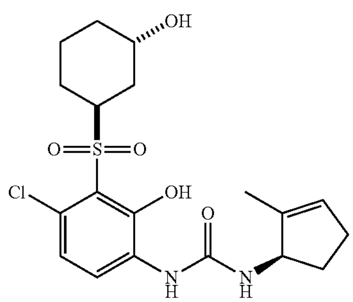 | 1-(4-chloro-2-hydroxy-3-((trans-3-hydroxycyclohexyl)sulfonyl)phenyl)-3-((R)-2-methylcyclopent-2-en-1-yl)urea | Int 2 and 39, method 2 | $^1$H-NMR (400 MHz, DMSO-$d_6$) δ ppm 10.70 (s, 1H), 8.36 (d, J = 9.0 Hz, 1H), 8.17 (s, 1H), 7.13 (d, J = 8.8 Hz, 1H), 7.07 (d, J = 8.3 Hz, 1H), 5.51 (br. s., 1H), 4.48-4.59 (m, 1H), 3.61-3.73 (m, 1H), 3.41-3.52 (m, 1H), 2.09-2.37 (m, 3H), 1.96 (d, J = 11.5 Hz, 1H), 1.81 (d, J = 10.0 Hz, 3H), 1.66 (s, 3H), 1.46-1.58 (m, 1H), 1.24-1.46 (m, 3H), 0.98-1.16 (m, 1H); MS(ES$^+$) m/z 429 (MH$^+$). |
| 54 | 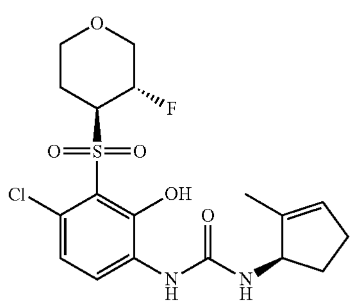 [SMILES: CC1=CCC[C@H]1NC(=O)Nc1ccc(Cl)c(S(=O)(=O)[C@H]2CCOC[C@@H]2F)c1O] | 1-(4-chloro-3-(((3S,4S)-3-fluorotetrahydro-2H-pyran-4-yl)sulfonyl)-2-hydroxyphenyl)-3-((R)-2-methylcyclopent-2-en-1-yl)urea | Int 2 and 41, method 1 | $^1$H-NMR (400 MHz, DMSO-$d_6$) δ ppm 10.66 (br. s., 1H), 8.35 (d, J = 8.8 Hz, 1H), 8.17 (s, 1H), 7.14 (d, J = 8.8 Hz, 1H), 7.05 (d, J = 8.3 Hz, 1H), 5.51 (br. s., 1H), 4.97 (d, J = 48.4 Hz, 1H), 4.49-4.59 (m, 1H), 4.07-4.25 (m, 1H), 3.92-4.05 (m, 2H), 3.44-3.66 (m, 2H), 2.10-2.35 (m, 5H), 1.72-1.83 (m, 1H), 1.66 (s, 3H), 1.47-1.58 (m, 1H); MS(ES$^+$) m/z 433 (MH$^+$). |
| 55 | 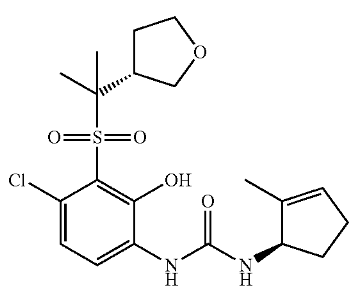 [SMILES: CC1=CCC[C@H]1NC(=O)Nc1ccc(Cl)c(S(=O)(=O)C(C)(C)[C@@H]2CCOC2)c1O] | 1-(4-chloro-2-hydroxy-3-((2-((R)-tetrahydrofuran-3-yl)propan-2-yl)sulfonyl)phenyl)-3-((R)-2-methylcyclopent-2-en-1-yl)urea | Int 2 and 42, method 1 | $^1$H-NMR (400 MHz, DMSO-$d_6$) δ ppm 10.39 (s, 1H), 8.41 (d, J = 8.8 Hz, 1H), 8.16 (s, 1H), 7.14 (d, J = 9.0 Hz, 1H), 7.07 (d, J = 8.3 Hz, 1H), 5.49-5.52 (m, 1H), 4.47-4.57 (m, 1H), 3.79 (t, J = 8.6 Hz, 1H), 3.73 (td, J = 8.3, 3.5 Hz, 1H), 3.54-3.64 (m, 2H), 2.78 (t, J = 8.6 Hz, 1H), 2.12-2.33 (m, 3H), 1.93-2.03 (m, 1H), 1.77 (dd, J = 12.5, 9.0 Hz, 1H), 1.66 (s, 3H), 1.39-1.57 (m, 1H), 1.29 (s, 3H), 1.33 (s, 3H); MS(ES$^+$) m/z 443 (MH$^+$). |

TABLE 1-continued

| No. | Structure | Name | Starting material and method | HNMR and LCMS |
|---|---|---|---|---|
| 56 | 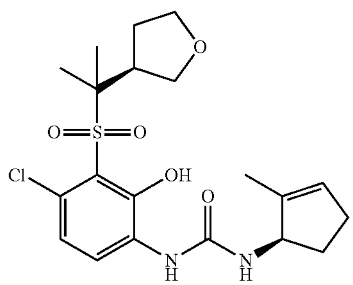 [SMILES: CC1=CCC[C@H]1NC(=O)Nc1ccc(Cl)c(S(=O)(=O)C(C)(C)[C@H]2CCOC2)c1O] | 1-(4-chloro-2-hydroxy-3-((2-((S)-tetrahydrofuran-3-yl)propan-2-yl)sulfonyl)phenyl)-3-((R)-2-methylcyclopent-2-en-1-yl)urea | Int 2 and 43, method 1 | $^1$H-NMR (400 MHz, DMSO-$d_6$) δ ppm 10.39 (s, 1H), 8.42 (d, J = 8.8 Hz, 1H), 8.17 (s, 1H), 7.15 (d, J = 8.8 Hz, 1H), 7.08 (d, J = 8.3 Hz, 1H), 5.51 (s, 1H), 4.49-4.57 (m, 1H), 3.65-3.95 (m, 2H), 3.53-3.65 (m, 2H), 2.79 (t, J = 8.7 Hz, 1H), 2.10-2.34 (m, 3H), 1.93-2.03 (m, 1H), 1.78 (dd, J = 12.6, 8.9 Hz, 1H), 1.66 (s, 3H), 1.44-1.55 (m, 1H), 1.33 (s, 3H), 1.29 (s, 3H); MS(ES$^+$) m/z 443 (MH$^+$). |
| 57 | 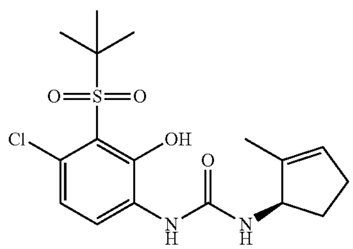 [SMILES: CC1=CCC[C@H]1NC(=O)Nc1ccc(Cl)c(S(=O)(=O)C(C)(C)C)c1O] | (R)-1-(3-(tert-butylsulfonyl)-4-chloro-2-(2-hydroxyphenyl)-3-(2-methylcyclopent-2-en-1-yl)urea | Int 2 and 44, method 1 | $^1$H-NMR (400 MHz, DMSO-$d_6$) δ ppm 10.42 (s, 1H), 8.42 (d, J = 9.0 Hz, 1H), 8.15 (s, 1H), 7.13 (d, J = 8.8 Hz, 1H), 7.07 (d, J = 8.3 Hz, 1H), 5.51 (s, 1H), 4.48-4.57 (m, 1H), 2.08-2.35 (m, 3H), 1.66 (s, 3H), 1.45-1.55 (m, 1H), 1.36 (s, 9H); MS(ES$^+$) m/z 387 (MH$^+$). |
| 58 | 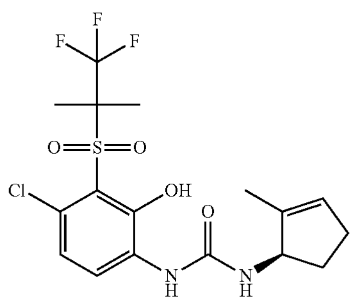 [SMILES: CC1=CCC[C@H]1NC(=O)Nc1ccc(Cl)c(S(=O)(=O)C(C)(C)C(F)(F)F)c1O] | (R)-1-(4-chloro-2-hydroxy-3-((1,1,1-trifluoro-2-methylpropan-2-yl)sulfonyl)phenyl)-3-(2-methylcyclopent-2-en-1-yl)urea | Int 2 and 12, method 1 | 1H-NMR (400 MHz, DMSO-$d_6$) δ ppm 10.32 (br. s., 1H), 8.35 (d, J = 9.0 Hz, 1H), 8.26 (s, 1H), 7.18 (d, J = 8.8 Hz, 1H), 7.09 (d, J = 8.6 Hz, 1H), 5.50-5.53 (m, 1H), 4.49-4.57 (m, 1H), 2.10-2.35 (m, 3H), 1.66 (s, 3H), 1.63 (s, 6H), 1.45-1.59 (m, 1H); MS(ES$^+$) m/z 441 (MH$^+$). |
| 59 | 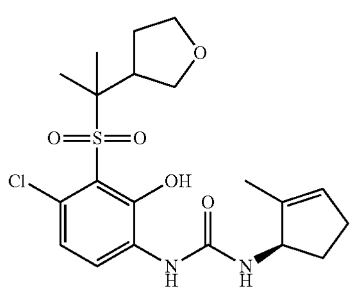 [SMILES: CC1=CCC[C@H]1NC(=O)Nc1ccc(Cl)c(S(=O)(=O)C(C)(C)C2CCOC2)c1O] | 1-(4-chloro-2-hydroxy-3-((2-(tetrahydrofuran-3-yl)propan-2-yl)sulfonyl)phenyl)-3-((R)-2-methylcyclopent-2-en-1-yl)urea | Int 2 and 45, method 1 | $^1$H-NMR (400 MHz, DMSO-$d_6$) δ ppm 10.40 (s, 1H), 8.41 (d, J = 8.8 Hz, 1H), 8.14 (s, 1H), 7.14 (d, J = 8.8 Hz, 1H), 7.05 (d, J = 8.5 Hz, 1H), 5.51 (s, 1H), 4.49-4.58 (m, 1H), 3.77-3.85 (m, 1H), 3.74 (td, J = 8.3, 3.8 Hz, 1H), 3.53-3.66 (m, 2H), 2.79 (quin, J = 8.5 Hz, 1H), 2.11-2.37 (m, 3H), 1.93-2.04 (m, 1H), 1.79 (dq, J = 12.4, 8.7 Hz, 1H), 1.67 (s, 3H), 1.44-1.59 (m, 1H), 1.34 (s, 3H), 1.30 (s, 3H); MS(ES$^+$) m/z 443 (MH$^+$). |
| 60 | 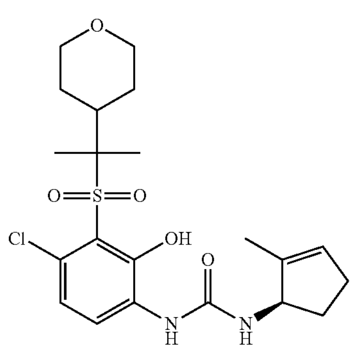 [SMILES: CC1=CCC[C@H]1NC(=O)Nc1ccc(Cl)c(S(=O)(=O)C(C)(C)C2CCOCC2)c1O] | (R)-1-(4-chloro-2-hydroxy-3-((2-(tetrahydro-2H-pyran-4-yl)propan-2-yl)sulfonyl)phenyl)-3-(2-methylcyclopent-2-en-1-yl)urea | Int 2 and 46, method 1 | $^1$H-NMR (400 MHz, DMSO-$d_6$) δ ppm 10.45 (s, 1H), 8.40 (d, J = 8.8 Hz, 1H), 8.13 (s, 1H), 7.13 (d, J = 9.0 Hz, 1H), 7.05 (d, J = 8.3 Hz, 1H), 5.51 (br. s., 1H), 4.49-4.58 (m, 1H), 3.90 (dd, J = 11.2, 3.1 Hz, 2H), 3.32 (t, J = 11.4 Hz, 2H), 2.10-2.36 (m, 4H), 1.76 (d, J = 12.5 Hz, 2H), 1.67 (s, 3H), 1.40-1.57 (m, 3H), 1.29 (s, 6H); MS(ES$^+$) m/z 457 (MH$^+$). |

TABLE 1-continued

| No. | Structure | Name | Starting material and method | HNMR and LCMS |
|---|---|---|---|---|
| 61 | (structure) | (R)-1-(4-chloro-2-hydroxy-3-((2-(oxetan-3-yl)propan-2-yl)sulfonyl)phenyl)-3-(2-methylcyclopent-2-en-1-yl)urea | Int 2 and 47, method 1 | $^1$H-NMR (400 MHz, DMSO-d$_6$) δ ppm 10.29 (br. s., 1H), 8.41 (d, J = 8.5 Hz, 1H), 8.17 (br. s., 1H), 7.15 (d, J = 8.8 Hz, 1H), 7.08 (d, J = 8.0 Hz, 1H), 5.51 (br. s., 1H), 4.59 (1, J = 7.0 Hz, 3H), 4.35-4.54 (m, 3H), 2.08-2.38 (m, 3H), 1.67 (br. s., 3H), 1.47-1.58 (m, 1H), 1.40 (br. s., 6H); MS(ES$^+$) m/z 429 (MH$^+$). |
| 62 | (structure) | (R)-1-(4-chloro-3-((1-fluoro-2-methylpropan-2-yl)sulfonyl)-2-hydroxyphenyl)-3-(2-methylcyclopent-2-en-1-yl)urea | Int 2 and 48, method 1 | $^1$H-NMR (400 MHz, DMSO-d$_6$) δ ppm 10.31 (s, 1H), 8.38 (d, J = 8.8 Hz, 1H), 8.16 (s, 1H), 7.12 (d, J = 8.8 Hz, 1H), 7.07 (d, J = 8.3 Hz, 1H), 5.51 (br. s., 1H), 4.73 (s, 1H), 4.62 (s, 1H), 4.45-4.57 (m, 1H), 2.10-2.37 (m, 3H), 1.66 (s, 3H), 1.45-1.57 (m, 1H), 1.35-1.42 (m, 6H); MS(ES$^+$) m/z 405 (MH$^+$). |
| 63 | (structure) | (R)-1-(4-chloro-3-((difluoro(pyridin-2-yl)methyl)sulfonyl)-2-hydroxyphenyl)-3-(2-methylcyclopent-2-en-1-yl)urea, trifluoroacetic acid salt | Int 2 and 49, method 1 | $^1$H-NMR (400 MHz, DMSO-d$_6$) δ ppm 10.44 (br. s., 1H), 8.70 (d, J = 4.5 Hz, 1H), 8.19-8.32 (m, 2H), 8.08 (1, J = 7.4 Hz, 1H), 7.85 (d, J = 7.8 Hz, 1H), 7.70 (dd, J = 7.8, 4.8 Hz, 1H), 7.13 (d, J = 8.8 Hz, 1H), 7.06 (d, J = 8.5 Hz, 1H), 5.52 (br. s., 1H), 4.48-4.67 (m, 1H), 2.09-2.38 (m, 3H), 1.68 (s, 3H), 1.43-1.61 (m, 1H); MS(ES$^+$) m/z 458 (MH$^+$). |
| 64 | (structure) | 1-(4-chloro-3-((fluoro(pyridin-2-yl)methyl)sulfonyl)-2-hydroxyphenyl)-3-((R)-2-methylcyclopent-2-en-1-yl)urea trifluoroacetic acid salt | Int 2 and 50, method 1 | $^1$H-NMR (400 MHz, DMSO-d$_6$) δ ppm 8.65 (d, J = 4.5 Hz, 1H), 8.28 (s, 1H), 8.18 (d, J = 8.8 Hz, 1H), 7.99 (t, J = 7.7 Hz, 1H), 7.69 (d, J = 8.0 Hz, 1H), 7.57 (dd, J = 7.3, 5.0 Hz, 1H), 7.14 (d, J = 8.8 Hz, 1H), 6.95-7.10 (m, 2H), 5.53 (br. s., 1H), 4.50-4.60 (m, 1H), 2.09-2.38 (m, 3H), 1.68 (s, 3H), 1.47-1.62 (m, 1H); MS(ES$^+$) m/z 440 (MH$^+$). |
| 65 | (structure) | (R)-1-(4-chloro-2-hydroxy-3-((6-methyl-2-oxaspiro[3.3]heptan-6-yl)sulfonyl)phenyl)-3-(2-methylcyclopent-2-en-1-yl)urea | Int 2 and 51, method 1 | $^1$H-NMR (400 MHz, DMSO-d$_6$) δ ppm 10.72 (s, 1H), 8.32 (d, J = 9.0 Hz, 1H), 8.15 (s, 1H), 7.11 (d, J = 9.0 Hz, 1H), 7.04 (d, J = 8.3 Hz, 1H), 5.51 (br. s., 1H), 4.66 (s, 2H), 4.54 (s, 3H), 3.01 (d, J = 14.1 Hz, 2H), 2.35 (d, J = 14.1 Hz, 2H), 2.09-2.32 (m, 3H), 1.67 (s, 3H), 1.45-1.58 (m, 1H), 1.32 (s, 3H); MS(ES$^+$) m/z 441 (MH$^+$). |

TABLE 1-continued

| No. | Structure | Name | Starting material and method | HNMR and LCMS |
|---|---|---|---|---|
| 66 | 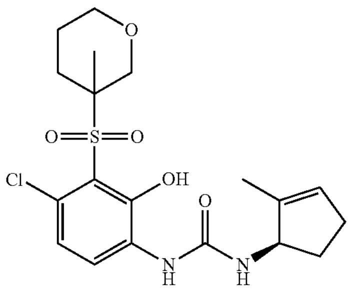 | 1-(4-chloro-2-hydroxy-3-((3-methyltetrahydro-2H-pyran-3-yl)sulfonyl)phenyl)-3-((R)-2-methylcyclopent-2-en-1-yl)urea | Int 2 and 52, method 1 | $^1$H-NMR (500 MHz, DMSO-d$_6$) δ ppm 10.32 (br, 1H), 8.41 (d, J = 8.9 Hz, 1H), 8.18 (s, 1H), 7.12 (m, 2H), 5.51 (s, 1H), 4.39-4.70 (m, 1H), 3.72 (d, J = 7.3 Hz, 3H), 2.08-2.35 (m, 5H), 1.78-1.89 (m, 1H), 1.66 (s, 5H), 1.45-1.58 (m, 1H), 1.41 (s, 3H); MS(ES$^+$) m/z 429 (MH$^+$). |
| 67 | 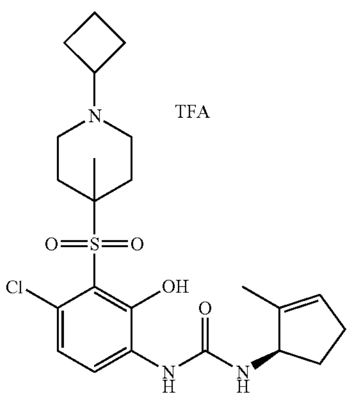 | (R)-1-(4-chloro-3-((1-cyclobutyl-4-methylpiperidin-4-yl)sulfonyl)-2-hydroxyphenyl)-3-(2-methylcyclopent-2-en-1-yl)urea, trifluoroacetic acid salt | Int 2 and 53, method 1 | $^1$H-NMR (400 MHz, DMSO-d$_6$) δ ppm 10.35 (br. s., 1H), 9.31 (br. s., 1H), 8.39 (d, J = 8.8 Hz, 1H), 8.21 (s, 1H), 7.19 (d, J = 8.8 Hz, 1H), 7.09 (d, J = 8.5 Hz, 1H), 5.52 (br. s., 1H), 4.48-4.60 (m, 1H), 3.61-3.76 (m, 1H), 2.82-3.09 (m, 2H), 2.07-2.37 (m, 9H), 1.90-2.07 (m, 2H), 1.62-1.81 (m, 5H), 1.46-1.62 (m, 4H); MS(ES$^+$) m/z 482 (MH$^+$). |
| 68 | 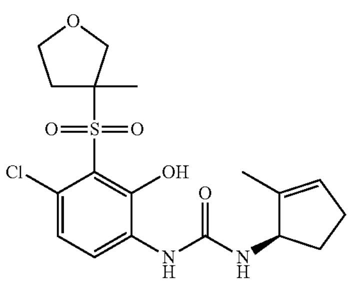 [SMILES: CC1=CCC[C@H]1NC(=O)Nc1ccc(Cl)c(S(=O)(=O)C2(C)CCOC2)c1O] | 1-(4-chloro-2-hydroxy-3-((3-methyltetrahydro-furan-3-yl)sulfonyl)phenyl)-3-((R)-2-methylcyclopent-2-en-1-yl)urea | Int 2 and 29, method 1 | $^1$H-NMR (400 MHz, DMSO-d$_6$) δ ppm 10.51 (s, 1H), 8.37 (d, J = 9.0 Hz, 1H), 8.20 (s, 1H), 7.15 (d, J = 8.8 Hz, 1H), 7.08 (d, J = 8.6 Hz, 1H), 5.51 (s, 1H), 4.47-4.58 (m, 1H), 4.33 (d, J = 10.0 Hz, 1H), 3.75-3.89 (m, 2H), 3.60 (d, J = 10.0 Hz, 1H), 2.67 (dt, J = 13.3, 7.9 Hz, 1H), 2.09-2.37 (m, 3H), 1.90-2.02 (m, 1H), 1.66 (s, 3H), 1.44-1.60 (m, 4H); MS(ES$^+$) m/z 415 (MH$^+$). |
| 69 | 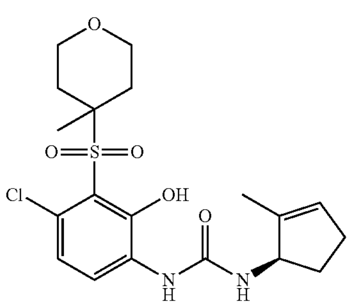 [SMILES: CC1=CCC[C@H]1NC(=O)Nc1ccc(Cl)c(S(=O)(=O)C2(C)CCOCC2)c1O] | (R)-1-(4-chloro-2-hydroxy-3-((4-methyltetrahydro-2H-pyran-4-yl)sulfonyl)phenyl)-3-(2-methylcyclopent-2-en-1-yl)urea | Int 2 and 30, method 1 | $^1$H-NMR (400 MHz, DMSO-d$_6$) δ ppm 10.38 (s, 1H), 8.42 (d, J = 8.8 Hz, 1H), 8.16 (s, 1H), 7.15 (d, J = 9.0 Hz, 1H), 7.07 (d, J = 8.3 Hz, 1H), 5.51 (br. s., 1H), 4.48-4.59 (m, 1H), 3.84 (dd, J = 11.7, 4.4 Hz, 2H), 3.45-3.55 (m, 2H), 2.09-2.35 (m, 3H), 2.02 (td, J = 12.5, 5.0 Hz, 2H), 1.66 (s, 3H), 1.57 (d, J = 12.8 Hz, 2H), 1.43-1.53 (m, 4H); MS(ES$^+$) m/z 429 (MH$^+$). |
| 70 | 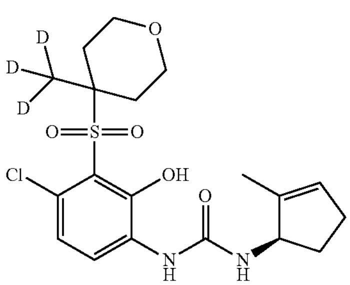 [SMILES: [2H]C([2H])([2H])C1(S(=O)(=O)c2c(Cl)ccc(NC(=O)N[C@@H]3CCC=C3C)c2O)CCOCC1] | (R)-1-(4-chloro-2-hydroxy-3-((4-d3-methyl)tetrahydro-2H-pyran-4-yl)sulfonyl)phenyl)-3-(2-methylcyclopent-2-en-1-yl)urea | Int 2 and 31, method 1 | $^1$H-NMR (400 MHz, DMSO-d$_6$) δ ppm 10.40 (br. s., 1H), 8.40 (d, J = 8.8 Hz, 1H), 8.14 (s, 1H), 7.11 (d, J = 8.8 Hz, 1H), 7.04 (d, J = 8.3 Hz, 1H), 5.51 (br. s., 1H), 4.49-4.57 (m, 1H), 3.84 (dd, J = 11.7, 4.1 Hz, 2H), 3.48 (t, J = 11.2 Hz, 2H), 2.10-2.35 (m, 3H), 2.03 (td, J = 12.4, 5.0 Hz, 2H), 1.67 (s, 3H), 1.46-1.63 (m, 3H); MS(ES$^+$) m/z 432 (MH$^+$). |

TABLE 1-continued

| No. | Structure | Name | Starting material and method | HNMR and LCMS |
|---|---|---|---|---|
| 71 | 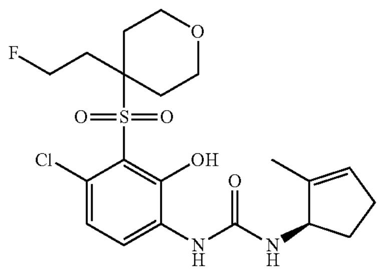 [SMILES: CC1=CCC[C@H]1NC(=O)Nc1ccc(Cl)c(S(=O)(=O)C2(CCF)CCOCC2)c1O] | (R)-1-(4-chloro-3-((4-(2-fluoroethyl)tetrahydro-2H-pyran-4-yl)sulfonyl)-2-hydroxyphenyl)-3-(2-methylcyclopent-2-en-1-yl)urea | Int 2 and 54, method 1 | $^{1}$H-NMR (400 MHz, DMSO-d$_{6}$) δ ppm 10.34 (s, 1H), 8.40 (d, J = 9.0 Hz, 1H), 8.17 (s, 1H), 7.17 (d, J = 9.0 Hz, 1H), 7.07 (d, J = 8.3 Hz, 1H), 5.51 (s, 1H), 4.86 (t, J = 6.3 Hz, 1H), 4.74 (t, J = 6.3 Hz, 1H), 4.49-4.58 (m, 1H), 3.83 (dd, J = 11.8, 3.5 Hz, 2H), 3.55 (t, J = 11.2 Hz, 2H), 2.43-2.59 (m, 2H), 2.11-2.35 (m, 3H), 1.91 (td, J = 12.4, 5.0 Hz, 2H), 1.75-1.83 (m, 2H), 1.67 (s, 3H), 1.47-1.57 (m, 1H); MS(ES$^{+}$) m/z 461 (MH$^{+}$). |
| 72 | 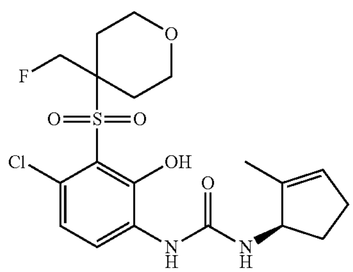 [SMILES: CC1=CCC[C@H]1NC(=O)Nc1ccc(Cl)c(S(=O)(=O)C2(CF)CCOCC2)c1O] | (R)-1-(4-chloro-3-((4-(fluoromethyl)tetrahydro-2H-pyran-4-yl)sulfonyl)-2-hydroxyphenyl)-3-(2-methylcyclopent-2-en-1-yl)urea | Int 2 and 55, method 1 | $^{1}$H-NMR (400 MHz, DMSO-d$_{6}$) δ ppm 10.34 (s, 1H), 8.36 (d, J = 9.0 Hz, 1H), 8.16 (s, 1H), 7.13 (d, J = 8.8 Hz, 1H), 7.05 (d, J = 8.3 Hz, 1H), 5.51 (br. s., 1H), 5.11 (s, 1H), 4.99 (s, 1H), 4.49-4.58 (m, 1H), 3.86 (dd, J = 11.7, 3.9 Hz, 2H), 3.54 (t, J = 11.4 Hz, 2H), 2.06-2.35 (m, 5H), 1.94-2.05(m, 1H), 1.76 (d, J = 13.6 Hz, 2H), 1.67 (s, 3H), 1.43-1.58 (m, 1H); MS(ES$^{+}$) m/z 447 (MH$^{+}$). |
| 73 | 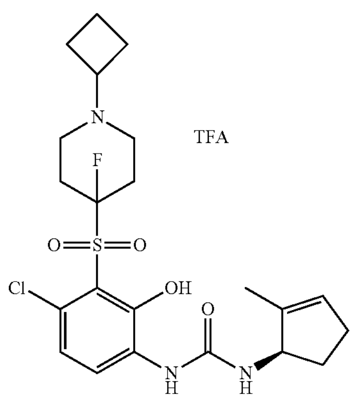 | (R)-1-(4-chloro-3-((1-cyclobutyl-4-fluoropiperidin-4-yl)sulfonyl)-2-hydroxyphenyl)-3-(2-methylcyclopent-2-en-1-yl)urea, trifluoroacetic acid salt | Int 2 and 56, method 1 | $^{1}$H-NMR (400 MHz, DMSO-d$_{6}$) δ ppm 10.10 (br. s., 1H), 8.24-8.33 (m, 2H), 7.16 (d, J = 8.8 Hz, 1H), 7.10 (d, J = 8.5 Hz, 1H), 5.52 (br. s., 1H), 4.50-4.59 (m, 1H), 3.69 (br. s., 1H), 3.42-3.55 (m, 3H), 2.91 (br. s., 2H), 2.41-2.59 (m, 1H), 2.22-2.38 (m, 4H), 2.09-2.22 (m, 5H), 1.70-1.84 (m, J = 9.0 Hz, 2H), 1.67 (s, 3H), 1.46-1.59 (m, 1H); MS(ES$^{+}$) m/z 486 (MH$^{+}$). |
| 74 | 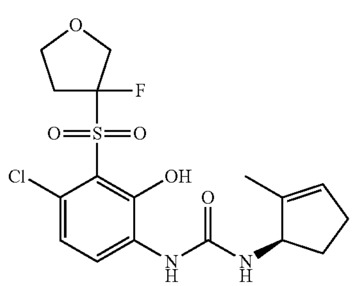 [SMILES: CC1=CCC[C@H]1NC(=O)Nc1ccc(Cl)c(S(=O)(=O)C2(F)CCOC2)c1O] | 1-(4-chloro-3-((3-fluorotetrahydrofuran-3-yl)sulfonyl)-2-hydroxyphenyl)-3-((R)-2-methylcyclopent-2-en-1-yl)urea | Int 2 and 57, method 1 | $^{1}$H-NMR (400 MHz, DMSO-d$_{6}$) δ ppm 8.26 (s, 1H), 8.19 (d, J = 8.8 Hz, 1H), 7.05 (d, J = 8.3 Hz, 2H), 5.51 (br. s., 1H), 4.49-4.59 (m, 1H), 4.35-4.49 (m, 1H), 3.91-4.10 (m, 3H), 2.74-2.94 (m, 1H), 2.11-2.41 (m, 4H), 1.67 (s, 3H), 1.47-1.61 (m, 1H); MS(ES$^{+}$) m/z 419 (MH$^{+}$). |
| 75 | 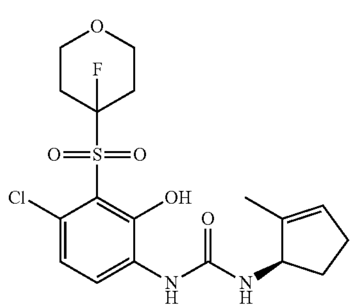 | (R)-1-(4-chloro-3-((4-fluorotetrahydro-2H-pyran-4-yl)sulfonyl)-2-hydroxyphenyl)-3-(2-methylcyclopent-2-en-1-yl)urea | Int 2 and 58, method 1 | $^{1}$H-NMR (400 MHz, DMSO-d$_{6}$) δ ppm 10.19 (br. s., 1H), 8.39 (d, J = 9.0 Hz, 1H), 8.20 (s, 1H), 7.17 (d, J = 9.0 Hz, 1H), 7.10 (d, J = 8.3 Hz, 1H), 5.51 (br. s., 1H), 4.53 (d, J = 6.5 Hz, 1H), 3.97 (dd, J = 5.3, 11.5 Hz, 2H), 3.49 (t, J = 11.3 Hz, 2H), 2.10-2.40(m, 5H), 1.91 (t, J = 12.3 Hz, 2H), 1.66 (s, 3H), 1.45-1.60 (m, 1H); MS(ES$^{+}$) m/z 433 (MH$^{+}$). |

TABLE 1-continued

| No. | Structure | Name | Starting material and method | HNMR and LCMS |
|---|---|---|---|---|
| 76 | *TFA salt structure* | (R)-1-(4-chloro-3-((3,3-difluorocyclobutyl)sulfonyl)-2-hydroxyphenyl)-3-(2-methylcyclopent-2-en-1-yl)urea trifluoroacetic acid salt | Int 2 and 59, method 5 | $^1$H-NMR (400 MHz, CDCl$_3$) δ ppm 10.71 (s, 1H), 8.44 (d, J = 8.9 Hz, 1H), 7.04 (d, J = 8.9 Hz, 1H), 6.94 (s, 1H), 5.58 (s, 1H), 4.68 (s, 2H), 4.30-4.42 (m, 1H), 3.12 (m, 2H), 2.75-3.01 (m, 2H), 2.35-2.49 (m, 2H), 2.15-2.35 (m, 1H), 1.53-1.72 (m, 4H); MS(ES$^+$) m/z 421 (MH$^+$). |
| 77 | 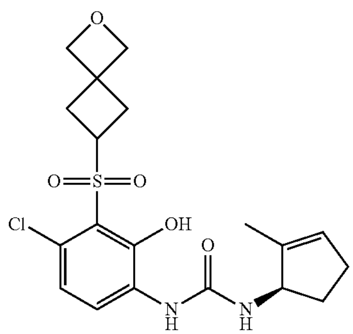 [SMILES: CC1=CCC[C@H]1NC(=O)Nc1ccc(Cl)c(S(=O)(=O)C2CC3(COC3)C2)c1O] | (R)-1-(3-(2-oxaspiro[3.3]heptan-6-ylsulfonyl)-4-chloro-2-hydroxyphenyl)-3-(2-methylcyclopent-2-en-1-yl)urea | Int 2 and 60, method 1 | $^1$H-NMR (400 MHz, CDCl$_3$) δ ppm 10.75 (br. s., 1H), 8.30 (d, J = 8.5 Hz, 1H), 8.18 (br. s., 1H), 7.01-7.29 (m, 2H), 5.51 (br. s., 1H), 4.54 (br. s., 5H), 4.41 (br. s., 1H), 2.51-2.70 (m, 4H), 2.11-2.40 (m, 3H), 1.66 (br. s., 3H), 1.32-1.58 (m, 1H); MS(ES$^+$) m/z 427 (MH$^+$). |
| 78 | 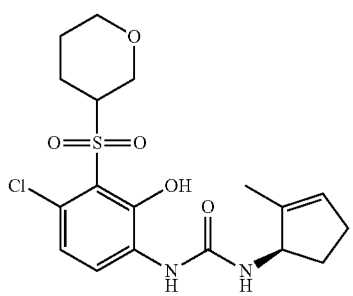 [SMILES: CC1=CCC[C@H]1NC(=O)Nc1ccc(Cl)c(S(=O)(=O)C2CCCOC2)c1O] | 1-(4-chloro-2-hydroxy-3-((tetrahydro-2H-pyran-3-yl)sulfonyl)phenyl)-3-((R)-2-methylcyclopent-2-en-1-yl)urea | Int 2 and 61, method 1 | $^1$H-NMR (500 MHz, DMSO-d$_6$) δ ppm 10.70 (br, 1H), 8.21 (s, 2H), 6.93-7.17 (m, 1H), 6.63-6.93 (m, 1H), 5.50 (s, 1H), 4.32-4.67 (m, 1H), 3.83-4.19 (m, 2H), 3.70-3.80 (m, 1H), 3.50-3.65 (m, 1H), 3.33-3.36 (m, 1H), 2.07-2.33 (m, 3H), 1.69-2.01 (m, 3H), 1.66 (s, 3H), 1.43-1.61 (m, 2H); MS(ES$^+$) m/z 415 (MH$^+$). |
| 79 | 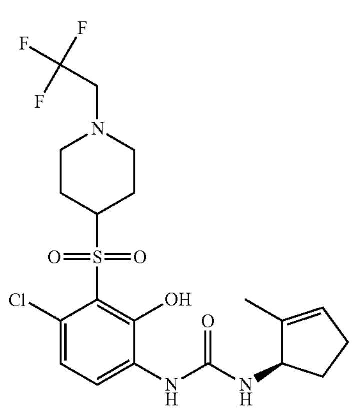 [SMILES: CC1=CCC[C@H]1NC(=O)Nc1ccc(Cl)c(S(=O)(=O)C2CCN(CC(F)(F)F)CC2)c1O] | (R)-1-(4-chloro-2-hydroxy-3-((1-(2,2,2-trifluoroethyl)piperidin-4-yl)sulfonyl)phenyl)-3-(2-methylcyclopent-2-en-1-yl)urea | Int 2 and 62, method 1 | $^1$H-NMR (400 MHz, DMSO-d$_6$) δ ppm 8.09 (s, 1H), 7.87 (br. s., 1H), 6.88-6.95 (m, 1H), 6.26 (br. s., 1H), 5.46 (br. s., 1H), 4.48-4.57 (m, 1H), 4.16-4.23 (m, 3H), 3.38-3.49 (m, 2H), 3.19 (d, J = 11.5 Hz, 2H), 2.08-2.35 (m, 5H), 1.86-1.95 (m, 1H), 1.65 (s, 3H), 1.44-1.56 (m, 1H), 1.42 (br. s., 1H); MS(ES$^+$) m/z 496 (MH$^+$). |

TABLE 1-continued

| No. | Structure | Name | Starting material and method | HNMR and LCMS |
|---|---|---|---|---|
| 80 | 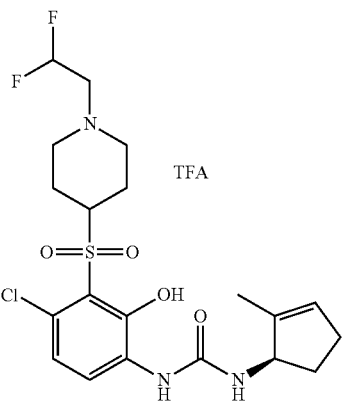 [SMILES: CC1=CCC[C@H]1NC(=O)Nc1ccc(Cl)c(S(=O)(=O)C2CCN(CC(F)F)CC2)c1O] | (R)-1-(4-chloro-3-((1-(2,2-difluoroethyl)piperidin-4-yl)sulfonyl)-2-hydroxyphenyl)-3-(2-methylcyclopent-2-en-1-yl)urea trifluoroacetic acid salt | Int 2 and 63, method 5 | $^1$H-NMR (400 MHz, DMSO-d$_6$) δ ppm 10.71 (s, 1H), 8.33 (d, J = 8.9 Hz, 1H), 8.21 (s, 1H), 7.15 (d, J = 8.9 Hz, 1H), 7.10 (d, J = 8.4 Hz, 1H), 6.28 (t, J = 55.0 Hz, 1H), 5.52 (s, 1H), 4.53 (d, J = 7.0 Hz, 1H), 3.75-3.83 (m, 1H), 3.06-3.27 (m, 4H), 2.62-2.76 (m, 1H), 2.09-2.39 (m, 4H), 1.82-1.98 (m, 4H), 1.66 (s, 3H), 1.52 (m, 1H); MS(ES$^+$) m/z 478 (MH$^+$). |
| 81 | 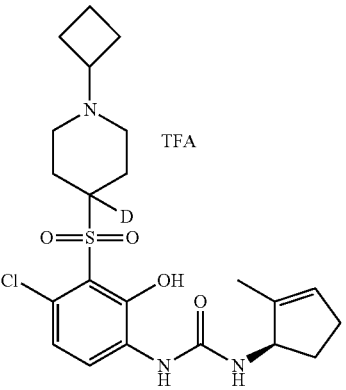 [SMILES: [2H]C1(S(=O)(=O)c2c(Cl)ccc(NC(=O)N[C@@H]3CCC=C3C)c2O)CCN(C2CCC2)CC1] | (R)-1-(4-chloro-3-((1-cyclobutylpiperidin-4-yl)sulfonyl)-2-hydroxyphenyl)-3-(2-methylcyclopent-2-en-1-yl)urea-d$_1$, trifluoroacetic acid salt | Int 2 and 64, method 1 | $^1$H-NMR (400 MHz, DMSO-d$_6$) δ ppm 10.78 (br. s., 1H), 9.49 (br. s., 1H), 8.22-8.31 (m, 2H), 7.16 (t, J = 4.4 Hz, 1H), 7.10 (d, J = 8.3 Hz, 1H), 5.52 (br. s., 1H), 4.54 (d, J = 6.5 Hz, 1H), 3.40-3.65 (m, 4H), 2.87 (br. s., 2H), 2.05-2.35 (m, 9H), 1.96 (d, J = 11.3 Hz, 2H), 1.62-1.81 (m, 5H), 1.48-1.58 (m, 1H); MS(ES$^+$) m/z 469 (MH$^+$). |
| 82 | 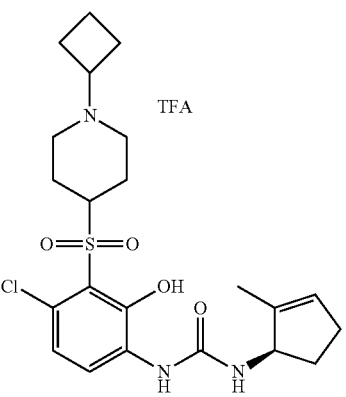 [SMILES: CC1=CCC[C@H]1NC(=O)Nc1ccc(Cl)c(S(=O)(=O)C2CCN(C3CCC3)CC2)c1O] | (R)-1-(4-chloro-3-((1-cyclobutylpiperidin-4-yl)sulfonyl)-2-hydroxyphenyl)-3-(2-methylcyclopent-2-en-1-yl)urea trifluoroacetic acid salt | Int 2 and 65, method 1 | $^1$H-NMR (400 MHz, DMSO-d$_6$) δ ppm 10.78 (br. s., 1H), 9.44 (br. s., 1H), 8.25 (d, J = 8.0 Hz, 2H), 7.15 (d, J = 8.8 Hz, 1H), 7.09 (d, J = 8.3 Hz, 1H), 5.52 (br. s., 1H), 4.50-4.58 (m, 1H), 3.95-4.09 (m, 1H), 3.42-3.64 (m, 4H), 2.75-2.95 (m, 2H), 2.05-2.37 (m, 9H), 1.85-2.04 (m, 2H), 1.63-1.81 (m, 5H), 1.44-1.60 (m, 1H); MS(ES$^+$) m/z 468 (MH$^+$). |

TABLE 1-continued

| No. | Structure | Name | Starting material and method | HNMR and LCMS |
|---|---|---|---|---|
| 83 | 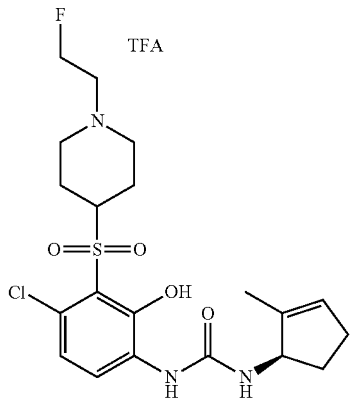 | (R)-1-(4-chloro-3-((1-cyclobutylpiperidin-4-yl)sulfonyl)-2-hydroxyphenyl)-3-(2-methylcyclopent-2-en-1-yl)urea trifluoroacetic acid salt | Int 2 and 66, method 5 | $^1$H-NMR (400 MHz, DMSO-d$_6$) δ ppm 10.78 (br. s., 1H), 9.44 (br. s., 1H), 8.25 (d, J = 8.0 Hz, 2H), 7.15 (d, J = 8.8 Hz, 1H), 7.09 (d, J = 8.3 Hz, 1H), 5.52 (br. s., 1H), 4.50-4.58 (m, 1H), 3.95-4.09 (m, 1H), 3.42-3.64 (m, 4H), 2.75-2.95 (m, 2H), 2.05-2.37 (m, 9H), 1.85-2.04 (m, 2H), 1.63-1.81 (m, 5H), 1.44-1.60 (m, 1H); MS(ES$^+$) m/z 468 (MH$^+$). |
| 84 & 85 | | 1-(4-chloro-2-hydroxy-3-(((8aR)-octahydroindolizin-7-yl)sulfonyl)phenyl)-3-((R)-2-methylcyclopent-2-en-1-yl)urea, trifluoroacetic acid salt and 1-(4-chloro-2-hydroxy-3-(((8aS)-octahydroindolizin-7-yl)sulfonyl)phenyl)-3-((R)-2-methylcyclopent-2-en-1-yl)urea, trifluoroacetic acid salt | Int 2 and 67, method 1 | Compound 84: Chiral HPLC (Column AD-H, 4.6*250 mm, 5 μm, co-solvent: MeOH (0.1% DEA), CO$_2$ flow rate: 2.25 mL/min, Co-solvent flow rate: 0.75 mL/min, back pressure: 151 bar): t$_R$ = 4.25 min, ee %: >99%; $^1$H-NMR (400 MHz, MeOD-d$_4$) δ ppm 8.31 (d, J = 8.3 Hz, 1H), 7.14 (d, J = 8.8 Hz, 1H), 5.55 (s, 1H), 4.93-5.03 (m, 1H), 4.65 (br. s., 1H), 4.17 (d, J = 5.4 Hz, 1H), 4.03 (br. s., 1H), 3.70 (br. s., 1H), 3.45-3.56 (m, 2H), 3.33 (br. s., 1H), 3.21 (d, J = 8.3 Hz, 3H), 1.92-2.45 (m, 10H), 1.73 (s, 3H), 1.58-1.70 (m, 1H); MS(ES$^+$) m/z 454 (MH$^+$). Compound 85: Chiral HPLC (Column AD-H, 4.6*250 mm, 5 μm, co-solvent: MeOH (0.1% DEA), CO$_2$ flow rate: 2.25 mL/min, Co-solvent flow rate: 0.75 mL/min, back pressure: 151 bar): t$_R$ = 3.34 min, ee %: >99%; $^1$H-NMR (400 MHz, MeOD-d$_4$) δ ppm 8.24-8.41 (m, 1H), 7.14 (d, J = 9.0 Hz, 1H), 5.53-5.57 (m, 1H), 4.65 (br. s., 1H), 4.10-4.22 (m, 1H), 3.86-4.10 (m, 1H), 3.59-3.86 (m, 1H), 3.41-3.59 (m, 2H), 2.71-3.25 (m, 2H), 1.97-2.60 (m, 10H), 1.73 (s, 3H), 1.58-1.69 (m, 1H); MS(ES$^+$) m/z 454 (MH$^+$). |
| 86 | 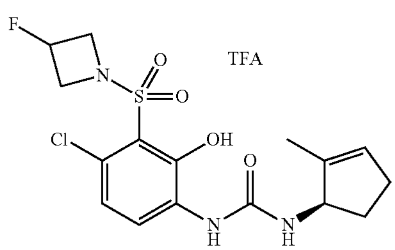 [SMILES: CC1=CCC[C@H]1NC(=O)Nc1ccc(Cl)c(S(=O)(=O)N2CC(F)C2)c1O] | (R)-1-(4-chloro-3-((3-fluoroazetidin-1-yl)sulfonyl)-2-hydroxyphenyl)-3-(2-methylcyclopent-2-en-1-yl)urea trifluoroacetic acid salt | Int 2 and 68, method 2 | $^1$H-NMR (400 MHz, DMSO-d$_6$) δ ppm 10.27 (s, 1H), 8.28 (d, J = 8.8 Hz, 1H), 8.18 (s, 1H), 7.13 (d, J = 8.8 Hz, 1H), 7.08 (d, J = 8.4 Hz, 1H), 5.51 (s, 1H), 5.28-5.48 (m, 1H), 4.49-4.58 (m, 1H), 4.35 (dd, J = 10.5, 5.9 Hz, 1H), 4.30 (dd, J = 10.5, 5.9 Hz, 1H), 4.11 (dd, J = 10.5, 3.1 Hz, 1H), 4.05 (dd, J = 10.5, 3.1 Hz, 1H), 2.10-2.35 (m, 3H), 1.67 (s, 3H), 1.46-1.57 (m, 1H); MS(ES$^+$) m/z 404 (MH$^+$). |
| 87 | 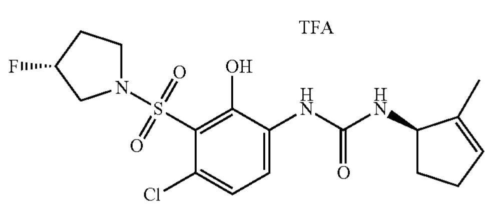 [SMILES: CC1=CCC[C@H]1NC(=O)Nc1ccc(Cl)c(S(=O)(=O)N2CC[C@@H](F)C2)c1O] | 1-(4-chloro-3-(((R)-3-fluoropyrrolidin-1-yl)sulfonyl)-2-hydroxyphenyl)-3-((R)-2-methylcyclopent-2-en-1-yl)urea, trifluoroacetic acid salt | Int 2 and 69, method 2 | $^1$H-NMR (400 MHz, CDCl$_3$) δ ppm 10.59 (s, 1H), 8.33 (d, J = 8.7 Hz, 1H), 7.08 (s, 1H), 7.00 (d, J = 8.7 Hz, 1H), 5.55 (s, 1H), 5.27 (d, J = 52.3 Hz, 1H), 4.90 (d, J = 7.6 Hz, 1H), 4.68 (s, 1H), 3.68-3.83 (m, 2H), 3.54-3.65 (m, 2H), 2.32-2.47 (m, 2H), 2.17-2.32 (m, 2H), 2.01 (s, 1H), 1.75 (s, 3H), 1.64-1.71 (m, 1H); MS(ES$^+$) m/z 418 (MH$^+$). |

TABLE 1-continued

| No. | Structure | Name | Starting material and method | HNMR and LCMS |
|---|---|---|---|---|
| 88 | 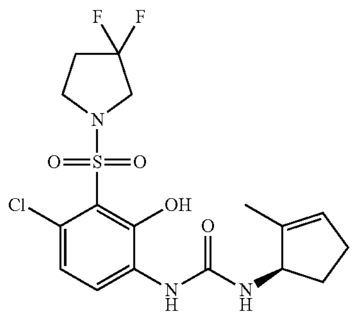 [SMILES: CC1=CCC[C@H]1NC(=O)Nc1ccc(Cl)c(S(=O)(=O)N2CCC(F)(F)C2)c1O] | (R)-1-(4-chloro-3-((3,3-difluoropyrrolidin-1-yl)sulfonyl)-2-hydroxyphenyl)-3-(2-methylcyclopent-2-en-1-yl)urea | Int 2 and 70, method 2 | $^1$H-NMR (500 MHz, DMSO-d$_6$) δ ppm 10.48 (s, 1H), 8.21 (s, 1H), 8.10 (d, J = 8.4 Hz, 1H), 7.07 (d, J = 8.4 Hz, 1H), 6.85 (s, 1H), 5.50 (s, 1H), 4.53 (d, J = 7.5 Hz, 1H), 3.81 (t, J = 12.7 Hz, 2H), 3.58 (t, J = 7.4 Hz, 2H), 2.40-2.49 (m, 2H), 2.07-2.35 (m, 3H), 1.66 (s, 3H), 1.44-1.56 (m, 1H); MS(ES$^+$) m/z 436 (MH$^+$). |
| 89 | 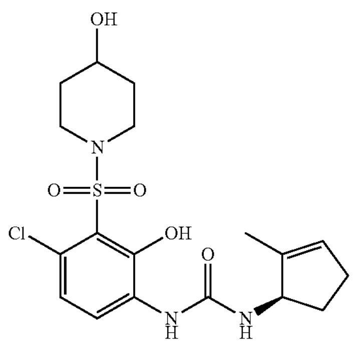 [SMILES: CC1=CCC[C@H]1NC(=O)Nc1ccc(Cl)c(S(=O)(=O)N2CCC(O)CC2)c1O] | (R)-1-(4-chloro-2-hydroxy-3-((4-hydroxypiperidin-1-yl)sulfonyl)phenyl)-3-(2-methylcyclopent-2-en-1-yl)urea | Int 2 and 71, method 2 | $^1$H-NMR (400 MHz, DMSO-d$_6$) δ ppm 10.42 (s, 1H), 8.30 (d, J = 8.8 Hz, 1H), 8.13 (s, 1H), 7.06-7.10 (m, 2H), 5.51 (s, 1H), 4.79 (s, 1H), 4.53 (d, J = 6.9 Hz, 1H), 3.65 (dd, J = 7.8, 4.1 Hz, 1H), 3.40-3.52 (m, 2H), 2.99-3.11 (m, 2H), 2.10-2.39 (m, 3H), 1.73-1.78 (m, 2H), 1.66 (s, 3H), 1.33-1.57 (m, 3H); MS(ES$^+$) m/z 430 (MH$^+$). |
| 90 | 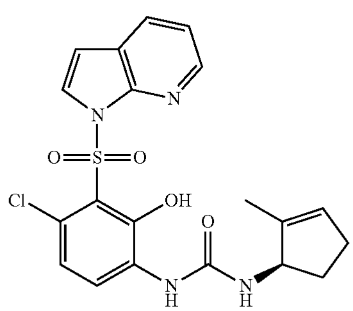 [SMILES: CC1=CCC[C@H]1NC(=O)Nc1ccc(Cl)c(S(=O)(=O)n2ccc3cccnc32)c1O] | (R)-1-(3-((1H-pyrrolo[2,3-b]pyridin-1-yl)sulfonyl)-4-chloro-2-hydroxyphenyl)-3-(2-methylcyclopent-2-en-1-yl)urea | Int 2 and 72, method 1 | $^1$H-NMR (400 MHz, DMSO-d$_6$) δ ppm 10.83 (br. s., 1H), 8.34 (s, 1H), 8.27 (d, J = 4.5 Hz, 1H), 8.23 (d, J = 8.8 Hz, 1H), 8.14 (d, J = 7.8 Hz, 1H), 7.97 (d, J = 4.0 Hz, 1H), 7.33 (dd, J = 7.8, 4.8 Hz, 1H), 6.99-7.10 (m, 2H), 6.86 (d, J = 4.0 Hz, 1H), 5.51 (br. s., 1H), 4.48-4.58 (m, 1H), 2.09-2.37 (m, 3H), 1.67 (s, 3H), 1.48-1.59 (m, 1H); MS(ES$^+$) m/z 447 (MH$^+$). |
| 91 | 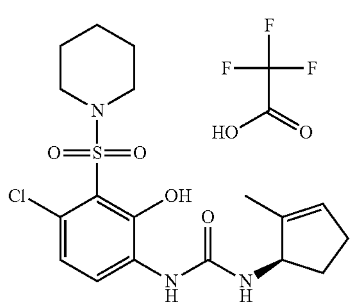 [SMILES: CC1=CCC[C@H]1NC(=O)Nc1ccc(Cl)c(S(=O)(=O)N2CCCCC2)c1O ; O=C(O)C(F)(F)F] | (R)-1-(4-chloro-2-hydroxy-3-(piperidin-1-ylsulfonyl)phenyl)-3-(2-methylcyclopent-2-en-1-yl)urea trifluoroacetic acid salt | Int 2 and 73, method 5 | $^1$H-NMR (400 MHz, DMSO-d$_6$) δ ppm 10.45 (s, 1H), 8.31 (d, J = 8.8 Hz, 1H), 8.13 (s, 1H), 7.08 (dd, J = 8.6, 4.1 Hz, 2H), 5.51 (s, 1H), 4.54 (d, J = 7.0 Hz, 1H), 3.17-3.22 (m, 4H), 2.15-2.40 (m, 3H), 1.67 (s, 3H), 1.42-1.62 (m, 7H); MS(ES$^+$) m/z 414 (MH$^+$). |

TABLE 1-continued

| No. | Structure | Name | Starting material and method | HNMR and LCMS |
|---|---|---|---|---|
| 92 | 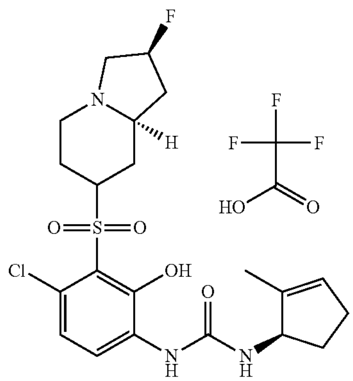 [SMILES: CC1=CCC[C@H]1NC(=O)Nc1ccc(Cl)c(S(=O)(=O)C2CCN3C[C@@H](F)C[C@H]3C2)c1O ; O=C(O)C(F)(F)F] | 1-(4-chloro-3-(((7S,8aS)-7-fluorohexahydro-pyrrolo[1,2-a]pyrazin-2(1H)-yl)sulfonyl)-2-hydroxyphenyl)-3-((R)-2-methylcyclopent-2-en-1-yl)urea, trifluoroacetic acid salt | Int 2 and 74, method 5 | $^1$H-NMR (400 MHz, DMSO-d$_6$) δ ppm 10.54 (br, 1H), 8.23 (d, J = 4.0 Hz, 2H), 7.11 (d, J = 8.8 Hz, 2H), 5.16-5.52 (m, 2H), 4.44-4.61 (m, 1H), 2.81-4.20 (m, 9H), 2.04-2.40 (m, 4H), 1.37-1.67 (m, 5H); MS(ES$^+$) m/z 473 (MH$^+$). |
| 93 | 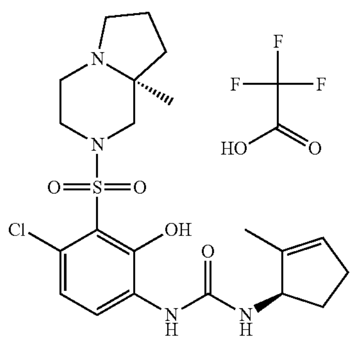 [SMILES: CC1=CCC[C@H]1NC(=O)Nc1ccc(Cl)c(S(=O)(=O)N2CCN3CCC[C@@]3(C)C2)c1O ; O=C(O)C(F)(F)F] | 1-(4-chloro-2-hydroxy-3-(((S)-8a-methylhexahydro-pyrrolo[1,2-a]pyrazin-2(1H)-yl)sulfonyl)phenyl)-3-((R)-2-methylcyclopent-2-en-1-yl)urea, trifluoroacetic acid salt | Int 2 and 75, method 5 | $^1$H-NMR (400 MHz, DMSO-d$_6$) δ ppm 10.49 (br, 1H), 8.14-8.32 (m, 2H), 7.13 (t, J = 8.4 Hz, 2H), 5.52 (s, 1H), 4.54 (d, J = 6.7 Hz, 1H), 3.20-3.82 (m, 8H), 2.15-2.33 (m, 3H), 1.81-2.10 (m, 4H), 1.66 (s, 3H), 1.46-1.59 (m, 1H), 1.37 (s, 3H); MS(ES$^+$) m/z 469 (MH$^+$). |
| 94 | 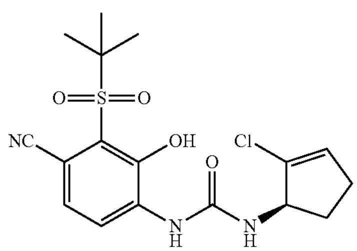 | (R)-1-(3-(tert-butylsulfonyl)-4-cyano-2-hydroxyphenyl)-3-(2-chlorocyclopent-2-en-1-yl)urea | Int 1 and 76, method 1 | $^1$H-NMR (400 MHz, DMSO-d$_6$) δ ppm 10.16 (br. s., 1H), 8.63 (s, 1H), 8.54 (d, J = 8.3 Hz, 1H), 7.63 (d, J = 8.8 Hz, 1H), 7.56 (d, J = 8.3 Hz, 1H), 6.01 (d, J = 1.7 Hz, 1H), 4.65-4.82 (m, 1H), 2.25-2.46 (m, 3H), 1.63-1.72 (m, 1H), 1.26-1.46 (m, 10H); MS(ES$^+$) m/z 398 (MH$^+$). |
| 95 | 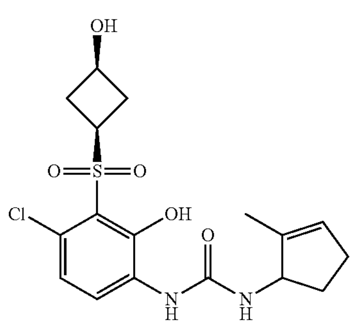 [SMILES: CC1=CCCC1NC(=O)Nc1ccc(Cl)c(S(=O)(=O)[C@H]2C[C@@H](O)C2)c1O] | 1-(4-chloro-2-hydroxy-3-((cis-3-hydroxycyclobutyl)sulfonyl)phenyl)-3-(2-methylcyclopent-2-en-1-yl)urea | Int 3 and 77, method 1 | $^1$H-NMR (400 MHz, DMSO-d$_6$) δ ppm 10.77 (s, 1H), 8.32 (d, J = 8.8 Hz, 1H), 8.14-8.20 (m, 1H), 7.05-7.14 (m, 2H), 5.51 (br. s., 1H), 4.48-4.57 (m, 1H), 4.00-4.13 (m, 2H), 2.37-2.47 (m, 2H), 2.10-2.37 (m, 5H), 1.66 (s, 3H), 1.46-1.56 (m, 1H); MS(ES$^+$) m/z 401 (MH$^+$). |

TABLE 1-continued

| No. | Structure | Name | Starting material and method | HNMR and LCMS |
|---|---|---|---|---|
| 96 | 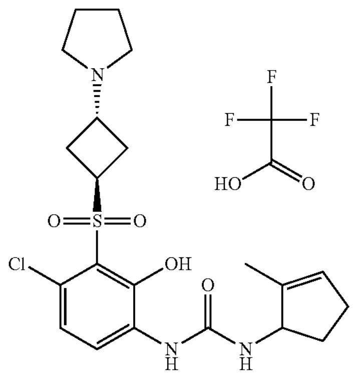 [SMILES: CC1=CCCC1NC(=O)Nc1ccc(Cl)c(S(=O)(=O)[C@H]2C[C@H](N3CCCC3)C2)c1O ; O=C(O)C(F)(F)F] | 1-(4-chloro-2-hydroxy-3-(((1r,3r)-3-(pyrrolidin-1-yl)cyclobutyl)sulfonyl)phenyl)-3-(2-methylcyclopent-2-en-1-yl)urea, trifluoroacetic acid salt | Int 3 and 78, method 1 | $^1$H-NMR (400 MHz, DMSO-d$_6$) δ ppm 10.91 (br. s., 1H), 10.20 (br. s., 1H), 8.28 (s, 1H), 8.19 (d, J = 8.5 Hz, 1H), 7.07-7.17 (m, 2H), 5.52 (br. s., 1H), 4.48-4.60 (m, 2H), 3.96-4.08 (m, 1H), 3.71-3.80 (m, 1H), 2.96 (br. s., 2H), 2.56-2.77 (m, 5H), 2.11-2.36 (m, 3H), 1.93-2.06 (m, 2H), 1.78-1.93 (m, 2H), 1.66 (s, 3H), 1.46-1.58 (m, 1H); MS(ES$^+$) m/z 454 (MH$^+$). |
| 97 | 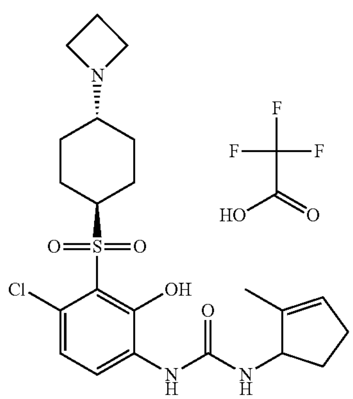 [SMILES: CC1=CCCC1NC(=O)Nc1ccc(Cl)c(S(=O)(=O)[C@H]2CC[C@H](N3CCC3)CC2)c1O ; O=C(O)C(F)(F)F] | 1-(3-(((1r,4r)-4-(azetidin-1-yl)cyclohexyl)sulfonyl)-4-chloro-2-hydroxyphenyl)-3-(2-methylcyclopent-2-en-1-yl)urea trifluoroacetic acid salt | Int 3 and 79, method 1 | $^1$H-NMR (400 MHz, MeOD-d$_4$) δ ppm 8.28 (d, J = 8.8 Hz, 1H), 7.08 (d, J = 8.8 Hz, 1H), 5.54 (br. s., 1H), 4.59-4.68 (m, 1H), 4.10-4.22 (m, 4H), 3.81 (br. s., 1H), 3.38 (br. s., 1H), 2.52-2.68 (m, 1H), 2.17-2.45 (m, 5H), 2.03-2.17 (m, 2H), 1.85-2.03 (m, 6H), 1.72 (s, 3H), 1.56-1.69 (m, 1H); MS(ES$^+$) m/z 468 (MH$^+$). |
| 98 | 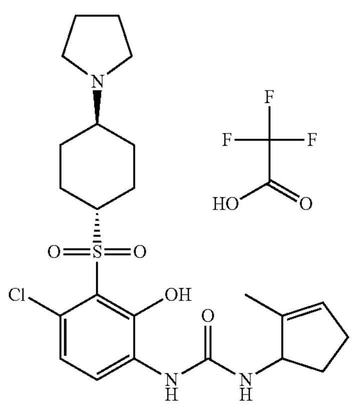 [SMILES: CC1=CCCC1NC(=O)Nc1ccc(Cl)c(S(=O)(=O)[C@H]2CC[C@H](N3CCCC3)CC2)c1O ; O=C(O)C(F)(F)F] | 1-(4-chloro-2-hydroxy-3-(((1R,4R)-4-(pyrrolidin-1-yl)cyclohexyl)sulfonyl)phenyl)-3-(2-methylcyclopent-2-en-1-yl)urea, trifluoroacetic acid salt | Int 3 and 80, method 1 | $^1$H-NMR (400 MHz, DMSO-d$_6$) δ ppm 10.83 (br. s., 1H), 9.50 (br. s., 1H), 8.29 (d, J = 8.8 Hz, 1H), 8.24 (s, 1H), 7.10 (d, J = 8.5 Hz, 1H), 7.15 (d, J = 8.8 Hz, 1H), 5.52 (s, 1H), 4.47-4.63 (m, 1H), 3.73-3.87 (m, 1H), 3.56-3.68 (m, 2H), 3.17-3.29 (m, 1H), 2.95-3.08 (m, 2H), 2.12-2.36 (m, 3H), 1.75-2.10 (m, 11H), 1.66 (s, 3H), 1.39-1.59 (m, 1H); MS(ES$^+$) m/z 482 (MH$^+$). |
| 99 | 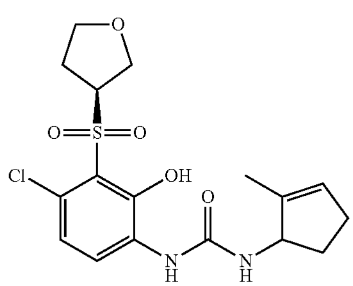 [SMILES: CC1=CCCC1NC(=O)Nc1ccc(Cl)c(S(=O)(=O)[C@H]2CCOC2)c1O] | 1-(4-chloro-2-hydroxy-3-(((S)-tetrahydrofuran-3-yl)sulfonyl)phenyl)-3-(2-methylcyclopent-2-en-1-yl)urea | Int 3 and 81, method 1 | $^1$H-NMR (400 MHz, DMSO-d$_6$) δ ppm 10.77 (br. s., 1H), 8.26 (d, J = 8.8 Hz, 1H), 8.19 (s, 1H), 7.01-7.11 (m, 2H), 5.51 (s, 1H), 4.49-4.66 (m, 2H), 4.03 (dd, J = 10.3, 4.0 Hz, 1H), 3.87-3.95 (m, 2H), 3.65-3.74 (m, 1H), 2.08-2.37 (m, 5H), 1.67 (s, 3H), 1.47-1.58 (m, 1H); MS(ES$^+$) m/z 401 (MH$^+$). |

TABLE 1-continued

| No. | Structure | Name | Starting material and method | HNMR and LCMS |
|---|---|---|---|---|
| 100 | 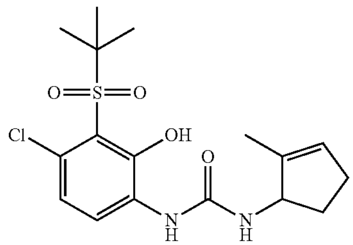 [SMILES: CC1=CCCC1NC(=O)Nc1ccc(Cl)c(S(=O)(=O)C(C)(C)C)c1O] | 1-(3-(tert-butylsulfonyl)-4-chloro-2-hydroxyphenyl)-3-(2-methylcyclopent-2-en-1-yl)urea | Int 3 and 44, method 1 | $^1$H-NMR (400 MHz, DMSO-$d_6$) δ ppm 10.43 (s, 1H), 8.41 (d, J = 9.0 Hz, 1H), 8.13 (s, 1H), 7.13 (d, J = 8.8 Hz, 1H), 7.04 (d, J = 8.3 Hz, 1H), 5.51 (br. s., 1H), 4.49-4.58 (m, 1H), 2.09-2.35 (m, 3H), 1.67 (s, 3H), 1.46-1.58 (m, 1H), 1.37 (s, 9H); MS(ES$^+$) m/z 387 (MH$^+$). |
| 101 | 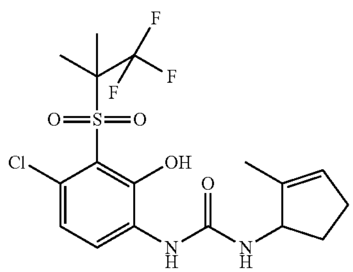 [SMILES: CC1=CCCC1NC(=O)Nc1ccc(Cl)c(S(=O)(=O)C(C)(C)C(F)(F)F)c1O] | 1-(4-chloro-2-hydroxy-3-((1,1,1-trifluoro-2-methylpropan-2-yl)sulfonyl)phenyl)-3-(2-methylcyclopent-2-en-1-yl)urea | Int 3 and 12, method 1 | $^1$H-NMR (400 MHz, DMSO-$d_6$) δ ppm 10.33 (br. s., 1H), 8.34 (d, J = 8.8 Hz, 1H), 8.23 (s, 1H), 7.17 (d, J = 9.0 Hz, 1H), 7.06 (d, J = 8.3 Hz, 1H), 5.51 (s, 1H), 4.50-4.58 (m, 1H), 2.12-2.36 (m, 3H), 1.67 (s, 3H), 1.63 (s, 6H), 1.45-1.59 (m, 1H); MS(ES$^+$) m/z 441 (MH$^+$). |
| 102 | 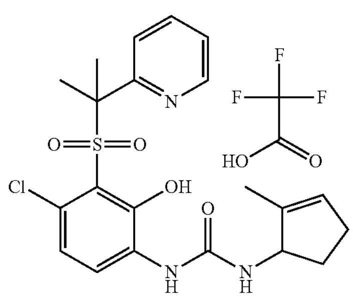 | 1-(4-chloro-2-hydroxy-3-((2-(pyridin-2-yl)propan-2-yl)sulfonyl)phenyl)-3-(2-methylcyclopent-2-en-1-yl)urea, trifluoroacetic acid salt | Int 3 and 14, method 1 | $^1$H-NMR (400 MHz, DMSO-$d_6$) δ ppm 9.99 (s, 1H), 8.44 (d, J = 3.8 Hz, 1H), 8.33 (d, J = 8.8 Hz, 1H), 7.91 (s, 1H), 7.80 (td, J = 7.8, 1.8 Hz, 1H), 7.65 (d, J = 8.0 Hz, 1H), 7.38 (dd, J = 6.9, 4.9 Hz, 1H), 7.00 (d, J = 8.3 Hz, 1H), 6.96 (d, J = 9.0 Hz, 1H), 5.50 (s, 1H), 4.46-4.59 (m, 1H), 2.10-2.35 (m, 3H), 1.88 (s, 6H), 1.66 (s, 3H), 1.46-1.56 (m, 1H); MS(ES$^+$) m/z 450 (MH$^+$). |
| 103 | 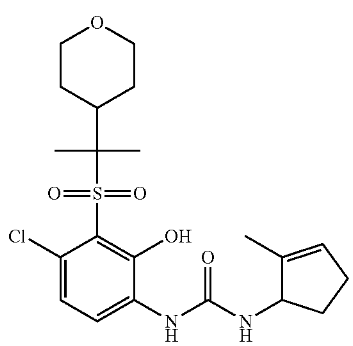 [SMILES: CC1=CCCC1NC(=O)Nc1ccc(Cl)c(S(=O)(=O)C(C)(C)C2CCOCC2)c1O] | 1-(4-chloro-2-hydroxy-3-((2-(tetrahydro-2H-pyran-4-yl)propan-2-yl)sulfonyl)phenyl)-3-(2-methylcyclopent-2-en-1-yl)urea | Int 3 and 82, method 1 | $^1$H-NMR (400 MHz, DMSO-$d_6$) δ ppm 10.45 (s, 1H), 8.40 (d, J = 8.8 Hz, 1H), 8.13 (s, 1H), 7.13 (d, J = 8.8 Hz, 1H), 7.05 (d, J = 8.3 Hz, 1H), 5.51 (s, 1H), 4.49-4.57 (m, 1H), 3.90 (dd, J = 11.2, 3.4 Hz, 2H), 3.25-3.32 (m, 2H), 2.09-2.36 (m, 4H), 1.76 (d, J = 12.5 Hz, 2H), 1.67 (s, 3H), 1.40-1.56 (m, 3H), 1.29 (s, 6H); MS(ES$^+$) m/z 457 (MH$^+$). |
| 104 | 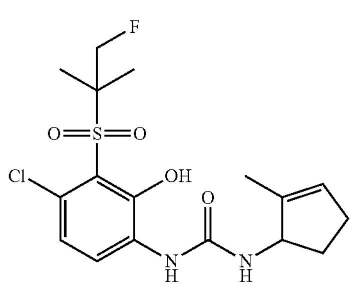 [SMILES: CC1=CCCC1NC(=O)Nc1ccc(Cl)c(S(=O)(=O)C(C)(C)CF)c1O] | 1-(4-chloro-3-((1-fluoro-2-methylpropan-2-yl)sulfonyl)-2-hydroxyphenyl)-3-(2-methylcyclopent-2-en-1-yl)urea | Int 3 and 48, method 1 | $^1$H-NMR (400 MHz, DMSO-$d_6$) δ ppm 10.32 (s, 1H), 8.38 (d, J = 9.0 Hz, 1H), 8.14 (s, 1H), 7.12 (d, J = 9.0 Hz, 1H), 7.04 (d, J = 8.5 Hz, 1H), 5.51 (s, 1H), 4.73 (s, 1H), 4.61 (s, 1H), 4.44-4.58 (m, 1H), 2.09-2.37 (m, 3H), 1.67 (s, 3H), 1.45-1.58 (m, 1H), 1.40 (s, 3H), 1.38-1.40 (m, 3H); MS(ES$^+$) m/z 405 (MH$^+$). |

TABLE 1-continued

| No. | Structure | Name | Starting material and method | HNMR and LCMS |
|---|---|---|---|---|
| 105 | 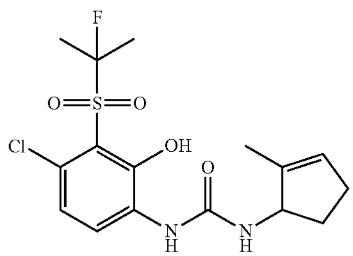 [SMILES: CC1=CCCC1NC(=O)Nc1ccc(Cl)c(S(=O)(=O)C(C)(C)F)c1O] | 1-(4-chloro-3-((2-fluoropropan-2-yl)sulfonyl)-2-hydroxyphenyl)-3-(2-methylcyclopent-2-en-1-yl)urea | Int 3 and 20, method 1 | $^1$H-NMR (400 MHz, DMSO-d$_6$) δ ppm 10.18 (br. s., 1H), 8.40 (d, J = 9.0 Hz, 1H), 8.17 (s, 1H), 7.15 (d, J = 8.8 Hz, 1H), 7.06 (d, J = 8.3 Hz, 1H), 5.51 (br. s., 1H), 4.49-4.58 (m, 1H), 2.09-2.36 (m, 3H), 1.76 (d, J = 21.6 Hz, 6H), 1.67 (s, 3H), 1.43-1.58 (m, 1H); MS(ES$^+$) m/z 391 (MH$^+$). |
| 106 | 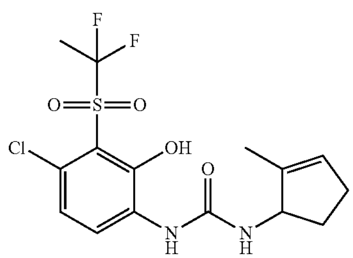 | 1-(4-chloro-3-((1,1-difluoroethyl)sulfonyl)-2-hydroxyphenyl)-3-(2-methylcyclopent-2-en-1-yl)urea | Int 3 and 83, method 1 | $^1$H-NMR (400 MHz, MeOD-d$_4$) δ ppm 8.39 (d, J = 8.8 Hz, 1H), 7.14 (d, J = 8.8 Hz, 1H), 5.51-5.58 (m, 1H), 4.58-4.70 (m, 1H), 2.29-2.43 (m, 2H), 2.24 (dtd, J = 9.4, 4.7, 2.1 Hz, 1H), 2.08 (t, J = 18.8 Hz, 3H), 1.73 (s, 3H); MS(ES$^+$) m/z 395 (MH$^+$). |
| 108 | 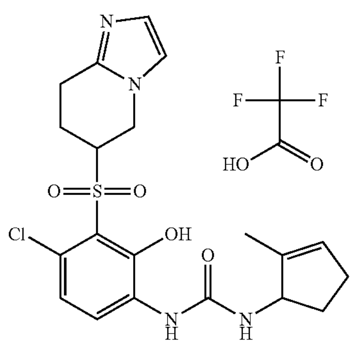 [SMILES: CC1=CCCC1NC(=O)Nc1ccc(Cl)c(S(=O)(=O)C2CCc3nccn3C2)c1O ; O=C(O)C(F)(F)F] | 1-(4-chloro-2-hydroxy-3-((5,6,7,8-etrahydroimidazo[1,2-a]pyridin-6-yl)sulfonyl)phenyl)-3-(2-methylcyclopent-2-en-1-yl)urea, trifluoroacetic acid salt | Int 3 and 84, method 1 | $^1$H-NMR (400 MHz, DMSO-d$_6$) δ ppm 8.37 (s, 1H), 8.17 (d, J = 8.5 Hz, 1H), 7.62 (s, 1H), 7.59 (s, 1H), 7.10-7.20 (m, 2H), 5.53 (br. s., 1H), 4.31-4.61 (m, 5H), 3.07-3.25 (m, 3H), 2.37-2.46 (m, 2H), 2.10-2.37 (m, 5H), 1.67 (s, 3H), 1.49-1.60 (m, 1H); MS(ES$^+$) m/z 451 (MH$^+$). |
| 109 | 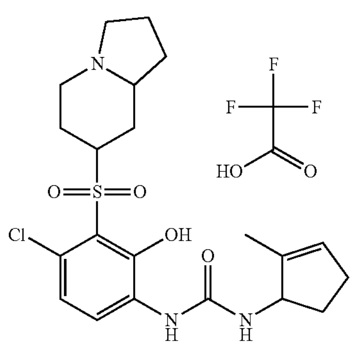 [SMILES: CC1=CCCC1NC(=O)Nc1ccc(Cl)c(S(=O)(=O)C2CCN3CCCC3C2)c1O ; O=C(O)C(F)(F)F] | 1-(4-chloro-2-hydroxy-3-((octahydroindolizin-7-yl)sulfonyl)phenyl)-3-(2-methylcyclopent-2-en-1-yl)urea, trifluoroacetic acid salt | Int 3 and 85, method 1 | $^1$H-NMR (400 MHz, DMSO-d$_6$) δ ppm 8.18-8.29 (m, 2H), 7.15 (d, J = 8.8 Hz, 1H), 7.09 (d, J = 8.3 Hz, 1H), 5.52 (br. s., 1H), 4.50-4.58 (m, 1H), 4.06-4.16 (m, 1H), 3.90 (br. s., 1H), 3.04-3.45 (m, 4H), 1.78-2.38 (m, 11H), 1.67 (s, 3H), 1.48-1.59 (m, 1H); MS(ES$^+$) m/z 454 (MH$^+$). |
| 110 | 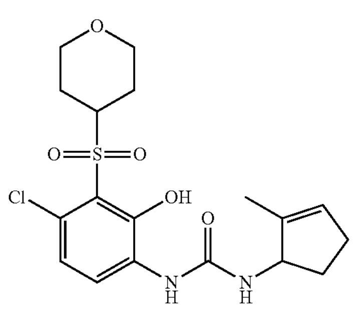 | 1-(4-chloro-2-hydroxy-3-((tetrahydro-2H-pyran-4-yl)sulfonyl)phenyl)-3-(2-methylcyclopent-2-en-1-yl)ureac | Int 3 and 86, method 1 | $^1$H-NMR (400 MHz, DMSO-d$_6$) δ ppm 10.67 (br. s., 1H), 8.36 (d, J = 9.0 Hz, 1H), 8.17 (s, 1H), 7.14 (d, J = 8.8 Hz, 1H), 7.07 (d, J = 8.3 Hz, 1H), 5.51 (br. s., 1H), 4.48-4.59 (m, 1H), 3.88-4.02 (m, 3H), 3.31-3.41 (m, 2H), 2.09-2.36 (m, 3H), 1.69-1.81 (m, 4H), 1.66 (s, 3H), 1.45-1.56 (m, 1H); MS(ES$^+$) m/z 415 (MH$^+$). |

TABLE 1-continued

| No. | Structure | Name | Starting material and method | HNMR and LCMS |
|---|---|---|---|---|
| 111 | 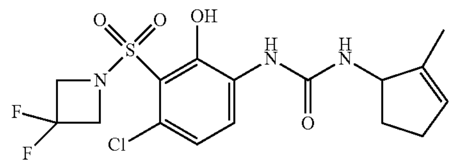 [SMILES: CC1=CCCC1NC(=O)Nc1ccc(Cl)c(S(=O)(=O)N2CC(F)(F)C2)c1O] | 1-(4-chloro-3-((3,3-difluoroazetidin-1-yl)sulfonyl)-2-hydroxyphenyl)-3-(2-methylcyclopent-2-en-1-yl)urea | Int 3 and 87, method 5 | ¹H-NMR (400 MHz, DMSO-d₆) δ ppm 10.42 (s, 1H), 8.24 (s, 1H), 8.20 (d, J = 8.9 Hz, 1H), 7.13 (d, J = 8.8 Hz, 1H), 7.09 (d, J = 8.4 Hz, 1H), 5.52 (s, 1H), 4.52 (t, J = 12.6 Hz, 5H), 2.07-2.43 (m, 3H), 1.67 (s, 3H), 1.42-1.62 (m, 1H); MS(ES⁺) m/z 422 (MH⁺). |
| 112 | 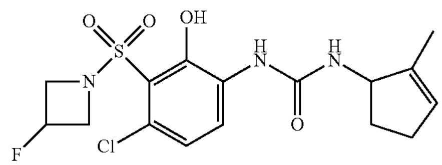 [SMILES: CC1=CCCC1NC(=O)Nc1ccc(Cl)c(S(=O)(=O)N2CC(F)C2)c1O] | 1-(4-chloro-3-((3-fluoroazetidin-1-yl)sulfonyl)-2-hydroxyphenyl)-3-(2-methylcyclopent-2-en-1-yl)urea | Int 3 and 88, method 5 | ¹H-NMR (400 MHz, DMSO-d₆) δ ppm 10.27 (s, 1H), 8.28 (d, J = 8.8 Hz, 1H), 8.18 (s, 1H), 7.13 (d, J = 8.8 Hz, 1H), 7.08 (d, J = 8.4 Hz, 1H), 5.52 (s, 1H), 5.26-5.50 (m, 1H), 4.54 (d, J = 7.2 Hz, 1H), 4.33 (m, 2H), 4.08 (m, 2H), 2.13-2.39 (m, 3H), 1.67 (s, 3H), 1.51 (m, 1H); MS(ES⁺) m/z 404 (MH⁺). |
| 113 | 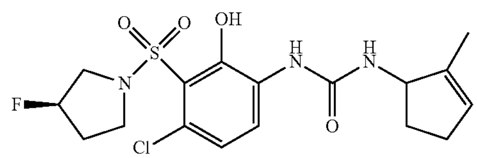 [SMILES: CC1=CCCC1NC(=O)Nc1ccc(Cl)c(S(=O)(=O)N2CC[C@@H](F)C2)c1O] | 1-(4-chloro-3-(((R)-3-fluoropyrrolidin-1-yl)sulfonyl)-2-hydroxyphenyl)-3-(2-methylcyclopent-2-en-1-yl)urea | Int 3 and 89, method 5 | ¹H-NMR (400 MHz, DMSO-d₆) δ ppm 10.50 (br, 1H), 8.27 (d, J = 8.8 Hz, 1H), 8.16 (s, 1H), 7.07 (d, J = 9.0 Hz, 2H), 5.51 (s, 1H), 5.23-5.45 (m, 1H), 4.41-4.59 (m, 1H), 3.36-3.71 (m, 4H), 2.01-2.36 (m, 5H), 1.67 (s, 3H), 1.43-1.58 (m, 1H); MS(ES⁺) m/z 418 (MH⁺). |
| 114 | 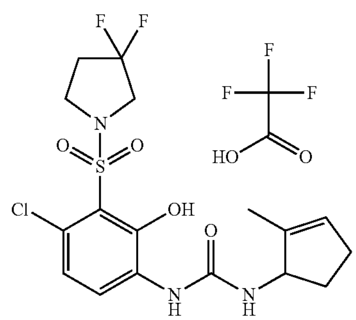 | 1-(4-chloro-3-((3,3-difluoropyrrolidin-1-yl)sulfonyl)-2-hydroxyphenyl)-3-(2-methylcyclopent-2-en-1-yl)urea, trifluoroacetic acid salt | Int 3 and 90, method 5 | ¹H-NMR (400 MHz, DMSO-d₆) δ ppm 10.48 (s, 1H), 8.23 (d, J = 12.5 Hz, 2H), 7.10 (dd, J = 13.4, 8.6 Hz, 2H), 5.52 (s, 1H), 4.54 (s, 1H), 3.80 (t, J = 12.6 Hz, 2H), 3.59 (t, J = 7.3 Hz, 2H), 2.11-2.47 (m, 5H), 1.67(s, 3H), 1.51 (d, J = 3.8 Hz, 1H); MS(ES⁺) m/z 436 (MH⁺). |
| 115 | 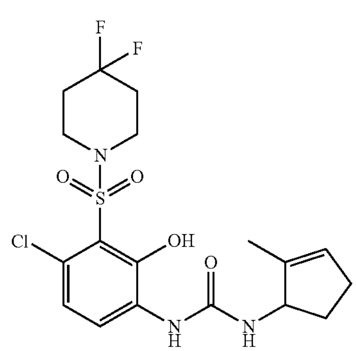 [SMILES: CC1=CCCC1NC(=O)Nc1ccc(Cl)c(S(=O)(=O)N2CCC(F)(F)CC2)c1O] | 1-(4-chloro-3-((4,4-difluoropiperidin-1-yl)sulfonyl)-2-hydroxyphenyl)-3-(2-methylcyclopent-2-en-1-yl)urea | Int 3 and 91, method 5 | ¹H-NMR (400 MHz, DMSO-d₆) δ ppm 10.43 (s, 1H), 8.26 (d, J = 8.9 Hz, 1H), 8.18 (s, 1H), 7.10 (t, J = 8.9 Hz, 2H), 5.52 (s, 1H), 4.54 (s, 1H), 3.40-3.53 (m, 4H), 3.29 (s, 1H), 2.00-2.31 (m, 7H), 1.67 (s, 3H), 1.51 (d, J = 4.1 Hz, 1H); MS(ES⁺) m/z 450 (MH⁺). |
| 116 | 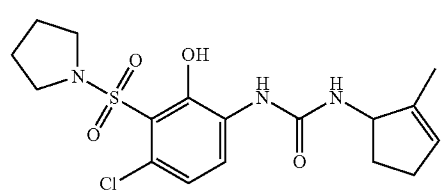 [SMILES: CC1=CCCC1NC(=O)Nc1ccc(Cl)c(S(=O)(=O)N2CCCC2)c1O] | 1-(4-chloro-2-hydroxy-3-(pyrrolidin-1-ylsulfonyl)phenyl)-3-(2-methylcyclopent-2-en-1-yl)urea | Int 3 and 92, method 5 | ¹H-NMR (400 MHz, DMSO-d₆) δ ppm 10.59 (s, 1H), 8.30 (d, J = 8.8 Hz, 1H), 8.14 (s, 1H), 6.87-7.34 (m, 2H), 5.52 (s, 1H), 4.54 (s, 1H), 3.34 (m, 4H), 2.25 (m, 3H), 1.86 (t, J = 6.4 Hz, 4H), 1.67 (s, 3H), 1.45-1.58 (m, 1H); MS(ES⁺) m/z 400 (MH⁺). |

TABLE 1-continued

| No. | Structure | Name | Starting material and method | HNMR and LCMS |
|---|---|---|---|---|
| 117 | 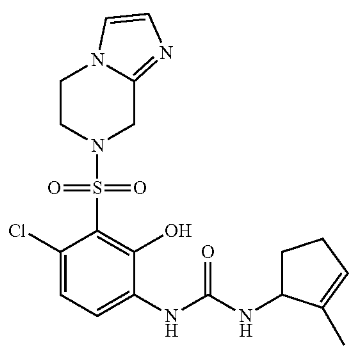 [SMILES: CC1=CCCC1NC(=O)Nc1ccc(Cl)c(S(=O)(=O)N2CCn3ccnc3C2)c1O] | 1-(4-chloro-3-((5,6-dihydroimidazo[1,2-a]pyrazin-7(8H)-yl)sulfonyl)-2-hydroxyphenyl)-3-(2-methylcyclopent-2-en-1-yl)urea | Int 3 and 93, method 5 | $^1$H-NMR (400 MHz, DMSO-d$_6$) δ ppm 8.27 (s, 1H), 8.12 (d, J = 9.0 Hz, 1H), 7.27 (s, 1H), 7.14 (s, 1H), 7.10 (d, J = 8.2 Hz, 1H), 6.91 (s, 2H), 5.50 (s, 1H), 4.48-4.60 (m, 3H), 3.99 (t, J = 4.7 Hz, 2H), 3.80 (t, J = 4.8 Hz, 2H), 2.14-2.33 (m, 3H), 1.66 (s, 3H), 1.45-1.55 (m, 1H); MS(ES$^-$) m/z 450 ((M − H)$^-$). |
| 118 | 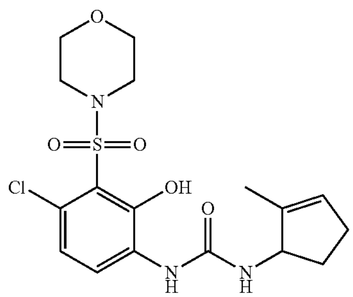 | 1-(4-chloro-2-hydroxy-3-(morpholinosulfonyl)phenyl)-3-(2-methylcyclopent-2-en-1-yl)urea | Int 3 and 94, method 5 | $^1$H-NMR (400 MHz, DMSO-d$_6$) δ ppm 10.38 (s, 1H), 8.30 (d, J = 8.9 Hz, 1H), 8.16 (s, 1H), 7.10 (dd, J = 11.8, 8.8 Hz, 2H), 5.51 (s, 1H), 4.53 (d, J = 6.4 Hz, (m, 1H), 3.59-3.66 4H), 3.24 (d, J = 4.2 Hz, 4H), 2.10-2.35 (m, 3H), 1.66 (s, 3H), 1.46-1.56 (m, 1H); MS(ES$^+$) m/z 416 (MH$^+$). |
| 119 | 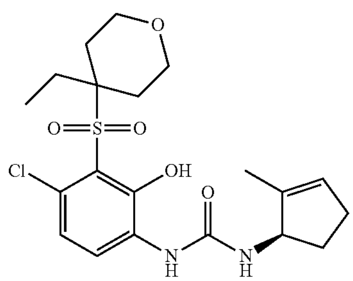 [SMILES: CCC1(S(=O)(=O)c2c(Cl)ccc(NC(=O)N[C@@H]3CCC=C3C)c2O)CCOCC1] | (R)-1-(4-chloro-3-((4-ethyltetrahydro-2H-pyran-4-yl)sulfonyl)-2-hydroxyphenyl)-3-(2-methylcyclopent-2-en-1-yl)urea | Int 2 and 95, method 1 | $^1$H-NMR (400 MHz, DMSO-d$_6$) δ ppm 10.43 (s, 1H), 8.41 (d, J = 8.8 Hz, 1H), 8.15 (s, 1H), 7.14 (d, J = 8.8 Hz, 1H), 7.05 (d, J = 8.3 Hz, 1H), 5.51 (br. s., 1H), 4.53 (d, J = 6.3 Hz, 1H), 3.81 (dd, J = 11.7, 3.1 Hz, 2H), 3.46-3.51 (m, 2H), 2.06-2.35 (m, 5H), 1.90 (td, J = 12.3, 4.8 Hz, 2H), 1.71-1.82 (m, 2H), 1.67 (s, 3H), 1.46-1.58 (m, 1H), 1.00 (t, J = 7.4 Hz, 3H); MS(ES$^+$) m/z 443 (MH$^+$). |
| 120 | 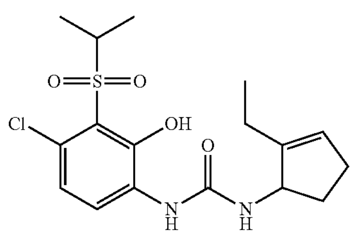 [SMILES: CCC1=CCCC1NC(=O)Nc1ccc(Cl)c(S(=O)(=O)C(C)C)c1O] | 1-(4-chloro-2-hydroxy-3-(isopropylsulfonyl)phenyl)-3-(2-ethylcyclopent-2-en-1-yl)urea | Int 9 and 21, method 1 | $^1$H-NMR (400 MHz, CDCl$_3$) δ ppm 10.90 (s, 1H), 8.43 (d, J = 8.0 Hz, 1H), 7.02 (d, J = 8.0 Hz, 1H), 6.98 (s, 1H), 5.56 (s, 1H), 4.76 (s, 1H), 3.89 (m, 1H), 2.13-2.42 (m, 4H), 1.70 (m, 6H), 1.62 (m, 6H), 1.10 (t, J = 8.0 Hz, 2H); MS(ES$^+$) m/z 387 (MH$^+$). |
| 121 | 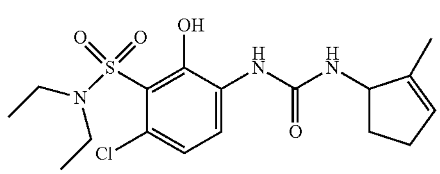 [SMILES: CCN(CC)S(=O)(=O)c1c(Cl)ccc(NC(=O)NC2CCC=C2C)c1O] | 6-chloro-N,N-diethyl-2-hydroxy-3-(3-(2-methylcyclopent-2-en-1-yl)ureido)benzenesulfonamide | Int 3 and 96, method 5 | $^1$H-NMR (400 MHz, DMSO-d$_6$) δ ppm 10.64 (s, 1H), 8.31 (d, J = 8.7 Hz, 1H), 8.14 (s, 1H), 7.08 (d, J = 8.7 Hz, 2H), 5.52 (s, 1H), 4.54 (d, J = 6.9 Hz, 1H), 3.33-3.41 (m, 4H), 2.07-2.41 (m, 3H), 1.67 (s, 3H), 1.50 (m, 1H), 1.06 (t, J = 6.9 Hz, 6H); MS(ES$^+$) m/z 402 (MH$^+$). |

TABLE 1-continued

| No. | Structure | Name | Starting material and method | HNMR and LCMS |
|---|---|---|---|---|
| 122 | 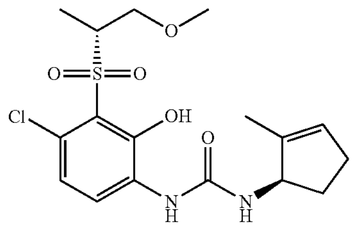 [SMILES: COC[C@@H](C)S(=O)(=O)c1c(Cl)ccc(NC(=O)N[C@@H]2CCC=C2C)c1O] | 1-(4-chloro-2-hydroxy-3-(((R)-1-methoxypropan-2-yl)sulfonyl)phenyl)-3-((R)-2-methylcyclopent-2-en-1-yl)urea | Int 2 and 97, method 5 | $^1$H-NMR (400 MHz, DMSO-d$_6$) δ ppm 10.65 (s, 1H), 8.34 (d, J = 8.8 Hz, 1H), 8.15 (s, 1H), 7.10 (d, J = 9.0 Hz, 1H), 7.06 (d, J = 8.5 Hz, 1H), 5.51 (s, 1H), 4.53 (d, J = 7.3 Hz, 1H), 4.03 (td, J = 5.0, 6.9 Hz, 1H), 3.67 (dd, J = 7.0, 10.8 Hz, 1H), 3.58 (dd, J = 4.8, 10.8 Hz, 1H), 3.09 (s, 3H), 2.10-2.36 (m, 3H), 1.66 (s, 3H), 1.45-1.58 (m, 1H), 1.30 (d, J = 7.0 Hz, 3H); MS(ES$^+$) m/z 403 (MH$^+$). |
| 123 | 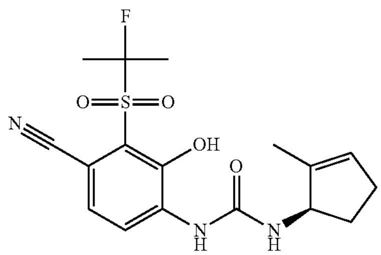 [SMILES: CC1=CCC[C@H]1NC(=O)Nc1ccc(C#N)c(S(=O)(=O)C(C)(C)F)c1O] | (R)-1-(4-cyano-3-((2-fluoropropan-2-yl)sulfonyl)-2-hydroxyphenyl)-3-(2-methylcyclopent-2-en-1-yl)urea | Int 2 and 98, method 1 | $^1$H-NMR (400 MHz, DMSO-d$_6$) δ ppm 10.22 (br. s., 1H), 8.62 (s, 1H), 8.55 (d, J = 8.6 Hz, 1H), 7.55-7.66 (m, 1H), 7.34 (d, J = 8.3 Hz, 1H), 5.52 (s, 1H), 4.54 (d, J = 6.9 Hz, 1H), 2.12-2.39 (m, 3H), 1.78 (s, 3H), 1.72 (s, 3H), 1.66 (s, 3H), 1.47-1.59 (m, 1H); MS(ES$^+$) m/z 382 (MH$^+$). |
| 124 | 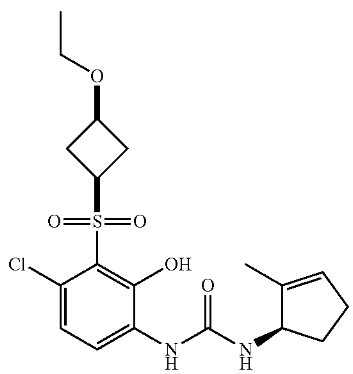 | (R)-1-(4-chloro-3-((cis-3-ethoxycyclobutyl)sulfonyl)-2-hydroxyphenyl)-3-(2-methylcyclopent-2-en-1-yl)urea | Int 2 and 99, method 1 | $^1$H-NMR (400 MHz, DMSO-d$_6$) δ ppm 10.75 (br. s., 1H), 8.30 (d, J = 8.8 Hz, 1H), 8.15 (s, 1H), 7.09 (d, J = 8.8 Hz, 1H), 7.05 (d, J = 8.5 Hz, 1H), 5.50 (br. s., 1H), 4.47-4.59 (m, 1H), 4.19 (quin, J = 8.0 Hz, 1H), 3.93 (quin, J = 7.0 Hz, 1H), 3.35-3.39 (m, 2H), 3.31-3.34 (m, 2H), 2.08-2.34 (m, 5H), 1.66 (s, 3H), 1.45-1.62 (m, 1H), 1.08 (1, J = 7.0 Hz, 3H); MS(ES$^+$) m/z 429 (MH$^+$). |
| 125 | 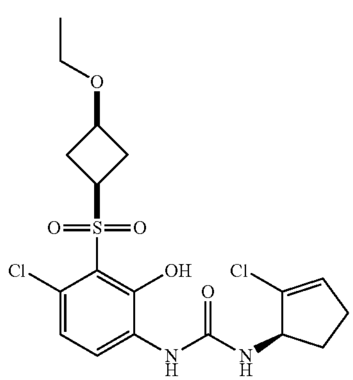 | 1-(4-chloro-3-(((1s,3s)-3-ethoxycyclobutyl)sulfonyl)-2-hydroxyphenyl)-3-(2-chlorocyclopent-2-en-1-yl)urea | Int 1 and 99, method 1 | $^1$H-NMR (400 MHz, DMSO-d$_6$) δ ppm 10.71 (br. s., 1H), 8.31 (d, J = 8.8 Hz, 1H), 8.21 (s, 1H), 7.36 (d, J = 8.8 Hz, 1H), 7.12 (d, J = 8.8 Hz, 1H), 5.94-6.02 (m, 1H), 4.68-4.79 (m, 1H), 4.13-4.27 (m, 1H), 3.81-4.00 (m, 1H), 3.35 (q, J = 7.0 Hz, 2H), 2.46-2.56 (m, 1H), 2.17-2.46 (m, 6H), 1.60-1.72 (m, 1H), 1.05-1.12 (m, 3H); MS(ES$^+$) m/z 449 (MH$^+$). |

TABLE 1-continued

| No. | Structure | Name | Starting material and method | HNMR and LCMS |
|---|---|---|---|---|
| 126 | 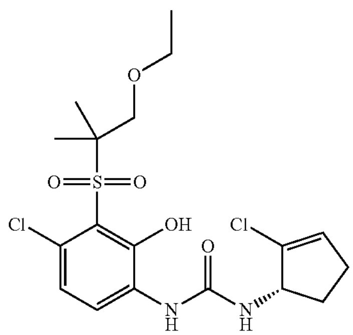 [SMILES: CCOCC(C)(C)S(=O)(=O)c1c(Cl)ccc(NC(=O)N[C@H]2CCC=C2Cl)c1O] | (S)-1-(4-chloro-3-((1-ethoxy-2-methylpropan-2-yl)sulfonyl)-2-hydroxyphenyl)-3-(2-chlorocyclopent-2-en-1-yl)urea | Int 5 and 100, method 1 | $^1$H-NMR (400 MHz, DMSO-d$_6$) δ ppm 10.34 (s, 1H), 8.35 (d, J = 9.0 Hz, 1H), 8.16 (s, 1H), 7.36 (d, J = 8.8 Hz, 1H), 7.09 (d, J = 8.8 Hz, 1H), 5.98 (s, 1H), 4.69-4.79 (m, 1H), 3.58 (s, 2H), 3.25-3.34 (m, 2H), 2.21-2.45 (m, 3H), 1.58-1.69 (m, 1H), 1.38 (s, 6H), 0.93 (t, J = 6.9 Hz, 3H); MS(ES$^+$) m/z 451 (MH$^+$). |
| 127 | 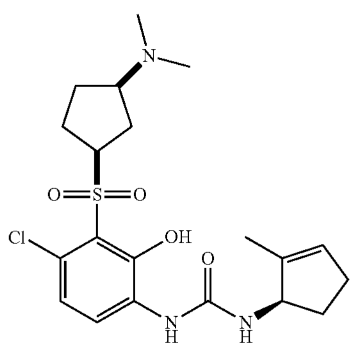 | cis-1-(4-chloro-3-((3-(dimethylamino)cyclopentyl)sulfonyl)-2-hydroxyphenyl)-3-((R)-2-methylcyclopent-2-en-1-yl)urea | Int 2 and 101, method 5 | $^1$H-NMR (400 MHz, DMSO-d$_6$) δ ppm 9.95 (br. s., 1H), 8.14 (s, 1H), 7.82 (d, J = 8.1 Hz, 1H), 6.98 (d, J = 8.1 Hz, 1H), 6.20 (d, J = 8.4 Hz, 1H), 5.46 (s, 1H), 4.82 (d, J = 5.6 Hz, 1H), 4.52 (t, J = 6.4 Hz, 1H), 3.33 (s, 1H), 2.53 (s, 6H), 2.07-2.30 (m, 5H), 1.82-1.91 (m, 3H), 1.46-1.64 (m, 5H); MS(ES$^+$) m/z 442 (MH$^+$). |
| 128 | 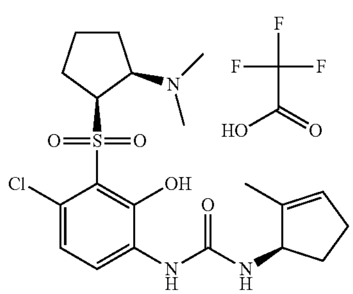 | Cis-1-(4-chloro-3-((3-(dimethylamino)cyclopentyl)sulfonyl)-2-hydroxyphenyl)-3-((R)-2-methylcyclopent-2-en-1-yl)urea | Int 2 and 102, method 5 | $^1$H-NMR (400 MHz, DMSO-d$_6$) δ ppm 9.95 (br. s., 1H), 8.14 (s, 1H), 7.82 (d, J = 8.1 Hz, 1H), 6.98 (d, J = 8.1 Hz, 1H), 6.20 (d, J = 8.4 Hz, 1H), 5.46 (s, 1H), 4.82 (d, J = 5.6 Hz, 1H), 4.52 (t, J = 6.4 Hz, 1H), 3.33 (s, 1H), 2.53 (s, 6H), 2.07-2.30 (m, 5H), 1.82-1.91 (m, 3H), 1.46-1.64 (m, 5H); MS(ES$^+$) m/z 442 (MH$^+$). |
| 129 | 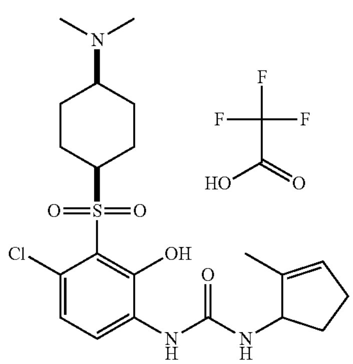 | 1-(4-chloro-3-(((1s,4s)-4-(dimethylamino)cyclohexyl)sulfonyl)-2-hydroxyphenyl)-3-(2-methylcyclopent-2-en-1-yl)urea, trifluoroacetic acid salt | Int 3 and 103, method 1 | $^1$H-NMR (400 MHz, DMSO-d$_6$) δ ppm 10.82 (br. s., 1H), 9.55 (br. s., 1H), 8.27 (d, J = 8.8 Hz, 1H), 8.22 (s, 1H), 7.14 (d, J = 8.8 Hz, 1H), 7.09 (d, J = 8.5 Hz, 1H), 5.52 (br. s., 1H), 4.49-4.60 (m, 1H), 3.80 (t, J = 4.6 Hz, 1H), 3.18-3.30 (m, 1H), 2.77 (s, 6H), 2.06-2.36 (m, 4H), 1.80-2.07 (m, 6H), 1.67 (s, 3H), 1.46-1.59 (m, 1H); MS(ES$^+$) m/z 456 (MH$^+$). |

TABLE 1-continued

| No. | Structure | Name | Starting material and method | HNMR and LCMS |
|---|---|---|---|---|
| 130 | 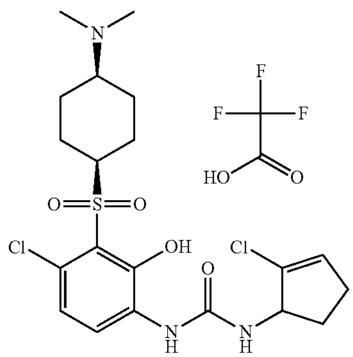 [SMILES: CN(C)[C@H]1CC[C@@H](S(=O)(=O)c2c(Cl)ccc(NC(=O)NC3CCC=C3Cl)c2O)CC1 ; O=C(O)C(F)(F)F] | 1-(4-chloro-3-((cis-4-(dimethylamino)cyclohexyl)sulfonyl)-2-hydroxyphenyl)-3-(2-chlorocyclopent-2-en-1-yl)urea, trifluoroacetic acid salt | Int 10 and 103, method 1 | $^1$H-NMR (400 MHz, DMSO-d$_6$) δ ppm 8.29 (d, J = 8.8 Hz, 1H), 8.23 (s, 1H), 7.36 (d, J = 8.8 Hz, 1H), 7.15 (d, J = 8.8 Hz, 1H), 5.97-6.01 (m, 1H), 4.71-4.79 (m, 1H), 3.78-3.84 (m, 1H), 3.19-3.35 (m, 1H), 2.77 (s, 6H), 2.24-2.46 (m, 3H), 2.06-2.19 (m, 2H), 1.82-2.06 (m, 6H), 1.61-1.72 (m, 1H); MS(ES$^+$) m/z 476 (MH$^+$). |
| 131 | 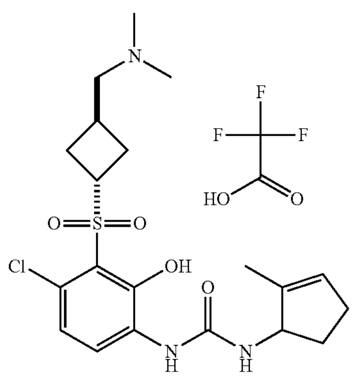 | 1-(4-chloro-3-(((1r,3r)-3-((dimethylamino)methyl)cyclobutyl)sulfonyl)-2-hydroxyphenyl)-3-(2-methylcyclopent-2-en-1-yl)urea, trifluoroacetic acid salt | Int 3 and 104, method 1 | $^1$H-NMR (400 MHz, DMSO-d$_6$) δ ppm 10.85 (br. s., 1H), 9.45 (br. s., 1H), 8.26 (d, J = 8.8 Hz, 1H), 8.22 (s, 1H), 7.08-7.17 (m, 2H), 5.52 (s, 1H), 4.45-4.60 (m, 2H), 3.17 (d, J = 6.8 Hz, 2H), 2.61-2.78 (m, 7H), 2.35-2.46 (m, 2H), 2.10-2.34 (m, 4H), 1.66 (s, 3H), 1.45-1.58 (m, 1H); MS(ES$^+$) m/z 442 (MH$^+$). |
| 132 | 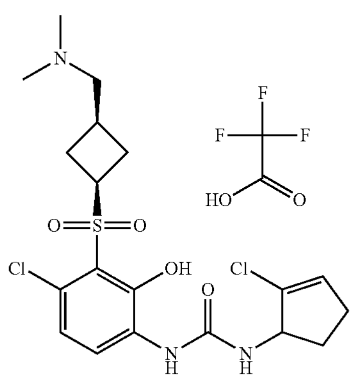 [SMILES: CN(C)C[C@H]1C[C@@H](S(=O)(=O)c2c(Cl)ccc(NC(=O)NC3CCC=C3Cl)c2O)C1 ; O=C(O)C(F)(F)F] | 1-(4-chloro-3-((cis-3-((dimethylamino)methyl)cyclobutyl)sulfonyl)-2-hydroxyphenyl)-3-(2-chlorocyclopent-2-en-1-yl)urea, trifluoroacetic acid salt | Int 10 and 105, method 1 | $^1$H-NMR (400 MHz, DMSO-d$_6$) δ ppm 10.77 (br. s., 1H), 9.42 (br. s., 1H), 8.22-8.33 (m, 2H), 7.40 (d, J = 8.5 Hz, 1H), 7.13 (d, J = 8.8 Hz, 1H), 6.00 (br. s., 1H), 4.68-4.79 (m, 1H), 4.54 (quin, J = 8.6 Hz, 1H), 3.17 (d, J = 6.8 Hz, 2H), 2.62-2.78 (m, 7H), 2.16-2.46 (m, 7H), 1.58-1.70 (m, 1H); MS(ES$^+$) m/z 462 (MH$^+$). |
| 133 | 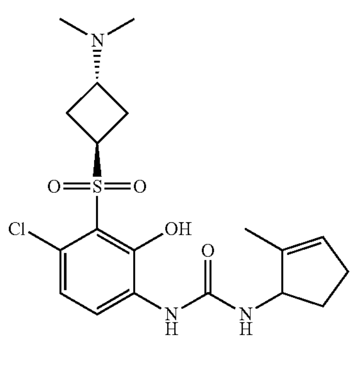 [SMILES: CC1=CCCC1NC(=O)Nc1ccc(Cl)c(S(=O)(=O)[C@H]2C[C@H](N(C)C)C2)c1O] | 1-(4-chloro-3-((trans-3-(dimethylamino)cyclobutyl)sulfonyl)-2-hydroxyphenyl)-3-(2-methylcyclopent-2-en-1-yl)urea | Int 3 and 106, method 1 | $^1$H-NMR (400 MHz, DMSO-d$_6$) δ ppm 8.14 (d, J = 10.8 Hz, 1H), 7.92-8.09 (m, 1H), 6.98 (t, J = 8.0 Hz, 1H), 6.63 (d, J = 8.5 Hz, 1H), 6.39-6.56 (m, 1H), 5.46-5.51 (m, 1H), 4.48-4.68 (m, 2H), 4.43 (t, J = 8.4 Hz, 1H), 2.92-3.02 (m, 1H), 2.37-2.47 (m, 2H), 2.08-2.37 (m, 11H), 1.65 (br. s., 3H), 1.44-1.55 (m, 1H); MS(ES$^+$) m/z 428 (MH$^+$). |

TABLE 1-continued

| No. | Structure | Name | Starting material and method | HNMR and LCMS |
|---|---|---|---|---|
| 134 | 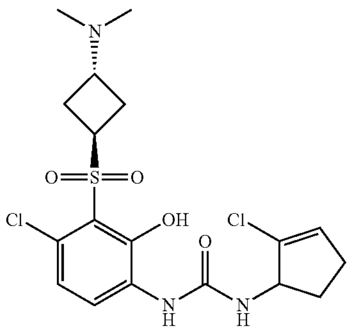 | 1-(4-chloro-3-((trans-3-(dimethylamino)cyclobutyl)sulfonyl)-2-hydroxyphenyl)-3-(2-chlorocyclopent-2-en-1-yl)urea | Int 10 and 106, method 1 | $^1$H-NMR (400 MHz, DMSO-$d_6$) δ ppm 8.17-8.23 (m, 1H), 7.88-8.04 (m, 1H), 7.26-7.33 (m, 1H), 6.40-6.65 (m, 1H), 5.93-5.97 (m, 1H), 4.58-4.78 (m, 2H), 4.45 (quin, J = 8.6 Hz, 1H), 3.01-3.11 (m, 1H), 2.20-2.47 (m, 16H), 1.57-1.71 (m, 1H); MS(ES$^+$) m/z 448 (MH$^+$). |
| 135 | 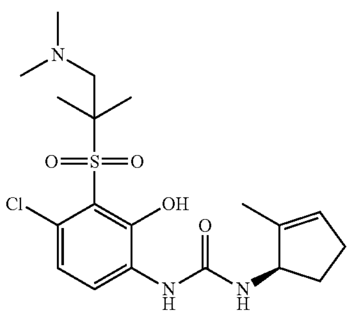 [SMILES: CC1=CCC[C@H]1NC(=O)Nc1ccc(Cl)c(S(=O)(=O)C(C)(C)CN(C)C)c1O] | (R)-1-(4-chloro-3-((1-(dimethylamino)-2-methylpropan-2-yl)sulfonyl)-2-hydroxyphenyl)-3-(2-methylcyclopent-2-en-1-yl)urea | Int 2 and 107, method 1 | $^1$H-NMR (400 MHz, DMSO-$d_6$) δ ppm 8.14 (s, 1H), 8.00 (d, J = 8.3 Hz, 1H), 7.03 (d, J = 8.3 Hz, 1H), 6.46 (d, J = 8.3 Hz, 1H), 5.48 (s, 1H), 4.48-4.57 (m, 1H), 3.14 (s, 2H), 2.70 (s, 6H), 2.10-2.34 (m, 3H), 1.65 (s, 3H), 1.44-1.56 (m, 1H), 1.40 (s, 3H), 1.40 (s, 3H); MS(ES$^+$) m/z 430 (MH$^+$). |
| 136 | 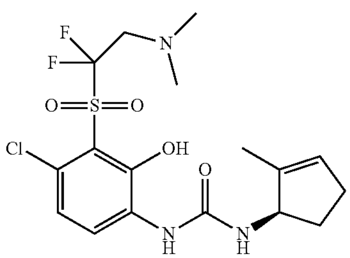 [SMILES: CC1=CCC[C@H]1NC(=O)Nc1ccc(Cl)c(S(=O)(=O)C(F)(F)CN(C)C)c1O] | (R)-1-(4-chloro-3-((2-(dimethylamino)-1,1-difluoroethyl)sulfonyl)-2-hydroxyphenyl)-3-(2-methylcyclopent-2-en-1-yl)urea | Int 2 and 108, method 1 | $^1$H-NMR (400 MHz, DMSO-$d_6$) δ ppm 8.18 (s, 1H), 8.08 (d, J = 8.5 Hz, 1H), 7.02 (d, J = 8.5 Hz, 1H), 6.64 (d, J = 8.3 Hz, 1H), 5.49 (br. s., 1H), 4.48-4.58 (m, 1H), 3.66-3.77 (m, 2H), 2.56 (s, 6H), 2.08-2.35 (m, 3H), 1.66 (s, 3H), 1.46-1.57 (m, 1H); MS(ES$^+$) m/z 438 (MH$^+$). |
| 137 | 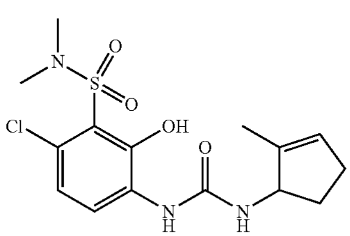 | 6-chloro-2-hydroxy-N,N-dimethyl-3-(3-(2-methylcyclopent-2-en-1-yl)ureido)benzenesulfonamide | Int 3 and 109, method 1 | $^1$H-NMR (400 MHz, DMSO-$d_6$) δ ppm 10.49 (br, 1H), 8.25 (d, J = 8.5 Hz, 1H), 8.16 (s, 1H), 7.06 (d, J = 8.4 Hz, 2H), 5.51 (s, 1H), 4.54 (s, 1H), 2.85 (s, 6H), 2.10-2.39 (m, 3H), 1.66 (s, 3H), 1.49 (dd, J = 15.3, 9.6 Hz, 1H); MS(ES$^-$) m/z 472 (M − H)$^-$. |
| 138 | 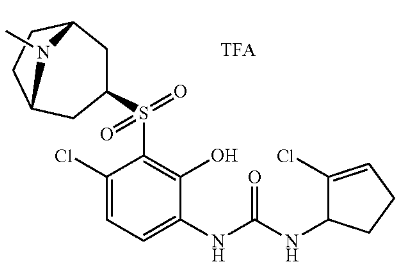 [SMILES: CN1[C@@H]2CC[C@H]1C[C@H](S(=O)(=O)c1c(Cl)ccc(NC(=O)NC3CCC=C3Cl)c1O)C2] | 1-(4-chloro-2-hydroxy-3-(((1R,3s,5S)-8-methyl-8-azabicyclo[3.2.1]octan-3-yl)sulfonyl)phenyl)-3-(2-chlorocyclopent-2-en-1-yl)urea, trifluoroacetic acid salt | Int 10 and 110, method 1 | $^1$H-NMR (400 MHz, DMSO-$d_6$) δ ppm 10.63 (br. s., 1H), 9.63 (br. s., 1H), 8.25-8.32 (m, 2H), 7.37 (d, J = 8.8 Hz, 1H), 7.16 (d, J = 9.0 Hz, 1H), 5.97-6.01 (m, 1H), 4.70-4.79 (m, 1H), 4.03-4.16 (m, 1H), 3.99 (br. s., 2H), 2.65 (br. s., 3H), 2.15-2.45 (m, 7H), 1.96-2.05 (m, 2H), 1.85-1.96 (m, 2H), 1.60-1.73 (m, 1H); MS(ES$^+$) m/z 474 (MH$^+$). |

TABLE 1-continued

| No. | Structure | Name | Starting material and method | HNMR and LCMS |
|---|---|---|---|---|
| 139 | 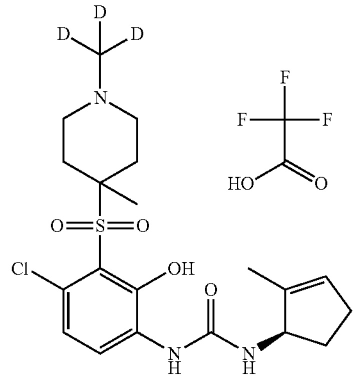 [SMILES: [2H]C([2H])([2H])N1CCC(C)(S(=O)(=O)c2c(Cl)ccc(NC(=O)N[C@@H]3CCC=C3C)c2O)CC1 ; O=C(O)C(F)(F)F] | (R)-1-(4-chloro-2-hydroxy-3-((4-methyl-1-(d3-methyl)piperidin-4-yl)sulfonyl)phenyl)-3-(2-methylcyclopent-2-en-1-yl)urea, trifluoroacetic acid salt | Int 2 and 111, method 1 | $^1$H-NMR (400 MHz, DMSO-d$_6$) δ ppm 10.34 (s, 1H), 8.40 (d, J = 9.0 Hz, 1H), 8.17 (s, 1H), 7.17 (d, J = 9.0 Hz, 1H), 7.07 (d, J = 8.3 Hz, 1H), 5.51 (s, 1H), 4.86 (t, J = 6.3 Hz, 1H), 4.74 (t, J = 6.3 Hz, 1H), 4.49-4.59 (m, 1H), 3.79-3.90 (m, 2H), 3.55 (t, J = 11.2 Hz, 2H), 2.43-2.58 (m, 1H), 2.10-2.36 (m, 3H), 1.91 (td, J = 12.4, 5.0 Hz, 2H), 1.74-1.84 (m, 2H), 1.67 (s, 3H), 1.46-1.59 (m, 1H); MS(ES$^+$) m/z 445 (MH$^+$). |
| 140 | 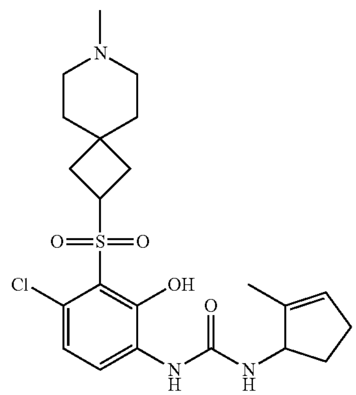 [SMILES: CC1=CCCC1NC(=O)Nc1ccc(Cl)c(S(=O)(=O)C2CC3(CCN(C)CC3)C2)c1O] | 1-(4-chloro-2-hydroxy-3-((7-methyl-7-azaspiro[3.5]nonan-2-yl)sulfonyl)phenyl)-3-(2-methylcyclopent-2-en-1-yl)urea | Int 3 and 112, method 1 | $^1$H-NMR (400 MHz, DMSO-d$_6$) δ ppm 8.15 (s, 1H), 7.82 (d, J = 8.3 Hz, 1H), 6.93 (d, J = 8.3 Hz, 1H), 6.24 (d, J = 7.8 Hz, 1H), 5.46 (br. s., 1H), 4.85 (quin, J = 8.5 Hz, 1H), 4.48-4.58 (m, 1H), 2.79 (br. s., 3H), 2.04-2.36 (m, 4H), 1.91-2.04 (m, 2H), 1.59-1.73 (m, 6H), 1.43-1.55 (m, 1H); MS(ES$^+$) m/z 468 (MH$^+$). |
| 141 | 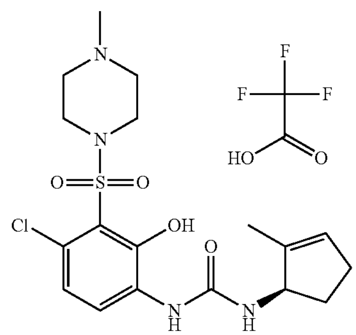 [SMILES: CC1=CCC[C@H]1NC(=O)Nc1ccc(Cl)c(S(=O)(=O)N2CCN(C)CC2)c1O ; O=C(O)C(F)(F)F] | (R)-1-(4-chloro-2-hydroxy-3-((4-methylpiperazin-1-yl)sulfonyl)phenyl)-3-(2-methylcyclopent-2-en-1-yl)urea, trifluoroacetic acid salt | Int 2 and 113, method 5 | $^1$H-NMR (400 MHz, DMSO-d$_6$) δ ppm 10.19 (br. s., 1H), 8.35 (s, 1H), 8.15 (d, J = 8.8 Hz, 1H), 7.11-7.18 (m, 2H), 5.52 (s, 1H), 4.54 (d, J = 6.5 Hz, 1H), 3.63-3.78 (m, 8H), 2.84 (s, 3H), 2.07-2.41 (m, 3H), 1.67 (s, 3H), 1.42-1.60 (m, 1H); MS(ES$^+$) m/z 429 (MH$^+$). |
| 142 | 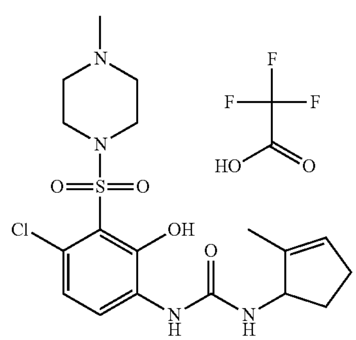 [SMILES: CC1=CCCC1NC(=O)Nc1ccc(Cl)c(S(=O)(=O)N2CCN(C)CC2)c1O ; O=C(O)C(F)(F)F] | 1-(4-chloro-2-hydroxy-3-((4-methylpiperazin-1-yl)sulfonyl)phenyl)-3-(2-methylcyclopent-2-en-1-yl)urea, trifluoroacetic acid salt | Int 3 and 113, method 5 | $^1$H-NMR (400 MHz, DMSO-d$_6$) δ ppm 10.45 (s, 1H), 8.32 (s, 1H), 8.16 (d, J = 8.8 Hz, 1H), 7.14 (m, 2H), 5.52 (s, 1H), 4.54 (m, 4H), 3.54 (m, 4H), 2.83 (s, 3H), 1.96-2.40 (m, 3H), 1.67 (s, 3H), 1.44-1.60 (m, 1H); MS(ES$^+$) m/z 429 (MH$^+$). |

TABLE 1-continued

| No. | Structure | Name | Starting material and method | HNMR and LCMS |
|---|---|---|---|---|
| 143 | 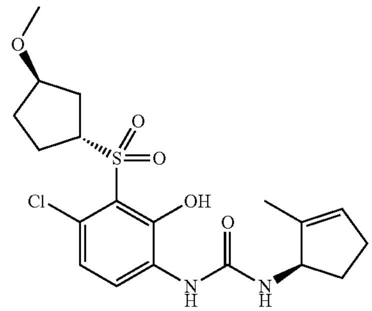 [SMILES: CO[C@@H]1CC[C@@H](S(=O)(=O)c2c(Cl)ccc(NC(=O)N[C@@H]3CCC=C3C)c2O)C1] | trans-1-(4-chloro-2-hydroxy-3-((3-methoxycyclopentyl)sulfonyl)phenyl)-3-((R)-2-methylcyclopent-2-en-1-yl)urea | Int 2 and 114, method 2 | $^1$H-NMR (400 MHz, DMSO-d$_6$) δ ppm 10.78 (s, 1H), 8.36 (d, J = 8.8 Hz, 1H), 8.17 (s, 1H), 7.13 (d, J = 8.9 Hz, 1H), 7.08 (d, J = 8.4 Hz, 1H), 5.52 (s, 1H), 4.59-4.47 (m, 1H), 4.30-4.16 (m, 1H), 3.90-3.77 (m, 1H), 3.18 (s, 3H), 2.36-2.12 (m, 4H), 2.03-1.91 (m, 1H), 1.87-1.72 (m, 4H), 1.67 (s, 3H), 1.56-1.46 (m, 1H); MS(ES$^+$) m/z 429 (MH$^+$). |
| 144 | 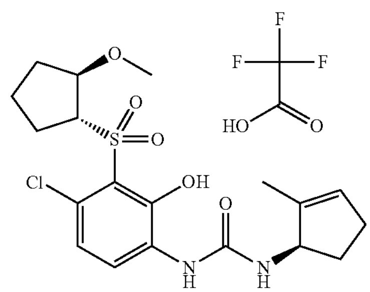 | (±)trans-1-(4-chloro-2-hydroxy-3-((2-methoxycyclopentyl)sulfonyl)phenyl)-3-((R)-2-methylcyclopent-2-en-1-yl)urea, trifluoroacetic acid salt | Int 2 and 115, method 2 | $^1$H-NMR (400 MHz, DMSO-d$_6$) δ ppm 10.74 (s, 1H), 8.33 (dd, J = 8.8, 2.6 Hz, 1H), 8.18 (s, 1H), 7.14 (d, J = 8.9 Hz, 1H), 7.08 (d, J = 8.4 Hz, 1H), 5.52 (s, 1H), 4.47-4.58 (m, 1H), 4.04-4.13 (m, 2H), 3.06 (s, 3H), 2.13-2.36 (m, 3H), 1.99-2.09 (m, 1H), 1.81-1.94 (m, 2H), 1.69-1.78 (m, 3H), 1.67 (s, 3H), 1.46-1.57 (m, 1H); MS(ES$^+$) m/z 429 (MH$^+$). |
| 145 | 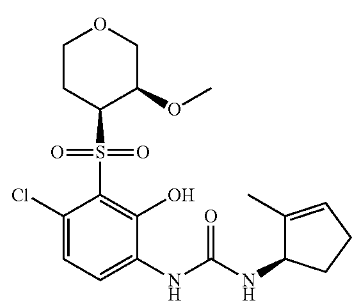 [SMILES: CO[C@@H]1COCC[C@@H]1S(=O)(=O)c1c(Cl)ccc(NC(=O)N[C@@H]2CCC=C2C)c1O] | 1-(4-chloro-2-hydroxy-3-(((3R,4S)-3-methoxytetrahydro-2H-pyran-4-yl)sulfonyl)phenyl)-3-((R)-2-methylcyclopent-2-en-1-yl)urea | Int 2 and 116, method 1 | $^1$H-NMR (400 MHz, DMSO-d$_6$) δ ppm 10.69 (s, 1H), 8.28 (d, J = 8.8 Hz, 1H), 8.14 (s, 1H), 7.05-7.10 (m, 1H), 7.03 (d, J = 8.3 Hz, 1H), 5.51 (br. s., 1H), 4.48-4.58 (m, 1H), 4.13 (dd, J = 10.8, 4.8 Hz, 1H), 3.86-3.99 (m, 2H), 3.63 (td, J = 9.9, 4.8 Hz, 1H), 3.40-3.45 (m, 1H), 3.11 (s, 3H), 3.03 (t, J = 10.4 Hz, 1H), 2.11-2.35 (m, 3H), 2.04 (dd, J = 13.3, 4.0 Hz, 1H), 1.71-1.81 (m, 1H), 1.67 (s, 3H), 1.47-1.58 (m, 1H); MS(ES$^+$) m/z 445 (MH$^+$). |
| 146 | 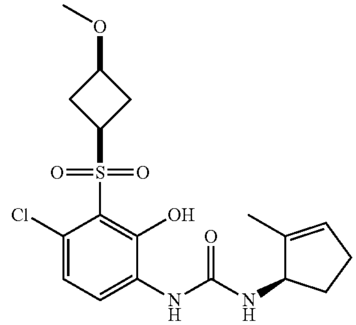 | 1-(4-chloro-2-hydroxy-3-((cis-3-methoxycyclobutyl)sulfonyl)phenyl)-3-((R)-2-methylcyclopent-2-en-1-yl)urea | Int 2 and 117, method 1 | $^1$H-NMR (400 MHz, DMSO-d$_6$) δ ppm 10.74 (br. s., 1H), 8.30 (d, J = 8.8 Hz, 1H), 8.16 (s, 1H), 7.10 (d, J = 8.8 Hz, 1H), 7.04 (s, 1H), 5.51 (br. s., 1H), 4.53 (d, J = 6.5 Hz, 1H), 4.21 (t, J = 8.4 Hz, 1H), 3.86 (t, J = 6.9 Hz, 1H), 3.14 (s, 3H), 2.10-2.39 (m, 5H), 1.67 (s, 3H), 1.45-1.59 (m, 1H); MS(ES$^+$) m/z 415 (MH$^+$). |

TABLE 1-continued

| No. | Structure | Name | Starting material and method | HNMR and LCMS |
|---|---|---|---|---|
| 147 | 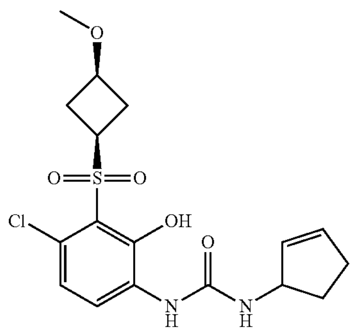 [SMILES: CO[C@H]1C[C@@H](S(=O)(=O)c2c(Cl)ccc(NC(=O)NC3C=CCC3)c2O)C1] | 1-(4-chloro-2-hydroxy-3-((cis-3-methoxycyclobutyl)sulfonyl)phenyl)-3-(cyclopent-2-en-1-yl)urea | Int 4 and 117, method 1 | $^1$H-NMR (400 MHz, DMSO-d$_6$) δ ppm 10.74 (br. s., 1H), 8.28 (d, J = 8.8 Hz, 1H), 8.15 (s, 1H), 7.01-7.19 (m, 2H), 5.84-5.99 (m, 1H), 5.65-5.76 (m, 1H), 4.61-4.75 (m, 1H), 4.10-4.31 (m, 1H), 3.80-3.93 (m, 1H), 3.13 (s, 3H), 2.31-2.46 (m, 2H), 2.11-2.29 (m, 4H), 1.41-1.53 (m, 1H); MS(ES$^+$) m/z 401 (MH$^+$). |
| 148 | 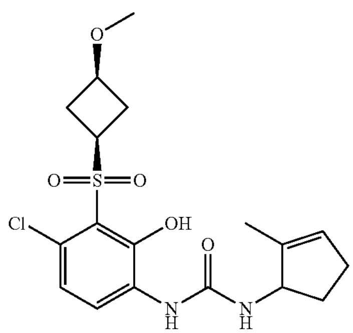 [SMILES: CO[C@H]1C[C@@H](S(=O)(=O)c2c(Cl)ccc(NC(=O)NC3CCC=C3C)c2O)C1] | 1-(4-chloro-2-hydroxy-3-((cis-3-methoxycyclobutyl)sulfonyl)phenyl)-3-(2-methylcyclopent-2-en-1-yl)urea | Int 3 and 117, method 1 | $^1$H-NMR (400 MHz, DMSO-d$_6$) δ ppm 10.74 (br. s., 1H), 8.31 (d, J = 9.0 Hz, 1H), 8.18 (s, 1H), 7.08 (d, J = 8.5 Hz, 1H), 7.11 (d, J = 8.8 Hz, 1H), 5.51 (br. s., 1H), 4.53 (br. s., 1H), 4.22 (quin, J = 8.5 Hz, 1H), 3.85 (quin, J = 7.0 Hz, 1H), 3.02-3.21 (m, 3H), 2.10-2.38 (m, 5H), 1.66 (s, 3H), 1.40-1.58 (m, 1H); MS(ES$^+$) m/z 415 (MH$^+$). |
| 149 | 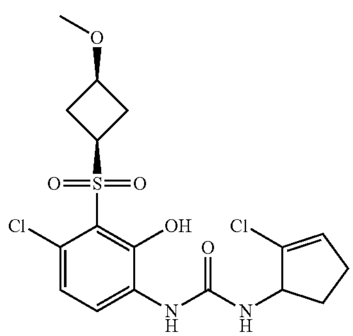 [SMILES: CO[C@H]1C[C@@H](S(=O)(=O)c2c(Cl)ccc(NC(=O)NC3CCC=C3Cl)c2O)C1] | 1-(4-chloro-2-hydroxy-3-((cis-3-methoxycyclobutyl)sulfonyl)phenyl)-3-(2-chlorocyclopent-2-en-1-yl)urea | Int 10 and 117, method 1 | $^1$H-NMR (400 MHz, DMSO-d$_6$) δ ppm 10.70 (br. s., 1H), 8.31 (d, J = 8.8 Hz, 1H), 8.23 (s, 1H), 7.38 (d, J = 8.8 Hz, 1H), 7.13 (d, J = 8.8 Hz, 1H), 5.99 (br. s., 1H), 4.73 (br. s., 1H), 4.14-4.31 (m, 1H), 3.85 (quin, J = 7.0 Hz, 1H), 3.03-3.18 (m, 3H), 2.33-2.45 (m, 2H), 2.30 (d, J = 9.0 Hz, 1H), 2.21 (q, J = 9.5 Hz, 2H), 1.54-1.75 (m, 1H); MS(ES$^+$) m/z 435 (MH$^+$). |
| 150 | 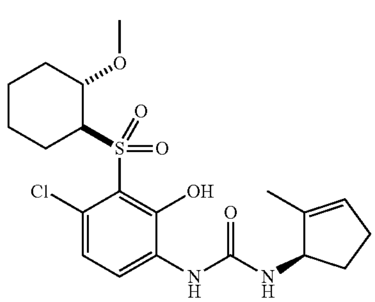 | (±)trans-1-(4-chloro-2-hydroxy-3-((2-methoxycyclohexyl)sulfonyl)phenyl)-3-((R)-2-methylcyclopent-2-en-1-yl)urea | Int 2 and 118, method 2 | $^1$H-NMR (500 MHz, DMSO-d$_6$) δ ppm 10.68 (s, 1H), 8.29 (t, J = 8.4 Hz, 1H), 8.12 (br. s., 1H), 6.93-7.14 (m, 2H), 5.51 (br. s., 1H), 4.53 (br. s., 1H), 3.62-3.70 (m, 1H), 3.52-3.61 (m, 1H), 3.42 (br. s., 1H), 2.22-2.37 (m, 2H), 2.21 (br. s., 1H), 2.17 (br. s., 3H), 1.81 (d, J = 12.3 Hz, 1H), 1.66 (br. s., 4H), 1.40-1.58 (m, 2H), 1.18-1.37 (m, 2H), 1.03-1.16 (m, 1H); MS(ES$^+$) m/z 443 (MH$^+$). |

TABLE 1-continued

| No. | Structure | Name | Starting material and method | HNMR and LCMS |
|---|---|---|---|---|
| 151 | 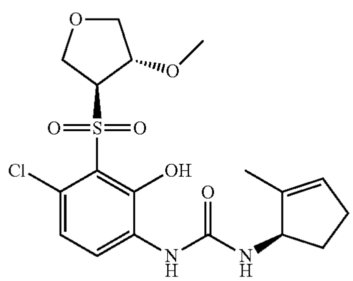 [SMILES: CO[C@H]1COC[C@@H]1S(=O)(=O)c1c(Cl)ccc(NC(=O)N[C@@H]2CCC=C2C)c1O] | 1-(4-chloro-2-hydroxy-3-(((3S,4S)-4-methoxytetrahydrofuran-3-yl)sulfonyl)phenyl)-3-((R)-2-methylcyclopent-2-en-1-yl)urea | Int 2 and 119, method 1 | $^1$H-NMR (400 MHz, DMSO-$d_6$) δ ppm 10.84 (br. s., 1H), 8.19-8.30 (m, 2H), 7.15 (d, J = 8.8 Hz, 1H), 7.07 (d, J = 8.8 Hz, 1H), 5.52 (br. s., 1H), 4.55 (br. s., 1H), 4.37-4.43 (m, 1H), 4.33 (br. s., 1H), 4.16 (dd, J = 8.0, 10.3 Hz, 1H), 3.97 (dt, J = 5.2, 10.2 Hz, 2H), 3.72 (dd, J = 3.3, 9.8 Hz, 1H), 3.14 (s, 3H), 2.09-2.37 (m, 3H), 1.67 (s, 3H), 1.47-1.59 (m, 1H); MS(ES$^+$) m/z 431 (MH$^+$). |
| 152 | 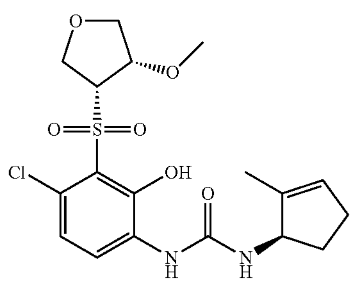 [SMILES: CO[C@H]1COC[C@H]1S(=O)(=O)c1c(Cl)ccc(NC(=O)N[C@@H]2CCC=C2C)c1O] | 1-(4-chloro-2-hydroxy-3-(((3R,4S)-4-methoxytetrahydrofuran-3-yl)sulfonyl)phenyl)-3-((R)-2-methylcyclopent-2-en-1-yl)urea | Int 2 and 120, method 1 | $^1$H-NMR (400 MHz, DMSO-$d_6$) δ ppm 10.56 (s, 1H), 8.37 (d, J = 8.8 Hz, 1H), 8.15 (s, 1H), 7.12 (d, J = 8.8 Hz, 1H), 7.03 (d, J = 8.3 Hz, 1H), 5.51 (br. s., 1H), 4.71-4.84 (m, 1H), 4.54 (d, J = 7.0 Hz, 1H), 4.31 (dd, J = 6.2, 9.4 Hz, 1H), 4.05-4.17 (m, 2H), 3.88 (dd, J = 3.0, 9.5 Hz, 1H), 3.70 (dd, J = 4.0, 9.5 Hz, 1H), 2.93 (s, 3H), 2.09-2.39 (m, 3H), 1.67 (s, 3H), 1.44-1.58 (m, 1H); MS(ES$^+$) m/z 431 (MH$^+$). |
| 153 | 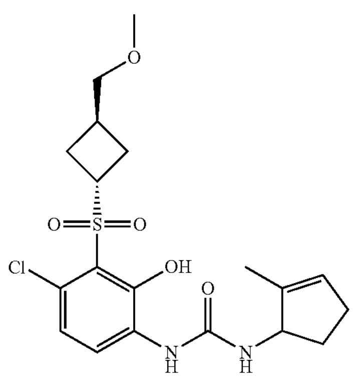 [SMILES: COC[C@H]1C[C@H](S(=O)(=O)c2c(Cl)ccc(NC(=O)NC3CCC=C3C)c2O)C1] | 1-(4-chloro-2-hydroxy-3-((trans-3-(methoxymethyl)cyclobutyl)sulfonyl)phenyl)-3-(2-methylcyclopent-2-en-1-yl)urea | Int 3 and 121, method 1 | $^1$H-NMR (400 MHz, DMSO-$d_6$) δ ppm 10.81 (br. s., 1H), 8.31 (d, J = 8.8 Hz, 1H), 8.16 (s, 1H), 7.10 (d, J = 8.8 Hz, 1H), 7.07 (d, J = 8.5 Hz, 1H), 5.51 (br. s., 1H), 4.39-4.62 (m, 2H), 3.37 (d, J = 6.3 Hz, 2H), 3.18-3.27 (m, 3H), 2.54-2.70 (m, 1H), 2.39-2.48 (m, 2H), 2.14-2.35 (m, 3H), 2.08 (ddd, J = 5.1, 8.9,13.6 Hz, 2H), 1.66 (s, 3H), 1.36-1.58 (m, 1H); MS(ES$^+$) m/z 429 (MH$^+$). |
| 154 | 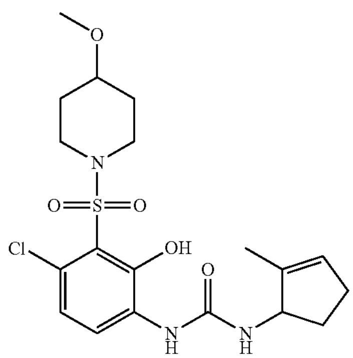 [SMILES: COC1CCN(S(=O)(=O)c2c(Cl)ccc(NC(=O)NC3CCC=C3C)c2O)CC1] | 1-(4-chloro-2-hydroxy-3-((4-methoxypiperidin-1-yl)sulfonyl)phenyl)-3-(2-methylcyclopent-2-en-1-yl)urea | Int 3 and 122, method 4 | $^1$H-NMR (400 MHz, CDCl$_3$) δ ppm 10.60 (s, 1H), 8.31 (d, J = 8.8 Hz, 1H), 7.10 (s, 1H), 6.98 (d, J = 8.8 Hz, 1H), 5.54 (br. s., 1H), 4.95 (d, J = 8.3 Hz, 1H), 4.69 (br. s., 1H), 3.45-3.56 (m, 2H), 3.41 (tt, J = 3.3, 6.7 Hz, 1H), 3.33 (s, 3H), 3.15-3.28 (m, 2H), 2.31-2.48 (m, 2H), 2.17-2.31 (m, 1H), 1.78-1.95 (m, 4H), 1.64-1.72 (m, 2H); MS(ES$^+$) m/z 444 (MH$^+$). |

TABLE 1-continued

| No. | Structure | Name | Starting material and method | HNMR and LCMS |
|---|---|---|---|---|
| 155 | 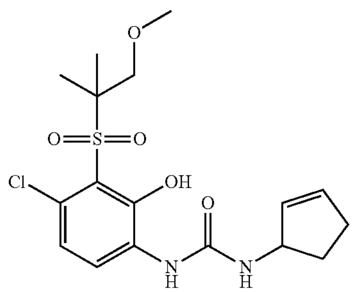 [SMILES: COCC(C)(C)S(=O)(=O)c1c(Cl)ccc(NC(=O)NC2C=CCC2)c1O] | 1-(4-chloro-2-hydroxy-3-((1-methoxy-2-methylpropan-2-yl)sulfonyl)phenyl)-3-(cyclopent-2-en-1-yl)urea | Int 4 and 123, method 1 | $^1$H-NMR (400 MHz, CDCl$_3$) δ ppm 10.55 (br. s., 1H), 8.39 (br. s., 1H), 7.04 (br. s., 2H), 5.99 (br. s., 1H), 5.76 (br. s., 1H), 4.90 (br. s., 1H), 4.73 (br. s., 1H), 3.48-3.68 (m, 2H), 3.12-3.42 (m, 3H), 2.39 (br. s., 3H), 1.61 (br. s., 5H), 1.27-1.57 (m, 8H); MS(ES$^+$) m/z 403 (MH$^+$). |
| 156 | 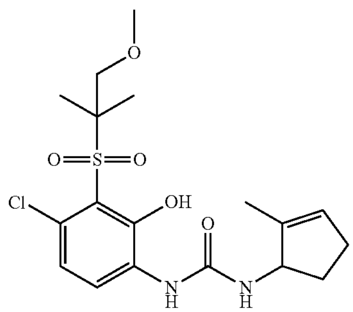 [SMILES: COCC(C)(C)S(=O)(=O)c1c(Cl)ccc(NC(=O)NC2CCC=C2C)c1O] | 1-(4-chloro-2-hydroxy-3-((1-methoxy-2-methylpropan-2-yl)sulfonyl)phenyl)-3-(2-methylcyclopent-2-en-1-yl)urea | Int 3 and 123, method 1 | $^1$H-NMR (400 MHz, DMSO-d$_6$) δ ppm 10.32 (s, 1H), 8.37 (d, J = 8.8 Hz, 1H), 8.11 (s, 1H), 7.04 (d, J = 8.5 Hz, 1H), 7.08 (d, J = 8.8 Hz, 1H), 5.51 (s, 1H), 4.46-4.62 (m, 1H), 3.54 (s, 2H), 3.18 (s, 3H), 2.12-2.38 (m, 3H), 1.67 (s, 3H), 1.47-1.60 (m, 1H), 1.37 (s, 6H); MS(ES$^+$) m/z 417 (MH$^+$). |
| 157 | 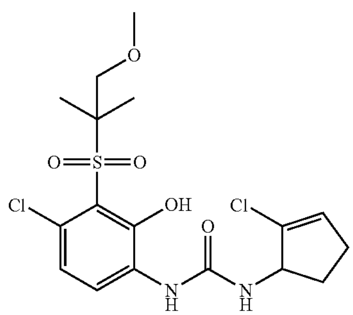 | 1-(4-chloro-2-hydroxy-3-((1-methoxy-2-methylpropan-2-yl)sulfonyl)phenyl)-3-(2-chlorocyclopent-2-en-1-yl)urea | Int 10 and 123, method 1 | $^1$H-NMR (400 MHz, DMSO-d$_6$) δ ppm 10.31 (s, 1H), 8.35 (d, J = 8.8 Hz, 1H), 8.16 (s, 1H), 7.33 (d, J = 8.5 Hz, 1H), 7.09 (d, J = 8.8 Hz, 1H), 5.98 (d, J = 1.8 Hz, 1H), 4.64-4.81 (m, 1H), 3.54 (s, 2H), 3.17 (s, 3H), 2.20-2.45 (m, 3H), 1.59-1.71 (m, 1H), 1.37 (s, 6H); MS(ES$^+$) m/z 403 (MH$^+$). |
| 158 | 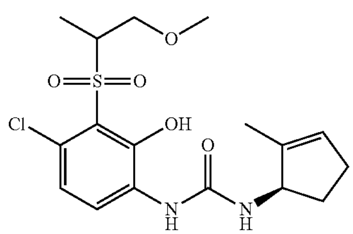 | 1-(4-chloro-2-hydroxy-3-((1-methoxypropan-2-yl)sulfonyl)phenyl)-3-((R)-2-methylcyclopent-2-en-1-yl)urea | Int 2 and 124, method 1 | $^1$H-NMR (400 MHz, DMSO-d$_6$) δ ppm 10.66 (br. s., 1H), 8.31 (dd, J = 2.4, 8.9 Hz, 1H), 8.13 (s, 1H), 7.03 (d, J = 8.3 Hz, 1H), 7.07 (d, J = 8.8 Hz, 1H), 5.51 (br. s., 1H), 4.53 (d, J = 6.3 Hz, 1H), 3.94-4.13 (m, 1H), 3.68 (dd, J = 6.8, 10.8 Hz, 1H), 3.58 (dd, J = 5.0, 10.8 Hz, 1H), 3.11 (s, 3H), 2.09-2.36 (m, 3H), 1.67 (s, 3H), 1.44-1.58 (m, 1H), 1.20-1.37 (m, 3H); MS(ES$^+$) m/z 403 (MH$^+$). |
| 159 | 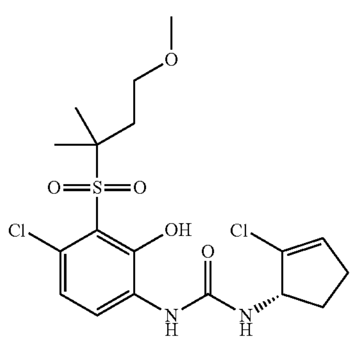 | (S)-1-(4-chloro-2-hydroxy-3-((4-methoxy-2-methylbutan-2-yl)sulfonyl)phenyl)-3-(2-chlorocyclopent-2-en-1-yl)urea | Int 5 and 125, method 1 | $^1$H-NMR (400 MHz, DMSO-d$_6$) δ ppm 10.39 (s, 1H), 8.40 (d, J = 8.8 Hz, 1H), 8.21 (s, 1H), 7.36 (d, J = 8.8 Hz, 1H), 7.15 (d, J = 9.0 Hz, 1H), 5.99 (d, J = 1.8 Hz, 1H), 4.74 (dt, J = 2.8, 5.5 Hz, 1H), 3.48 (t, J = 6.7 Hz, 2H), 3.21 (s, 3H), 2.35-2.46 (m, 2H), 2.21-2.35 (m, 1H), 1.97 (t, J = 6.7 Hz, 2H), 1.64 (dd, J = 5.5, 9.8 Hz, 1H), 1.36 (s, 6H); MS(ES$^+$) m/z 451 (MH$^+$). |

TABLE 1-continued

| No. | Structure | Name | Starting material and method | HNMR and LCMS |
|---|---|---|---|---|
| 160 | 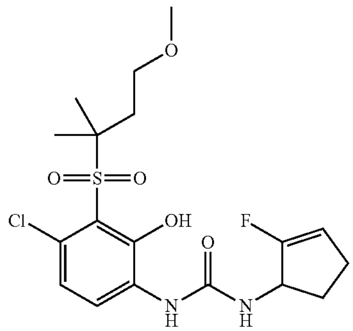 [SMILES: COCCC(C)(C)S(=O)(=O)c1c(Cl)ccc(NC(=O)NC2CCC=C2F)c1O] | 1-(4-chloro-2-hydroxy-3-((4-methoxy-2-methylbutan-2-yl)sulfonyl)phenyl)-3-(2-fluorocyclopent-2-en-1-yl)urea | Int 8 and 125, method 1 | $^1$H-NMR (400 MHz, DMSO-d$_6$) δ ppm 10.40 (s, 1H), 8.38 (d, J = 8.8 Hz, 1H), 8.15 (s, 1H), 7.37 (d, J = 8.3 Hz, 1H), 7.14 (d, J = 9.0 Hz, 1H), 5.31 (br. s., 1H), 4.75 (br. s., 1H), 3.48 (t, J = 6.5 Hz, 2H), 3.21 (s, 3H), 2.31-2.42 (m, 1H), 2.26 (m, 1H), 2.19 (d, J = 7.3 Hz, 1H), 1.97 (t, J = 6.5 Hz, 2H), 1.54-1.67 (m, 1H), 1.36 (s, 6H); MS(ES$^+$) m/z 435 (MH$^+$). |
| 161 | 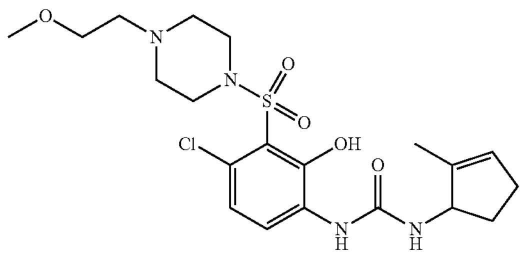 [SMILES: COCCN1CCN(S(=O)(=O)c2c(Cl)ccc(NC(=O)NC3CCC=C3C)c2O)CC1] | 1-(4-chloro-2-hydroxy-3-((4-(2-methoxyethyl)piperazin-1-yl)sulfonyl)phenyl)-3-(2-methylcyclopent-2-en-1-yl)urea | Int 3 and 126, method 5 | $^1$H-NMR (400 MHz, DMSO-d$_6$) δ ppm 10.48 (br. s., 1H), 8.23 (s, 2H), 7.10 (d, J = 8.0 Hz, 1H), 6.92 (br. s., 1H), 5.54 (br. s., 1H), 4.58 (br. s., 1H), 3.43-3.48 (m, 3H), 3.26-3.31 (m, 4H), 3.25 (s, 4H), 2.53 (br. s., 2H), 2.12-2.39 (m, 4H), 1.64-1.75 (m, 4H), 1.46-1.63 (m, 1H); MS(ES$^+$) m/z 473 (MH$^+$). |
| 162 | 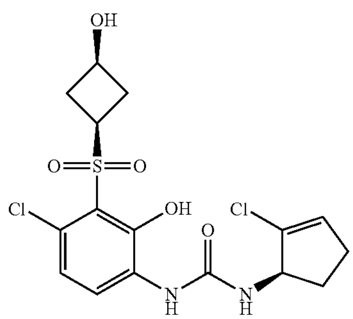 [SMILES: O=C(Nc1ccc(Cl)c(S(=O)(=O)[C@H]2C[C@@H](O)C2)c1O)N[C@@H]1CCC=C1Cl] | 1-(4-chloro-2-hydroxy-3-((cis-3-hydroxycyclobutyl)sulfonyl)phenyl)-3-((R)-2-chlorocyclopent-2-en-1-yl)urea | Int 1 and 77, method 1 | $^1$H-NMR (400 MHz, DMSO-d$_6$) δ ppm 10.74 (br. s., 1H), 8.31 (d, J = 8.8 Hz, 1H), 8.20 (s, 1H), 7.34 (d, J = 8.8 Hz, 1H), 7.09 (d, J = 9.0 Hz, 1H), 5.99 (s, 1H), 5.52 (d, J = 6.5 Hz, 1H), 4.73 (br. s., 1H), 3.93-4.13 (m, 2H), 2.35-2.47 (m, 4H), 2.27-2.34 (m, 1H), 2.14-2.27 (m, 2H), 1.59-1.72 (m, 1H); MS(ES$^+$) m/z 421 (MH$^+$). |
| 163 | 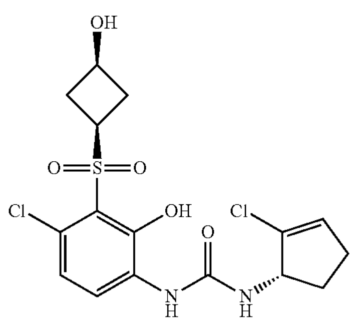 [SMILES: O=C(Nc1ccc(Cl)c(S(=O)(=O)[C@H]2C[C@@H](O)C2)c1O)N[C@H]1CCC=C1Cl] | 1-(4-chloro-2-hydroxy-3-((cis-3-hydroxycyclobutyl)sulfonyl)phenyl)-3-((S)-2-chlorocyclopent-2-en-1-yl)urea | Int 5 and 77, method 1 | $^1$H-NMR (400 MHz, DMSO-d$_6$) δ ppm 10.75 (s, 1H), 8.32 (d, J = 8.8 Hz, 1H), 8.22 (s, 1H), 7.33-7.42 (m, 1H), 7.05-7.17 (m, 1H), 5.99 (d, J = 1.8 Hz, 1H), 4.69-4.81 (m, 2H), 4.03-4.12 (m, 2H), 2.44-2.48 (m, 1H), 2.35-2.40 (m, 2H), 2.27-2.35 (m, 1H), 2.14-2.26 (m, 2H), 1.55-1.76 (m, 1H); MS(ES$^+$) m/z 421 (MH$^+$). |
| 164 | 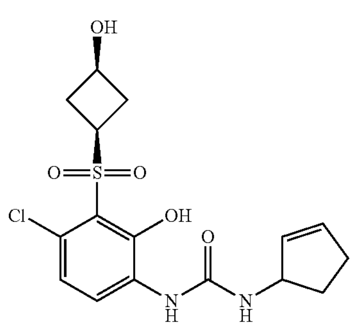 [SMILES: O=C(Nc1ccc(Cl)c(S(=O)(=O)[C@H]2C[C@@H](O)C2)c1O)NC1C=CCC1] | 1-(4-chloro-2-hydroxy-3-((cis-3-hydroxycyclobutyl)sulfonyl)phenyl)-3-(cyclopent-2-en-1-yl)urea | Int 4 and 77, method 1 | $^1$H-NMR (400 MHz, DMSO-d$_6$) δ ppm 10.76 (s, 1H), 8.30 (d, J = 9.0 Hz, 1H), 8.13 (s, 1H), 7.05-7.17 (m, 2H), 5.93 (dd, J = 1.9, 5.4 Hz, 1H), 5.71 (dd, J = 2.0, 5.5 Hz, 1H), 4.64-4.74 (m, 1H), 4.02-4.13 (m, 2H), 2.32-2.46 (m, 3H), 2.10-2.31 (m, 4H), 1.40-1.54 (m, 1H); MS(ES$^+$) m/z 387 (MH$^+$). |

| No. | Structure | Name | Starting material and method | HNMR and LCMS |
|---|---|---|---|---|
| 165 | 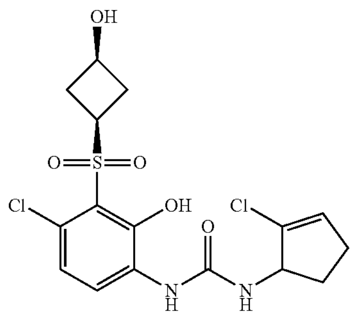 [SMILES: O=C(Nc1ccc(Cl)c(S(=O)(=O)[C@H]2C[C@@H](O)C2)c1O)NC1CCC=C1Cl] | 1-(4-chloro-2-hydroxy-3-((cis-3-hydroxycyclobutyl)sulfonyl)phenyl)-3-(2-chlorocyclopent-2-en-1-yl)urea | Int 10 and 77, method 1 | $^1$H-NMR (400 MHz, DMSO-$d_6$) δ ppm 10.75 (s, 1H), 8.32 (d, J = 8.8 Hz, 1H), 8.10-8.27 (m, 1H), 7.37 (d, J = 8.8 Hz, 1H), 7.12 (d, J = 8.8 Hz, 1H), 5.99 (br. s., 1H), 4.73 (br. s., 1H), 3.98-4.16 (m, 2H), 2.34-2.47 (m, 4H), 2.25-2.34 (m, 1H), 2.10-2.24 (m, 2H), 1.53-1.71 (m, 1H); MS(ES$^+$) m/z 421 (MH$^+$). |
| 166 | 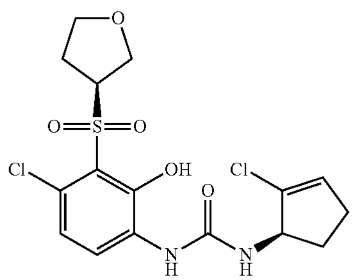 [SMILES: O=C(Nc1ccc(Cl)c(S(=O)(=O)[C@H]2CCOC2)c1O)N[C@@H]1CCC=C1Cl] | 1-(4-chloro-2-hydroxy-3-(((S)-tetrahydrofuran-3-yl)sulfonyl)phenyl)-3-((R)-2-chlorocyclopent-2-en-1-yl)urea | Int 1 and 81, method 1 | $^1$H-NMR (400 MHz, DMSO-$d_6$) δ ppm 10.72 (br. s., 1H), 8.26 (d, J = 8.8 Hz, 1H), 8.24 (s, 1H), 7.35 (d, J = 8.8 Hz, 1H), 7.05 (d, J = 8.8 Hz, 1H), 5.98 (d, J = 1.8 Hz, 1H), 4.70-4.87 (m, 1H), 4.57-4.68 (m, 1H), 4.02-4.07 (m, 1H), 3.86-3.95 (m, 2H), 3.64-3.74 (m, 1H), 2.36-2.45 (m, 2H), 2.26-2.36 (m, 1H), 2.09-2.23 (m, 2H), 1.57-1.73 (m, 1H); MS(ES$^+$) m/z 421 (MH$^+$). |
| 167 | 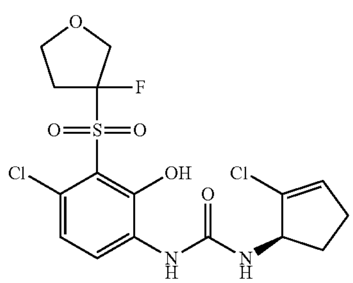 [SMILES: O=C(Nc1ccc(Cl)c(S(=O)(=O)C2(F)CCOC2)c1O)N[C@@H]1CCC=C1Cl] | 1-(4-chloro-3-((3-fluorotetrahydrofuran-3-yl)sulfonyl)-2-hydroxyphenyl)-3-((R)-2-chlorocyclopent-2-en-1-yl)urea | Int 1 and 57, method 1 | $^1$H-NMR (400 MHz, DMSO-$d_6$) δ ppm 8.18-8.43 (m, 2H), 7.37 (d, J = 9.0 Hz, 1H), 7.19 (d, J = 8.8 Hz, 1H), 5.99 (d, J = 1.8 Hz, 1H), 4.67-4.82 (m, 1H), 4.34-4.51 (m, 1H), 3.94-4.12 (m, 4H), 2.73-2.96 (m, 1H), 2.17-2.46 (m, 4H), 1.56-1.79 (m, 1H); MS(ES$^+$) m/z 439 (MH$^+$). |
| 168 | 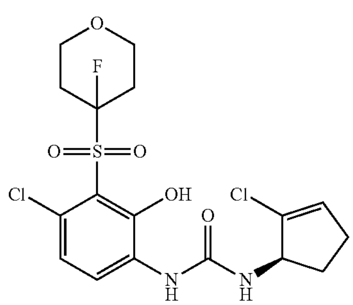 | (R)-1-(4-chloro-3-((4-fluorotetrahydro-2H-pyran-4-yl)sulfonyl)-2-hydroxyphenyl)-3-(2-chlorocyclopent-2-en-1-yl)urea | Int 1 and 58, method 1 | $^1$H-NMR (400 MHz, DMSO-$d_6$) δ ppm 10.16 (br. s., 1H), 8.39 (d, J = 8.8 Hz, 1H), 8.25 (s, 1H), 7.40 (d, J = 8.8 Hz, 1H), 7.18 (d, J = 8.8 Hz, 1H), 5.99 (br. s., 1H), 4.73 (br. s., 1H), 3.98 (dd, J = 5.0, 11.5 Hz, 2H), 3.48-3.56 (m, 3H), 2.16-2.45 (m, 5H), 1.91 (t, J = 12.1 Hz, 2H), 1.54-1.70 (m, 1H); MS(ES$^+$) m/z 453 (MH$^+$). |

TABLE 1-continued

| No. | Structure | Name | Starting material and method | HNMR and LCMS |
|---|---|---|---|---|
| 169 | 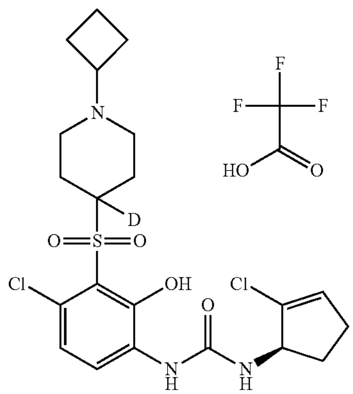 [SMILES: [2H]C1(S(=O)(=O)c2c(Cl)ccc(NC(=O)N[C@@H]3CCC=C3Cl)c2O)CCN(C2CCC2)CC1 ; O=C(O)C(F)(F)F] | (R)-1-(4-chloro-3-((1-cyclobutylpiperidin-4-yl)sulfonyl)-2-hydroxyphenyl)-3-(2-chlorocyclopent-2-en-1-yl)urea-d₁, trifluoroacetic acid salt | Int 1 and 64, method 1 | $^1$H-NMR (400 MHz, DMSO-d$_6$) δ ppm 10.66 (br. s., 1H), 9.45 (br. s., 1H), 8.20-8.39 (m, 2H), 7.38 (d, J = 8.8 Hz, 1H), 7.17 (t, J = 4.4 Hz, 1H), 5.95-6.03 (m, 1H), 4.66-4.83 (m, 1H), 3.45 (br. s., 3H), 3.17 (s, 1H), 2.75-3.00 (m, 2H), 2.25-2.47 (m, 3H), 2.04-2.24 (m, 6H), 1.95 (br. s., 2H), 1.60-1.83 (m, 3H); MS(ES$^+$) m/z 489 (MH$^+$). |
| 170 | 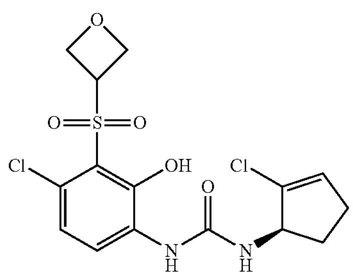 [SMILES: O=C(Nc1ccc(Cl)c(S(=O)(=O)C2COC2)c1O)N[C@@H]1CCC=C1Cl] | (R)-1-(4-chloro-2-hydroxy-3-(oxetan-3-ylsulfonyl)phenyl)-3-(2-chlorocyclopent-2-en-1-yl)urea | Int 1 and 126, method 1 | $^1$H-NMR (400 MHz, DMSO-d$_6$) δ ppm 8.30 (d, J = 8.8 Hz, 1H), 8.23 (s, 1H), 7.27 (dd, J = 3.3, 8.5 Hz, 1H), 7.15 (d, J = 8.8 Hz, 1H), 5.99 (br. s., 1H), 4.65-4.92 (m, 3H), 3.98 (dd, J = 5.1, 11.2 Hz, 1H), 3.81-3.91 (m, 1H), 3.66-3.75 (m, 2H), 2.20-2.45 (m, 3H), 1.51-1.69 (m, 1H); MS(ES+) m/z 407 (MH+). |
| 171 | 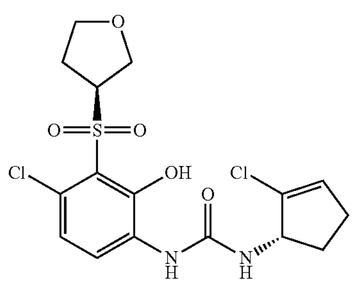 [SMILES: O=C(Nc1ccc(Cl)c(S(=O)(=O)[C@H]2CCOC2)c1O)N[C@H]1CCC=C1Cl] | 1-(4-chloro-2-hydroxy-3-(((S)-tetrahydrofuran-3-yl)sulfonyl)phenyl)-3-((S)-2-chlorocyclopent-2-en-1-yl)urea | Int 5 and 81, method 1 | $^1$H-NMR (400 MHz, DMSO-d$_6$) δ ppm 10.71 (br. s., 1H), 8.31 (d, J = 8.8 Hz, 1H), 8.24 (s, 1H), 7.36 (d, J = 8.8 Hz, 1H), 7.15 (d, J = 8.8 Hz, 1H), 5.99 (s, 1H), 4.68-4.87 (m, 1H), 4.46-4.67 (m, 1H), 4.04 (dd, J = 4.0, 10.3 Hz, 1H), 3.87-3.98 (m, 2H), 3.63-3.76 (m, 1H), 2.35-2.46 (m, 2H), 2.10-2.35 (m, 3H), 1.52-1.73 (m, 1H); MS(ES$^+$) m/z 421 (MH$^+$). |
| 172 | 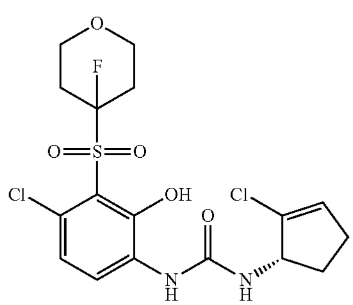 | (S)-1-(4-chloro-3-((4-fluorotetrahydro-2H-pyran-4-yl)sulfonyl)-2-hydroxyphenyl)-3-(2-chlorocyclopent-2-en-1-yl)urea | Int 5 and 58, method 1 | $^1$H-NMR (400 MHz, DMSO-d$_6$) δ ppm 10.16 (br. s., 1H), 8.39 (d, J = 8.8 Hz, 1H), 8.25 (s, 1H), 7.39 (d, J = 8.8 Hz, 1H), 7.18 (d, J = 8.8 Hz, 1H), 5.99 (s, 1H), 4.65-4.80 (m, 1H), 3.97 (dd, J = 5.3, 11.5 Hz, 2H), 3.49 (t, J = 11.4 Hz, 3H), 2.17-2.47 (m, 5H), 1.91 (t, J = 12.3 Hz, 2H), 1.55-1.73 (m, 1H); MS(ES$^+$) m/z 453 (MH$^+$). |
| 173 | 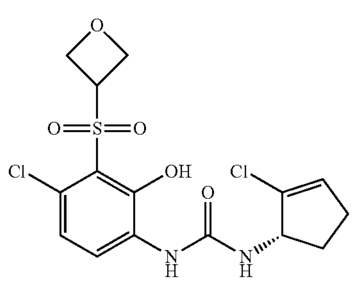 [SMILES: O=C(Nc1ccc(Cl)c(S(=O)(=O)C2COC2)c1O)N[C@H]1CCC=C1Cl] | (S)-1-(4-chloro-2-hydroxy-3-(oxetan-3-ylsulfonyl)phenyl)-3-(2-chlorocyclopent-2-en-1-yl)urea | Int 5 and 126, method 1 | $^1$H-NMR (400 MHz, DMSO-d$_6$) δ ppm 8.29 (dd, J = 1.5, 8.8 Hz, 1H), 8.21 (s, 1H), 7.25 (dd, J = 2.9, 8.7 Hz, 1H), 7.14 (d, J = 8.8 Hz, 1H), 5.99 (s, 1H), 5.29-5.43 (m, 1H), 4.77-4.88 (m, 2H), 4.66-4.76 (m, 1H), 3.99 (dt, J = 5.2, 10.9 Hz, 1H), 3.81-3.91 (m, 1H), 3.62-3.77 (m, 1H), 2.23-2.45 (m, 3H), 1.57-1.72 (m, 1H); MS(ES$^+$) m/z 407 (MH$^+$). |

TABLE 1-continued

| No. | Structure | Name | Starting material and method | HNMR and LCMS |
|---|---|---|---|---|
| 174 | 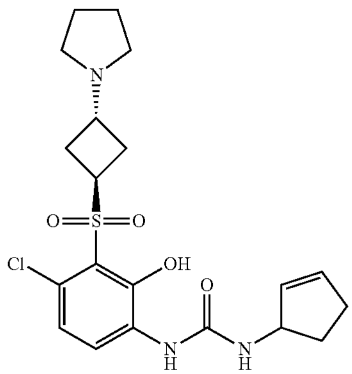 [SMILES: O=C(Nc1ccc(Cl)c(S(=O)(=O)[C@H]2C[C@H](N3CCCC3)C2)c1O)NC1C=CCC1] | 1-(4-chloro-2-hydroxy-3-((trans-3-(pyrrolidin-1-yl)cyclobutyl)sulfonyl)phenyl)-3-(cyclopent-2-en-1-yl)urea | Int 4 and 78, method 1 | $^1$H-NMR (400 MHz, DMSO-$d_6$) δ ppm 7.06 (d, J = 8.0 Hz, 1H), 6.19-6.40 (m, 1H), 5.79-5.95 (m, 1H), 5.59-5.75 (m, 1H), 5.20-5.48 (m, 1H), 4.67 (br. s., 1H), 4.57 (t, J = 8.5 Hz, 1H), 3.61 (br. s., 2H), 3.09 (br. s., 3H), 2.87 (br. s., 2H), 2.59-2.81 (m, 4H), 2.37 (d, J = 7.3 Hz, 3H), 2.07-2.25 (m, 2H), 1.81 (br. s., 2H), 1.67 (br. s., 3H), 1.38 (d, J = 15.3 Hz, 1H); MS(ES$^+$) m/z 440 (MH$^+$). |
| 175 | 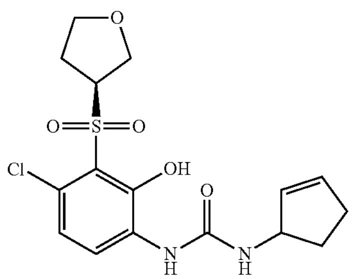 [SMILES: O=C(Nc1ccc(Cl)c(S(=O)(=O)[C@H]2CCOC2)c1O)NC1C=CCC1] | 1-(4-chloro-2-hydroxy-3-(((S)-tetrahydrofuran-3-yl)sulfonyl)phenyl)-3-(cyclopent-2-en-1-yl)urea | Int 4 and 81, method 1 | $^1$H-NMR (400 MHz, DMSO-$d_6$) δ ppm 10.77 (br. s., 1H), 8.29 (d, J = 8.8 Hz, 1H), 8.16 (s, 1H), 7.15 (s, 1H), 7.06-7.13 (m, 1H), 5.87-6.02 (m, 1H), 5.66-5.76 (m, 1H), 4.64-4.81 (m, 1H), 4.57 (td, J = 4.6, 8.6 Hz, 1H), 4.04 (dd, J = 4.1, 10.4 Hz, 1H), 3.88-3.99 (m, 2H), 3.62-3.74 (m, 1H), 2.33-2.46 (m, 1H), 2.06-2.32 (m, 4H), 1.50 (td, J = 4.9, 8.0 Hz, 1H); MS(ES$^+$) m/z 387 (MH$^+$). |
| 176 | 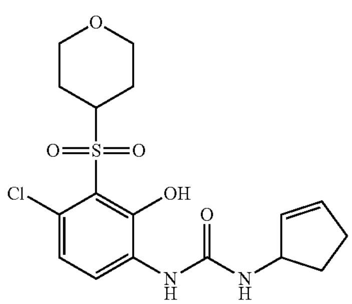 [SMILES: O=C(Nc1ccc(Cl)c(S(=O)(=O)C2CCOCC2)c1O)NC1C=CCC1] | 1-(4-chloro-2-hydroxy-3-((tetrahydro-2H-pyran-4-yl)sulfonyl)phenyl)-3-(cyclopent-2-en-1-yl)urea | Int 4 and 86, method 1 | $^1$H-NMR (400 MHz, DMSO-$d_6$) δ ppm 10.68 (br. s., 1H), 8.33 (d, J = 8.8 Hz, 1H), 8.13 (s, 1H), 7.11-7.15 (m, 2H), 5.93-5.95 (m, 1H), 5.71-5.73 (m, 1H), 4.69-4.71 (m, 1H), 3.94-3.97 (m, 3H), 3.30-3.45 (m, 2H), 2.37-2.44 (m, 1H), 2.21-2.29 (m, 2H), 1.73-1.78 (m, 4H), 1.25-1.53 (m, 1H); MS(ES$^+$) m/z 401 (MH$^+$). |
| 177 | 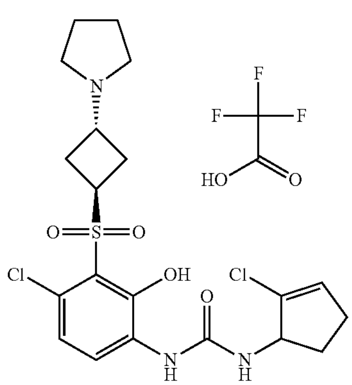 [SMILES: O=C(Nc1ccc(Cl)c(S(=O)(=O)[C@H]2C[C@H](N3CCCC3)C2)c1O)NC1CCC=C1Cl ; O=C(O)C(F)(F)F] | 1-(4-chloro-2-hydroxy-3-((trans-3-(pyrrolidin-1-yl)cyclobutyl)sulfonyl)phenyl)-3-(2-chlorocyclopent-2-en-1-yl)urea, trifluoroacetic acid salt | Int 10 and 78, method 1 | $^1$H-NMR (400 MHz, DMSO-$d_6$) δ ppm 11.25 (br. s., 1H), 10.83 (br. s., 1H), 8.40 (d, J = 6.3 Hz, 1H), 8.21 (d, J = 8.8 Hz, 1H), 7.39-7.52 (m, 1H), 7.10-7.25 (m, 1H), 5.99 (br. s., 1H), 4.74 (br. s., 1H), 4.62 (br. s., 1H), 4.34-4.52 (m, 1H), 3.99 (br. s., 1H), 2.93 (br. s., 2H), 2.64-2.87 (m, 4H), 2.35-2.45 (m, 2H), 2.20-2.35 (m, 1H), 1.96 (br. s., 4H), 1.66 (d, J = 5.8 Hz, 1H); MS(ES$^+$) m/z 474 (MH$^+$). |

TABLE 1-continued

| No. | Structure | Name | Starting material and method | HNMR and LCMS |
|---|---|---|---|---|
| 178 | 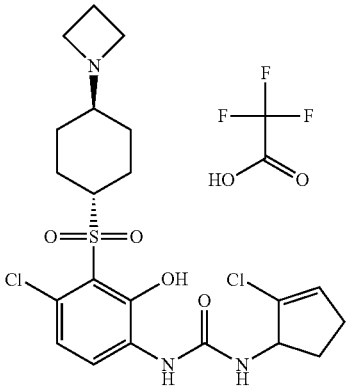 [SMILES: O=C(Nc1ccc(Cl)c(S(=O)(=O)[C@H]2CC[C@H](N3CCC3)CC2)c1O)NC1CCC=C1Cl ; O=C(O)C(F)(F)F] | 1-(3-((trans-4-(azetidin-1-yl)cyclohexyl)sulfonyl)-4-chloro-2-hydroxyphenyl)-3-(2-chlorocyclopent-2-en-1-yl)urea, trifluoroacetic acid salt | Int 10 and 79, method 1 | $^1$H-NMR (400 MHz, DMSO-d$_6$) δ ppm 10.74 (br. s., 1H), 9.82 (br. s., 1H), 8.30 (d, J = 8.8 Hz, 1H), 8.24 (s, 1H), 7.35 (d, J = 8.5 Hz, 1H), 7.15 (d, J = 9.0 Hz, 1H), 5.99 (br. s., 1H), 4.74 (br. s., 1H), 3.92-4.18 (m, 4H), 3.69-3.79 (m, 1H), 2.25-2.46 (m, 5H), 2.16 (br. s., 1H), 1.88 (br. s., 2H), 1.79 (br. s., 6H), 1.54-1.70 (m, 1H); MS(ES$^+$) m/z 487 (MH$^+$). |
| 179 | 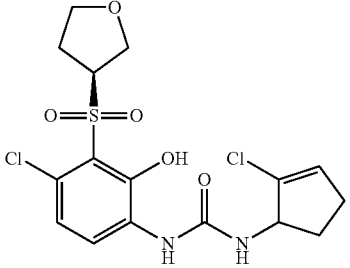 [SMILES: O=C(Nc1ccc(Cl)c(S(=O)(=O)[C@H]2CCOC2)c1O)NC1CCC=C1Cl] | 1-(4-chloro-2-hydroxy-3-(((S)-tetrahydrofuran-3-yl)sulfonyl)phenyl)-3-(2-chlorocyclopent-2-en-1-yl)urea | Int 10 and 81, method 1 | $^1$H-NMR (400 MHz, DMSO-d$_6$) δ ppm 10.71 (br. s., 1H), 8.32 (d, J = 8.8 Hz, 1H), 8.25 (s, 1H), 7.38 (d, J = 8.8 Hz, 1H), 7.16 (d, J = 9.0 Hz, 1H), 5.91-6.06 (m, 1H), 4.70-4.81 (m, 1H), 4.57 (dt, J = 4.3, 8.2 Hz, 1H), 4.04 (dd, J = 4.0, 10.3 Hz, 1H), 3.87-3.99 (m, 2H), 3.69 (q, J = 7.3 Hz, 1H), 2.34-2.46 (m, 2H), 2.10-2.34 (m, 3H), 1.49-1.73 (m, 1H); MS(ES$^+$) m/z 421 (MH$^+$). |
| 180 | 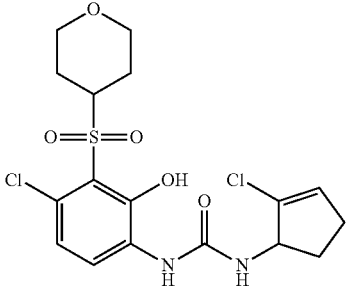 [SMILES: O=C(Nc1ccc(Cl)c(S(=O)(=O)C2CCOCC2)c1O)NC1CCC=C1Cl] | 1-(4-chloro-2-hydroxy-3-((tetrahydro-2H-pyran-4-yl)sulfonyl)phenyl)-3-(2-chlorocyclopent-2-en-1-yl)urea | Int 10 and 86, method 1 | $^1$H-NMR (400 MHz, DMSO-d$_6$) δ ppm 10.64 (br. s., 1H), 8.33-8.43 (m, 1H), 8.20 (br. s., 1H), 7.35 (d, J = 7.8 Hz, 1H), 7.04-7.22 (m, 1H), 5.98 (br. s., 1H), 4.73 (br. s., 1H), 3.95 (d, J = 8.8 Hz, 3H), 2.39 (dd, J = 1.9, 4.4 Hz, 2H), 2.19-2.35 (m, 1H), 1.74 (br. s., 4H), 1.60-1.71 (m, 1H); MS(ES$^+$) m/z 435 (MH$^+$). |
| 181 | 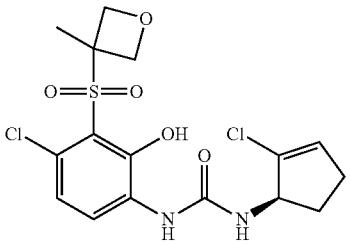 [SMILES: CC1(S(=O)(=O)c2c(Cl)ccc(NC(=O)N[C@@H]3CCC=C3Cl)c2O)COC1] | (R)-1-(4-chloro-2-hydroxy-3-((3-methyloxetan-3-yl)sulfonyl)phenyl)-3-(2-chlorocyclopent-2-en-1-yl)urea | Int 1 and 127, method 1 | $^1$H-NMR (400 MHz, DMSO-d$_6$) δ ppm 8.30-8.39 (m, 1H), 8.24 (s, 1H), 7.30 (s, 1H), 7.16 (d, J = 8.8 Hz, 1H), 5.99 (br. s., 1H), 4.72 (br. s., 1H), 4.63 (dd, J 3.5, 12.8 Hz, 1H), 4.51 (dd, J = 5.9, 12.7 Hz, 1H), 3.67-3.77 (m, 3H), 2.25-2.45 (m, 3H), 1.59-1.72 (m, 1H), 1.35 (s, 3H); MS(ES$^+$) m/z 421 (MH$^+$). |
| 182 | 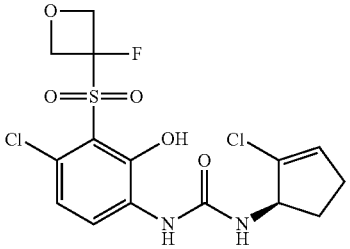 [SMILES: O=C(Nc1ccc(Cl)c(S(=O)(=O)C2(F)COC2)c1O)N[C@@H]1CCC=C1Cl] | (R)-1-(4-chloro-3-((3-fluorooxetan-3-yl)sulfonyl)-2-hydroxyphenyl)-3-(2-chlorocyclopent-2-en-1-yl)urea | Int 1 and 128, method 1 | $^1$H-NMR (400 MHz, DMSO-d$_6$) δ ppm 8.24-8.45 (m, 2H), 7.18-7.34 (m, 2H), 6.00 (m, 1H), 5.04-5.15 (m, 1H), 4.90-5.04 (m, 1H), 4.72 (br. s., 1H), 3.98-4.21 (m, 2H), 2.16-2.45 (m, 3H), 1.64 (d, J = 5.3 Hz, 1H); MS(ES$^+$) m/z 425 (MH$^+$). |

TABLE 1-continued

| No. | Structure | Name | Starting material and method | HNMR and LCMS |
|---|---|---|---|---|
| 183 | 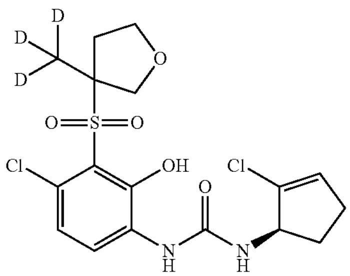 [SMILES: [2H]C([2H])([2H])C1(S(=O)(=O)c2c(Cl)ccc(NC(=O)N[C@@H]3CCC=C3Cl)c2O)CCOC1] | 1-(4-chloro-2-hydroxy-3-((3-(d₃-methyl)tetrahydro-furan-3-yl)sulfonyl)phenyl)-3-((R)-2-chlorocyclopent-2-en-1-yl)urea | Int 1 and 129, method 1 | ¹H-NMR (400 MHz, DMSO-d₆) δ ppm 10.48 (br. s., 1H), 8.38 (br. s., 1H), 8.25 (br. s., 1H), 7.29-7.52 (m, 1H), 7.17 (br. s., 1H), 5.99 (br. s., 1H), 4.74 (br. s., 1H), 4.34 (br. s., 1H), 3.82 (br. s., 3H), 2.66 (br. s., 1H), 2.38 (br. s., 3H), 1.96 (br. s., 1H), 1.65 (br. s., 1H); MS(ES⁺) m/z 438 (MH⁺). |
| 184 | 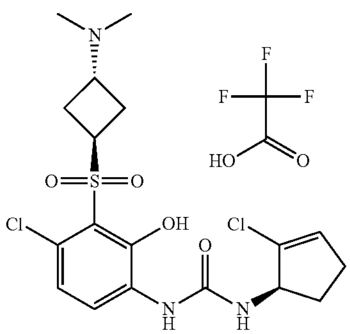 [SMILES: CN(C)[C@H]1C[C@H](S(=O)(=O)c2c(Cl)ccc(NC(=O)N[C@@H]3CCC=C3Cl)c2O)C1 ; O=C(O)C(F)(F)F] | 1-(4-chloro-3-((trans-3-(dimethylamino)cyclobutyl)sulfonyl)-2-hydroxyphenyl)-3-((R)-2-chlorocyclopent-2-en-1-yl)urea, trifluoroacetic acid salt | Int 1 and 106, method 1 | ¹H-NMR (400 MHz, DMSO-d₆) δ ppm 10.40 (br. s., 1H), 8.34 (s, 1H), 8.20 (d, J = 8.8 Hz, 1H), 7.40 (d, J = 8.8 Hz, 1H), 7.13 (d, J = 8.8 Hz, 1H), 5.99 (d, J = 1.7 Hz, 1H), 4.68-4.81 (m, 1H), 4.39-4.53 (m, 1H), 3.98 (quin, J = 7.9 Hz, 1H), 2.59-2.83 (m, 13H), 2.21-2.45 (m, 4H), 1.59-1.73 (m, 1H); MS(ES⁺) m/z 448 (MH⁺). |
| 185 | 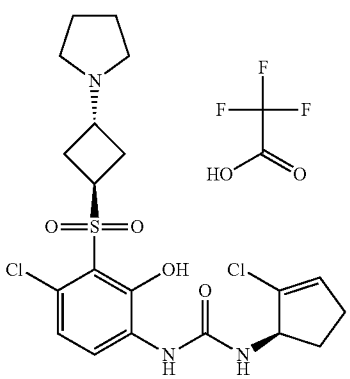 [SMILES: O=C(Nc1ccc(Cl)c(S(=O)(=O)[C@H]2C[C@H](N3CCCC3)C2)c1O)N[C@@H]1CCC=C1Cl ; O=C(O)C(F)(F)F] | 1-(4-chloro-2-hydroxy-3-((trans-3-(pyrrolidin-1-yl)cyclobutyl)sulfonyl)phenyl)-3-((R)-2-chlorocyclopent-2-en-1-yl)urea, trifluoroacetic acid salt | Int 1 and 78, method 1 | ¹H-NMR (400 MHz, DMSO-d₆) δ ppm 10.47 (br. s., 1H), 8.30 (br. s., 1H), 8.22 (d, J = 8.8 Hz, 1H), 7.38 (d, J = 8.6 Hz, 1H), 7.14 (d, J = 8.8 Hz, 1H), 5.96-6.06 (m, 1H), 4.69-4.81 (m, 1H), 4.52-4.65 (m, 1H), 3.96-4.09 (m, 1H), 3.06 (br. s., 2H), 2.60-2.84 (m, 5H), 2.24-2.47 (m, 4H), 1.94 (br. s., 4H), 1.63-1.76 (m, 1H); MS(ES⁺) m/z 474 (MH⁺). |
| 186 | | 1-(4-chloro-2-hydroxy-3-(((S)-1-methoxypropan-2-yl)sulfonyl)phenyl)-3-((R)-2-methylcyclopent-2-en-1-yl)urea | Int 2 and 130, method 5 | ¹H-NMR (400 MHz, DMSO-d₆) δ ppm 10.66 (s, 1H), 8.34 (d, J = 8.9 Hz, 1H), 8.15 (s, 1H), 7.11 (d, J = 8.9 Hz, 1H), 7.06 (d, J = 8.4 Hz, 1H), 5.51 (s, 1H), 4.53 (d, J = 7.1 Hz, 1H), 4.01-4.06 (m, 1H), 3.67 (dd, J = 10.8, 6.9 Hz, 1H), 3.58 (dd, J = 10.8, 4.9 Hz, 1H), 3.10 (s, 3H), 2.13-2.32 (m, 3H), 1.67 (s, 3H), 1.45-1.56 (m, 1H), 1.30 (d, J = 7.0 Hz, 3H); MS(ES⁺) m/z 403 (MH⁺). | ced

TABLE 1-continued

| No. | Structure | Name | Starting material and method | HNMR and LCMS |
|---|---|---|---|---|
| 187 & 188 | | 1-(4-chloro-2-hydroxy-3-(((R)-3-d₃-methyltetrahydro-furan-3-yl)sulfonyl)phenyl)-3-((R)-2-methylcyclopent-2-en-1-yl)urea and 1-(4-chloro-2-hydroxy-3-(((S)-3-d₃-methyltetrahydro-furan-3-yl)sulfonyl)phenyl)-3-((R)-2-methylcyclopent-2-en-1-yl)urea | Int 2 and 129, method 1 | Isomer 1: HPLC (OJ-H column (4.6*250 mm, 5 uM), 1:1 ACN/IPA (containing 0.1% DEA), $CO_2$ flow rate: 2.4 mL/min; co-solvent flow rate: 0.6 mL/min; back pressure: 123 bar); $t_r$ = 5.66 min; >99% ee; $^1$H-NMR (400 MHz, DMSO-$d_6$) δ ppm 10.51 (br. s., 1H), 8.29 (d, J = 8.3 Hz, 1H), 8.20 (s, 1H), 7.07 (d, J = 8.3 Hz, 1H), 6.91-7.04 (m, 1H), 5.50 (s, 1H), 4.47-4.58 (m, 1H), 4.36 (d, J = 10.0 Hz, 1H), 3.72-3.88 (m, 2H), 3.59 (d, J = 10.0 Hz, 1H), 2.52-2.76 (m, 1H), 2.09-2.36 (m, 3H), 1.85-1.98 (m, 1H), 1.66 (s, 3H), 1.45-1.57 (m, 1H); MS(ES$^+$) m/z 418 (MH$^+$). Isomer 2: HPLC (OJ-H column (4.6*250 mm, 5 uM), 1:1 ACN/IPA (containing 0.1% DEA), $CO_2$ flow rate: 2.4 mL/min; co-solvent flow rate: 0.6 mL/min; back pressure: 123 bar); $t_r$ = 6.30 min; >99% ee; $^1$H-NMR (400 MHz, DMSO-$d_6$) δ ppm 10.51 (br. s., 1H), 8.27 (d, J = 8.6 Hz, 1H), 8.20 (s, 1H), 7.06 (d, J = 8.3 Hz, 1H), 6.96 (br. s., 1H), 5.50 (s, 1H), 4.49-4.57 (m, 1H), 4.37 (d, J = 10.0 Hz, 1H), 3.74-3.86 (m, 2H), 3.59 (d, J = 10.0 Hz, 1H), 2.69 (dt, J = 13.3, 7.9 Hz, 1H), 2.11-2.34 (m, 3H), 1.87-1.95 (m, 1H), 1.66 (s, 3H), 1.46-1.55 (m, 1H); MS(ES$^+$) m/z 418 (MH$^+$). |
| 189 & 190 | | 1-(4-chloro-2-hydroxy-3-(((R)-3-d₃-methyltetrahydro-furan-3-yl)sulfonyl)phenyl)-3-((R)-2-chlorocyclopent-2-en-1-yl)urea and 1-(4-chloro-2-hydroxy-3-(((S)-3-d₃-methyltetrahydro-furan-3-yl)sulfonyl)phenyl)-3-((R)-2-chlorocyclopent-2-en-1-yl)urea | Int 1 and 129, method 1 | Isomer 1: $^1$H-NMR (400 MHz, DMSO-$d_6$) δ ppm 10.49 (s, 1H), 8.37 (d, J = 8.8 Hz, 1H), 8.24 (s, 1H), 7.37 (d, J = 8.6 Hz, 1H), 7.16 (d, J = 8.8 Hz, 1H), 5.87-6.07 (m, 1H), 4.69-4.82 (m, 1H), 4.33 (d, J = 10.0 Hz, 1H), 3.77-3.91 (m, 2H), 3.59 (s, 4H), 3.62 (s, 3H), 2.66 (dt, J = 7.9, 13.4 Hz, 1H), 2.23-2.43 (m, 3H), 1.96 (ddd, J = 5.1, 7.3,13.0 Hz, 1H), 1.56-1.75 (m, 1H); MS(ES$^+$) m/z 438 (MH$^+$). Isomer 2: $^1$H-NMR (400 MHz, DMSO-$d_6$) δ ppm 10.48 (s, 1H), 8.37 (d, J = 8.8 Hz, 1H), 8.24 (s, 1H), 7.37 (d, J = 8.8 Hz, 1H), 7.16 (d, J = 9.1 Hz, 1H), 5.90-6.07 (m, 1H), 4.66-4.84 (m, 1H), 4.33 (d, J = 10.0 Hz, 1H), 3.69-3.99 (m, 10H), 3.60 (d, J = 10.0 Hz, 1H), 2.66 (dt, J = 7.9, 13.3 Hz, 1H), 2.20-2.44 (m, 3H), 1.95 (ddd, J = 5.0, 7.4, 13.0 Hz, 1H), 1.56-1.73 (m, 1H); MS(ES$^+$) m/z 438 (MH$^+$). |

Compound 191: (R)-1-(3-(tert-butylsulfonyl)-4-cyano-2-hydroxphenyl)-3-(2-methylcyclopent-2-en-1-yl)urea

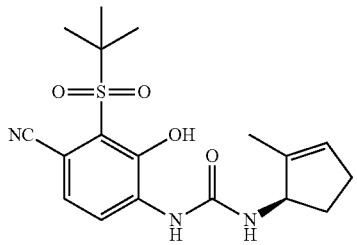 [SMILES: CC1=CCC[C@H]1NC(=O)Nc1ccc(C#N)c(S(=O)(=O)C(C)(C)C)c1O]

To a solution of 4-amino-2-(tert-butylsulfonyl)-3-hydroxybenzonitrile (Intermediate 76, 450 mg) in pyridine (20 mL) was added fresh (R)-5-isocyanato-1-methylcyclopent-1-ene (Intermediate 2, 327 mg) in toluene (20 mL). The reaction mixture was stirred at RT overnight. The mixture was quenched with water (5 mL) and concentrated. the residue was purified with MDAP (acidic condition) to afford (R)-1-(3-(tert-butylsulfonyl)-4-cyano-2-hydroxphenyl)-3-(2-methylcyclopent-2-en-1-yl)urea (120 mg). $^1$H-NMR (400 MHz, DMSO-d$_6$) δ ppm 10.13 (br. s., 1H), 8.51-8.64 (m, 2H), 7.60 (d, J=8.6 Hz, 1H), 7.34 (d, J=8.3 Hz, 1H), 5.52 (s, 1H), 4.54 (d, J=6.8 Hz, 1H), 2.11-2.37 (m, 3H), 1.66 (s, 3H), 1.46-1.60 (m, 1H), 1.30-1.46 (m, 9H); MS(ES$^+$) m/z 378 (MH$^+$).

Compound 192: 1-(4-chloro-2-hydroxy-3-((trans-3-(pyrrolidin-1-yl)cyclobutyl)sulfonyl)phenyl)-3-((R)-2-methylcyclopent-2-en-1-yl)urea, trifluoroacetic acid salt

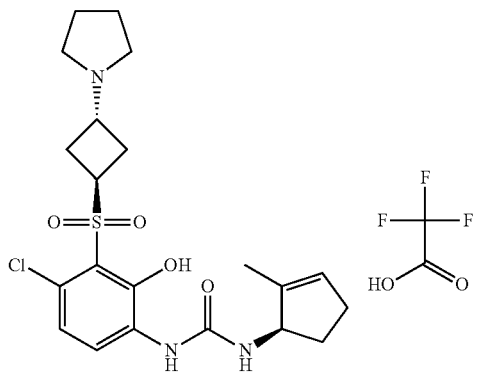

To a solution of 6-amino-3-chloro-2-((trans-3-(pyrrolidin-1-yl)cyclobutyl)sulfonyl)phenol (Intermediate 78, 80 mg) in pyridine (5 mL) was added (R)-5-isocyanato-1-methylcyclopent-1-ene (Intermediate 2, 74 mg) solution in toluene (5 mL) dropwise. The mixture was stirred at RT overnight. The mixture was concentrated and the resulting residue was redissolved in DMF (8 mL) and purified by MDAP to afford 1-(4-chloro-2-hydroxy-3-((trans-3-(pyrrolidin-1-yl)cyclobutyl)sulfonyl)phenyl)-3-((R)-2-methylcyclopent-2-en-1-yl)urea as a trifluoroacetic acid salt (21 mg) as a white solid. $^1$H-NMR (400 MHz, DMSO-d$_6$) δ ppm 10.44 (br. s., 2H), 8.28 (br. s., 1H), 8.18 (d, J=8.8 Hz, 1H), 7.13 (d, J=8.8 Hz, 1H), 7.10 (d, J=8.6 Hz, 1H), 5.52 (s, 1H), 4.49-4.62 (m, 2H), 4.02 (quin, J=7.5 Hz, 1H), 2.82-3.23 (m, 2H), 2.64-2.80 (m, 5H), 2.11-2.36 (m, 3H), 1.80-2.08 (m, 4H), 1.67 (s, 3H), 1.45-1.64 (m, 1H); MS(ES$^+$) m/z 454 (MH$^+$).

Compound 193: 1-(4-chloro-3-((trans-3-(dimethylamino)cyclobutyl)sulfonyl)-2-hydroxyphenyl)-3-((R)-2-methylcyclopent-2-en-1-yl)urea, trifluoroacetic acid salt

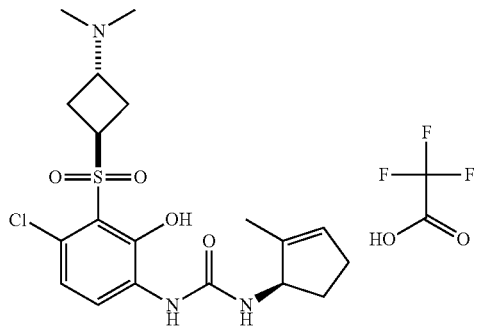

To a solution of 6-amino-3-chloro-2-((trans-3-(dimethylamino)cyclobutyl)sulfonyl)phenol (Intermediate 106, 100 mg) in pyridine (5 mL) was added fresh (R)-5-isocyanato-1-methylcyclopent-1-ene (Intermediate 2, 40 mg) in toluene (5 mL). The reaction mixture was stirred at RT overnight, and then quenched with water (5 mL). The solvent was removed. The residue was purified by MDAP (acidic condition) to afford 1-(4-chloro-3-((trans-3-(dimethylamino)cyclobutyl)sulfonyl)-2-hydroxyphenyl)-3-((R)-2-methylcyclopent-2-en-1-yl)urea as a trifluoroacetic acid salt (40 mg). $^1$H-NMR (400 MHz, DMSO-d$_6$) δ ppm 10.46 (br. s., 1H), 8.32 (s, 1H), 8.16 (d, J=8.8 Hz, 1H), 7.06-7.17 (m, 2H), 5.52 (s, 1H), 4.50-4.58 (m, 1H), 4.40-4.50 (m, 1H), 3.98 (quin, J=7.9 Hz, 1H), 2.62-2.82 (m, 10H), 2.11-2.36 (m, 3H), 1.67 (s, 3H), 1.49-1.59 (m, 1H); MS(ES$^+$) m/z 428 (MH$^+$).

Compound 194: (R)-1-(4-chloro-3-((1,1-difluoroethyl)sulfonyl)-2-hydroxphenyl)-3-(2-methylcyclopent-2-en-1-yl)urea

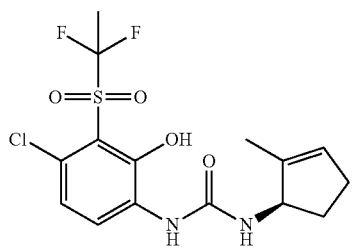 [SMILES: CC1=CCC[C@H]1NC(=O)Nc1ccc(Cl)c(S(=O)(=O)C(C)(F)F)c1O]

To a solution of 6-amino-3-chloro-2-((1,1-difluoroethyl)sulfonyl)phenol (Intermediate 83, 84 mg) in pyridine (5 mL) was added (R)-5-isocyanato-1-methylcyclopent-1-ene (Intermediate 2, 0.15 M in toluene, 4 mL). The reaction mixture was stirred at RT overnight. The mixture was concentrated and the residue was dissolved in DMF (8 mL) and purified by MDAP to afford (R)-1-(4-chloro-3-((1,1-difluoroethyl)sulfonyl)-2-hydroxyphenyl)-3-(2-methylcyclopent-2-en-1-yl)urea (15 mg) as a white solid. $^1$H-NMR (400 MHz, DMSO-d$_6$) δ ppm 10.53 (br. s., 1H), 8.28 (s, 1H), 8.26 (d, J=9.0 Hz, 1H), 7.17 (d, J=8.8 Hz, 1H), 7.07 (d, J=8.3 Hz, 1H), 5.52 (br. s., 1H), 4.44-4.62 (m, 1H), 2.23-2.36 (m, 2H), 2.16-2.23 (m, 1H), 2.09 (t, J=19.2 Hz, 3H), 1.67 (s, 3H), 1.47-1.59 (m, 1H); MS(ES$^+$) m/z 395 (MH$^+$).

Compound 195: 1-(4-chloro-2-hydroxy-3-(((S)-3-methyltetrahydrofuran-3-yl)sulfonyl)phenyl)-3-((R)-2-methylcyclopent-2-en-1-yl)urea

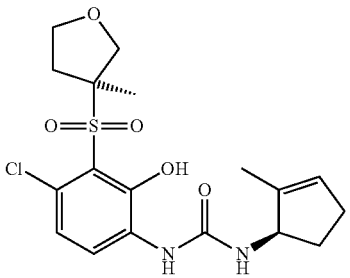

and Compound 196: 1-(4-chloro-2-hydroxy-3-(((R)-3-methyltetrahydrofuran-3-yl)sulfonyl)phenyl)-3-((R)-2-methylcyclopent-2-en-1-yl)urea

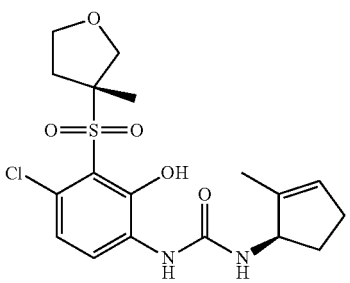 [SMILES: CC1=CCC[C@H]1NC(=O)Nc1ccc(Cl)c(S(=O)(=O)[C@]2(C)CCOC2)c1O]

To a solution of 6-amino-3-chloro-2-((3-methyltetrahydrofuran-3-yl)sulfonyl)phenol (Intermediate 29, 3000 mg) in pyridine (20 mL) was added (R)-5-isocyanato-1-methylcyclopent-1-ene (Intermediate 2, 2279 mg). The resulting mixture was stirred at 40° C. for 12 hours. Cold water (30 mL) was added and aqueous layer was extracted with DCM (2×100 mL). The combined organic layers were dried over Na$_2$SO$_4$, filtered and concentrated to give 1-(4-chloro-2-hydroxy-3-((3-methyltetrahydrofuran-3-yl)sulfonyl)phenyl)-3-((R)-2-methylcyclopent-2-en-1-yl)urea (4.1 g) as a dark solid. A part of this compound (3.0 g) was purified by SFC and MDAP under acidic condition to afford the pure two enantiomers: 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195, 666 mg) and 1-(4-chloro-2-hydroxy-3-(((R)-3-methyltetrahydrofuran-3-yl)sulfonyl)phenyl)-3-((R)-2-methylcyclopent-2-en-1-yl)urea (Compound 196, 626 mg).

Compound 195: HPLC (Chiralpak IC column (4.6*250 mm, 5 uM), 1:1 ACN/IPA (containing 0.5% DEA), CO$_2$ flow rate: 2.55 mL/min; co-solvent flow rate: 0.45 mL/min; back pressure: 120 bar); t$_r$=16.9 min; >93% ee; $^1$H-NMR (400 MHz, DMSO-d$_6$) δ ppm 10.53 (s, 1H), 8.36 (d, J=8.8 Hz, 1H), 8.17 (s, 1H), 7.14 (d, J=8.8 Hz, 1H), 7.05 (d, J=8.3 Hz, 1H), 5.51 (s, 1H), 4.49-4.63 (m, 1H), 4.33 (d, J=10.3 Hz, 1H), 3.76-3.89 (m, 2H), 3.61 (d, J=10.0 Hz, 1H), 2.68 (dt, J=13.3, 7.9 Hz, 1H), 2.10-2.35 (m, 3H), 1.91-2.02 (m, 1H), 1.67 (s, 3H), 1.44-1.58 (m, 4H); MS(ES$^+$) m/z 415 (MH$^+$);

Compound 196: HPLC (Chiralpak IC column (4.6*250 mm, 5 uM), 1:1 ACN/IPA (containing 0.5% DEA), CO$_2$ flow rate: 2.55 mL/min; co-solvent flow rate: 0.45 mL/min; back pressure: 120 bar); t$_r$=14.3 min; >99% ee; $^1$H-NMR (400 MHz, DMSO-d$_6$) δ ppm 10.52 (s, 1H), 8.36 (d, J=9.0 Hz, 1H), 8.17 (s, 1H), 7.14 (d, J=8.8 Hz, 1H), 7.05 (d, J=8.3 Hz, 1H), 5.51 (s, 1H), 4.49-4.61 (m, 1H), 4.33 (d, J=10.0 Hz, 1H), 3.75-3.91 (m, 2H), 3.61 (d, J=10.0 Hz, 1H), 2.68 (dt, J=13.3, 7.9 Hz, 1H), 2.09-2.37 (m, 3H), 1.90-2.02 (m, 1H), 1.67 (s, 3H), 1.42-1.59 (m, 4H); MS(ES$^+$) m/z 415 (MH$^+$).

Alternative Synthesis of Compound 195

1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) may be prepared by an alternative synthetic route as follows:

a) Preparation of oxolan-3-yl methylsulfonate

Step 1a

To the ice-water cooled solution of tetrahydrofuran-3-ol (490.0 g, 5.57 mol) in dichloromethane (4 L) was added triethylamine (731.1 g, 7.24 mol) followed by MsCl (701.3 g, 6.12 mol) dropwise over 30 min. The mixture was stirred at room temperature overnight. The reaction was quenched with water and extracted with ethyl acetate three times. The combined organic layers were washed, dried and concentrated to give the title compound (747 g) which was used in the next step without purification.

b) Preparation of (R)-2-methylcyclopent-2-enamine hydrochloride

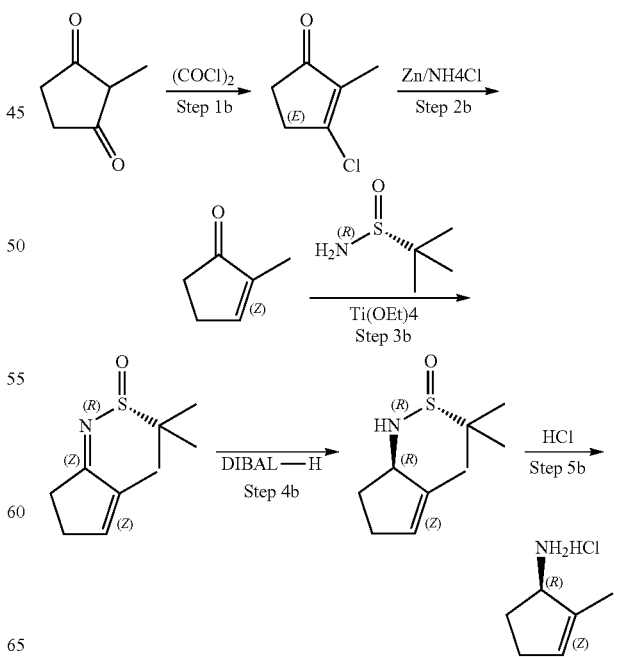

Step 1b: 3-chloro-2-methylcyclopent-2-en-1-one

To a solution of 2-methylcyclopentane-1,3-dione (245.0 g, 2.00 mol) and DMF (207 mL, 2.60 mol) in DCM (3 L) cooled to 0° C. was added (COCl)$_2$ (212 mL, 2.40 mol) over 30 min. The reaction was allowed to warm to ambient temperature over 1 hour with stirring and the mixture poured into a mixture of ether and water (1:1, 4 L). The organic layer was separated, dried over anhydrous sodium sulfate and filtered. After removal of the solvent, the crude product was purified by chromatography through a short column of silica gel (PE/EA=4:1). The solvent was removed to give the title compound (267 g) as a brown oil.

Step 2b: 2-Methylcyclopent-2-en-1-one (3)

To a solution of the product from Step 1 b (250.0 g, 1.78 mol) in methanol (3 L) was added Zinc (870.0 g, 13.4 mol) and NH$_4$Cl (1380.0 g, 25.79 mol) and the reaction mixture was heated under reflux with stirring for 2 hours. The mixture was cooled and filtered and the solvent was evaporated to afford the title compound (154 g) as a colorless oil, which was used without purification in the next step.

Step 3b: (R,Z)-2-methyl-N-(2-methylcyclopent-2-en-1-ylidene)propane-2-sulfinamide A 500 mL three-necked flask equipped with a dean and stark apparatus was charged with (R)-2-methyl-2-propane-sulfinamide (9.5 g, 78.4 mmol) and toluene (95 mL) and the mixture was heated under reflux for 30 min. The product from Step 2b (5 g, 52.0 mmol, 1.0 equiv) and Ti(OH)$_4$ (17.8 g, 78.0 mmol, 1.5 equiv) were added to the solution and the resulting mixture was heated to reflux for 15 h. Further Ti(OH)$_4$ (4.8 g, 20.8 mmol, 0.4 equiv) was added and the reaction mixture was stirred under reflux for additional 24 h. The reaction mixture was allowed to cool to room temperature and quenched with water (3 mL) in MTBE (50 mL). The solution was stirred at room temperature for 30 min and the resulting precipitate was filtered. The filter cake was washed with MTBE (50 mL) twice and the combined organic phases were washed with water (100 mL) twice, dried over MgSO$_4$, filtered and concentrated in vacuum to afford the title product (8.1 g) as an oil, which was used directly in the next step.

Step 4b: (R)-2-methyl-N—((R)-2-methylcyclopent-2-en-1-yl) propane-2-sulfinamide A 3 L three-necked flask equipped with a thermometer was charged with the product from Step 3b (64 g, 320 mmol, 1.0 equiv.) and THF (640 mL) under N2 and DIBAL-H (1 M solution in toluene, 320 mL) was added dropwise over 30 min at −70 deg C. Stirring was continued at −70 deg C. for a further 1 h until the no more starting material was observed by HPLC. The mixture was quenched with water (10 mL) at −70 deg C. and an aqueous solution of 9% potassium sodium tartrate tetrahydrate (1 L) was added at 10° C. over a period of 30 min. The mixture was stirred for an additional 30 min. The aqueous phase was separated and the organic phase was filtered. The filter cake was washed with aqueous solution of 9% potassium sodium tartrate tetrahydrate (500 mL) and MTBE (200 mL). The combined aqueous phases were extracted with MTBE (250 mL×2). All orgainic phases were combined, dried over MgSO$_4$ and concentrated. The residue was purified by column chromatography (EA:n-heptane=1:9 to 1:2) to give the title product (38 g).

Step 5b: (R)-2-methylcyclopent-2-enamine hydrochloride

To a solution of the product from Step 4b (35 g, 155.4 mmol) in methanol (700 mL) was added HCl solution (4M in dioxane, 140 mL 3.2 equiv.) dropise at room temperature and the resulting mixture was stirred at room temperature overnight until HPLC indicated no starting material. The mixture was concentrated to (approximately 100 mL) and the residue was purified twice by azeotropic distillation using MTBE (200 mL×2) to get give an oil. MTBE (100 mL) was added and the mixture stirred for 2 h at 40-50 deg C. The resulting mixture was cooled to 20 deg C. The resulting precipitate was filtered, washed with MTBE and the filter cake was dried to give the title product (21.5 g).

c) Propitiation of 1-(4-chloro-2-hydroxy-3-(((S)-3-methyl-tetrahydrofuran-3-yl)sulfonyl)phenyl)-3-((R)-2-methylcyclopent-2-en-1-yl)urea (Compound 195)

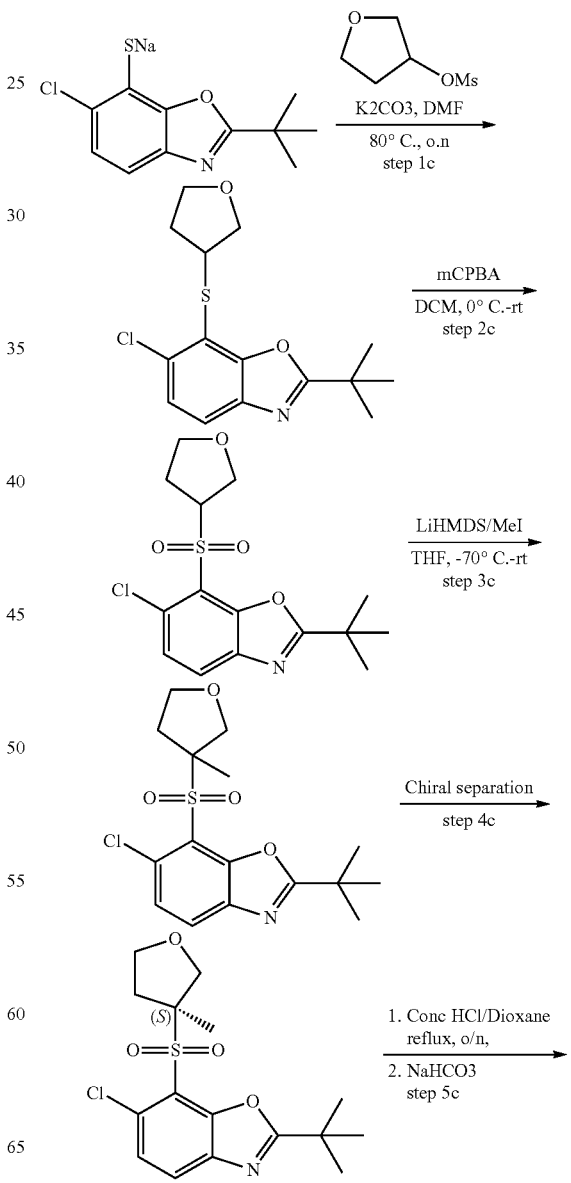

-continued

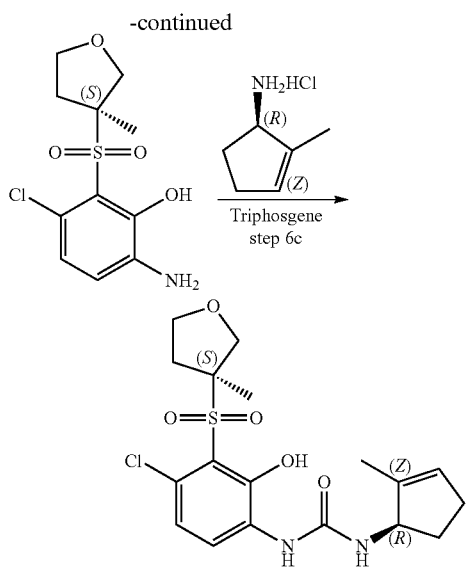

Step 1c: 2-(tert-butyl)-6-chloro-7-oxolan-3-ylthiobenzoxazole

To a solution of sodium 2-(tert-butyl)-6-chlorobenzo[d]oxazole-7-thiolate (for prepatation see US patent application No US 2007/02496782) (1185.7 g, 4.50 mol) in N,N-dimethylformamide (6 L), was added potassium carbonate (745.0 g, 5.40 mol) and oxolan-3-yl methylsulfonate (the product from Step 1a above) (747.0 g, 4.50 mol) and the resulting reaction mixture was stirred at 80° C. overnight. TLC showed the reaction was completed. After cooling, the reaction mixture was poured into water (3.5 L) and extratced with ethyl acetate three times. The combined organic layers were washed and dried, then concentrated to afford the title compound (1244 g) which used in the next step without purification.

Step 2c: 2-(tert-butyl)-6-chloro-7-(oxolan-3-ylsulfonyl)benzoxazole

To an ice-water cooled solution of the product from Step 1c (350.0 g, 1.12 mol) in dichloromethane (3.5 L) was added m-CPBA (500.0 g, 2.46 mol) slowly in portions. The resulting reaction mixture was stirred at room temperature overnight. TLC showed the starting material had disappeared. The reaction was quenched with aq.NaHCO3 and aq. $Na_2S_2O_3$ and extracted with ethyl acetate. The combined organic layers were washed and dried, then concentrated to give the crude product which was purified by silica gel column chromatography (PE/EA=100:1 to 3:1) to give title product.

Step 3c: 2-(tert-butyl)-6-chloro-7-[(3-methyloxolan-3-yl)sulfonyl]benzoxazole

To a solution of the product from Step 2c (272.0 g, 0.79 mol) and iodomethane (280.7 g, 1.98 mol) in tetrahydrofuran (2.7 L) cooled to −78° C. under a nitrogen atmosphere was added LiHMDS (1 M/L, 1980 mL, 1.98 mol) dropwise slowly and carefully over 45 min. The resulting reaction mixture was stirred at −70° C. for 2 hours, then warmed up to room temperature slowly and stirred overnight. TLC showed that the starting material was completely consumed. After cooling, the mixture was quenched with aq.NH4Cl and extracted with ethyl acetate. The organic layer was wash with brine, dried, filtered and concentrated. Trituration with PE/EA (20:1) gave the title compound (254 g) as an off-white solid.

Step 4c: 2-(tert-butyl)-6-chloro-7-[((3S)-3-methyl-oxolan-3-yl)sulfonyl]benzoxazole The racemic product from Step 3c was separated into its chiral components using preparative chiral chromatography. The product from Step 3c (100 g) was dissolved in a 1:1 mixture of DCM: IPA (1000 ml). The separation equipment and conditions were as follows:

| | |
|---|---|
| Instrument | Thar 200 Preparative SFC |
| Column | ChiralPak IC, 300 × 50 mmI.D. 10 um |
| | Mobile phase A for CO2 and B for IPA |
| Gradient | B 35% |
| Flow rate | 200 mL/min |
| Back pressure | 100 bar |
| Column temperature | 40 deg C. |
| Wavelength | 254 nm |
| Cycle time | 4 min |
| Injection | 6 ml per injection |

This method gave the title product in 95.8% yield (47.9 g).

The product from Step 3c was purified using analytical chiral chromatography. The separation equipment and conditions were as follows:

| | |
|---|---|
| Instrument | Thar analytical SFC |
| Column | Chiralpak IC 150 × 4.6 mm I.D., 3 um Mobile phase A for CO2 and B for IPA (0.05% DEA) |
| Gradient | B 5~40% |
| Flow rate | 2.4 mL/min |
| Back pressure | 100 bar |
| Column temperature | 35 deg C. |
| Wavelength | 220 nm |

Analytical chiral chromatoraphy gave the title product with the following $^1$H NMR spectrum: $^1$HNMR (CDCl3, 400 MHz): δ 7.83 (d, J=8.4 Hz, 1H), 7.51 (d, J=8.4 Hz, 1H), 4.63 (d, J=10 Hz, 1H), 3.92-3.88 (m, 2H), 3.62 (d, J=10 Hz, 1H), 3.01-2.94 (m, 1H), 1.92-1.85 (m, 1H), 1.60 (s, 3H), 1.52 (s, 9H).

Step 5c: 2-[((3S)-3-methyloxolan-3-yl)sulfonyl]-6-amino-3-chlorophenol

To a solution of the product from Step 4c (155.0 g, 0.43 mmol) in 1,4-dioxane (150 mL) was added conc. aqueous hydrochloric acid (1100 mL, 13.2 mmol) and the mixture was heated under reflux overnight. TLC showed that the starting material was completely consumed. The mixture was cooled to room temperature and the solvent removed under reduced pressure. The resulting residue was dissolved in EA and the pH adjusted to 8 with aq.NaHCO3. The mixture was extracted, washed and concentated. The residue was purified by silica gel column chromatography (PE/EA=10:1) to give the title compound (114 g).

Step 6c: 1-(4-chloro-2-hydroxy-3-(((S)-3-methyltetrahydrofuran-3-yl)sulfonyl)phenyl)-3-((R)-2-methyl-cyclopent-2-en-1-yl)urea (Compound 195)

To a solution of the product from Step 5b (1.1 g, 78.6% pure, 6.5 mmol) in toluene (10 mL) was added triphosgene (1.6 g, 5.4 mmol) at room temperature and the resulting mixture was stirred under reflux for 3 hours. Additional triphosgene (0.2 g, 0.6 mmol) was added and the mixture was stirred for 5.5 hours under reflux. The reaction was cooled to room temperature and a solution of the product of Step 5c (1.55 g, 4.7 mmol) in pyridine (10 mL) was added dropwise. The reaction mixture was stirred at room temperature for 69 hours until no starting material (from Step 5c) was observed by HPLC. The reaction was quenched with water (10 mL) and ethyl acetate (20 mL) added. The mixture was stirred for 30 min and the resulting suspension was filtered. The phases were separated and the aqueous phase was extracted with ethyl acetate (20 mL×3) three times. The combined organic phases were dried over MgSO₄ and concentrated. The resided was azeotropically distilled with IPA (10 mL) to give a crude product as a solid. This solid was dissolved in a mixture solution of IPA (6 mL) and heptane (12 mL) at 60 deg C. The resulting mixture was stirred at 60 deg C. and then at 20 deg C. for 1 hour respectively to obtain a suspension which was filtered to give a solid. This solid was dissolved in ethyl acetate/heptane (1:1) and passed through a silica pad. The filtrate was concentrated to give the desired product (1.7 g) as a yellow solid. The product was recrystallised by dissolving the yellow solid in isopropanol (15 mL) at 70 deg C. and stirring for 30 mins until a clear solution was obtained. The solution was cooled to room temperature over 30 min, and then to 0 deg C. over 30 min. The resulting precipitate was filtered, washed and dried to give the title product (1.0 g, 99.2% pure, 95.2% d.e) as a white solid.

The further recrystallization twice provided the product (0.7 g, 99.95% pure, 98.6% d.e) as a white solid. ¹H NMR: (DMSO-d6, 400 MHz): δ 10.522 (s, 1H), 8.382 (d, J=8.8 Hz, 1H), 8.198 (s, ¹H), 7.154 (d, J=8.8 Hz, 1H), 7.086 (d, J=8.4 Hz, 1H), 5.518 (s, 1H), 4.538 (d, J=6.8 Hz, 1H), 4.339 (d, J=10.4 Hz, 1H), 3.854-3.794 (m, 2H), 3.612 (d, J=10 Hz, 1H), 2.716-2.663 (m, 1H), 2.289-2.243 (m, 3H), 1.980-1.942 (m, 1H), 1.672 (s, 1H), 1.521-1.491 (m, 4H); MS Calcd.: 414.9; MS Found: 415.1 (M+1)+.

Piperazine salt of Compound 195: 1-(4-chloro-2-hydroxy-3-(((S)-3-methyltetrahydrofuran-3-yl)sulfonyl)phenyl)-3-((R)-2-methylcyclopent-2-en-1-yl)urea

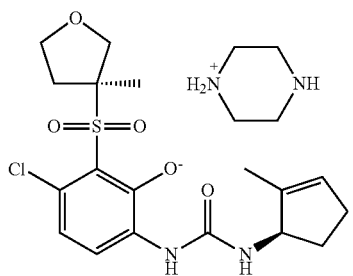 [SMILES: CC1=CCC[C@H]1NC(=O)Nc1ccc(Cl)c(S(=O)(=O)[C@@]2(C)CCOC2)c1[O-] ; C1CNCCN1]

To a 50 mL flask equipped with a thermometer, condenser, magnetic stir and nitrogen inlet/outlet was added 1-(4-chloro-2-hydroxy-3-(((S)-3-methyltetrahydrofuran-3-yl)sulfonyl)phenyl)-3-((R)-2-methylcyclopent-2-en-1-yl)urea (Compound 195) (600 mg, purity 97.7%) in methyl isobutyl ketone (5 mL) and the mixture was heated to 50° C. to form a clear solution. Piperazine (131 mg, 1.05 eq.) was added in one portion to obtain a white suspension. Additional methyl isobutyl ketone (5 mL) was added and the suspension was stirred for 3 hours at 50° C. The mixture was cooled to RT over 1 hour and filtered to give a white solid. The white solid was rinsed with TBME (1 mL) and dried in vacuo overnight at RT to give the title product as a white solid (657 mg) (process recovery yield 89.0%; purity is 97.7%). Differential scanning calorimetry (DSC) showed a single peak of magnitude 164.3 J/g at 194.05° C., indicating a single crystalline form.

Compound 197 and 198: 1-(4-chloro-2-hydroxy-3-(((S)-3-methyltetrahydrofuran-3-yl)sulfonyl)phenyl)-3-((R)-2-chlorocyclopent-2-en-1-yl)urea and 1-(4-chloro-2-hydroxy-3-(((R)-3-methyltetrahydrofuran-3-yl)sulfonyl)phenyl)-3-((R)-2-chlorocyclopent-2-en-1-yl)urea

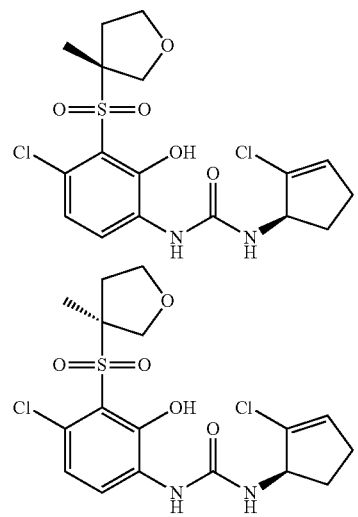

To a solution of 6-amino-3-chloro-2-((3-methyltetrahydrofuran-3-yl)sulfonyl)phenol (Intermediate 29, 600 mg) in pyridine (20 mL) was added the fresh (R)-1-chloro-5-isocyanatocyclopent-1-ene (Intermediate 1, 443 mg) in toluene (20 mL). The mixture was stirred at RT overnight. The resulting solution was quenched with water (5 mL) and concentrated. The residue was purified with MDAP (acidic condition) to afford 1-(4-chloro-2-hydroxy-3-((3-methyltetrahydrofuran-3-yl)sulfonyl)phenyl)-3-((R)-2-chlorocyclopent-2-en-1-yl)urea (205 mg). A part of this compound (160 mg) was purified by chiral separation (AD-H (4.6*250 mm,5 um), co-solvent MeOH, 1% DEA) and then MDAP (acidic condition) to give 1-(4-chloro-2-hydroxy-3-(((S)-3-methyltetrahydrofuran-3-yl)sulfonyl)phenyl)-3-((R)-2-chlorocyclopent-2-en-1-yl)urea and 1-(4-chloro-2-hydroxy-3-(((R)-3-methyltetrahydrofuran-3-yl)sulfonyl)phenyl)-3-((R)-2-chlorocyclopent-2-en-1-yl)urea (compounds 197 and 198, 37 mg and 31 mg, respectively) as violet solids.

Isomer 1: HPLC (AD-H column (4.6*250 mm, 5 uM), IPA (containing 0.1% DEA), CO₂ flow rate: 2.25 mL/min; co-solvent flow rate: 0.75 mL/min; back pressure: 149 bar); $t_r$=4.7 min; >99% ee; ¹H-NMR (400 MHz, DMSO-d₆) δ ppm 10.49 (s, 1H), 8.37 (d, J=8.9 Hz, 1H), 8.25 (s, 1H), 7.38 (d, J=8.8 Hz, 1H), 7.16 (d, J=8.9 Hz, 1H), 5.99 (d, J=1.7 Hz, 1H), 4.73 (s, 1H), 4.34 (d, J=10.1 Hz, 1H), 3.72-3.97 (m, 2H), 3.61 (d, J=10.1 Hz, 1H), 2.67 (m, 1H), 2.18-2.47 (m, 3H), 1.84-2.04 (m, 1H), 1.57-1.78 (m, 1H), 1.49 (s, 3H); MS(ES⁺) m/z 435 (MH⁺).

Isomer 2: HPLC (AD-H column (4.6*250 mm, 5 uM), IPA (containing 0.1% DEA), CO$_2$ flow rate: 2.25 mL/min; co-solvent flow rate: 0.75 mL/min; back pressure: 149 bar); t$_r$=5.5 min; >93% ee; $^1$H-NMR (400 MHz, DMSO-d$_6$) δ ppm 10.49 (s, 1H), 8.37 (d, J=8.9 Hz, 1H), 8.24 (s, 1H), 7.37 (d, J=8.7 Hz, 1H), 7.16 (d, J=8.9 Hz, 1H), 5.99 (s, 1H), 4.73 (s, 1H), 4.34 (d, J=10.1 Hz, 1H), 3.71-3.96 (m, 2H), 3.61 (d, J=10.1 Hz, 1H), 2.62-2.78 (m, 1H), 2.19-2.44 (m, 3H), 1.84-2.06 (m, 1H), 1.56-1.78 (m, 1H), 1.49 (s, 3H); MS(ES$^+$) m/z 435 (MH$^+$).

Compound 199: (R)-1-(4-chloro-2-hydroxy-3-(piperazin-1-ylsulfonyl)phenyl)-3-(2-methylcyclopent-2-en-1-yl)urea, trifluoroacetic acid salt

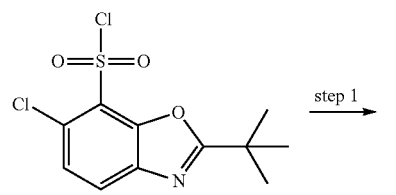

step 1

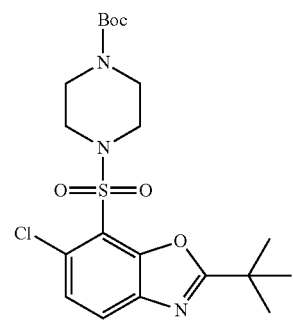

step 2

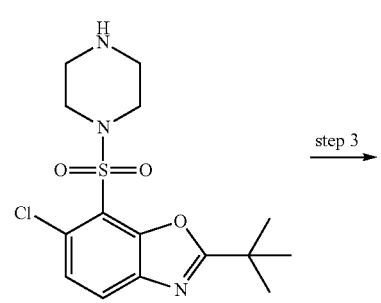

step 3

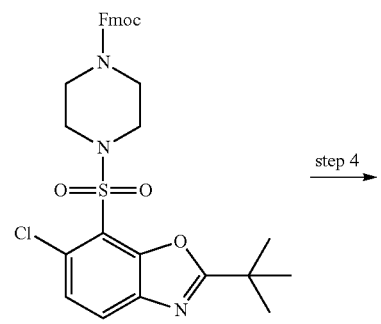

step 4

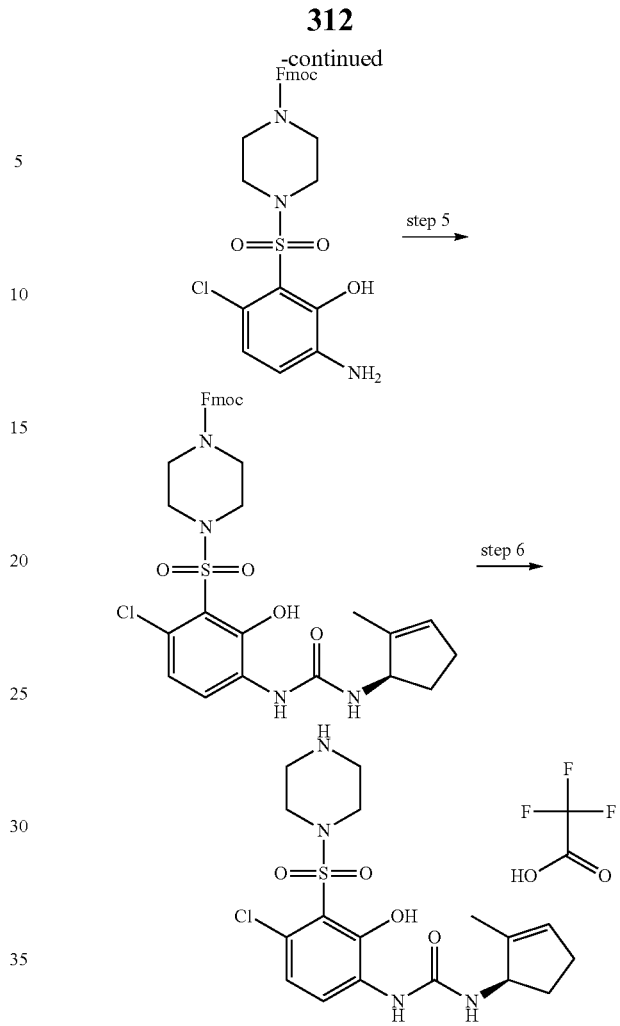

Step 1: TEA (0.8 g) was added to a solution of 2-(tert-butyl)-6-chlorobenzo[d]oxazole-7-sulfonyl chloride (2.5 g) and tert-butyl piperazine-1-carboxylate (2.2 g) in THF (50 mL) at RT. The reaction mixture was stirred for 3 hours. The reaction mixture was poured into ice-water (50 mL), and extracted with EA (3×40 mL). The combined organic layers were washed with brine (20 mL), dried over Na$_2$SO$_4$, filtered and concentrated under reduced pressure. The residue was purified by column chromatography (eluting with PE:EA=30:1) to give tert-butyl 4-((2-(tert-butyl)-6-chlorobenzo[d]oxazol-7-yl)sulfonyl)piperazine-1-carboxylate (3.0 g) as a light yellow oil. MS(ES$^+$) m/z 402 (M-t-Bu+H+).

Step 2: To a stirred solution of tert-butyl 4-((2-(tert-butyl)-6-chlorobenzo[d]oxazol-7-yl)sulfonyl)piperazine-1-carboxylate (700 mg) in DCM (20 mL) at RT was added 2,2,2-trifluoroacetic acid (0.5 mL). The reaction mixture was stirred at this temperature for 2 hours. Cold water (50 mL) was added. The resulting mixture was neutralized with sat. NaHCO$_3$ solution. The aq. layer was extracted with DCM (2×50 mL). The combined organic layers were dried over Na$_2$SO$_4$, filtered and concentrated in vacuo to give 2-(tert-butyl)-6-chloro-7-(piperazin-1-ylsulfonyl)benzo[d]oxazole (500 mg) as a light yellow solid. MS(ES$^+$) m/z 358 (MH$^+$).

Step 3: 2-(Tert-butyl)-6-chloro-7-(piperazin-1-ylsulfonyl)benzo[d]oxazole (500 mg) was added to a solution of sodium hydrogencarbonate (141 mg) and (9H-fluoren-9-yl)methyl carbonochloridate (380 mg) in 1,4-dioxane (10 mL) and water (10 mL) at RT. The reaction mixture was stirred at RT for 16 hours. Cold water (30 mL) was added. The aq. layer was extracted with DCM (2×50 mL). The combined organic layers were dried over Na$_2$SO$_4$, filtered and concentrated in vacuo to give (9H-fluoren-9-yl)methyl 4-((2-(tert-butyl)-6-chloro-2,3-dihydrobenzo[d]oxazol-7-yl)sulfonyl)piperazine-1-carboxylate (320 mg) as a light yellow solid.

Step 4: To a solution of (9H-fluoren-9-yl)methyl 4-((2-(tert-butyl)-6-chlorobenzo[d]oxazol-7-yl)sulfonyl)piperazine-1-carboxylate (320 mg) in 1,4-dioxane (2 mL) was added sulfuric acid (65% w/w, 0.05 mL). The resulting mixture was stirred for 1 hour at 100° C. Cold water (30 mL) was added. The resulting mixture was neutralized with sat. NaHCO$_3$ solution. The mixture was extracted with DCM (2×100 mL). The combined organic layers were dried over Na$_2$SO$_4$, filtered and concentrated in vacuo to give (9H-fluoren-9-yl)methyl 4-((3-amino-6-chloro-2-hydroxyphenyl)sulfonyl)piperazine-1-carboxylate (150 mg) as a light yellow solid. MS(ES$^+$) m/z 514 (MH$^+$).

Step 5: To a solution of (9H-fluoren-9-yl)methyl 4-((3-amino-6-chloro-2-hydroxyphenyl)sulfonyl)piperazine-1-carboxylate (130 mg) in pyridine (1 mL) was added (R)-5-isocyanato-1-methylcyclopent-1-ene (Intermediate 2, 62 mg). The resulted mixture was stirred for 12 hours at 40° C. Cold water (30 mL) was added. The mixture was extracted with CH2Cl2 (2×100 mL). The combined organic layers were dried over Na$_2$SO$_4$, filtered and concentrated to give (R)-(9H-fluoren-9-yl)methyl 4-((6-chloro-2-hydroxy-3-(3-(2-methylcyclopent-2-en-1-yl)ureido)phenyl)sulfonyl)piperazine-1-carboxylate (100 mg) as a white solid.

Step 6: To a solution of (R)-(9H-fluoren-9-yl)methyl 4-((6-chloro-2-hydroxy-3-(3-(2-methylcyclopent-2-en-1-yl)ureido)phenyl)sulfonyl)piperazine-1-carboxylate (130 mg) in DMF (2 mL) was added piperidine (174 mg). The resulting mixture was stirred for 2 hours at RT. Cold water (30 mL) was added. The mixture was extracted with DCM (2×100 mL). The combined organic layers were dried over Na$_2$SO$_4$, filtered and concentrated in vacuo. The residue was purified by MDAP under basic condition to give the title compound (36 mg) as a white solid. $^1$H-NMR (400 MHz, DMSO-d$_6$) δ ppm 8.22 (s, 1H), 7.79 (d, J=8.1 Hz, 1H), 7.13 (br s, 1H), 6.96 (d, J=8.6 Hz, 1H), 6.20 (d, J=8.0 Hz, 1H), 5.45 (s, 1H), 4.49-4.55 (m, 1H), 3.25-3.30 (s, 4H), 2.78-2.93 (m, 4H), 2.13-2.23 (m, 3H), 1.64 (s, 3H), 1.44-1.50 (m, 1H); MS(ES$^+$) m/z 415 (MH$^+$).

Compound 200: (R)-1-(4-chloro-3-((1-ethyl-4-fluoropiperidin-4-yl)sulfonyl)-2-hydroxphenyl)-3-(2-chlorocyclopent-2-en-1-yl)urea

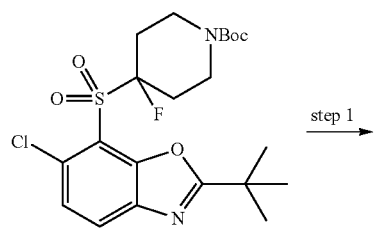

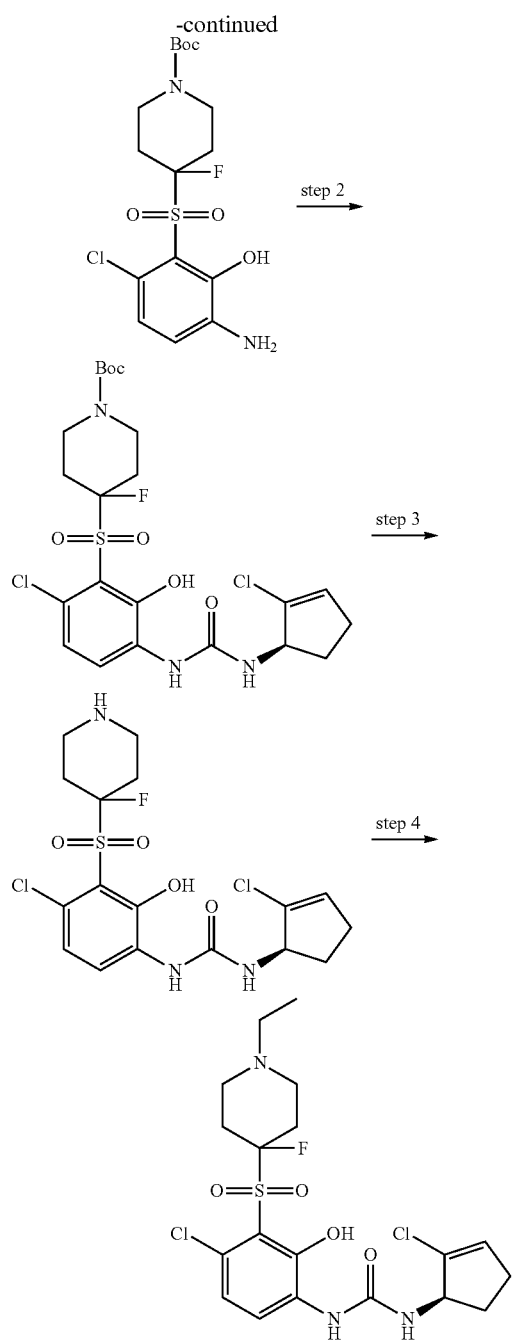

Step 1: To a solution of tert-butyl 4-((2-(tert-butyl)-6-chlorobenzo[d]oxazol-7-yl)sulfonyl)-4-fluoropiperidine-1-carboxylate (Intermediate 56, Step 4, 2.6 g) in 1,4-dioxane (15 mL) was added aq. HCl solution (37%, 15 mL). The mixture was refluxed at 110° C. for 2 hours, and then concentrated. The resulting residue was dissolved in EA (40 mL). The pH was adjusted to 8-9 using TEA. Boc-anhydride (1.2 mL) was added. The mixture was stirred for 15 mins under ice bath temperature. The organic layer was separated, washed with sat. brine, dried over anhydrous sodium sulfate, and filtered. The filtrate was concentrated and purified by column chromatography (eluting with a gredient of 0-60% EA in PE) to afford tert-butyl 4-((3-amino-6-chloro-2-hydroxyphenyl)sulfonyl)-4-fluoropiperidine-1-carboxylate (695 mg). MS(ES$^+$) m/z 431 (MNa$^+$).

Step 2: To a solution of tert-butyl 4-((3-amino-6-chloro-2-hydroxyphenyl)sulfonyl)-4-fluoropiperidine-1-carboxylate (220 mg) in pyridine (5 mL) was added a solution of (R)-1-chloro-5-isocyanatocyclopent-1-ene (Intermediate 1, 77 mg) in toluene (8 mL). The reaction mixture was stirred at RT overnight. The mixture was concentrated. The resulting residue was dissolved in DMF (8 mL) and purified by MDAP to afford (R)-tert-butyl 4-((6-chloro-3-(3-(2-chlorocyclopent-2-en-1-yl)ureido)-2-hydroxyphenyl)sulfonyl)-4-fluoropiperidine-1-carboxylate (188 mg) as a white solid. MS(ES$^+$) m/z 574 (MNa$^+$).

Step 3: To a solution of (R)-tert-butyl 4-((6-chloro-3-(3-(2-chlorocyclopent-2-en-1-yl)ureido)-2-hydroxyphenyl)sulfonyl)-4-fluoropiperidine-1-carboxylate (188 mg) in DCM (10 mL) was added TFA (0.03 mL). The reaction mixture was stirred at RT for 1 hour, and then concentrated to afford (R)-1-(4-chloro-3-((4-fluoropiperidin-4-yl)sulfonyl)-2-hydroxphenyl)-3-(2-chlorocyclopent-2-en-1-yl)urea, trifluoroacetic acid salt (193 mg) as a brown solid. MS(ES$^+$) m/z 452 (MH$^+$).

Step 4: To a solution of (R)-1-(4-chloro-3-((4-fluoropiperidin-4-yl)sulfonyl)-2-hydroxyphenyl)-3-(2-chlorocyclopent-2-en-1-yl)urea, trifluoroacetic acid salt (193 mg) in acetonitrile (10 mL) was added acetaldehyde (0.3 mL). The reaction mixture was stirred at 0° C. for 20 mins. Sodium triacetoxyborohydride (289 mg) was added. The reaction mixture was stirred at RT for 1 hour. DCM (60 mL) was added. The organic layer was washed with brine, dried over anhydrous sodium sulfate. The solution was concentrated and the resulting residue was purified by MADP to afford the title compound (75 mg) as a white solid. $^1$H-NMR (400 MHz, DMSO-d$_6$) δ ppm 8.03 (s, 1H), 7.92 (d, J=8.3 Hz, 1H), 7.34 (d, J=9.0 Hz, 1H), 6.34-6.44 (m, 1H), 5.94-5.98 (m, 1H), 4.72-4.82 (m, 1H), 3.45-3.65 (m, 2H), 2.74-2.94 (m, 5H), 2.59-2.73 (m, 1H), 2.15-2.45 (m, 6H), 1.58-1.73 (m, 1H), 1.04 (t, J=7.3 Hz, 3H); MS(ES$^+$) m/z 480 (MH$^+$).

Compound 201: (S)-1-(4-chloro-3-((1-ethyl-4-fluoropiperidin-4-yl)sulfonyl)-2-hydroxphenyl)-3-(2-chlorocyclopent-2-en-1-yl)urea, trifluoroacetic acid salt

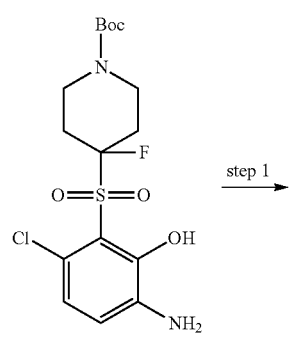

step 1 →

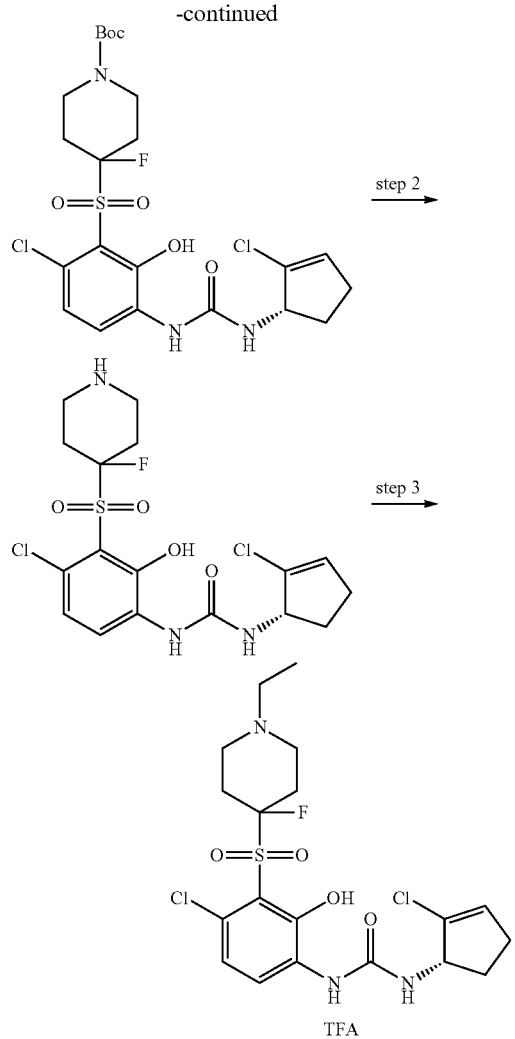

Step 1: To a solution of tert-butyl 4-((3-amino-6-chloro-2-hydroxyphenyl)sulfonyl)-4-fluoropiperidine-1-carboxylate (Compound 200, Step 1, 220 mg) in pyridine (5 mL) was added a solution of (S)-1-chloro-5-isocyanatocyclopent-1-ene (Intermediate 5, 0.1 M in toluene, 8 mL). The reaction mixture was stirred at RT overnight. The mixture was concentrated. The resulting residue was dissolved in DMF (8 mL) and purified by MDAP to afford (S)-tert-butyl 4-((6-chloro-3-(3-(2-chlorocyclopent-2-en-1-yl)ureido)-2-hydroxyphenyl)sulfonyl)-4-fluoropiperidine-1-carboxylate (210 mg) as a white solid. MS(ES$^+$) m/z 574 (MNa$^+$).

Step 2: To a solution of (S)-tert-butyl 4-((6-chloro-3-(3-(2-chlorocyclopent-2-en-1-yl)ureido)-2-hydroxyphenyl)sulfonyl)-4-fluoropiperidine-1-carboxylate (210 mg) in DCM (10 mL) was added TFA (0.03 mL). The reaction mixture was stirred at RT for 1 hour, and then concentrated to afford (S)-1-(4-chloro-3-((4-fluoropiperidin-4-yl)sulfonyl)-2-hydroxyphenyl)-3-(2-chlorocyclopent-2-en-1-yl)urea, trifluoroacetic acid salt (215 mg) as a brown solid. MS(ES$^+$) m/z 452 (MH$^+$).

Step 3: To a solution of (S)-1-(4-chloro-3-((4-fluoropiperidin-4-yl)sulfonyl)-2-hydroxyphenyl)-3-(2-chlorocyclopent-2-en-1-yl)urea, trifluoroacetic acid salt (215 mg) in acetonitrile (10 mL) was added acetaldehyde (0.3 mL). The reaction mixture was stirred at 0° C. for 20 mins. Sodium triacetoxyborohydride (322 mg) was added. The reaction mixture was stirred at RT for 1 hour. DCM (60 mL) was added, and the mixture was washed by sat. brine. The organic layer was separated, washed with brine, dried over anhydrous sodium sulfate and concentrated. The residue was purified by MADP to afford (S)-1-(4-chloro-3-((1-ethyl-4-fluoropiperidin-4-yl)sulfonyl)-2-hydroxyphenyl)-3-(2-chlorocyclopent-2-en-1-yl)urea as a trifluoroacetic acid salt (110 mg) as a white solid. $^1$H-NMR (400 MHz, DMSO-d$_6$) δ ppm 9.89 (br. s., 1H), 8.34 (s, 1H), 8.29 (d, J=8.8 Hz, 1H), 7.41 (d, J=8.8 Hz, 1H), 7.16 (d, J=8.5 Hz, 1H), 5.97-6.02 (m, 1H), 4.70-4.79 (m, 1H), 3.63 (d, J=11.8 Hz, 2H), 3.02-3.21 (m, 4H), 2.53-2.69 (m, 1H), 2.23-2.48 (m, 6H), 1.61-1.72 (m, 1H), 1.21 (t, J=7.3 Hz, 3H); MS(ES$^+$) m/z 480 (MH$^+$).

Compound 202: 1-(4-chloro-2-hydroxy-3-((1-(1-methyl-1H-imidazol-2-yl)ethyl)sulfonyl)phenyl)-3-(cyclopent-2-en-1-yl)urea, trifluoroacetic acid salt

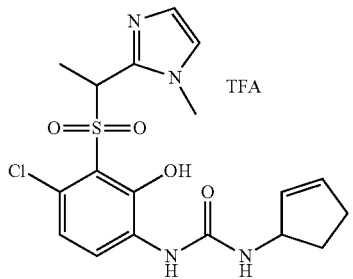 [SMILES: CC(c1nccn1C)S(=O)(=O)c1c(Cl)ccc(NC(=O)NC2C=CCC2)c1O]

To a solution of 6-amino-3-chloro-2-((1-(1-methyl-1H-imidazol-2-yl)ethyl)sulfonyl)phenol (Intermediate 25, 100 mg) in pyridine (5 mL) was added fresh 3-isocyanatocyclopent-1-ene solution (Intermediate 4, 0.08 M in toluene, 4 mL). The resulting mixture was stirred at room temperature overnight, and then quenched with ethanol (10 mL). The resulting mixture was concentrated under reduced pressure, and then purified with MDAP (acidic condition) to afford the title compound (22.1 mg). MS(ES$^+$) m/z 425 (MH$^+$).

Compound 203: 1-(4-chloro-3-((trans-3-((dimethylamino)methyl)cyclobutyl)sulfonyl)-2-hydroxyphenyl)-3-(2-chlorocyclopent-2-en-1-yl)urea, trifluoroacetic acid salt

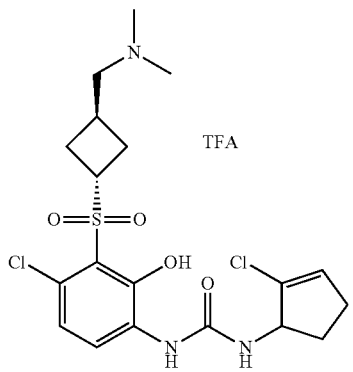 [SMILES: CN(C)C[C@H]1C[C@H](S(=O)(=O)c2c(Cl)ccc(NC(=O)NC3CCC=C3Cl)c2O)C1]

To a solution of 6-amino-3-chloro-2-((trans-3-((dimethylamino)methyl)cyclobutyl)sulfonyl)phenol (Intermediate 104, 20 mg) in pyridine (5 mL) was added fresh 1-chloro-5-isocyanatocyclopent-1-ene solution (Intermediate 1, 0.1 M in toluene, 4.5 mL) dropwise. The mixture was stirred at room temperature overnight. The mixture was concentrated and the resulting residue was dissolved in DMF (8 mL) and purified by MDAP (acid condition) to afford the title compound (1.4 mg) as a white solid. $^1$H NMR (400 MHz, methanol-d$_4$) δ ppm 8.30 (dd, J=8.9, 4.1 Hz, 1H), 7.10 (d, J=8.8 Hz, 1H), 5.94 (d, J=1.5 Hz, 1H), 4.86-4.82 (m, 1H), 4.66-4.56 (m, 1H), 3.29 (d, J=7.3 Hz, 1H), 2.97-3.14 (m, 1H), 2.88 (s, 6H), 2.67-2.86 (m, 2H), 2.44-2.61 (m, 3H), 2.27-2.44 (m, 3H), 1.72-1.87 (m, 1H); $^{19}$F-NMR (376 MHz, methanol-d$_4$) δ ppm −76.9; MS(ES$^+$) m/z 462 (MH$^+$).

Compound 204: 1-(4-chloro-3-((cis-3-((dimethylamino)methyl)cyclobutyl)sulfonyl)-2-hydroxyphenyl)-3-(2-chlorocyclopent-2-en-1-yl)urea, trifluoroacetic acid salt

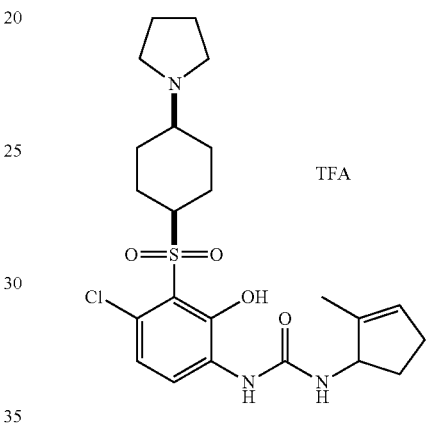

To a solution of 6-amino-3-chloro-2-((cis-4-(pyrrolidin-1-yl)cyclohexyl)sulfonyl)phenol (Intermediate 131, 20 mg) in pyridine (5 mL) was added fresh 5-isocyanato-1-methylcyclopent-1-ene solution (Intermediate 2, 0.1 M in toluene, 4.5 mL) dropwise. The mixture was stirred at room temperature overnight. The mixture was concentrated and the resulting residue was dissolved in DMF (8 mL) and purified by MDAP (acid condition) to afford the title compound (1.7 mg) as a white solid. $^1$H-NMR (400 MHz, DMSO-d$_6$) δ ppm 8.34 (d, J=8.8 Hz, 1H), 7.12 (d, J=8.8 Hz, 1H), 5.57 (br. s., 1H), 4.66 (br. s., 1H), 3.69-3.79 (m, 1H), 3.63 (br. s., 2H), 3.08-3.28 (m, 3H), 2.10-2.45 (m, 9H), 1.92-2.09 (m, 2H), 1.77-1.90 (m, 2H), 1.75 (s, 3H), 1.51-1.70 (m, 3H); MS(ES$^+$) m/z 482 (MH$^+$).

Compound 205: 1-(4-chloro-2-hydroxy-3-(((S)-3-methyltetrahydrofuran-3-yl)sulfonyl)phenyl)-3-((S)-2-methylcyclopent-2-en-1-yl)urea

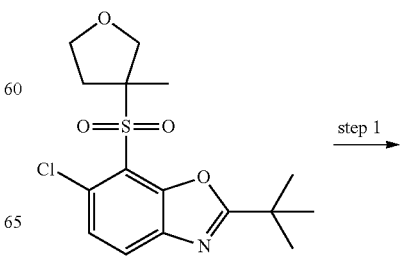

step 1

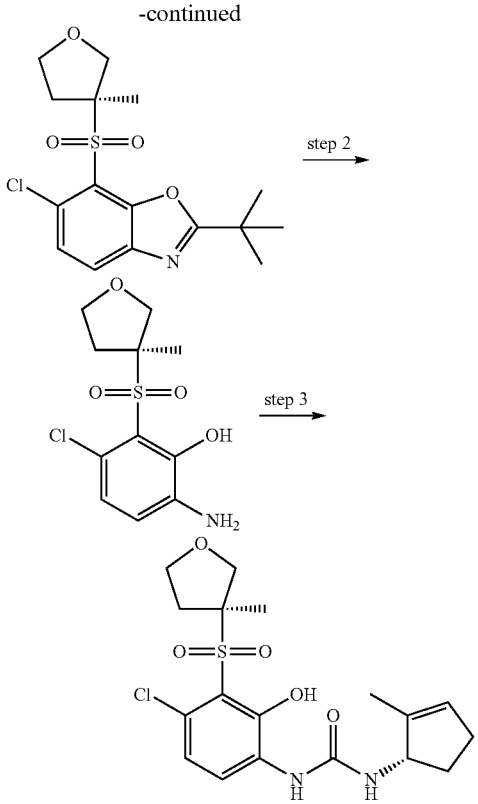

Step 1: 6-Amino-3-chloro-2-((3-methyltetrahydrofuran-3-yl)sulfonyl)phenol (Intermediate 25, 10.15 g) was purified by chiral HPLC to afford (S)-2-(tert-butyl)-6-chloro-7-((3-methyltetrahydrofuran-3-yl)sulfonyl)benzo[d]oxazole (6.77 g). HPLC (CHIRALCEL OJ-H column (4.6*150 mm), Hexane/EtOH=95/5 (v/v), flow rate: 1.0 mL/min); $t_r$=7.85 min; >99% ee; The other enantiomer (R)-2-(tert-butyl)-6-chloro-7-((3-methyltetrahydrofuran-3-yl)sulfonyl)benzo[d]oxazole(S)-2-(tert-butyl)-6-chloro-7-((3-methyltetrahydrofuran-3-yl)sulfonyl)benzo[d]oxazole was also collected. HPLC (CHIRALCEL OJ-H column (4.6*150 mm), Hexane/EtOH=95/5 (v/v), flow rate: 1.0 mL/min); $t_r$=10.32 min; >99% ee;

Step 2: To a solution of (S)-2-(tert-butyl)-6-chloro-7-((3-methyltetrahydrofuran-3-yl)sulfonyl)benzo[d]oxazole (155.0 g) in 1,4-dioxane (150 mL) was added conc. aqueous hydrochloric acid (1100 mL). The mixture was heated to reflux overnight. TLC showed that the starting material was completely consumed. After cooled to room temperature, the solvent was removed under reduced pressure. The resulting residue was dissolved in EtOAc. The pH of the solution was adjusted to 8 with aq.NaHCO₃, extratced, washed and concentrated. The resulting residue was purified by silica gel column chromatography (Petroleum Ether/EtOAc=10:1) to afford (S)-6-amino-3-chloro-2-((3-methyltetrahydrofuran-3-yl)sulfonyl)phenol (114 g).

Step 3: To a solution of (S)-2-methylcyclopent-2-enamine, hydrochloride (synthesized using the similar method for intermediate 2, Step 6, 1.1 g) in toluene (20 mL) was added triphosgene (2.44 g) portionwise. The resulting mixture was stirred at 120° C. for 6 hours. Then (S)-5-isocyanato-1-methylcyclopent-1-ene was cooled and used without work-up. To a solution of (S)-6-amino-3-chloro-2-((3-methyltetrahydrofuran-3-yl)sulfonyl)phenol (1.6 g) in pyridine (20 mL) was added the freshly prepared (S)-5-isocyanato-1-methylcyclopent-1-ene in toluene (20 mL) dropwise. The reaction mixture was stirred at room temperature overnight. Then it was quenched with water (50 mL) and extracted with EtOAc (100 mL*2). The combined organic layers were washed with 0.1 M HCl (50 mL*3), sat. aq. NaHCO₃ (50 mL) and brine (50 mL*2), dried over Na₂SO₄. After filtration, the solution was concentrated and part of the residue was purified by prep-HPLC to afford the title compound (200 mg). ¹H-NMR (300 MHz, DMSO-$d_6$) δ ppm 10.50 (br, 1H), 8.34 (d, 1H), 8.16 (s, 1H), 7.08 (dd, 2H), 5.49 (br, 1H), 4.50 (d, 1H), 4.30 (d, 1H), 3.77-3.82 (m, 2H), 3.27 (d, 1H), 2.64-2.70 (m, 1H), 2.14-2.27 (m, 3H), 1.88-1.93 (m, 1H), 1.63 (s, 3H), 1.48 (s, 4H); MS(ES⁺) m/z 415 (MH⁺).

Compound 206: 1-(4-chloro-2-hydroxy-3-(((R)-3-methyltetrahydrofuran-3-yl)sulfonyl)phenyl)-3-((S)-2-methylcyclopent-2-en-1-yl)urea

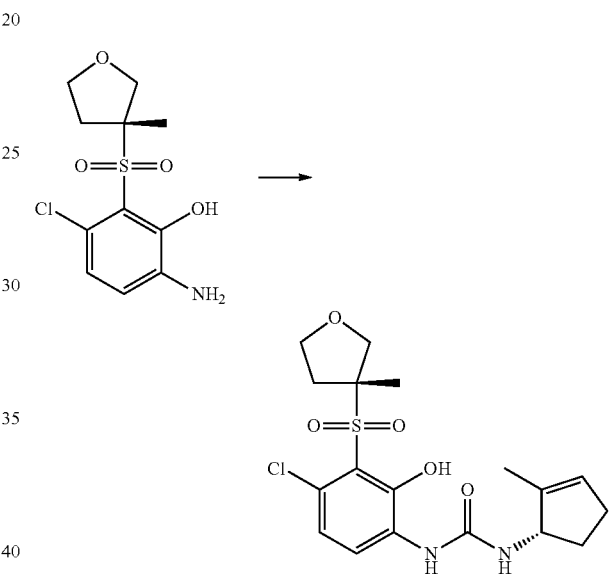

To a solution of (S)-2-methylcyclopent-2-enamine, hydrochloride (synthesized using the similar method for intermediate 2, Step 6, 1.75 g) in toluene (20 mL) was added triphosgene (3.0 g, 10.28 mmol) portionwise. The resulting mixture was stirred at 120° C. for 6 hours. Then the product (S)-5-isocyanato-1-methylcyclopent-1-ene was cooled and used without work-up. To a solution of (R)-6-amino-3-chloro-2-((3-methyltetrahydrofuran-3-yl)sulfonyl)phenol (synthesized using the samilar method for compound 205, Step 2, 2.0 g) in pyridine (20 mL) was added the freshly prepared (S)-5-isocyanato-1-methylcyclopent-1-ene in toluene (20 mL) dropwise. The reaction mixture was stirred at room temperature overnight. Then it was quenched with water (50 mL) and extracted with EtOAc (100 mL*2), the combined organic layers were washed with 0.1 M HCl (50 mL*3), sat. aq. NaHCO₃ (50 mL) and brine (50 mL*2), dried over Na₂SO₄. After filtration, the solution was concentrated and part of the residue was purified by prep-HPLC to afford the title compound (300 mg). ¹H-NMR (300 MHz, DMSO-$d_6$) δ ppm 10.50 (br, 1H), 8.34 (d, 1H), 8.16 (s, 1H), 7.08 (dd, 2H), 5.49 (br, 1H), 4.50 (d, 1H), 4.30 (d, 1H), 3.77-3.82 (m, 2H), 3.27 (d, 1H), 2.64-2.70 (m, 1H), 2.14-2.27 (m, 3H), 1.88-1.93 (m, 1H), 1.63 (s, 3H), 1.48 (s, 4H); MS(ES⁺) m/z 415 (MH⁺).

As stated above, the compounds of the invention are CXCR2 antagonists and are useful in the treatment or prevention of diseases mediated by CXCR2. The biological activities of the compounds of the invention can be determined using any suitable assay for determining the activity of a candidate compound as a CXCR2 antagonist, as well as tissue and in vivo models.

Assays a) CXCR2 Tango Assay

The assay measures ligand-induced activation of the receptor CXCR2 in a stable cell line containing the recombinant human CXCR2 linked to a TEV protease site and a Gal4-VP16 transcription factor (Invitrogen). Ligand binding to the receptor results in the recruitment of arrestin proteins (tagged with protease) to the receptor and triggers the release of a tethered transcription factor. The transcription factor enters the nucleus and activates the transcription of the reporter gene. The ability of a compound to inhibit CXCR2 activation is indirectly assessed by measuring the reporter gene activity.

A vial of cryopreserved cells was removed from liquid nitrogen and rapidly thawed in a water bath at 37° C. with gentle agitation. The contents of the vial were transferred drop-wise into Thawing Medium in a sterile 15 ml conical tube and then centrifuged at 1000 rpm for 4-5 min. Then the cell pellets were resuspended in Assay Medium at a density of ~200,000 cells/ml. All test compounds were dissolved in DMSO at a concentration of 10 mM and were prepared in 100% DMSO to provide 10 point dose response curves. A reference CXCR2 antagonist was added to wells in row 2, columns 1-5 & 7-11. Exemplified compounds 1-4, 7, 8-10, 13-22, 24-26, 28-30, 32, 33, 36, 37, 40, 42-44. 95-110, 115-118, 120, 121, 125, 126, 129-134, 137, 138, 140, 142, 147-149, 153-157, 159-162, 163-166, 168, 170, 172, 174-180 and 202 were tested using the CXCR2 antagonist sodium 3-chloro-6-(3-(2,3-dichlorophenyl)ureido)-2-sulfamoylphenolate as reference compound (Reference Compound 1) (published International patent application WO2002/079122). Exemplified compounds 5-7, 11, 12, 23, 27, 31, 34, 35, 38-42, 45-94, 111-114, 117, 119, 122-124, 127, 128, 135, 136, 139, 141, 143-146, 150-152, 158, 163, 166, 167, 169, 171-173, 181-201, 205 and 206 were tested using the CXCR2 antagonist 1-(4-chloro-3-((1,4-dimethylpiperidin-4-yl)sulfonyl)-2-hydroxyphenyl)-3-(2-chloro-3-fluorophenyl)urea as reference compound (Reference Compound 2; the procedure for making Reference Compound 2 is shown below). Test compounds were added to wells in row 2, columns 13-17 & 19-23 and rows 3-15, columns 1-5 & 7-11/13-17 & 19-23 (columns 6 and 18 as positive controls and un-stimulated controls respectively; columns 12 and 24 as cell-free control). Compounds in solution were added to the assay plate (Greiner 781090) using an Echo (Labcyte) concentration-response program (50 nl/well). The cell-free, un-stimulated and positive controls were loaded with 50 nl/well pure DMSO to ensure that the DMSO concentration was constant across the plate for all assays. Using Multi-drop Combi (Thermo) with standard cassette, 50 μl of Assay Medium was added to each well in the cell-free controls (columns 12 and 24); 50 μl of the cell suspension without hCXCL1 (a CXCR2 ligand) was added to each well in column 18 of the plate (~10,000 cells per well); and 50 μl of the cell suspension with 80 nM hCXCL1 was added to the rest of wells of the plate (~10,000 cells per well). The cells were incubated overnight at 37° C./5% $CO_2$. 10 μl of 6× substrate mixture (LiveBLAzer™-FRET B/G substrate (CCF4-AM) Cat # K1096 from Invitrogen, Inc.) was added to each well using Multi-drop Combi (Thermo) with small-tube cassette and the plates incubated at room temperature for 2 h in the dark. The plate was finally read on EnVision using one excitation channel (409 nm) and two emission channels (460 nm and 530 nm).

The blue/green emission ratio (460 nm/530 nm) was calculated for each well, by dividing the background-subtracted Blue emission values by the background-subtracted Green emission values. The dose response curve was based on sigmoidal dose-response model. All ratio data was normalized based upon the maximum emission ratio of positive control (hCXCL1) and minimum emission ratio of negative control (DMSO) on each plate. The intrinsic activity (IA) of each compound would be the normalized percentage of its maximum response after curve fitting.

All exemplified compounds (except for Compounds 203 and 204) were tested in the CXCR2 Tango assay or a similar assay described above. The data mentioned below represents a mean pIC 50 value of multiple test results. It is understood that the data illustrated below may have reasonable variation depending on the specific conditions and procedures used by the person conducting the testing.

All tested compounds exhibited a pIC50≥5.5 (except for Compound 181 which exhibited a pIC50<5). Compounds 1-6, 9, 10, 12, 14-18, 20-27, 29-31, 34, 36-41, 44-46, 48-52, 55-63, 65-70, 72-78, 80-125, 127-134, 136, 137, 139-151, 153, 154, 156-158, 161, 162, 164-169, 174-180 and 183-200 exhibited a pIC50≥8.0. Compounds 2, 6, 20, 21, 23, 31, 37-39, 41, 45, 46, 48-52, 57-63, 69, 70, 73-77, 81-83, 85, 88-91, 94, 95, 98, 101, 106, 119, 122-124, 127, 129, 130, 143, 144, 146, 162, 166-169, 186, 189-196 and 200 exhibited a pIC50≥9.0. Compound 195 exhibited a pIC50 of 9.0. Compound 196 exhibited a pIC50 of 9.0.

b) Human Whole Blood Assay

The whole blood assay tested the compounds' ability to inhibit the upregulation of CD11b in GROα stimulated neutrophils in human whole blood.

Blood was withdrawn by venipuncture from consented adults and poured into a Sterilin tube containing an anti-coagulant Heparin (10 uL/mL of blood). All the test compounds were dissolved in DMSO to 4 mM and serial diluted across the plate, 1 in 3 to provide 10 point dose response curves. The compounds were then diluted 100 fold in -PBS [Phosphate buffered saline (without Calcium Chloride and Magnesium Chloride)] after which, 1 uL was dispensed in 96 U bottom Costar plates using an FX. This was done to reduce the final DMSO concentration to 0.25% and for compounds to be screened at 10 uM final assay concentration, after addition of blood.

10 uL of blood was transferred to the compound plate using a multi-channel pipette, gently tapped and incubated for 15 minutes, at 37° C. After 15 minutes, the stimulant GROα was diluted to 100 nM in 0.1% BSA (Albumin Bovine Serum)-PBS and 5 uL is dispensed across the whole plate for a final concentration of 33 nM. The plate was gently tapped and incubated further for 15 minutes at 37° C. The plate was placed on ice for 1 minute before addition of 10 uL of an antibody cocktail consisting of CD11b-FITC (40 ug/mL) purchased from BioLegend (address: Cambridge Bioscience, Munro House, Trafalgar Way, Bar Hill, Cambridge, UK) and CD16-PE purchased from BD Pharmingen (address: The Danby Building, Edmung Halley Road, Oxford Science Park, Oxford, UK) (stock concentration 100 tests, 2 mL stock volume is diluted 1 in 5). The plate was placed on ice for 1 hour in the dark. The cells were then fixed using 200 uL/well of 1×FACS (Flow Activated Cell Sorting) Lyse solution (Becton and Dickinson-BD) and on ice for 20 minutes in the dark. The plate was centrifuged at 1600 rpm for 5 minutes and re-suspended with 200 uL of ice cold PBS. This step was repeated twice and on the final step the plate was re-suspended with 50 uL of ice cold -PBS for flow Cytometric analysis.

Samples were run on a Becton and Dickinson (BD)-Acurri C6 Flow Cytometer using a HyperCyt sampling apparatus (IntelliCyt) with a flow rate 2 uL/sec. CD11b upregulation is monitored in neutrophils and identified using a combination of both side scatter and CD16 expression.

Compounds 5, 20, 23, 27, 31, 39-42, 49, 56, 57, 59, 60, 62, 66, 68-70, 72, 75, 76, 78, 82, 83, 90, 92-94, 104, 107, 110, 112, 114, 119, 122, 123, 128, 136, 141, 142, 144, 146, 151, 158, 165, 184-186, 191-196, 199 and 200 were tested in this assay and exhibited a between pIC50≥5.6 to 7.6. Compound 195 exhibited pIC50 of 7.4. Compound 196 exhibited pIC50 of 6.8.

c) OPC Differentiation Assay

In the oligodendrocyte precursor cell (OPC) in vitro differentiation assay, purified or enriched OPCs are cultured and differentiated into immature oligodendrocytes, mature oligodendrocytes, and myelinating oligodendrocytes (Watkins et al. (2008) *Neuron* 60:555-569). Specific markers have been identified for each specific stage of OPC differentiation. Myelin basic proteins (MBP), a specific marker for matured and myelinating oligodendrocytes, is used as an indicator for OPC differentiation and maturation (Franklin et al. (2008) *J Neurosci*, 255 Suppl 1:19-25). The OPC differentiation assay provides a tool to screen the compounds with the potency of promoting OPC differentiation, which is an initial step for downstream remyelination repair in vivo after demyelination occurs in mutiple scelerosis (MS) patients.

Rat oligodendrocyte precursor cells (OPCs) were obtained from P1 pups and were cultured in DMEM/20S medium (DMEM with 20% FBS, 4 mM L-Glutamine, 1 mM sodium pyruvate and penicillin) (Zhang et al. (2007) *Nature Protocol* 2 (5):1044). After isolation of enriched OPCs from mix glia cells, 7000-10000 viable cells were planted into each well in opaque-walled 96-well-plate (Costar3603) in normal OPC proliferative medium BDM (DMEM with 4 mM L-Glutamine, 1 mM sodium pyruvate, 0.1% BSA, 50 ug/ml Apo-transferrin, 5 µg/ml insulin, 30 nM sodium selenite, 10 nM D-biotin, 10 nM hydrocortisone and 1/100 N2 and penicillin.) with 10 ng/ml PDGF and 10 ng/ml bFGF; The medium was changed next day into basal differentiation medium (DMEM/F12 with 6 ng/ml Glucose, 2 mM L-Glutamine, 0.1 mg/ml BSA, 50 ug/ml transferrin, 30 nM Triiodothyronine, 20 nM hydrocortisone, 20 nM progesterone, 10 nM D-biotin and 30 nM sodium selenite and 5 ug/ml insulin and penicillin) (Mabie et al. 1999. *J. Neurosci.* 19 (16):9074-83) with or without the test compounds added to the media. The blank group was carried out without adding the tested compounds to the media. Culture media were changed around 3-5 days followed by fixation of the cells and immunostaining for MBP (Millipore cat. no. LV1519581). The plate was read on Cellomics (SN: 04080019LH; P/N no 1-0117) using target activation protocol to calculate the percentage of MBP+ cells to reflect the differentiation of OPCs.

Compound 195 was tested in the OPC differentiation assay and was found to promote OPC differentiation. Compound 195 exhibited a pIC50 in this assay of 5.2.

1-(4-Chloro-3-((1,4-dimethylpiperidin-4-yl)sulfonyl)-2-hydroxyphenyl)-3-(2-chloro-3-fluorophenyl) urea [Reference Compound 2 in Assay a)]

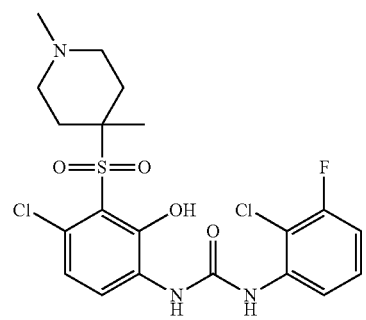 [SMILES: CN1CCC(C)(S(=O)(=O)c2c(Cl)ccc(NC(=O)Nc3cccc(F)c3Cl)c2O)CC1]

To a solution of 6-amino-3-chloro-2-[(1,4-dimethyl-4-piperidinyl)sulfonyl]phenol, hydrochloride (see below for prearation of the free base) (0.35 g) in 1,4-dioxane (10 mL) and water (1 mL) was added NaHCO$_3$ (0.225 g). The mixture was stirred at rt for 10 min. Then 2-chloro-1-fluoro-3-isocyanatobenzene (0.153 g) was added. Stirring continued for additional 10 min. Afterwards, the reaction mixture was diluted with water (50 mL), extracted with EA (2×50 mL). The solution was then washed with brine, dried over anhydrous Na$_2$SO$_4$ and purified by MDAP to give the title product as its trifluoroacetic acid salt (130 mg).

6-Amino-3-chloro-2-((1,4-dimethylpiperidin-4-yl) sulfonyl)phenol

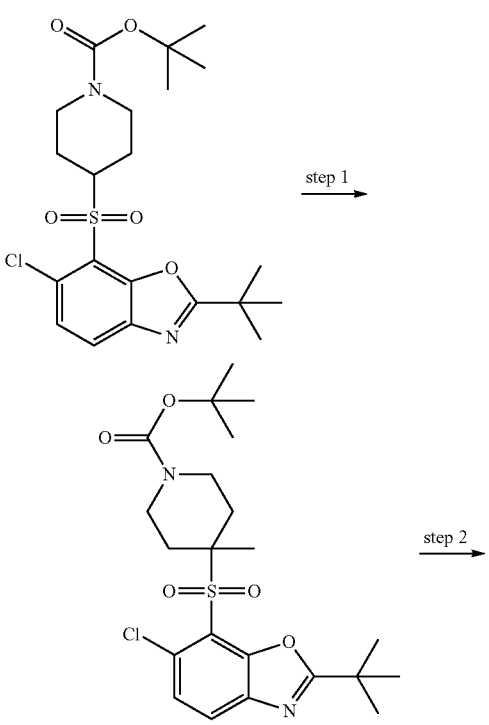

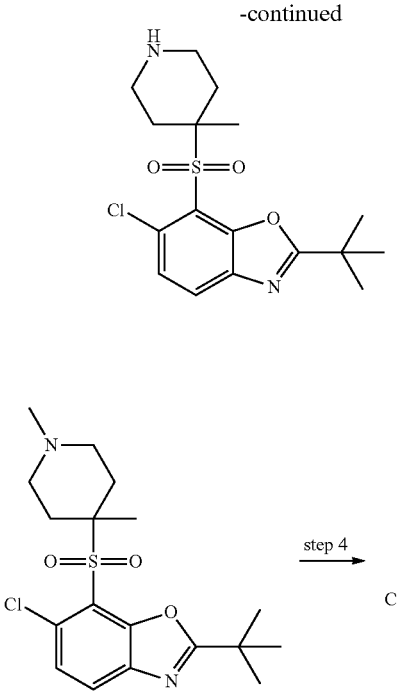

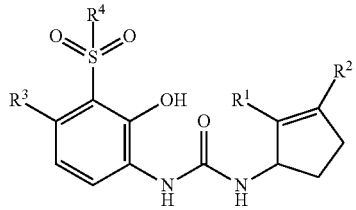

Step 1: To a solution of tert-butyl 4-((2-(tert-butyl)-6-chlorobenzo[d]oxazol-7-yl)sulfonyl)piperidine-1-carboxylate (0.35 g) (see Intermediate 56, step 3) in tetrahydrofuran (THF) (25 mL) at −78° C. was added n-butyllithium (0.383 mL, 1.6 M in n-hexane). The mixture was stirred at −78° C. for 1 h. Then MeI (0.048 mL) was added. Stirring continued for 4 h at −78° C. Afterwards, the reaction was quenched with aq.NH$_4$Cl, extracted with EA (2×50 mL). The solution was then washed with brine, dried over anhydrous Na$_2$SO$_4$, and concentrated to give tert-butyl 4-((2-(tert-butyl)-6-chlorobenzo[d]oxazol-7-yl)sulfonyl)-4-methylpiperidine-1-carboxylate (0.4 g).

Step 2: To a solution of the product from Step 1 (0.35 g) in dichloromethane (DCM) (20 mL) was added TFA (0.572 mL). The mixture was stirred at rt overnight. The resulting solution was concentrated under vacuo to give 2-(tert-butyl)-6-chloro-7-((4-methylpiperidin-4-yl)sulfonyl)benzo[d]oxazole, trifluoroacetic acid salt (0.35 g).

Step 3: To a solution of the product from Step 2 (0.35 g) in N,N-dimethylformamide (DMF) (10 mL) was added AcOH (0.054 mL) and formaldehyde (0.788 mL). Then the reaction mixture was cooled to 0° C., stirred for 10 min and sodium triacetoxyborohydride (0.6 g) was added portionwise. Stirring was continued for additional 20 min. Afterwards, the reaction was quenched with sat. aq. NaHCO$_3$ (20 mL) and extracted with DCM (2×50 mL). The solution was then washed with brine, dried over anhydrous Na$_2$SO$_4$, and concentrated to give 2-(tert-butyl)-6-chloro-7-((1,4-dimethylpiperidin-4-yl)sulfonyl)benzo[d]oxazole (0.3 g).

Step 4: To a solution of the product from Step 3 (0.35 g) in 1,4-dioxane (10 mL) and water (10 mL) was added HCl (0.747 mL, 37% in water). The mixture was heated at 120° C. overnight. Afterwards, the resulting solution was concentrated under vacuo to give 6-amino-3-chloro-2-((1,4-dimethylpiperidin-4-yl)sulfonyl)phenol hydrochloride (0.3 g), which was used in the next step without further purification.

The invention claimed is:
1. A compound of formula (I) or a pharmaceutically acceptable salt thereof,

(I)

wherein
$R^1$ is H, $C_{1-3}$alkyl, $C_{1-3}$haloalkyl or halo;
$R^2$ is H, $C_{1-3}$alkyl, $C_{1-3}$haloalkyl or halo;
$R^3$ is fluoro, chloro or cyano; and
$R^4$ is selected from the group consisting of:
a) $C_{1-6}$alkyl optionally substituted by one or more substituents independently selected from the group consisting of: fluoro, $C_{1-3}$alkoxy, $C_{1-3}$fluoroalkyl, $C_{1-3}$fluoroalkoxy and hydroxy;
b) —(CH$_2$)$_n$—N(R$^{4a}$)(R$^{4b}$); wherein
n is 0, 1 or 2;
the —(CH$_2$)$_n$— linker is optionally substituted by one or more groups independently selected from the group consisting of fluoro and methyl optionally substituted by one or more deuterium; and
wherein R$^{4a}$ and R$^{4b}$ are independently $C_{1-3}$alkyl, or R$^{4a}$ and R$^{4b}$, together with the nitrogen to which they are attached, form a 4, 5 or 6-membered ring, which ring
  i) optionally contains one additional ring-heteroatom selected from nitrogen and oxygen;
  ii) may be saturated, or when the ring is a 5 or 6-membered, be unsaturated or aromatic;
  iii) is optionally substituted by one or more substituents independently selected from $C_{1-3}$alkyl optionally substituted by one or more substituent independently selected from the group consisting of deuterium, fluoro, $C_{1-3}$fluoroalkyl, hydroxy, $C_{1-3}$alkoxy, $C_{1-3}$alkoxy$C_{1-3}$alkyl and $C_{1-3}$fluoroalkoxy; or
  iv) is ortho-fused to a further 5 or 6-membered ring which further ring is saturated, unsaturated or aromatic, which further ring optionally contains one additional ring-heteroatom selected from nitrogen and oxygen, and which further ring is optionally independently substituted by one or more fluoro or methyl substituents;
c) —(CH$_2$)$_p$-heteroaryl; wherein
p is 1 or 2;
the —(CH$_2$)$_p$— linker is optionally substituted by one or more groups independently selected from fluoro and methyl optionally substituted by one or more deuterium; the heteroaryl is 5 or 6-membered and is attached to the —(CH$_2$)$_p$— via a ring carbon atom; and
wherein the heteroaryl is optionally substituted by one or more substituents independently selected from the group consisting of $C_{1-3}$alkyl, fluoro, $C_{1-3}$fluoroalkyl; $C_{1-3}$alkoxy, $C_{1-3}$alkoxy$C_{1-3}$alkyl and $C_{1-3}$fluoroalkoxy, or wherein two substituents on adjacent ring-atoms, together with the interconnecting atoms form a further 5 or 6-membered ring ortho-fused to the heteroaryl group; which further ring is saturated, unsaturated or aromatic, and which further ring contains one additional heteroatom selected from nitrogen and oxygen; and which further ring is independently substituted by one or more fluoro or methyl substituents;
d) —(CH$_2$)$_q$-heterocyclyl; wherein
q is 0, 1 or 2;
the —(CH$_2$)$_q$— linker is optionally substituted by one or more groups independently selected from fluoro and methyl optionally substituted by one or more deuterium;
the heterocyclyl group is 3, 4, 5, or 6-membered and is attached to the —(CH$_2$)$_q$— via a ring carbon atom;
the heterocyclyl is saturated or unsaturated; and
wherein the heterocyclyl group is optionally substituted by one or more substituents independently selected from the group consisting of deuterium, C$_{1-3}$alkyl optionally substituted by one or more deuterium, fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy, C$_{3-6}$cycloalkyl and —(CH$_2$)$_s$NR$^{4c}$R$^{4d}$; or two substituents on the heterocyclyl group together with the interconnecting atom(s), foam a further 5 or 6-membered ring which further ring is saturated, unsaturated or aromatic when the further ring is ortho-fused; and which further ring optionally contains one additional heteroatom selected from nitrogen and oxygen, and which further ring is optionally independently substituted by one or more fluoro or methyl substituents; wherein s is 0 or 1, and wherein R$^{4c}$ and R$^{4d}$ are independently C$_{1-3}$alkyl, or R$^{4c}$ and R$^{4d}$, together with the nitrogen to which they are attached, form a 4, 5 or 6-membered saturated ring which ring is optionally substituted by one or more fluoro substituent; and
e) —(CH$_2$)$_r$—C$_{3-6}$cycloalkyl; wherein
r is 0, 1 or 2;
the —(CH$_2$)$_r$— linker is optionally substituted by one or more groups independently selected from fluoro and methyl optionally substituted by one or mote deuterium; and
wherein the C$_{3-6}$cycloalkyl group is optionally substituted by one or more substituents independently selected from the group consisting of C$_{1-3}$alkyl optionally substituted by one or more deuterium, fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy and —(CH$_2$)$_t$NR$^{4e}$R$^{4f}$, or wherein two substituents on the cycloalkyl group together with the interconnecting atom(s) form a further 5 or 6-membered ring which further ring is saturated, unsaturated or aromatic when the further ring is ortho-fused, and which further ring optionally contains one heteroatom selected from nitrogen and oxygen, and which further ring is optionally independently substituted by one or more fluoro or methyl substituents; wherein t is 0 or 1, and wherein R$^{4e}$ and R$^{4f}$ are independently C$_{1-3}$alkyl, or R$^{4e}$ and R$^{4f}$, together with the nitrogen to which they are attached, form a 4, 5 or 6-membered saturated ring which ring is optionally substituted by one or more fluoro substituent.

2. The compound according to claim 1 or a pharmaceutically acceptable salt thereof wherein R$^1$ is methyl, fluoro or chloro.

3. The compound according to claim 1 or a pharmaceutically acceptable salt thereof wherein R$^2$ is H, fluoro or chloro.

4. The compound according to claim 1 or a pharmaceutically acceptable salt thereof wherein R$^3$ is chloro or cyano.

5. The compound according to claim 1 or a pharmaceutically acceptable salt thereof wherein R$^4$ is selected from the group consisting of:
a) C$_{1-6}$alkyl optionally substituted by one or more substituents independently selected from the group consisting of: fluoro, C$_{1-3}$alkoxy, C$_{1-3}$fluoroalkyl, C$_{1-3}$fluoroalkoxy and hydroxy;
d) —(CH$_2$)$_q$-heterocyclyl; wherein
q is 0, 1 or 2;
the —(CH$_2$)$_q$— linker is optionally substituted by one or more groups independently selected from fluoro and methyl optionally substituted by one or more deuterium;
the heterocyclyl group is 3, 4, 5 or 6-membered and is attached to the —(CH$_2$)$_q$— via a ring carbon atom;
the heterocyclyl is saturated or unsaturated; and
wherein the heterocyclyl group is optionally substituted by one or more substituents independently selected from the group consisting of deuterium, C$_{1-3}$alkyl optionally substituted by one or more deuterium, fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy, C$_{3-6}$cycloalkyl and —(CH$_2$)$_s$NR$^{4c}$R$^{4d}$, or two substituents on the heterocyclyl group together with the interconnecting atom(s), form a further 5 or 6-membered ring which further ring is saturated, unsaturated or aromatic when the further ring is ortho-fused, and which further ring optionally contains one additional heteroatom selected from nitrogen and oxygen, and which further ring is optionally independently substituted by one or more fluoro or methyl substituents, wherein s is 0 or 1, and wherein R$^{4c}$ and R$^{4d}$ are independently C$_{1-3}$alkyl, or R$^{4c}$ and R$^{4d}$, together with the nitrogen to which they are attached, form a 4, 5 or 6-membered saturated ring which ring is optionally substituted by one or more fluoro substituent; and
e) —(CH$_2$)$_r$—C$_{3-6}$cycloalkyl; wherein
r is 0, 1, or 2;
the —(CH$_2$)$_r$— linker is optionally substituted by independently selected from fluoro and methyl optionally subtituted one or more deuterium; and wherein the C$_{3-6}$cycloalkyl group is optionally substituted by one or more substituents independently selected from the group consisting of C$_{1-3}$alkyl optionally substituted by one or more deuterium, fluoro, C$_{1-3}$fluoroalkyl, hydroxy, C$_{1-3}$alkoxy, C$_{1-3}$alkoxyC$_{1-3}$alkyl, C$_{1-3}$fluoroalkoxy and —(CH$_2$)$_t$NR$^{4e}$R$^{4f}$; or wherein two substituents on the cycloalkyl group together with the interconnecting atom(s) form a further 5 or 6-membered ring which further ring is saturated, unsaturated or aromatic when the further ring is ortho-fused; and
which further ring optionally contains one heteroatom selected from nitrogen and oxygen; and which further ring is optionally independently substituted by one or more fluoro or methyl substituents; wherein t is 0 or 1, and wherein R$^{4e}$ and R$^{4f}$ are independently C$_{1-3}$alkyl, or R$^{4e}$ and R$^{4f}$, together with the nitrogen to which they are attached, form a 4, 5 or 6-membered saturated ring which ring is optionally substituted by one or more fluoro substituent.

6. The compound according to claim 1 or a pharmaceutically acceptable salt thereof wherein, $R^4$ is selected from the group consisting of:
a) $C_{1-4}$alkyl optionally substituted by one, two or three substituents independently selected from the group consisting of: fluoro, $C_{1-3}$alkoxy and $C_{1-3}$fluoroalkyl;
d) a 5 or 6-membered, saturated heterocyclyl group directly attached to the sulfone via a ring carbon atom, which heterocyclyl group is optionally substituted by one, two or three substituents independently selected from the group consisting of $C_{1-3}$alkyl optionally substituted by one or more deuterium, fluoro, $C_{1-3}$fluoroalkyl, hydroxy, $C_{1-3}$alkoxy and —$NR^{4c}R^{4d}$, wherein $R^{4c}$ and $R^{4d}$ are independently $C_{1-3}$alkyl; and
which heterocyclyl group contains one or two ring-heteroatoms independently selected from nitrogen and oxygen; and
e) a $C_{4-6}$cycloalkyl group directly attached to the sulfone; which cycloalkyl group is optionally substituted by one or two substituents independently selected from the group consisting of fluoro, $C_{1-3}$fluoroalkyl, hydroxy, $C_{1-3}$alkoxy and —$(CH_2)_tNR^{4e}R^{4f}$; wherein t is 0 or 1, and wherein $R^{4e}$ and $R^{4f}$ are independently $C_{1-3}$alkyl, or $R^{4e}$ and $R^{4f}$, together with the nitrogen to which they are attached, form a 4, 5 or 6-membered saturated ring which ring is optionally substituted by one or more fluoro substituent.

7. The compound according to claim 1 or a pharmaceutically acceptable salt thereof wherein $R^4$ is selected from the group consisting of:
a) $C_{1-4}$alkyl optionally substituted by one, two or three fluoro;
d) a 5 or 6-membered, saturated heterocyclyl directly attached to the sulfone, via a ring carbon atom which heterocyclyl group is optionally substituted by one, two or three substituents independently selected from methyl, deuteromethyl and fluoro; and
which heterocyclyl group contains one ring-heteroatom selected from nitrogen and oxygen; and
e) a $C_{4-6}$cycloalkyl directly attached to the sulfone; which cycloalkyl group is optionally substituted by one or two substituents independently selected from the group consisting of fluoro, hydroxy, methoxy and -$NR^{4e}R^{4f}$; and wherein $R^{4e}$ and $R^{4f}$ are independently $C_{1-2}$alkyl, or $R^{4e}$ and $R^{4f}$, together with the nitrogen to which they are attached, form a 4, 5 or 6-membered saturated ring which ring is optionally substituted by one or more fluoro substituent.

8. The compound according to claim 1 or a pharmaceutically acceptable salt thereof, having the formula (Ic)

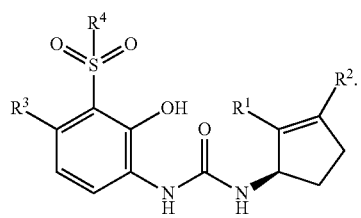

(Ic)

9. The compound according to claim 1, which is selected from the group consisting of:
(R)-1-(4-chloro-2-hydroxy-3-((4-methyltetrahydro-2H-pyran-4-yl)sulfonyl)phenyl)-3-(2-chlorocyclopent-2-en-1-yl)urea;
(R)-1-(3-(tert-butylsulfonyl)-4-cyano-2-hydroxyphenyl)-3-(2-methylcyclopent-2-en-1-yl)urea;
1-(4-chloro-2-hydroxy-3-((trans-3-(pyrrolidin-1-yl)cyclobutyl)sulfonyl)phenyl)-3-((R)-2-methylcyclopent-2-en-1-yl)urea;
1-(4-chloro-3-((trans-3-(dimethylamino)cyclobutyl)sulfonyl)-2-hydroxyphenyl)-3-((R)-2-methylcyclopent-2-en-1-yl)urea;
(R)-1-(4-chloro-3-((1,1-difluoroethyl)sulfonyl)-2-hydroxyphenyl)-3-(2-methylcyclopent-2-en-1-yl)urea;
1-(4-chloro-2-hydroxy-3-(((S)-3-methyltetrahydrofuran-3-yl)sulfonyl)phenyl)-3-((R)-2-methylcyclopent-2-en-11-yl)urea;
1-(4-chloro-2-hydroxy-3-(((R)-3-methyltetrahydrofuran-3-yl)sulfonyl)phenyl)-3-((R)-2-methylcyclopent-2-en-1-yl)urea;
1-(4-chloro-2-hydroxy-3-(((S)-3-methyltetrahydrofuran-3-yl)sulfonyl)phenyl)-3-((R)-2-chlorocyclopent-2-en-1-yl)urea; and
1-(4-chloro-2-hydroxy-3-(((R)-3-methyltetrahydrofuran-3-yl)sulfonyl)phenyl)-3-((R)-2-chlorocyclopent-2-en-1-yl)urea;
or a pharmaceutically acceptable salt thereof.

10. The compound according to claim 1 which is 1-(4-chloro-2-hydroxy-3-(((S)-3-methyltetrahydrofuran-3-yl)sulfonyl)phenyl)-3-((R)-2-methylcyclopent-2-en-1-yl)urea of formula (Id) or a pharmaceutically acceptable salt thereof

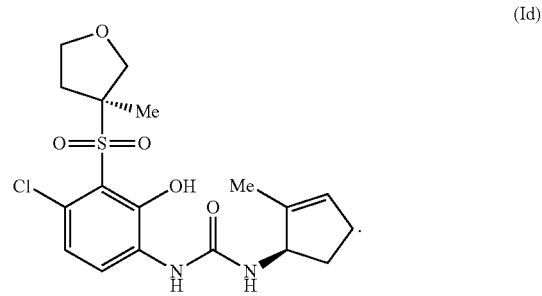 [SMILES: CC1=CCC[C@H]1NC(=O)Nc1ccc(Cl)c(S(=O)(=O)[C@@]2(C)CCOC2)c1O]

(Id)

11. The compound according to claim 10 or pharmaceutically acceptable salt thereof wherein the salt is piperazine salt.

12. A pharmaceutical composition comprising a) a compound defined in claim 1 or a pharmaceutically acceptable salt thereof and b) one or more pharmaceutically acceptable excipients.

* * * * *